(12) United States Patent
Smolke et al.

(10) Patent No.: US 10,738,335 B2
(45) Date of Patent: Aug. 11, 2020

(54) METHODS OF PRODUCING NOR-OPIOID AND NAL-OPIOID BENZYLISOQUINOLINE ALKALOIDS

(71) Applicant: Antheia, Inc., Menlo Park, CA (US)

(72) Inventors: Christina D. Smolke, Menlo Park, CA (US); Catherine Thodey, Mountain View, CA (US); Isis Trenchard, Redwood City, CA (US)

(73) Assignee: Antheia, Inc., Menlo Park, CA (US)

( * ) Notice: Subject to any disclaimer, the term of this patent is extended or adjusted under 35 U.S.C. 154(b) by 0 days.

(21) Appl. No.: 16/127,084

(22) Filed: Sep. 10, 2018

(65) Prior Publication Data

US 2019/0144900 A1    May 16, 2019

Related U.S. Application Data

(63) Continuation of application No. PCT/US2017/057237, filed on Oct. 18, 2017.

(60) Provisional application No. 62/473,215, filed on Mar. 17, 2017, provisional application No. 62/409,837, filed on Oct. 18, 2016.

(51) Int. Cl.
| | |
|---|---|
| C12P 17/18 | (2006.01) |
| C12N 9/02 | (2006.01) |
| C12N 9/06 | (2006.01) |
| C12N 9/04 | (2006.01) |
| C12N 9/14 | (2006.01) |
| C12N 15/85 | (2006.01) |
| C12P 17/12 | (2006.01) |
| C12N 9/90 | (2006.01) |

(52) U.S. Cl.
CPC .......... *C12P 17/182* (2013.01); *C12N 9/0006* (2013.01); *C12N 9/0028* (2013.01); *C12N 9/0071* (2013.01); *C12N 9/14* (2013.01); *C12N 9/90* (2013.01); *C12N 15/85* (2013.01); *C12P 17/12* (2013.01); *C12P 17/18* (2013.01); *C12Y 105/01027* (2013.01); *C12Y 114/16002* (2013.01); *C12Y 114/21004* (2013.01); *C12N 2015/8518* (2013.01); *C12Y 305/04016* (2013.01)

(58) Field of Classification Search
CPC ........ C12N 17/182; C12N 9/90; C12N 15/85; C12P 17/12; C12Y 305/040016
See application file for complete search history.

(56) References Cited

U.S. PATENT DOCUMENTS

| | | | |
|---|---|---|---|
| 6,067,749 A * | 5/2000 | Fist | A01H 4/001 47/58.1 R |
| 7,037,674 B1 | 5/2006 | Kutchan et al. | |
| 7,514,251 B2 | 4/2009 | Kutchan et al. | |
| 7,767,428 B2 | 8/2010 | Kutchan et al. | |
| 8,710,226 B2 | 4/2014 | Patel et al. | |
| 8,993,280 B2 | 3/2015 | Sato et al. | |
| 9,200,261 B2 | 12/2015 | Winzer et al. | |
| 9,447,444 B2 | 9/2016 | Winzer et al. | |
| 9,458,481 B2 | 10/2016 | Winzer et al. | |
| 9,725,732 B2 | 8/2017 | Winzer et al. | |
| 9,862,979 B2 | 1/2018 | Winzer et al. | |
| 9,926,329 B2 | 3/2018 | Huntley et al. | |
| 10,006,010 B2 | 6/2018 | Winzer et al. | |
| 2006/0185032 A1 | 8/2006 | Kutchan et al. | |
| 2008/0196123 A1 | 8/2008 | Kutchan et al. | |
| 2010/0075385 A1 | 3/2010 | Kutchan et al. | |
| 2014/0013465 A1 | 1/2014 | Coombs et al. | |
| 2014/0273109 A1 | 9/2014 | Smolke et al. | |
| 2016/0201101 A1 | 7/2016 | Facchini et al. | |
| 2016/0251688 A1 | 9/2016 | Siddiqui et al. | |
| 2016/0312256 A1 | 10/2016 | Facchini et al. | |
| 2016/0340704 A1 | 11/2016 | Martin et al. | |
| 2017/0058305 A1 | 3/2017 | Facchini et al. | |
| 2017/0130250 A1 | 5/2017 | Facchini et al. | |
| 2017/0198299 A1 | 7/2017 | Winzer et al. | |
| 2017/0267686 A1 | 9/2017 | Facchini et al. | |
| 2017/0280647 A1 | 10/2017 | Fist et al. | |
| 2017/0306301 A1 | 10/2017 | Martin et al. | |
| 2017/0362617 A1 | 12/2017 | Peralta-Yahya et al. | |
| 2018/0251801 A1 | 9/2018 | Aharoni et al. | |

FOREIGN PATENT DOCUMENTS

| | | |
|---|---|---|
| WO | WO-9802033 A1 | 1/1998 |
| WO | WO-0058333 A1 | 10/2000 |
| WO | WO-02101052 A2 | 12/2002 |
| WO | WO-2005021763 A2 | 3/2005 |

(Continued)

OTHER PUBLICATIONS

Abel et al., Synthesis of potential bupreneomorphine intermediates by selective microbial N- and O-demethylation. Biotechnol Lett., 2002, vol. 24: 1291-1294. (Year: 2002).*

Abel et al., The synthesis of bupreneomorphine intermediates by regioselective microbial N- and O-demethylation reactions using Cunninghamella echinulata NRRL 1384. Enz. Mirobial Technol., 2003: 743-748. (Year: 2003).*

Boonstra et al., Engineering novel biocatalytic routes for production of semisynthetic opiate drugs. Biomol. Eng., 2001, vol. 41: 41-47. (Year: 2001).*

(Continued)

*Primary Examiner* — Ganapathirama Raghu
(74) *Attorney, Agent, or Firm* — Wilson Sonsini Goodrich & Rosati

(57) ABSTRACT

A method of demethylizing an opioid to a nor-opioid is provided. The method comprises contacting an opioid with at least one enzyme. Contacting the opioid with the at least one enzyme converts the opioid to a nor-opioid. A method of converting a nor-opioid to a nal-opioid is provided. The method comprises contacting a nor-opioid with at least one enzyme. Contacting the nor-opioid with the at least one enzyme converts the nor-opioid to a nal-opioid.

11 Claims, 32 Drawing Sheets

Specification includes a Sequence Listing.

(56) References Cited

FOREIGN PATENT DOCUMENTS

| WO | WO-2006015887 A2 | 2/2006 |
| WO | WO-2009122436 A2 | 10/2009 |
| WO | WO-2011058446 A2 | 5/2011 |
| WO | WO-2011161431 A2 | 12/2011 |
| WO | WO-2012039438 A1 | 3/2012 |
| WO | WO-2015192233 A1 | 12/2015 |
| WO | WO-2016026048 A1 | 2/2016 |
| WO | WO-2016049364 A2 | 3/2016 |
| WO | WO-2016149821 A1 | 9/2016 |
| WO | WO-2016207643 A1 | 12/2016 |
| WO | WO-2017083632 A1 | 5/2017 |
| WO | WO-2017122011 A1 | 7/2017 |
| WO | WO-2018000089 A1 | 1/2018 |
| WO | WO-2018005553 A1 | 1/2018 |
| WO | WO-2018027324 A1 | 2/2018 |
| WO | WO-2018029282 A1 | 2/2018 |
| WO | WO-2018039749 A1 | 3/2018 |
| WO | WO-2018075670 A1 | 4/2018 |
| WO | WO-2018136654 A1 | 7/2018 |

OTHER PUBLICATIONS

Broun et al., Catalytic plasticity of fatty acid modification enzymes underlying chemical diversity of plant lipids. Science, 1998, vol. 282: 1315-1317. (Year: 1998).*

Devos et al., Practical limits of function prediction. Proteins: Structure, Function, and Genetics. 2000, vol. 41: 98-107. (Year: 2000).*

Dragan et al., Convenient gram-scale metabolite synthesis by engineering fission yeast strains expressing functional human P450 systems. 2011, vol. 163: 965-980. (Year: 2011).*

Kummer et al., Effect of the inhibition of CYP3A4 or CYP2D6 on the pharmacokinetics and pharmacodynamics of oxycodone. Eur J. Clin. Pharmacol., 2011, vol. 67: 63-71. (Year: 2011).*

Samer et al., The effects of CYP2D6 and CYP3A activities on the pharmacokinetics of immediate release oxycodone. Brit. J. Pharmacol., 2010, vol. 160: 907-918. (Year: 2010).*

Seffernick et al., Melamine deaminase and Atrazine chlorohydrolase: 98 percent identical but functionally different. J. Bacteriol., 2001, vol. 183 (8): 2405-2410. (Year: 2001).*

Whisstock et al., Prediction of protein function from protein sequence. Q. Rev. Biophysics., 2003, vol. 36 (3): 307-340. (Year: 2003).*

Witkowski et al., Conversion of b-ketoacyl synthase to a Malonyl Decarboxylase by replacement of the active cysteine with glutamine. Biochemistry, 1999, vol. 38: 11643-11650. (Year: 1999).*

Berenyi et al., Recent developments in the chemistry of thebaine and its transformation products as pharmacological products. curr. Med. Chem., 2009, vol. 16: 3215-3242 (Year: 2009).*

Bruce et al., Towards engineering pathways for the synthesis of analgesics and antitussive. Annals of New York Academy of Sciences, 1994: 85-99. (Year: 1994).*

Chaudhary V., Fungal biotransformation of morphine alkaloids. M.Sc., Thesis, Brock Univ., St. Catharines, Ontarioo, 2009, pp. 1-110. (Year: 2009).*

Romand et al., Characterization of oxycodone in vitro metabolism by human cytochrome P450 and UDP-glucuronosyltransferases. J. Pharma. Biomed. Analysis. 2017, vol. 144: 129-137. (Year: 2017).*

Galanie et al. Complete biosynthesis of opioids in yeast. Science 349(6252):1095-1100 (2015).

Grönlund, J. Effect of Cytochrome P450 2d6 and 3a Enzyme Inhibition on the Metabolism of Oxycodone. Dissertation (online). University of Turku. Turku, Finland (2011). 88 pages. Retrieved from the internet Jun. 14, 2018, available at: http://www.utupub.fi/bitstream/handle/10024/69970/AnnalesD971Gr%C3%B6nlund.pdf?sequence=1.

Hagel et al. Biochemistry and occurrence of O-demethylation in plant metabolism. Frontiers in Physiology. vol. 1 Article 14 (2010). 7 pages.

Hudlicky, T. Recent advances in process development for opiate-derived pharmaceutical agents. Canadian Journal of Chemistry. 93(5):492-501 (2015).

Kumarihamy et al. In Vitro Opioid Receptor Affinity and in Vivo Behavioral Studies of Nelumbo nucifera Flower. J Ethnopharmacol. 174:57-65 (2015).

Kutchan et al. Characterization and Mechanism of the Berberine Bridge Enzyme, a Covalently Flavinylated Oxidase of Benzophenanthridine Alkaloid Biosynthesis in Plants. Journal of Biochemical Chemistry 270(41):24475-24481 (1995).

Lalovic et al. Quantitative Contribution of Cyp2d6 and Cyp3a to Oxycodone Metabolism in Human Liver and Intestinal Microsomes. Drug Metabolism and Disposition. 32(4):447-454 (2004).

PCT/US2017/057237 International Search Report and Written Opinion dated Mar. 19, 2018.

\* cited by examiner

\>RQNK-2062398
MELQYISYFQPTSSVVALLLALVSILSSVVVLRKTFLNNYSSSPASSTKTAVLSH
QRQQSCALPISGLLHIFMNKNGLIHVTLGNMADKYGPIFSFPTGSHRTLVVSS
WEMVKECFTGNNDTAFSNRPIPLAFKTIFYACGGIDSYGLSSVPYGKYWREL
RKVCVHNLLSNQQLLKFRHLIISQVDTSFNKLYELCKNSEDNHGNYTTTTTA
AGMVRIDDWLAELSFNVIGRIVCGFQSGPKTGAPSRVEQFKEAINEASYFMS
TSPVSDNVPMLGWIDQLTGLTRNMKHCGKKLDLVVESIINDHRQKRRFSRTK
GGDEKDDEQDDFIDICLSIMEQPQLPGNNNPSQIPIKSIVLDMIGGGTDTTKLT
TIWTLSLLLNNPHVLDKAKQEVDAHFRTKRRSTNDAAAAVVDFDDIRNLVYIQ
AIIKESMRLYPASPVVERLSGEDCVVGGFHVPAGTRLWANVWKMQRDPKVW
DDPLVFRPDRFLSDEQKMVDVRGQNYELLPFGAGRRVCPGVSFSLDLMQLV
LTRLILEFEMKSPSGKVDMTATPGLMSYKVIPLDILLTHRRIKPCVQSAASERD
MESSGVPVITLGSGKVMPVLGMGTFEKVGKSERERLAILKAIEVGYRYFDT
AAAYETEEVLGEAIAEALQLGLVKSRDELFISSMLWCTDAHADRVLLALQNSL
RNLKLEYVDLYMLPFPASLKPGKITMDIPEEDICRMDYRSVWAAMEECQNLG
FTKSIGVSNFSCKKLQELMATANIPPAVNQVEMSPAFQQKKLREYCNANNILV
SAISVLGSNGTPWGSNAVLGSEVLKKIAMAKGKSVAQVSMRWVYEQGASLV
VKSFSEERLRENLNIFDWELTKEDHEKIGEIPQCRILSAYFLVSPNGPFKSQEE
LWDDEA*

FIG. 4

** results in mixture of R- and S-BIA

Genotype:

YDR514CΔ::$P_{PYK1}$-PsCNMT-$T_{MFa1}$, $P_{PGK1}$-Ps6OMT-$T_{PHO5}$, $P_{TPI1}$-DRS-DRR-$T_{STE2}$ LEU2 marker, $P_{TEF1}$-PsCPR-$T_{CYC1}$, $P_{GPD}$-BsCYP80A1-$T_{ADH1}$

Schematic representation:

Four genetic constructs integrated into the yeast genome:
1. YBR197CΔ::$P_{TPI1}$-RnSepR-$T_{STE2}$, $P_{TEF1}$-RnPTPS-$T_{CYC1}$, *KanMX marker*, $P_{GPD}$-RnQDHPR-$T_{AHD1}$, $P_{PGK1}$-RnPCD-$T_{PHO5}$
2. HIS3 Δ ::$P_{GPD}$-RnTyrH-$T_{ADH1}$, $P_{TPI1}$-PpDODC-$T_{STE2}$, *HIS5 marker*, $P_{TEF1}$-RnDHFR-$T_{CYC1}$, $P_{PGK1}$-CjNCS-$T_{PHO5}$
3. YDR514CΔ::$P_{PYK1}$-PsCNMT-$T_{MFa1}$, $P_{PGK1}$-Ps6OMT-$T_{PHO5}$, $P_{GPD}$-EcCYP80B1-$T_{ADH1}$, *LEU2 marker*, $P_{TEF1}$-PsCPR-$T_{CYC1}$, $P_{TPI1}$-Ps4OMT-$T_{STE2}$
4. ARO4Δ::$P_{TEF1}$-ARO4$^{FBR}$-$T_{CYC1}$, $P_{GPD}$-ARO7$^{FBR}$-$T_{ADH1}$, *HygR marker*, $P_{PGK1}$-TKL1-$T_{PHO5}$, $P_{TPI1}$-ARO10-$T_{STE2}$

Schematic of the integrated constructs indicating the orientation of each expression cassette:

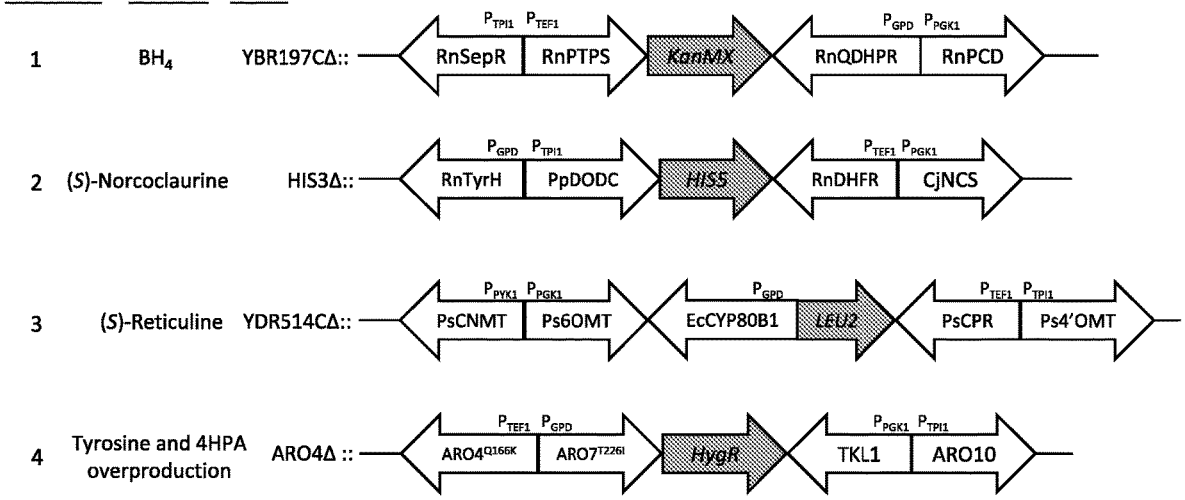

FIG. 22

*3-O-demethylase (ODM):*

| | Substrate | Product |
|---|---|---|
| | Substrate | Product |
| | Codeine | Morphine |
| | Oxycodone | Oxymorphone |
| | Thebaine | Oripavine |
| | Hydrocodone | Hydromorphone |
| | Dihydrocodeine | Dihydromorphine |
| | 14-hydroxycodeine | 14-hydroxymorphine |
| | Codeinone | Morphinone |
| | 14-hydroxycodeinone | 14-hydroxymorphinone |

Figure 23

N-demethylase (NDM):

SUBSTRATE → PRODUCT + Formaldehyde

| A | Substrate R = CH₃ | R = H | Product R = CH₃ | R = H |
|---|---|---|---|---|
| HO | Codeine | Morphine | Norcodeine | Normorphine |
| O, HO | Oxycodone | Oxymorphone | Noroxycodone | Noroxymorphone |
| H₃C-O | Thebaine | Oripavine | Northebaine | Nororipavine |
| O | Hydrocodone | Hydromorphone | Norhydrocodone | Norhydromorphone |
| HO | Dihydrocodeine | Dihydromorphine | Nordihydrocodeine | Nordihydromorphine |
| HO, HO | 14-hydroxycodeine | 14-hydroxymorphine | Nor-14-hydroxycodeine | Nor-14-hydroxymorphine |
| O | Codeinone | Morphinone | Norcodeinone | Normorphinone |
| O, HO | 14-hydroxycodeinone | 14-hydroxymorphinone | Nor-14-hydroxycodeinone | Nor-14-hydroxymorphinone |

Figure 24

Example reaction scheme:

Plasmid/YAC vectors for enzyme expression and engineering

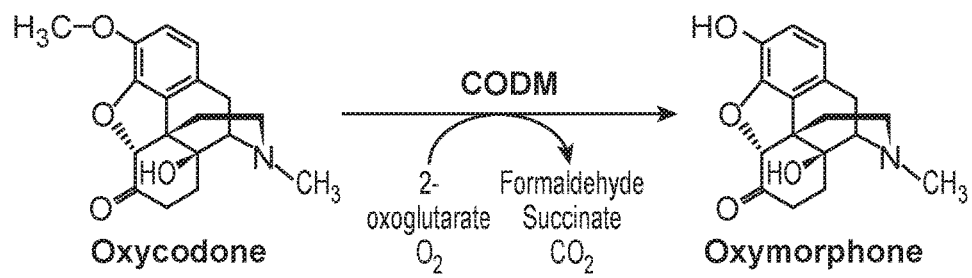
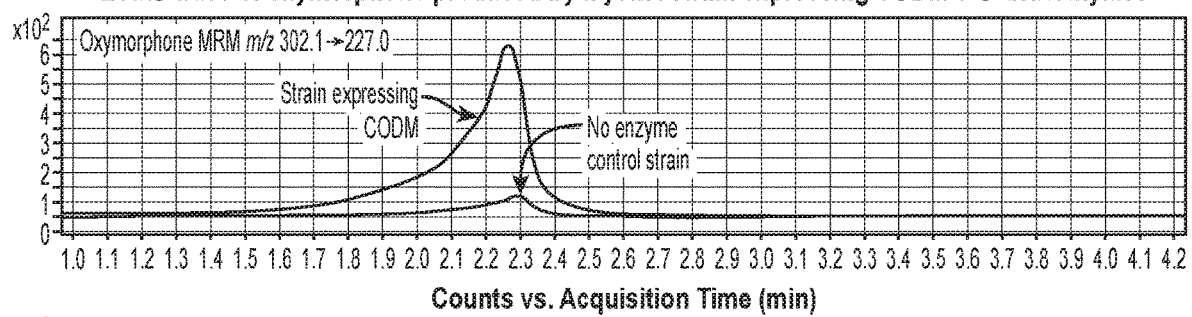
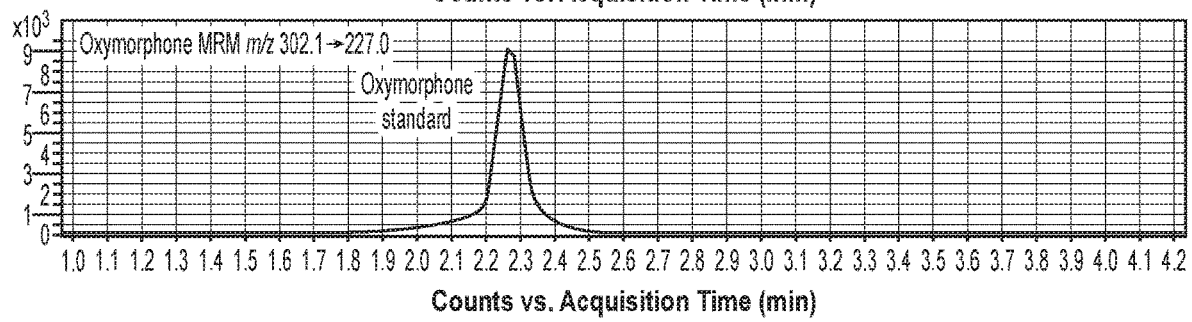
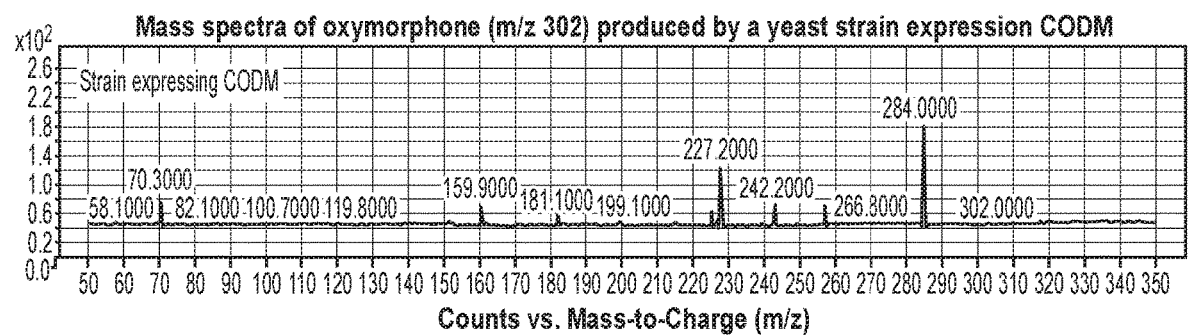
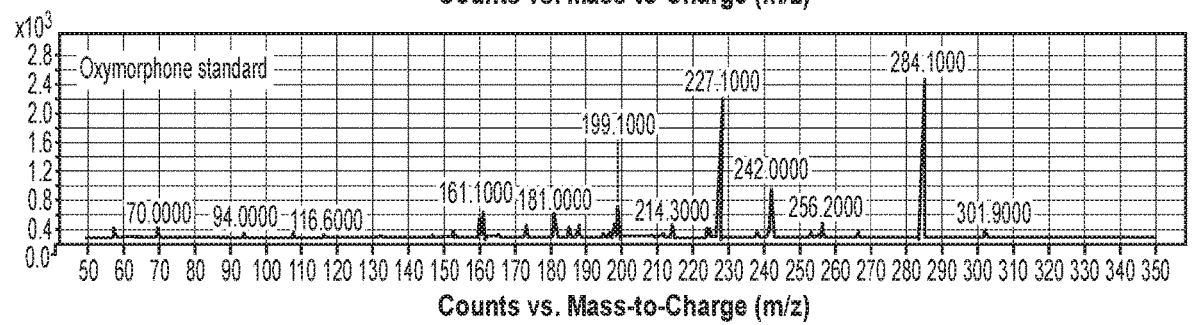
FIG. 29

METHODS OF PRODUCING NOR-OPIOID AND NAL-OPIOID BENZYLISOQUINOLINE ALKALOIDS

CROSS-REFERENCE

This application is a continuation application of International Patent Application No. PCT/US2017/057237, filed Oct. 18, 2017, which application claims the benefit of U.S. Provisional Application No. 62/409,837, filed Oct. 18, 2016, and U.S. Provisional Application No. 62/473,215, filed Mar. 17, 2017, which applications are incorporated herein by reference.

SEQUENCE LISTING

The instant application contains a Sequence Listing which has been submitted electronically in ASCII format and is hereby incorporated by reference in its entirety. Said ASCII copy, created on Dec. 10, 2018, is named 47840-706_301_SL.txt and is 515,044 bytes in size.

BACKGROUND OF THE INVENTION

Medicinal opioids are used for treating moderate to severe pain, but may exhibit addictive properties. Due to the mechanism by which medicinal opioids relieve pain, these medications are among the most effective painkillers in modern medicine. Additionally, however, medicinal opioids are also widely abused. In addressing the use of medicinal opioids, policy makers are tasked with balancing the under-treatment of pain, while mitigating the risk for opioid abuse. Pharmacotherapies have proven effective in treating and preventing opioid addiction but the high cost of these therapeutics is a limiting factor in the scope and reach of treatment programs.

SUMMARY OF THE INVENTION

The present disclosure provides methods for demethylating a first opioid to a second opioid. The present disclosure further provides methods for demethylating an opioid to a nor-opioid. Additionally, the present disclosure provides methods for altering an opioid to a nal-opioid. Further, the present disclosure provides engineered cells for producing a nor-opioid from an opioid present within the engineered cell. The present disclosure also provides engineered cells for producing a nal-opioid from a nor-opioid present within the engineered cell.

An aspect of the invention provides a method for demethylating a first opioid to a second opioid. The method comprises contacting the first opioid with at least one enzyme, wherein contacting the first opioid with the at least one enzyme converts the first opioid to a second opioid through loss of an O-linked methyl group, wherein the first opioid is not selected from the group consisting of codeine and thebaine.

Another aspect of the invention provides a method of demethylating an opioid to a nor-opioid. The method comprises contacting the first opioid with at least one enzyme, wherein contacting the first opioid with the at least one enzyme converts the first opioid to a second opioid through loss of an O-linked methyl group. The method also comprises contacting the second opioid with at least one enzyme, wherein contacting the opioid with the at least one enzyme converts the second opioid to a nor-opioid through loss of an N-linked methyl group.

An additional aspect of the invention provides another method of demethylating an opioid to a nor-opioid. The method comprises contacting the opioid with at least one enzyme, wherein contacting the opioid with the at least one enzyme converts the opioid to a nor-opioid through removal of an N-linked methyl group from the opioid, wherein the opioid is not thebaine when the opioid contacts the at least one enzyme in vitro.

A further aspect of the invention provides a method of altering an opioid to a nal-opioid. The method comprises contacting the opioid with at least a first enzyme, wherein contacting the opioid with the at least a first enzyme converts the opioid to a nor-opioid through removal of an N-linked methyl group from the opioid. The method also comprises contacting the nor-opioid with at least a second enzyme, wherein contacting the nor-opioid with the at least a second enzyme in the presence of a cofactor converts the nor-opioid to a nal-opioid through transfer of a sidechain from the cofactor.

Another aspect of the invention provides another method of altering an opioid to a nal-opioid. The method comprises contacting the first opioid with at least one enzyme, wherein contacting the first opioid with the at least one enzyme converts the first opioid to a second opioid through loss of an O-linked methyl group. The method also comprises contacting the second opioid with at least a second enzyme, wherein contacting the opioid with the at least a second enzyme converts the second opioid to a nor-opioid through loss of an N-linked methyl group. Additionally, the method comprises contacting the nor-opioid with at least a third enzyme, wherein contacting the nor-opioid with the at least a third enzyme in the presence of a cofactor converts the nor-opioid to a nal-opioid through transfer of a sidechain from the cofactor.

An additional aspect of the invention provides an engineered cell that produces a nor-opioid from an opioid present within the engineered cell, the engineered cell comprising a heterologous coding sequence encoding an N-demethylase produced by the engineered cell, wherein the N-demethylase converts the opioid within the engineered cell to the nor-opioid and wherein the nor-opioid is produced within the engineered cell.

A further aspect of the invention provides an engineered cell that produces a nal-opioid from a nor-opioid present within the engineered cell, the engineered cell comprising a heterologous coding sequence encoding an N-methyltransferase produced by the engineered cell, wherein the N-methyltransferase converts the nor-opioid within the engineered cell to the nal-opioid.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the invention will be obtained by reference to the following detailed description that sets forth illustrative embodiments, in which the principles of the invention are utilized, and the accompanying drawings of which:

FIG. 4 illustrates an amino acid sequence of a CYP-COR enzyme (SEQ ID NO: 1), in accordance with embodiments of the invention.

FIG. 14 illustrates an LC/MS-MS analysis of yeast strains engineered to convert (S)-reticuline to salutaridine, in accordance with embodiments of the invention.

FIG. 22 illustrates yeast platform strains for the production of the key branch point intermediate reticuline from L-tyrosine, in accordance with embodiments of the invention.

FIG. 23 illustrates an enzyme having opioid 3-O-demethylase activity, in accordance with embodiments of the invention.

FIG. 24 illustrates an enzyme having opioid N-demethylase activity, in accordance with embodiments of the invention.

FIG. 29 illustrates the functional expression of CODM, in accordance with embodiments of the invention.

DETAILED DESCRIPTION OF THE INVENTION

Figure 1:
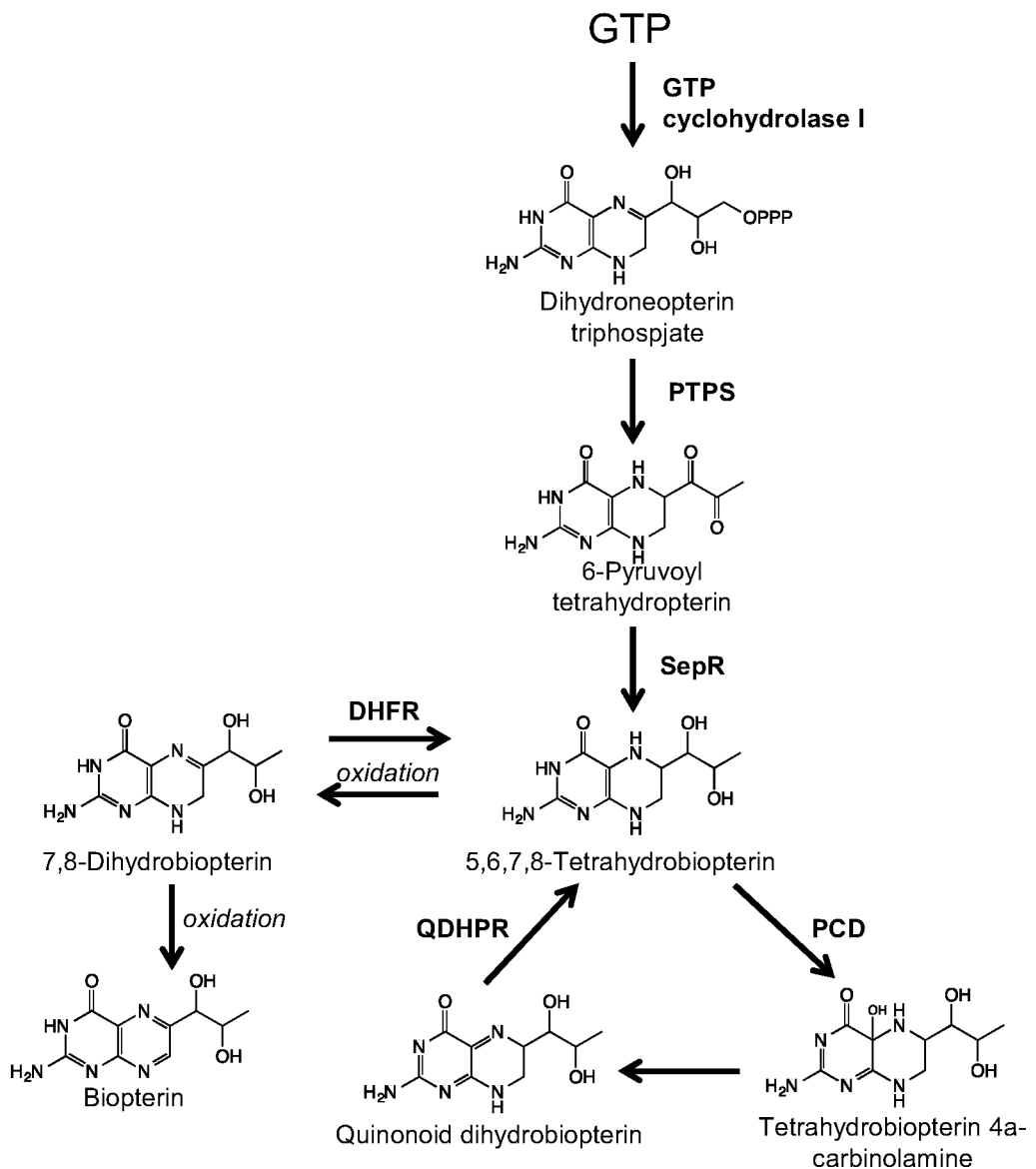
FIG. 1 illustrates examples of synthesis, recycling, and salvage pathways of tetrahydrobiopterin, in accordance with embodiments of the invention.

Nal-opioids are an important class of pharmacotherapies for combating opioid addiction and opioid-associated side effects. Opiates like codeine and morphine are plant molecules from opium poppy, which have a unique five-ring structure that allows them to bind μ-opioid receptors in the brain, spine, gut, and peripheral sensors and mimic the body's natural attenuation of pain. These same opiate molecules can be modified to act as antagonists, e.g., naltrexone and naloxone. In some examples opioid molecules can be modified by introducing chemical modifications that permit binding to opioid receptors but prevent activation of the downstream signaling response. Other molecules, such as buprenorphine, may bind to opioid receptors and act as mixed partial agonists.

The suite of antagonist and mixed partial-agonist opioids, collectively called nal-opioids, may form a toolkit of competitive modulators that can occupy receptor binding sites in patients that have ingested a strong opioid agonist. As examples, in the addicted patient population nal-opioids may be used for: (1) treating overdose, by administering a strong antagonist, such as naloxone; (2) detoxification, by managing symptoms with mixed partial agonists, such as buprenorphine; and/or (3) maintenance, by blocking the reward response, for example with a buprenorphine/naloxone combination drug. In the patient population with severe pain, nal-opioids may be used for: (4) prevention, e.g. through abuse deterrent combination agonist/antagonist formulations, such as morphine/naltrexone combinations, which may block euphoria and intoxication when the drug is misused; and/or (5) reducing side effects by administering peripherally acting antagonists that may displace opioid agonists from receptors in the gut where they may cause constipation, for example, a polymer conjugate of naloxone (Movantik™).

The raw starting materials for nal-opioid synthesis are natural opiates, such as thebaine, that are extracted from opium poppy drug crops. Traditionally, these molecules are then chemically modified to the semi-synthetic antagonists, weak agonists, and mixed partial agonists through a series of inefficient reaction steps that require the use of catalysts, solvents, reagents, and purification methods to isolate the nal-opioid product from the starting material and reaction intermediates. The current semi-synthetic production methods are inefficient and add substantial cost to the overall process.

The present disclosure provides methods for the production of diverse nal-opioids in engineered host cells. The present disclosure also provides methods for the production of diverse nor-opioids in engineered host cells. Additionally, the present disclosure provides methods for the production of an O-demethylase and an N-demethylase in engineered host cells. In particular cases, the disclosure provides methods for producing nor-opioid products through the demethylization of an opioid to a nor-opioid in an engineered host cell. In further particular cases, the present disclosure provides methods for producing diverse nal-opioids by modifying a nor-opioid with an enzyme that can add an N-linked side chain, such as an N-methyltransferase.

The present disclosure provides methods for the production of nal-opioids and nor-opioid compounds in engineered host cells. Throughout this disclosure the term "compound" may be used to refer to something comprising two or more elements, for example a nal-opioid molecule, or a nal-opioid composition. A nal-opioid compound may refer to a largely pure composition of a nal-opioid, or a composition of a nal-opioid which may or may not contain impurities.

Nal-Opioids of Interest

Host cells which produce BIAs of interest are provided. In some examples, engineered strains of host cells such as the engineered strains of embodiments discussed herein may provide a platform for producing Nal-opioids of interest including, but not limited to: naltrexone, naloxone, nalmefene, nalorphine, nalorphine, nalodeine, naldemedine, naloxegol, 6β-naltrexol, naltrindole, methylnaltrexone, methylsamidorphan, alvimopan, axelopran, bevenpran, dinicotinate, levallorphan, samidorphan, buprenorphine, dezocine, eptazocine, butorphanol, levorphanol, nalbuphine, pentazocine, phenazocine, norbinaltorphimine, and diprenorphine.

Nor-Opioids of Interest

Host cells which produce nor-opioids of interest are provided. In some examples, engineered strains of host cells such as the engineered strains of embodiments discussed herein may provide a platform for producing Nor-opioids of interest including, but not limited to: norcodeine, noroxycodone, northebaine, norhydrocodone, nordihydro-codeine, nor-14-hydroxy-codeine, norcodeinone, nor-14-hydroxy-codeinone, normorphine, noroxymorphone, nororipavine, norhydro-morphone, nordihydro-morphine, nor-14-hydroxy-morphine, normorphinone, nor-14-hydroxy-morphinone.

Benzylisoquinoline Alkaloids (BIAs) of Interest

Host cells which produce BIAs of interest are provided. In some examples, engineered strains of host cells such as the engineered strains of embodiments discussed herein may provide a platform for producing benzylisoquinoline alkaloids of interest and modifications thereof across several structural classes including, but not limited to, precursor BIAs, benzylisoquinolines, promorphinans, morphinans and others. Each of these classes is meant to include biosynthetic precursors, intermediates, and metabolites thereof, of any convenient member of an engineered host cell biosynthetic pathway that may lead to a member of the class. Non-limiting examples of compounds are given below for each of these structural classes. In some cases, the structure of a given example may or may not be characterized itself as a benzylisoquinoline alkaloid. In some cases, the present chemical entities are meant to include all possible isomers, including single enantiomers, racemic mixtures, optically pure forms, mixtures of diastereomers, and intermediate mixtures.

BIA precursors may include, but are not limited to, norcoclaurine (NC) and norlaudanosoline (NL), as well as NC and NL precursors, such as tyrosine, tyramine, 4-hydroxyphenylacetaldehyde (4-HPA), 4-hydroxyphenylpyruvic acid (4-HPPA), L-3,4-dihydroxyphenylalanine (L-DOPA), 3,4-dihydroxyphenylacetaldehyde (3,4-DHPA), and dopamine. In some embodiments, the one or more BIA precursors are 3,4-dihydroxyphenylacetaldehyde (3,4-DHPA) and dopamine. In certain instances, the one or more BIA precursors are 4-hydroxyphenylacetaldehyde (4-HPA) and dopamine. In particular, NL and NC may be synthesized, respectively, from precursor molecules via a Pictet-Spengler condensation reaction, where the reaction may occur spontaneously or may by catalyzed by any convenient enzymes.

Benzylisoquinolines may include, but are not limited to, norcoclaurine, norlaudanosoline, coclaurine, 3'-hydroxycoclaurine, 4'-O-methylnorlaudanosoline, 4'-O-methyl-laudanosoline, N-methylnorcoclaurine, laudanosoline, N-methylcoclaurine, 3'-hydroxy-N-methylcoclaurine, reticuline, norreticuline, papaverine, laudanine, laudanosine, tetrahydropapaverine, 1,2-dihydropapaverine, and orientaline.

Promorphinans may include, but are not limited to, salutaridine, salutaridinol, and salutaridinol-7-O-acetate.

Morphinans may include, but are not limited to, thebaine, codeinone, codeine, morphine, morphinone, oripavine, neopinone, neopine, neomorphine, hydrocodone, dihydrocodeine, 14-hydroxycodeinone, oxycodone, 14-hydroxycodeine, morphinone, hydromorphone, dihydromorphine, dihydroetorphine, ethylmorphine, etorphine, metopon, buprenorphine, pholcodine, and heterocodeine.

Host Cells

Any convenient cells may be utilized in the subject host cells and methods. In some cases, the host cells are non-plant cells. In some instances, the host cells may be characterized as microbial cells. In certain cases, the host cells are insect cells, vertebrate cells, mammalian cells, plant cells, fungal cells, bacterial cells, or yeast cells. Any convenient type of host cell may be utilized in producing the subject nor-opioid- or nal-opioid-producing cells, see, e.g., US2008/0176754, and US2014/0273109 the disclosures of which are incorporated by reference in their entirety. Host cells of interest include, but are not limited to, bacterial cells, such as Bacillus subtilis, Escherichia coli, Streptomyces, and Salmonella typhimuium cells, insect cells such as Drosophila melanogaster S2 and Spodoptera frugiperda Sf9 cells, mammalian cells such as HeLa and 293 cells, plant cells such as Tobacco BY-2 cells, and yeast cells such as Saccharomyces cerevisiae, Schizosaccharomyces pombe, and Pichia pastoris cells. In some examples, the host cells are yeast cells or E. coli cells. In some cases, the host cell is a yeast cell. In some instances, the host cell is from a strain of yeast engineered to produce a nor-opioid or nal-opioid BIA of interest, such as a northebaine or naloxone. In some instances, the host cell is from a strain of yeast engineered to produce an enzyme of interest. In some instances, the host cell is from a strain of yeast engineered to produce an O-demethylase. The O-demethylase may be able to convert a substrate, such as a first opioid, into a second opioid. In some instances, the host cell is from a strain of yeast engineered to produce an N-demethylase. The N-demethylase may be able to convert a substrate, such as a second opioid, into a nor-opioid. In some instances, the host cell is from a strain of yeast engineered to produce a methyltransferase. Additionally the methyltransferase may be able to convert a nor-opioid into a nal-opioid. In some instances, the host cell is from a strain of yeast engineered to produce an epimerase. The epimerase may have an oxidase and a reductase. Additionally, the epimerase may be able to convert an (S)-1-benzylisoquinoline alkaloid to an (R)-1-benzylisoquinoline alkaloid. Further, the epimerase may be separated into smaller enzymes that retain oxidase or reductase activity so as to be used to convert an (S)-1-benzylisoquinoline alkaloid to an (R)-1-benzylisoquinoline alkaloid.

Any of the host cells described in US2008/0176754 and US2014/0273109 by Smolke et al. may be adapted for use in the subject cells and methods. In certain embodiments, the yeast cells may be of the species Saccharomyces cerevisiae (S. cerevisiae). In certain embodiments, the yeast cells may be of the species Schizosaccharomyces pombe. In certain embodiments, the yeast cells may be of the species Pichia pastoris. Yeast is of interest as a host cell because cytochrome P450 proteins are able to fold properly into the endoplasmic reticulum membrane so that their activity is maintained. In examples, cytochrome P450 proteins are involved in some biosynthetic pathways of interest. In additional examples, cytochrome P450 proteins are involved in the production of BIAs of interest such as naloxone or naltrexone. In further examples, cytochrome P450 proteins are involved in the production of an enzyme of interest, such as an epimerase having an oxidase and a reductase.

Yeast strains of interest that may find use in the invention include, but are not limited to, CEN.PK (Genotype: MATa/α ura3-52/ura3-52 trp1-289/trp1-289 leu2-3_112/leu2-3_112 his3 Δ1/his3 Δ1 MAL2-8C/MAL2-8C SUC2/SUC2), S288C, W303, D273-10B, X2180, A364A, Σ1278B, AB972, SKI, and FL100. In certain cases, the yeast strain is any of S288C (MATa; SUC2 mal mel gal2 CUP1 flo1 flo8-1 hap1), BY4741 (MATα; his3Δ1; leu2Δ0; met15Δ0; ura3Δ0), BY4742 (MATα; his3Δ1; leu2Δ0; lys2Δ0; ura3Δ0), BY4743 (MATa/MATα; his3Δ1/his3Δ1; leu2Δ0/leu2Δ0; met15Δ0/MET15; LYS2/lys2Δ0; ura3Δ0/ura3Δ0), and WAT11 or W(R), derivatives of the W303-B strain (MATa; ade2-1; his3-11, -15; leu2-3, -112; ura3-1; canR; cyr+) which express the Arabidopsis thaliana NADPH-P450 reductase ATR1 and the yeast NADPH-P450 reductase CPR1, respectively. In another embodiment, the yeast cell is W303alpha (MATα; his3-11,15 trp1-1 leu2-3 ura3-1 ade2-1). The identity and genotype of additional yeast strains of interest may be found at EUROSCARF (web.uni-frankfurt.de/fb15/mikro/euroscarf/col_index.html).

In some instances the host cell is a fungal cell. In certain embodiments, the fungal cells may be of the Aspergillus species and strains include Aspergillus niger (ATCC 1015, ATCC 9029, CBS 513.88), Aspergillus oryzae (ATCC 56747, RIB40), Aspergillus terreus (NIH 2624, ATCC 20542) and Aspergillus nidulans (FGSC A4).

In certain embodiments, heterologous coding sequences may be codon optimized for expression in Aspergillus sp. and expressed from an appropriate promoter. In certain embodiments, the promoter may be selected from phosphoglycerate kinase promoter (PGK), MbfA promoter, cytochrome c oxidase subunit promoter (CoxA), SrpB promoter, TvdA promoter, malate dehydrogenase promoter (MdhA), beta-mannosidase promoter (ManB). In certain embodiments, a terminator may be selected from glucoamylase terminator (GlaA) or TrpC terminator. In certain embodiments, the expression cassette consisting of a promoter, heterologous coding sequence, and terminator may be expressed from a plasmid or integrated into the genome of the host. In certain embodiments, selection of cells maintaining the plasmid or integration cassette may be performed with antibiotic selection such as hygromycin or nitrogen source utilization, such as using acetamide as a sole nitrogen source. In certain embodiments, DNA constructs may be introduced into the host cells using established transformation methods such as protoplast transformation, lithium acetate, or electroporation. In certain embodiments, cells may be cultured in liquid ME or solid MEA (3% malt extract, 0.5% peptone, and +1.5% agar) or in Vogel's minimal medium with or without selection.

In some instances the host cell is a bacterial cell. The bacterial cell may be selected from any bacterial genus. Examples of genuses from which the bacterial cell may come include Anabaena, Arthrobacter, Acetobacter, Acetobacterium, Bacillus, Bifidobacterium, Brachybacterium, Brevibacterium, Carnobacterium, Clostridium, Corynebacterium, Enterobacter, Escherichia, Gluconacetobacter, Gluconobacter, Hafnia, Halomonas, Klebsiella, Kocuria, Lactobacillus, Leucononstoc, Macrococcus, Methylomonas, Methylobacter, Methylocella, Methylococcus, Microbacterium, Micrococcus, Microcystis, Moorella, Oenococcus, Pediococcus, Prochlorococcus, Propionibacterium, Proteus, Pseudoalteromonas, Pseudomonas, Psychrobacter, Rhodobacter, Rhodococcus, Rhodopseudomonas, Serratia, Staphylococcus, Streptococcus, Streptomyces, Synechococcus, Synechocystis, Tetragenococcus, Weissella, and Zymomonas. Examples of bacterial species which may be used with the methods of this disclosure include Arthrobacter nicotianae, Acetobacter aceti, Arthrobacter arilaitensis, Bacillus cereus, Bacillus coagulans, Bacillus licheniformis, Bacillus pumilus, Bacillus sphaericus, Bacillus stearothermophilus, Bacillus subtilis, Bifidobacterium adolescentis, Brachybacterium tyrofermentans, Brevibacterium linens, Carnobacterium divergens, Corynebacterium flavescens, Enterococcus faecium, Gluconacetobacter europaeus, Gluconacetobacter johannae, Gluconobacter oxydans, Hafnia alvei, Halomonas elongata, Kocuria rhizophila, Lactobacillus acidifarinae, Lactobacillus jensenii, Lactococcus lactis, Lactobacillus yamanashiensis, Leuconostoc citreum, Macrococcus caseolyticus, Microbacterium foliorum, Micrococcus lylae, Oenococcus oeni, Pediococcus acidilactici, Propionibacterium acidipropionici, Proteus vulgaris, Pseudomonas fluorescens, Psychrobacter celer, Staphylococcus condimenti, Streptococcus thermophilus, Streptomyces griseus, Tetragenococcus halo-

*philus, Weissella cibaria, Weissella koreensis, Zymomonas mobilis, Corynebacterium glutamicum, Bifidobacterium bifidum/breve/longum, Streptomyces lividans, Streptomyces coelicolor, Lactobacillus plantarum, Lactobacillus sakei, Lactobacillus casei, Pseudoalteromonas citrea, Pseudomonas putida, Clostridium ljungdahlii/aceticum/acetobutylicum/beijerinckii/butyricum,* and *Moorella themocellum/thermoacetica.*

In certain embodiments, the bacterial cells may be of a strain of *Escherichia coli*. In certain embodiments, the strain of *E. coli* may be selected from BL21, DH5α, XL1-Blue. HB101, BL21, and K12, In certain embodiments, heterologous coding sequences may be codon optimized for expression in *E. coli* and expressed from an appropriate promoter. In certain embodiments, the promoter may be selected from T7 promoter, tac promoter, trc promoter, atetracycline-inducible promoter (tet), lac operon promoter (lac), lacO1 promoter. In certain embodiments, the expression cassette consisting of a promoter, heterologous coding sequence, and terminator may be expressed from a plasmid or integrated into the genome. In certain embodiments, the plasmid is selected from pUC19 or pBAD. In certain embodiments, selection of cells maintaining the plasmid or integration cassette may be performed with antibiotic selection such as kanamycin, chloramphenicol, streptomycin, spectinomycin, gentamycin, erythromycin or ampicillin. In certain embodiments, DNA constructs may be introduced into the host cells using established transformation methods such as conjugation, heat shock chemical transformation, or electroporation. In certain embodiments, cells may be cultured in liquid Luria-Bertani (LB) media at 37° C. with or without antibiotics.

In certain embodiments, the bacterial cells may be a strain of *Bacillus subtilis*. In certain embodiments, the strain of *B. subtilis* may be selected from 1779, GP25, RO-NN-1, 168, BSn5, BEST195, 1A382, and 62178. In certain embodiments, heterologous coding sequences may be codon optimized for expression in *Bacillus* sp. and expressed from an appropriate promoter. In certain embodiments, the promoter may be selected from grac promoter, p43 promoter, or trnQ promoter. In certain embodiments, the expression cassette consisting of the promoter, heterologous coding sequence, and terminator may be expressed from a plasmid or integrated into the genome. In certain embodiments, the plasmid is selected from pHP13 pE194, pC194, pHT01, or pHT43. In certain embodiments, integrating vectors such as pDG364 or pDG1730 may be used to integrate the expression cassette into the genome. In certain embodiments, selection of cells maintaining the plasmid or integration cassette may be performed with antibiotic selection such as erythromycin, kanamycin, tetracycline, and spectinomycin. In certain embodiments, DNA constructs may be introduced into the host cells using established transformation methods such as natural competence, heat shock, or chemical transformation. In certain embodiments, cells may be cultured in liquid Luria-Bertani (LB) media at 37° C. or M9 medium plus glucose and tryptophan.

Genetic Modifications to Host Cells

The host cells may be engineered to include one or more modifications (such as two or more, three or more, four or more, five or more, or even more modifications) that provide for the production of BIAs of interest. Additionally or alternatively, the host cells may be engineered to include one or more modifications (such as two or more, three or more, four or more, five or more, or even more modifications) that provide for the production of enzymes of interest. In some cases, a modification is a genetic modification, such as a mutation, addition, or deletion of a gene or fragment thereof, or transcription regulation of a gene or fragment thereof. As used herein, the term "mutation" refers to a deletion, insertion, or substitution of an amino acid(s) residue or nucleotide(s) residue relative to a reference sequence or motif. The mutation may be incorporated as a directed mutation to the native gene at the original locus. In some cases, the mutation may be incorporated as an additional copy of the gene introduced as a genetic integration at a separate locus, or as an additional copy on an episomal vector such as a 2μ or centromeric plasmid. In certain instances, the substrate inhibited copy of the enzyme is under the native cell transcriptional regulation. In some instances, the substrate inhibited copy of the enzyme is introduced with engineered constitutive or dynamic regulation of protein expression by placing it under the control of a synthetic promoter. In some examples, the object of one or more modifications may be a native gene. In some examples, the object of one or more modifications may be a non-native gene. In some examples, a non-native gene may be inserted into a host cell. In further examples, a non-native gene may be altered by one or more modifications prior to being inserted into a host cell.

An engineered host cell may overproduce one or more nor-opioid BIAs of interest. An engineered host cell may overproduce one or more nal-opioid BIAs of interest. By overproduce is meant that the cell has an improved or increased production of a nor-opioid and/or nal-opioid BIA molecule of interest relative to a control cell (e.g., an unmodified cell). By improved or increased production is meant both the production of some amount of the nor-opioid and/or nal-opioid BIA of interest where the control has no nor-opioid and/or nal-opioid BIA of interest production, as well as an increase of about 10% or more, such as about 20% or more, about 30% or more, about 40% or more, about 50% or more, about 60% or more, about 80% or more, about 100% or more, such as 2-fold or more, such as 5-fold or more, including 10-fold or more in situations where the control has some nor-opioid and/or nal-opioid BIA of interest production.

An engineered host cell may overproduce one or more nor-opioids. In some cases, the engineered host cell may produce some amount of the nor-opioid of interest where the control has no nor-opioid production, as well as an increase of about 10% or more, such as about 20% or more, about 30% or more, about 40% or more, about 50% or more, about 60% or more, about 80% or more, about 100% or more, such as 2-fold or more, such as 5-fold or more, including 10-fold or more in situations where the control has some nor-opioid of interest production.

An engineered host cell may further overproduce one or more nal-opioids. In some cases, the engineered host cell may produce some amount of the nal-opioid of interest where the control has no nal-opioid production, as well as an increase of about 10% or more, such as about 20% or more, about 30% or more, about 40% or more, about 50% or more, about 60% or more, about 80% or more, about 100% or more, such as 2-fold or more, such as 5-fold or more, including 10-fold or more in situations where the control has some nal-opioid of interest production.

An engineered host cell may overproduce one or more BIAs of interest. By overproduce is meant that the cell has an improved or increased production of a BIA molecule of interest relative to a control cell (e.g., an unmodified cell). By improved or increased production is meant both the production of some amount of the BIA of interest where the control has no BIA of interest production, as well as an increase of about 10% or more, such as about 20% or more, about 30% or more, about 40% or more, about 50% or more, about 60% or more, about 80% or more, about 100% or more, such as 2-fold or more, such as 5-fold or more, including 10-fold or more in situations where the control has some BIA of interest production.

An engineered host cell may overproduce one or more (S)-1-benzylisoquinoline alkaloids. In some cases, the engineered host cell may produce some amount of the (S)-1-benzylisoquinoline alkaloid of interest where the control has no (S)-1-benzylisoquinoline alkaloid production, as well as an increase of about 10% or more, such as about 20% or more, about 30% or more, about 40% or more, about 50% or more, about 60% or more, about 80% or more, about 100% or more, such as 2-fold or more, such as 5-fold or more, including 10-fold or more in situations where the control has some (S)-1-benzylisoquinoline alkaloid of interest production.

An engineered host cell may further overproduce one or more (R)-1-benzylisoquinoline alkaloids. In some cases, the engineered host cell may produce some amount of the (R)-1-benzylisoquinoline alkaloid of interest where the control has no (R)-1-benzylisoquinoline alkaloid production, as well as an increase of about 10% or more, such as about 20% or more, about 30% or more, about 40% or more, about 50% or more, about 60% or more, about 80% or more, about 100% or more, such as 2-fold or more, such as 5-fold or more, including 10-fold or more in situations where the control has some (R)-1-benzylisoquinoline alkaloid of interest production. An engineered host cell may further overproduce one or more of morphinan and pro-morphinan alkaloids.

In some cases, the engineered host cell is capable of producing an increased amount of (R)-reticuline relative to a control host cell that lacks the one or more modifications (e.g., as described herein). In certain instances, the increased amount of (R)-reticuline is about 10% or more relative to the control host cell, such as about 20% or more, about 30% or more, about 40% or more, about 50% or more, about 60% or more, about 80% or more, about 100% or more, about 2-fold or more, about 5-fold or more, or even about 10-fold or more relative to the control host cell. In some cases, (R)-reticuline is the product of an epimerization reaction within an engineered host cell. In these cases, (S)-reticuline may be the substrate of the epimerization reaction.

Additionally, an engineered host cell may overproduce one or more enzymes of interest. By overproduce is meant that the cell has an improved or increased production of an enzyme of interest relative to a control cell (e.g., an unmodified cell). By improved or increased production is meant both the production of some amount of the enzyme of interest where the control has no production, as well as an increase of about 10% or more, such as about 20% or more, about 30% or more, about 40% or more, about 50% or more, about 60% or more, about 80% or more, about 100% or more, such as 2-fold or more, such as 5-fold or more, including 10-fold or more in situations where the control has some enzyme of interest production.

An engineered host cell may overproduce one or more O-demethylase (ODM) enzymes. Examples of ODM enzymes that may be utilized in embodiments described herein are found in Table 3. In some cases, the engineered host cell may produce some amount of the ODM enzyme where the control has no ODM enzyme production, as well as an increase of about 10% or more, such as about 20% or more, about 30% or more, about 40% or more, about 50% or more, about 60% or more, about 80% or more, about 100% or more, such as 2-fold or more, such as 5-fold or more, including 10-fold or more in situations where the control has some ODM enzyme production.

An engineered host cell may overproduce one or more N-demethylase (NDM) enzymes. Examples of NDM enzymes that may be utilized in embodiments described herein are found in Table 4. In some cases, the engineered host cell may produce some amount of the ODM enzyme where the control has no NDM enzyme production, as well as an increase of about 10% or more, such as about 20% or more, about 30% or more, about 40% or more, about 50% or more, about 60% or more, about 80% or more, about 100% or more, such as 2-fold or more, such as 5-fold or more, including 10-fold or more in situations where the control has some NDM enzyme production.

An engineered host cell may overproduce one or more N-methyltransferase (NMT) enzymes. Examples of NMT enzymes that may be utilized in embodiments described herein are found in Table 5. In some cases, the engineered host cell may produce some amount of the NMT enzyme where the control has no NMT enzyme production, as well as an increase of about 10% or more, such as about 20% or more, about 30% or more, about 40% or more, about 50% or more, about 60% or more, about 80% or more, about 100% or more, such as 2-fold or more, such as 5-fold or more, including 10-fold or more in situations where the control has some NMT enzyme production.

An engineered host cell may overproduce one or more CYP-COR enzymes. In some cases, the engineered host cell may produce some amount of the CYP-COR enzyme where the control has no CYP-COR enzyme production, as well as an increase of about 10% or more, such as about 20% or more, about 30% or more, about 40% or more, about 50% or more, about 60% or more, about 80% or more, about 100% or more, such as 2-fold or more, such as 5-fold or more, including 10-fold or more in situations where the control has some CYP-COR enzyme production.

An engineered host cell may further overproduce one or more enzymes that are derived from the CYP-COR enzyme. In some cases, the engineered host cell may produce some amount of the enzymes that are derived from the CYP-COR enzyme, where the control has no production of enzymes that are derived from the CYP-COR enzyme, as well as an increase of about 10% or more, such as about 20% or more, about 30% or more, about 40% or more, about 50% or more, about 60% or more, about 80% or more, about 100% or more, such as 2-fold or more, such as 5-fold or more, including 10-fold or more in situations where the control has some production of enzymes that are derived from the CYP-COR enzyme.

In some cases, the one or more (such as two or more, three or more, or four or more) modifications may be selected from: a substrate inhibition alleviating mutation in a biosynthetic enzyme gene; a product inhibition alleviating mutation in a biosynthetic enzyme gene; a cofactor recovery promoting mechanism; a feedback inhibition alleviating mutation in a biosynthetic enzyme gene; a transcriptional modulation modification of a biosynthetic enzyme gene; an inactivating mutation in an enzyme gene; an epimerization modification; a bisBIA generating modification; and a heterologous coding sequence that encodes an enzyme. A cell that includes one or more modifications may be referred to as an engineered cell.

Substrate Inhibition Alleviating Mutations

In some instances, the engineered host cells are cells that include one or more substrate inhibition alleviating mutations (such as two or more, three or more, four or more, five or more, or even more) in one or more biosynthetic enzyme genes of the cell. In some examples, the one or more biosynthetic enzyme genes are native to the cell (e.g., is present in an unmodified cell). In some examples, the one or more biosynthetic enzyme genes are non-native to the cell. As used herein, the term "substrate inhibition alleviating mutation" refers to a mutation that alleviates a substrate inhibition control mechanism of the cell.

A mutation that alleviates substrate inhibition reduces the inhibition of a regulated enzyme in the cell of interest relative to a control cell and provides for an increased level of the regulated compound or a downstream biosynthetic product thereof. In some cases, by alleviating inhibition of the regulated enzyme is meant that the $IC_{50}$ of inhibition is increased by 2-fold or more, such as by 3-fold or more, 5-fold or more, 10-fold or more, 30-fold or more, 100-fold or more, 300-fold or more, 1000-fold or more, or even more. By increased level is meant a level that is 110% or more of that of the regulated compound in a control cell or a downstream product thereof, such as 120% or more, 130% or more, 140% or more, 150% or more, 160% or more, 170% or more, 180% or more, 190% or more, or 200% or more, such as at least 3-fold or more, at least 5-fold or more, at least 10-fold or more or even more of the regulated compound in the engineered host cell or a downstream product thereof.

A variety of substrate inhibition control mechanisms and biosynthetic enzymes in the engineered host cell that are directed to regulation of levels of nal-opioid or nor-opioid BIAs of interest, or precursors thereof, may be targeted for substrate inhibition alleviation. The engineered host cell may include one or more substrate inhibition alleviating mutations in one or more biosynthetic enzyme genes. The one or more mutations may be located in any convenient biosynthetic enzyme genes where the biosynthetic enzyme is subject to regulatory control. In some embodiments, the one or more biosynthetic enzyme genes encode one or more tyrosine hydroxylase enzymes. In certain instances, the one or more substrate inhibition alleviating mutations are present in a biosynthetic enzyme gene that is TyrH. In some embodiments, the engineered host cell may include one or more substrate inhibition alleviating mutations in one or more biosynthetic enzyme genes such as one of those genes described in Table 2.

In certain embodiments, the one or more substrate inhibition alleviating mutations are present in the TyrH gene. The TyrH gene encodes tyrosine hydroxylase, which is an enzyme that converts tyrosine to L-DOPA. However, TyrH is inhibited by its substrate, tyrosine. Mammalian tyrosine hydroxylase activity, such as that seen in humans or rats, can be improved through mutations to the TyrH gene that relieve substrate inhibition. In particular, substrate inhibition from tyrosine can be relieved by a point mutation W166Y in the TyrH gene. The point mutation W166Y in the TyrH gene may also improve the binding of the cosubstrate of tyrosine hydroxylase, $BH_4$, to catalyze the reaction of tyrosine to L-DOPA. The mutants of TyrH, when expressed in yeast strains to produce BIAs from sugar (such as those described in U.S. Provisional Patent Application Ser. No. 61/899,496) can significantly improve the production of BIAs.

Any convenient numbers and types of mutations may be utilized to alleviate a substrate inhibition control mechanism. In certain embodiments, the engineered host cells of the present invention may include 1 or more, 2 or more, 3 or more, 4 or more, 5 or more, 6 or more, 7 or more, 8 or more, 9 or more, 10 or more, 11 or more, 12 or more, 13 or more, 14 or more, or even 15 or more substrate inhibition alleviating mutations, such as 1, 2, 3, 4, 5, 6, 7, 8, 9, 10, 11, 12, 13, 14 or 15 substrate inhibition alleviating mutations in one or more biosynthetic enzyme genes within the engineered host cell.

Cofactor Recovery Promoting Mechanisms

In some instances, the engineered host cells are cells that include one or more cofactor recovery promoting mechanisms (such as two or more, three or more, four or more, five or more, or even more) in one or more biosynthetic enzyme genes of the cell. In some examples, the one or more biosynthetic enzyme genes are native to the cell (e.g., is present in an unmodified cell). In some examples, the one or more biosynthetic enzyme genes are non-native to the cell. As used herein, the term "cofactor recovery promoting mechanism" refers to a mechanism that promotes a cofactor recovery control mechanism of the cell.

A variety of cofactor recovery control mechanisms and biosynthetic enzymes in the engineered host cell that are directed to regulation of levels of nor-opioid or nal-opioid BIAs of interest, or precursors thereof, may be targeted for cofactor recovery promotion. The engineered host cell may include one or more cofactor recovery promoting mechanism in one or more biosynthetic enzyme genes. In examples, the engineered host cell may include a heterologous coding sequence that encodes dihydrofolate reductase (DHFR). When DHFR is expressed, it may convert 7,8-dihydrobiopterin ($BH_2$) to the tetrahydrobiopterin ($BH_4$), thereby recovering $BH_4$ as a TyrH cosubstrate. In some examples, the engineered host cell may include one or more cofactor recovery promoting mechanisms in one or more biosynthetic enzyme genes such as one of those genes described in Table 2.

Any convenient numbers and types of mechanisms may be utilized to promote a cofactor recovery control mechanism. In certain embodiments, the engineered host cells of the present invention may include 1 or more, 2 or more, 3 or more, 4 or more, 5 or more, 6 or more, 7 or more, 8 or more, 9 or more, 10 or more, 11 or more, 12 or more, 13 or more, 14 or more, or even 15 or more cofactor recovery promoting mechanisms such as 1, 2, 3, 4, 5, 6, 7, 8, 9, 10, 11, 12, 13, 14 or 15 cofactor recovery promoting mechanisms in one or more biosynthetic enzyme genes within the engineered host cell.

Product Inhibition Alleviating Mutations

In some instances, the engineered host cells are cells that include one or more product inhibition alleviating mutations (such as two or more, three or more, four or more, five or more, or even more) in one or more biosynthetic enzyme genes of the cell. In some examples, the one or more biosynthetic enzyme genes are native to the cell (e.g., is present in an unmodified cell). In some examples, the one or more biosynthetic enzyme genes are non-native to the cell. As used herein, the term "product inhibition alleviating mutation" refers to a mutation that alleviates a short term and/or long term product inhibition control mechanism of an engineered host cell. Short term product inhibition is a control mechanism of the cell in which there is competitive binding at a cosubstrate binding site. Long term product inhibition is a control mechanism of the cell in which there is irreversible binding of a compound away from a desired pathway.

A mutation that alleviates product inhibition reduces the inhibition of a regulated enzyme in the cell of interest relative to a control cell and provides for an increased level of the regulated compound or a downstream biosynthetic product thereof. In some cases, by alleviating inhibition of the regulated enzyme is meant that the $IC_{50}$ of inhibition is increased by 2-fold or more, such as by 3-fold or more, 5-fold or more, 10-fold or more, 30-fold or more, 100-fold or more, 300-fold or more, 1000-fold or more, or even more. By increased level is meant a level that is 110% or more of that of the regulated compound in a control cell or a downstream product thereof, such as 120% or more, 130% or more, 140% or more, 150% or more, 160% or more, 170% or more, 180% or more, 190% or more, or 200% or more, such as at least 3-fold or more, at least 5-fold or more, at least 10-fold or more or even more of the regulated compound in the engineered host cell or a downstream product thereof.

A variety of product inhibition control mechanisms and biosynthetic enzymes in the engineered host cell that are directed to regulation of levels of nor-opioid or nal-opioid BIAs of interest may be targeted for product inhibition alleviation. The engineered host cell may include one or more product inhibition alleviating mutations in one or more biosynthetic enzyme genes. The mutation may be located in any convenient biosynthetic enzyme genes where the biosynthetic enzyme is subject to regulatory control. In some embodiments, the one or more biosynthetic enzyme genes encode one or more tyrosine hydroxylase enzymes. In certain instances, the one or more product inhibition alleviating mutations are present in a biosynthetic enzyme gene that is TyrH. In some embodiments, the engineered host cell includes one or more product inhibition alleviating mutations in one or more biosynthetic enzyme genes such as one of those genes described in Table 2.

In certain embodiments, the one or more product inhibition alleviating mutations are present in the TyrH gene. The TyrH gene encodes tyrosine hydroxylase, which is an enzyme that converts tyrosine to L-DOPA. TyrH requires tetrahydrobiopterin ($BH_4$) as a cosubstrate to catalyze the hydroxylation reaction. Some microbial strains, such as Saccharomyces cerevisiae, do not naturally produce $BH_4$, but can be engineered to produce this substrate through a four-enzyme synthesis and recycling pathway, as illustrated in FIG. 1. FIG. 1 illustrates examples of synthesis, recycling, and salvage pathways of tetrahydrobiopterin, in accordance with embodiments of the invention. FIG. 1 provides the use of the enzymes PTPS, pyruvoyl tetrahydropterin synthase; SepR, sepiapterin reductase; PCD, pterin 4a-carbinolamine dehydratase; QDHPR, dihydropteridine reductase; and DHFR, dihydrofolate reductase. Of the enzymes that are illustrated in FIG. 1, yeast synthesizes an endogenous GTP cyclohydrolase I. GTP and dihydroneopterin triphosphate are naturally synthesized in yeast. Additionally, other metabolites in FIG. 1 are not naturally produced in yeast.

TyrH is inhibited by its product L-DOPA, as well as other catecholamines, particularly dopamine. Mammalian tyrosine hydroxylase activity, such as from humans or rats, can be improved through mutations that relieve product inhibition. For example, short term product inhibition, such as competitive binding at the cosubstrate binding site, can be relieved by a point mutation W166Y on the TyrH gene. In particular, the point mutation W166Y on the TyrH gene may improve binding of the cosubstrate. Additionally, short term product inhibition to relieve competitive binding at the cosubstrate binding site may be improved by a point mutation S40D on the TyrH gene. Short term product inhibition may also be improved by the joint mutations of R37E, R38E on the TyrH gene. In particular, R37E, R38E mutations may together specifically improve tyrosine hydroxylase activity in the presence of dopamine.

Additionally, long term product inhibition may be relieved by point mutations on the TyrH gene. Long term product inhibition relief may include the irreversible binding of catecholamine to iron in the active site such that there is less catecholamine present to act as a product inhibitor of tyrosine hydroxylase activity. Long term product inhibition can be relieved by the mutations E332D and Y371F, respectively, in the TyrH gene.

Combinations of the mutations can be made (such as two or three or more mutations at once) to relieve multiple types of substrate and product inhibition to further improve the activity of TyrH. The mutants of TyrH, when expressed in yeast strains to produce nor-opioid and/or nal-opioid BIAs of interest from sugar (such as those described in U.S. Provisional Patent Application Ser. No. 61/899,496) can significantly improve the production of nor-opioid and/or nal-opioid products.

Any convenient numbers and types of mutations may be utilized to alleviate a product inhibition control mechanism. In certain embodiments, the engineered host cells of the present invention may include 1 or more, 2 or more, 3 or more, 4 or more, 5 or more, 6 or more, 7 or more, 8 or more, 9 or more, 10 or more, 11 or more, 12 or more, 13 or more, 14 or more, or even 15 or more product inhibition alleviating mutations, such as 1, 2, 3, 4, 5, 6, 7, 8, 9, 10, 11, 12, 13, 14 or 15 product inhibition alleviating mutations in one or more biosynthetic enzyme genes within the engineered host cell.

Feedback Inhibition Alleviating Mutations

In some instances, the engineered host cells are cells that include one or more feedback inhibition alleviating mutations (such as two or more, three or more, four or more, five or more, or even more) in one or more biosynthetic enzyme genes of the cell. In some cases, the one or more biosynthetic enzyme genes are native to the cell (e.g., is present in an unmodified cell). Additionally or alternatively, in some examples the one or more biosynthetic enzyme genes are non-native to the cell. As used herein, the term "feedback inhibition alleviating mutation" refers to a mutation that alleviates a feedback inhibition control mechanism of an engineered host cell. Feedback inhibition is a control mechanism of the cell in which an enzyme in the synthetic pathway of a regulated compound is inhibited when that compound has accumulated to a certain level, thereby balancing the amount of the compound in the cell. A mutation that alleviates feedback inhibition reduces the inhibition of a regulated enzyme in the engineered host cell relative to a control cell. In this way, engineered host cell provides for an increased level of the regulated compound or a downstream biosynthetic product thereof. In some cases, by alleviating inhibition of the regulated enzyme is meant that the $IC_{50}$ of inhibition is increased by 2-fold or more, such as by 3-fold or more, 5-fold or more, 10-fold or more, 30-fold or more, 100-fold or more, 300-fold or more, 1000-fold or more, or even more. By increased level is meant a level that is 110% or more of that of the regulated compound in a control cell or a downstream product thereof, such as 120% or more, 130% or more, 140% or more, 150% or more, 160% or more, 170% or more, 180% or more, 190% or more, or 200% or more, such as at least 3-fold or more, at least 5-fold or more, at least 10-fold or more or even more of the regulated compound in the host cell or a downstream product thereof.

A variety of feedback inhibition control mechanisms and biosynthetic enzymes that are directed to regulation of levels of BIAs of interest may be targeted for alleviation in the host cell. The host cell may include one or more feedback inhibition alleviating mutations in one or more biosynthetic enzyme genes native to the cell. The one or more mutations may be located in any convenient biosynthetic enzyme genes where the biosynthetic enzyme is subject to regulatory control. In some embodiments, the one or more biosynthetic enzyme genes may encode one or more enzymes selected from a 3-deoxy-d-arabinose-heptulosonate-7-phosphate (DAHP) synthase and a chorismate mutase. In some embodiments, the one or more biosynthetic enzyme genes encode a 3-deoxy-d-arabinose-heptulosonate-7-phosphate (DAHP) synthase. In some instances, the one or more biosynthetic enzyme genes may encode a chorismate mutase. In certain instances, the one or more feedback inhibition alleviating mutations may be present in a biosynthetic enzyme gene selected from ARO4 and ARO7. In certain instances, the one or more feedback inhibition alleviating mutations may be present in a biosynthetic enzyme gene that is ARO4. In certain instances, the one or more feedback inhibition alleviating mutations are present in a biosynthetic enzyme gene that is ARO7. In some embodiments, the engineered host cell may include one or more feedback inhibition alleviating mutations in one or more biosynthetic enzyme genes such as one of those genes described in Table 2.

Any convenient numbers and types of mutations may be utilized to alleviate a feedback inhibition control mechanism. As used herein, the term "mutation" refers to a deletion, insertion, or substitution of an amino acid(s) residue or nucleotide(s) residue relative to a reference sequence or motif. The mutation may be incorporated as a directed mutation to the native gene at the original locus. In some cases, the mutation may be incorporated as an additional copy of the gene introduced as a genetic integration at a separate locus, or as an additional copy on an episomal vector such as a 2μ or centromeric plasmid. In certain instances, the feedback inhibited copy of the enzyme is under the native cell transcriptional regulation. In some instances, the feedback inhibited copy of the enzyme is introduced with engineered constitutive or dynamic regulation of protein expression by placing it under the control of a synthetic promoter.

In certain embodiments, the one or more feedback inhibition alleviating mutations may be present in the ARO4 gene. ARO4 mutations of interest may include, but are not limited to, substitution of the lysine residue at position 229 with a leucine, a substitution of the glutamine residue at position 166 with a lysine residue, or a mutation as described by Hartmann M, et al. ((2003) Proc Natl Acad Sci USA 100(3):862-867) or Fukuda, et al. ((1992) J Ferment Bioeng 74(2):117-119). In some instances, mutations for conferring feedback inhibition may be selected from a mutagenized library of enzyme mutants. Examples of such selections may include rescue of growth of o-fluoro-D,L-phenylalanine or growth of aro3 mutant yeast strains in media with excess tyrosine as described by Fukuda, et al. ((1990) Breeding of Brewing Yeast Producing a Large Amount of Beta-Phenylethyl Alcohol and Beta-Phenylethyl Acetate. Agr Biol Chem Tokyo 54(1):269-271).

In certain embodiments, the engineered host cells of the present invention may include 1 or more, 2 or more, 3 or more, 4 or more, 5 or more, 6 or more, 7 or more, 8 or more, 9 or more, 10 or more, 11 or more, 12 or more, 13 or more, 14 or more, or even 15 or more feedback inhibition alleviating mutations, such as 1, 2, 3, 4, 5, 6, 7, 8, 9, 10, 11, 12, 13, 14 or 15 feedback inhibition alleviating mutations in one or more biosynthetic enzyme genes within the engineered host cell.

Transcriptional Modulation Modifications

The host cells may include one or more transcriptional modulation modifications (such as two or more, three or more, four or more, five or more, or even more modifications) of one or more biosynthetic enzyme genes of the cell. In some examples, the one or more biosynthetic enzyme genes are native to the cell. In some examples, the one or more biosynthetic enzyme genes are non-native to the cell. Any convenient biosynthetic enzyme genes of the cell may be targeted for transcription modulation. By transcription modulation is meant that the expression of a gene of interest in a modified cell is modulated, e.g., increased or decreased, enhanced or repressed, relative to a control cell (e.g., an unmodified cell). In some cases, transcriptional modulation of the gene of interest includes increasing or enhancing expression. By increasing or enhancing expression is meant that the expression level of the gene of interest is increased by 2-fold or more, such as by 5-fold or more and sometimes by 25-, 50-, or 100-fold or more and in certain embodiments 300-fold or more or higher, as compared to a control, i.e., expression in the same cell not modified (e.g., by using any convenient gene expression assay). Alternatively, in cases where expression of the gene of interest in a cell is so low that it is undetectable, the expression level of the gene of interest is considered to be increased if expression is increased to a level that is easily detectable. In certain instances, transcriptional modulation of the gene of interest includes decreasing or repressing expression. By decreasing or repressing expression is meant that the expression level of the gene of interest is decreased by 2-fold or more, such as by 5-fold or more and sometimes by 25-, 50-, or 100-fold or more and in certain embodiments 300-fold or more or higher, as compared to a control. In some cases, expression is decreased to a level that is undetectable. Modifications of host cell processes of interest that may be adapted for use in the subject host cells are described in U.S. Publication No. 20140273109 (Ser. No. 14/211,611) by Smolke et al., the disclosure of which is herein incorporated by reference in its entirety.

Figure 2:
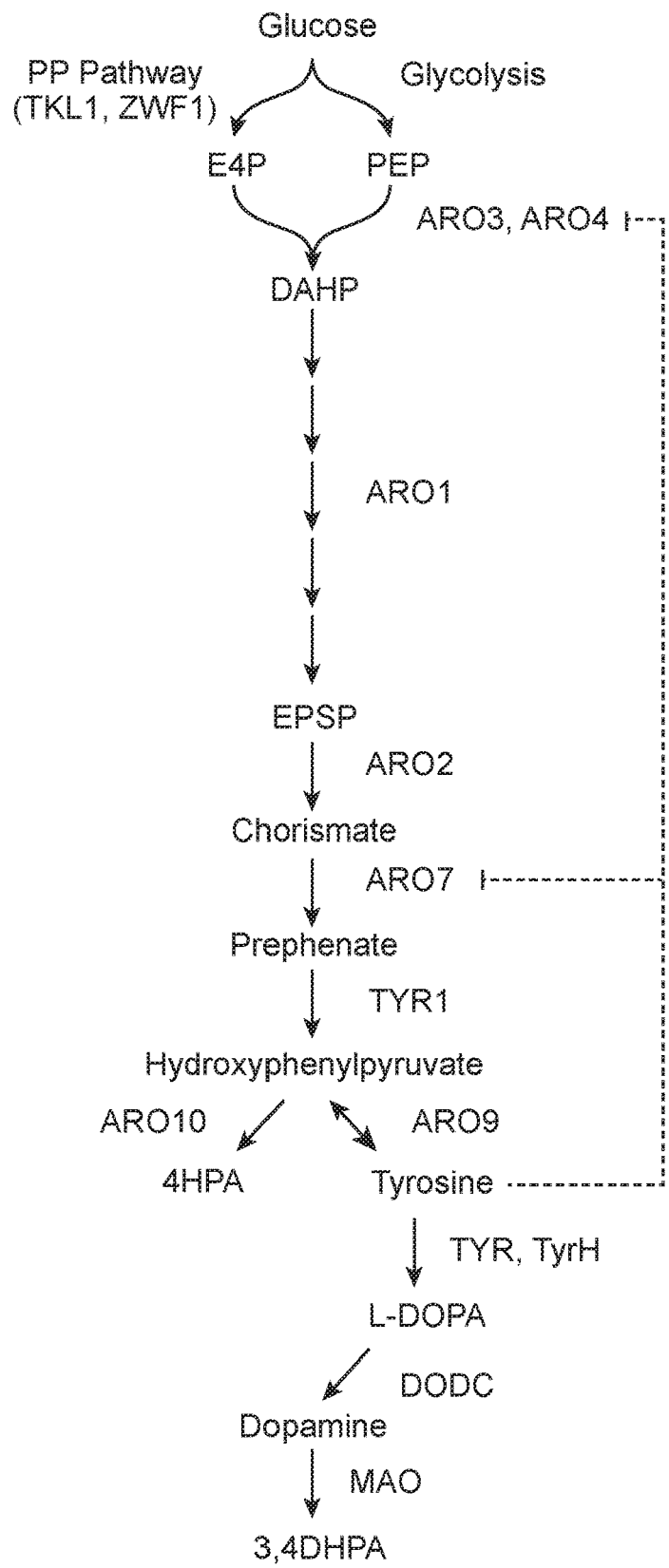
FIG. 2 illustrates a biosynthetic scheme for conversion of glucose to 4-HPA, dopamine, and 3,4-DHPA, in accordance with embodiments of the invention.

Any convenient biosynthetic enzyme genes may be transcriptionally modulated, and include but are not limited to, those biosynthetic enzymes described in FIG. 2. In particular, FIG. 2 illustrates a biosynthetic scheme for conversion of glucose to 4-HPA, dopamine, and 3,4-DHPA, in accordance with embodiments of the invention. Examples of enzymes described in FIG. 2 include ARO3, ARO4, ARO1, ARO7, TYR1, TYR, TyrH, DODC, MAO, ARO10, ARO9, and TKL. In some instances, the one or more biosynthetic enzyme genes may be selected from ARO10, ARO9, and TKL. In some cases, the one or more biosynthetic enzyme genes may be ARO10. In certain instances, the one or more biosynthetic enzyme genes may be ARO9. In some embodiments, the one or more biosynthetic enzyme genes may be TKL. In some embodiments, the host cell includes one or more transcriptional modulation modifications to one or more genes such as one of those genes described in Table 2.

In some embodiments, the transcriptional modulation modification may include a substitution of a strong promoter for a native promoter of the one or more biosynthetic enzyme genes or the expression of an additional copy(ies) of the gene or genes under the control of a strong promoter. The promoters driving expression of the genes of interest may be constitutive promoters or inducible promoters, provided that the promoters may be active in the host cells. The genes of interest may be expressed from their native promoters. Additionally or alternatively, the genes of interest may be expressed from non-native promoters. Although not a requirement, such promoters may be medium to high strength in the host in which they are used. Promoters may be regulated or constitutive. In some embodiments, promoters that are not glucose repressed, or repressed only mildly by the presence of glucose in the culture medium, may be used. There are numerous suitable promoters, examples of which include promoters of glycolytic genes such as the promoter of the *B. subtilis* tsr gene (encoding fructose biphosphate aldolase) or GAPDH promoter from yeast *S. cerevisiae* (coding for glyceraldehyde-phosphate dehydrogenase) (Bitter G. A., *Meth. Enzymol.* 152:673-684 (1987)). Other strong promoters of interest include, but are not limited to, the ADHI promoter of baker's yeast (Ruohonen L., et al, *J. Biotechnol.* 39:193-203 (1995)), the phosphate-starvation induced promoters such as the PHO5 promoter of yeast (Hinnen A., et al, in *Yeast Genetic Engineering*, Barr P. J., et al. eds, Butterworths (1989), the alkaline phosphatase promoter from *B. licheniformis* (Lee. J. W. K., et al, *J. Gen. Microbiol.* 137:1127-1133 (1991)), GPD1, and TEF1. Yeast promoters of interest include, but are not limited to, inducible promoters such as Gal1-10, Gal1, GalL, GalS, repressible promoter Met25, tetO, and constitutive promoters such as glyceraldehyde 3-phosphate dehydrogenase promoter (GPD), alcohol dehydrogenase promoter (ADH), translation-elongation factor-1-alpha promoter (TEF), cytochrome c-oxidase promoter (CYC1), MRP7 promoter, etc. In some instances, the strong promoter is GPD1. In certain instances, the strong promoter is TEF1. Autonomously replicating yeast expression vectors containing promoters inducible by hormones such as glucocorticoids, steroids, and thyroid hormones are also known and include, but are not limited to, the glucorticoid responsive element (GRE) and thyroid hormone responsive element (TRE), see e.g., those promoters described in U.S. Pat. No. 7,045,290. Vectors containing constitutive or inducible promoters such as alpha factor, alcohol oxidase, and PGH may be used. Additionally any promoter/enhancer combination (as per the Eukaryotic Promoter Data Base EPDB) could also be used to drive expression of genes of interest. It is understood that any convenient promoters specific to the host cell may be selected, e.g., *E. coli* T7 promoter, lac promoter or tetO promoter. In some cases, promoter selection may be used to optimize transcription, and hence, enzyme levels to maximize production while minimizing energy resources.

Inactivating Mutations

The engineered host cells may include one or more inactivating mutations to an enzyme of the cell (such as two or more, three or more, four or more, five or more, or even more). The inclusion of one or more inactivating mutations may modify the flux of a synthetic pathway of an engineered host cell to increase the levels of a nor-opioid or nal-opioid BIAs of interest or a desirable enzyme or precursor leading to the same. In some examples, the one or more inactivating mutations are to an enzyme native to the cell. Additionally or alternatively, the one or more inactivating mutations are to an enzyme non-native to the cell. As used herein, by "inactivating mutation" is meant one or more mutations to a gene or regulatory DNA sequence of the cell, where the mutation(s) inactivates a biological activity of the protein expressed by that gene of interest. In some cases, the gene is native to the cell. In some instances, the gene encodes an enzyme that is inactivated and is part of or connected to the synthetic pathway of a nor-opioid and/or nal-opioid BIAs of interest produced by the host cell. In some instances, an inactivating mutation is located in a regulatory DNA sequence that controls a gene of interest. In certain cases, the inactivating mutation is to a promoter of a gene. Any convenient mutations (e.g., as described herein) may be utilized to inactivate a gene or regulatory DNA sequence of interest. By "inactivated" or "inactivates" is meant that a biological activity of the protein expressed by the mutated gene is reduced by 10% or more, such as by 20% or more, 30% or more, 40% or more, 50% or more, 60% or more, 70% or more, 80% or more, 90% or more, 95% or more, 97% or more, or 99% or more, relative to a control protein expressed by a non-mutated control gene. In some cases, the protein is an enzyme and the inactivating mutation reduces the activity of the enzyme.

In some examples, the engineered host cell includes an inactivating mutation in an enzyme native to the cell. Any convenient enzymes may be targeted for inactivation. Enzymes of interest may include, but are not limited to those enzymes, described in Table 2 whose action in the synthetic pathway of the engineered host cell tends to reduce the levels of a nor-opioid or nal-opioid of interest. In some cases, the enzyme has glucose-6-phosphate dehydrogenase activity. In certain embodiments, the enzyme that includes an inactivating mutation is ZWF1. In some cases, the enzyme has alcohol dehydrogenase activity. In some embodiments, the enzyme that includes an inactivating mutation is selected from ADH2, ADH3, ADH4, ADH5, ADH6, ADH7, and SFA1. In certain embodiments, the enzyme that includes an inactivating mutation(s) is ADH2. In certain embodiments, the enzyme that includes an inactivating mutation(s) is ADH3. In certain embodiments, the enzyme that includes an inactivating mutation(s) is ADH4. In certain embodiments, the enzyme that includes an inactivating mutation(s) is ADH5. In certain embodiments, the enzyme that includes an inactivating mutation(s) is ADH6. In certain embodiments, the enzyme that includes an inactivating mutation(s) is ADH7. In some cases, the enzyme has aldehyde oxidoreductase activity. In certain embodiments, the enzyme that includes an inactivating mutation is selected from ALD2, ALD3, ALD4, ALD5, and ALD6. In certain embodiments, the enzyme that includes an inactivating mutation(s) is ALD2. In certain embodiments, the enzyme that includes an inactivating mutation(s) is ALD3. In certain embodiments, the enzyme that includes an inactivating mutation(s) is ALD4. In certain embodiments, the enzyme that includes an inactivating mutation(s) is ALD5. In certain embodiments, the enzyme that includes an inactivating mutation(s) is ALD6. In some embodiments, the host cell includes one or more inactivating mutations to one or more genes described in Table 2.

Epimerization Modifications

Figure 3:
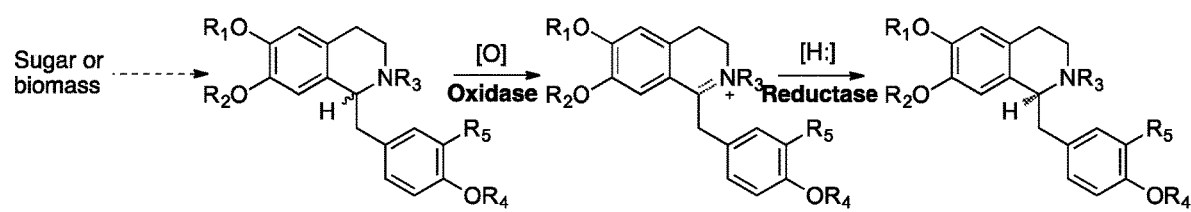
FIG. 3 illustrates a schematic example of (R)-1-benzylisoquinoline alkaloid formation, in accordance with embodiments of the invention.

Some methods, processes, and systems provided herein describe the conversion of (S)-1-benzylisoquinoline alkaloids to (R)-1-benzylisoquinoline alkaloids. Some of these methods, processes, and systems may comprise an engineered host cell. In some examples, the conversion of (S)-1-benzylisoquinoline alkaloids to (R)-1-benzylisoquinoline alkaloids is a key step in the conversion of a substrate to a diverse range of alkaloids. In some examples, the conversion of (S)-1-benzylisoquinoline alkaloids to (R)-1-benzylisoquinoline alkaloids comprises an epimerization reaction. In some cases, epimerization of a substrate alkaloid may be performed by oxidizing an (S)-substrate to the corresponding Schiff base or imine intermediate, then stereospecifically reducing this intermediate to an (R)-product as provided in FIG. 3 and as represented generally in Scheme 1. As provided in Scheme 1, $R_1$, $R_2$, $R_3$, and $R_4$ may be H or $CH_3$. $R_5$ may be H, OH, or $OCH_3$.

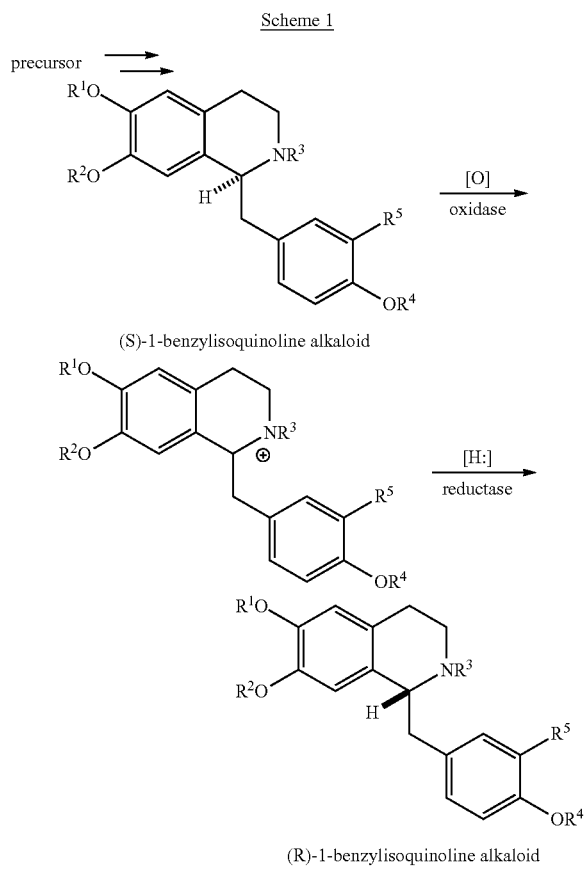

Scheme 1

(S)-1-benzylisoquinoline alkaloid (R)-1-benzylisoquinoline alkaloid

In some examples, the conversion of the (S)-substrate to the (R)-product may involve at least one oxidation reaction and at least one reduction reaction. In some cases, an oxidation reaction is optionally followed by a reduction reaction. In some cases, at least one of the oxidation and reduction reactions is carried out in the presence of an enzyme. In some cases, at least one of the oxidation and reduction reactions is catalyzed by an enzyme. In some cases, the oxidation and reduction reactions are both carried out in the presence of at least one enzyme. In some cases, at least one enzyme is useful to catalyze the oxidation and reduction reactions. The oxidation and reduction reactions may be catalyzed by the same enzyme.

In some methods, processes and systems described herein, an oxidation reaction may be performed in the presence of an enzyme. In some examples, the enzyme may be an oxidase. The oxidase may use an (S)-1-benzylisoquinoline as a substrate. The oxidase may convert the (S)-substrate to a corresponding imine or Schiff base derivative. The oxidase may be referred to as 1,2-dehydroreticuline synthase (DRS). Non-limiting examples of enzymes suitable for oxidation of (S)-1-benzylisoquinoline alkaloids in this disclosure include a cytochrome P450 oxidase, a 2-oxoglutarate-dependent oxidase, and a flavoprotein oxidase. For example, (S)-tetrahydroprotoberberine oxidase (STOX, E.C 1.3.3.8) may oxidize (S)-norreticuline and other (S)-1-benzylisoquinoline alkaloids to 1,2-dehydronorreticuline and other corresponding 1,2-dehydro products. In some examples, a protein that comprises an oxidase domain of any one of the preceding examples may perform the oxidation. In some examples, the oxidase may catalyze the oxidation reaction within a host cell, such as an engineered host cell, as described herein.

In some examples, a reduction reaction may follow the oxidation reaction. The reduction reaction may be performed by an enzyme. In some examples, the reductase may use an imine or Schiff base derived from a 1-benzylisoquinoline as a substrate. The reductase may convert the imine or Schiff base derivative to an (R)-1-benzylisoquinoline. The reductase may be referred to as 1,2-dehydroreticuline reductase (DRR). Non-limiting examples of enzymes suitable for reduction of an imine or Schiff base derived from an (S)-1-benzylisoquinoline alkaloid include an aldo-keto reductase (e.g., a codeinone reductase-like enzyme (EC 1.1.1.247)) and a short chain dehydrogenase (e.g., a salutaridine reductase-like enzyme (EC 1.1.1.248)). In some examples, a protein that comprises a reductase domain of any one of the preceding examples may perform the reduction. In a further embodiment, the reduction is stereospecific. In some examples, the reductase may catalyze the reduction reaction within a host cell, such as an engineered host cell, as described herein.

An example of an enzyme that can perform an epimerization reaction that converts (S)-1-benzylisoquinoline alkaloids to (R)-1-benzylisoquinoline alkaloids includes an epimerase having an oxidase domain and a reductase domain. In particular, the epimerase may have a cytochrome P450 oxidase 82Y2-like domain. Additionally, the epimerase may have a codeinone reductase-like domain. Further, an epimerase having a cytochrome P450 oxidase 82Y2-like domain and also having a codeinone reductase-like domain may be referred to as a CYP-COR enzyme. In particular, a CYP-COR enzyme may be a fusion enzyme. The CYP-COR enzyme may also be referred to as DRS-DRR (dehydroreticuline synthase-dehydroreticuline reductase).

An example of an amino acid sequence of a CYP-COR enzyme that may be used to perform the conversion of (S)-1-benzylisoquinoline alkaloids to (R)-1-benzylisoquinoline alkaloids is provided in FIG. 4. In particular, FIG. 4 illustrates an amino acid sequence of a CYP-COR enzyme, in accordance with embodiments of the invention. As seen in FIG. 4, underlined text denotes the cytochrome P450 CYP82Y2-like domain (59% identity to AFB74617.1). The dotted underlined text denotes the aldo-keto reductase NADPH-dependent codeinone reductase-like domain (75% identity to ACM44066.1). Additional amino acid sequences of a CYP-COR enzyme are set forth in Table 1. An amino acid sequence for an epimerase that is utilized in converting an (S)-1-benzylisoquinoline alkaloid to an (R)-1-benzylisoquinoline alkaloid may be 75% or more identical to a given amino acid sequence as listed in Table 1. For example, an amino acid sequence for such an epimerase may comprise an amino acid sequence that is at least 75% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, or 99% or more identical to an amino acid sequence as provided herein. Additionally, in certain embodiments, an "identical" amino acid sequence contains at least 80%-99% identity at the amino acid level to the specific amino acid sequence. In some cases an "identical" amino acid sequence contains at least about 85%, 86%, 87%, 88%, 89%, 90%, 91%, 92%, 93%, 94% and more in certain cases, at least 95%, 96%, 97%, 98% and 99% identity, at the amino acid level. In some cases, the amino acid sequence may be identical but the DNA sequence is altered such as to optimize codon usage for the host organism, for example.

An engineered host cell may be provided that produces an epimerase that converts (S)-1-benzylisoquinoline alkaloid to (R)-1-benzylisoquinoline alkaloid, wherein the epimerase comprises an amino acid sequence selected from the group consisting of: SEQ ID NOs: 1, 2, 3, 4, 5, 6, 7, 8, 9, 10, 11, 12, 13, 14, and 15. The epimerase that is produced within the engineered host cell may be recovered and purified so as to form a biocatalyst. In some cases, the epimerase may be split into one or more enzymes. Additionally, one or more enzymes that are produced by splitting the epimerase may be recovered from the engineered host cell. These one or more enzymes that result from splitting the epimerase may also be used to catalyze the conversion of (S)-1-benzylisoquinoline alkaloids to (R)-1-benzylisoquinoline alkaloids. In particular, the one or more enzymes that are recovered from the engineered host cell that produces the epimerase may be used in a process for converting an (S)-1-benzylisoquinoline alkaloid to an (R)-1-benzylisoquinoline alkaloid. The process may include contacting the (S)-1-benzylisoquinoline alkaloid with an epimerase in an amount sufficient to convert said (S)-1-benzylisoquinoline alkaloid to (R)-1-benzylisoquinoline alkaloid. In examples, the (S)-1-benzylisoquinoline alkaloid may be contacted with a sufficient amount of the one or more enzymes such that at least 5% of said (S)-1-benzylisoquinoline alkaloid is converted to (R)-1-benzylisoquinoline alkaloid. In further examples, the (S)-1-benzylisoquinoline alkaloid may be contacted with a sufficient amount of the one or more enzymes such that at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 82%, at least 84%, at least 86%, at least 88%, at least 90%, at least 91%, at least 92%, at least 93%, at least 94%, at least 95%, at least 96%, at least 97%, at least 98%, at least 99%, at least 99.5%, at least 99.7%, or 100% of said (S)-1-benzylisoquinoline alkaloid is converted to (R)-1-benzylisoquinoline alkaloid.

The one or more enzymes that may be used to convert an (S)-1-benzylisoquinoline alkaloid to an (R)-1-benzylisoquinoline alkaloid may contact the (S)-1-benzylisoquinoline alkaloid in vitro. Additionally, or alternatively, the one or more enzymes that may be used to convert an (S)-1-benzylisoquinoline alkaloid to an (R)-1-benzylisoquinoline alkaloid may contact the (S)-1-benzylisoquinoline alkaloid in vivo. Additionally, the one or more enzymes that may be used to convert an (S)-1-benzylisoquinoline alkaloid to an (R)-1-benzylisoquinoline alkaloid may be provided to a cell having the (S)-1-benzylisoquinoline alkaloid within, or may be produced within an engineered host cell.

In some examples, the methods provide for engineered host cells that produce an alkaloid product, wherein the epimerization of an (S)-substrate to an (R)-product may comprise a key step in the production of an alkaloid product. In some examples, the alkaloid produced is an (R)-1-benzylisoquinoline alkaloid. In still other embodiments, the alkaloid produced is derived from an (R)-1-benzylisoquinoline alkaloid, including, for example, 4-ring promorphinan and 5-ring morphinan alkaloids. In another embodiment, an (S)-1-benzylisoquinoline alkaloid is an intermediate toward the product of the engineered host cell. In still other embodiments, the alkaloid product is selected from the group consisting of morphinan and promorphinanalkaloids.

In some examples, the (S)-substrate is an (S)-1-benzylisoquinoline alkaloid selected from the group consisting of (S)-norreticuline, (S)-reticuline, (S)-tetrahydropapaverine, (S)-norcoclaurine, (S)-coclaurine, (S)—N-methylcoclaurine, (S)-3'-hydroxy-N-methylcoclaurine, (S)-norisoorientaline, (S)-orientaline, (S)-isoorientaline, (S)-norprotosinomenine, (S)-protosinomenine, (S)-norlaudanosoline, (S)-laudanosoline, (S)-4'-O-methyllaudanosoline, (S)-6-O-methylnorlaudanosoline, (S)-4'-O-methylnorlaudanosoline.

In some examples, the (S)-substrate is a compound of Formula I:

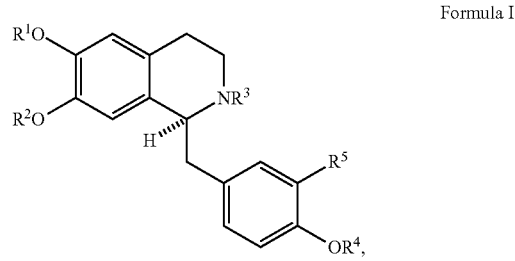

Formula I or a salt thereof, wherein:
$R^1$, $R^2$, $R^3$, and $R^4$ are independently selected from hydrogen and methyl; and
$R^5$ is selected from hydrogen, hydroxy, and methoxy.
In some other examples, at least one of $R^1$, $R^2$, $R^3$, $R^4$, and $R^5$ is hydrogen.

In still other examples, the (S)-substrate is a compound of Formula II:

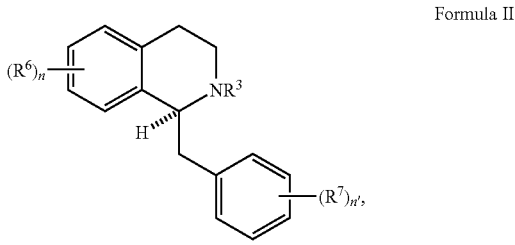

Formula II or a salt thereof, wherein:
$R^3$ is selected from hydrogen and $C_1$-$C_4$ alkyl;
$R^6$ and $R^7$ are independently selected at each occurrence from hydroxy, fluoro, chloro, bromo, carboxaldehyde, $C_1$-$C_4$ acyl, $C_1$-$C_4$ alkyl, and $C_1$-$C_4$ alkoxy;
n is 0, 1, 2, 3, or 4; and
n' is 0, 1, 2, 3, 4 or 5.

When a bond is drawn across a ring, it means substitution may occur at a non-specific ring atom or position. For example, in Formula II shown above, the hydrogen of any —CH— in the 6-membered ring may be replaced with $R^7$ to form —$CR^7$—.

In some examples, $R^6$ and $R^7$ are independently methyl or methoxy. In some other examples, n and n' are independently 1 or 2. In still other embodiments, $R^3$ is hydrogen or methyl.

In some examples, the methods provide for engineered host cells that produce alkaloid products from (S)-reticuline. The epimerization of (S)-reticuline to (R)-reticuline may comprise a key step in the production of diverse alkaloid products from a precursor. In some examples, the precursor is L-tyrosine or a sugar (e.g., glucose). The diverse alkaloid products can include, without limitation, morphinan and promorphinan alkaloids.

Any suitable carbon source may be used as a precursor toward an epimerized 1-benzylisoquinoline alkaloid. Suitable precursors can include, without limitation, monosaccharides (e.g., glucose, fructose, galactose, xylose), oligosaccharides (e.g., lactose, sucrose, raffinose), polysaccharides (e.g., starch, cellulose), or a combination thereof. In some examples, unpurified mixtures from renewable feedstocks can be used (e.g., corn steep liquor, sugar beet molasses, barley malt, biomass hydrolysate). In still other embodiments, the carbon precursor can be a one-carbon compound (e.g., methanol, carbon dioxide) or a two-carbon compound (e.g., ethanol). In yet other embodiments, other carbon-containing compounds can be utilized, for example, methylamine, glucosamine, and amino acids (e.g., L-tyrosine). In some examples, a 1-benzylisoquinoline alkaloid may be added directly to an engineered host cell, including, for example, norlaudanosoline, laudanosoline, norreticuline, and reticuline. In still further embodiments, a 1-benzylisoquinoline alkaloid may be added to the engineered host cell as a single enantiomer (e.g., an (S)-1-benzylisoquinoline alkaloid), or a mixture of enantiomers, including, for example, a racemic mixture.

In some examples, the methods provide for the epimerization of a stereocenter of a 1-benzylisoquinoline alkaloid, or a derivative thereof. In a further embodiment, the method comprises contacting the 1-benzylisoquinoline alkaloid with at least one enzyme. The at least one enzyme may invert the stereochemistry of a stereocenter of a 1-benzylisoquinoline alkaloid, or derivative thereof, to the opposite stereochemistry. In some examples, the at least one enzyme converts an (S)-1-benzylisoquinoline alkaloid to an (R)-1-benzylisoquinoline alkaloid. In some examples of this conversion of an (S)-1-benzylisoquinoline alkaloid to an (R)-1-benzylisoquinoline alkaloid utilizing the at least one enzyme, the (S)-1-benzylisoquinoline alkaloid is selected from the group consisting of (S)-norreticuline, (S)-reticuline, (S)-tetrahydropapaverine, (S)-norcoclaurine, (S)-coclaurine, (S)—N-methylcoclaurine, (S)-3'-hydroxy-N-methylcoclaurine, (S)-norisoorientaline, (S)-orientaline, (S)-isoorientaline, (S)-norprotosinomenine, (S)-protosinomenine, (S)-norlaudanosoline, (S)-laudanosoline, (S)-4'-O-methyllaudanosoline, (S)-6-O-methylnorlaudanosoline, and (S)-4'-O-methylnorlaudanosoline.

In still other embodiments, the 1-benzylisoquinoline alkaloid that is epimerized may comprise two or more stereocenters, wherein only one of the two or more stereocenters is inverted to produce a diastereomer of the substrate (e.g., (S, R)-1-benzylisoquinoline alkaloid converted to (R, R)-1-benzylisoquinoline alkaloid). In examples where only one stereocenter of a 1-benzylisoquinoline alkaloid is inverted when contacted with the at least one enzyme, the product is referred to as an epimer of the 1-benzylisoquinoline alkaloid.

In some examples, the 1-benzylisoquinoline alkaloid is presented to the enzyme as a single stereoisomer. In some other examples, the 1-benzylisoquinoline alkaloid is presented to the enzyme as a mixture of stereoisomers. In still further embodiments, the mixture of stereoisomers may be a racemic mixture. In some other examples, the mixture of stereoisomers may be enriched in one stereoisomer as compared to another stereoisomer.

In some examples, an 1-benzylisoquinoline alkaloid, or a derivative thereof, is recovered. In some examples, the 1-benzylisoquinoline alkaloid is recovered from a cell culture. In still further embodiments, the recovered 1-benzylisoquinoline alkaloid is enantiomerically enriched in one stereoisomer as compared to the original mixture of 1-benzylisoquinoline alkaloids presented to the enzyme. In still further embodiments, the recovered 1-benzylisoquinoline alkaloid has an enantiomeric excess of at least 50%, at least 55%, at least 60%, at least 65%, at least 70%, at least 75%, at least 80%, at least 82%, at least 84%, at least 86%, at least 88%, at least 90%, at least 91%, at least 92%, at least 93%, at least 94%, at least 95%, at least 96%, at least 97%, at least 98%, at least 99%, at least 99.5%, at least 99.7%, or 100%.

"Isomers" are different compounds that have the same molecular formula. "Stereoisomers" are isomers that differ only in the way the atoms are arranged in space. "Enantiomers" are a pair of stereoisomers that are non-superimposable mirror images of each other. A 1:1 mixture of a pair of enantiomers is a "racemic" mixture. "Diastereoisomers" or "diastereomers" are stereoisomers that have at least two asymmetric atoms but are not mirror images of each other. The term "epimer" as used herein refers to a compound having the identical chemical formula but a different optical configuration at a particular position. For example, the (R,S) and (S,S) stereoisomers of a compound are epimers of one another. In some examples, a 1-benzylisoquinoline alkaloid is converted to its epimer (e.g., epi-1-benzylisoquinoline alkaloid). The absolute stereochemistry is specified according to the Cahn-Ingold-Prelog R-S system. When a compound is a pure enantiomer, the stereochemistry at each chiral carbon can be specified by either R or S. Resolved compounds whose absolute configuration is unknown can be designated (+) or (−) depending on the direction (dextro- or levorotatory) in which they rotate plane polarized light at the wavelength of the sodium D line. Certain compounds described herein contain one or more asymmetric centers and can thus give rise to enantiomers, diastereomers, and other stereoisomeric forms that can be defined, in terms of absolute stereochemistry, as (R)- or (S)-.

TABLE 1

Example partial and full-length amino acid sequences of CYP-COR fusion enzymes.

| Sequence | Description | SEQ. ID NO. |
|---|---|---|
| MELQYISYFQPTSSVVALLLALVSILSSVVVLRKTFLNNYSS SPASSTKTAVLSHQRQQSCALPISGLLHIFMNKNGLIHVTLG NMADKYGPIFSFPTGSHRTLVVSSWEMVKECFTGNNDTAF SNRPIPLAFKTIFYACGGIDSYGLSSVPYGKYWRELRKVCV HNLLSNQQLLKFRHLIISQVDTSFNKLYELCKNSEDNHGNY TTTTTTAAGMVRIDDWLAELSFNVIGRIVCGFQSGPKTGAP SRVEQFKEAINEASYFMSTSPVSDNVPMLGWIDQLTGLTRN MKHCGKKLDLVVESIINDHRQKRRFSRTKGGDEKDDEQDD FIDICLSIMEQPQLPGNNNPSQIPIKSIVLDMIGGGTDTTKLTT IWTLSLLLNNPHVLDKAKQEVDAHFRTKRRSTNDAAAAVV DFDDIRNLVYIQAIIKESMRLYPASPVVERLSGEDCVVGGFH VPAGTRLWANVWKMQRDPKVWDDPLVFRPDRFLSDEQK | P. somniferum plant source; full-length amino acid sequence >RQNK-2062398 (also FPYZ-2037562, BMRX-2007040, and MLPX- | SEQ. ID NO. 1 |

TABLE 1-continued

Example partial and full-length amino acid sequences of CYP-COR fusion enzymes.

| Sequence | Description | SEQ. ID NO. |
| --- | --- | --- |
| MVDVRGQNYELLPFGAGRRVCPGVSFSLDLMQLVLTRLIL EFEMKSPSGKVDMTATPGLMSYKVIPLDILLTHRRIKPCVQ SAASERDMESSGVPVITLGSGKVMPVLGMGTFEKVGKGSE RERLAILKAIEVGYRYFDTAAAYETEEVLGEAIAEALQLGL VKSRDELFISSMLWCTDAHADRVLLALQNSLRNLKLEYVD LYMLPFPASLKPGKITMDIPEEDICRMDYRSVWAAMEECQ NLGFTKSIGVSNFSCKKLQELMATANIPPAVNQVEMSPAFQ QKKLREYCNANNILVSAISVLGSNGTPWGSNAVLGSEVLK KIAMAKGKSVAQVSMRWVYEQGASLVVKSFSEERLRENL NIFDWELTKEDHEKIGEIPQCRILSAYFLVSPNGPFKSQEEL WDDEA* | 2016197) | |
| MELQYISYFQPTSSVVALLLALVSILSSVVVLRKTFLNNYSS SPASSTKTAVLSHQRQQSCALPISGLLHIFMNKNGLIHVTLG NMADKYGPIFSFPTGSHRTLVVSSWEMVKECFTGNNDTAF SNRPIPLAFKTIFYACGGIDSYGLSSVPYGKYWRELRKVCV HNLLSNQQLLKFRHLIISQVDTSFNKLYELCKNSEDNHGNY TTXLLLPQLAWRQPWKLYYXTTTTAAGMVRIDDWLAELS FNVIGRIVCGFQSGPKTGAPSRVEQFKEAINEASYFMSTSPV SDNVPMLGWIDQLTGLTRNMKHCGKKLDLVVESIINDHRQ KRRFSRTKGGDEKDDEQDDFIDICLSIMEQPQLPGNNNPSQI PIKSIVLDMIGGGTDTTKLTTIWTLSLLLNNPHVLDKAKQE VDAHFRTKRRSTNDAAAAVVDFDDIRNLVYIQAIIKESMRL YPASPVVERLSGEDCVVGGFHVPAGTRLWANVWKMQRDP KVWDDPLVFRPDRFLSDEQKMVDVRGQNYELLPFGAGRR VCPGVSFSLDLMQLVLTRLILEFEMKSPSGKVDMTATPGL MSYKVIPLDILLTHRRIKPCVQSAASERDMESSGVPVITLGS GKVMPVLGMGTFEKVGKGSERERLAILKAIEVGYRYFDTA AAYETEEVLGEAIAEALQLGLVKSRDELFISSMLWCTDAHA DRVLLALQNSLRNLKLEYVDLYMLPFPASLKPGKITMDIPE EDICRMDYRSVWAAMEECQNLGFTKSIGVSNFSCKKLQEL MATANIPPAVNQVEMSPAFQQKKLREYCNANNILVSAISVL GSNGTPWGSNAVLGSEVLKKIAMAKGKSVAQVSMRWVY EQGASLVVKSFSEERLRENLNIFDWELTKEDHEKIGEIPQCR ILSAYFLVSPNGPFKSQEELWDDEA* | P. somniferum plant source; full-length amino acid sequence >KKCW-2026866 (also FPYZ-2037562, MLPX-2016197) | SEQ. ID NO. 2 |
| MELQYISYFQPTSSVVALLLALVSILSSVVVLRKTFLNNYSS SPASSTKTAVLSHQRQQSCALPISGLLHIFMNKNGLIHVTLG NMADKYGPIFSFPTGSHRTLVVSSWEMVKECFTGNNDTAF SNRPIPLAFKTIFYACGGIDSYGLSSVPYGKYWRELRKVCV HNLLSNQQLLKFRHLIISQVDTSFNKLYELCKNSEDNHGNY TTTTTTAAGMVRIDDWLAELSFNVIGRIVCGFQSGPKTGAP SRVEQFKEAINEASYFMSTSPVSDNVPMLGWIDQLTGLTRN MKHCGKKLDLVVESIINDHRQKRRFSRTKGGDEKDDEQDD FIDICLSIMEQPQLPGNNNPSQIPIKSIVLDMIGGGTDTTKLTT IWTLSLLLNNPHVLDKAKQEVDAHFRTKRRSTNDAAAAVV DFDDIRNLVYIQAIIKESMRLYPASPVVERLSGEDCVVGGFH VPAGTRLWANVWKMQRDPKVWDDPLVFRPDRFLSDEQK MVDVRGQNYELLPFGAGRRVCPGVSFSLDLMQLVLTRLIL EFEMKSPSGKVDMTATPGLMSYKVIPLDILLTHRRIKPCVQ SAASERDMESSGVPVITLGSGKVMPVLGMGTFEKVGKGSE RERLAILKAIEVGYRYFDTAAAYETEEVLGEAIAEALQLGL VKSRDELFISSMLWCTDAHADRVLLALQNSLRNLKLEYVD LYMLPFPASLKPGKITMDIPEEDICRMDYRXVSKPWLH* | P. somniferum plant source; partial-length amino acid sequence >SUFP-2025636 | SEQ. ID NO. 3 |
| MRWHRXIDSYGLSSVPYGKYWRELRKVCVHNLLSNQQLL KFRHLIISQVDTSFNKLYELCKNSEDNQGNYPTTTTAAGMV RIDDWLAELSFNVIGRIVCGFQSGPKTGAPSRVEQFKEAINE ASYFMSTSPVSDNVPMLGWIDQLTGLTRNMKHCGKKLDL VVESIINDHRQKRRFSRTKGGDEKDDEQDDFIDICLSIMEQP QLPGNNNPSQIPIKSIVLDMIGGGTDTTKLTTIWTLSLLLNNP HVLDKAKQEVDAHFRTKRRSTNDAAAAVVDFDDIRNLVYI QAIIKESMRLYPASPVVERLSGEDCVVGGFHVPAGTRLWA NVWKMQRDPKVWDDPLVFRPDRFLSDEQKMVDVRGQNY ELLPFGAGRRVCPGVSFSLDLMQLVLTRLILEFEMKSPSGK VDMTATPGLMSYKVIPLDILLTHRRIKPCVQSAASERDMES SGVPVITLGSGKVMPVLGMGTFEKVGKGSERERLAILKAIE VGYRYFDTAAAYETEEVLGEAIAEALQLGLVKSRDELFISS MLWCTDAHADRVLLALQNSLRNLKLEYVDLYMLPFPASL KPGKITMDIPEEDICRMDYRSVWAAMEECQNLGFTKSIGVS NFSCKKLQELMATANIPPAVNQVEMSPAFQQKKLREYCNA NNILVSAISVLGSNGTPWGSNAVLGSEVLKKIAMAKGKSV AQVSMRWVYEQGASLVVKSFSEERLRENLNIFDWELTKED HEKIGEIPQCRILSAYFLVSPNGPFKSQEELWDDEA* | P. somniferum plant source; partial-length amino acid sequence >MIKW-2013651 | SEQ. ID NO. 4 |

TABLE 1-continued

Example partial and full-length amino acid sequences of CYP-COR fusion enzymes.

| Sequence | Description | SEQ. ID NO. |
|---|---|---|
| MELQYISYFQPTSSVVALLLALVSILSSVVVLRKTFLNNYSS SPASSTKTAVLSHQRQQSCALPISGLLHIFMNKNGLIHVTLG NMADKYGPIFSFPTGSHRTLVVSSWEMVKECFTGNNDTAF SNRPIPLAFKTIFYACGGIDSYGLSSVPYGKYWRELRKVCV HNLLSNQQLLKFRHLIISQVDTSFNKLYELCKNSEDNQGNY TTTTTAAGMVRIDDWLAELSFNVIGRIVCGFQSGPKTGAPS RVEQFKEAINEASYFMSTSPVSDNVPMLGWIDQLTGLTRN MKHCGKKLDLVVESIINDHRQKRRFSRTKGGDEKDDEQDD FIDICLSIMEQPQLPGNNNPSQIPIKSIVLDMIGGGTDTTKLTT IWTLSLLLNNPHVLDKAKQEVDAHFRTKRRSTNDAAAAVV DFDDIRNLVYIQAIIKESMRLYPASPVVERLSGEDCVVGGFH VPAGTRLWANVWKMQRDPKVWDDPLVFRPDRFLSDEQK MVDVRGQNYELLPFGAGRRVCPGVSFSLDLMQLVLTRLIL EFEMKSPSGKVDMTATPGLMSYKVIPLDILLTHRRIKPCVQ SAASERDMESSGVPVITLGSGKVMPVLGMGTFEKVGKGSE RERLAILKAIEVGYRYFDTAAAYETEEVLGEAIAEALQLGL VKSRDELFISSMLWCTDAHADRVLLALQNSLRNLKLEYVD LYMLPFPASLKPGKITMDIPEEDICRMDYRSVWAAMEECQ NLGFTKSIGVSNFSCKKLQELMATANIPPAVNQVEMSPAFQ QKKLREYCNANNILVSAISVLGSNGTPWGSNAVLGSEVLK KIAMAKGKSVAQVSMRWVYEQGASLVVKSFSEERLRENL NIFDWELTKEDHEKIGEIPQCRILSAYFLVSPNGPFKSQEEL WDDEA* | *P. setigerum* plant source; full-length amino acid sequence >EPRK-2027940 (also FPYZ-2037562, STDO-2019715, FNXH-2029312, MLPX-2016196, MLPX-2016197) | SEQ. ID NO. 5 |
| MELQYISYFQPTSSVVALLLALVSILSSVVVLRKTFLNNYSS SPASSTKTAVLSHQRQQSCALPISGLLHIFMNKNGLIHVTLG NMADKYGPIFSFPTGSHRTLVVSSWEMVKECFTGNNDTAF SNRPIPLAFKTIFYACGGIDSYGLSSVPYGKYWRELRKVCV HNLLSNQQLLKFRHLIISQVDTSFNKLYELCKNSEDNQGNY TTTTTAAGMVRIDDWLAELSFNVIGRIVCGFQSGPKTGAPS RVEQFKEAINEASYFMSTSPVSDNVPMLGWIDQLTGLTRN MKHCGKKLDLVVESIINDHRQKRRFSRTKGGDEKDDEQDD FIDICLSIMEQPQLPGNNNPSQIPIKSIVLDMIGGGTDTTKLTT IWTLSLLLNNPHVLDKAKQEVDAHFRTKRRSTNDAAAAVV DFDDIRNLVYIQALYPASPVVERLSGEDCVVGGFHVPAGTR LWANVWKMQRDPKVWDDPLVFRPDRFLSDEQKMVDVRG QNYELLPFGAGRRVCPGVSFSLDLMQLVLTRLILEFEMKSP SGKVDMTATPGLMSYKVIPLDILLTHRRIKPCVQSAASERD MESSGVPVITLGSGKVMPVLGMGTFEKVGKGSERERLAIL KAIEVGYRYFDTAAAYETEEVLGEAIAEALQLGLVKSRDEL FISSMLWCTDAHADRVLLALQNSLRNLKLEYVDLYMLPFP ASLKPGKITMDIPEEDICRMDYRSVWAAMEE | *P. setigerum* plant source; partial-length amino acid sequence >QCOU-2000833 | SEQ. ID NO. 6 |
| MELQYFSYFQPTSSVVALLLALVSILFSVVVLRKTFSNNYSS PASSTETAVLCHQRQQSCALPISGLLHVFMNKNGLIHVTLG NMADKYGPIFSFPTGSHRTLVVSSWEMVKECFTGNNDTAF SNRPIPLAFQTIFYACGGIDSYGLSSVPYGKYWRELRKVCV HNLLSNQQLLKFRHLIISQVDTSFNKLYELCKNSEDNQGMV RMDDWLAQLSFNVIGRIVCGFQSDPKTGAPSRVEQFKEVIN EASYFMSTSPVSDNVPMLGWIDQLTGLTRNMKHCGKKLD LVVESIIKDHRQKRRFSRTKGGDEKDDEQDDFIDICLSIMEQ PQLPGNNSPPQIPIKSIVLDMIGGGTDTTKLTTIWTLSLLLNN PHVLDKAKQEVDAHFRKKRRSTDDAAAAVVDFDDIRNLV YIQAIIKESMRLYPASPVVERLSGEDCVVGGFHVPAGTRLW ANVWKMQRDPKVWDDPLVFRPERFLSDEQKMVDVRGQN YELLPFGAGRRICPGVSFSLDLMQLVLTRLILEFEMKSPSGK VDMTATPGLMSYKVVPLDILLTHRRIKSCVQLASSERDMES SGVPVITLSSGKVMPVLGMGTFEKVGKGSERERLAILKAIE VGYRYFDTAAAYETEEVLGEAIAEALQLGLIESRDELFISSM LWCTDAHPDRVLLALQNSLRNLKLEYLDLYMLPFPASLKP GKITMDIPEEDICRMDYRSVWSAMEECQNLGFTKSIGVSNF SSKKLQELMATANIPPAVNQVEMSPAFQQKKLREYCNANN ILVSAVSILGSNGTPWGSNAVLGSEVLKQIAMAKGKSVAQ VSMRWVYEQGASLVVKSFSEERLRENLNIFDWELTKEDNE KIGEIPQCRILTAYFLVSPNGPFKSQEELWDDKA* | *P. bracteatum* plant source; full-length amino acid sequence >SSDU-2015634 (also SSDU-2015636, ZSNV-2027701, RRID-2004435) | SEQ. ID NO. 7 |
| MELQYFSYFQPTSSVVALLLALVSILFSVVVLRKTFSNNYSS PASSTETAVLCHQRQQSCALPISGLLHVFMNKNGLIHVTLG NMADKYGPIFSFPTGSHRTLVVSSWEMVKECFTGNNDTAF SNRPIPLAFQTIFYACGGIDSYGLSSVPYGKYWRELRKVCV HNLLSNQQLLKFRHLIISQVDTSFNKLYELCKNSEDNQGMV RMDDWLAQLSFNVIGRIVCGFQSDPKTGAPSRVEQFKEVIN EASYFMSTSPVSDNVPMLGWIDQLTGLTRNMKHCGKKLD | *P. bracteatum* plant source; full-length amino acid sequence >TMWO-2027322 | SEQ. ID NO. 8 |

TABLE 1-continued

Example partial and full-length amino acid sequences of CYP-COR fusion enzymes.

| Sequence | Description | SEQ. ID NO. |
|---|---|---|
| LVVESIIKDHRQKRRFSRTKGGDEKDDEQDDFIDICLSIMEQ<br>PQLPGNNSPPQIPIKSIVLDMIGGGTDTTKLTTIWTLSLLLNN<br>PHVLDKAKQEVDAHFRKKRRSTDDAAAAVVDFDDIRNLV<br>YIQAAIIKESMRLYPASPVVERLSGEDCVVGGFHVPAGTRLW<br>ANVWKMQRDPKVWDDPLVFRPERFLSDEQKMVDVRGQN<br>YELLPFGAGRRICPGVSFSLDLMQLVLTRLILEFEMKSPSGK<br>VDMTATPGLMSYKVVPLDILLTHRRIKSCVQLASSERDMES<br>SGVPVITLSSGKVMPVLGMGTFEKVGKGSERERLAILKAIE<br>VGYRYFDTAAAYETEEVLGEAIAEALQLGLIESRDELFISSM<br>LWCTDAHPDRVLLALQNSLRNLKLEYLDLYMLPFPASLKP<br>GKITMDIPEEDICRMDYRSVWSAMEECQNLGFTKSIGVSNF<br>SCKKLQELMATANIPPAVNQVEMSPAFQQKKLREYCNANN<br>ILVSAVSILGSNGTPWGSNAVLGSEVLKQIAMAKGKSVAQ<br>VSMRWVYEQGASLVVKSFSEERLRENLNIFDWELTKEDNE<br>KIGEIPQCRILTAYFLVSPNGPFKSQEELWDDKA* | (also RRID-<br>2004435) | |
| SSPASSTETAVLCHQRQQSCALPISGLLHIFMNKNGLIHVTL<br>GNMADKYGPIFSFPTGSHRILVVSSWEMVKECFTGNNDTA<br>FSNRPIPLAFKTIFYACRGIDSYGLSSVPYGKYWRELRKVCV<br>HNLLSNQQLLKFRHLIISQVDTSFNKLYELCKNSEDNQGMV<br>RMDDWLAQLSFSVIGRIVCGFQSDPKTGAPSRVEQFKEAIN<br>EASYFMSTSPVSDNVPMLGWIDQLTGLTRNMTHCGKKLDL<br>VVESIINDHRQKRRFSRTKGGDEKDDEQDDFIDICLSIMEQP<br>QLPGNNNPPKIPIKSIVLDMIGAGTDTTKLTIIWTLSLLLNNP<br>NVLAKAKQEVDAHFETKKRSTNEASVVVDFDDIGNLVYIQ<br>AAIIKESMRLYPVSPVVERLSSEDCVVGGFHVPAGTRLWANV<br>WKMQRDPKVWDDPLVFRPERFLSDEQKMVDVRGQNYEL<br>LPFGAGRRICPGVSFSLDLMQLVLTRLILEFEMKSPSGKVD<br>MTATPGLMSYKVVPLDILLTHRRIKSCVQLASSERDMESSG<br>VPVITLRSGKVMPVLGMGTFEKAGKGSERERLAILKAIEVG<br>YRYFDTAAAYETEEVLGEAIAEALQLGLIKSRDELFISSML<br>WCTDAHPDRVLLALQNSLRNLKLEYVDLYMLPFPASLKPG<br>KITMDIPEEDICPMDYRSVWSAMEECQNLGLTKSIGVSNFS<br>CKKLEELMATANIPPAVNQVEMSPAFQQKKLREYCNANNI<br>LVSAVSILGSNGTPWGSNAVLGSEVLKKIAMAKGKSVAQV<br>SMRWVYEQGASLVVKSFSEERLRENLNIFDWQLTKEDNEK<br>IGEIPQCRILSAYFLVSPKGPFKSQEELWDDKA* | *P. bracteatum* plant source; partial-length amino acid sequence >pbr.PBRST1 PF_89405 | SEQ. ID NO. 9 |
| SSPASSTETAVLCHQRQQSCALPISGLLHIFMNKNGLIHVTL<br>GNMADKYGPIFSFPTGSHRILVVSSWEMVKECFTGNNDTFF<br>SNRPIPLAFKIIFYAGGVDSYGLALVPYGKYWRELRKICVH<br>NLLSNQQLLKFRHLIISQVDTSFNKLYELCKNSEDNQGMVR<br>MDDWLAQLSFSVIGRIVCGFQSDPKTGAPSRVEQFKEAINE<br>ASYFMSTSPVSDNVPMLGWIDQLTGLTRNMTHCGKKLDL<br>VVESIINDHRQKRRFSRTKGGDEKDDEQDDFIDICLSIMEQP<br>QLPGNNNPPKIPIKSIVLDMIGGGTDTTKLTTIWTLSLLLNNP<br>HVLDKAKQEVDAHFLTKRRSTNDAAVVDFDDIRNLVYIQA<br>IIKESMRLYPASPVVERLSGEDCVVGGFHVPAGTRLWVNV<br>WKMQRDPNVWADPMVFRPERFLSHGQKKMVDVRGKNYE<br>LLPFGAGRRICPGISFSLDLMQLVLTRLILEFEMKSPSGKVD<br>MTATPGLMSYKVVPLDILLTHRRIKSCVQLASSERDMESSG<br>VPVITLRSGKVMPVLGMGTFEKAGKGSERERLAILKAIEVG<br>YRYFDTAAAYETEEVLGEAIAEALQLGLIKSRDELFISSML<br>WCTDAHPDRVLLALQNSLRNLKLEYVDLYMLPFPASLKPG<br>KITMDIPEEDICPMDYRSVWSAMEECQNLGLTKSIGVSNFS<br>CKKLEELMATANIPPAVNQVEMSPAFQQKKLREYCNANNI<br>LVSAVSILGSNGTPWGSNAVLGSEVLKKIAMAKGKSVAQV<br>SMRWVYEQGASLVVKSFSEERLRENLNIFDWQLTKEDNEK<br>IGEIPQCRILSAYFLVSPKGPFKSQEELWDDKA* | *P. bracteatum* plant source; partial-length amino acid sequence >pbr.PBRST1 PF_4328 | SEQ. ID NO. 10 |
| SSPASSTETAVLCHQRQQSCALPISGLLHIFMNKNGLIHVTL<br>GNMADKYGPIFSFPTGSHRILVVSSWEMVKECFTGNNDTFF<br>SNRPIPLAFKIIFYAGGVDSYGLALVPYGKYWRELRKICVH<br>NLLSNQQLLNFRHLIISQVDTSFNKLYDLSNKKKNTTTDSG<br>TVRMDDWLAQLSFNVIGRIVCGFQTHTETSATSSVERFTEA<br>IDEASRFMSIATVSDTFPWLGWIDQLTGLTRKMKHYGKKL<br>DLVVESIIEDHRQNRRISGTKQGDDFIDICLSIMEQPQIIPGN<br>NDPPRQIPIKSIVLDMIGGGTDTTKLTTTWTLSLLLNNPHVL<br>EKAREEVDAHFGTKRRPTNDDAVMVEFDDIRNLVYIQAIIK<br>ESMRLYPASPVVERLSGEDCVVGGFHVPAGTRLWVNVWK<br>MQRDPNVWADPMVFRPERFLSDEQKMVDVRGQNYELLPF<br>GAGRRICPGVSFSLDLMQLVLTRLILEFEMKSPSGKVDMTA<br>TPGLMSYKVVPLDILLTHRRIKSCVQLASSERDMESSGVPVI<br>TLRSGKVMPVLGMGTFEKAGKGSERERLAILKAIEVGYRY | *P. bracteatum* plant source; partial-length amino acid sequence >pbr.PBRST1 PF_12180 | SEQ. ID NO. 11 |

TABLE 1-continued

Example partial and full-length amino acid sequences of CYP-COR fusion enzymes.

| Sequence | Description | SEQ. ID NO. |
|---|---|---|
| FDTAAAYETEEVLGEAIAEALQLGLIKSRDELFISSMLWCT DAHPDRVLLALQNSLRNLKLEYVDLYMLPFFPASLKPGKIT MDIPEEDICPMDYRSVWSAMEECQNLGLTKSIGVSNFSCKK LEELMATANIPPAVNQVEMSPAFQQKKLREYCNANNILVS AVSILGSNGTPWGSNAVLGSEVLKKIAMAKGKSVAQVSMR WVYEQGASLVVKSFSEERLRENLNIFDWQLTKEDNEKIGEI PQCRILSAYFLVSPKGPFKSQEELWDDKA* | | |
| VALRKKILKNYYSSSSSTATAVSHQWPKASRALPLIDLLHV FFNKTDLMHVTLGNMADKFGPIFSFPTGSHRTLVVSSWEK AKECFTGNNDIVFSGRPLPLAFKLIFYAGGIDSYGISQVPYG KKWRELRNICVHNILSNQQLLKFRHLMISQVDNSFNKLYEV CNSNKDEGDSATSTTAAGIVRMDDWLGKLAFDVIARIVCG FQSQTETSTTSSMERFTEAMDEASRFMSVTAVSDTVPWLG WIDQLTGLKRNMKHCGKKLNLVVKSIIEDHRQKRRLSSTK KGDENIIDEDEQDDFIDICLSIMEQPQLPGNNNPPKIPIKSIVL DMIGGGTDTTKLTTIWTLSLLLNNPHVLDKAKQEVDAHFL TKRRSTNDAAVVDFDDIRNLVYIQAIIKESMRLYPASPVVE RLSGEDCVVGGFHVPAGTRLWVNVWKMQRDPNVWADP MVFRPERFLSDEQKMVDVRGQNYELLPFGAGRRICPGVSFS LDLMQLVLTRLILEFEMKSPSGKVDMTATPGLMSYKVVPL DILLTHRRIKSCVQLASSERDMESSGVPVITLRSGKVMPVLG MGTFEKAGKGSERERLAILKAIEVGYRYFDTAAAYETEEVL GEAIAEALQLGLIKSRDELFISSMLWCTDAHPDRVLLALQN SLRNLKLEYVDLYMLPFPASLKPGKITMDIPEEDICPMDYRS VWSAMEECQNLGLTKSIGVSNFSCKKLEELMATANIPPAV NQVEMSPAFQQKKLREYCNANNILVSAVSILGSNGTPWGS NAVLGSEVLKKIAMAKGKSVAQVSMRWVYEQGASLVVKS FSEERLRENLNIFDWQLTKEDNEKIGEIPQCRILSAYFLVSPK GPFKSQEELWDDKA* | P. bracteatum plant source; partial-length amino acid sequence >pbr. PBRST1 PF_4329 | SEQ. ID NO. 12 |
| MELQYFSYFQPTSSVVALLLALVSILFSVVVLRKTFSNNYSS PASSTETAVLCHQRQQSCALPISGLLHVFMNKNGLIHVTLG NMADKYGPIFSFPTGSHRTLVVSSWEMVKECFTGNNDTAF SNRPIPLAFQTIFYACGGIDSYGLSSVPYGKYWRELRKVCV HNLLSNQQLLKFRHLIISQVDTSFNKLYELCKNSEDNQGMV RMDDWLAQLSFNVIGRIVCGFQSDPKTGAPSRVEQFKEVIN EASYFMSTSPVSDNVPMLGWIDQLTGLTRNMKHCGKKLD LVVESIIKDHRQKRRFSRTKGGDEKDDEQDDFIDICLSIMEQ PQLPGNNSPPQIPIKSIVLDMIGGGTDTTKLTTIWTLSLLLNN PHVLDKAKQEVDAHFRKKRSTDDAAAAVVDFDDIRNLV YIQAIIKESMRLYPASPVVERLSGEDCVVGGFHVPAGTRLW ANVWKMQRDPKVWDDPLVFRPERFLSDEQKMVDVRGQN YELLPFGAGRRICPGVSFSLDLMQLVLTRLILEFEMKSPSGK VDMTATPGLMSYKVVPLDILLTHRRIKSCVQLASSERDMES SGVPVITLSSGKVMPVLGMGTFEKVGKGSERERLAILKAIE VGYRYFDTAAAYETEEVLGEAIAEALQLGLIESRDELFISSM LWCTDAHPDRVLLALQNSLRNLKLEYLDYMLPFPASLKP GKITMDIPEEDICRMDYRSVWSAMEECQNLGFTKSIGVSNF SSKKLQELMATANIPPAVNQVEMSPAFQQKKLREYCNANN ILVSAVSILGSNGTPWGSNAVLGSEVLKQIAMAKGKSVAQ VSMRWVXKFSAYAIVWSLFFGHRICITLYSFLIRNVAYICIT Y* | P. bracteatum plant source; partial-length amino acid sequence >SSDU-2015635 | SEQ. ID NO. 13 |
| MELQYFSYFQPTSSVVALLLALVSILFSVVVLRKTFSNNYSS PASSTETAVLCHQRQQSCALPISGLLHVFMNKNGLIHVTLG NMADKYGPIFSFPTGSHRTLVVSSWEMVKECFTGNNDTAF SNRPIPLAFQTIFYACGGIDSYGLSSVPYGKYWRELRKVCV HNLLSNQQLLKFRHLIISQVDTSFNKLYELCKNSEDNQGMV RMDDWLAQLSFNVIGRIVCGFQSDPKTGAPSRVEQFKEVIN EASYFMSTSPVSDNVPMLGWIDQLTGLTRNMKHCGKKLD LVVESIIKDHRQKRRFSRTKGGDEKDDEQDDFIDICLSIMEQ PQLPGNNSPPQIPIKSIVLDMIGGGTDTTKLTTIWTLSLLLNN PHVLDKAKQEVDAHFRKKRSTDDAAAAVVDFDDIRNLV YIQAIIKESMRLYPASPVVERLSGEDCVVGGFHVPAGTRLW ANVWKMQRDPKVWDDPLVFRPERFLSDEQKMVDVRGQN YELLPFGAGRRICPGVSFSLDLMQLVLTRLILEFEMKSPSGK VDMTATPGLMSYKVVPLDILLTHRRIKSCVQLASSERDMES SGVPVITLSSGKVMPVLGMGTFEKVGKGSERERLAILKAIE VGYRYFDTAAAYETEEVLGEAIAEALQLGLIESRDELFISSM LWCTDAHPDRVLLALQNSLRQVFLMQIRLIYICTYQQVHL NIYFQINEFVLCDMYRNLKLEY | P. bracteatum plant source; partial-length amino acid sequence >SSDU-2015637 | SEQ. ID NO. 14 |

TABLE 1-continued

Example partial and full-length amino acid sequences of CYP-COR fusion enzymes.

| Sequence | Description | SEQ. ID NO. |
|---|---|---|
| LNNYSSSPASSTKTAVLSHQRQQSCALPISGLLHIFMNKNGL IHVTLGNMADKYGPIFSFPTGSHRTLVVSSWEMVKECFTGN NDTAFSNRPIPLAFKTIFYACGGIDSYGLSSVPYGKYWRELR KVCVHNLLSNQQLLKFRHLIISQVDTSFNKLYELCKNSEDN QGNYPTTTTAAGMVRIDDWLAELSFNVIGRIVCGFQSGPKT GAPSRVEQFKEAINEASYFMSTSPVSDNVPMLGWIDQLTGL TRNMKHCGKKLDLVVESIINDHRQKRRFSRTKGGDEKDDE QDDFIDICLSIMEQPQLPGNNNPSQIPIKSIVLDMIGGGTDTT KLTTIWTLSLLLNNPHVLDKAKQEVDAHFRTKRRSTNDAA AAVVDFDDIRNLVYIQAIIKESMRLYPASPVVERLSGEDCV VGGFHVPAGTRLWANVWKMQRDPKVWDDPLVFRPDRFL SDEQKMVDVRGQNYELLPFGAGRRVCPGVSFSLDLMQLV LTRLILEFEMKSPSGKVDMTATPGLMSYKVIPLDILLTHRRI KPCVQSAASERDMESSGVPVITLGSGKVMPVLGMGTFEKV GKGSERERLAFLKAIEVGYRYFDTAAAYETEEFLGEAIAEA LQLGLIKSRDELFITSKLWPCDAHPDLVVPALQNSLRNLKL EYVDLYMLPFPASLKPGKITMDIPEEDICRMDYRSVWAAM EECQNLGFTKSIGVSNFSCKKLQELMATANIPPAVNQVEMS PAFQQKKLREYCNANNILVSAISVLGSNGTPWGSNAVLGSE VLKKIAMAKGKSVAQVSMRWVYEQGASLVVKSFSEERLR ENLNIFDWELTKEDHEKIGEIPQCRILSAYFLVSPNGPFKSQE ELWDDEA* | C. majus plant source; partial-length amino acid sequence >chm.CMAST 2PF_14984 | SEQ. ID NO. 15 |

BisBIA Generating Modifications

Some methods, processes, and systems provided herein describe the production of bisbenzylisoquinoline alkaloids (bisBIAs). BisBIAs are dimeric molecules that may be formed by coupling reactions between two BIA monomers. In examples, bisBIAs may be formed by carbon-oxygen coupling reactions. In other examples, bisBIAs may be formed by carbon-carbon coupling reactions. In some examples, the bisBIA dimeric molecule is a homodimer, comprising two identical BIA monomers. In examples, an engineered host cell may produce one BIA monomer. In these examples, the BIA monomers may form homodimers when contacted with one or more coupling enzymes. In other examples, the bisBIA dimeric molecule is a heterodimer, comprising two different BIA monomers. For example, a bisBIA may be a heterodimer that comprises BIA monomers that are enantiomers of each other. In some examples, an engineered host cell may produce two or more BIA monomers. In these examples, the BIA monomers may form homodimers and heterodimers when contacted with one or more coupling enzymes.

Some of these methods, processes, and systems that describe the production of bisBIAs may comprise an engineered host cell. In some examples, the engineered host cell may be engineered to produce BIA monomers which, in turn, may be used as building block molecules for forming bisBIAs. Examples of BIA monomers that may be used to form bisBIAs include coclaurine, N-methylcoclaurine, laudanine, norcoclaurine, norlaudanosoline, 6-O-methyl-norlaudanosoline, 3'-hydroxy-N-methylcoclaurine, 3'-hydroxycoclaurine, reticuline, norreticuline, norlaudanine, laudanosine, and papaverine. In particular, engineered host cells may synthesize BIA monomers from norcoclaurine or norlaudanosoline by expression of heterologous enzymes including O-methyltransferases, N-methyltransferases, and 3'-hydroxylases. Examples of O-methyltransferases may include norcoclaurine 6-O-methyltransferase (6OMT) from *Thalicrum flavum, Nelumbo nucifera, Populus euphratica*, or another species. Further examples of O-methyltransferases may include catechol O-methyltransferase (COMT) from *Homo sapiens, Mus musculus, Rattus norvegicus, Gorilla gorilla*, or another species. Further examples of N-methyltransferases may include coclaurine N-methyltransferase (CNMT) from *T. flavum, N. nucifera, Aristolochia fimbriata*, or another species. Examples of 3'hydroxylases may include N-methylcoclaurine 3'-hydroxylase (CYP80B1) from *Eschscholzia californica, T. flavum, N. nucifera*, or another species.

The engineered host cells may produce either (S) or (R) enantiomers of any given BIA monomer. Additionally or alternatively, the engineered host cells may produce a mixture of both enantiomers. The ratio of (S) and (R) enantiomers may be determined by the substrate and product specificities of the one or more enzymes that synthesize the BIA monomers. Alternatively, the amount of each enantiomer present may be modified by the expression of an additional enzyme or enzymes that perform the epimerization of one stereoisomer into another, as discussed above.

These BIA monomers may be fused into a dimeric bisBIA scaffold. In particular, the BIA monomers may be fused into a dimeric bisBIA scaffold utilizing one or more enzymes that are produced by the engineered host cell. Additionally or alternatively, the BIA monomers may be fused into a dimeric bisBIA scaffold utilizing one or more enzymes that are provided to the BIA monomers from a source that is external to the engineered host cell. The one or more enzymes may be used to form carbon-oxygen and/or carbon-carbon coupling reactions to fuse two BIA monomers at one, two, or three positions. In some examples, two BIA monomers may be linked by an ether bridge. In some examples, a direct carbon-carbon bond may be used to connect the two BIA monomers. In some examples, a bisBIA that is formed by fusing two BIA monomers may comprise one diphenyl ether linkage. In some examples, two BIA monomers may be fused to form a bisBIA that comprises two diphenyl ether linkages. In some examples, a bisBIA that is formed from two BIA monomers may comprise three diphenyl ether linkages. In some examples, the bisBIA may comprise one diphenyl ether linkage and one benzyl phenyl ether linkage.

In some cases, the bisBIA may comprise one benzyl phenyl ether linkage and two diphenyl ether linkages.

In examples, the BIA monomers may be contacted with a sufficient amount of the one or more enzymes that may be used to form coupling reactions to fuse two BIA monomers such that at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 82%, at least 84%, at least 86%, at least 88%, at least 90%, at least 91%, at least 92%, at least 93%, at least 94%, at least 95%, at least 96%, at least 97%, at least 98%, at least 99%, at least 99.5%, at least 99.7%, or 100% of said BIA monomers are converted to bisBIAs. The one or more enzymes that may be used to dimerize the BIA monomers into bisBIAs may contact the BIA monomers in vitro. Additionally, or alternatively, the one or more enzymes that may be used to dimerize the BIA monomers into bisBIAs may contact the BIA monomers in vivo. Additionally, the one or more bisBIA dimerizing enzyme may be expressed in a host cell that produces BIA monomers. Alternatively, the BIA monomers may be provided to the engineered host cell that expresses the bisBIA dimerizing enzyme. Alternatively, the one or more bisBIA dimerizing enzymes may be provided to a cell having BIA monomers within.

In some examples, the bisbenzylisoquinoline alkaloid is a compound of any one of Formulas Va-Vu:

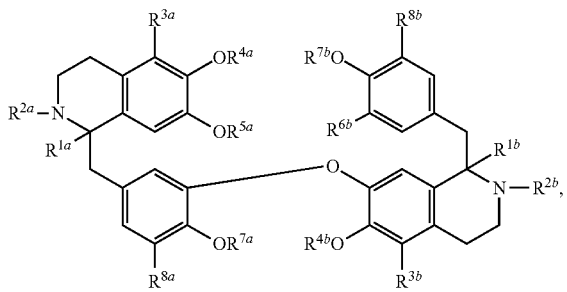

Formula Va

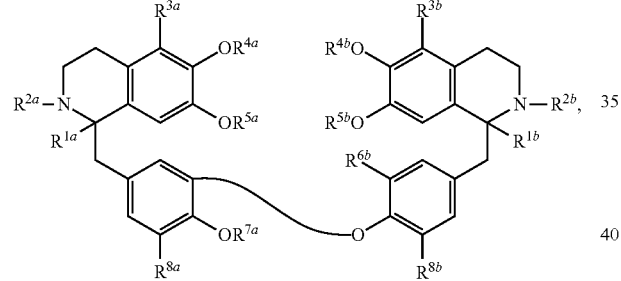

Formula Vb

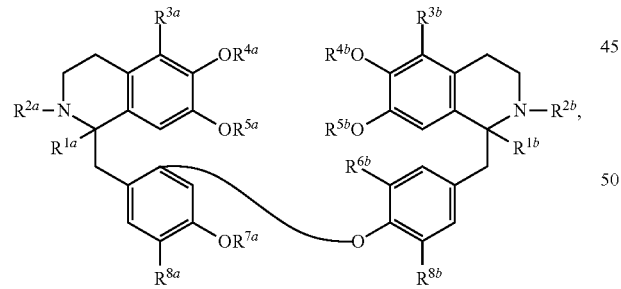

Formula Vc

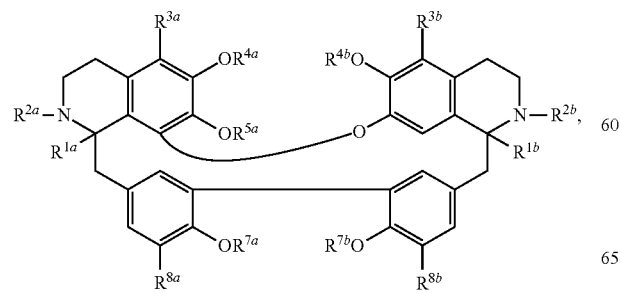

-continued

Formula Vd

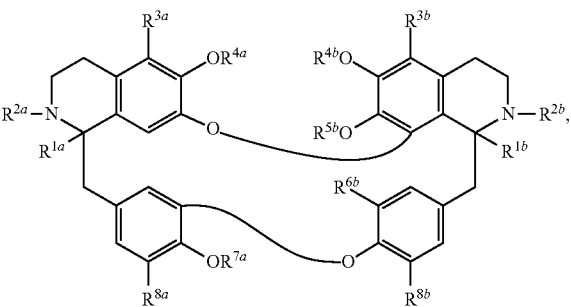

Formula Ve

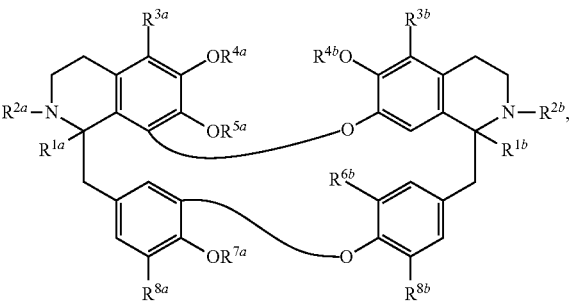

Formula Vf

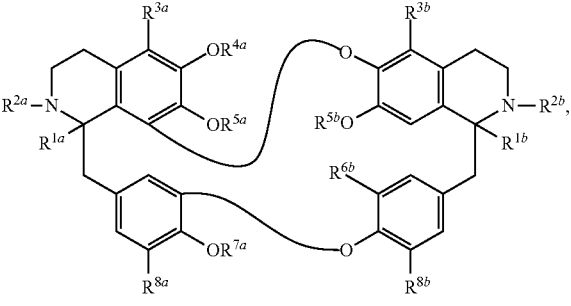

Formula Vg

Formula Vh

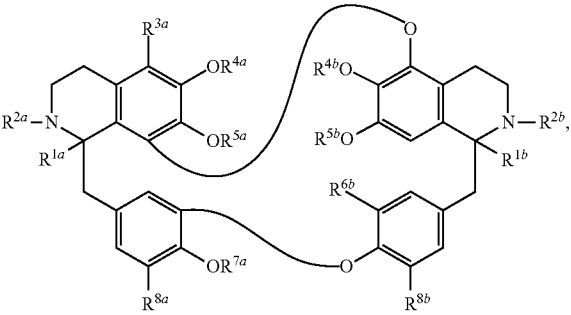

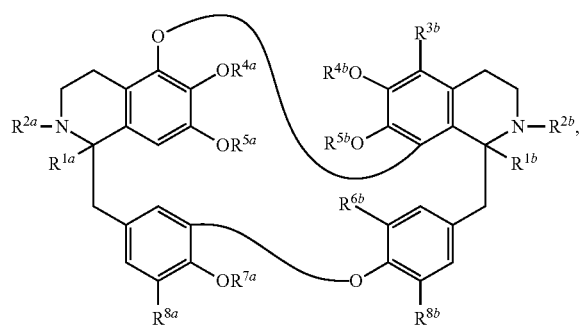

Formula Vq

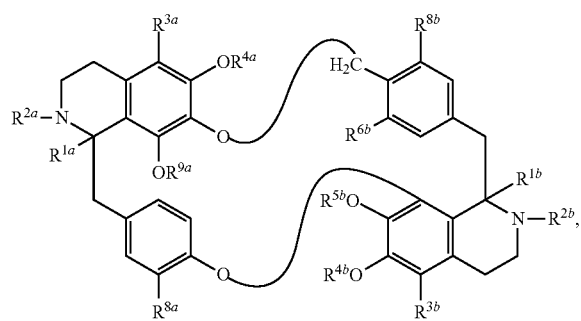

Formula Vu

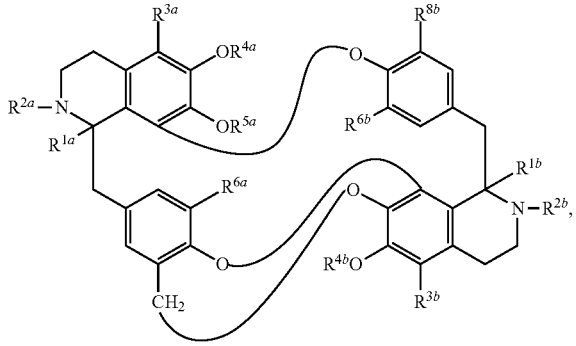

Formula Vr

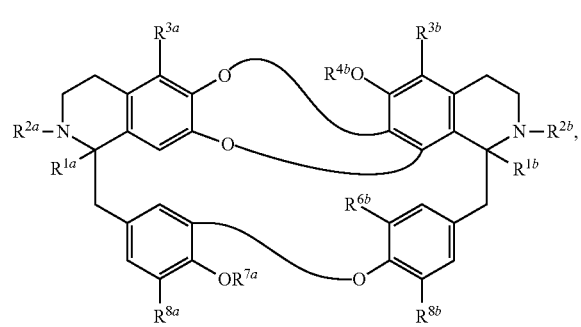

Formula Vs

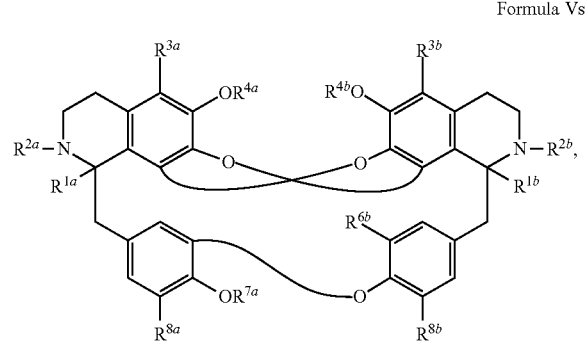

Formula Vt

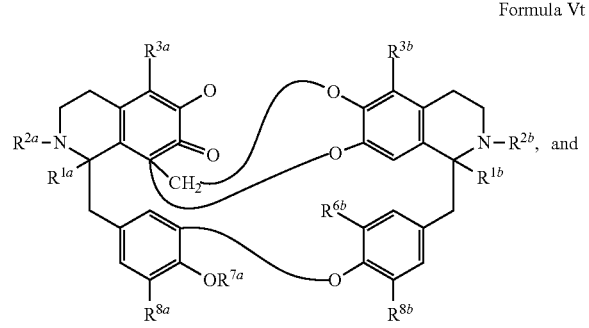

and or a salt thereof, wherein:
$R^{1a}$, $R^{1b}$, $R^{2a}$, and $R^{2b}$ are independently selected from hydrogen and $C_1$-$C_4$ alkyl;
$R^{3a}$, $R^{3b}$, $R^{6a}$, $R^{6b}$, $R^{8a}$, and $R^{8b}$ are independently selected from hydrogen, hydroxy, fluoro, chloro, bromo, carboxaldehyde, $C_1$-$C_4$ acyl, $C_1$-$C_4$ alkyl, and $C_1$-$C_4$ alkoxy;
$R^{4a}$ and $R^{5a}$ are independently selected from hydrogen and $C_1$-$C_4$ alkyl, or $R^{4a}$ and $R^{5a}$ together form a methylene bridge;
$R^{4b}$ and $R^{5b}$ are independently selected from hydrogen and $C_1$-$C_4$ alkyl, or $R^{4b}$ and $R^{5b}$ together form a methylene bridge; and
$R^{7a}$, $R^{7b}$, and $R^{9a}$ are independently selected from hydrogen and $C_1$-$C_4$ alkyl.

In some examples, $R^{1a}$ and $R^{1b}$ are each hydrogen; $R^{2a}$ and $R^{2b}$ are each methyl; $R^{3a}$ and $R^{3b}$ are each hydrogen; $R^{4a}$ and $R^{5a}$ are independently hydrogen or methyl; $R^{4b}$ and $R^{5b}$ are independently hydrogen or methyl, or $R^{4b}$ and $R^{5b}$ together form a methylene bridge; $R^{6a}$, $R^{6b}$, $R^{8a}$, and $R^{8b}$ are each hydrogen; and $R^{7a}$, $R^{7b}$, and $R^{9a}$ are independently hydrogen or methyl.

As illustrated above, the bisBIA compounds of Formulas Va, Vb, and Vd are formed by fusing two BIA monomers using a carbon-oxygen coupling reaction. Additionally, the bisBIA compounds of Formulas Vc, Vf, and Vh are formed by fusing two BIA monomers using both a carbon-oxygen coupling reaction and a carbon-carbon coupling reaction. Further, the bisBIA compounds of Formulas Ve, Vg, Vi, Vj, Vk, Vl, Vm, Vo, Vp, and Vq are formed by fusing two BIA monomers using two carbon-oxygen coupling reactions. The bisBIA compound of Formula Vn is formed by fusing two BIA monomers using two carbon-oxygen coupling reactions and a carbon-carbon coupling reaction. Additionally, the bisBIA compound of Formula Vr is formed by fusing two BIA monomers using three carbon-oxygen coupling reactions.

The one or more enzymes that may be used to form the coupling reactions may include known cytochrome P450s such as *Berberis stolonifera* CYP80A1 or similar cytochrome P450 enzymes from other plants that naturally synthesize these compounds. Alternatively, the coupling reaction may be performed by an enzyme that is not a cytochrome P450. The one or more enzymes that may be used to form the coupling reactions may be engineered to accept non-native substrates. Accordingly, the one or more enzymes that may be used to form the coupling reactions may be used to generate non-natural bisBIA molecules. In examples, the one or more enzymes may fuse a natural BIA monomer with a non-natural BIA monomer to produce a non-natural bisBIA molecule. In other examples, the one or more enzymes may fuse two non-natural BIA monomers to produce a non-natural bisBIA molecule. Enzyme engineered strategies may be used to identify one or more enzymes that may be used to form the coupling reactions that fuse BIA monomers to produce bisBIAs. In examples, enzyme engineering strategies may include site directed mutagenesis, random mutagenesis and screening, DNA shuffling, and screening.

shown in Scheme 2, wherein $R^a$, $R^b$, $R^c$, and $R^d$ are independently selected from hydrogen, hydroxy, fluoro, chloro, bromo, carboxaldehyde, $C_1$-$C_4$ acyl, $C_1$-$C_4$ alkyl, and alkoxy. In some examples, $R^a$, $R^b$, and the carbon atoms to which they are attached optionally form a carbocycle or heterocycle. In some examples, $R^c$, $R^d$, and the carbon atoms to which they are attached optionally form a carbocycle or heterocycle.

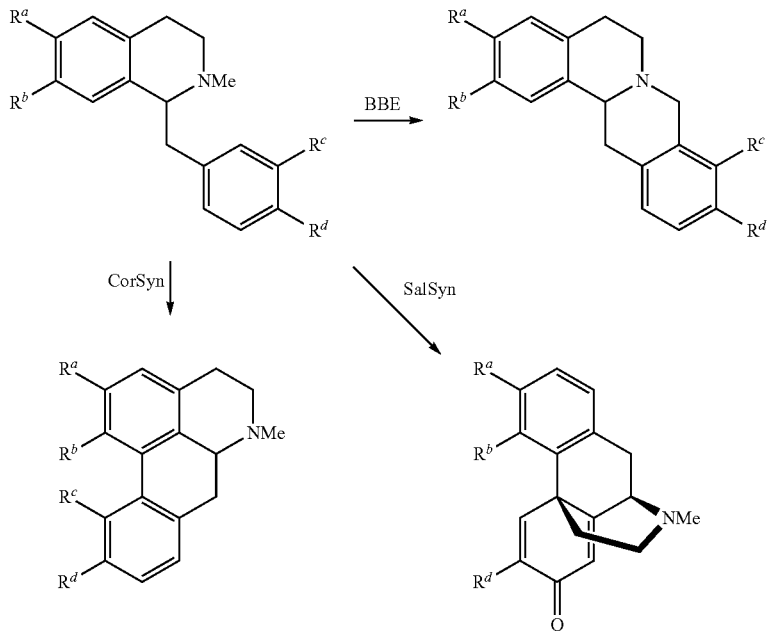

Scheme 2

Once bisBIAs are formed, the bisBIAs may be further derivatized or modified. The bisBIAs may be derivatized or modified utilizing one or more enzymes that are produced by the engineered host cell. In particular, the bisBIAs may be derivatized or modified by contacting the bisBIAs with one or more enzymes that are produced by the engineered host cell. Additionally or alternatively, the bisBIAs may be derivatized or modified by contacting the bisBIAs with one or more enzymes that are provided to the bisBIAs from a source that is external to the engineered host cell. The one or more enzymes that may be used to derivatize or modify the bisBIAs may be used to perform tailoring reactions. Examples of tailoring reactions include oxidation, reduction, O-methylation, N-methylation, O-demethylation, acetylation, methylenedioxybridge formation, and O,O-demethylenation. A bisBIA may be derivatized or modified using one or more tailoring reactions.

Examples of tailoring reactions are provided in Table 8. In some examples, tailoring enzymes may be used to catalyze carbon-carbon coupling reactions performed on a bisBIA, or a derivative thereof. Examples of tailoring enzymes that may be used to catalyze carbon-carbon coupling reactions include a Berberine bridge enzyme (BBE) from *Papaver somniferum, Eschscholzia californica, Coptis japonica, Berberis stolonifer, Thalictrum flavum*, or another species; Salutaridine synthase (SalSyn) from *Papaver somniferum* or another species; and Corytuberine synthase (CorSyn) from *Coptis japonica* or another species. Non-limiting examples of reactions that can be catalyzed by tailoring enzymes are In some examples, tailoring enzymes may be used to catalyze oxidation reactions performed on a bisBIA, or a derivative thereof. Examples of tailoring enzymes that may be used to catalyze oxidation reactions include a Tetrahydroprotoberberine oxidase (STOX) from *Coptis japonica, Argemone mexicana, Berberis wilsonae*, or another species; Dihydrobenzophenanthridine oxidase (DBOX) from *Papaver somniferum* or another species; Methylstylopine hydroxylase (MSH) from *Papaver somniferum* or another species; and Protopine 6-hydroxylase (P6H) from *Papaver somniferum, Eschscholzia californica*, or another species.

Tailoring enzymes may also be used to catalyze methylenedioxy bridge formation reactions performed on a bisBIA, or a derivative thereof. Examples of tailoring enzymes that may be used to catalyze methylenedioxy bridge formation reactions include a Stylopine synthase (StySyn or STS) from *Papaver somniferum, Eschscholzia californica, Argemone mexicana*, or another species; Cheilanthifoline synthase (CheSyn or CFS) from *Papaver somniferum, Eschscholzia californica, Argemone mexicana*, or another species; and Canadine synthase (CAS) from *Thalictrum flavum, Coptis chinensis*, or another species.

In other examples, tailoring enzymes may be used to catalyze O-methylation reactions performed on a bisBIA, or a derivative thereof. Examples of tailoring enzymes that may be used to catalyze O-methylation reactions include a Norcoclaurine 6-O-methyltransferase (6OMT) from *Papaver somniferum, Thalictrum flavum, Coptis japonica, Papaver bracteatum*, or another species; 3'hydroxy-N-methylcoclaurine 4'-O-methyltransferase (4'OMT) from *Papaver somniferum, Thalictrum flavum, Coptis japonica, Coptis chinensis*, or another species; Reticuline 7-O-methyltransferase (7OMT) from *Papaver somniferum, Eschscholzia californica*, or another species; and Scoulerine 9-O-methyltransferase (9OMT) from *Papaver somniferum, Thalictrum flavum, Coptis japonica, Coptis chinensis*, or another species.

Additionally, tailoring enzymes may be used to catalyze N-methylation reactions performed on a bisBIA, or a derivative thereof. Examples of tailoring enzymes that may be used to catalyze N-methylation reactions include Coclaurine N-methyltransferase (CNMT) from *Papaver somniferum, Thalictrum flavum, Coptis japonica*, or another species; Tetrahydroprotoberberine N-methyltransferase (TNMT) from *Papaver somniferum, Eschscholzia californica, Papaver bracteatum*, or another species.

Further, tailoring enzymes may be used to catalyze O-demethylation reactions performed on a bisBIA, or a derivative thereof. Examples of tailoring enzymes that may be used to catalyze O-demethylation reactions include Thebaine demethylase (T6ODM) from *Papaver somniferum* or another species; and Codeine demethylase (CODM) from *Papaver somniferum*, or another species.

Tailoring enzymes may also be used to catalyze reduction reactions performed on a bisBIA, or a derivative thereof. Examples of tailoring enzymes that may be used to catalyze reduction reactions include Salutaridine reductase (SalR) from *Papaver somniferum, Papaver bracteatum*, or another species; Codeinone reductase (COR) from *Papaver somniferum* or another species; and Sanguinarine reductase (SanR) from *Eschscholzia californica* or another species. In other examples, tailoring enzymes may be used to catalyze acetylation reactions performed on a bisBIA, or a derivative thereof. An example of a tailoring enzyme that may be used to catalyze acetylation reactions includes Salutaridine acetyltransferase (SalAT) from *Papaver somniferum* or another species.

O-Demethylation Modifications

Some methods, processes, and systems provided herein describe the conversion of a first benzylisoquinoline alkaloid to a second benzylisoquinoline alkaloid by the removal of an O-linked methyl group. Some of these methods, processes, and systems may comprise an engineered host cell. In some examples, the conversion of a first benzylisoquinoline alkaloid to a second benzylisoquinoline alkaloid is a key step in the conversion of a substrate to a nor-opioids or nal-opioids. In some examples, the conversion of a first alkaloid to a second alkaloid comprises a demethylase reaction.

FIG. 23 illustrates an enzyme having opioid 3-O-demethylase activity, in accordance with embodiments of the invention. Specifically, the enzyme may act on any morphinan alkaloid structure to remove the methyl group from the oxygen bound to carbon 3.

Examples of amino acid sequences of ODM enzymes are set forth in Table 3. An amino acid sequence for an ODM that is utilized in converting a first alkaloid to a second alkaloid may be 75% or more identical to a given amino acid sequence as listed in Table 3. For example, an amino acid sequence for such an epimerase may comprise an amino acid sequence that is at least 75% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, or 99% or more identical to an amino acid sequence as provided herein. Additionally, in certain embodiments, an "identical" amino acid sequence contains at least 80%-99% identity at the amino acid level to the specific amino acid sequence. In some cases an "identical" amino acid sequence contains at least about 85%, 86%, 87%, 88%, 89%, 90%, 91%, 92%, 93%, 94% and more in certain cases, at least 95%, 96%, 97%, 98% and 99% identity, at the amino acid level. In some cases, the amino acid sequence may be identical but the DNA sequence is altered such as to optimize codon usage for the host organism, for example.

An engineered host cell may be provided that produces an ODM that converts a first alkaloid to a second alkaloid, wherein the ODM comprises a given amino acid sequence as listed in Table 3. An engineered host cell may be provided that produces one or more ODM enzymes. The ODM that is produced within the engineered host cell may be recovered and purified so as to form a biocatalyst. The process may include contacting the first alkaloid with an ODM in an amount sufficient to convert said first alkaloid to a second alkaloid. In examples, the first alkaloid may be contacted with a sufficient amount of the one or more enzymes such that at least 5% of said first alkaloid is converted to a second alkaloid. In further examples, the first alkaloid may be contacted with a sufficient amount of the one or more enzymes such that at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 82%, at least 84%, at least 86%, at least 88%, at least 90%, at least 91%, at least 92%, at least 93%, at least 94%, at least 95%, at least 96%, at least 97%, at least 98%, at least 99%, at least 99.5%, at least 99.7%, or 100% of said first alkaloid is converted to a second alkaloid.

The one or more enzymes that may be used to convert a first alkaloid to a second alkaloid may contact the first alkaloid in vitro. Additionally, or alternatively, the one or more enzymes that may be used to convert a first alkaloid to a second alkaloid may contact the first alkaloid in vivo. In some examples, the one or more enzymes that may be used to convert a first alkaloid to a second alkaloid may be provided to a cell having the first alkaloid within. In some examples, the one or more enzymes that may be used to convert a first alkaloid to a second alkaloid may be produced within an engineered host cell.

In some examples, the methods provide for engineered host cells that produce an alkaloid product, wherein the O-demethylation of a substrate to a product may comprise a key step in the production of an alkaloid product. In some examples, the alkaloid produced is a nor-opioid or a nal-opioid. In still other embodiments, the alkaloid produced is derived from a nor-opioid or a nal-opioid. In another embodiment, a first alkaloid is an intermediate toward the product of the engineered host cell. In still other embodiments, the alkaloid product is selected from the group consisting of morphine, oxymorphine, oripavine, hydromorphone, dihydromorphine, 14-hydroxymorphine, morphinone, and 14-hydroxymorphinone.

In some examples, the substrate alkaloid is an opioid selected from the group consisting of codeine, oxycodone, thebaine, hydrocodone, dihydrocodeine, 14-hydroxycodeine, codeinone, and 14-hydroxycodeinone.

N-Demethylation Modifications

Some methods, processes, and systems provided herein describe the conversion of a first alkaloid to a second alkaloid by the removal of an N-linked methyl group. Some of these methods, processes, and systems may comprise an engineered host cell. In some examples, the conversion of a first alkaloid to a second alkaloid is a key step in the conversion of a substrate to a nor-opioids or nal-opioids. In some examples, the conversion of a first alkaloid to a second alkaloid comprises a demethylase reaction.

FIG. 24 illustrates an enzyme having opioid N-demethylase activity, in accordance with embodiments of the invention. Specifically, the enzyme may act on any morphinan alkaloid structure to remove the methyl group from the nitrogen.

Examples of an amino acid sequence of an N-demethylase enzyme that may be used to perform the conversion a first alkaloid to a second alkaloid are provided in Table 4. An amino acid sequence for an NDM that is utilized in converting a first alkaloid to a second alkaloid may be 75% or more identical to a given amino acid sequence as listed in Table 4. For example, an amino acid sequence for such an epimerase may comprise an amino acid sequence that is at least 75% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, or 99% or more identical to an amino acid sequence as provided herein. Additionally, in certain embodiments, an "identical" amino acid sequence contains at least 80%-99% identity at the amino acid level to the specific amino acid sequence. In some cases an "identical" amino acid sequence contains at least about 85%, 86%, 87%, 88%, 89%, 90%, 91%, 92%, 93%, 94% and more in certain cases, at least 95%, 96%, 97%, 98% and 99% identity, at the amino acid level. In some cases, the amino acid sequence may be identical but the DNA sequence is altered such as to optimize codon usage for the host organism, for example.

An engineered host cell may be provided that produces an NDM that converts a first alkaloid to a second alkaloid, wherein the NDM comprises an amino acid sequence as listed in Table 4. An engineered host cell may be provided that produces one or more NDM enzymes. The NDM that is produced within the engineered host cell may be recovered and purified so as to form a biocatalyst. The process may include contacting the first alkaloid with an NDM in an amount sufficient to convert said first alkaloid to a second alkaloid. In examples, the first alkaloid may be contacted with a sufficient amount of the one or more enzymes such that at least 5% of said first alkaloid is converted to a second alkaloid. In further examples, the first alkaloid may be contacted with a sufficient amount of the one or more enzymes such that at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 82%, at least 84%, at least 86%, at least 88%, at least 90%, at least 91%, at least 92%, at least 93%, at least 94%, at least 95%, at least 96%, at least 97%, at least 98%, at least 99%, at least 99.5%, at least 99.7%, or 100% of said first alkaloid is converted to a second alkaloid.

The one or more enzymes that may be used to convert a first alkaloid to a second alkaloid may contact the first alkaloid in vitro. Additionally, or alternatively, the one or more enzymes that may be used to convert a first alkaloid to a second alkaloid may contact the first alkaloid in vivo. In some examples, the one or more enzymes that may be used to convert a first alkaloid to a second alkaloid may be provided to a cell having the first alkaloid within. In some examples, the one or more enzymes that may be used to convert a first alkaloid to a second alkaloid may be produced within an engineered host cell.

In some examples, the methods provide for engineered host cells that produce an alkaloid product, wherein the N-demethylation of a substrate to a product may comprise a key step in the production of an alkaloid product. In some examples, the alkaloid produced is a nor-opioid or a nal-opioid. In still other embodiments, the alkaloid produced is derived from a nor-opioid or a nal-opioid. In another embodiment, a first alkaloid is an intermediate toward the product of the engineered host cell. In still other embodiments, the alkaloid product is selected from the group consisting of norcodeine, noroxycodone, northebaine, norhydrocodone, nordihydro-codeine, nor-14-hydroxy-codeine, norcodeinone, nor-14-hydroxy-codeinone, normorphine, noroxymorphone, nororipavine, norhydro-morphone, nordihydro-morphine, nor-14-hydroxy-morphine, normorphinone, and nor-14-hydroxy-morphinone.

In some examples, the substrate alkaloid is an opioid selected from the group consisting of codeine, oxycodone, thebaine, hydrocodone, dihydrocodeine, 14-hydroxycodeine, codeinone, and 14-hydroxycodeinone, morphine, oxymorphone, oripavine, hydromorphone, dihydromorphine, 14-hydroxy-morphine, morphinone, or 14-hydroxy-morphinone.

N-Methyltransferase Modifications

Some methods, processes, and systems provided herein describe the conversion of a first alkaloid to a second alkaloid by the addition of an N-linked sidechain group. Some methods, processes, and systems provided herein describe the conversion of a first alkaloid to a second alkaloid by the transfer of a sidechain group from a cosubstrate to the first alkaloid. Some of these methods, processes, and systems may comprise an engineered host cell. In some examples, the conversion of a first alkaloid to a second alkaloid is a key step in the conversion of a substrate to a nal-opioid. In some examples, the conversion of a first alkaloid to a second alkaloid comprises a methyltransferase reaction.

Figure 25:
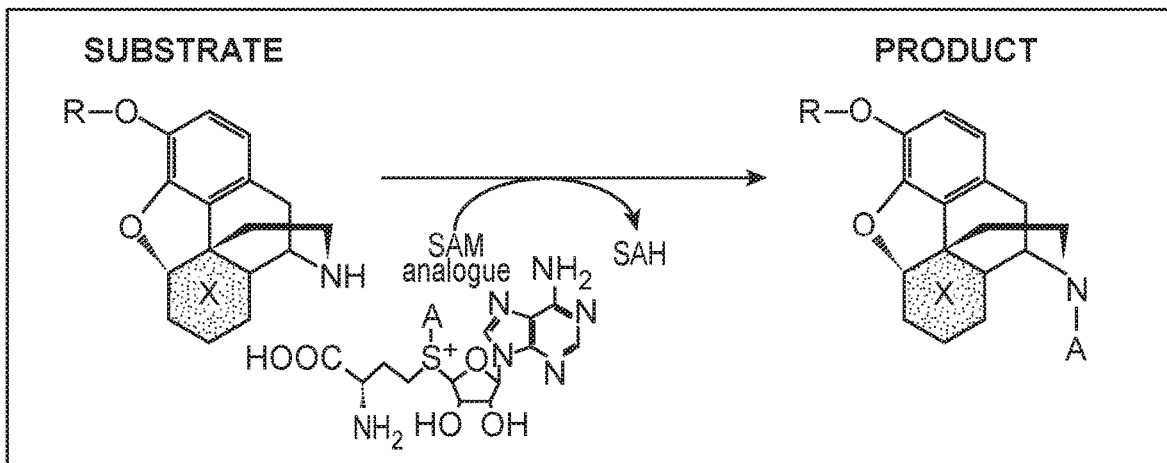
FIG. 25 illustrates an enzyme having N-methyltransferase activity, in accordance with embodiments of the invention.

FIG. 25 illustrates an enzyme having N-methyltransferase activity, in accordance with embodiments of the invention. Specifically, the enzyme may act on any morphinan alkaloid structure to add a methyl group or other carbon moiety to the nitrogen. S-Adenosyl methionine (SAM) may act as the donor of the functional group (methyl, allyl, cyclopropyl-methyl, or other).

Examples of amino acid sequences of NMT enzymes are set forth in Table 5. An amino acid sequence for an NMT that is utilized in converting a first alkaloid to a second alkaloid may be 75% or more identical to a given amino acid sequence as listed in Table 5. For example, an amino acid sequence for such an epimerase may comprise an amino acid sequence that is at least 75% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, or 99% or more identical to an amino acid sequence as provided herein. Additionally, in certain embodiments, an "identical" amino acid sequence contains at least 80%-99% identity at the amino acid level to the specific amino acid sequence. In some cases an "identical" amino acid sequence contains at least about 85%, 86%, 87%, 88%, 89%, 90%, 91%, 92%, 93%, 94% and more in certain cases, at least 95%, 96%, 97%, 98% and 99% identity, at the amino acid level. In some cases, the amino acid sequence may be identical but the DNA sequence is altered such as to optimize codon usage for the host organism, for example.

An engineered host cell may be provided that produces an NMT that converts a first alkaloid to a second alkaloid, wherein the NMT comprises an amino acid sequence as provided in Table 5. An engineered host cell may be provided that produces one or more NMT enzymes. The NMT that is produced within the engineered host cell may be recovered and purified so as to form a biocatalyst. The process may include contacting the first alkaloid with an NMT in an amount sufficient to convert said first alkaloid to a second alkaloid. In examples, the first alkaloid may be contacted with a sufficient amount of the one or more enzymes such that at least 5% of said first alkaloid is converted to a second alkaloid. In further examples, the first alkaloid may be contacted with a sufficient amount of the one or more enzymes such that at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 82%, at least 84%, at least 86%, at least 88%, at least 90%, at least 91%, at least 92%, at least 93%, at least 94%, at least 95%, at least 96%, at least 97%, at least 98%, at least 99%, at least 99.5%, at least 99.7%, or 100% of said first alkaloid is converted to a second alkaloid.

The one or more enzymes that may be used to convert a first alkaloid to a second alkaloid may contact the first alkaloid in vitro. Additionally, or alternatively, the one or more enzymes that may be used to convert a first alkaloid to a second alkaloid may contact the first alkaloid in vivo. In some examples, the one or more enzymes that may be used to convert a first alkaloid to a second alkaloid may be provided to a cell having the first alkaloid within. In some examples, the one or more enzymes that may be used to convert a first alkaloid to a second alkaloid may be produced within an engineered host cell.

In some examples, the methods provide for engineered host cells that produce an alkaloid product, wherein the N-methyltransferase of a substrate to a product may comprise a key step in the production of an alkaloid product. In some examples, the alkaloid produced is a nal-opioid. In still other embodiments, the alkaloid produced is derived from a nor-opioid or a nal-opioid. In another embodiment, a first alkaloid is an intermediate toward the product of the engineered host cell. In still other embodiments, the alkaloid product is selected from the group including naloxone, naltrexone, and nalmefene.

In some examples, the substrate alkaloid is an opioid selected from the group consisting of norcodeine, noroxycodone, northebaine, norhydrocodone, nordihydro-codeine, nor-14-hydroxy-codeine, norcodeinone, nor-14-hydroxy-codeinone, normorphine, noroxymorphone, nororipavine, norhydro-morphone, nordihydro-morphine, nor-14-hydroxy-morphine, normorphinone, and nor-14-hydroxy-morphinone. In some examples, the cosubstrate is S-adenosyl-methionine, Allyl-S-adenosylmethionine, or cyclopropylmethyl-S-adenosylmethionine.

Heterologous Coding Sequences

In some instances, the engineered host cells harbor one or more heterologous coding sequences (such as two or more, three or more, four or more, five or more) which encode activity(ies) that enable the engineered host cells to produce desired enzymes of interest and/or BIAs of interest, e.g., as described herein. As used herein, the term "heterologous coding sequence" is used to indicate any polynucleotide that codes for, or ultimately codes for, a peptide or protein or its equivalent amino acid sequence, e.g., an enzyme, that is not normally present in the host organism and may be expressed in the host cell under proper conditions. As such, "heterologous coding sequences" includes multiple copies of coding sequences that are normally present in the host cell, such that the cell is expressing additional copies of a coding sequence that are not normally present in the cells. The heterologous coding sequences may be RNA or any type thereof, e.g., mRNA, DNA or any type thereof, e.g., cDNA, or a hybrid of RNA/DNA. Coding sequences of interest include, but are not limited to, full-length transcription units that include such features as the coding sequence, introns, promoter regions, 3'-UTRs, and enhancer regions.

The engineered host cells may also be modified to possess one or more genetic alterations to accommodate the heterologous coding sequences. Alterations of the native host genome include, but are not limited to, modifying the genome to reduce or ablate expression of a specific protein that may interfere with the desired pathway. The presence of such native proteins may rapidly convert one of the intermediates or final products of the pathway into a metabolite or other compound that is not usable in the desired pathway. Thus, if the activity of the native enzyme were reduced or altogether absent, the produced intermediates would be more readily available for incorporation into the desired product.

Heterologous coding sequences include but are not limited to sequences that encode enzymes, either wild-type or equivalent sequences, that are normally responsible for the production of BIAs of interest in plants. In some cases, the enzymes for which the heterologous sequences code may be any of the enzymes in the 1-BIA pathway, and may be from any convenient source. The choice and number of enzymes encoded by the heterologous coding sequences for the particular synthetic pathway may be selected based upon the desired product. In certain embodiments, the host cells may include 1 or more, 2 or more, 3 or more, 4 or more, 5 or more, 6 or more, 7 or more, 8 or more, 9 or more, 10 or more, 11 or more, 12 or more, 13 or more, 14 or more, or even 15 or more heterologous coding sequences, such as 1, 2, 3, 4, 5, 6, 7, 8, 9, 10, 11, 12, 13, 14, or 15 heterologous coding sequences.

As used herein, the term "heterologous coding sequences" also includes the coding portion of the peptide or enzyme, i.e., the cDNA or mRNA sequence, of the peptide or enzyme, as well as the coding portion of the full-length transcriptional unit, i.e., the gene including introns and exons, as well as "codon optimized" sequences, truncated sequences or other forms of altered sequences that code for the enzyme or code for its equivalent amino acid sequence, provided that the equivalent amino acid sequence produces a functional protein. Such equivalent amino acid sequences may have a deletion of one or more amino acids, with the deletion being N-terminal, C-terminal, or internal. Truncated forms are envisioned as long as they have the catalytic capability indicated herein. Fusions of two or more enzymes are also envisioned to facilitate the transfer of metabolites in the pathway, provided that catalytic activities are maintained.

Operable fragments, mutants, or truncated forms may be identified by modeling and/or screening. In some cases, this is achieved by deletion of, for example, N-terminal, C-terminal, or internal regions of the protein in a step-wise fashion, followed by analysis of the resulting derivative with regard to its activity for the desired reaction compared to the original sequence. If the derivative in question operates in this capacity, it is considered to constitute an equivalent derivative of the enzyme proper.

In examples, some heterologous proteins may show occurrences where they are incorrectly processed when expressed in a recombinant host. For example, plant proteins such as cytochrome P450 enzymes expressed in microbial production hosts may have occurrences of incorrect processing. In particular, salutaridine synthase may undergo N-linked glycosylation when heterologously expressed in yeast. This N-linked glycosylation may not be observed in plants, which may be indicative of incorrect N-terminal sorting of the nascent SalSyn transcript so as to reduce the activity of the enzyme in the heterologous microbial host. In such examples, protein engineering directed at correcting N-terminal sorting of the nascent transcript so as to remove the N-linked glycosylation pattern may result in improved activity of the salutaridine synthase enzyme in the recombinant production host. This is explained further in Example 8 below.

Some aspects of the invention also relate to heterologous coding sequences that code for amino acid sequences that are equivalent to the native amino acid sequences for the various enzymes. An amino acid sequence that is "equivalent" is defined as an amino acid sequence that is not identical to the specific amino acid sequence, but rather contains at least some amino acid changes (deletions, substitutions, inversions, insertions, etc.) that do not essentially affect the biological activity of the protein as compared to a similar activity of the specific amino acid sequence, when used for a desired purpose. The biological activity refers to, in the example of an epimerase, its catalytic activity. Equivalent sequences are also meant to include those which have been engineered and/or evolved to have properties different from the original amino acid sequence. Mutable properties of interest include catalytic activity, substrate specificity, selectivity, stability, solubility, localization, etc.

In some instances, the expression of each type of enzyme is increased through additional gene copies (i.e., multiple copies), which increases intermediate accumulation and/or BIA of interest production. Some embodiments of the invention include increased BIA of interest production in a host cell through simultaneous expression of multiple species variants of a single or multiple enzymes. In some cases, additional gene copies of a single or multiple enzymes are included in the host cell. Any convenient methods may be utilized including multiple copies of a heterologous coding sequence for an enzyme in the host cell.

In some examples, the engineered host cell includes multiple copies of a heterologous coding sequence for an enzyme, such as 2 or more, 3 or more, 4 or more, 5 or more, or even 10 or more copies. In certain embodiments, the engineered host cell includes multiple copies of heterologous coding sequences for one or more enzymes, such as multiple copies of two or more, three or more, four or more, etc. In some cases, the multiple copies of the heterologous coding sequence for an enzyme are derived from two or more different source organisms as compared to the host cell. For example, the engineered host cell may include multiple copies of one heterologous coding sequence, where each of the copies is derived from a different source organism. As such, each copy may include some variations in explicit sequences based on inter-species differences of the enzyme of interest that is encoded by the heterologous coding sequence.

The engineered host cell medium may be sampled and monitored for the production of BIAs of interest. The BIAs of interest may be observed and measured using any convenient methods. Methods of interest include, but are not limited to, LC-MS methods (e.g., as described herein) where a sample of interest is analyzed by comparison with a known amount of a standard compound. Additionally, there are other ways that BIAs of interest may be observed and/or measured. Examples of alternative ways of observing and/or measuring BIAs include GC-MS, UV-vis spectroscopy, NMR, LC-NMR, LC-UV, TLC, capillary electrophoresis, among others. Identity may be confirmed, e.g., by m/z and MS/MS fragmentation patterns, and quantitation or measurement of the compound may be achieved via LC trace peaks of know retention time and/or EIC MS peak analysis by reference to corresponding LC-MS analysis of a known amount of a standard of the compound.

Additionally, a culture of the engineered host cell may be sampled and monitored for the production of enzymes of interest, such as a CYP-COR enzyme. The enzymes of interest may be observed and measured using any convenient methods. Methods of interest include enzyme activity assays, polyacrylamide gel electrophoresis, carbon monoxide spectroscopy, and western blot analysis.

Methods

Methods for Culturing Host Cells for BIA Production

As summarized above, some aspects of the invention include methods of preparing nor-opioid and nal-opioid BIAs of interest. Additionally, some aspects of the invention include methods of preparing enzymes of interest. As such, some aspects of the invention include culturing an engineered host cell under conditions in which the one or more host cell modifications (e.g., as described herein) are functionally expressed such that the cell converts starting compounds of interest into product nor-opioid and/or nal-opioid BIAs of interest. Also provided are methods that include culturing an engineered host cell under conditions suitable for protein production such that one or more heterologous coding sequences are functionally expressed and convert starting compounds of interest into product enzymes or nor-opioid and/or nal-opioid BIAs of interest. In examples, the method is a method of preparing a nor-opioid and/or nal-opioid BIA of interest that includes culturing an engineered host cell (e.g., as described herein); adding a starting compound to the cell culture; and recovering the nor-opioid and/or nal-opioid from the cell culture. In some examples, the method is a method of preparing an enzyme that includes culturing an engineered host cell (e.g., as described herein); adding a starting compound to the cell culture; and recovering the enzyme from the cell culture.

Fermentation media may contain suitable carbon substrates. The source of carbon suitable to perform the methods of this disclosure may encompass a wide variety of carbon containing substrates. Suitable substrates may include, without limitation, monosaccharides (e.g., glucose, fructose, galactose, xylose), oligosaccharides (e.g., lactose, sucrose, raffinose), polysaccharides (e.g., starch, cellulose), or a combination thereof. In some cases, unpurified mixtures from renewable feedstocks may be used (e.g., cornsteep liquor, sugar beet molasses, barley malt). In some cases, the carbon substrate may be a one-carbon substrate (e.g., methanol, carbon dioxide) or a two-carbon substrate (e.g., ethanol). In other cases, other carbon containing compounds may be utilized, for example, methylamine, glucosamine, and amino acids.

Any convenient methods of culturing engineered host cells may be employed for producing the nor-opioid and/or nal-opioid BIAs of interest. The particular protocol that is employed may vary, e.g., depending on the engineered host cell, the heterologous coding sequences, the enzymes of interest, the nor-opioid and/or nal-opioid BIAs of interest, etc. The cells may be present in any convenient environment, such as an environment in which the cells are capable of expressing one or more functional heterologous enzymes.

In some embodiments, the cells are cultured under conditions that are conducive to enzyme expression and with appropriate substrates available to allow production of nor-opioid and/or nal-opioid BIAs of interest in vivo. In some embodiments, the functional enzymes are extracted from the engineered host for production of nor-opioid and/or nal-opioid BIAs of interest under in vitro conditions. In some instances, the engineered host cells are placed back into a multicellular host organism. The engineered host cells are in any phase of growth, including, but not limited to, stationary phase and log-growth phase, etc. In addition, the cultures themselves may be continuous cultures or they may be batch cultures.

Cells may be grown in an appropriate fermentation medium at a temperature between 14-40° C. Cells may be grown with shaking at any convenient speed (e.g., 200 rpm). Cells may be grown at a suitable pH. Suitable pH ranges for the fermentation may be between pH 5-9. Fermentations may be performed under aerobic, anaerobic, or microaerobic conditions. Any suitable growth medium may be used. Suitable growth media may include, without limitation, common commercially prepared media such as synthetic defined (SD) minimal media or yeast extract peptone dextrose (YEPD) rich media. Any other rich, defined, or synthetic growth media appropriate to the microorganism may be used.

Cells may be cultured in a vessel of essentially any size and shape. Examples of vessels suitable to perform the methods of this disclosure may include, without limitation, multi-well shake plates, test tubes, flasks (baffled and non-baffled), and bioreactors. The volume of the culture may range from 10 microliters to greater than 10,000 liters.

The addition of agents to the growth media that are known to modulate metabolism in a manner desirable for the production of alkaloids may be included. In a non-limiting example, cyclic adenosine 2'3'-monophosphate may be added to the growth media to modulate catabolite repression.

Any convenient cell culture conditions for a particular cell type may be utilized. In certain embodiments, the host cells that include one or more modifications are cultured under standard or readily optimized conditions, with standard cell culture media and supplements. As one example, standard growth media when selective pressure for plasmid maintenance is not required may contain 20 g/L yeast extract, 10 g/L peptone, and 20 g/L dextrose (YPD). Host cells containing plasmids are grown in synthetic complete (SC) media containing 1.7 g/L yeast nitrogen base, 5 g/L ammonium sulfate, and 20 g/L dextrose supplemented with the appropriate amino acids required for growth and selection. Alternative carbon sources which may be useful for inducible enzyme expression include, but are not limited to, sucrose, raffinose, and galactose. Cells are grown at any convenient temperature (e.g., 30° C.) with shaking at any convenient rate (e.g., 200 rpm) in a vessel, e.g., in test tubes or flasks in volumes ranging from 1-1000 mL, or larger, in the laboratory.

Culture volumes may be scaled up for growth in larger fermentation vessels, for example, as part of an industrial process. The industrial fermentation process may be carried out under closed-batch, fed-batch, or continuous chemostat conditions, or any suitable mode of fermentation. In some cases, the cells may be immobilized on a substrate as whole cell catalysts and subjected to fermentation conditions for alkaloid production.

Batch fermentation is a closed system, in which the composition of the medium is set at the beginning of the fermentation and not altered during the fermentation process. The desired organism(s) are inoculated into the medium at the beginning of the fermentation. In some instances, the batch fermentation is run with alterations made to the system to control factors such as pH and oxygen concentration (but not carbon). In this type of fermentation system, the biomass and metabolite compositions of the system change continuously over the course of the fermentation. Cells typically proceed through a lag phase, then to a log phase (high growth rate), then to a stationary phase (growth rate reduced or halted), and eventually to a death phase (if left untreated).

A continuous fermentation is an open system, in which a defined fermentation medium is added continuously to the bioreactor and an equal amount of fermentation media is continuously removed from the vessel for processing. Continuous fermentation systems are generally operated to maintain steady state growth conditions, such that cell loss due to medium being removed must be balanced by the growth rate in the fermentation. Continuous fermentations are generally operated at conditions where cells are at a constant high cell density. Continuous fermentations allow for the modulation of one or more factors that affect target product concentration and/or cell growth.

The liquid medium may include, but is not limited to, a rich or synthetic defined medium having an additive component described above. Media components may be dissolved in water and sterilized by heat, pressure, filtration, radiation, chemicals, or any combination thereof. Several media components may be prepared separately and sterilized, and then combined in the fermentation vessel. The culture medium may be buffered to aid in maintaining a constant pH throughout the fermentation.

Process parameters including temperature, dissolved oxygen, pH, stirring, aeration rate, and cell density may be monitored or controlled over the course of the fermentation. For example, temperature of a fermentation process may be monitored by a temperature probe immersed in the culture medium. The culture temperature may be controlled at the set point by regulating the jacket temperature. Water may be cooled in an external chiller and then flowed into the bioreactor control tower and circulated to the jacket at the temperature required to maintain the set point temperature in the vessel.

Additionally, a gas flow parameter may be monitored in a fermentation process. For example, gases may be flowed into the medium through a sparger. Gases suitable for the methods of this disclosure may include compressed air, oxygen, and nitrogen. Gas flow may be at a fixed rate or regulated to maintain a dissolved oxygen set point.

The pH of a culture medium may also be monitored. In examples, the pH may be monitored by a pH probe that is immersed in the culture medium inside the vessel. If pH control is in effect, the pH may be adjusted by acid and base pumps which add each solution to the medium at the required rate. The acid solutions used to control pH may be sulfuric acid or hydrochloric acid. The base solutions used to control pH may be sodium hydroxide, potassium hydroxide, or ammonium hydroxide.

Further, dissolved oxygen may be monitored in a culture medium by a dissolved oxygen probe immersed in the culture medium. If dissolved oxygen regulation is in effect, the oxygen level may be adjusted by increasing or decreasing the stirring speed. The dissolved oxygen level may also be adjusted by increasing or decreasing the gas flow rate. The gas may be compressed air, oxygen, or nitrogen.

Stir speed may also be monitored in a fermentation process. In examples, the stirrer motor may drive an agitator. The stirrer speed may be set at a consistent rpm throughout the fermentation or may be regulated dynamically to maintain a set dissolved oxygen level.

Additionally, turbidity may be monitored in a fermentation process. In examples, cell density may be measured using a turbidity probe. Alternatively, cell density may be measured by taking samples from the bioreactor and analyzing them in a spectrophotometer. Further, samples may be removed from the bioreactor at time intervals through a sterile sampling apparatus. The samples may be analyzed for alkaloids produced by the host cells. The samples may also be analyzed for other metabolites and sugars, the depletion of culture medium components, or the density of cells.

In another example, a feed stock parameter may be monitored during a fermentation process. In particular, feed stocks including sugars and other carbon sources, nutrients, and cofactors that may be added into the fermentation using an external pump. Other components may also be added during the fermentation including, without limitation, antifoam, salts, chelating agents, surfactants, and organic liquids.

Any convenient codon optimization techniques for optimizing the expression of heterologous polynucleotides in host cells may be adapted for use in the subject host cells and methods, see e.g., Gustafsson C., et al. (2004) *Trends Biotechnol*, 22, 346-353, which is incorporated by reference in its entirety.

The subject method may also include adding a starting compound to the cell culture. Any convenient methods of addition may be adapted for use in the subject methods. The cell culture may be supplemented with a sufficient amount of the starting materials of interest (e.g., as described herein), e.g., an amount in the mM to μM range such as between about 1-5 mM of a starting compound. It is understood that the amount of starting material added, the timing and rate of addition, the form of material added, etc., may vary according to a variety of factors. The starting material may be added neat or pre-dissolved in a suitable solvent (e.g., cell culture media, water, or an organic solvent). The starting material may be added in concentrated form (e.g., 10× over desired concentration) to minimize dilution of the cell culture medium upon addition. The starting material may be added in one or more batches, or by continuous addition over an extended period of time (e.g., hours or days).

Methods for Isolating Products from the Fermentation Medium

The subject methods may also include recovering the nor-opioid and/or nal-opioid BIAs of interest from the cell culture. Any convenient methods of separation and isolation (e.g., chromatography methods or precipitation methods) may be adapted for use in the subject methods to recover the nor-opioid and/or nal-opioid BIAs of interest from the cell culture. Filtration methods may be used to separate soluble from insoluble fractions of the cell culture. In some cases, liquid chromatography methods (e.g., reverse phase HPLC, size exclusion, or normal phase chromatography) may be used to separate the BIA of interest from other soluble components of the cell culture. In some cases, extraction methods (e.g., liquid extraction, pH based purification, solid phase extraction, affinity chromatography, ion exchange, etc.) may be used to separate the nor-opioid and/or nal-opioid BIAs of interest from other components of the cell culture.

The produced alkaloids may be isolated from the fermentation medium using methods known in the art. A number of recovery steps may be performed immediately after (or in some instances, during) the fermentation for initial recovery of the desired product. Through these steps, the alkaloids (e.g., nor-opioids or nal-opioids) may be separated from the cells, cellular debris and waste, and other nutrients, sugars, and organic molecules may remain in the spent culture medium. This process may be used to yield a nor-opioid or nal-opioid-enriched product.

In an example, a product stream having a nor-opioid or nal-opioid product is formed by providing engineered yeast cells and a feedstock including nutrients and water to a batch reactor. In particular, the engineered yeast cells may be subjected to fermentation by incubating the engineered yeast cells for a time period of at least about 5 minutes to produce a solution comprising the nor-opioid or nal-opioid product and cellular material. Once the engineered yeast cells have been subjected to fermentation, at least one separation unit may be used to separate the nor-opioid or nal-opioid product from the cellular material to provide the product stream comprising the nor-opioid or nal-opioid product. In particular, the product stream may include the nor-opioid or nal-opioid product as well as additional components, such as a clarified yeast culture medium. Additionally, a nor-opioid or nal-opioid product may comprise one or more nor-opioids or nal-opioids of interest, such as one or more nor-opioid or nal-opioid compounds.

Different methods may be used to remove cells from a bioreactor medium that include an enzyme and/or nor-opioid or nal-opioid of interest. In examples, cells may be removed by sedimentation over time. This process of sedimentation may be accelerated by chilling or by the addition of fining agents such as silica. The spent culture medium may then be siphoned from the top of the reactor or the cells may be decanted from the base of the reactor. Alternatively, cells may be removed by filtration through a filter, a membrane, or other porous material. Cells may also be removed by centrifugation, for example, by continuous flow centrifugation or by using a continuous extractor.

Different methods may be used to remove cells from a bioreactor medium that include a BIA of interest such as naloxone or naltrexone. In examples, cells may be removed by sedimentation over time. This process of sedimentation may be accelerated by chilling or by the addition of fining agents such as silica. The spent culture medium may then be siphoned from the top of the reactor or the cells may be decanted from the base of the reactor. Alternatively, cells may be removed by filtration through a filter, a membrane, or other porous material. Cells may also be removed by centrifugation, for example, by continuous flow centrifugation or by using a continuous extractor.

If some valuable nor-opioid and/or nal-opioid BIAs of interest are present inside the cells, the cells may be permeabilized or lysed and the cell debris may be removed by any of the methods described above. Agents used to permeabilize the cells may include, without limitation, organic solvents (e.g., DMSO) or salts (e.g., lithium acetate). Methods to lyse the cells may include the addition of surfactants such as sodium dodecyl sulfate, or mechanical disruption by bead milling or sonication.

Nor-opioid and/or nal-opioid BIAs of interest may be extracted from the clarified spent culture medium through liquid-liquid extraction by the addition of an organic liquid that is immiscible with the aqueous culture medium. In examples, the use of liquid-liquid extraction may be used in addition to other processing steps. Examples of suitable organic liquids include, but are not limited to, isopropyl myristate, ethyl acetate, chloroform, butyl acetate, methylisobutyl ketone, methyl oleate, toluene, oleyl alcohol, ethyl butyrate. The organic liquid may be added to as little as 10% or as much as 100% of the volume of aqueous medium.

In some cases, the organic liquid may be added at the start of the fermentation or at any time during the fermentation. This process of extractive fermentation may increase the yield of nor-opioid and/or nal-opioid BIAs of interest from the host cells by continuously removing nor-opioids and/or nal-opioids to the organic phase.

Agitation may cause the organic phase to form an emulsion with the aqueous culture medium. Methods to encourage the separation of the two phases into distinct layers may include, without limitation, the addition of a demulsifier or a nucleating agent, or an adjustment of the pH. The emulsion may also be centrifuged to separate the two phases, for example, by continuous conical plate centrifugation.

Alternatively, the organic phase may be isolated from the aqueous culture medium so that it may be physically removed after extraction. For example, the solvent may be encapsulated in a membrane.

In examples, nor-opioid and/or nal-opioid BIAs of interest may be extracted from a fermentation medium using adsorption methods. In examples, nor-opioids or nal-opioids of interest may be extracted from clarified spent culture medium by the addition of a resin such as Amberlite® XAD4 or another agent that removes nor-opioids or nal-opioids by adsorption. The nor-opioids or nal-opioids of interest may then be released from the resin using an organic solvent. Examples of suitable organic solvents include, but are not limited to, methanol, ethanol, ethyl acetate, or acetone.

Nor-opioids or nal-opioids of interest may also be extracted from a fermentation medium using filtration. At high pH, the nor-opioids or nal-opioids of interest may form a crystalline-like precipitate in the bioreactor. This precipitate may be removed directly by filtration through a filter, membrane, or other porous material. The precipitate may also be collected by centrifugation and/or decantation.

The extraction methods described above may be carried out either in situ (in the bioreactor) or ex situ (e.g., in an external loop through which media flows out of the bioreactor and contacts the extraction agent, then is recirculated back into the vessel). Alternatively, the extraction methods may be performed after the fermentation is terminated using the clarified medium removed from the bioreactor vessel.

Methods for Purifying Products from Alkaloid-Enriched Solutions

Subsequent purification steps may involve treating the post-fermentation solution enriched with nor-opioid or nal-opioid product(s) of interest using methods known in the art to recover individual product species of interest to high purity.

In one example, nor-opioids or nal-opioids of interest extracted in an organic phase may be transferred to an aqueous solution. In some cases, the organic solvent may be evaporated by heat and/or vacuum, and the resulting powder may be dissolved in an aqueous solution of suitable pH. In a further example, the BIAs of interest may be extracted from the organic phase by addition of an aqueous solution at a suitable pH that promotes extraction of the nor-opioids or nal-opioids of interest into the aqueous phase. The aqueous phase may then be removed by decantation, centrifugation, or another method.

The nor-opioid or nal-opioid-containing solution may be further treated to remove metals, for example, by treating with a suitable chelating agent. The nor-opioid or nal-opioid of interest-containing solution may be further treated to remove other impurities, such as proteins and DNA, by precipitation. In one example, the nor-opioid or nal-opioid of interest-containing solution is treated with an appropriate precipitation agent such as ethanol, methanol, acetone, or isopropanol. In an alternative example, DNA and protein may be removed by dialysis or by other methods of size exclusion that separate the smaller alkaloids from contaminating biological macromolecules.

In further examples, the solution containing nor-opioids or nal-opioids of interest may be extracted to high purity by continuous cross-flow filtration using methods known in the art.

If the solution contains a mixture of nor-opioids or nal-opioids of interest, it may be subjected to acid-base treatment to yield individual nor-opioid or nal-opioid of interest species using methods known in the art. In this process, the pH of the aqueous solution is adjusted to precipitate individual nor-opioids or nal-opioids.

For high purity, small-scale preparations, the nor-opioids or nal-opioids may be purified in a single step by liquid chromatography.

LCMS Method:

The BIA compounds of interest such as naloxone or naltrexone may be separated using liquid chromatography, and detected and quantified using mass spectrometry. Compound identity may be confirmed by characteristic elution time, mass-to-charge ratio (m/z) and fragmentation patterns (MS/MS). Quantitation may be performed by comparison of compound peak area to a standard curve of a known reference standard compound. Additionally, BIAs of interest may be detected by alternative methods such as GC-MS, UV-vis spectroscopy, NMR, LC-NMR, LC-UV, TLC, and capillary electrophoresis.

Purpald Assay Method

For high throughput screening of demethylation reactions a purpald assay may be used. For example, demethylation catalyzed by 2-oxoglutarate dependent dioxygenases produces formaldehyde a as product as shown in the generalized chemical equation: [substrate]+2-oxoglutarate+$O_2$ ⇌ [product]+formaldehyde+succinate+$CO_2$. Purpald reagent in alkaline conditions undergoes a color change in the presence of formaldehyde that can be quantified to concentrations as low as 1 nM with a spectrophotometer at 510 nm.

Yeast-Derived Alkaloid APIs Versus Plant-Derived APIs

The clarified yeast culture medium (CYCM) may contain a plurality of impurities. The clarified yeast culture medium may be dehydrated by vacuum and/or heat to yield an alkaloid-rich powder. This product is analogous to the concentrate of poppy straw (CPS), which is exported from poppy-growing countries and purchased by Active Pharmaceutical Ingredients (API) manufacturers. For the purposes of this invention, CPS is a representative example of any type of purified plant extract from which the desired alkaloids product(s) may ultimately be further purified. Table 9 and Table 10 highlight the impurities in these two products that may be specific to either CYCM or CPS or may be present in both. Accordingly, these nor-opioids or nal-opioids may be assessed for impurities based on non-pigment impurities. By analyzing a product of unknown origin for a subset of these impurities, a person of skill in the art could determine whether the product originated from a yeast or plant production host.

API-grade pharmaceutical ingredients are highly purified molecules. As such, impurities that could indicate the plant- or yeast-origin of an API (such as those listed in Table 9 and Table 10) may not be present at the API stage of the product.

Indeed, many of the API products derived from yeast strains of the present invention may be largely indistinguishable from the traditional plant-derived APIs. In some cases, however, conventional alkaloid compounds may be subjected to chemical modification using chemical synthesis approaches, which may show up as chemical impurities in plant-based products that require such chemical modifications. For example, chemical derivatization may often result in a set of impurities related to the chemical synthesis processes. In certain situations, these modifications may be performed biologically in the yeast production platform, thereby avoiding some of the impurities associated with chemical derivation from being present in the yeast-derived product. In particular, these impurities from the chemical derivation product may be present in an API product that is produced using chemical synthesis processes but may be absent from an API product that is produced using a yeast-derived product. Alternatively, if a yeast-derived product is mixed with a chemically-derived product, the resulting impurities may be present but in a lesser amount than would be expected in an API that only or primarily contains chemically-derived products. In this example, by analyzing the API product for a subset of these impurities, a person of skill in the art could determine whether the product originated from a yeast production host or the traditional chemical derivatization route.

Non-limiting examples of impurities that may be present in chemically-derivatized morphinan APIs but not in biosynthesized APIs include a codeine-O(6)-methyl ether impurity in API codeine; 8,14-dihydroxy-7,8-dihydrocodeinone in API oxycodone; and tetrahydrothebaine in API hydrocodone. The codeine-O(6)-methyl ether may be formed by chemical over-methylation of morphine. The 8,14-dihydroxy-7,8-dihydrocodeinone in API oxycodone may be formed by chemical over-oxidation of thebaine. Additionally, the tetrahydrothebaine in API hydrocodone may be formed by chemical over-reduction of thebaine.

However, in the case where the yeast-derived compound and the plant-derived compound are both subjected to chemical modification through chemical synthesis approaches, the same impurities associated with the chemical synthesis process may be expected in the products. In such a situation, the starting material (e.g., CYCM or CPS) may be analyzed as described above.

Host Cell Derived Nal-Opioids Vs Chemically Derived Nal-Opioids

Nal-opioids produced by chemical synthesis may contain a plurality of impurities. These impurities may arise from many different causes, for example, unreacted starting materials, incomplete reactions, the formation of byproducts, persistence of intermediates, dimerization, or degradation. An example of an unreacted starting material could be oxymorphone remaining in a preparation of naltrexone. An example of an impurity arising from an incomplete reaction could be 3-O-Methylbuprenorphine resulting from the incomplete 3-O-demethylation of thebaine. Chemical modification can result in the addition or removal of functional groups at off-target sites. For example, the oxidation of C10 to create 10-hydroxynaltrexone and 10-ketonaltrexone during naltrexone synthesis, or the removal of the 6-O-methyl group to give 6-O-desmethylbuprenorphine during buprenorphine synthesis. Impurities may arise from the persistence of reaction intermediates, for example the persistence of N-oxides like oxymorphone N-oxide formed during the N-demethylation process. Another source of impurities is dimerization, the conjugation of two opioid molecules, for example two buprenorphine molecules (2,2'-bisbuprenorphine), two naltrexone molecules (2,2'-bisnaltrexone), or two naloxone molecules (2,2'-bisnaloxone). Impurities may arise from degradation of starting materials, reaction intermediates, or reaction products. The extreme physical conditions used in chemical syntheses may make the presence of degradation more likely. An example of an impurity that may arise from degradation is dehydrobuprenorphine produced by oxidizing conditions during buprenorphine synthesis.

Nal-opioids produced by enzyme catalysis in a host cell may contain different impurities than nal-opioids produced by chemical synthesis. Nal-opioids produced by enzyme catalysis in a host cell may contain fewer impurities than nal-opioids produced by chemical synthesis. Nal-opioids produced by enzyme catalysis in a host cell may lack certain impurities that are found in nal-opioids produced by chemical synthesis. In examples, key features of enzyme synthesis may include, (1) enzymes target a specific substrate and residue with high fidelity; (2) enzymes perform reactions in the mild physiological conditions within the cell which do not compromise the stability of the molecules; and (3) enzymes are engineered to be efficient catalysts that drive reactions to completion.

Table 11 highlights some of the impurities that may be specific to chemically produced nal-opioids. Accordingly, nal-opioids may be assessed for impurities to determine the presence or absence of any impurity from Table 11. By analyzing a product of unknown origin for a subset of these impurities, a person of skill in the art could determine whether the product originated from a chemical or enzymatic synthesis.

Methods of Engineering Host Cells

Also included are methods of engineering host cells for the purpose of producing nor-opioid and/or nal-opioid BIAs of interest. Inserting DNA into host cells may be achieved using any convenient methods. The methods are used to insert the heterologous coding sequences into the engineered host cells such that the host cells functionally express the enzymes and convert starting compounds of interest into product nor-opioid and/or nal-opioid BIAs of interest.

Any convenient promoters may be utilized in the subject engineered host cells and methods. The promoters driving expression of the heterologous coding sequences may be constitutive promoters or inducible promoters, provided that the promoters are active in the engineered host cells. The heterologous coding sequences may be expressed from their native promoters, or non-native promoters may be used. Such promoters may be low to high strength in the host in which they are used. Promoters may be regulated or constitutive. In certain embodiments, promoters that are not glucose repressed, or repressed only mildly by the presence of glucose in the culture medium, are used. Promoters of interest include but are not limited to, promoters of glycolytic genes such as the promoter of the *B. subtilis* tsr gene (encoding the promoter region of the fructose bisphosphate aldolase gene) or the promoter from yeast *S. cerevisiae* gene coding for glyceraldehyde 3-phosphate dehydrogenase (GPD, GAPDH, or TDH3), the ADH1 promoter of baker's yeast, the phosphate-starvation induced promoters such as the PHO5 promoter of yeast, the alkaline phosphatase promoter from *B. licheniformis*, yeast inducible promoters such as Gal1-10, Gal1, GalL, GalS, repressible promoter Met25, tetO, and constitutive promoters such as glyceraldehyde 3-phosphate dehydrogenase promoter (GPD), alcohol dehydrogenase promoter (ADH), translation-elongation factor-1-α promoter (TEF), cytochrome c-oxidase promoter (CYC1), MRP7 promoter, etc. Autonomously replicating yeast expression vectors containing promoters inducible by hormones such as glucocorticoids, steroids, and thyroid hormones may also be used and include, but are not limited to, the glucorticoid responsive element (GRE) and thyroid hormone responsive element (TRE). These and other examples are described U.S. Pat. No. 7,045,290, which is incorporated by reference, including the references cited therein. Additional vectors containing constitutive or inducible promoters such as a factor, alcohol oxidase, and PGH may be used. Additionally any promoter/enhancer combination (as per the Eukaryotic Promoter Data Base EPDB) could also be used to drive expression of genes. Any convenient appropriate promoters may be selected for the host cell, examples of promoters that could be used in an *E. coli* cell include T7, lac and tetO promoters. One may also use promoter selection to optimize transcript, and hence, enzyme levels to maximize production while minimizing energy resources.

Any convenient vectors may be utilized in the subject engineered host cells and methods. Vectors of interest include vectors for use in yeast and other cells. The types of yeast vectors may be broken up into 4 general categories: integrative vectors (YIp), autonomously replicating high copy-number vectors (YEp or 2μ, plasmids), autonomously replicating low copy-number vectors (YCp or centromeric plasmids) and vectors for cloning large fragments (YACs). Vector DNA is introduced into prokaryotic or eukaryotic cells via any convenient transformation or transfection techniques. DNA of another source (e.g. PCR-generated double stranded DNA product, or synthesized double stranded or single stranded oligonucleotides) may be used to engineer the yeast by integration into the genome. Any single transformation event may include one or several nucleic acids (vectors, double stranded or single stranded DNA fragments) to genetically modify the host cell.

Utility

The engineered host cells and methods disclosed herein, e.g., as described above, find use in a variety of applications. Applications of interest include, but are not limited to: research applications and therapeutic applications. Methods disclosed herein find use in a variety of different applications including any convenient application where the production of nor-opioid and/or nal-opioid BIAs of interest.

The subject engineered host cells and methods find use in a variety of therapeutic applications. Therapeutic applications of interest include those applications in which the preparation of pharmaceutical products that include nor-opioids or nal-opioids is of interest. The engineered host cells described herein produce nor-opioids or nal-opioids of interest and enzymes of interest. Reticuline is a major branch point intermediate of interest in the synthesis of BIAs including engineering efforts to produce end products such as opioid products. The subject host cells may be utilized to produce nor-opioids or nal-opioids of interest from simple and inexpensive starting materials that may find use in the production of BIAs of interest, including reticuline, and BIA end products, such as nor-opioids or nal-opioids. As such, the subject host cells find use in the supply of therapeutically active nor-opioids or nal-opioids of interest.

In some instances, the engineered host cells and methods find use in the production of commercial scale amounts of nor-opioids or nal-opioids thereof where chemical synthesis of these compounds is low yielding and not a viable means for large-scale production. In certain cases, the host cells and methods are utilized in a fermentation facility that would include bioreactors (fermenters) of e.g., 5,000-200,000 liter capacity allowing for rapid production of nor-opioids or nal-opioids of interest thereof for therapeutic products. Such applications may include the industrial-scale production of nor-opioids or nal-opioids of interest from fermentable carbon sources such as cellulose, starch, and free sugars.

The subject engineered host cells and methods find use in a variety of research applications. The subject host cells and methods may be used to analyze the effects of a variety of enzymes on the biosynthetic pathways of a variety of nor-opioid and/or nal-opioid BIAs of interest. In addition, the engineered host cells may be engineered to produce nor-opioid and/or nal-opioid BIAs of interest that find use in testing for bioactivity of interest in as yet unproven therapeutic functions. In some cases, the engineering of host cells to include a variety of heterologous coding sequences that encode for a variety of enzymes elucidates the high yielding biosynthetic pathways towards nor-opioid and/or nal-opioid BIAs of interest. In certain cases, research applications include the production of nor-opioid and/or nal-opioid BIAs of interest for therapeutic molecules of interest that may then be further chemically modified or derivatized to desired products or for screening for increased therapeutic activities of interest. In some instances, host cell strains are used to screen for enzyme activities that are of interest in such pathways, which may lead to enzyme discovery via conversion of nor-opioid or nal-opioid metabolites produced in these strains.

The subject engineered host cells and methods may be used as a production platform for plant specialized metabolites. The subject host cells and methods may be used as a platform for drug library development as well as plant enzyme discovery. For example, the subject engineered host cells and methods may find use in the development of natural product based drug libraries by taking yeast strains producing interesting scaffold molecules, such as norcodeine, or northebaine, and further functionalizing the compound structure through combinatorial biosynthesis or by chemical means. By producing drug libraries in this way, any potential drug hits are already associated with a production host that is amenable to large-scale culture and production. As another example, these subject engineered host cells and methods may find use in plant enzyme discovery. The subject host cells provide a clean background of defined metabolites to express plant EST libraries to identify new enzyme activities. The subject host cells and methods provide expression methods and culture conditions for the functional expression and increased activity of plant enzymes in yeast.

Kits and Systems

Some aspects of the invention further include kits and systems, where the kits and systems may include one or more components employed in methods disclosed herein, e.g., engineered host cells, starting compounds, heterologous coding sequences, vectors, culture medium, etc., as described herein. In some embodiments, the subject kit includes an engineered host cell (e.g., as described herein), and one or more components selected from the following: starting compounds, a heterologous coding sequence and/or a vector including the same, vectors, growth feedstock, components suitable for use in expression systems (e.g., cells, cloning vectors, multiple cloning sites (MCS), bi-directional promoters, an internal ribosome entry site (IRES), etc.), and a culture medium.

Any of the components described herein may be provided in the kits, e.g., host cells including one or more modifications, starting compounds, culture medium, etc. A variety of components suitable for use in making and using heterologous coding sequences, cloning vectors and expression systems may find use in the subject kits. Kits may also include tubes, buffers, etc., and instructions for use. The various reagent components of the kits may be present in separate containers, or some or all of them may be pre-combined into a reagent mixture in a single container, as desired.

Also provided are systems for producing nor-opioid and/or nal-opioid BIAs of interest, where the systems may include engineered host cells including one or more modifications (e.g., as described herein), starting compounds, culture medium, a fermenter and fermentation equipment, e.g., an apparatus suitable for maintaining growth conditions for the host cells, sampling and monitoring equipment and components, and the like. A variety of components suitable for use in large scale fermentation of yeast cells may find use in the subject systems.

In some cases, the system includes components for the large scale fermentation of engineered host cells, and the monitoring and purification of nor-opioid or nal-opioid compounds produced by the fermented host cells. In certain embodiments, one or more starting compounds (e.g., as described herein) are added to the system, under conditions by which the engineered host cells in the fermenter produce one or more desired nor-opioid or nal-opioid products of interest. In some instances, the host cells produce a nor-opioid or nal-opioid of interest (e.g., as described herein). In certain cases, the nor-opioid or nal-opioid products of interest are opioid antagonists, such as naloxone, naltrexone, nalmefene, or nalorphine. In certain cases, the nor-opioid or nal-opioid products of interest are opioid antagonists such as naltrindole or norbinaltorphimine. In some examples, the nor-opioid or nal-opioid products of interest are partial agonists such as buprenorphine.

In some cases, the system includes processes for monitoring and or analyzing one or more nor-opioid and/or nal-opioid BIAs of interest compounds produced by the subject host cells. For example, a LC-MS analysis system as described herein, a chromatography system, or any convenient system where the sample may be analyzed and compared to a standard, e.g., as described herein. The fermentation medium may be monitored at any convenient times before and during fermentation by sampling and analysis. When the conversion of starting compounds to nor-opioid or nal-opioid products of interest is complete, the fermentation may be halted and purification of the nor-opioid or nal-opioid products may be done. As such, in some cases, the subject system includes a purification component suitable for purifying the nor-opioid or nal-opioid products of interest from the host cell medium into which it is produced. The purification component may include any convenient means that may be used to purify the nor-opioid or nal-opioid products of interest produced by fermentation, including but not limited to, silica chromatography, reverse-phase chromatography, ion exchange chromatography, HIC chromatography, size exclusion chromatography, liquid extraction, and pH extraction methods. In some cases, the subject system provides for the production and isolation of enzyme and/or nor-opioid or nal-opioid fermentation products of interest following the input of one or more starting compounds to the system.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.), but some experimental errors and deviations should be accounted for. Unless indicated otherwise, parts are parts by weight, molecular weight is weight average molecular weight, temperature is in degrees Centigrade, and pressure is at or near atmospheric.

Discussion of Enzyme List

The host cells may be engineered to include one or more modifications (such as two or more, three or more, four or more, five or more, or even more modifications) that provide for the production of nor-opioid and/or nal-opioid BIAs of interest. Table 2 provides a list of exemplary genes that may be acted upon by one or more modifications so as to provide for the production of nor-opioid and/or nal-opioid BIAs of interest and/or enzymes of interest in an engineered host cell.

Modifications of genes as provided in Table 2 may be used to produce nor-opioid and/or nal-opioid BIAs of interest from engineered host cells that are supplied with a medium containing the minimal nutrients required for growth. This minimal medium may contain a carbon source, a nitrogen source, amino acids, vitamins, and salts. For example, modifications of genes as provided in Table 2 may be used to produce nor-opioid and/or nal-opioid BIAs of interest from engineered host cells that are fed sugar. Additionally, modifications of one or more genes as provided in Table 2 may be used to augment the biosynthetic processes of host cells that may be engineered for drug production.

Additionally, the use of these modifications to provide for the production of nor-opioid and/or nal-opioid BIAs of interest and/or enzymes of interest in engineered host cells is not readily apparent from the mere identification of enzymes that may be produced by the genes. In particular, synthetic pathways that have been reconstructed in host cells, such as yeast cells, as described herein comprise a variety of enzymes that do not act together in nature within a single organism. Additionally, some of the enzymes discussed herein do not act for nor-opioid and/or nal-opioid BIA biosynthesis in their natural context. Further, some of the enzymes described herein are not evolved to function in particular host cells, such as yeast cells, and are not evolved to function together. Further, some of the nor-opioids or nal-opioids produced do not occur naturally. In these cases, it would not be obvious that the enzymes would exhibit sufficient activity in the context of the synthetic nor-opioid and/or nal-opioid pathway in a host cell, such as yeast, to have sufficient flux through the pathway to produce downstream nor-opioid or nal-opioid end products.

For example, plant enzymes are often difficult to functionally express in heterologous microbial hosts, such as yeast. In many cases the enzymes may be misfolded, not correctly localized within the host cell, and/or incorrectly processed. The differences in protein translation and processing between yeast and plants can lead to these enzymes exhibiting substantially reduced to no detectable activities in the yeast host. These challenges arise commonly for endomembrane localized enzymes, such as cytochrome P450s, which are strongly represented in the BIA pathways which produce precursors for nor-opioids or nal-opioids. Even reduced enzyme activities may pose a substantial challenge to engineering yeast to produce complex BIAs, which requires sufficient activity at each step to ensure high-level accumulation of the desired BIA products.

Additionally, there are endogenous enzymes/pathways in some host cells, such as yeast, that may act on many of the early precursors in the BIA pathway (i.e., intermediates from tyrosine to norcoclaurine), and thus it may not be readily apparent that there would be sufficient flux through the heterologous pathway to achieve substantial BIA production given these competing endogenous pathways. For example, the Erlich pathway (Hazelwood, et al. 2008. Appl. Environ. Microbiol. 74: 2259-66; Larroy, et al. 2003. Chem. Biol. Interact. 143-144: 229-38; Larroy, et al. 2002. Eur. J. Biochem. 269: 5738-45) in yeast is the main endogenous pathway that would act to convert many of the intermediates in the early BIA pathway to undesired products and divert flux from the synthetic pathway.

Further, many of the enzymes as discussed herein, and as provided in Table 2, may function under very specific regulation strategies, including spatial regulation, in the native plant hosts, which may be lost upon transfer to the heterologous yeast host. In addition, plants present very different biochemical environments than yeast cells under which the enzymes are evolved to function, including pH, redox state, and substrate, cosubstrate, coenzyme, and cofactor availabilities. Given the differences in biochemical environments and regulatory strategies between the native hosts and the heterologous yeast hosts, it is not obvious that the enzymes would exhibit substantial activities when in the context of the yeast environment and further not obvious that they would work together to direct simple precursors such as sugar to complex BIA compounds. Maintaining the activities of the enzymes in the yeast host is particularly important as many of the pathways have many reaction steps (>10), such that if these steps are not efficient then one would not expect accumulation of desired downstream products.

In addition, in the native plant hosts, the associated metabolites in these pathways may be localized across different cell and tissue types. In several examples, there are cell types that may be specialized for biosynthesis and cell types that may be synthesized for metabolite accumulation. This type of cell specialization may be lost when expressing the pathways within a heterologous yeast host, and may play an important role in controlling the toxicity of these metabolites on the cells. Thus, it is not obvious that yeast could be successfully engineered to biosynthesize and accumulate these metabolites without being harmed by the toxicity of these compounds.

As one example, in the native plant hosts, the enzyme BBE is reported to have dynamic subcellular localization. In particular, the enzyme BBE initially starts in the ER and then is sorted to the vacuole (Bird and Facchini. 2001. Planta. 213: 888-97). It has been suggested that the ER-association of BBE in plants (Alcantara, et al. 2005. Plant Physiol. 138: 173-83) provides the optimal basic pH (pH ~8.8) for BBE activity (Ziegler and Facchini. 2008. Annu. Rev. Plant Biol. 59: 735-69). As another example, there is evidence that sanguinarine biosynthesis occurs in specialized vesicles within plant cells (Amann, et al. 1986. Planta. 167: 310-20), but only some of the intermediates accumulate in the vesicles. This may occur so as to sequester them from other enzyme activities and/or toxic effects.

As another example, the biosynthetic enzymes in the morphinan pathway branch are all localized to the phloem, which is part of the vascular tissue in plants. In the phloem, the pathway enzymes may be further divided between two cell types: the sieve elements common to all plants, and the laticifer which is a specialized cell type present only in certain plants which make specialized secondary metabolites. The upstream enzymes (i.e., from NCS through to SalAT) are predominantly in the sieve elements, and the downstream enzymes (i.e., T6ODM, COR, CODM) are mostly in the laticifer (Onoyovwe, et al. 2013. Plant Cell. 25: 4110-22). Additionally, it was discovered that the final steps in the noscapine biosynthetic pathway take place in the laticifer (Chen and Facchini. 2014. Plant J. 77: 173-84). This compartmentalization is thought to be highly important for regulating biosynthesis by isolating or trafficking intermediates, providing optimal pH, enhancing supply of cofactors, although the nature of the poppy laticifer microenvironment is still under investigation (Ziegler and Facchini. 2008. Annu. Rev. Plant Biol. 59: 735-69). Further, it is predicted that several of the enzymes may function as multi-enzyme complexes or metabolic channels common to plant secondary metabolism (Kempe, et al. 2009. Phytochemistry. 70: 579-89; Allen, et al. 2004. Nat. Biotechnol. 22: 1559-66). When biosynthetic enzymes are combined from different hosts and/or expressed recombinantly in a heterologous yeast cell it is not clear that these complexes or channels will form as they would in the native host. In an additional example, in *Coptis japonica*, berberine is biosynthesized in root tissues and then accumulated within the rhizome via the action of specialized ATP-binding cassette transport proteins (Shitan, et al. 2013. Phytochemistry. 91: 109-16). In opium poppy, morphinan alkaloids are accumulated within the latex (cytoplasm of laticifer cells) (Martin, et al. 1967. Biochemistry. 6: 2355-63).

Further, even without these considerations, it is also the case that the plant enzymes for several of the steps in the pathways described herein have not yet been characterized. For example, the conversion of tyrosine to the early benzylisoquinoline alkaloid scaffold norcoclaurine has not yet been characterized. Thus, for several of the steps in the pathways described herein, alternative biosynthetic scheme were produced by bringing together enzyme activities that do not normally occur together in nature for the biosynthesis of BIAs or identifying new enzyme activities from genome sequence information to use in the reconstructed pathways.

For example, the two-step conversion of tyrosine to dopamine may be achieved by combining at least 5 mammalian enzymes and 1 bacterial enzyme, which do not naturally occur together and were not evolved to function in the context of this pathway or with plant enzymes. In these instances, it may not be obvious to utilize these enzymes for the biosynthesis of compounds they were not evolved for in nature and that they would function effectively in the context of a heterologous microbial host and this pathway.

Examples of the genes that are the object of modifications so as to produce nor-opioid and/or nal-opioid BIAs of interest and/or enzymes of interest are discussed below. Additionally, the genes are discussed in the context of a series of Figures that illustrate pathways that are used in generating BIAs and nor-opioid and/or nal-opioid BIAs of interest and/or enzymes of interest.

[TKL1] In some examples, the engineered host cell may modify the expression of the enzyme transketolase. Transketolase is encoded by the TKL1 gene. In examples, transketolase catalyzes the reaction of fructose-6-phosphate+glyceraldehyde-3-phosphate xylulose-5-phosphate+erythrose-4-phosphate, as referenced in FIG. 2. An engineered host cell may be modified to include constitutive overexpression of the TKL1 gene in the engineered host cell. Additionally or alternatively, the engineered host cell may be modified to synthetically regulate the expression of the TKL1 gene in the engineered host cell. In examples, the engineered host cell may be modified to incorporate a copy, copies, or additional copies, of the TKL1 gene. Additionally or alternatively, the engineered host cell may be modified to incorporate the introduction of a strong promoter element for the overexpression of the TKL1 gene within the engineered host cell. The TKL1 gene may be derived from *Saccharomyces cerevisiae* or another species. In some examples, the TKL1 gene may be 100% similar to the naturally occurring gene.

[ZWF1] In some examples, the engineered host cell may modify the expression of the enzyme glucose-6-phosphate dehydrogenase. Glucose-6-phosphate dehydrogenase is encoded by the ZWF1 gene. In examples, glucose-6-phosphate dehydrogenase catalyzes the reaction of glucose-6-phosphate→6-phosphogluconolactone, as referenced in FIG. 2. An engineered host cell may be modified to delete the coding region of the ZWF1 gene in the engineered host cell. Alternatively, the engineered host cell may be modified to disable the functionality of the ZWF1 gene, such as by introducing an inactivating mutation.

[ARO4] In some examples, the engineered host cell may modify the expression of the enzyme 3-deoxy-D-arabino-heptulosonate-7-phosphate (DAHP) synthase. DAHP synthase is encoded by the ARO4 gene. In examples, DAHP synthase catalyzes the reaction of erythrose-4-phosphate+ phosphoenolpyruvic acid→DAHP, as referenced in FIG. 2. An engineered host cell may modify the ARO4 gene to incorporate one or more feedback inhibition alleviating mutations. In particular, a feedback inhibition alleviating mutation (e.g., ARO4$^{FBR}$) may be incorporated as a directed mutation to a native ARO4 gene at the original locus; as an additional copy introduced as a genetic integration at a separate locus; or as an additional copy on an episomal vector such as a 2-μm or centromeric plasmid. The identifier "FBR" in the mutation ARO4$^{FBR}$ refers to feedback resistant mutants and mutations. The feedback inhibited copy of the DAHP synthase enzyme may be under a native yeast transcriptional regulation, such as when the engineered host cell is a yeast cell. Alternatively, the feedback inhibited copy of the DAHP synthase enzyme may be introduced to the engineered host cell with engineered constitutive or dynamic regulation of protein expression by placing it under the control of a synthetic promoter. In some cases, the ARO4 gene may be derived from *Saccharomyces cerevisiae*. In some cases, the ARO4 gene may be 100% similar to the naturally occurring gene. Examples of modifications to the ARO4 gene include a feedback inhibition resistant mutation, K229L, or Q166K.

[ARO7] In some examples, the engineered host cell may modify the expression of the enzyme chorismate mutase. Chorismate mutase is encoded by the ARO7 gene. In examples, chorismate mutase catalyzes the reaction of chorismate→prephenate, as referenced in FIG. 2. An engineered host cell may modify the ARO7 gene to incorporate one or more feedback inhibition alleviating mutations. In particular, a feedback inhibition alleviating mutation (e.g., ARO7$^{FBR}$) may be incorporated as a directed mutation to a native ARO7 gene at the original locus; as an additional copy introduced as a genetic integration at a separate locus; or as an additional copy on an episomal vector such as a 2-μm or centromeric plasmid. The identifier "FBR" in the mutation ARO7$^{FBR}$ refers to feedback resistant mutants and mutations. The feedback inhibited copy of the chorismate mutase enzyme may be under a native yeast transcriptional regulation, such as when the engineered host cell is a yeast cell. Alternatively, the feedback inhibited copy of the chorismate mutase enzyme may be introduced to the engineered host cell with engineered constitutive or dynamic regulation of protein expression by placing it under the control of a synthetic promoter. In some cases, the ARO7 gene may be derived from *Saccharomyces cerevisiae*. In some cases, the ARO7 gene may be 100% similar to the naturally occurring gene. Examples of modifications to the ARO7 gene include a feedback inhibition resistant mutation or T226I.

[ARO10] In some examples, the engineered host cell may modify the expression of the enzyme phenylpyruvate decarboxylase. Phenylpyruvate decarboxylase is encoded by the ARO10 gene. In examples, phenylpyruvate decarboxylase catalyzes the reaction of hydroxyphenylpyruvate→4-hydroxyphenylacetate (4HPA), as referenced in FIG. 2. An engineered host cell may be modified to include constitutive overexpression of the ARO10 gene in the engineered host cell. Additionally or alternatively, the engineered host cell may be modified to synthetically regulate the expression of the ARO10 gene in the engineered host cell. In examples, the engineered host cell may be modified to incorporate a copy, copies, or additional copies, of the ARO10 gene. Additionally or alternatively, the engineered host cell may be modified to incorporate the introduction of a strong promoter element for the overexpression of the ARO10 gene within the engineered host cell. The ARO10 gene may be derived from *Saccharomyces cerevisiae* or another species. In some examples, the ARO10 gene may be 100% similar to the naturally occurring gene.

[ADH2-7, SFA1] In some examples, the engineered host cell may modify the expression of alcohol dehydrogenase enzymes. Alcohol dehydrogenase enzymes may be encoded by one or more of the ADH2, ADH3, ADH4, ADH5, ADH6, ADH7, and SFA1 genes. In examples, alcohol dehydrogenase catalyzes the reaction of 4HPA→tyrosol. An engineered host cell may be modified to delete the coding region of one or more of the ADH2, ADH3, ADH4, ADH5, ADH6, ADH7, and SFA1 genes in the engineered host cell. Alternatively, the engineered host cell may be modified to disable the functionality of one or more of the ADH2, ADH3, ADH4, ADH5, ADH6, ADH7, and SFA1 genes, such as by introducing an inactivating mutation.

[ALD2-6] In some examples, the engineered host cell may modify the expression of aldehyde oxidase enzymes. Aldehyde oxidase enzymes may be encoded by one or more of the ALD2, ALD3, ALD4, ALD5, and ALD6 genes. In examples, aldehyde oxidase catalyzes the reaction of 4HPA hydroxyphenylacetic acid. An engineered host cell may be modified to delete the coding region of one or more of the ALD2, ALD3, ALD4, ALD5, and ALD6 genes in the engineered host cell. Alternatively, the engineered host cell may be modified to disable the functionality of one or more of the ALD2, ALD3, ALD4, ALD5, and ALD6 genes, such as by introducing an inactivating mutation.

[ARO9] In some examples, the engineered host cell may modify the expression of the enzyme aromatic aminotransferase. Aromatic aminotransferase is encoded by the ARO9 gene. In examples, aromatic aminotransferase catalyzes the reaction of hydroxyphenylpyruvate+glutamate→tyrosine+ alpha-ketogluterate, as referenced in FIG. 2. An engineered host cell may be modified to include constitutive overexpression of the ARO9 gene in the engineered host cell. Additionally or alternatively, the engineered host cell may be modified to synthetically regulate the expression of the ARO9 gene in the engineered host cell. In examples, the engineered host cell may be modified to incorporate a copy, copies, or additional copies, of the ARO9 gene. Additionally or alternatively, the engineered host cell may be modified to incorporate the introduction of a strong promoter element for the overexpression of the ARO9 gene within the engineered host cell. The ARO9 gene may be derived from *Saccharomyces cerevisiae* or another species. In some examples, the ARO9 gene may be 100% similar to the naturally occurring gene.

[TYR] In some examples, the engineered host cell may modify the expression of the enzyme tyrosinase. Tyrosinase is encoded by the TYR gene. In examples, tyrosinase catalyzes the reaction of tyrosine→L-DOPA, as referenced in FIG. 2. In other examples, tyrosinase catalyzes the reaction of L-DOPA→dopaquinone. An engineered host cell may be modified to include constitutive expression of the TYR gene in the engineered host cell. Additionally or alternatively, the engineered host cell may be modified to synthetically regulate the expression of the TYR gene in the engineered host cell. In examples, the engineered host cell may be modified to incorporate a copy, copies, or additional copies, of the TYR gene. Additionally or alternatively, the engineered host cell may be modified to incorporate the introduction of a strong promoter element for the overexpression of the TYR gene within the engineered host cell. The TYR gene may be derived from *Ralstonia solanacearum, Agaricus bisporus*, or another species. In some examples, the TYR gene may be 100% similar to the naturally occurring gene.

[TyrH] In some examples, the engineered host cell may modify the expression of the enzyme tyrosine hydroxylase. Tyrosine hydroxylase is encoded by the TyrH gene. In examples, tyrosine hydroxylase catalyzes the reaction of tyrosine→L-DOPA, as referenced in FIGS. 2 and 5. An engineered host cell may be modified to include constitutive expression of the TyrH gene in the engineered host cell. Additionally or alternatively, the engineered host cell may be modified to synthetically regulate the expression of the TyrH gene in the engineered host cell. In examples, the engineered host cell may be modified to incorporate a copy, copies, or additional copies, of the TyrH gene. Additionally or alternatively, the engineered host cell may be modified to incorporate the introduction of a strong promoter element for the overexpression of the TyrH gene within the engineered host cell. The TyrH gene may be derived from *Homo sapiens, Rattus norvegicus, Mus musculus*, or another species. In some examples, the TyrH gene may be 100% similar to the naturally occurring gene.

[DODC] In some examples, the engineered host cell may modify the expression of the enzyme L-DOPA decarboxylase. L-DOPA decarboxylase is encoded by the DODC gene. In examples, L-DOPA decarboxylase catalyzes the reaction of L-DOPA→dopamine, as referenced in FIGS. 2 and 5. An engineered host cell may be modified to include constitutive expression of the DODC gene in the engineered host cell. Additionally or alternatively, the engineered host cell may be modified to synthetically regulate the expression of the DODC gene in the engineered host cell. In examples, the engineered host cell may be modified to incorporate a copy, copies, or additional copies, of the DODC gene. Additionally or alternatively, the engineered host cell may be modified to incorporate the introduction of a strong promoter element for the overexpression of the DODC gene within the engineered host cell. The DODC gene may be derived from *Pseudomonas putida, Rattus norvegicus*, or another species. In some examples, the DODC gene may be 100% similar to the naturally occurring gene.

[TYDC] In some examples, the engineered host cell may modify the expression of the enzyme tyrosine/DOPA decarboxylase. Tyrosine/DOPA decarboxylase is encoded by the TYDC gene. In examples, tyrosine/DOPA decarboxylase catalyzes the reaction of L-DOPA dopamine, as referenced in FIG. 2. An engineered host cell may be modified to include constitutive expression of the TYDC gene in the engineered host cell. Additionally or alternatively, the engineered host cell may be modified to synthetically regulate the expression of the TYDC gene in the engineered host cell. In examples, the engineered host cell may be modified to incorporate a copy, copies, or additional copies, of the TYDC gene. Additionally or alternatively, the engineered host cell may be modified to incorporate the introduction of a strong promoter element for the overexpression of the TYDC gene within the engineered host cell. The TYDC gene may be derived from *Papaver somniferum* or another species. In some examples, the TYDC gene may be 100% similar to the naturally occurring gene.

[MAO] In some examples, the engineered host cell may modify the expression of the enzyme monoamine oxidase. Monoamine oxidase is encoded by the MAO gene. In examples, monoamine oxidase catalyzes the reaction of dopamine→3,4-DHPA, as referenced in FIG. 2. An engineered host cell may be modified to include constitutive expression of the MAO gene in the engineered host cell. Additionally or alternatively, the engineered host cell may be modified to synthetically regulate the expression of the MAO gene in the engineered host cell. In examples, the engineered host cell may be modified to incorporate a copy, copies, or additional copies, of the MAO gene. Additionally or alternatively, the engineered host cell may be modified to incorporate the introduction of a strong promoter element for the overexpression of the MAO gene within the engineered host cell. In some cases, the MAO gene may be codon optimized for expression in *Saccharomyces cerevisiae*. The MAO gene may be derived from *Escherichia coli, Homo sapiens, Micrococcus luteus*, or another species. In some examples, the MAO gene may be 77% similar to the naturally occurring gene.

Figure 5:
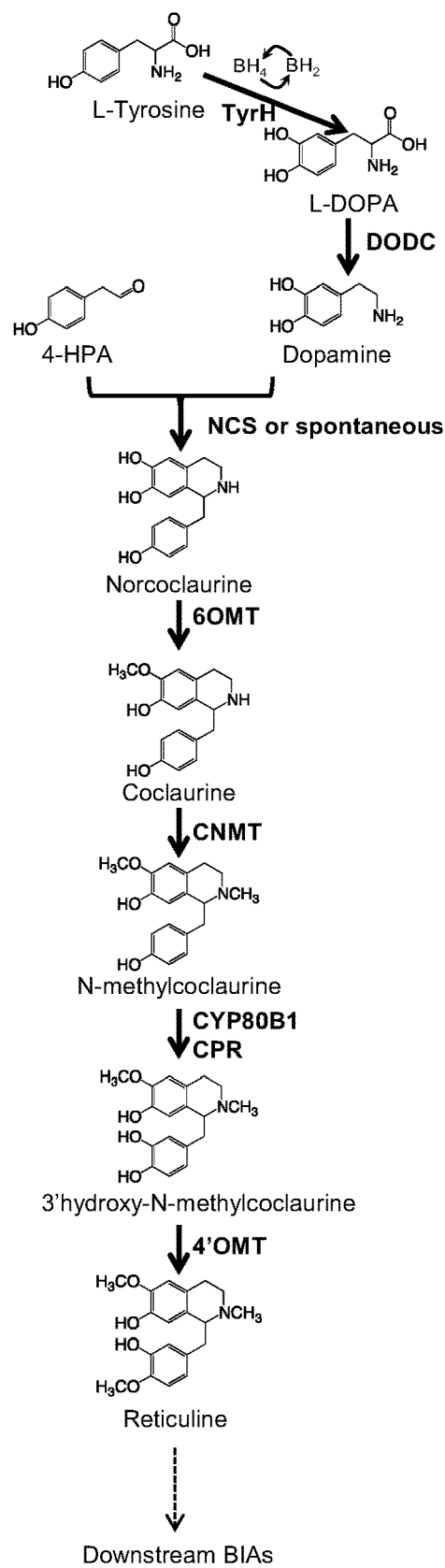
FIG. 5 illustrates a biosynthetic scheme for conversion of L-tyrosine to reticuline via norcoclaurine, in accordance with embodiments of the invention.

[NCS] In some examples, the engineered host cell may modify the expression of the enzyme norcoclaurine synthase. Norcoclaurine synthase is encoded by the NCS gene. In examples, norcoclaurine synthase catalyzes the reaction of 4HPA+dopamine→(S)-norcoclaurine, as referenced in FIG. 5. In particular, FIG. 5 illustrates a biosynthetic scheme for conversion of L-tyrosine to reticuline via norcoclaurine, in accordance with embodiments of the invention. FIG. 5 provides the use of the enzymes TyrH, tyrosine hydroxylase; DODC, DOPA decarboxylase; NCS, norcoclaurine synthase, as discussed herein; 6OMT, 6-O-methyltransferase; CNMT, coclaurine N-methyltransferase; CYP80B1, cytochrome P450 80B1; CPR, cytochrome P450 NADPH reductase; 4'OMT, 3'hydroxy-N-methylcoclaurine 4'-O-methyltransferase. L-DOPA, L-3,4-dihydroxyphenylalanine; and 4-HPA, 4-hydroxyphenylacetylaldehyde. Of the enzymes that are illustrated in FIG. 5, 4-HPA and L-tyrosine are naturally synthesized in yeast. All other metabolites shown are not naturally produced in yeast. Additionally, although TyrH is depicted as catalyzing the conversion of L-tyrosine to L-DOPA, other enzymes may also be used to perform this step as described in the specification. For example, tyrosinases may also be used to perform the conversion of L-tyrosine to L-DOPA. In addition, other enzymes such as cytochrome P450 oxidases may also be used to perform the conversion of L-tyrosine to L-DOPA. Such enzymes may exhibit oxidase activity on related BIA precursor compounds including L-DOPA and L-tyrosine.

Figure 6:
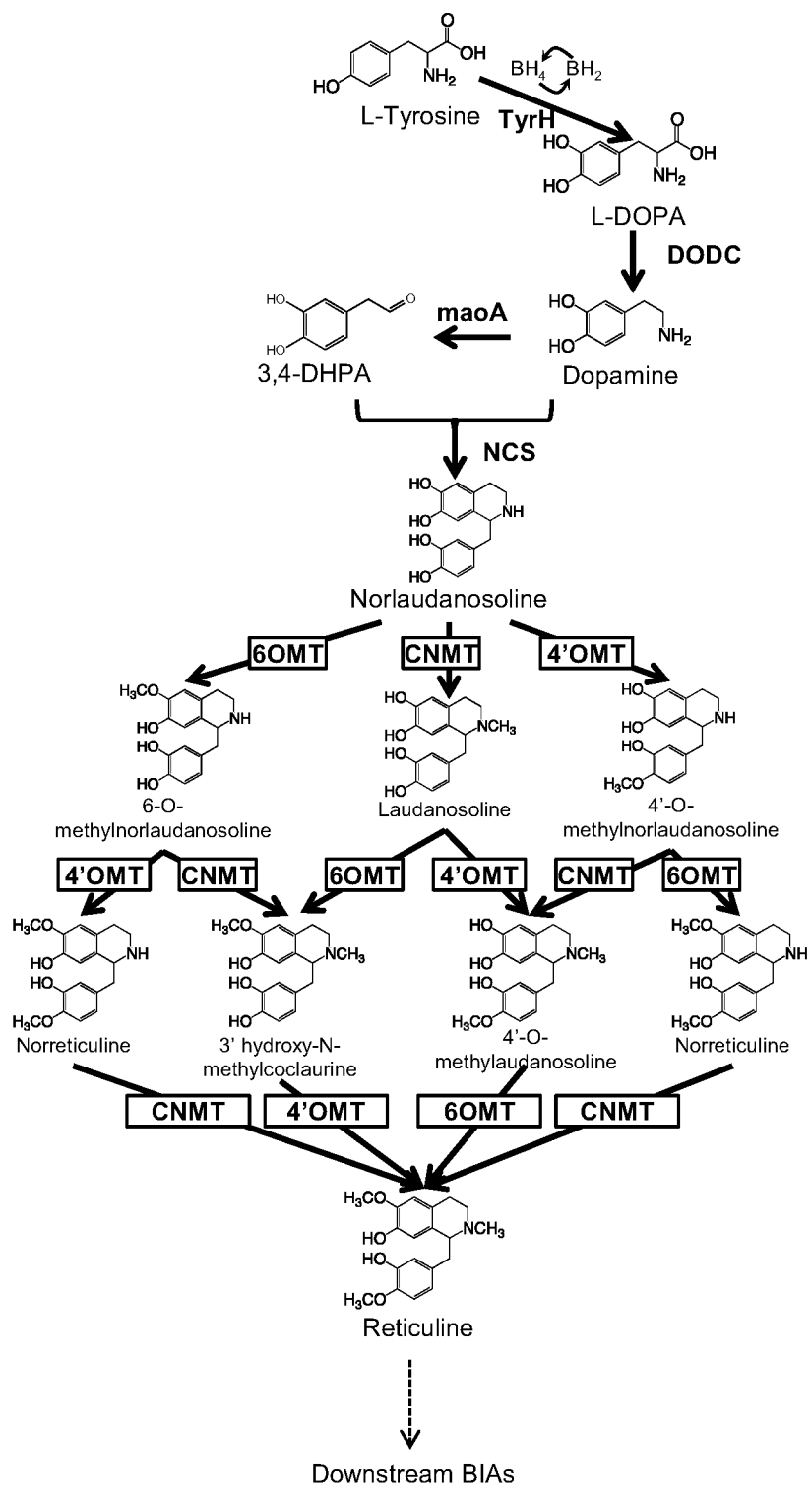
FIG. 6 illustrates a biosynthetic scheme for conversion of L-tyrosine to reticuline via norlaudanosoline, in accordance with embodiments of the invention.

Additionally, norcoclaurine synthase catalyzes the reaction of 3,4-DHPA+dopamine→(S)-norlaudanosoline, as referenced in FIG. 6. In particular, FIG. 6 illustrates a biosynthetic scheme for conversion of L-tyrosine to reticuline via norlaudanosoline, in accordance with embodiments of the invention. FIG. 6 provides the use of the enzymes TyrH, tyrosine hydroxylase; DODC, DOPA decarboxylase; maoA, monoamine oxidase; NCS, norcoclaurine synthase; 6OMT, 6-O-methyltransferase; CNMT, coclaurine N-methyltransferase; 4'OMT, 3'hydroxy-N-methylcoclaurine 4'-O-methyltransferase. L-DOPA, L-3,4-dihydroxyphenylalanine; and 3,4-DHPA, 3,4-dihydroxyphenylacetaldehyde. Of the enzymes that are illustrated in FIG. 6, L-tyrosine is naturally synthesized in yeast. Other metabolites that are shown in FIG. 6 are not naturally produced in yeast.

An engineered host cell may be modified to include constitutive expression of the NCS gene in the engineered host cell. Additionally or alternatively, the engineered host cell may be modified to synthetically regulate the expression of the NCS gene in the engineered host cell. In examples, the engineered host cell may be modified to incorporate a copy, copies, or additional copies, of the NCS gene. Additionally or alternatively, the engineered host cell may be modified to incorporate the introduction of a strong promoter element for the overexpression of the NCS gene within the engineered host cell. Additionally, the norcoclaurine synthase may have an N-terminal truncation. In some cases, the NCS gene may be codon optimized for expression in *Saccharomyces cerevisiae*. The NCS gene may be derived from *Coptis japonica, Papaver somniferum, Papver bracteatum, Thalicitum flavum, Corydalis saxicola*, or another species. In some examples, the NCS gene may be 80% similar to the naturally occurring gene.

[6OMT] In some examples, the engineered host cell may modify the expression of the enzyme norcoclaurine 6-O-methyltransferase. Norcoclaurine 6-O-methyltransferase is encoded by the 6OMT gene. In some examples, norcoclaurine 6-O-methyltransferase catalyzes the reaction of norcoclaurine→coclaurine, as referenced in FIG. 5. In other examples, norcoclaurine 6-O-methyltransferase catalyzes the reaction of norlaudanosoline→3'hydroxycoclaurine, as well as other reactions detailed herein, such as those provided in FIG. 6. Additionally, the engineered host cell may be modified to include constitutive expression of the 6OMT gene in the engineered host cell. Additionally or alternatively, the engineered host cell may be modified to synthetically regulate the expression of the 6OMT gene in the engineered host cell. In examples, the engineered host cell may be modified to incorporate a copy, copies, or additional copies, of the 6OMT gene. Additionally or alternatively, the engineered host cell may be modified to incorporate the introduction of a strong promoter element for the overexpression of the 6OMT gene within the engineered host cell. The 6OMT gene may be derived from *P. somniferum, T flavum, Coptis japonica*, or another species. In some examples, the 6OMT gene may be 100% similar to the naturally occurring gene.

[CNMT] In some examples, the engineered host cell may modify the expression of the enzyme coclaurine-N-methyltransferase. Coclaurine-N-methyltransferase is encoded by the CNMT gene. In some examples, coclaurine-N-methyltransferase catalyzes the reaction of coclaurine→N-methylcoclaurine, as referenced in FIG. 5. In other examples, the coclaurine-N-methyltransferase enzyme may catalyze the reaction of 3'hydroxy coclaurine→3'hydroxy-N-methylcoclaurine. In other examples, coclaurine-N-methyltransferase may catalyze the reaction of noroxymorphone→naloxone, as referenced in FIG. 26. In other examples, coclaurine-N-methyltransferase may catalyze other reactions detailed herein, such as those provided in FIG. 6. Additionally, the engineered host cell may be modified to include constitutive expression of the CNMT gene in the engineered host cell. Additionally or alternatively, the engineered host cell may be modified to synthetically regulate the expression of the CNMT gene in the engineered host cell. In examples, the engineered host cell may be modified to incorporate a copy, copies, or additional copies, of the CNMT gene. Additionally or alternatively, the engineered host cell may be modified to incorporate the introduction of a strong promoter element for the overexpression of the CNMT gene within the engineered host cell. The CNMT gene may be derived from *P. somniferum, T flavum, Coptis japonica*, or another species. In some examples, the CNMT gene may be 100% similar to the naturally occurring gene.

[4'OMT] In some examples, the engineered host cell may modify the expression of the enzyme 4'-O-methyltransferase. 4'-O-methyltransferase is encoded by the 4'OMT gene. In some examples, 4'-O-methyltransferase catalyzes the reaction of 3'-hydroxy-N-methylcoclaurine→reticuline, as referenced in FIG. 5. In other examples, 4'O-methyltransferase catalyzes other reactions detailed herein, such as those provided in FIG. 6. Additionally, the engineered host cell may be modified to include constitutive expression of the 4'OMT gene in the engineered host cell. Additionally or alternatively, the engineered host cell may be modified to synthetically regulate the expression of the 4'OMT gene in the engineered host cell. In examples, the engineered host cell may be modified to incorporate a copy, copies, or additional copies, of the 4'OMT gene. Additionally or alternatively, the engineered host cell may be modified to incorporate the introduction of a strong promoter element for the overexpression of the 4'OMT gene within the engineered host cell. The 4'OMT gene may be derived from *P. somniferum, T flavum, Coptis japonica*, or another species. In some examples, the 4'OMT gene may be 100% similar to the naturally occurring gene.

[CYP80B1] In some examples, the engineered host cell may modify the expression of the enzyme cytochrome P450 80B1. Cytochrome P450 80B1 is encoded by the CYP80B1 gene. In examples, cytochrome P450 80B1 catalyzes the reaction of N-methylcoclaurine→3'-hydroxy-N-methylcoclaurine, as referenced in FIG. 5. An engineered host cell may be modified to include constitutive expression of the cytochrome P450 80B1 gene in the engineered host cell. Additionally or alternatively, the engineered host cell may be modified to synthetically regulate the expression of the cytochrome P450 80B1 gene in the engineered host cell. In examples, the engineered host cell may be modified to incorporate a copy, copies, or additional copies, of the cytochrome P450 80B1 gene. Additionally or alternatively, the engineered host cell may be modified to incorporate the introduction of a strong promoter element for the overexpression of the cytochrome P450 80B1 gene within the engineered host cell. In some cases, the CYP80B1 gene may be codon optimized for expression in *Saccharomyces cerevisiae*. The cytochrome P450 80B1 gene may be derived from *P. somniferum, E. californica, T. flavum*, or another species. In some examples, the P450 80B1 gene may be 77% similar to the naturally occurring gene.

[FOL2] In some examples, the engineered host cell may modify the expression of the enzyme GTP cyclohydrolase. GTP cyclohydrolase is encoded by the FOL2 gene. In some examples, GTP cyclohydrolase catalyzes the reaction of GTP→dihydroneopterin triphosphate, as referenced in FIG. 1. The engineered host cell may be modified to include constitutive overexpression of the FOL2 gene in the engineered host cell. The engineered host cell may also be modified to include native regulation. Additionally or alternatively, the engineered host cell may be modified to synthetically regulate the expression of the FOL2 gene in the engineered host cell. In examples, the engineered host cell may be modified to incorporate a copy, copies, or additional copies, of the FOL2 gene. Additionally or alternatively, the engineered host cell may be modified to incorporate the introduction of a strong promoter element for the overexpression of the FOL2 gene within the engineered host cell. The FOL2 gene may be derived from *Saccharomyces cerevisiae, Homo sapiens, Mus musculus*, or another species. In some examples, the FOL2 gene may be 100% similar to the naturally occurring gene.

[PTPS] In some examples, the engineered host cell may modify the expression of the enzyme 6-pyruvoyl tetrahydrobiopterin (PTP) synthase. Pyruvoyl tetrahydrobiopterin synthase is encoded by the PTPS gene. In some examples, 6-pyruvoyl tetrahydrobiopterin synthase catalyzes the reaction of dihydroneopterin triphosphate→PTP, as referenced in FIG. 1. The engineered host cell may be modified to include constitutive expression of the PTPS gene in the engineered host cell. Additionally or alternatively, the engineered host cell may be modified to synthetically regulate the expression of the PTPS gene in the engineered host cell. In examples, the engineered host cell may be modified to incorporate a copy, copies, or additional copies, of the PTPS gene. Additionally or alternatively, the engineered host cell may be modified to incorporate the introduction of a strong promoter element for the overexpression of the PTPS gene within the engineered host cell. In some cases, the PTPS gene may be codon optimized for expression in *Saccharomyces cerevisiae*. The PTPS gene may be derived from *Rattus norvegicus, Homo sapiens, Mus musculus*, or another species. In some examples, the PTPS gene may be 80% similar to the naturally occurring gene.

[SepR] In some examples, the engineered host cell may modify the expression of the enzyme sepiapterin reductase. Sepiapterin reductase is encoded by the SepR gene. In some examples, sepiapterin reductase catalyzes the reaction of PTP→$BH_4$, as referenced in FIG. 1. The engineered host cell may be modified to include constitutive expression of the SepR gene in the engineered host cell. Additionally or alternatively, the engineered host cell may be modified to synthetically regulate the expression of the SepR gene in the engineered host cell. In examples, the engineered host cell may be modified to incorporate a copy, copies, or additional copies, of the SepR gene. Additionally or alternatively, the engineered host cell may be modified to incorporate the introduction of a strong promoter element for the overexpression of the SepR gene within the engineered host cell. In some cases, the SepR gene may be codon optimized for expression in *Saccharomyces cerevisiae*. The SepR gene may be derived from *Rattus norvegicus, Homo sapiens, Mus musculus*, or another species. In some examples, the SepR gene may be 72% similar to the naturally occurring gene.

[PCD] In some examples, the engineered host cell may modify the expression of the enzyme 4a-hydroxytetrahydrobiopterin (pterin-4α-carbinolamine) dehydratase. 4a-hydroxytetrahydrobiopterin dehydratase is encoded by the PCD gene. In some examples, 4a-hydroxytetrahydrobiopterin dehydratase catalyzes the reaction of 4a-hydroxytetrahydrobiopterin→$H_2O$+quinonoid dihydropteridine, as referenced in FIG. 1. The engineered host cell may be modified to include constitutive expression of the PCD gene in the engineered host cell. Additionally or alternatively, the engineered host cell may be modified to synthetically regulate the expression of the PCD gene in the engineered host cell. In examples, the engineered host cell may be modified to incorporate a copy, copies, or additional copies, of the PCD gene. Additionally or alternatively, the engineered host cell may be modified to incorporate the introduction of a strong promoter element for the overexpression of the PCD gene within the engineered host cell. In some cases, the PCD gene may be codon optimized for expression in *Saccharomyces cerevisiae*. The PCD gene may be derived from *Rattus norvegicus, Homo sapiens, Mus musculus*, or another species. In some examples, the PCD gene may be 79% similar to the naturally occurring gene.

[QDHPR] In some examples, the engineered host cell may modify the expression of the enzyme quinonoid dihydropteridine reductase. Quinonoid dihydropteridine reductase is encoded by the QDHPR gene. In some examples, quinonoid dihydropteridine reductase catalyzes the reaction of quinonoid dihydropteridine→$BH_4$, as referenced in FIG. 1. The engineered host cell may be modified to include constitutive expression of the QDHPR gene in the engineered host cell. Additionally or alternatively, the engineered host cell may be modified to synthetically regulate the expression of the QDHPR gene in the engineered host cell. In examples, the engineered host cell may be modified to incorporate a copy, copies, or additional copies, of the QDHPR gene. Additionally or alternatively, the engineered host cell may be modified to incorporate the introduction of a strong promoter element for the overexpression of the QDHPR gene within the engineered host cell. In some cases, the QDHPR gene may be codon optimized for expression in *Saccharomyces cerevisiae*. The QDHPR gene may be derived from *Rattus norvegicus, Homo sapiens, Mus musculus*, or another species. In some examples, the QDHPR gene may be 75% similar to the naturally occurring gene.

[DHFR] In some examples, the engineered host cell may modify the expression of the enzyme dihydrofolate reductase. Dihydrofolate reductase is encoded by the DHFR gene. In some examples, dihydrofolate reductase catalyzes the reaction of 7,8-dihydrobiopterin ($BH_2$)→5,6,7,8-tetrahydrobiopterin ($BH_4$), as referenced in FIG. 1. This reaction may be useful in recovering $BH_4$ as a co-substrate for the converstion of tyrosine to L-DOPA, as illustrated in FIG. 5. The engineered host cell may be modified to include constitutive expression of the DHFR gene in the engineered host cell. Additionally or alternatively, the engineered host cell may be modified to synthetically regulate the expression of the DHFR gene in the engineered host cell. In examples, the engineered host cell may be modified to incorporate a copy, copies, or additional copies, of the DHFR gene. Additionally or alternatively, the engineered host cell may be modified to incorporate the introduction of a strong promoter element for the overexpression of the DHFR gene within the engineered host cell. In some cases, the DHFR gene may be codon optimized for expression in *Saccharomyces cerevisiae*. The DHFR gene may be derived from *Rattus norvegicus, Homo sapiens*, or another species. In some examples, the DHFR gene may be 77% similar to the naturally occurring gene.

Figure 7:
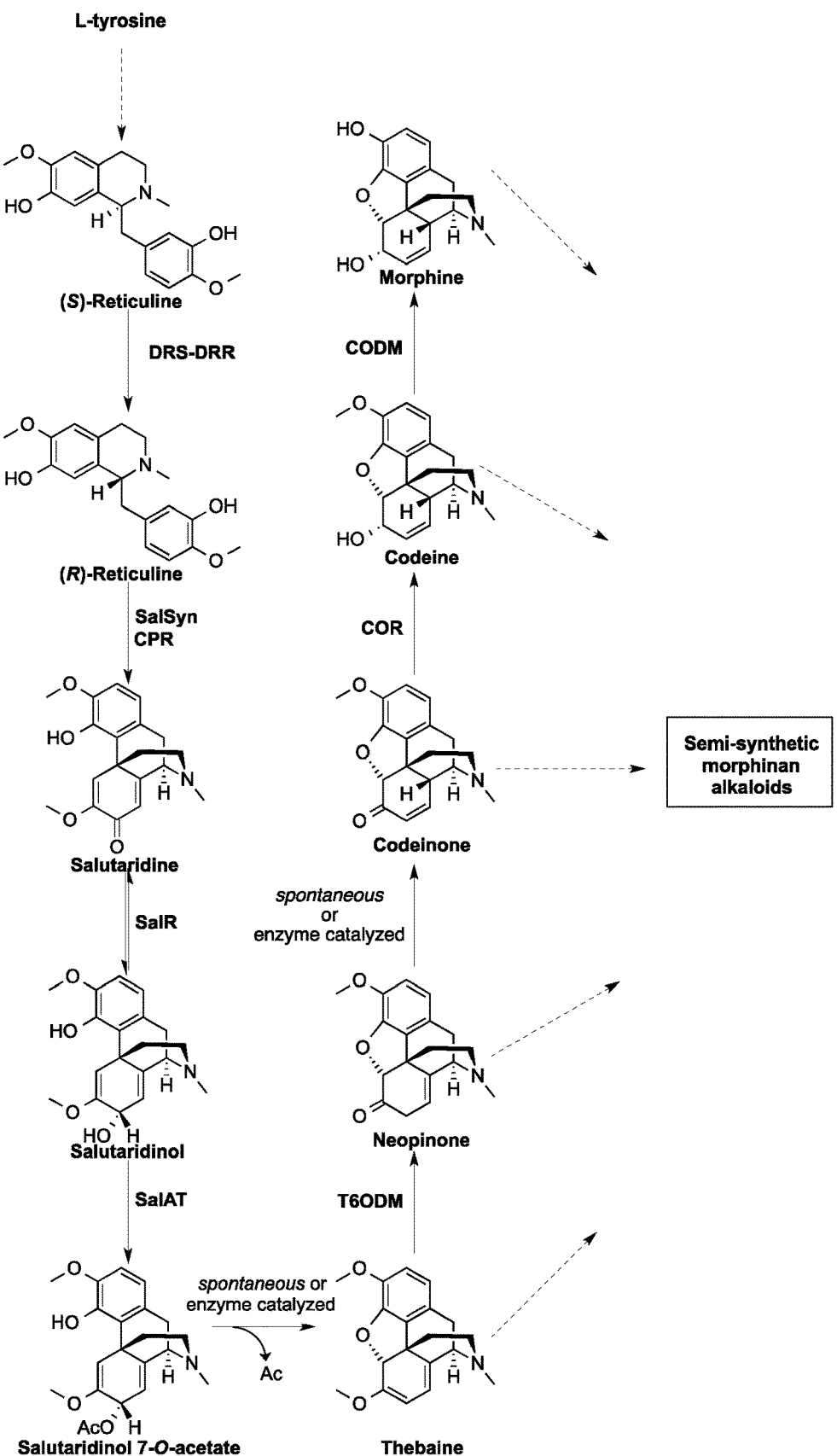
FIG. 7 illustrates a biosynthetic scheme for conversion of L-tyrosine to morphinan alkaloids, in accordance with embodiments of the invention.

[CYP-COR] As discussed above with regard to epimerizing 1-BIAs, the engineered host cell may modify the expression of a BIA epimerase. The BIA epimerase is encoded by the CYP-COR gene (e.g., CYP82Y2-COR gene). The CYP-COR gene may also be referred to as the DRS-DRR gene. In some examples, the BIA epimerase catalyzes the conversion of (S)-1-BIA→(R)-1-BIA, as referenced in FIG. 7. In particular, FIG. 7 illustrates a biosynthetic scheme for conversion of L-tyrosine to morphinan alkaloids, in accordance with embodiments of the invention. FIG. 7 provides the use of the enzymes CPR, cytochrome P450 reductase; CYP-COR, cytochrome P450 CYP82Y1-like codeinone reductase-like fusion; SalSyn, salutaridine synthase; SalR, salutaridine reductase; SalAT, salutaridinol 7-O- acetyltransferase; T6ODM, thebaine 6-O-demethylase; COR, codeinone reductase; and CODM, codeine-O-demethylase.

The engineered host cell may be modified to include constitutive expression of the CYP-COR gene in the engineered host cell. Additionally or alternatively, the engineered host cell may be modified to synthetically regulate the expression of the CYP-COR gene in the engineered host cell. In examples, the engineered host cell may be modified to incorporate a copy, copies, or additional copies, of the CYP-COR gene. Additionally or alternatively, the engineered host cell may be modified to incorporate the introduction of a strong promoter element for the overexpression of the CYP-COR gene within the engineered host cell. The CYP-COR gene may be derived from *Papaver bracteatum, Papaver somniferum, Papaver setigerum, Chelidonium majus*, or another species. In some examples, the CYP-COR gene may be 77% similar to the naturally occurring gene.

[CPR] In some examples, the engineered host cell may modify the expression of the enzyme cytochrome P450 reductase. The cytochrome P450 reductase is encoded by the CPR gene. In some examples, the cytochrome P450 reductase catalyzes the reaction of (R)-reticuline→salutaridine, as referenced in FIG. 7. Additionally, the cytochrome P450 reductase catalyzes other reactions such as those described in FIGs. throughout the application. The engineered host cell may be modified to include constitutive expression of the CPR gene in the engineered host cell. Additionally or alternatively, the engineered host cell may be modified to synthetically regulate the expression of the CPR gene in the engineered host cell. In examples, the engineered host cell may be modified to incorporate a copy, copies, or additional copies, of the CPR gene. Additionally or alternatively, the engineered host cell may be modified to incorporate the introduction of a strong promoter element for the overexpression of the CPR gene within the engineered host cell. The CPR gene may be derived from *E. californica, P. somniferum, H. sapiens, S. cerevisiae, A. thaliana*, or another species. In some examples, the CPR gene may be 100% similar to the naturally occurring gene.

[SalSyn] In some examples, the engineered host cell may modify the expression of the enzyme salutaridine synthase. The salutaridine synthase is encoded by the SalSyn gene. In some examples, the salutaridine synthase catalyzes the reaction of (R)-reticuline 4 salutaridine, as referenced in FIG. 7. The engineered host cell may be modified to include constitutive expression of the SalSyn gene in the engineered host cell. Additionally or alternatively, the engineered host cell may be modified to synthetically regulate the expression of the SalSyn gene in the engineered host cell. In examples, the engineered host cell may be modified to incorporate a copy, copies, or additional copies, of the SalSyn gene. Additionally or alternatively, the engineered host cell may be modified to incorporate the introduction of a strong promoter element for the overexpression of the SalSyn gene within the engineered host cell. In some cases, the SalSyn gene may be codon optimized for expression in *Saccharomyces cerevisiae*. In some examples the SalSyn may be modified at the N-terminus. The SalSyn gene may be derived from *Papaver somniferum, Papaver spp, Chelidonium majus*, or another species. In some examples, the SalSyn gene may be 78% similar to the naturally occurring gene.

[SalR] In some examples, the engineered host cell may modify the expression of the enzyme salutaridine reductase. Salutaridine reductase is encoded by the SalR gene. In some examples, salutaridine reductase reversibly catalyzes the reaction of salutaridinol 4 salutaridine, as referenced in FIG. 7. The engineered host cell may be modified to include constitutive expression of the SalR gene in the engineered host cell. Additionally or alternatively, the engineered host cell may be modified to synthetically regulate the expression of the SalR gene in the engineered host cell. In examples, the engineered host cell may be modified to incorporate a copy, copies, or additional copies, of the SalR gene. Additionally or alternatively, the engineered host cell may be modified to incorporate the introduction of a strong promoter element for the overexpression of the SalR gene within the engineered host cell. In some cases, the SalR gene may be codon optimized for expression in *Saccharomyces cerevisiae*. The SalR gene may be derived from *Papaver somniferum, Papaver bracteatum, Papaver spp., Chelidonium majus*, or another species. In some examples, the SalR gene may be 80-100% similar to the naturally occurring gene.

[SalAT] In some examples, the engineered host cell may modify the expression of the enzyme acetyl-CoA: salutaridinol 7-O-acetyltransferase. Acetyl-CoA: salutaridinol 7-O-acetyltransferase is encoded by the SalAT gene. In some examples, acetyl-CoA:salutaridinol 7-O-acetyltransferase catalyzes the reaction of acetyl-CoA+salutaridinol 4 CoA+7-O-acetylsalutaridinol, as referenced in FIG. 7. The engineered host cell may be modified to include constitutive expression of the SalAT gene in the engineered host cell. Additionally or alternatively, the engineered host cell may be modified to synthetically regulate the expression of the SalAT gene in the engineered host cell. In examples, the engineered host cell may be modified to incorporate a copy, copies, or additional copies, of the SalAT gene. Additionally or alternatively, the engineered host cell may be modified to incorporate the introduction of a strong promoter element for the overexpression of the SalAT gene within the engineered host cell. In some cases, the SalAT gene may be codon optimized for expression in *Saccharomyces cerevisiae*. The SalAT gene may be derived from *Papaver somniferum, Papaver bracteatum, Papaver orientate, Papaver spp.*, or another species. In some examples, the SalAT gene may be 77-80% similar to the naturally occurring gene.

[T6ODM] In some examples, the engineered host cell may modify the expression of the enzyme thebaine 6-O-demethylase. Thebaine 6-0 demethylase is encoded by the T6ODM gene. In some examples, thebaine 6-O-demethylase catalyzes the reaction of thebaine→neopinone, as referenced in FIG. 7. Once the neopinone has been produced, the neopinone may be converted to codeinone. The conversion of neopinone→codeinone may occur spontaneously. Alternatively, the conversion of neopinone→codeinone may occur as a result of a catalyzed reaction. In other examples, the T6ODM enzyme may catalyze the O-demethylation of substrates other than thebaine. For example, T6ODM may O-demethylate oripavine to produce morphinone. Alternatively, T6ODM may catalyze the O-demethylation of BIAs within the 1-benzylisoquinoline, protoberberine, or protopine classes such as papaverine, canadine, and allocryptopine, respectively. The engineered host cell may be modified to include constitutive expression of the T6ODM gene in the engineered host cell. Additionally or alternatively, the engineered host cell may be modified to synthetically regulate the expression of the T6ODM gene in the engineered host cell. In examples, the engineered host cell may be modified to incorporate a copy, copies, or additional copies, of the T6ODM gene. Additionally or alternatively, the engineered host cell may be modified to incorporate the introduction of a strong promoter element for the overexpression of the T6ODM gene within the engineered host cell. In some cases, the T6ODM gene may be codon optimized for expression in *Saccharomyces cerevisiae*. The T6ODM gene may be derived from *Papaver somniferum*, or another species. In some examples, the T6ODM gene may be 76.2% similar to the naturally occurring gene.

[COR] In some examples, the engineered host cell may modify the expression of the enzyme codeinone reductase. Codeinone reductase is encoded by the COR gene. In some examples, codeinone reductase catalyzes the reaction of codeinone to codeine, as referenced in FIG. 7. In some cases, codeinone reductase can catalyze the reaction of neopinone to neopine. In other examples, COR can catalyze the reduction of other morphinans including hydrocodone→dihydrocodeine, 14-hydroxycodeinone→14-hydroxycodeine, and hydromorphone→dihydromorphine. The engineered host cell may be modified to include constitutive expression of the COR gene in the engineered host cell. Additionally or alternatively, the engineered host cell may be modified to synthetically regulate the expression of the COR gene in the engineered host cell. In examples, the engineered host cell may be modified to incorporate a copy, copies, or additional copies, of the COR gene. Additionally or alternatively, the engineered host cell may be modified to incorporate the introduction of a strong promoter element for the overexpression of the COR gene within the engineered host cell. In some cases, the COR gene may be codon optimized for expression in *Saccharomyces cerevisiae*. Additionally or alternatively, the COR gene may be modified with the addition of targeting sequences for mitochondria, vacuole, endoplasmic reticulum, or a combination thereof. The COR gene may be derived from *Papaver somniferum*, or another species. In some examples, the COR gene may be 76-78% similar to the naturally occurring gene. In examples, the COR gene may be 76.8%, 77.0%, 77.3%, or 77.7% similar to the naturally occurring gene.

[CODM] In some examples, the engineered host cell may modify the expression of the enzyme codeine O-demethylase. Codeine O-demethylase is encoded by the CODM gene. In some examples, codeine O-demethylase catalyzes the reaction of codeine to morphine, as referenced in FIG. 7. Codeine O-demethylase can also catalyze the reaction of neopine to neomorphine. Codeine O-demethylase can also catalyze the reaction of thebaine to oripavine. In other examples, CODM may catalyze the O-demethylation of BIAs within the 1-benzylisoquinoline, aporphine, and protoberberine classes such as reticuline, isocorydine, and scoulerine, respectively. In other examples, the CODM enzyme may catalyze an O,O-demethylenation reaction to cleave the methylenedioxy bridge structures in protopines. The engineered host cell may be modified to include constitutive expression of the CODM gene in the engineered host cell. Additionally or alternatively, the engineered host cell may be modified to synthetically regulate the expression of the CODM gene in the engineered host cell. In examples, the engineered host cell may be modified to incorporate a copy, copies, or additional copies, of the CODM gene. Additionally or alternatively, the engineered host cell may be modified to incorporate the introduction of a strong promoter element for the overexpression of the CODM gene within the engineered host cell. In some cases, the CODM gene may be codon optimized for expression in *Saccharomyces cerevisiae*. Additionally or alternatively, the CODM gene may be modified with the addition of targeting sequences for mitochondria. The CODM gene may be derived from *Papaver somniferum*, *Papaver* spp., or another species. In some examples, the CODM gene may be 75% similar to the naturally occurring gene. In examples, the CODM gene may be 75.2% similar to the naturally occurring gene.

[BBE] In some examples, the engineered host cell may modify the expression of the enzyme berberine bridge enzyme. The berberine bridge enzyme is encoded by the BBE gene. In some examples, berberine bridge enzyme catalyzes the reaction of (S)-reticuline→(S)-scoulerine. The engineered host cell may be modified to include constitutive expression of the BBE gene in the engineered host cell. Additionally or alternatively, the engineered host cell may be modified to synthetically regulate the expression of the BBE gene in the engineered host cell. In examples, the engineered host cell may be modified to incorporate a copy, copies, or additional copies, of the BBE gene. Additionally or alternatively, the engineered host cell may be modified to incorporate the introduction of a strong promoter element for the overexpression of the BBE gene within the engineered host cell. The BBE gene may be derived from *Papaver somniferum*, *Argemone mexicana*, *Eschscholzia californica*, *Berberis stolonifera*, *Thalictrum flavum* subsp. *glaucum*, *Coptis japonica*, *Papaver* spp., or another species. In some examples, the BBE gene may be 99% similar to the naturally occurring gene.

[S9OMT] In some examples, the engineered host cell may modify the expression of the enzyme S-adenosyl-L-methionine:(S)-scoulerine 9-O-methyltransferase. S-adenosyl-L-methionine:(S)-scoulerine 9-O-methyltransferase is encoded by the S9OMT gene. In some examples, S-adenosyl-L-methionine:(S)-scoulerine 9-O-methyltransferase catalyzes the reaction of S-adenosyl-L-methionine+(S)-scoulerine S-adenosyl-L-homocysteine+(S)-tetrahydrocolumbamine. The engineered host cell may be modified to include constitutive expression of the S9OMT gene in the engineered host cell. Additionally or alternatively, the engineered host cell may be modified to synthetically regulate the expression of the S9OMT gene in the engineered host cell. In examples, the engineered host cell may be modified to incorporate a copy, copies, or additional copies, of the S9OMT gene. Additionally or alternatively, the engineered host cell may be modified to incorporate the introduction of a strong promoter element for the overexpression of the S9OMT gene within the engineered host cell. In some cases, the S9OMT gene may be codon optimized for expression in *Saccharomyces cerevisiae*. The S9OMT gene may be derived from *Thalictrum flavum* subsp. *glaucum*, *Coptis japonica*, *Coptis chinensis*, *Papaver somniferum*, *Thalictrum* spp., *Coptis* spp., *Papaver* spp., or another species. In some examples, the S9OMT gene may be 100% similar to the naturally occurring gene. In examples, the S9OMT gene may be 80% similar to the naturally occurring gene.

[CAS] In some examples, the engineered host cell may modify the expression of the enzyme (S)-canadine synthase. (S)-canadine synthase is encoded by the CAS gene. In some examples, (S)-canadine synthase catalyzes the reaction of (S)-tetrahydrocolumbamine→(S)-canadine. The engineered host cell may be modified to express the CAS gene in the engineered host cell. The engineered host cell may be modified to include constitutive expression of the CAS gene in the engineered host cell. Additionally or alternatively, the engineered host cell may be modified to synthetically regulate the expression of the CAS gene in the engineered host cell. In examples, the engineered host cell may be modified to incorporate a copy, copies, or additional copies, of the CAS gene. Additionally or alternatively, the engineered host cell may be modified to incorporate the introduction of a strong promoter element for the overexpression of the CAS gene within the engineered host cell. The CAS gene may be derived from *Thalictrum flavum* subsp. *glaucum, Coptis japonica, Thalictrum* spp., *Coptis* spp., or another species. In some examples, the CAS gene may be 100%

[STOX] In some examples, the engineered host cell may modify the expression of the enzyme (S)-tetrahydroprotoberberine oxidase. (S)-tetrahydroprotoberberine oxidase is encoded by the STOX gene. In some examples, (S)-tetrahydroprotoberberine oxidase catalyzes the reaction of (S)-tetrahydroberberine+2 $O_2 \rightarrow$ berberine+$2H_2O_2$. The engineered host cell may be modified to include constitutive expression of the STOX gene in the engineered host cell. Additionally or alternatively, the engineered host cell may be modified to synthetically regulate the expression of the STOX gene in the engineered host cell. In examples, the engineered host cell may be modified to incorporate a copy, copies, or additional copies, of the STOX gene. Additionally or alternatively, the engineered host cell may be modified to incorporate the introduction of a strong promoter element for the overexpression of the STOX gene within the engineered host cell. In some examples the STOX may be modified at the N-terminus. In some cases, the STOX gene may be codon optimized for expression in *Saccharomyces cerevisiae*. The STOX gene may be derived from *Berberis wilsonae, Coptis japonica, Berberis* spp., *Coptis* spp., or another species. In some examples, the STOX gene may be 78% similar to the naturally occurring gene.

[TNMT] In some examples, the engineered host cell may modify the expression of the enzyme tetrahydroprotoberberine-N-methyltransferase. Tetrahydroprotoberberine-N-methyltransferase is encoded by the TNMT gene. In some examples, tetrahydroprotoberberine-N-methyltransferase catalyzes the reaction of canadine→N-methylcanadine. In some examples, tetrahydroprotoberberine-N-methyltransferase catalyzes the reaction of noroxymorphone→naloxone, as referenced in FIG. 26.

In other examples, tetrahydroprotoberberine-N-methyltransferase catalyzes the reaction of stylopine→cis-N-methylstylopine. The engineered host cell may be modified to include constitutive expression of the TNMT gene in the engineered host cell. Additionally or alternatively, the engineered host cell may be modified to synthetically regulate the expression of the TNMT gene in the engineered host cell. In examples, the engineered host cell may be modified to incorporate a copy, copies, or additional copies, of the TNMT gene. Additionally or alternatively, the engineered host cell may be modified to incorporate the introduction of a strong promoter element for the overexpression of the TNMT gene within the engineered host cell. In some cases, the TNMT gene may be codon optimized for expression in *Saccharomyces cerevisiae*. The TNMT gene may be derived from *Papaver somniferum, Eschscholzia californica, Papaver bracteatum, Argemone mexicana*, or another species. In some examples, the TNMT gene may be 100% similar to the naturally occurring gene. In examples, the TNMT gene may be 81% similar to the naturally occurring gene.

[CFS] In some examples, the engineered host cell may modify the expression of the enzyme cheilanthifoline synthase. Cheilanthifoline synthase is encoded by the CFS gene. In examples, cheilanthifoline synthase catalyzes the reaction of scoulerine cheilanthifoline. An engineered host cell may be modified to include constitutive expression of the CFS gene in the engineered host cell. Additionally or alternatively, the engineered host cell may be modified to synthetically regulate the expression of the CFS gene in the engineered host cell. In examples, the engineered host cell may be modified to incorporate a copy, copies, or additional copies, of the CFS gene. Additionally or alternatively, the engineered host cell may be modified to incorporate the introduction of a strong promoter element for the overexpression of the CFS gene within the engineered host cell. The CFS gene may be derived from *P. somniferum, E. californica, A. mexicana*, or another species. In some examples, the CFS gene may be 77%, 78%, or 79% similar to the naturally occurring gene. Additionally, the CFS gene may be codon optimized for expression in *Saccharomyces cerevisiae*.

[STS] In some examples, the engineered host cell may modify the expression of the enzyme stylopine synthase. Stylopine synthase is encoded by the STS gene. In examples, stylopine synthase catalyzes the reaction of cheilanthifoline→stylopine. An engineered host cell may be modified to include constitutive expression of the STS gene in the engineered host cell. Additionally or alternatively, the engineered host cell may be modified to synthetically regulate the expression of the STS gene in the engineered host cell. In examples, the engineered host cell may be modified to incorporate a copy, copies, or additional copies, of the STS gene. Additionally or alternatively, the engineered host cell may be modified to incorporate the introduction of a strong promoter element for the overexpression of the STS gene within the engineered host cell. The STS gene may be derived from *P. somniferum, E. californica, A. mexicana*, or another species. In some examples, the STS gene may be 76%, 78%, or 79% similar to the naturally occurring gene. Additionally, the STS gene may be codon optimized for expression in *Saccharomyces cerevisiae*.

[MSH] In some examples, the engineered host cell may modify the expression of the enzyme cis-N-methylstylopine 14-hydroxylase. Cis-N-methylstylopine 14-hydroxylase is encoded by the MSH gene. In examples, cis-N-methylstylopine 14-hydroxylase catalyzes the reaction of cis-N-methylstylopine→protopine. An engineered host cell may be modified to include constitutive expression of the MSH gene in the engineered host cell. Additionally or alternatively, the engineered host cell may be modified to synthetically regulate the expression of the MSH gene in the engineered host cell. In examples, the engineered host cell may be modified to incorporate a copy, copies, or additional copies, of the MSH gene. Additionally or alternatively, the engineered host cell may be modified to incorporate the introduction of a strong promoter element for the overexpression of the MSH gene within the engineered host cell. The MSH gene may be derived from *P. somniferum* or another species. In some examples, the MSH gene may be 79% similar to the naturally occurring gene. Additionally, the MSH gene may be codon optimized for expression in *Saccharomyces cerevisiae*.

[P6H] In some examples, the engineered host cell may modify the expression of the enzyme protopine-6-hydroxylase. Protopine-6-hydroxylase is encoded by the P6H gene. In examples, protopine-6-hydroxylase catalyzes the reaction of Protopine→6-hydroxyprotopine. An engineered host cell may be modified to include constitutive expression of the P6H gene in the engineered host cell. Additionally or alternatively, the engineered host cell may be modified to synthetically regulate the expression of the P6H gene in the engineered host cell. In examples, the engineered host cell may be modified to incorporate a copy, copies, or additional copies, of the P6H gene. Additionally or alternatively, the engineered host cell may be modified to incorporate the introduction of a strong promoter element for the overexpression of the CFS gene within the engineered host cell.

The P6H gene may be derived from *P. somniferum, E. californica*, or another species. In some examples, the P6H gene may be 79% similar to the naturally occurring gene. Additionally, the P6H gene may be codon optimized for expression in *Saccharomyces cerevisiae*.

[DBOX] In some examples, the engineered host cell may modify the expression of the enzyme dihydrobenzophenanthridine oxidase. Dihydrobenzophenanthridine oxidase is encoded by the DBOX gene. In examples, dihydrobenzophenanthridine oxidase catalyzes the reaction of dihydrosanguinarine→sanguinarine. An engineered host cell may be modified to include constitutive expression of the DBOX gene in the engineered host cell. Additionally or alternatively, the engineered host cell may be modified to synthetically regulate the expression of the DBOX gene in the engineered host cell. In examples, the engineered host cell may be modified to incorporate a copy, copies, or additional copies, of the DBOX gene. Additionally or alternatively, the engineered host cell may be modified to incorporate the introduction of a strong promotor element for the overexpression of the DBOX gene within the engineered host cell. The DBOX gene may be derived from *P. somniferum* or another species. In some examples, the DBOX gene may be 100% similar to the naturally occurring gene. Additionally, the DBOX gene may be codon optimized for expression in *Saccharomyces cerevisiae*.

Figure 8:
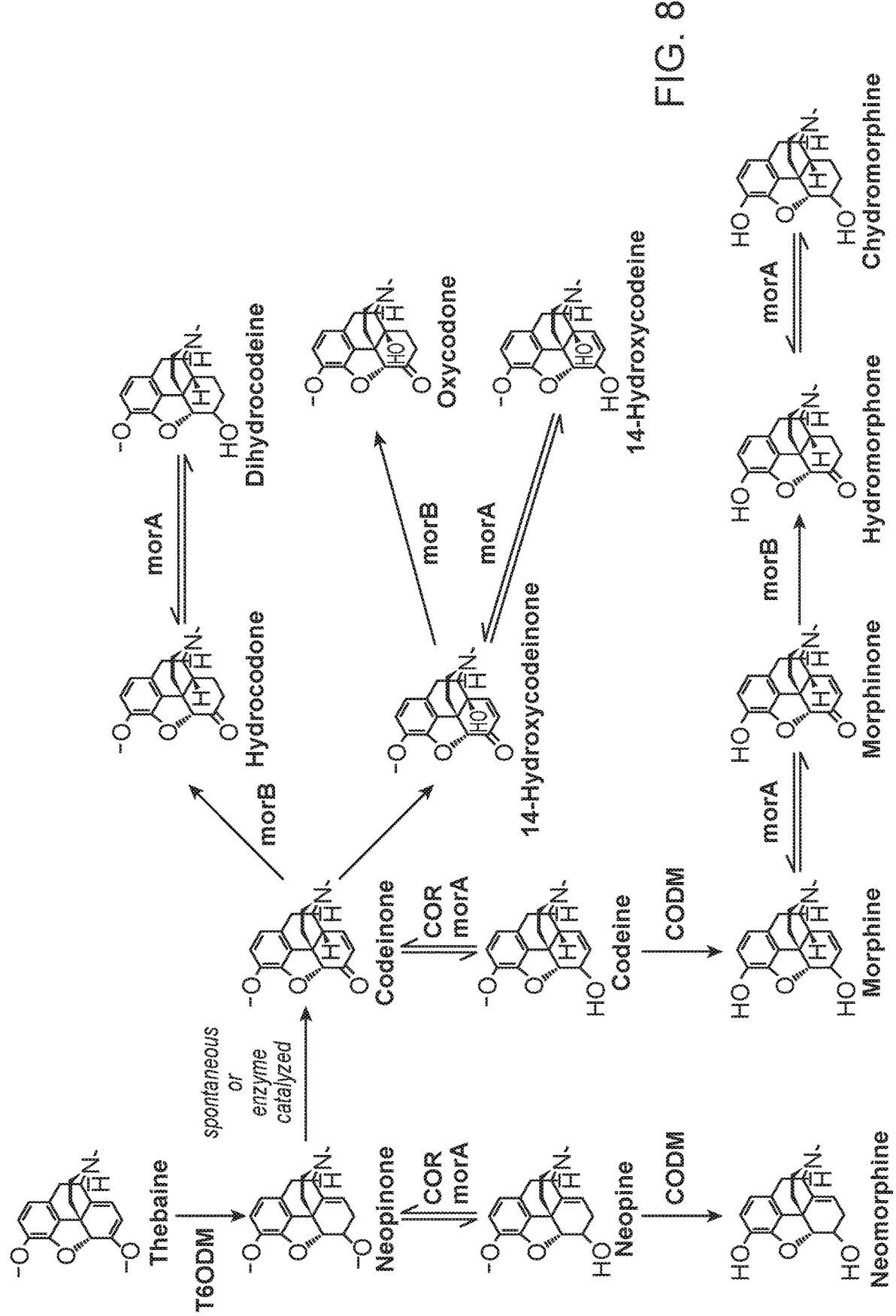
FIG. 8 illustrates a biosynthetic scheme for production of semi-synthetic opioids, in accordance with embodiments of the invention.
Figure 30:
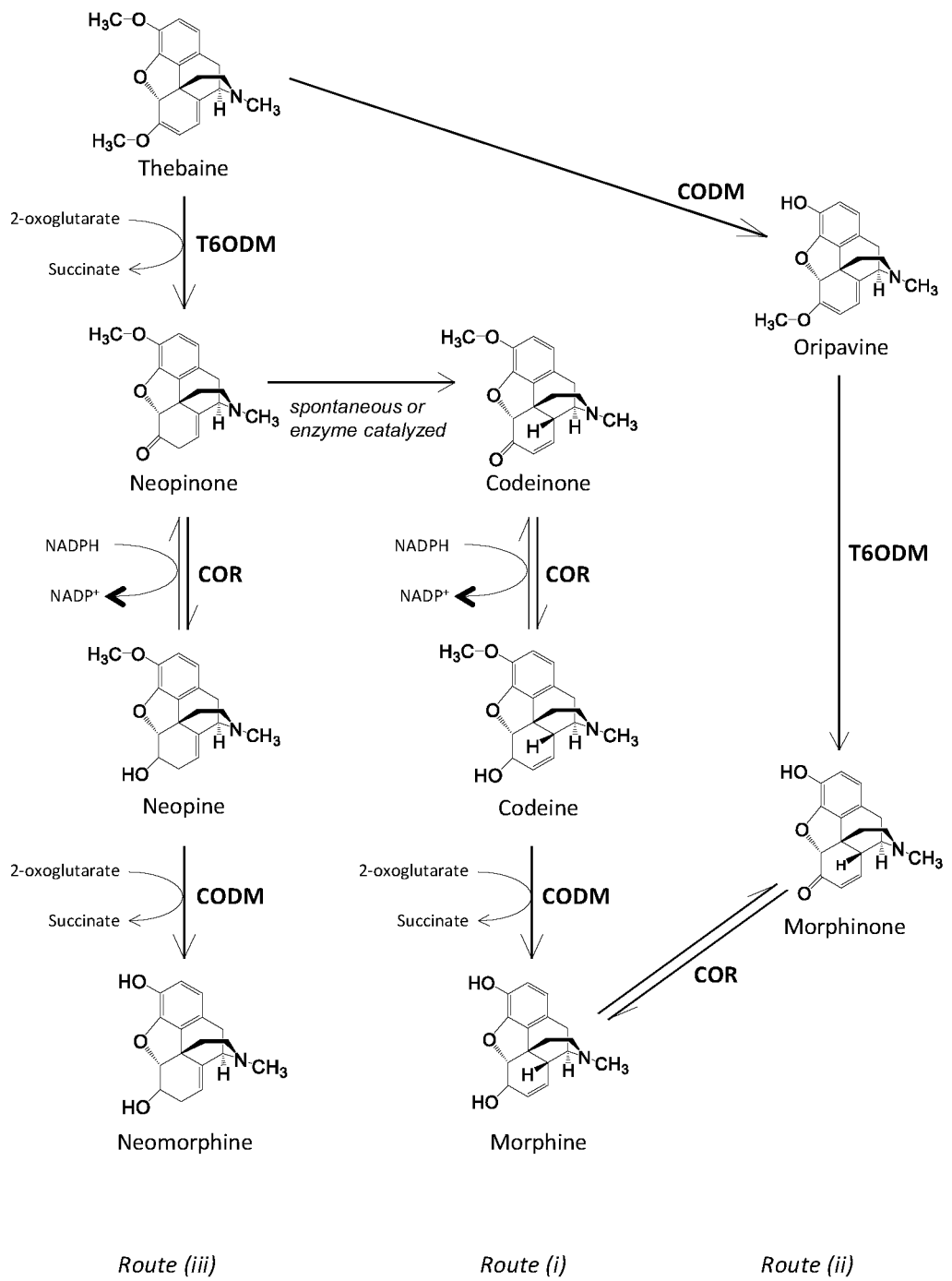
FIG. 30 illustrates a biosynthetic scheme for production of semi-synthetic opioids, in accordance with embodiments of the invention.

[morA] In some examples, the engineered host cell may modify the expression of the enzyme morphine dehydrogenase. Morphine dehydrogenase is encoded by the morA gene. In some examples, morphine dehydrogenase catalyzes the reaction of morphine→morphinone, as referenced in FIG. 8. In other examples, morphine dehydrogenase catalyzes the reaction of codeinone→codeine, also as referenced in FIG. 8. FIG. 8 illustrates a biosynthetic scheme for production of semi-synthetic opiods, in accordance with embodiments of the invention. In particular, FIG. 8 illustrates extended transformations of thebaine in yeast by incorporating morA, morphine dehydrogenase; and morB, morphine reductase. FIG. 30 illustrates an additional transformation of thebaine, in accordance with embodiments of the invention.

The engineered host cell may be modified to include constitutive expression of the morA gene in the engineered host cell. Additionally or alternatively, the engineered host cell may be modified to synthetically regulate the expression of the morA gene in the engineered host cell. In examples, the engineered host cell may be modified to incorporate a copy, copies, or additional copies, of the morA gene. Additionally or alternatively, the engineered host cell may be modified to incorporate the introduction of a strong promoter element for the overexpression of the morA gene within the engineered host cell. In some cases, the morA gene may be codon optimized for expression in *Saccharomyces cerevisiae*. The morA gene may be derived from *Pseudomonas putida* or another species. In some examples, the morA gene may be 73.7% similar to the naturally occurring gene.

[morB] In some examples, the engineered host cell may modify the expression of the enzyme morphinone reductase. Morphinone reductase is encoded by the morB gene. In some examples, morphinone reductase catalyzes the reaction of codeinone hydrocodone, as referenced in FIG. 8. In other examples, morphinone reductase catalyzes the reaction of morphinone→hydromorphone, also as referenced in FIG. 8. In other examples, morphinone reductase catalyzes the reaction 14-hydroxycodeinone→oxycodone. The engineered host cell may be modified to include constitutive expression of the morB gene in the engineered host cell. Additionally or alternatively, the engineered host cell may be modified to synthetically regulate the expression of the morB gene in the engineered host cell. In examples, the engineered host cell may be modified to incorporate a copy, copies, or additional copies, of the morB gene. Additionally or alternatively, the engineered host cell may be modified to incorporate the introduction of a strong promoter element for the overexpression of the morB gene within the engineered host cell. In some cases, the morB gene may be codon optimized for expression in *Saccharomyces cerevisiae*. The morB gene may be derived from *Pseudomonas putida* or another species. In some examples, the morB gene may be 67.2% similar to the naturally occurring gene.

[CYP80A1] In some examples, the engineered host cell may express the enzyme berbamunine synthase. Berbamunine synthase is encoded by the gene for cytochrome P450 enzyme 80A1 (CYP80A1). In some examples, CYP80A1 catalyzes the reaction (S)—N-methylcoclaurine+(R)—N-methylcoclaurine→berbamunine. In other examples, CYP80A1 catalyzes the reaction (R)—N-methylcoclaurine+(R)—N-methylcoclaurine→guattegaumerine. In other examples, CYP80A1 catalyzes the reaction (R)—N-methylcoclaurine+(S)-coclaurine→2'norberbamunine. The engineered host cell may be modified to include constitutive expression of the CYP80A1 gene in the engineered host cell. Additionally or alternatively, the engineered host cell may be modified to synthetically regulate the expression of the CYP80A1 gene in the engineered host cell. In examples, the engineered host cell may be modified to incorporate a copy, copies, or additional copies, of the CYP80A1 gene. Additionally or alternatively, the engineered host cell may be modified to incorporate the introduction of a strong promoter element for the overexpression of the CYP80A1 gene within the engineered host cell. In some cases, the CYP80A1 gene may be codon optimized for expression in *Saccharomyces cerevisiae*. The CYP80A1 gene may be derived from *Berberis stolonifera* or another species. In some examples, the CYP80A1 gene may be 76% similar to the naturally occurring gene.

[PODA] In some example, the engineered host cell may express the enzyme protopine O-dealkylase. Protopine O-dealkylase is encoded by the gene PODA. In some examples, PODA catalyzes the O,O-demethylenation of protoberberines and protopines such as canadine, stylopine, berberine, cryptopine, allocryptopine, and protopine. In some examples, PODA catalyzes the O-demethylation of BIAs including tetrahydropapaverine, tetrahydropalmatine, and cryptopine. The engineered host cell may be modified to include constitutive expression of the PODA gene in the engineered host cell. Additionally or alternatively, the engineered host cell may be modified to synthetically regulate the expression of the PODA gene in the engineered host cell. In examples, the engineered host cell may be modified to incorporate a copy, copies, or additional copies, of the PODA gene. Additionally or alternatively, the engineered host cell may be modified to incorporate the introduction of a strong promoter element for the overexpression of the PODA gene within the engineered host cell. In some cases, the PODA gene may be codon optimized for expression in *Saccharomyces cerevisiae*. The PODA gene may be derived from *Papaver somniferum* or other species. In some examples, the PODA gene may be 70-100% similar to the naturally occurring gene.

[BM3] In some examples, the engineered host cell may express the enzyme BM3. BM3 is a *Bacillus megaterium* cytochrome P450 involved in fatty acid monooxygenation in its native host. In some cases BM3 N-demethylates an opioid to produce a nor-opioid, as referenced in FIG. 27. It is also readily expressed as an active heterologous enzyme in yeast and bacteria. BM3 has several advantages as a biosynthetic enzyme including that it is soluble, comes with a fused reductase partner protein, and can readily be engineered to accept new substrates. Additionally, Table 6 illustrates variants of BM3 N-demethylase.

Examples of the aforementioned genes can be expressed from a number of different platforms in the host cell, including plasmid (2μ, ARS/CEN), YAC, or genome. In addition, examples of the aforementioned gene sequences can either be native or codon optimized for expression in the desired heterologous host (e.g., *Saccharomyces cerevisiae*).

EXAMPLES

The following examples are given for the purpose of illustrating various embodiments of the invention and are not meant to limit the invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Figure 9:
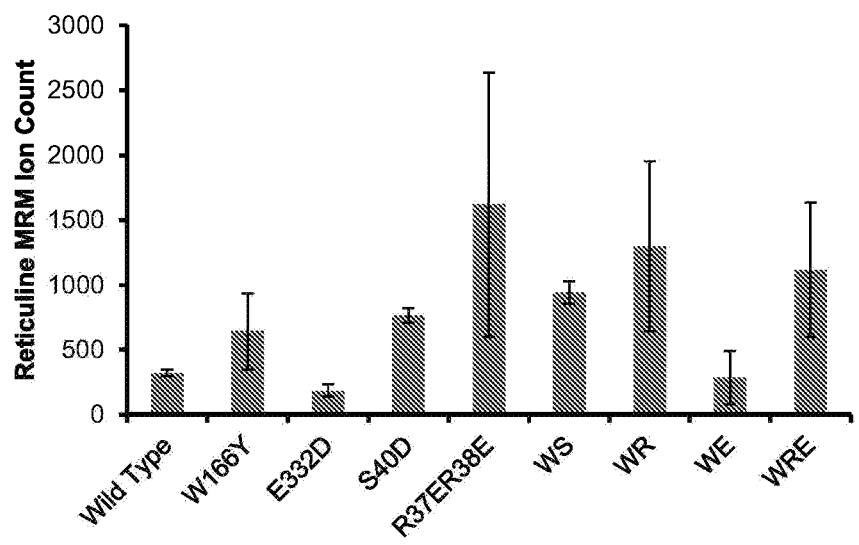
FIG. 9 illustrates tyrosine hydroxylase mutants that improve reticuline production from sugar in engineered yeast strains, in accordance with embodiments of the invention.

Example 1: Tyrosine Hydroxylase Mutants Improve Reticuline Production in Engineered Yeast Strains Tyrosine hydroxylase from *R. norvegicus* was yeast codon optimized, synthesized, and cloned into a low-copy plasmid. Single mutants (W166Y, E332D, S40D and R37ER38E), double mutants (W166Y and E332D, W166Y and 540D, W166Y and R37ER38E), and one triple mutant (W166Y, R37ER38E, and E332D) were generated through site-directed mutagenesis. Each TyrH mutant was expressed from a low-copy plasmid with the GPD promoter in a yeast strain containing the following mutations to central metabolism (as described in U.S. Provisional Patent Application Ser. No. 61/899,496): ARO4$^{FBR}$, ΔZWF1, and GPD-TKL1 promoter replacement. In addition, the strain expressed a chromosomally integrated copy of DOPA decarboxylase (DODC) from *P. putida*, four chromosomally integrated genes from *R. norvegicus* that generate the cosubstrate tetrahydrobiopterin (pyruvoyl tetrahydropterin synthase, PTPS; sepiapterin reductase, SepR; pterin 4a-carbinolamine dehydratase, PCD; dihydropteridine reductase, QDHPR), norcoclaurine synthase (NCS) from *C. japonica* expressed from a low-copy plasmid with a GPD promoter, and five genes for the biosynthesis of reticuline from norcoclaurine (*P. somniferum* 6-O-methyltransferase, Ps6OMT; *P. somniferum* coclaurine N-methyltransferase, PsCNMT; *E. californica* cytochrome P450 80B1, EcCYP80B1; *P. somniferum* cytochrome P450 NADPH reductase, PsCPR; and *P. somniferum* 3'hydroxy-N-methylcoclaurine 4'-O-methyltransferase, Ps4'OMT). The strains harboring TyrH mutants were grown in selective defined media (YNB) lacking tyrosine with 2% dextrose for 96 hours, and the production of reticuline was measured in the media via LC-MS/MS in MRM mode with the transition 330 m/z to 137 m/z. FIG. 9 shows the results of this assay and demonstrates that TyrH mutants can improve reticuline production by as much as 5-fold when compared to wild-type TyrH. As such, FIG. 9 illustrates tyrosine hydroxylase mutants that improve reticuline production from sugar in engineered yeast strains, in accordance with embodiments of the invention.

Figure 10:
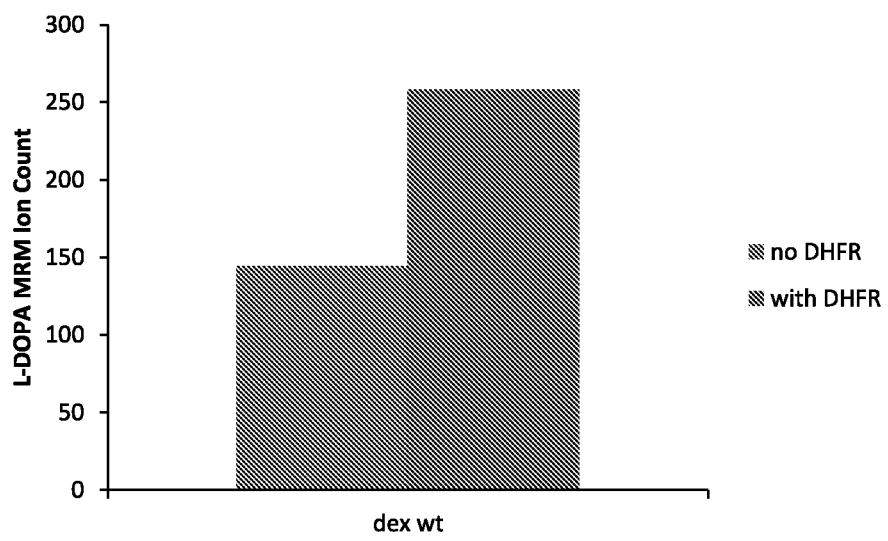
FIG. 10 illustrates coexpression of dihydrofolate reductase (DHFR) that improves L-DOPA production by tyrosine hydroxylase in engineered yeast strains, in accordance with embodiments of the invention.

Example 2: Expression of DHFR Improves Tyrosine Hydroxylase Activity in Engineered Yeast Strains Dihydrofolate reductase (DHFR) from *R. norvegicus* was yeast codon optimized, synthesized, and cloned into a low-copy plasmid under the control of a GPD promoter. DHFR was coexpressed with wild-type RnTyrH (low-copy plasmid with a GPD promoter) in a yeast strain containing the following mutations to central metabolism (as described in U.S. Provisional Patent Application Ser. No. 61/899,496): ARO4$^{FBR}$, ΔZWF1, and GPD-TKL1 promoter replacement. In addition, the strain expressed four chromosomally integrated genes from *R. norvegicus* that generate the cosubstrate tetrahydrobiopterin (pyruvoyl tetrahydropterin synthase, PTPS; sepiapterin reductase, SepR; pterin 4a-carbinolamine dehydratase, PCD; dihydropteridine reductase, QDHPR). The strains expressing DHFR and wild-type RnTyrH were grown in selective defined media (YNB) lacking tyrosine with 2% dextrose for 96 hours, and the production of L-DOPA was measured in the media via LC-MS/MS in MRM mode with the transition 198 m/z to 152 m/z. Expression of DHFR with wild-type RnTyrH increases L-DOPA production by 1.8-fold, as illustrated in FIG. 10. As such, FIG. 10 illustrates coexpression of dihydrofolate reductase (DHFR) that improves L-DOPA production by tyrosine hydroxylase in engineered yeast strains, in accordance with embodiments of the invention.

Example 3: Addition of Antioxidants to Growth Media Improve Tyrosine Hydroxylase Activity in Engineered Yeast Strains A yeast strain containing the following mutations to central metabolism (as described in U.S. Provisional Patent Application Ser. No. 61/899,496): ARO4$^{FBR}$, ΔZWF1, and GPD-TKL1 promoter replacement and expressing four chromosomally integrated genes from *R. norvegicus* that generate the cosubstrate tetrahydrobiopterin (pyruvoyl tetrahydropterin synthase, PTPS; sepiapterin reductase, SepR; pterin 4a-carbinolamine dehydratase, PCD; dihydropteridine reductase, QDHPR) as well as wild-type RnTyrH from a low-copy plasmid under the control of the GPD promoter was grown in selective defined media (YNB) lacking tyrosine with 2% galactose and 2 mM ascorbic acid for 96 hours.

The production of L-DOPA was measured in the media via LC-MS/MS in MRM mode with the transition 198 m/z to 152 m/z. The addition of 2 mM ascorbic acid improves L-DOPA production with wild-type RnTyrH by 1.8-fold. In addition, the concentration BH$_4$ intermediates were measured with LC-MS/MS in MRM mode with the following transitions: B, 238 m/z to 178 m/z; BH2, 240 m/z to 165 m/z and BH4, 242 m/z to 166 m/z. The addition of ascorbic acid also increases BH$_4$ in the media, which indicates the oxidation of BH$_4$ to BH$_2$ is prevented.

Figure 11A:
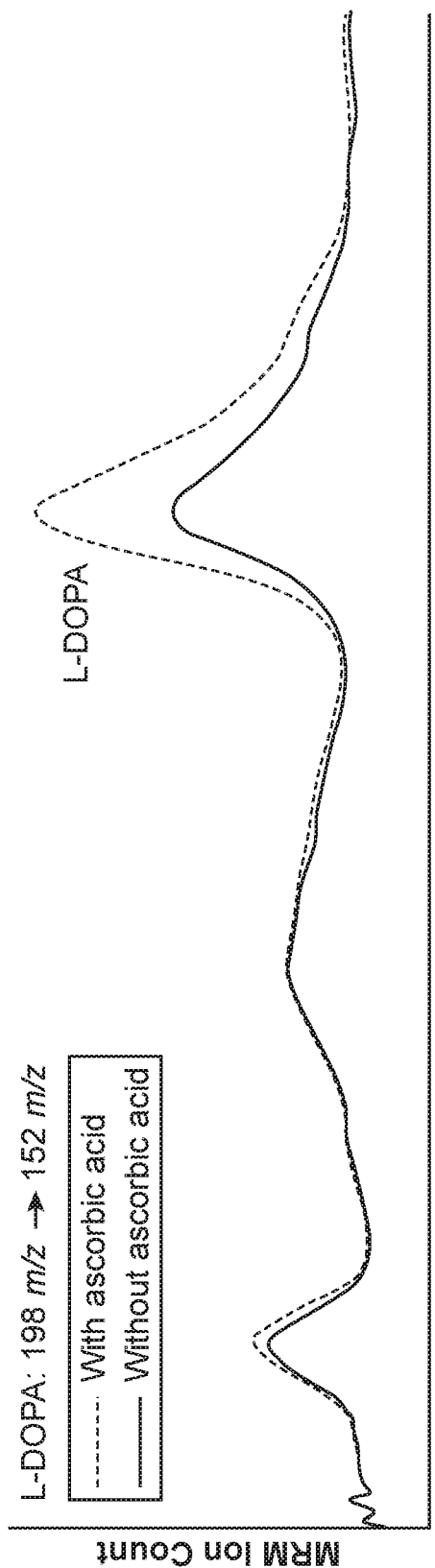
FIG. 11A illustrates the addition of antioxidants to culture media that improves L-DOPA production by tyrosine hydroxylase in engineered yeast strains.
Figure 11B:
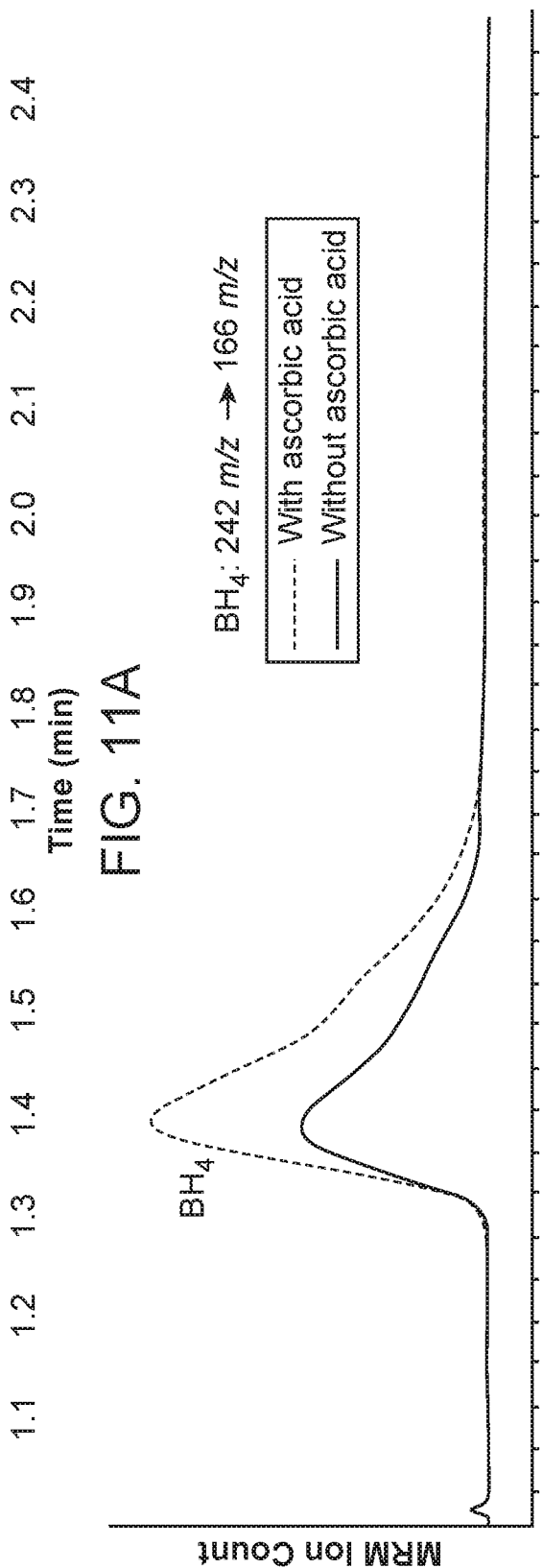
FIG. 11B illustrates the addition of antioxidants to culture media that increase $BH_4$ levels, in accordance with embodiments of the invention.
Figure 12A:
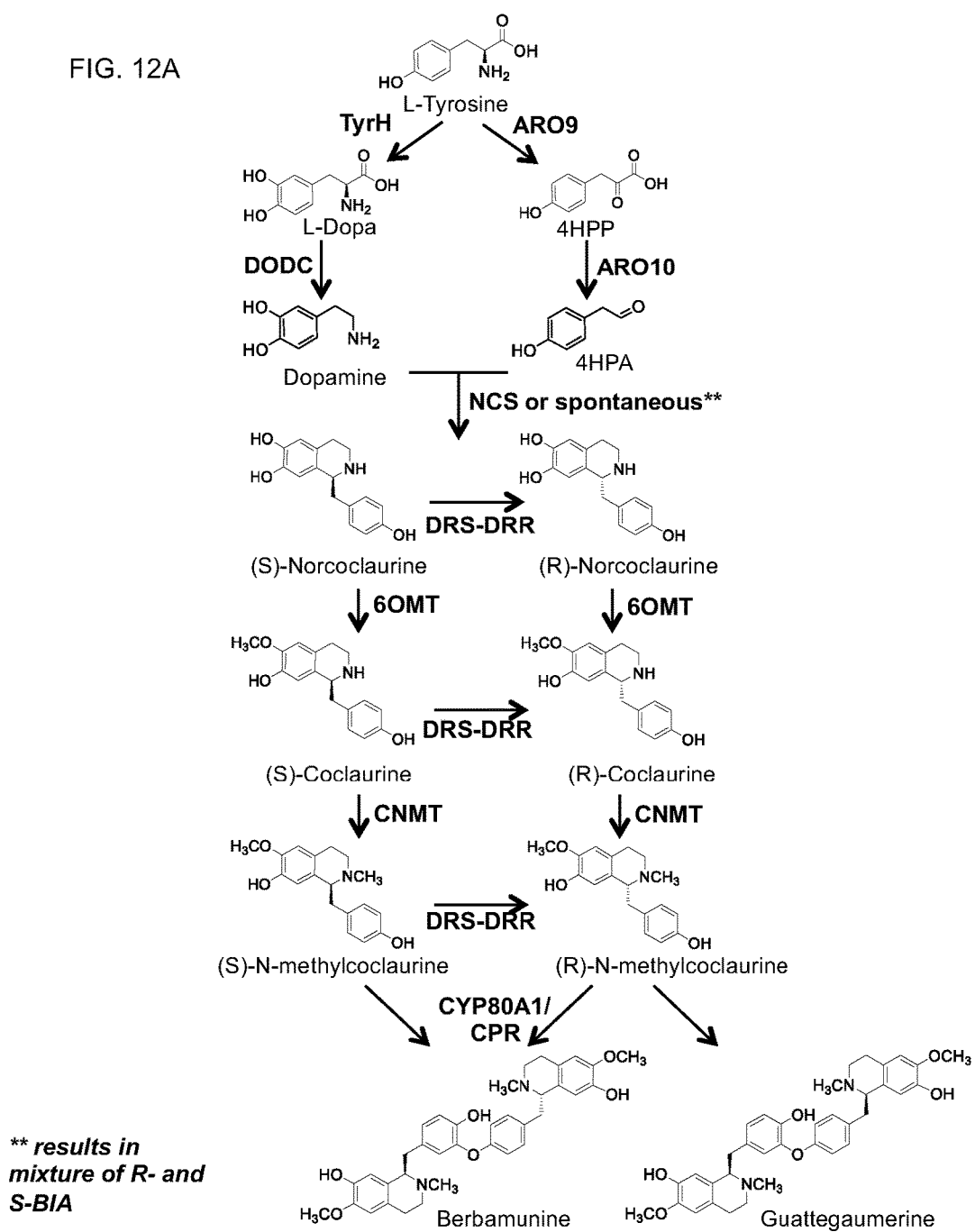
FIG. 12A illustrates a biosynthetic scheme for conversion of L-tyrosine to bisBIAs.
Figure 12B:
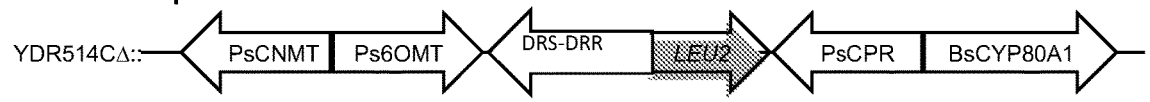
FIG. 12B illustrates yeast strains engineered to biosynthesize bisBIAs, in accordance with embodiments of the invention.

Accordingly, FIG. 11A illustrates addition of antioxidants to culture media that improves L-DOPA production by tyrosine hydroxylase in engineered yeast strains and (B) addition of antioxidants to culture media that increase BH$_4$ levels, in accordance with embodiments of the invention. In particular, FIG. 11A illustrate a wild-type RnTyrH (expressed from a low-copy plasmid under the control of a GPD promoter) was expressed in a yeast strain containing the following mutations to central metabolism (as described in U.S. Provisional Patent Application Ser. No. 61/899,496): ARO4$^{FBR}$, ΔZWF1, and GPD-TKL1 promoter replacement. In addition, the strain expressed four chromosomally integrated genes from R. norvegicus that generate the cosubstrate tetrahydrobiopterin (pyruvoyl tetrahydropterin synthase, PTPS; sepiapterin reductase, SepR; pterin 4a-carbinolamine dehydratase, PCD; dihydropteridine reductase, QDHPR). The strains expressing wild-type RnTyrH was grown in selective defined media (YNB) lacking tyrosine with 2% dextrose, with and without 2 mM ascorbic acid (aa) for 96 hours. The production of L-DOPA was measured in the media via LC-MS/MS in MRM mode with the transition 198 m/z to 152 m/z. Additionally, FIG. 11B illustrates, in the same strain described in FIG. 11A, the concentration of the BH$_4$ intermediate was measured in the media of strains grown with and without 2 mM ascorbic acid (aa) with LC-MS/MS in MRM mode with the following transition: BH$_4$, 242 m/z to 166 m/z.

Example 4. Identification of an Epimerase Enzyme

Figure 13:
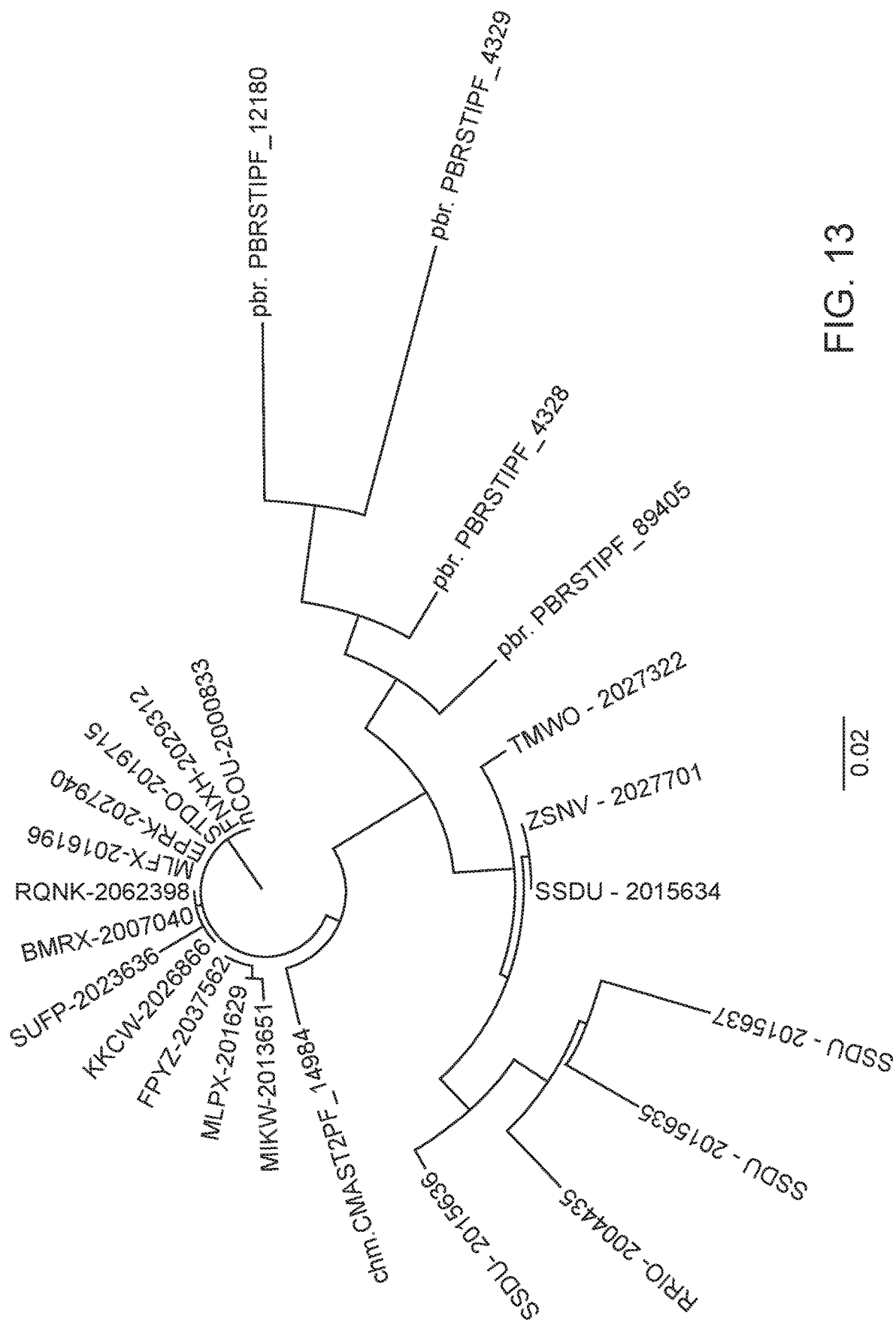
FIG. 13 illustrates a phylogenetic tree of cytochrome P450 oxidase-codeinone reductase-like (CYP-COR) fusions, in accordance with embodiments of the invention.

To identify an epimerase enzyme suitable for performing the epimerization reactions of the methods disclosed herein, a cytochrome P450 oxidase 82Y1-like domain and a codeinone reductase-like domain were identified in a single open reading frame (CYP-COR) in publically available plant transcriptomes. The CYP-COR fusions were identified from a BLAST search of the 1000 Plants Project (Matasci, et al. 2014. Gigascience. 3: 17) and PhytoMetaSyn (Facchini, et al. 2012. Trends Biotechnol. 30: 127-31; Xiao, et al. 2013. J. Biotechnol. 166: 122-34) transcriptomes using blastn with the query being the sequence of a previously published COR-silencing VIGS construct that resulted in reticuline accumulation (Wijekoon and Facchini. 2012. Plant J. 69: 1052-63). Once one CYP-COR fusion sequence was observed as a hit, that sequence was translated and the amino acid sequence was used as the query for a second search of both databases with tblastn. A phylogenetic tree of the CYP-COR fusion enzymes identified from the databases is provided in FIG. 13. The sequences were identified from The 1000 Plants Project and PhytoMetaSyn transcriptome databases based on a bioinformatic search. Additionally, an example amino acid sequence is provided in FIG. 4, as discussed above. Additionally, Table 1 lists various examples of amino acid sequences identified for this CYP-COR enzyme, which come from various plants including Papaver somniferum (opium poppy), Papaver setigerum (poppy of Troy), Papaver bracteatum (Iranian poppy), and Chelidonium majus (greater celandine).

Example 5. Epimerization of (S)-Reticuline to (R)-Reticuline in an Engineered Non Plant Host Cell Non-plant host cells were engineered to heterologously express enzymes described herein. For instance, yeast strains (Saccharomyces cerevisiae) were engineered to heterologously express the identified epimerases described in Example 4 and to verify their function in the context of this microbial host. The yeast-codon optimized DNA coding sequences for the partial amino acid sequences pbr.PBRST1PF_4328 and pbr.PBRST1PF_89405 were synthesized in-frame with the yeast-codon optimized coding sequence for amino acids 1-40 of SSDU-2015634 (Table 1) to generate CYP-COR_4328 and CYP-COR_89405, respectively. These CYP-COR coding sequences were cloned into a low-copy plasmid harboring a URA3 selection marker and expressed from the TDH3 promoter. The plasmids were transformed into yeast strains that harbored an expression cassette for a cytochrome P450 reductase (P$_{TEF1}$-ATR1 or P$_{TEF1}$-PsCPRv2) integrated into the chromosome. These yeast strains harboring the two plasmids were grown in synthetic complete media with the appropriated drop out solution (-Ura-Trp). The yeast strains were fed (S)-reticuline and BIA metabolites were analyzed after 72 hours of growth by LC-MS/MS analysis.

Figure 14A:
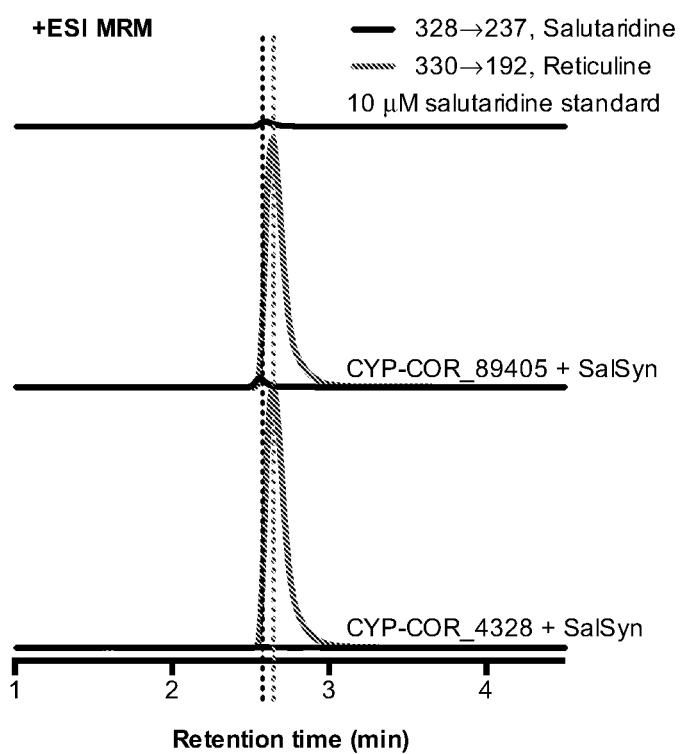
FIG. 14A illustrates chromatogram traces showing reticuline and salutaridine for two epimerase variants (CYP-COR_89405, CYP-COR_4328) and a standard.
Figure 14B:
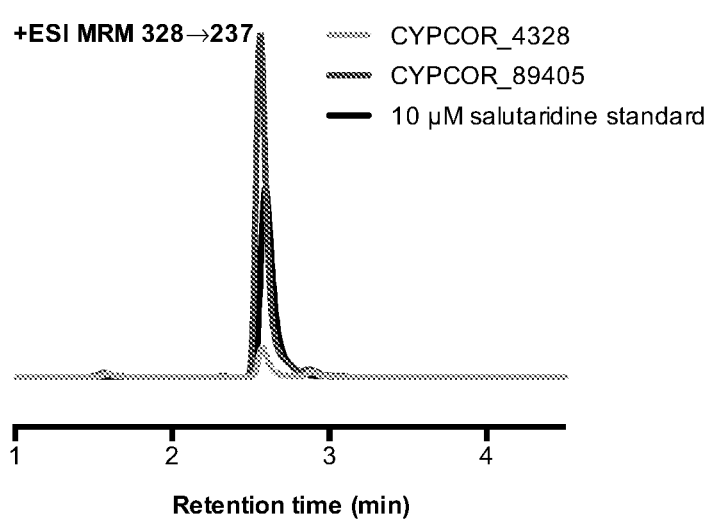
FIG. 14B illustrates the same chromatogram traces for salutaridine in (A) as replotted to demonstrate co-elution with the standard.

Example 6. Production of Salutaridine from (S)-Reticuline in an Engineered Yeast Cell Yeast strains (Saccharomyces cerevisiae) were engineered to heterologously express the identified epimerases described in Example 4 and to verify their function in the context of this microbial host. The yeast-codon optimized DNA coding sequences for the partial amino acid sequences pbr.PBRST1PF_4328 and pbr.PBRST1PF_89405 were synthesized in-frame with the yeast-codon optimized coding sequence for amino acids 1-40 of SSDU-2015634 (Table 1) to generate CYP-COR_4328 and CYP-COR_89405, respectively. These CYP-COR coding sequences were cloned into a low-copy plasmid harboring a URA3 selection marker and expressed from the TDH3 promoter. The salutaridine synthase (SalSyn) coding sequence was cloned into a low-copy plasmid harboring a TRP1 selection marker and expressed from the TDH3 promoter. The plasmids were transformed into yeast strains that harbored an expression cassette for a cytochrome P450 reductase (P$_{TEF1}$-ATR1 or P$_{TEF1}$-PsCPRv2) integrated into the chromosome. These yeast strains harboring the two plasmids were grown in synthetic complete media with the appropriated drop out solution (-Ura-Trp). The yeast strains were fed (S)-reticuline and BIA metabolites were analyzed after 72 hours of growth by LC-MS/MS analysis. The analysis indicated that the engineered yeast cells were able to convert (S)-reticuline to (R)-reticuline, which was then acted on by salutaridine synthase to form salutaridine, a 4-ring promorphinan alkaloid (FIG. 7, FIG. 14). Salutaridine synthase has been previously shown to act on (R)-reticuline and have no observable activity on (S)-reticuline (Gesell, et al. 2009. J. Biol. Chem. 284: 24432-42).

As shown in FIG. 7, CYP-COR catalyzes the conversion of (S)-reticuline to (R)-reticuline, which is then acted on by salutaridine synthase to make the promorphinan alkaloid salutaridine. FIG. 14 illustrates (A) chromatogram traces showing reticuline and salutaridine for two epimerase variants (CYP-COR_89405, CYP-COR_4328) and a standard. FIG. 14 also illustrates (B) the same chromatogram traces for salutaridine in (A) as replotted to demonstrate co-elution with the standard. In this experiment, the yeast contains two low-copy CEN/ARS plasmids with URA3 and TRP1 selective markers, TDH3 promoters, and the CYP-COR and SalSyn coding sequences. Yeast were grown from freshly transformed colonies in 3 mL selective media overnight, back-diluted into 3.5 mL media to OD 0.8, grown 7 hours, pelleted, and then resuspended into pH 7.4 HEPES buffer with 100 µM (S)-reticuline (Specs). After 16 hours on a spinner at 30° C., the yeast were pelleted and the buffer supernatant was analyzed by LC-MS/MS. Each trace is from a single sample representative of 2. Peaks are normalized such that the largest peak in all chromatograms is 100%.

Figure 15:
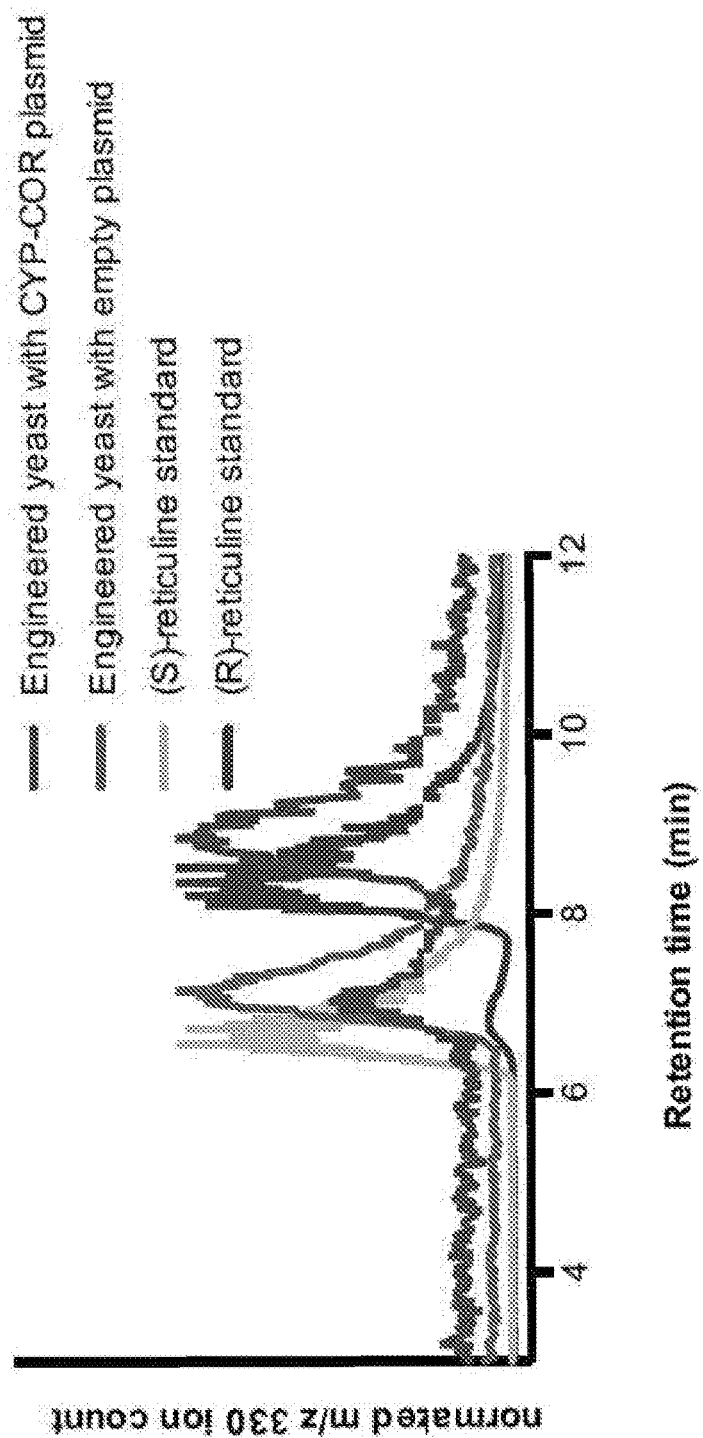
FIG. 15 illustrates a chiral LC/MS-MS analysis of yeast strains engineered to convert racemic norlaudanosoline to (R)-reticuline, in accordance with embodiments of the invention.

Example 7. Production of (R)-Reticuline from Racemic Norlaudanosoline in an Engineered Non Plant Host Cell Yeast strains (Saccharomyces cerevisiae) were engineered to heterologously express the identified epimerases described in Example 4 and to verify their function in the context of this microbial host. The yeast-codon optimized DNA coding sequence CYP-COR_89405 described in Example 5 was cloned into a low-copy plasmid harboring a URA3 selection marker and expressed from the TDH3 promoter. This plasmid was transformed into yeast strains that harbored expression cassettes for a cytochrome P450 reductase ($P_{TEF1}$-ATR1 or $P_{TEF1}$-PsCPRv2) and three methyltransferases (*Papaver somniferum* norcoclaurine-6-O-methyltransferase, coclaurine N-methyltransferase, and 3'-hydroxy-N-methylcoclaurine 4'-O-methyltransferase, all expressed from $P_{TEF1}$) integrated into the chromosome. This yeast strain harboring the plasmid was grown in synthetic complete media with the appropriated drop out solution (-Ura). The yeast strain was fed racemic norlaudanosoline and BIA metabolites were analyzed after 72 hours of growth by LC-MS/MS analysis. For chiral characterization, reticuline was concentrated from yeast media by pelleting 5 mL yeast culture and adding 120 mg XAD-4 resin to 4 mL supernatant, incubating on rotator overnight at room temperature, and eluting with 0.5 mL methanol. The concentrate was fractionated by reverse-phase HPLC (Pursuit XRs-C18, 5 μm, 50 mm×10 mm) with isocratic 15% methanol with 0.1% formic acid over 6.5 min with a flow rate of 5 mL/min and injection volume of 40-50 μL. Peak-pooled fractions were collected at approximately 4.5 min. Fractions were pooled, freeze-dried, and resuspended in 0.5 mL isopropanol. Depending on concentration, 0.5-5 μL were injected onto a chiral column (Phenomenex Lux cellulose-1, 3 μm, 150 mm×2 mm) and separated with isocratic 72% N-hexane, 28% isopropanol, 0.1% diethylamine with a flow rate of 0.3 mL/min and detection by MS and 250 nm UV. MS detection was performed with an Agilent 6320 Ion Trap mass spectrometer with ESI source gas temperature 350° C., gas flow of 10 L/min, nebulizer pressure 40 PSI and isolation of m/z 330.1 with width 1.0. The retention time of reticuline peaks was compared to that of authentic (S)-reticuline and (R)-reticuline standards. The analysis indicated that the engineered yeast cells containing the CYP-COR plasmid were able to convert racemic norlaudanosoline to (R)-reticuline, while engineered yeast cells with an empty plasmid produced exclusively (S)-reticuline (FIG. 15).

Figure 16A:
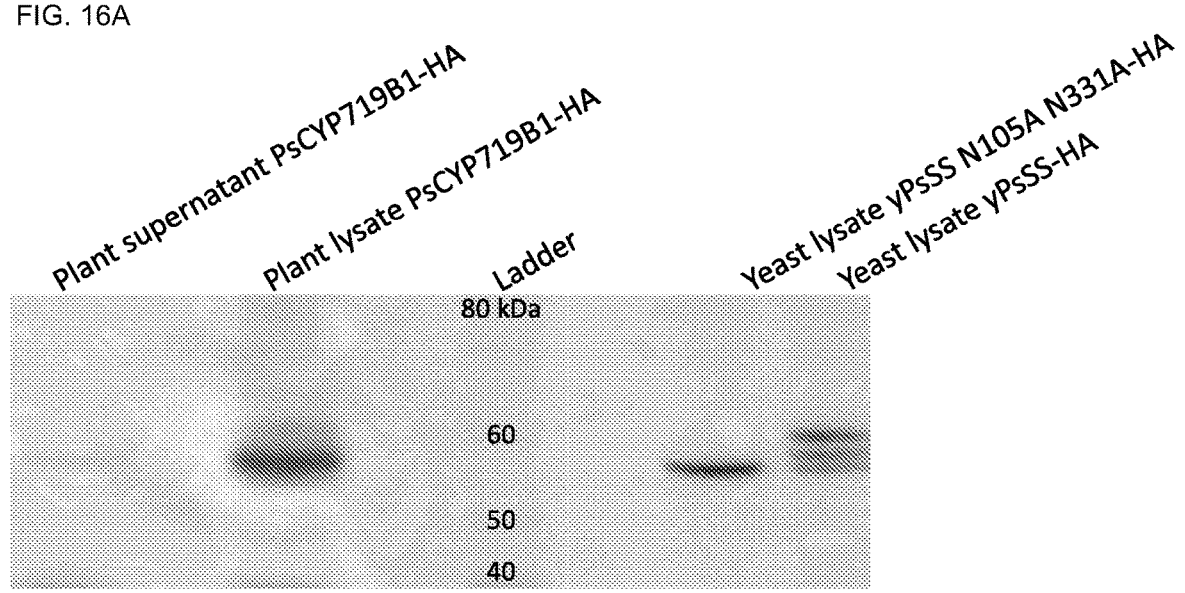
FIG. 16A illustrates N-linked glycosylation status of heterologously expressed salutarideine synthase.
Figure 16B:
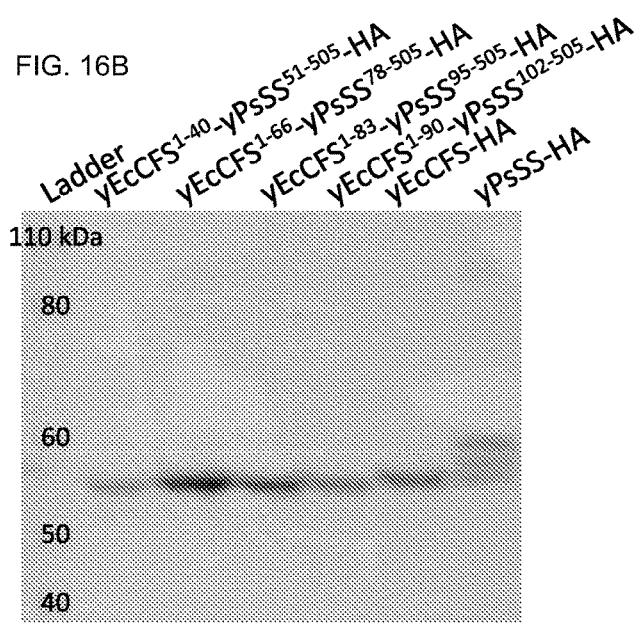
FIG. 16B illustrates engineered fusions of salutaridine synthase that eliminates N-linked glycosylation of the protein observed when heterologously expressed in yeast but not plants, in accordance with embodiments of the invention.

Example 8: Protein Engineering of Salutaridine Synthase to Improve its Processing and Activity when Expressed in a Microbial Host Heterologous proteins may be incorrectly processed when expressed in a recombinant host, for example, plant proteins such as cytochrome P450 enzymes expressed in microbial production hosts. For example, salutaridine synthase, which converts (R)-reticuline to salutaridine, undergoes N-linked glycosylation when heterologously expressed in yeast (FIG. 16A and FIG. 16B). The observed N-linked glycosylation pattern on salutaridine synthase is not observed when the enzyme is expressed in plants and is indicative of incorrect N-terminal sorting of the nascent SalSyn transcript, which reduces the activity of the enzyme in the heterologous microbial host. Thus, protein engineering directed at correcting N-terminal sorting of the nascent transcript and thereby removing the N-linked glycosylation pattern will result in improved activity of the salutaridine synthase enzyme in the recombinant production host.

Figure 17A:
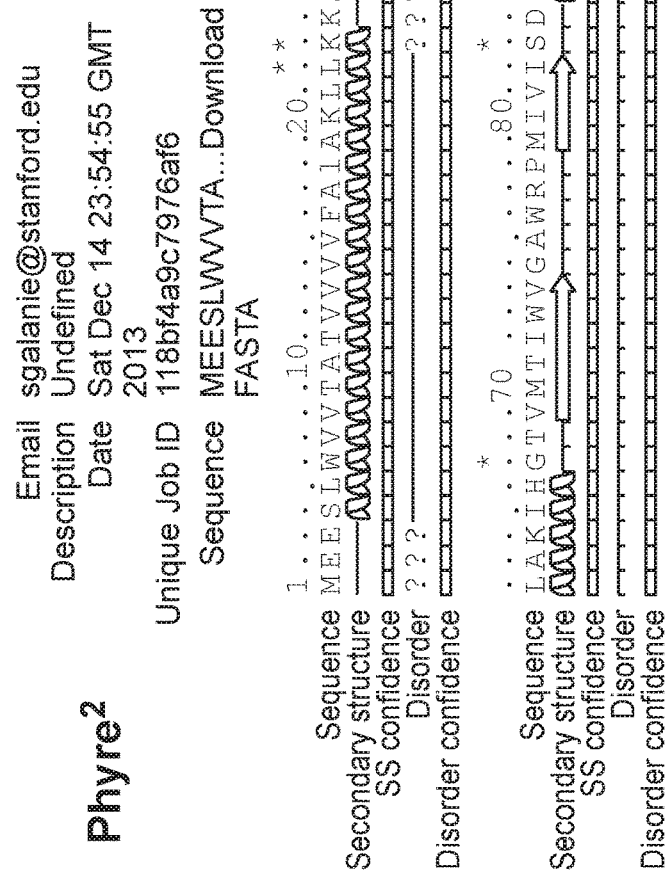
FIG. 17A and FIG. 17B illustrate cheilanthifoline synthase-salutaridine synthase fusion designs (SEQ ID NOS 117, and 115-116, respectively, in order of appearance), in accordance with embodiments of the invention.
Figure 17B:
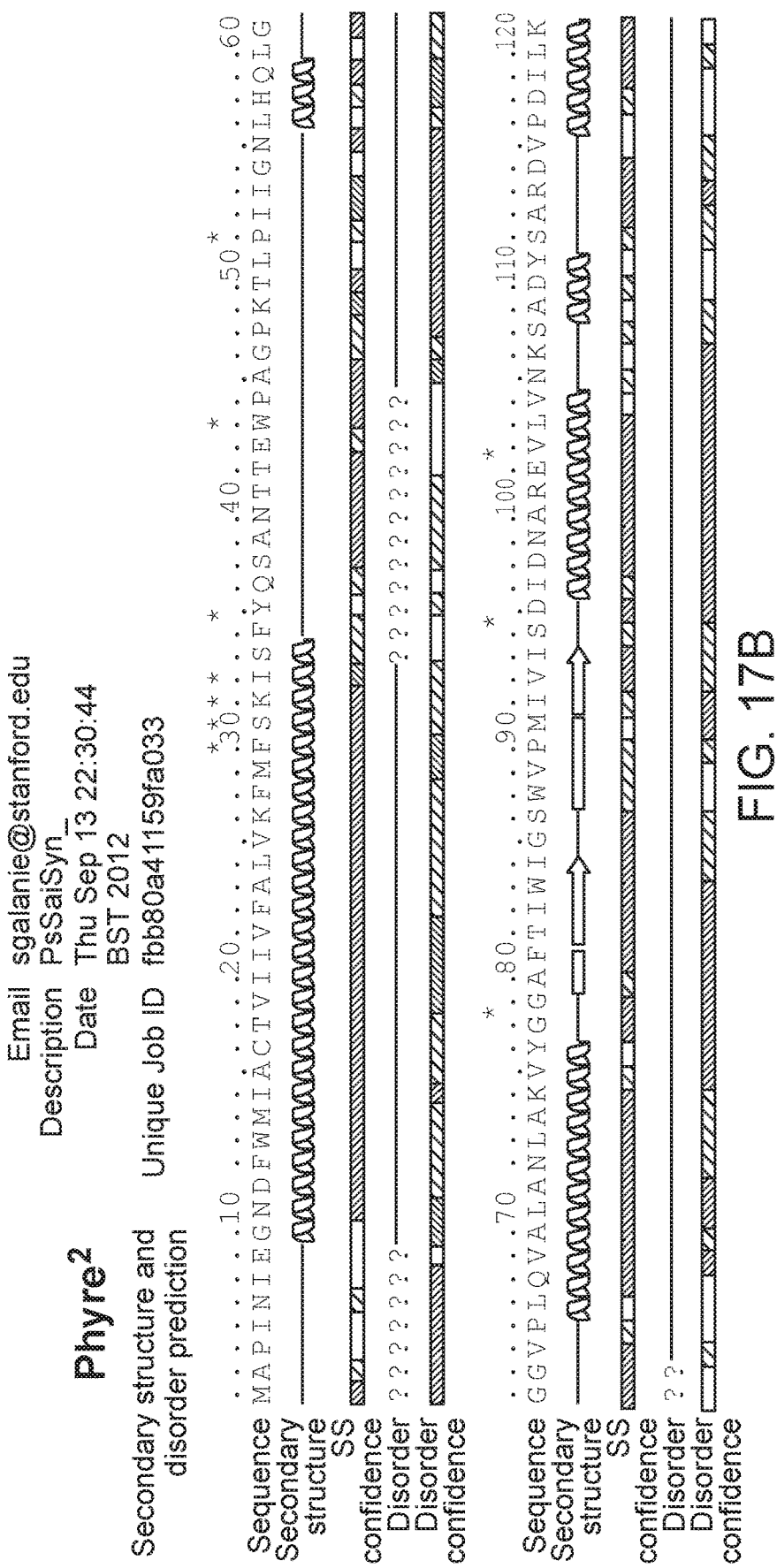

For example, N-terminal alpha-helices from cheilanthifoline synthase (CFS) were used to replace N-terminal alpha-helices from salutaridine synthase (SalSyn, FIG. 17). Junction points for these fusions were selected based on secondary structure motifs of CFS and SalSyn or based on amino acid alignments of CFS and SalSyn. The fusions were cloned by amplifying the N-terminal fragment from CFS and C-terminal fragment from SalSyn with 15-40 nucleotides of overlap with the other fragment, and then assembled with each other and a vector backbone by Gibson assembly to form the complete fusion open reading frame (Gibson, et al. 2009. Nat Methods. 6: 343-5).

As another example, the coding sequence for the cytochrome P450 domain from salutaridine synthase was placed directly into the P450 encoding region of other stably expressed cytochrome P450s such as the BM3 enzyme. For example, the conserved cytochrome P450 domain of the salutaridine synthase and the cytochrome P450 domain from an engineered variant of the *Bacillus megaterium* P450 monooxygenase CYP102A1 (BM3, (Michener and Smolke. 2012. Metab. Eng. 14: 306-16)) were identified by NCBI conserved domain search. Primers were designed to fuse the coding sequence of the first few amino acids of the BM3 to the coding sequence for the P450 domain of the salutaridine synthase, followed by the coding sequence for BM3 domains C-terminal to the P450 domain. As before, this construct was assembled via Gibson assembly.

The engineered salutaridine synthase protein fusions were analyzed by Western Blot analysis to confirm full-length expression and modification to or elimination of N-linked glycosylation patterns in yeast (FIG. 16A and FIG. 16B). The salutaridine synthase enzyme and protein fusions were C-terminally tagged with the human influenza hemagglutinin (HA) epitope and cloned into expression plasmids appropriate for yeast and plant expression. For yeast, the enzyme coding sequences were cloned into a low-copy yeast/*E. coli* shuttle vector harboring a URA3 selection marker and expressed from the TDH3 promoter. For plants, the sequences were cloned into an *E. coli/Agrobacterium tumefaciens* shuttle vector with kanamycin resistance and the Cauliflower mosaic virus (CaMV) 35S promoter with flanking 5' and 3'-untranslated regions from Cowpea mosaic virus RNA-2 for transient plant expression via *Agrobacterium tumefaciens*-infiltration. Yeast engineered to express salutaridine synthase exhibited a banding pattern indicative of N-linked glycosylation. We confirmed that this pattern was due to N-linked glycosylation by performing site-directed mutagenesis on the glycosylation site. In contrast, plant expression of this enzyme did not result in a banding pattern indicative of N-linked glycosylation, as seen in FIG. 16A. Although the N-linked glycosylation sites were unmodified, the engineered salutaridine synthase protein fusions were not N-glycosylated when expressed in yeast, as seen in FIG. 16B. By Western blot, we demonstrated that the yeast-expressed fusion enzymes were present as a single band, similar to the expression observed for the plant-expressed parent enzyme, indicating that the mis-processing of the nascent protein in yeast that resulted in N-linked glycosylation was repaired by the engineered fusions.

The engineered salutaridine synthase protein fusions were analyzed for improved enzyme activity when heterologously expressed in yeast. Coding sequences for salutaradine synthase and the engineered fusions were cloned into a low-copy plasmid harboring a URA3 selection marker and expressed from the TDH3 promoter. The yeast have $P_{TEF1}$-PsCPRv2 integrated into the TRP1 locus and contain a single low-copy plasmid with the URA3 selective marker and the salutaridine synthase coding sequence with the TDH3 promoter. Yeast were grown from freshly transformed colonies in 1 mL selective media (-Ura) overnight and back-diluted 1:20 into 0.5 mL selective media in 96-well plates with 10 αM (R)-reticuline (Toronto Research Chemicals). After 72-96 hours in the shaking incubator, the yeast were pelleted and the media supernatant was analyzed by LC-MS/MS. The analysis indicated that the engineered salutaradine synthase enzymes exhibited improved activity relative to that of the wild-type sequence when heterologously expressed in yeast (FIG. 18).

Figure 18:
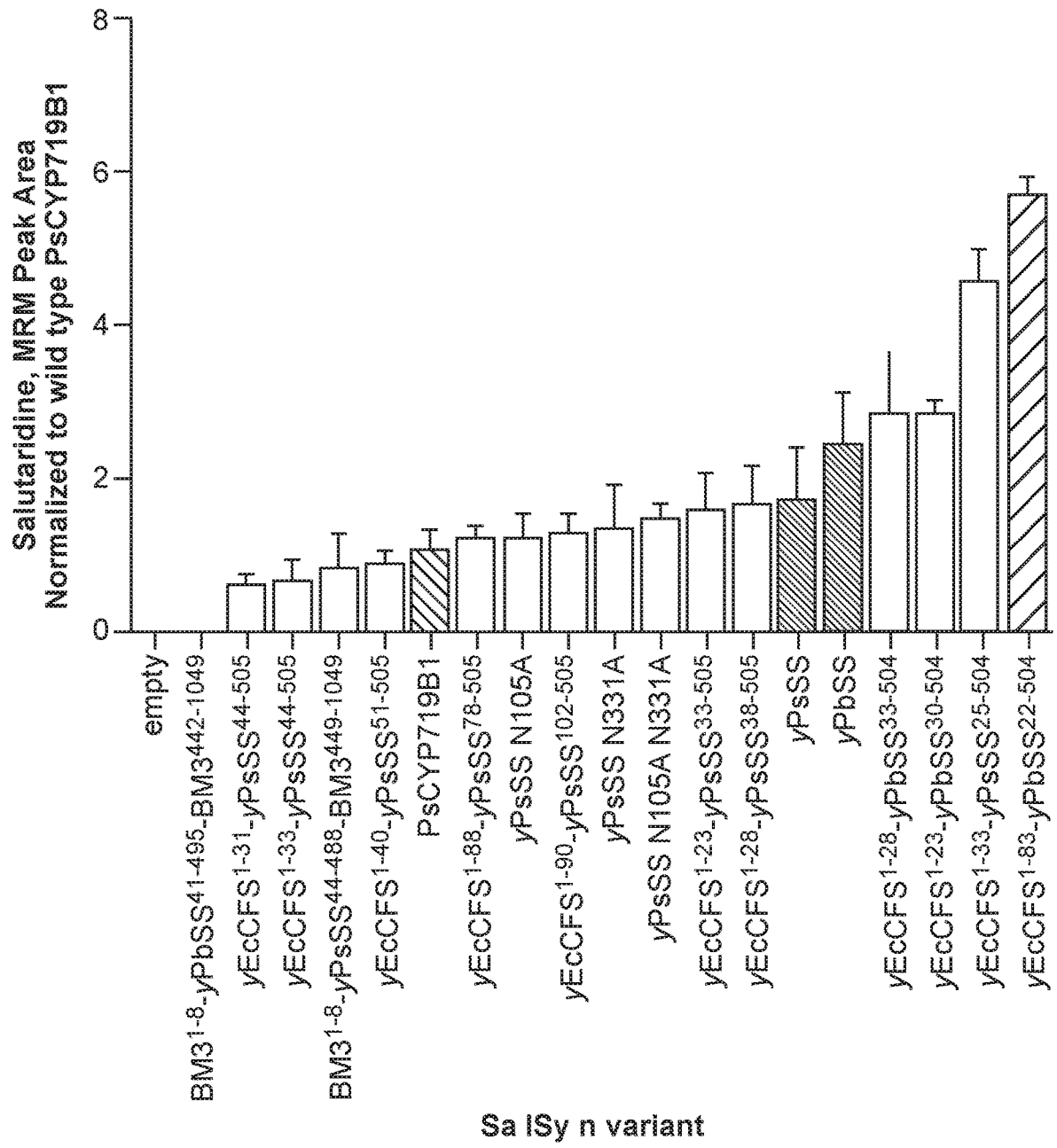
FIG. 18 illustrates salutaridine synthase codon-optimization and engineered fusions that improve activity in yeast, in accordance with embodiments of the invention.

FIG. 18 illustrates salutaridine synthase codon-optimization and engineered fusions that improve activity in yeast, in accordance with embodiments of the invention. As seen in FIG. 18, a black bar indicates a native wild-type sequence for salutaridine synthase, PsCYP719B1. Grey bars with black borders are yeast codon-optimized variants from *Papaver somniferum* and a newly identified sequence from *Papaver bracteatum*. The diagonally patterned bar indicates the most improved engineered fusion, which is based on the *P. bracteatum* sequence. Error bars indicate the range of at least two biological replicates. Natural, synthetic codon-optimized, and/or protein engineered variants of salutaridine synthase from *P. bracteatum*, *P. somniferum*, or *P. setigerum* (or related plant) may be used in these engineered strains.

The engineered salutaridine synthase protein fusions can be used in the context of a biosynthetic pathway to increase production of downstream benzylisoquinoline alkaloid products. In one example, yeast were engineered to heterologously express yeast codon optimized genes encoding an engineered salutaridine synthase fusion, *P. bracteatum* salutaridine reductase, and *P. somniferum* salutaridinol 7-O-acetyltransferase. The three expression cassettes ($P_{TDH3}$-31994yPsSS, $P_{TP11}$-yPbSalR, $P_{TEF1}$-yPsSalAT) were assembled into a yeast artificial chromosome (YAC) with a TRP1 section marker. The YAC was placed into yeast that harbored an expression cassette for a cytochrome P450 reductase ($P_{TEF1}$-ATR1 or $P_{TEF1}$-yPsCPRv2) integrated into the chromosome. The yeast strains were grown in synthetic complete media with the appropriated drop out solution (-Trp) and fed (R)-reticuline. BIA metabolites were analyzed after 96 hours of growth through LC-MS/MS analysis. The analysis indicates that yeast strains engineered with the engineered salutaridine synthase enzymes and other pathway enzymes produce the morphinan alkaloid thebaine, as illustrated in (A) of FIG. 19.

Figures 19A, 19B:
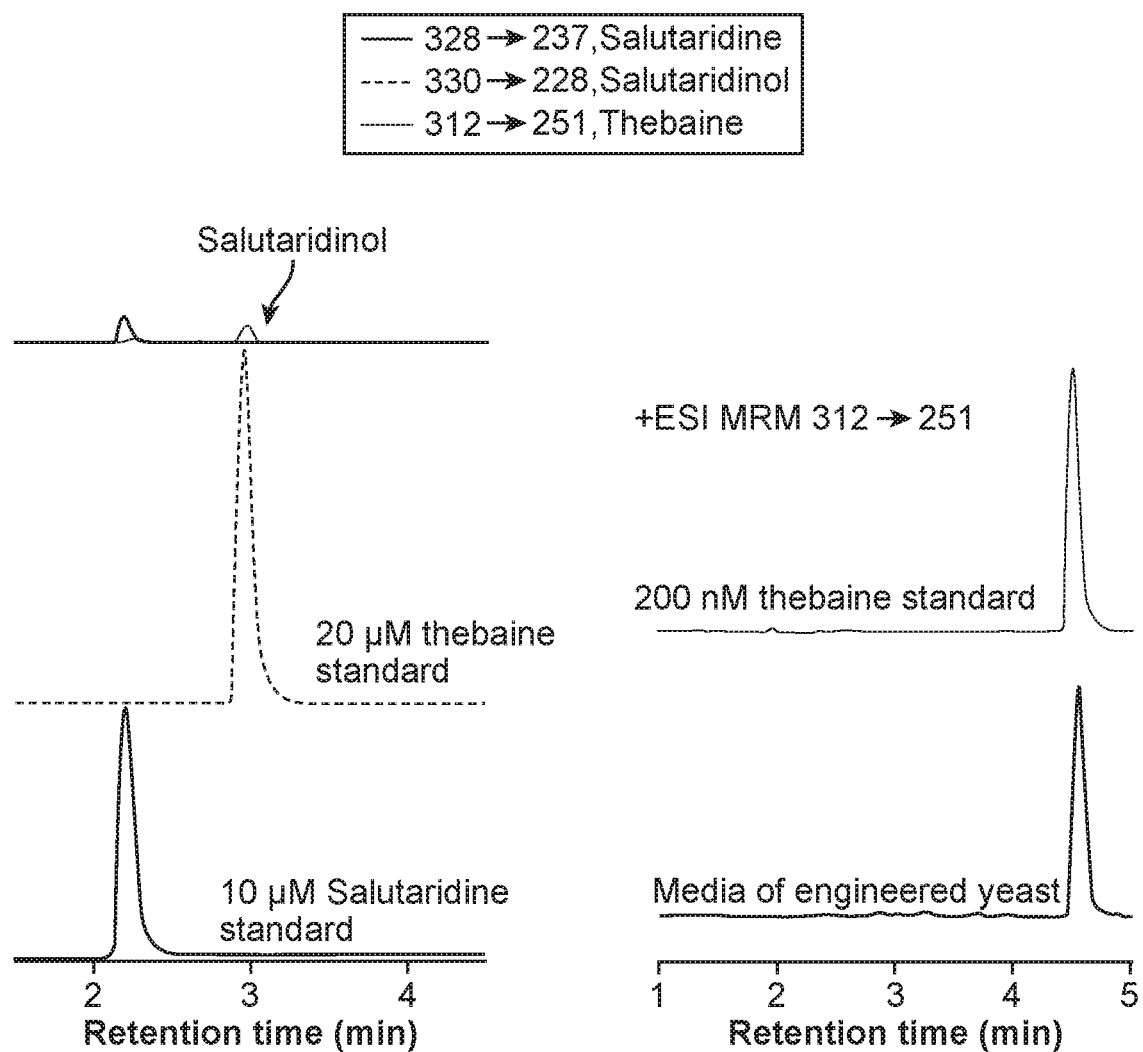
FIG. 19A and FIG. 19B illustrate LC/MS-MS analyses of small scale batch fermentation in which engineered yeast catalyze the conversion of (R)-reticuline to thebaine and the conversion of rac-norlaudanosoline to thebaine, in accordance with embodiments of the invention.

Accordingly, FIG. 19 illustrates (A) an LC/MS-MS analysis of small scale batch fermentation in which engineered yeast catalyze the conversion of (R)-reticuline to thebaine, in accordance with embodiments of the invention. As provided in (A) of FIG. 19, yeast strains are engineered to have a $P_{TEF1}$-ATR1 expression cassette integrated into the TRP1 locus and contain a single yeast artificial chromosome with the TRP1 selective marker and three expression cassettes: $P_{TDH3}$-yEcCFS$^{1-83}$-yPsSS$^{95-505}$, $P_{TP11}$-yPbSalR, and $P_{TEF1}$-yPsSalAT. Yeast were grown from freshly transformed colonies in 3 mL selective media overnight and back-diluted 1:20 into 0.5 mL selective media (-Trp) in culture tubes with 100 µM (R)-reticuline (Toronto Research Chemicals). After 72 hours in the shaking incubator, the yeast were pelleted and the media supernatant was analyzed by LC-MS/MS. Chromatogram traces show thebaine produced by this strain and salutaridinol and salutaridine accumulated, along with standards. These traces are representative of two samples.

Example 9: Protein Engineering of Enzymes in the Downstream Morphinan Branch to Improve Production of Morphinan Products from a Heterologous Microbial Host In one embodiment of the invention, pathway enzymes are engineered to exhibit increased activity to increase production of the BIA of interest. In this example, mutations were introduced into the open reading frame of a particular pathway enzyme by amplification with Mutazyme II (see Table 11). Sufficient template DNA was included in the amplification reaction to result in a mutation rate of 1-4 nucleotide substitutions per gene. The mutagenized library was cloned into the pYES1L vector by gap repair directly in yeast. In several instances, yeast strains selected for library expression contained integrated copies of genes that generate the substrate of the mutagenized enzyme. For example, a library of CODM variants was transformed into a strain with integrated copies of T6ODM and COR1.3 and fed thebaine in the culture medium. Expression of T6ODM and COR1.3 in these strains ensured that codeine and neopine would be available as substrates for each introduced CODM variant. Individual colonies were inoculated into 96-well plates and cultured 96 hours then assayed for production of their product by liquid chromatograph mass spectrometry (LC-MS). In the example of the CODM library, the products screened for were morphine and neomorphine. In each screen, variants with enhanced BIA production were sequenced and re-cloned for validation. Table 11 includes a summary of mutated enzyme variants identified through the screens that resulted in increased BIA production in yeast.

Figure 20:
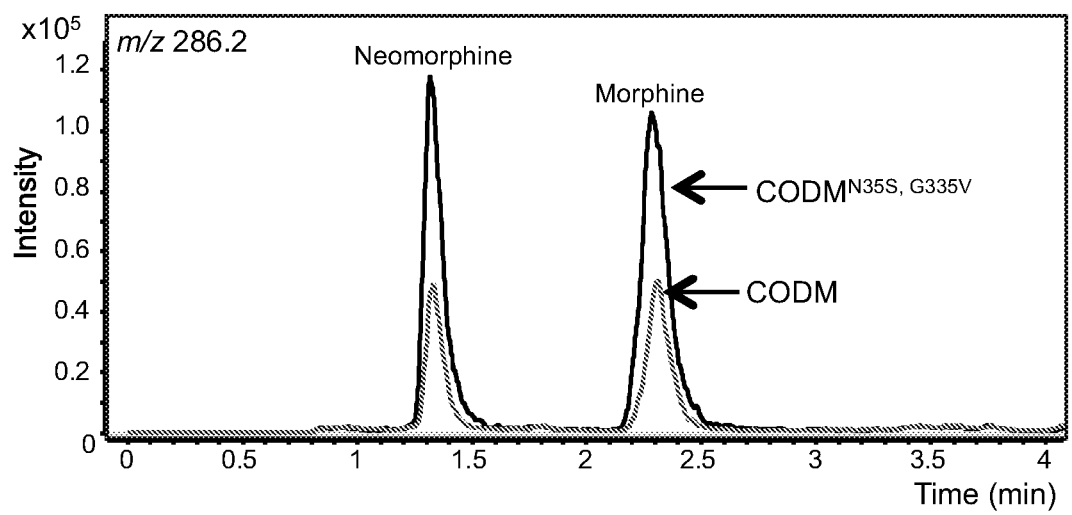
FIG. 20 illustrates generation of a CODM enzyme variant exhibiting enhanced activity in yeast through random mutagenesis and screening, in accordance embodiments of the invention.

FIG. 20 shows data of the validated enhanced activity of one of these mutants. In particular, FIG. 20 illustrates generation of a CODM enzyme variant exhibiting enhanced activity in yeast through random mutagenesis and screening, in accordance with embodiments of the invention. A library of CODM variants was generated by mutagenizing the coding region by error-prone PCR. A variant identified by screening of this library, CODM$^{N35S,G335V}$, was re-cloned and expressed in a yeast strain harboring integrated copies of T6ODM and COR1.3. This strain and another control strain expressing wild-type CODM were cultured in liquid medium with 1 mM thebaine. After 96 hours the culture medium was analyzed for CODM activity by LC-MS. Variant CODM$^{N35S,G335V}$ produced 1.4× more morphine and 2.6× more neomorphine than a strain expressing wild-type CODM.

Example 10: Optimization of Expression and Growth Conditions to Improve Benzylisoquinoline Alkaloid Production from a Heterologous Microbial Host Bezylisoquinoline alkaloid production from an engineered microbial host can be further improved by optimizing the expression of pathway enzymes and growth conditions. In one example, the expression of salutaridinol 7-O-acetyltransferase was altered in yeast by expressing the enzyme from a series of different promoters. The yeast were engineered to heterologously express yeast codon-optimized genes encoding *P. somniferum* salutaridinol 7-O-acetyltransferase from different promoters (as provided in FIG. 21A). Two expression cassettes ($P_{TP11}$-yPbSalR,$P_X$-yPsSalAT) were assembled into a yeast artificial chromosome (YAC) with a TRP1 section marker. The YAC was placed into yeast and cells were grown in synthetic complete media with the appropriated drop out solution (-Trp) and fed salutaridine. BIA metabolites were analyzed after 72 hours of growth by LC-MS/MS analysis. The optimization of pathway enzyme expression level can result in increased production of the morphinan alkaloid thebaine (as provided in FIG. 21A).

Figure 21A:
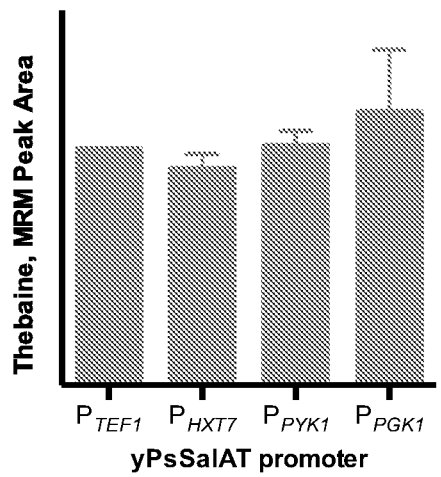
FIG. 21A, FIG. 21B, and FIG. 21C illustrate fermentation optimization for conversion of (R)-reticuline to thebaine by engineered yeast, in accordance with embodiments of the invention.
Figure 21B:
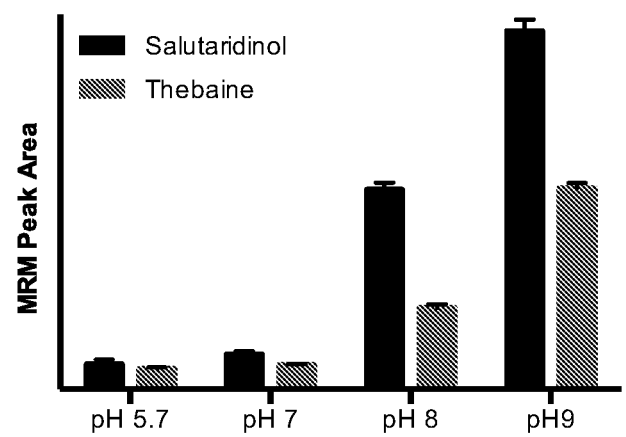
Figure 21C:
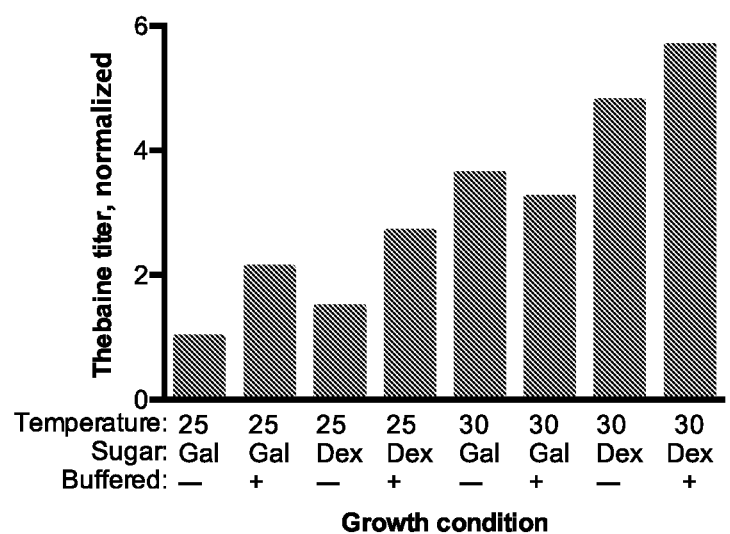

Optimization of strain cultivation conditions, including but not limited to sugar source, growth temperature, and pH, can be used to increase production of benzylisoquinoline alkaloids from engineered yeast strains (as provided in FIG. 21B and FIG. 21C). In one example, pH was varied to increase thebaine production from engineered yeast strains. Two expression cassettes ($P_{TP11}$-yPbSalR, $P_{TEF1}$-yPsSalAT) were assembled into a yeast artificial chromosome (YAC) with a TRP1 section marker. The YAC was placed into yeast and cells were grown in synthetic complete media with the appropriated drop out solution (-Trp), resuspended in buffer at pH 5.7-9, and fed salutaridine. BIA metabolites were analyzed after 16 hours of incubation by LC-MS/MS analysis. Levels of the 4-ring promorphinan alkaloid salutaridinol and the 5-ring morphinan alkaloid thebaine increased as a function of increasing pH (as provided in (B) of FIG. 21).

In another example, temperature, sugar, and media buffer content were varied to increase thebaine production from engineered yeast strains. Three expression cassettes ($P_{TDH3}$-D94yPsSS,$P_{TP11}$-yPbSalR,$P_{TEF1}$-yPsSalAT) were assembled into a yeast artificial chromosome (YAC) with a TRP1 section marker. The YAC was placed into yeast that harbored an expression cassette for a cytochrome P450 reductase ($P_{TEF1}$-ATR1 or $P_{TEF1}$-yPsCPRv2) integrated into the chromosome. The yeast strains were grown in synthetic complete media with the appropriated drop out solution (-Trp) and fed (R)-reticuline. BIA metabolites were analyzed after 72 hours of growth by LC-MS/MS analysis. The analysis indicates the microbial production of the morphinan alkaloid thebaine increases under certain cultivation conditions (buffered media with dextrose at 30° C., as provided in FIG. 21C).

Accordingly, FIG. 21A, FIG. 21B, and FIG. 21C illustrate fermentation optimization for conversion of (R)-reticuline to thebaine by engineered yeast, in accordance with embodiments of the invention. LC/MS-MS analysis of whole cell buffered assay of (A) SalAT promoter variants, (B) SalR and SalAT strain grown under different pH conditions, and (C) optimization of sugar source, growth temperature, and media buffer content. (A) Yeast strains engineered to contain a single yeast artificial chromosome with the TRP1 selective marker and two expression cassettes: $P_{TP11}$-yPbSalR and $P_X$-yPsSalAT with varied SalAT promoters. Yeast were grown from freshly transformed colonies in 3 mL selective media overnight and back-diluted 1:20 into 0.5 mL media in culture tubes with 100 µM salutaridine (Specs). After 72 hours in the shaking incubator, the yeast were pelleted and the media supernatant was analyzed by LC-MS/MS. (B) Yeast strains engineered to contain a single yeast artificial chromosome with the TRP1 selective marker and two expression cassettes: $P_{TP11}$-yPbSalR and $P_{TEF1}$-yPsSalAT. Yeast were grown from freshly transformed colonies in 3 mL selective media overnight, back-diluted into 3.5 mL media to OD 0.8, grown 7 hours, pelleted, and then resuspended into pH 5.7 MOPS, or pH 7, 8, or 9 Tris buffer with 10 µM salutaridine (Specs). After 16 hours on a spinner at 30° C., the yeast were pelleted and the buffer supernatant was analyzed by LC-MS/MS. Error bars represent the range of two samples. (C) Optimization of sugar source, growth temperature, and media buffer content. In this experiment, the yeast strains are engineered to have $P_{TEF1}$-ATR1 integrated into the TRP1 locus and contain a single yeast artificial chromosome with the TRP1 selective marker and three expression cassettes: $P_{TDH3}$-YEcCFS$^{1-83}$-yPsSS$^{95-505}$, $P_{TP11}$-yPbSalR, and $P_{TEF1}$-yPsSalAT. Yeast were grown from freshly transformed colonies in 3 mL selective media overnight and back-diluted 1:20 into 0.5 mL media in culture tubes with 100 µM (R)-reticuline (Toronto Research Chemicals). After 72 hours in the shaking incubator, the yeast were pelleted and the media supernatant was analyzed by LC-MS/MS.

Example 11: Yeast Engineered for the Production of Thebaine from an Early 1-Benzylisoquinoline Alkaloid Scaffold Yeast strains can be engineered for the production of the morphinan alkaloid thebaine, or morphinan alkaloids derived from thebaine, from early 1-benzylisoquinoline alkaloids. As an example, the engineered yeast strains can produce the morphinan alkaloid products from racemic or (S)-norcoclaurine or racemic or (S)-norlaudanosoline (FIGS. 5, 6, and 7, and (B) of 23). Yeast strains are engineered to produce (S)-reticuline from (S)-norcoclaurine or racemic or (S)-norlaudanosoline by the integration of three or five expression cassettes into the yeast genome. To produce (S)-reticuline from racemic or (S)-norlaudanosoline, the integrated expression cassettes encode *Papaver somniferum* norcoclaurine 6-O-methyltransferase (Ps6OMT, EC 2.1.1.128), 4'-O-methyltransferase (Ps4'OMT, EC 2.1.1.116), and coclaurine-N-methyltransferase (CNMT, EC 2.1.1.140), each with a TEF1 promoter (Hawkins and Smolke. 2008. Nat. Chem. Biol. 4: 564-73). To produce (S)-reticuline from racemic or (S)-norcoclaurine, the strain further harbors integrated expression cassettes for yeast codon-optimized *Eschscholzia californica* N-methylcoclaurine 3'-hydroxylase (yEcCYP80B1, EC 1.14.13.71) and ATR1 or yPsCPRv2 cytochrome P450 reductase expressed from the TDH3 or TEF1 promoter (CPR, EC 1.6.2.4). These strains are further engineered to incorporate epimerization-catalyzing enzymes (e.g., CYP-COR), salutaridine synthase, salutaridine reductase, and salutaridinol acetyltransferase to convert racemic or (S)-norcoclaurine or racemic or (S)-norlaudanosoline to the morphinan alkaloid thebaine, or morphinan alkaloids derived from thebaine (FIG. 7). As an alternative to expression of an epimerization-catalyzing enzyme, 6OMT, 4'OMT, CNMT, and/or CYP80B1 may be engineered such that rac-reticuline is produced from rac-norcoclaurine or rac-norlaudanosoline.

In one example, a yeast strain was engineered to convert rac-norlaudanosoline to thebaine. The yeast strain harbors integrated expression cassettes encoding Ps6OMT, Ps4'OMT, CNMT, and yPsCPRv2, each with a TEF1 promoter. Four expression cassettes ($P_{TDH3}$-yEcCFS$^{1-83}$-yPsSS$^{95-505}$, $P_{TP11}$-yPbSalR,$P_{TEF1}$-yPsSalAT, $P_{HXT7}$-CYP-COR_89405) were assembled into a yeast artificial chromosome (YAC) with a TRP1 selective marker in this strain. The yeast strain harboring the YAC and integrated cassettes was grown in synthetic complete media with the appropriated drop out solution (-Trp) and 1 mM rac-norlaudanosoline substrate. After 96 hours of growth, the media was analyzed for BIA metabolites by LC-MS/MS analysis. Nearly 200 nM thebaine was detected ((B) of FIG. 19). Other engineered salutaridine synthase variants may also be used in this strain (FIG. 18, Example 8).

Example 12: Platform Yeast Strains Engineered for the Production of Reticuline from L-Tyrosine A platform yeast strain that produces the key branch point BIA intermediate (S)-reticuline from L-tyrosine was constructed (FIG. 5). Specifically, four multi-gene expression constructs were integrated into the genome of a yeast strain. The composition of the four constructs is indicated in FIG. 22. Each construct is comprised of 4 or 5 genes expressed from strong constitutive promoters. Genes are positioned at each locus as complete expression cassettes comprising a promoter, gene open reading frame, and terminator as specified in the annotations above the schematic. The schematic shows the orientation of each expression cassette by the direction of the arrow representing a given gene. Selectable markers are italicized in the annotation and represented by grey arrows in the schematic. Each selection marker is flanked by loxP sites to allow removal of the marker from the locus. Additionally, each construct has a selectable marker flanked by loxP sites so that it can be removed by Cre recombinase.

In the first integration construct, four heterologous genes from *Rattus norvegicus* are integrated into the YBR197C locus together with a G418 selection marker (KanMX). RnPTPS, RnSepR, RnPCD, and RnQDHPR are required to synthesize and regenerate tetrahydrobiopterin ($BH_4$) from the yeast endogenous folate synthesis pathway. Each gene is codon optimized for expression in yeast.

In the second integration construct, four heterologous genes are integrated into the HIS3 locus together with the HISS selection marker. *Rattus norvegicus* tyrosine hydroxylase (RnTyrH) converts tyrosine to L-DOPA using the cosubstrate $BH_4$ generated by the preceding integration construct. The RnTyrH gene can be any of the wild-type or improved mutants which confer enhanced activity (e.g., W166Y, R37E, and R38E, Example 1). A second *Rattus norvegicus* gene, RnDHFR, encodes an enzyme that reduces dihydrobiopterin (an oxidation product of $BH_4$) to $BH_4$, in this way increasing the availability of this cosubstrate. Also included in the third construct is PpDODC from *Pseudomonas putida*, an enzyme that converts L-DOPA to dopamine. The fourth enzyme is CjNCS from *Coptis japonica*, which condenses 4-HPA and dopamine to make norcoclaurine. Each gene is codon optimized for expression in yeast.

In the third integration construct, five heterologous genes from plants and the LEU2 selection marker are integrated into the locus YDR514C. Ps6OMT, Ps4'OMT, and PsCNMT are methyltransferases from *Papaver somniferum* and are expressed as native plant nucleotide sequences. A fourth *P. somniferum* gene, yPsCPRv2, is codon optimized for yeast and encodes a reductase that supports the activity of a cytochrome P450 from *Eschscholzia californica*, EcCYP80A1. EcCYP80A1 is expressed as its native plant nucleotide sequence. The enzymes encoded in this construct perform two O-methylations, an N-methylation, and a hydroxylation to produce reticuline from the norcoclaurine produced by the preceding integration construct.

In the final integration construct, additional copies of *Saccharomyces cerevisiae* endogenous genes $ARO4^{Q166K}$, $ARO7^{T226I}$, TKL1, and ARO10 are integrated into the ARO4 locus together with a hygromycin resistance selection marker. $ARO4^{Q166K}$ and $ARO7^{T226I}$ are feedback-resistant mutants of ARO4 and ARO10 which each encode a single base pair substitution relative to the wild-type sequence. TKL1 and ARO10 are identical to the native yeast genes, but are expressed behind strong promoters. Aro4p and Aro7p are enzymes in the biosynthesis of aromatic amino acids including tyrosine. Removing feedback inhibition from these enzymes results in upregulation of endogenous tyrosine biosynthesis. Overexpression of Tkl1p upregulates the pentose phosphate pathway resulting in enhanced supply of erythrose 4-phosphate (E4P), a precursor for tyrosine. Overexpression of Aro10p increases the production of 4-HPA.

Platform yeast strains can be constructed with any number of the four expression cassettes. Specifically, platform yeast strains were constructed with integration constructs 1-4 and integration constructs 1-3. In the latter strain in which the tyrosine over-production construct (construct 4) is excluded, additional tyrosine may be supplied in the culture medium to support the biosynthesis of reticuline. Additional genetic modifications may be incorporated into the platform strains to support production of downstream BIAs and increased flux to BIA biosynthesis.

The yeast strains were grown in synthetic complete media with the appropriated amino acid drop out solution at 25 and 30° C. BIA metabolites in the media supernatant were analyzed after 48 and 96 hours of growth by LC-MS/MS analysis.

Example 13: Yeast Engineered for the Production of Thebaine and Other Morphinan Alkaloids from L-Tyrosine Yeast strains can be engineered for the production of the morphinan alkaloid thebaine, or morphinan alkaloids derived from thebaine, from early precursors such as tyrosine. As an example, the platform yeast strains described in Example 12 can be further engineered to produce the morphinan alkaloid products from L-tyrosine (FIG. 7).

The platform yeast strain producing (S)-reticuline from L-tyrosine (see description in Example 12) was further engineered to incorporate epimerization-catalyzing enzymes, such as the newly identified CYP-COR, salutaridine synthase, salutaridine reductase, and salutaridinol acetyltransferase to convert the biosynthesized (S)-reticuline to the morphinan alkaloid thebaine, or morphinan alkaloids derived from thebaine (FIG. 7). Three expression cassettes ($P_{TDH3}$-yEcCFS$^{1-26}$-yPbSS$^{33-504}$, $P_{TP11}$-yPbSalR, $P_{TEF1}$-yPsSalAT) were assembled into a yeast artificial chromosome (YAC) with a TRP1 selective marker directly in the platform yeast strain. Other engineered salutaridine synthase variants may also be incorporated into the YAC (FIG. 18, Example 8). The resulting yeast strain was also transformed with a low-copy CEN/ARS plasmid with a URA3 selective marker, TDH3 promoter, and a CYP-COR coding sequence.

The yeast strains harboring the YAC, low-copy plasmid, and integrated cassettes were grown in synthetic complete media with the appropriated drop out solution (-Ura-Trp) at 25 and 30° C. After 96 hours of growth, the media was analyzed for BIA metabolites by LC-MS/MS analysis. Further culture optimization with respect to temperature, carbon source, pH condition, and media composition was performed to improve BIA production.

Additional genetic modifications can be introduced into the yeast strains to produce morphinan alkaloids derived from thebaine (FIG. 7). In one example, the expression cassettes $P_{ADH1}$-T6ODM-$T_{ADH1}$, $P_{HXT7}$-COR-$T_{PGK1}$, and $P_{TEF1}$-CODM-$T_{CYC1}$ were directly assembled and integrated into the trp1 locus of the thebaine-producing yeast strain (Thodey et al., 2014). In another example, these yeast strains can be further engineered to produce additional morphine alkaloids by directly assembling the expression cassettes $P_{GPD}$-morA-$T_{CYC1}$, $P_{PGK1}$-morB-$T_{PHO5}$ and integrating this construct into the ura3 locus on the chromosome (Thodey et al., 2014).

Example 14: O-Demethylation of Opioid Molecules

For high throughput screening of demethylation reactions a purpald assay was used. For example, demethylation catalyzed by 2-oxoglutarate dependent dioxygenases produces formaldehyde as a product as shown in the generalized chemical equation: [substrate]+2-oxoglutarate+O2

[product]+formaldehyde+succinate+CO2. Purpald reagent in alkaline conditions undergoes a color change in the presence of formaldehyde that can be quantified to concentrations as low as 1 nM with a spectrophotometer at 510 nm.

An important step in the production of nor-opioid compounds is the O-demethylation of molecules such as oxycodone (see FIG. 23). To identify enzymes capable of performing this step, sequences from Table 3 were subjected to codon optimization for expression in S. cerevisiae, and ordered as synthetic genes (from Integrated DNA Technologies). Codon optimized sequences were cloned into expression vectors pA24, pA25, or pA26 (or similar vectors), shown in FIG. 28, which harbor promoter sequences of varying strength, by gap repair in the Cen.PK2 yeast host strain, according to standard molecular biology procedures. Individual colonies were isolated and verified by PCR and sequencing (ELIM biopharmaceuticals).

Figure 28:
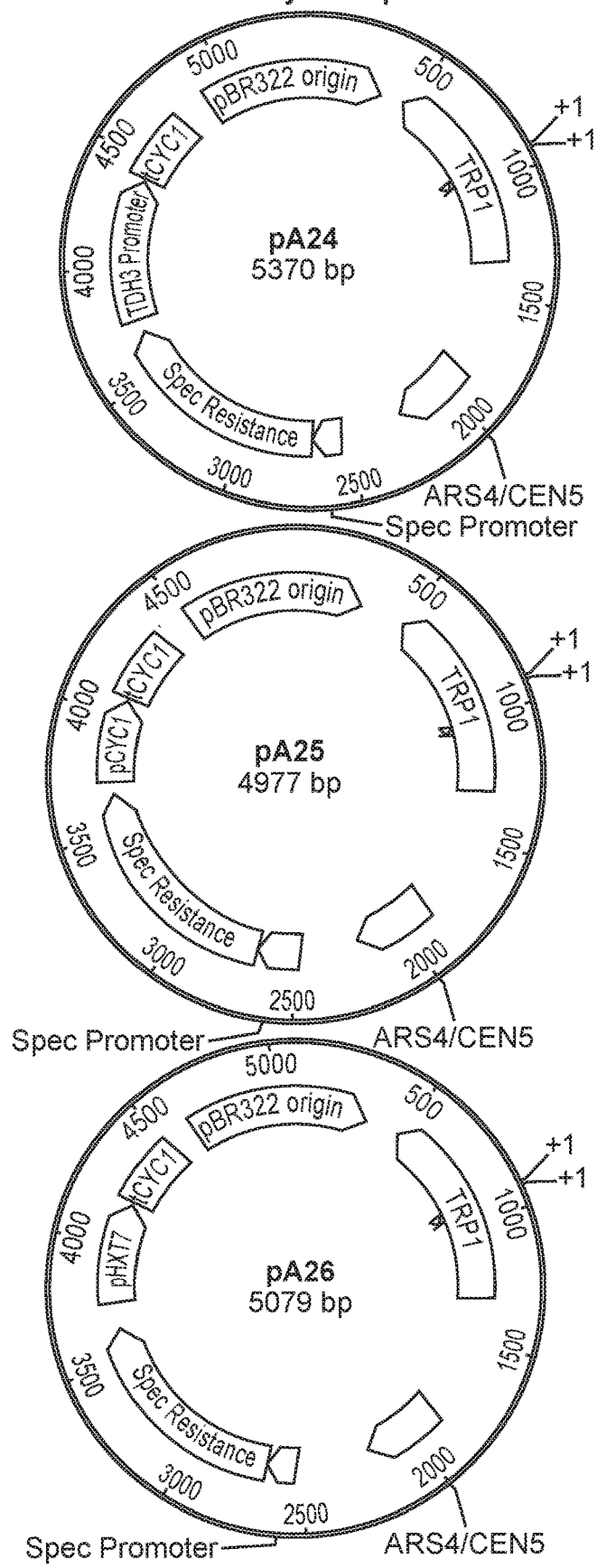
FIG. 28 illustrates plasmid/YAC vectors for enzyme expression and engineering, in accordance with embodiments of the invention.

FIG. 28 illustrates plasmid/YAC vectors for enzyme expression and engineering, in accordance with embodiments of the invention. Candidate and engineered enzymes were cloned into these vectors for expression in S. cerevisiae strains. Examples of pA24, pA25, and pA26 sequences are provided in Table 7.

Strains expressing putative O-demethylase enzymes were then tested for basal levels of activity on the various substrates listed in FIG. 23. To detect activity, cell cultures were grown in selective medium (as described above), lysed by glass bead disruption, and incubated with substrates in the presence of redox molecules and other cofactors (such as NADH, NADPH, and iron, at different concentrations depending on the enzyme requirements). O-demethylation of substrates, including but not limited to those listed in FIG. 23, was then detected by analysis via LC-MS of experimental and control samples (such as quantified amounts of oxycodone and oxymorphone, for example).

To identify engineered enzymes with improved O-demethylation activity, sequences encoding enzymes listed in Table 3 were subjected to random mutagenesis and then screened via a high-throughput colorimetric assay. Initial libraries were generated by error-prone PCR using Mutazyme II (Agilent Technologies), and variants were cloned into the pA24 (or similar) vector by gap repair in the Cen.PK2 screening host. Strains expressing mutated enzymes, with either individual mutations or combinations of mutations introduced by gene shuffling or other methods, were grown in selective medium in 96-well plate format under varying fermentation conditions (different media components, pH, and temperature, for example), pelleted, and lysed by glass bead disruption. Lysates were incubated with substrates (listed in FIG. 23) and assayed for formaldehyde production in the purpald assay. Enzymes with improved O-demethylation activity were verified by directly measuring O-demethylated product (oxymorphone, for example) formation in the culture medium by LC-MS.

Example 15: N-Demethylation of Opioid Molecules

N-demethylase activity removes the N-methyl group present in opioid substrate molecules (such as oxymorphone) and produces a nor-opioid compound (such as noroxymorphone), an important intermediate in the ultimate biosynthesis of nal-opioids. To identify enzymes capable of performing this step, sequences from Table 4 were subjected to codon optimization for expression in S. cerevisiae, and ordered as synthetic genes (from Integrated DNA Technologies). Codon optimized sequences were cloned into expression vectors pA24, pA25, or pA26 (or similar vectors), shown in FIG. 28, which harbor promoter sequences of varying strength, by gap repair in the Cen.PK2 yeast host strain, according to standard molecular biology procedures. Individual colonies were isolated and verified by PCR and sequencing (ELIM biopharmaceuticals).

Strains expressing putative O-demethylase enzymes were then tested for basal levels of activity on the various substrates listed in FIG. 24. To detect activity, cell cultures were grown in selective medium (as described above), lysed by glass bead disruption, and incubated with substrates in the presence of redox molecules and other cofactors (NADH, NADPH, and iron, for example). N-demethylation of substrates was then detected by analysis via LC-MS of experimental and control samples.

To identify engineered enzymes with improved N-demethylation activity, sequences encoding enzymes listed in Table 4 were subjected to random mutagenesis and then screened via a high-throughput colorimetric assay. Initial libraries were generated by error-prone PCR using Mutazyme II (Agilent Technologies), and variants were cloned into the pA24 (or similar) vector by gap repair in the Cen.PK2 screening host. Strains expressing mutated enzymes, with either individual mutations or combinations of mutations introduced by gene shuffling or other methods, were grown in selective medium in 96-well plate format under varying fermentation conditions (different media components, pH, and temperature, for example), pelleted, and lysed by glass bead disruption. Lysates were incubated with substrates (listed in FIG. 24) and assayed for formaldehyde production in the purpald assay. Enzymes with improved N-demethylation activity were verified by direct measurement of N-demethylated product (noroxymorphone, for example) formation in the culture medium by LC-MS.

Example 16: Modification of Nor-Opioid Compounds to Generate Nal-Opioids

Nor-opioid molecules can be modified at the exposed nitrogen to generate nal-opioids (see FIG. 25), an important class of pharmacotherapies for combating opioid addiction and opioid-associated side effects. To identify enzymes capable of modifying nor-opioid molecules, sequences from Table 5 were subjected to codon optimization for expression in S. cerevisiae, and ordered as synthetic genes (from Integrated DNA Technologies). Codon optimized sequences were cloned into expression vectors pA24, pA25, or pA26 (or similar vectors), shown in FIG. 28, which harbor promoter sequences of varying strength, by gap repair in the Cen.PK2 yeast host strain, according to standard molecular biology procedures. Individual colonies were isolated and verified by PCR and sequencing (ELIM biopharmaceuticals).

Strains expressing putative modifying enzymes were then tested for basal levels of activity on the various substrates listed in FIG. 25. To detect activity, cell cultures were grown in selective medium (as described above), lysed by glass bead disruption, and incubated with substrates in the presence of redox molecules and other cofactors (NADH, NADPH, and iron, for example). N-methylation of substrates was tested using S-adenosylmethionine (SAM) as the cosubstrate, and then additional modifying activity of enzymes was tested using SAM analogues (see "Cosubstrates" in FIG. 25). Modification of BIA substrates was detected via LC-MS of experimental and control samples.

To identify engineered enzymes with improved BIA modifying activity, sequences encoding enzymes listed in Table 5 were subjected to random mutagenesis and then screened via a high-throughput colorimetric assay. Initial libraries were generated by error-prone PCR using Mutazyme II (Agilent Technologies), and variants were cloned into the pA24 (or similar) vector by gap repair in the Cen.PK2 screening host. Strains expressing mutated enzymes, with either individual mutations or combinations of mutations introduced by gene shuffling or other methods, were grown in selective medium in 96-well plate format under varying fermentation conditions (different media components, pH, and temperature, for example), pelleted, and lysed by glass bead disruption. To detect N-methylation activity in a high-throughput screen, lysates were incubated with substrates (such as noroxymorphone) in the presence of a BM3 variant with demethylating activity, and assayed for formaldehyde production in the purpald assay (for indirect measurement of methylation). In this case, formaldehyde formation can only result from the activity of BM3 on a substrate that has been N-methylated by an enzyme of interest. Enzymes with improved modifying activity were additionally tested for activity in cell lysates using various SAM analogues as cosubstrates (see FIG. 25), and verified by direct measurement of product formation by LC-MS. The best variant enzymes were selected for the efficient bioconversion of substrate molecules to nal-opioid compounds.

Example 17: Demethylase Activity of BM3 Enzyme on Opioid Molecules

BM3 is a *Bacillus megaterium* cytochrome P450 involved in fatty acid monooxygenation in its native host. It is also readily expressed as an active heterologous enzyme in yeast and bacteria. BM3 has several advantages as a biosynthetic enzyme including that it is soluble, comes with a fused reductase partner protein, and can readily be engineered to accept new substrates. Several known BM3 variants have specific alanine substitutions which allow the rigid morphinan pentacyclic structure to access the active site. These variants were expressed in yeast and observed to N-demethylate thebaine to northebaine.

Specifically, BM3 variants 4H9, 7A1, and 8F11 (listed in Table 6) were integrated into the genomes of individual yeast strains (CEN.PK2) and incubated in citric acid-phosphate buffer (pH 5.0, 6.0, 7.0) and Tris-HCl buffer (pH 7.5, 8.0, 8.5) with 100 µM thebaine for 20 hours. A genetic construct which was identical except for the exclusion of the BM3 open reading frame was integrated to generate a no-enzyme control strain. The cells expressing BM3 produced northebaine at all tested pH levels above 7.0. The northebaine generated by the yeast strains was quantified by liquid chromatography mass spectrometry. The mass spectrum of northebaine (m/z 298) lacked the m/z 58 product ion consistent with a demethylated nitrogen (see FIG. 27C).

Figure 27A:
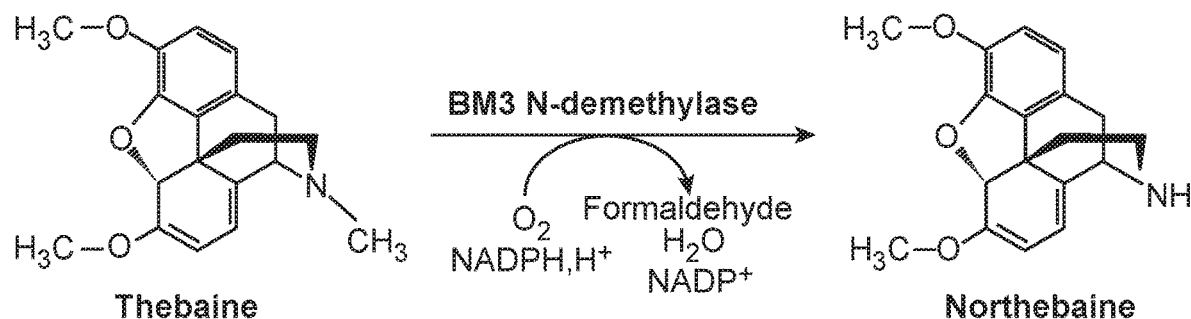
FIG. 27A, FIG. 27B, and FIG. 27C illustrates the functional expression of BM3 variants, in accordance with embodiments of the invention.
Figure 27B:
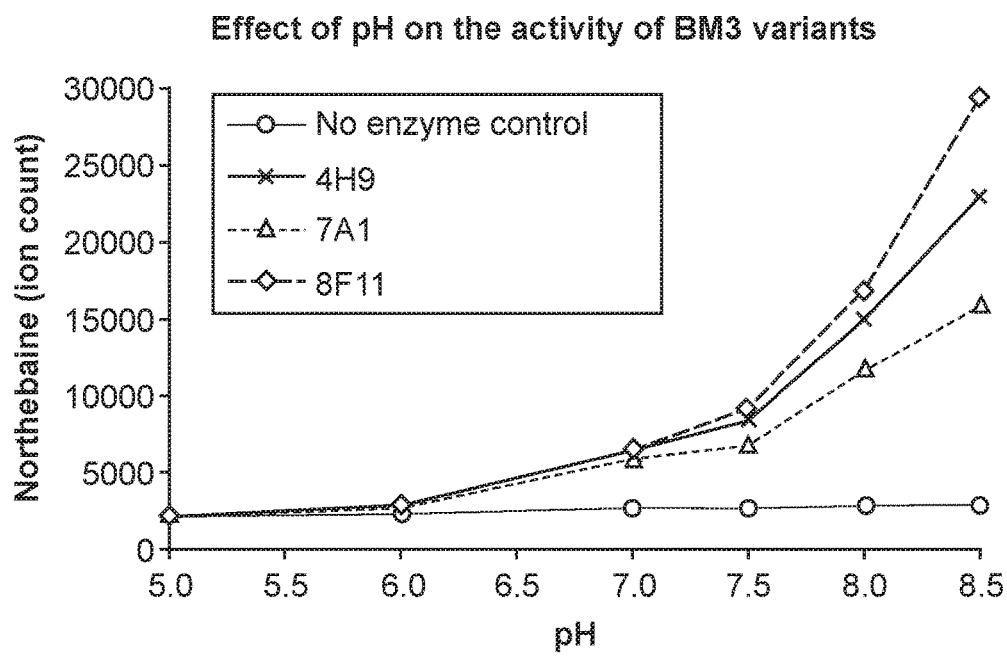
Figure 27C:
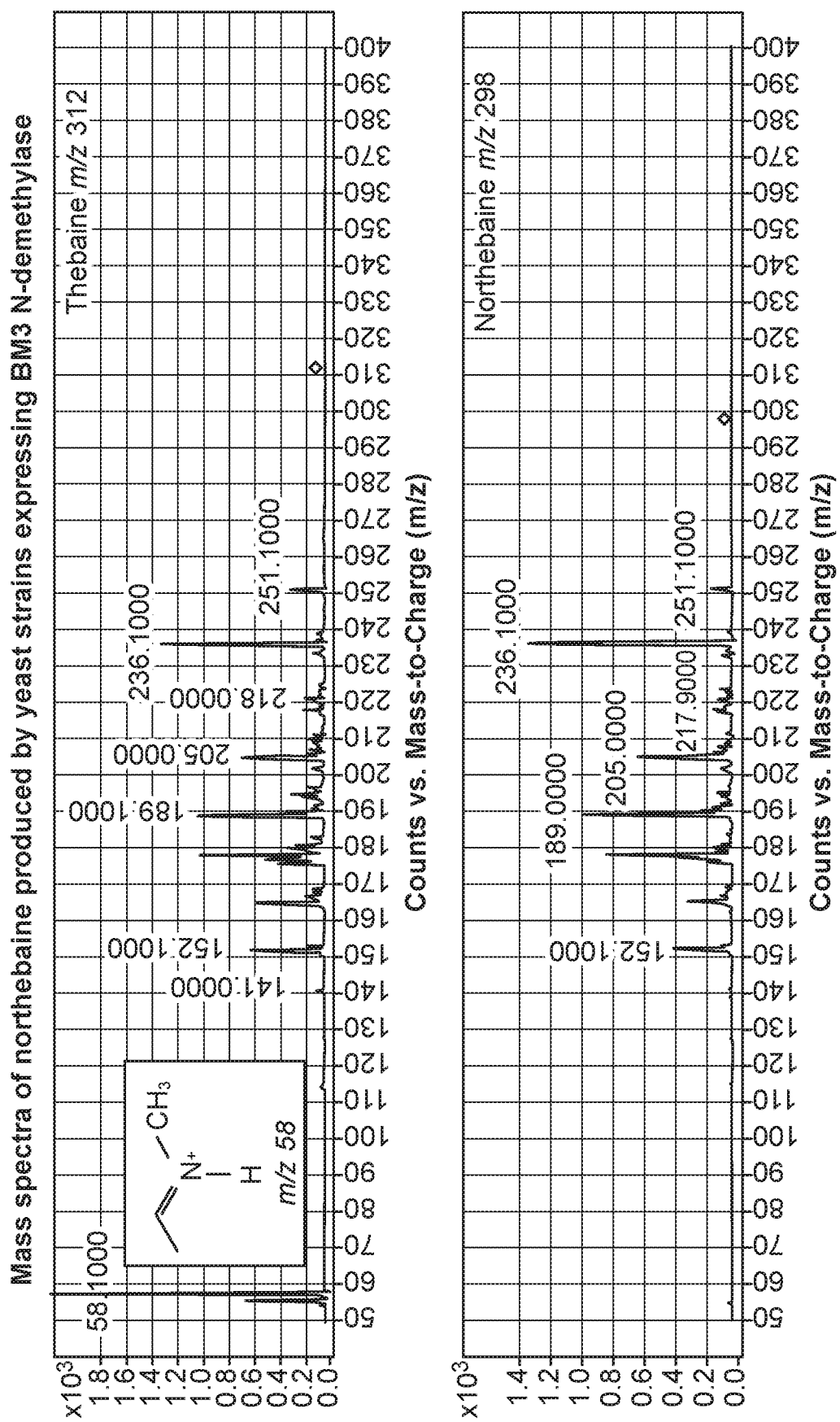

FIG. 27A, FIG. 27B and FIG. 27C illustrate the functional expression of BM3 variants, in accordance with embodiments of the invention. FIG. 27A shows the reaction mediated by the BM3 N-demethylase enzyme. FIG. 27B illustrates the functional expression of BM3 variants with thebaine N-demethylase activity in yeast. BM3 variants 4H9, 7A1, and 8F11 were integrated into the genomes of individual yeast strains (CEN.PK2) and incubated in citric acid-phosphate buffer (pH 5.0, 6.0, 7.0) and Tris-HCl buffer (pH 7.5, 8.0, 8.5) with 100 µM thebaine for 20 hours. A genetic construct which was identical except for the exclusion of the BM3 open reading frame was integrated to generate a no-enzyme control strain. The cells expressing BM3 produced northebaine at all tested pH levels above 7.0. The northebaine generated by the yeast strains was quantified by liquid chromatography mass spectrometry. The mass spectrum of northebaine (m/z 298) lacked the m/z 58 product ion consistent with a demethylated nitrogen (see FIG. 27C).

Example 18: Biological Production of O-Demethylated Opioid Molecules

Enzymes described in Example 14 and listed in Table 3, that displayed 0-demethylase activity on BIA molecules (such as those listed in Table 2), were incorporated into a microbial strain (either *Saccharomyces cerevisiae* or *Escherichia coli*) which biosynthesizes morphinan alkaloids de novo. The complete BIA biosynthetic pathway uses tyrosine produced by the host cell and/or supplemented in the culture medium. Two molecules of tyrosine are modified and condensed to form the first benzylisoquinoline structure which may be either norcoclaurine or norlaudanosoline. The benzylisoquinoline is further modified to form (S)-reticuline and then stereochemically inverted by the activity of an epimerase enzyme to yield (R)-reticuline. (R)-reticuline undergoes a carbon-carbon coupling reaction to form the first promorphinan, salutaridine, and is further modified before undergoing an oxygen-carbon coupling reaction to arrive at the first morphinan alkaloid structure, thebaine (see FIG. 26). Table 2 lists enzymes and activities in the complete pathway.

Figure 26:
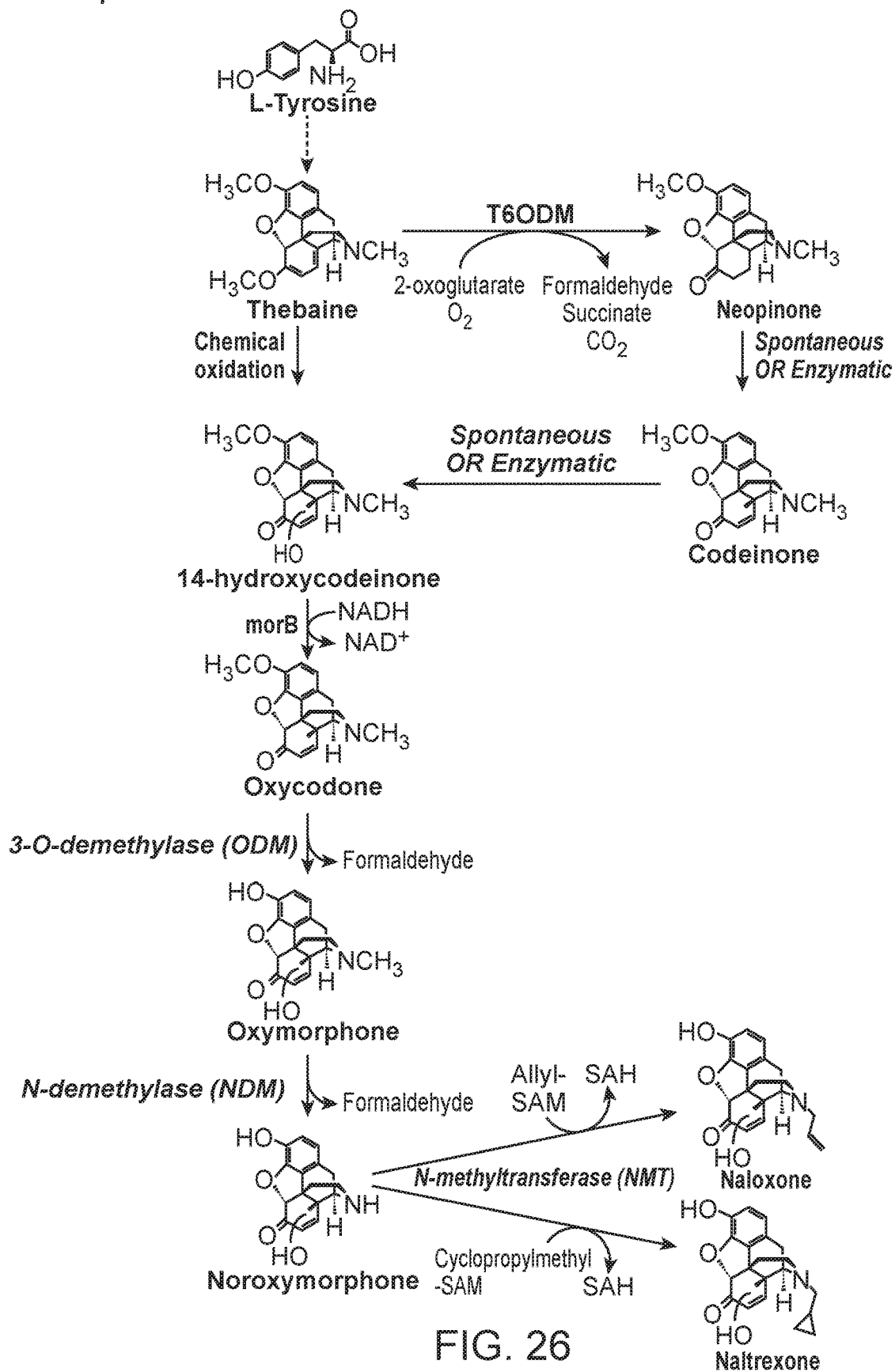
FIG. 26 illustrates a biosynthesis scheme in a microbial cell, in accordance with embodiments of the invention.

FIG. 26 illustrates a biosynthesis scheme in a microbial cell, in accordance with embodiments of the invention. Tyrosine produced endogenously by the cell and/or supplied in the culture medium is converted to oxycodone (broken arrows represent multiple enzymatic steps). The oxycodone is then 3-O-demethylated to oxymorphone and N-demethylated to noroxymorphone. Finally, an N-methyltransferase accepts allyl and cyclopropylmethyl carbon moieties from SAM analogues to produce naloxone and naltrexone, respectively.

To detect O-demethylase activity in strains producing morphinan alkaloid molecules (see FIG. 26), cells expressing candidate enzymes, either from plasmid vectors or chromosomally-integrated cassettes, were propagated by fermentation and cell supernatants were collected to analyze the total opioid profile (as described above). O-demethylation of opioid molecules in strains harboring the complete BIA pathway was detected by LC-MS (as described above). Specifically, the conversion of oxycodone to oxymorphone was detected. To detect 0-demethylation activity via biocatalysis, strains were cultured in selective medium and then lysed by glass bead disruption. Cell lysates were supplied exogenously with opioid substrates (see FIG. 23), and other cofactors necessary for enzyme function. O-demethylation of opioid molecules was detected by LC-MS.

Example 19: Biological Production of N-Demethylated Opioid Molecules

Enzymes described in Example 15 and listed in Table 4, that displayed N-demethylase activity on BIA molecules (such as those listed in Table 2), were incorporated into a microbial strain (either *Saccharomyces cerevisiae* or *Escherichia coli*) which biosynthesizes morphinan alkaloids de novo. The complete BIA biosynthetic pathway uses tyrosine produced by the host cell and/or supplemented in the culture medium. Two molecules of tyrosine are modified and condensed to form the first benzylisoquinoline structure which may be either norcoclaurine or norlaudanosoline. The benzylisoquinoline is further modified to form (S)-reticuline and then stereochemically inverted by the activity of an epimerase enzyme to yield (R)-reticuline. (R)-reticuline undergoes a carbon-carbon coupling reaction to form the first promorphinan, salutaridine, and is further modified before undergoing an oxygen-carbon coupling reaction to arrive at the first morphinan alkaloid structure, thebaine (see FIG. 26). Table 2 lists enzymes and activities in the complete pathway.

To detect N-demethylase activity in strains producing morphinan alkaloid molecules (see FIG. 26), cells expressing candidate enzymes, either from plasmid vectors or chromosomally-integrated cassettes, were propagated by fermentation and cell supernatants were collected to analyze the total opioid profile (as described above). N-demethylation of opioid molecules in strains harboring the complete BIA pathway was detected by LC-MS (as described above). Specifically, the conversion of oxymorphone to noroxymorphone was detected. To detect N-demethylation activity via biocatalysis, strains were cultured in selective medium and then lysed by glass bead disruption. Cell lysates were supplied exogenously with opioid substrates (see FIG. 24), and other cofactors necessary for enzyme function. N-demethylation of opioid molecules was detected by LC-MS.

Example 20: Biological Production of Nal-Opioid Compounds

Enzymes described in Example 16 and listed in Table 5, that displayed N-methylase activity on BIA molecules (such as those listed in Table 2), were incorporated into a microbial strain (either Saccharomyces cerevisiae or Escherichia coli) which biosynthesizes morphinan alkaloids de novo. FIG. 26 shows an example of the complete reaction scheme from the precursor molecule thebaine to the final nal-opioid compounds naloxone and naltrexone. These strains additionally express enzymes from Examples 1 and 2 and Tables 1 and 2, that are responsible for generating nor-opioid compounds from the complete BIA pathway. N-methylase enzymes were also expressed in a microbial strain (either Cen.PK2 for S. cerevisiae or BL21 for E. coli, for example) lacking the biosynthetic pathway, to generate a strain that is capable of biocatalysis of several different exogenously-supplied substrate molecules. The complete BIA biosynthetic pathway uses tyrosine produced by the host cell and/or supplemented in the culture medium. Two molecules of tyrosine are modified and condensed to form the first benzylisoquinoline structure which may be either norcoclaurine or norlaudanosoline. The benzylisoquinoline is further modified to form (S)-reticuline and then stereochemically inverted by the activity of an epimerase enzyme to yield (R)-reticuline. (R)-reticuline undergoes a carbon-carbon coupling reaction to form the first promorphinan, salutaridine, and is further modified before undergoing an oxygen-carbon coupling reaction to arrive at the first morphinan alkaloid structure, thebaine (see FIG. 26). Table 2 lists enzymes and activities in the complete pathway.

To detect N-modifying activity in strains with the complete BIA pathway to nor-opioids (see FIG. 26), cells expressing candidate enzymes were propagated by fermentation (as described above) and incubated with SAM or SAM analogs, such as those listed in FIG. 25. Enzymatic modification of nor-opioid or other BIA molecules in strains harboring the complete BIA pathway was detected in supernatants by LC-MS (as described above). To detect N-modifying activity via biocatalysis, strains were cultured in selective medium and then lysed by glass bead disruption. Cell lysates were supplied exogenously with SAM or SAM analogs, and other cofactors necessary for enzyme function. Specifically, the conversion of noroxymorphone to naloxone and naltrexone (using the SAM analogs allyl-SAM or cyclopropane-SAM, as shown in FIG. 25) was detected. Modification of nor-opioid or other BIA molecules was detected by LC-MS. To detect N-modifying activity by biocatalysis in a strain that does not have the complete BIA pathway, Cen.PK2 strains expressing enzymes described in Example 16 were grown in selective medium and lysed by glass bead disruption. Cell lysates were supplied exogenously with SAM or SAM analogs, cofactors necessary for enzyme function, and nor-opioid molecules such as those listed in FIG. 25 and Table 2. Modification of these compounds was detected by LC-MS.

Example 21: O-Demethylase Activity of CODM on Opioid Molecules

FIG. 29 illustrates the functional expression of CODM, in accordance with embodiments of the invention. In particular, FIG. 29 illustrates the functional expression of CODM with oxycodone 3-O-demethylase activity in yeast. The yeast codon-optimized CODM gene was integrated into the genome of yeast strain W303 and cultured in synthetic complete media for 16 hours. The parent W303 strain was also cultured in synthetic complete media for 16 hours as a no-enzyme control. The cells were pelleted and washed with 1 mL breaking buffer (100 mM Tris-HCl pH 7.5, 10% glycerol, 14 mM 2-mercaptoethanol, lx protease inhibitor). Cells were resuspended in 200 µL breaking buffer and lysed by glass bead disruption. The crude cell lysates were incubated with 10 mM ascorbic acid, 0.5 mM iron(II) sulfate, 0.1 mM oxycodone as substrate and 10 mM 2-oxoglutarate as cosubstrate in a total volume of 100 µL. 4 mM DTT was also added as a reducing agent to keep iron in the $Fe^{2+}$ state. The reaction was incubated at 30° C. for 3 h and quenched by diluting it 1:1 in ethanol with 0.1% acetic acid. The oxymorphone generated by the yeast strain expressing CODM was detected by LC-MS. The mass-charge ratio (m/z 302), retention time, and mass spectrum of oxymorphone produced by the yeast strain matched that of a purchased oxymorphone standard (see FIG. 29).

TABLE 2

| Enzyme list | | | | |
|---|---|---|---|---|
| Enzyme | Abbrev | Catalyzed Reactions | Source organisms | Genbank # |
| 3-deoxy-d-arabinose-heptulosonate-7-phosphate synthase | ARO4, DHAP synthase | erythrose-4-phosphate + PEP → DHAP (EC 2.5.1.54) | Saccharomyces cerevisiae | CAA85212.1 |
| Chorismate mutase | ARO7 | chorismate → prephenate (EC 5.4.99.5) | Saccharomyces cerevisiae | NP_015385.1 |
| Phenylpyruvate decarboxylase | ARO10 | hydroxyphenylpyruvate → 4HPA (EC 4.1.1.80) | Saccharomyces cerevisiae | NP_010668.3 |

TABLE 2-continued

Enzyme list

| Enzyme | Abbrev | Catalyzed Reactions | Source organisms | Genbank # |
|---|---|---|---|---|
| Aromatic aminotransferase | ARO9 | hydroxyphenylpyruvate + glutamate → tyrosine + alpha-ketogluterate (EC 2.6.1.57) | *Saccharomyces cerevisiae* | AEC14313.1 |
| Transketolase | TKL1 | fructose-6-phosphate + glyceraldehyde-3-phosphate ↔ xylulose-5-phosphate + erythrose-4-phosphate (EC 2.2.1.1) | *Saccharomyces cerevisiae* | NP_015399.1 |
| Glucose-6-phosphate dehydrogenase | ZWF1 | glucose-6-phosphate → 6-phosphogluconolactone (EC 1.1.1.49) | *Saccharomyces cerevisiae* | CAA96146.1 |
| Alcohol dehydrogenase | ADH2-7, SFA1 | 4HPA → tyrosol (EC 1.1.1.90) | *Saccharomyces cerevisiae* | NP_014032.1, AAT93007.1, NP_011258.2, NP_009703.3, NP_014051.3, NP_010030.1, NP_010113.1 |
| Aldehyde oxidase | ALD2-6 | 4HPA → hydroxyphenylacetic acid (EC 1.2.1.39) | *Saccharomyces cerevisiae* | NP_013893.1, NP_013892.1, NP_015019.1, NP_010996.2, NP_015264.1 |
| Tyrosinase | TYR | tyrosine → L-DOPA, L-DOPA → dopaquinone (EC 1.14.18.1) | *Ralstonia solanacearum*, *Agaricus bisporus* | NP_518458.1, AJ223816, |
| Tyrosine hydroxylase | TyrH | tyrosine → L-DOPA (EC 1.14.16.2) | *Homo sapiens*, *Rattus norvegicus*, *Mus musculus* | NM012740, NM000240, |
| GTP cyclohydrolase | FOL2 | GTP → dihydroneopterin triphosphate (EC 3.5.4.16) | *Saccharomyces cerevisiae*, *Homo sapiens*, *Mus musculus* | CAA97297.1, NP_001019195.1, NP_032128.1 |
| 6-pyruvoyl tetra-hydrobiopterin (PTP) synthase | PTPS | dihydroneopterin triphosphate → PTP (EC 4.2.3.12) | *Rattus norvegicus*, *Homo sapiens*, *Mus musculus* | AAH59140.1, BAA04224.1, AAH29013.1 |
| Sepiapterin reductase | SepR | PTP → BH4 (EC 1.1.1.153) | *Rattus norvegicus*, *Homo sapiens*, *Mus musculus* | NP_062054.1, NP_003115.1, NP_035597.2 |
| 4a-hydroxytetrahydro-biopterin (pterin-4α-carbinolamine) dehydratase | PCD | 4a-hydroxytetrahydrobiopterin → H2O + quinoid dihydropteridine (EC 4.2.1.96) | *Rattus norvegicus*, *Homo sapiens*, *Mus musculus* | NP_001007602.1, AAB25581.1, NP_079549.1 |
| Quinoid dihydropteridine reductase | QDHPR | quinoid dihydropteridine → BH4 (EC 1.5.1.34) | *Rattus norvegicus*, *Homo sapiens*, *Mus musculus* | AAH72536.1, NP_000311.2, AAH02107.1 |
| L-DOPA decarboxylase | DODC | L-DOPA → dopamine (EC 4.1.1.28) | *Pseudomonas putida*, *Rattus norvegicus* | AE015451.1, NP_001257782.1 |
| Tyrosine/DOPA decarboxylase | TYDC | L-DOPA → dopamine (EC 4.1.1.28) | *Papaver somniferum* | AAA97535.1, CAB56038.1 |
| Monoamine oxidase | MAO | dopamine → 3,4-DHPA (EC 1.4.3.4) | *E. coli*, *Homo sapiens*, *Micrococcus luteus* | J03792, D2367, AB010716.1 |
| Dihydrofolate reductase | DHFR | 7,8-Dihydrobiopterin → 5,6,7,8-Tetrahydrobiopterin (BH4) EC 1.5.1.3 | *Rattus norvegicus*, *Homo sapiens* | AF318150.1 |
| Norcoclaurine 6-O-methyltransferase | 6OMT | Norcoclaurine → coclaurine Norlaudanosoline → 3'hydroxycoclaurine EC 2.1.1.128 | *P. somniferum T. flavum* *Coptis japonica\** | AY268894 AY610507 D29811 |
| Coclaurine-N-methyltransferase | CNMT | Coclaurine → N-methylcoclaurine 3'hydroxycoclaurine → 3'-hydroxy-N-methylcoclaurine EC 2.1.1.140 | *P. somniferum T. flavum* *Coptis japonica\** | AY217336 AY610508 AB061863 |
| 4'-O-methyltransferase | 4'OMT | 3'-hydroxy-N-methylcoclaurine → Reticuline EC 2.1.1.116 | *P. somniferum T. flavum* *Coptis japonica\** | AY217333, AY217334 AY610510 D29812 |

TABLE 2-continued

Enzyme list

| Enzyme | Abbrev | Catalyzed Reactions | Source organisms | Genbank # |
|---|---|---|---|---|
| Norcoclaurine synthase | NCS | 4HPA + dopamine → S-norcoclaurine (EC 4.2.1.78) 3,4-DHPA + dopamine → S-norlaudanosoline | *Coptis japonica*, *Papaver somniferum*, *Papver bracteatum*, *Thalicitum flavum*, *Corydalis saxicola* | BAF45337.1, ACI45396.1, ACO90258.1, ACO90247.1, AEB71889.1 |
| Cytochrome P450 80B1 | CYP80B1 | N-methylcoclaurine → 3'-hydroxy-N-methylcoclaurine | *P. somniferum*, *E. californica*, *T. flavum* | AAF61400.1, AAC39453.1, AAU20767.1 |
| Cheilanthifoline synthase | CFS | Scoulerine → cheilanthifoline EC 1.14.21.2 | *P. somniferum* *E. californica* *A. mexicana* | GU325749 AB434654 EF451152 |
| Stylopine synthase | STS | Cheilanthifoline → stylopine EC 1.14.21.1 | *P. somniferum* *E. californica* *A. mexicana* | GU325750 AB126257 EF451151 |
| Tetrahydroprotoberberine-N-methyltransferase | TNMT | Stylopine → cis-N-methylstylopine EC 2.1.1.122 | *P. somniferum* *E. californica* *P. bracteatum* *A. mexicana* | DQ028579 EU882977 EU882994 HQ116698 |
| Cis-N-methylstylopine 14-hydroxylase | MSH | cis-N-methylstylopine → protopine EC 1.14.13.37 | *P. somniferum* | KC154003 |
| Protopine-6-hydroxylase | P6H | Protopine → 6-hydroxyprotopine EC 1.14.13.55 | *E. californica* *P. somniferum* | AB598834 AGC92397 |
| Dihydrobenzo-phenanthridine oxidase | DBOX | Dihydrosanguinarine → sanguinarine EC 1.5.3.12 | *P. somniferum* | [not in genbank] |
| (S)-tetrahydro-protoberberine oxidase | STOX | (S)-tetrahydroberberine + 2 O$_2$ = berberine + 2 H$_2$O$_2$ EC 1.3.3.8 | *Berberis wilsonae*, *Coptis japonica*, *Berberis* spp, *Coptis* spp | HQ116697, AB564543 |
| S-adenosyl-L-methionine:(S)-scoulerine 9-O-methyltransferase | S9OMT | S-adenosyl-L-methionine + (S)-scoulerine = S-adenosyl-L-homocysteine + (S)-tetrahydrocolumbamine EC 2.1.1.117 | *Thalictrum flavum* subsp. *glaucum*, *Coptis japonica*, *Coptis chinensis*, *Papaver somniferum*, *Thalictrum* spp, *Coptis* spp, *Papaver* spp | AY610512, D29809, EU980450, JN185323 |
| (S)-tetrahydrocolumbamine, NADPH:oxygen oxido-reductase (methylenedioxy-bridge-forming), also known as (S)-canadine synthase | CAS | (S)-tetrahydrocolumbamine + NADPH + H+ + O2 = (S)-canadine + NADP+ + 2 H2O EC 1.14.21.5 | *Thalictrum flavum* subsp. *glaucum*, *Coptis japonica*, *Thalictrum* spp, *Coptis* spp | AY610513, AB026122, AB374407, AB374408 |
| (S)-reticuline:oxygen oxidoreductase (methylene-bridge-forming), also known as berberine bridge enzyme | BBE | (S)-reticuline + O2 = (S)-scoulerine + H2O2 EC 1.21.3.3 | *Papaver somniferum*, *Argemone mexicana*, *Eschscholzia californica*, *Berberis stolonifera*, *Thalictrum flavum* subsp. *glaucum*, *Coptis japonica*, *Papaver* spp, *Eschscholzia* spp, *Berberis* spp, *Thalictrum* spp, *Coptis* spp | AF025430, EU881889, EU881890, S65550, AF005655, AF049347, AY610511, AB747097 |
| NADPH:hemoprotein oxido-reductase, also known as cytochrome P450 reductase | ATR1, CPR | NADPH + H+ + n oxidized hemoprotein = NADP+ + n reduced hemoprotein EC 1.6.2.4 | *Arabidopsis thaliana*, *Eschscholzia californica*, *Papaver somniferum*, *Homo sapiens*, *Saccharomyces cerevisiae*, *Papaver bracteatum*, *Papaver* spp, all plants | CAB58576.1, CAB58575.1, AAC05021.1, AAC05022.1, NM118585, many others (Ref PMID 19931102) |
| salutaridinol:NADP+ 7-oxidoreductase, also known as salutaridine reductase | SalR | salutaridinol + NADP+ = salutaridine + NADPH + H+ EC 1.1.1.248 | *Papaver somniferum*, *Papaver bracteatum*, *Papaver* spp *Chelidonium majus* | DQ316261, EF184229 (Ref PMID 22424601) |
| acetyl-CoA:salutaridinol 7-O-acetyltransferase, also known as salutaridinol 7-O-acetyltransferase | SalAT | acetyl-CoA + salutaridinol = CoA + 7-O-acetylsalutaridinol EC 2.3.1.150 | *Papaver somniferum*, *Papaver bracteatum*, *Papaver orientale*, *Papaver* spp | AF339913, FJ200355, FJ200358, FJ200356, JQ659008 |
| (R)-reticuline, NADPH:oxygen oxidoreductase (C—C phenol-coupling), also known as salutaridine synthase | SalSyn | (R)-reticuline + NADPH + H+ + O2 = salutaridine + NADP+ + 2 H2O EC 1.14.21.4 | *Papaver somniferum*, *Papaver* spp *Chelidonium majus* | EF451150 (Ref PMID 22424601) |

TABLE 2-continued

Enzyme list

| Enzyme | Abbrev | Catalyzed Reactions | Source organisms | Genbank # |
|---|---|---|---|---|
| 1-benzylisoquinoline alkaloid epimerase (cytochrome P450 82Y1-like codeinone reductase-like) | CYP-COR or DRS- DRR | (S)-reticuline –> (R)-reticuline (S)-1-benzylisoquinoline–> (R)-1-benzylisoquinoline EC 1.5.1.27 | *Papaver bracteatum*, *Papaver somniferum*, *Papaver setigerum*, *Chelidonium majus* | P0DKI7.1, AKO60175.1, AKO60180.1, AKO60179.1, AKO60175.1 |
| Cytochrome P450, family 2, subfamily D, polypeptide 6 | CYP2D6 | Promiscuous oxidase, can perform(R)-reticuline + NADPH + H+ + O2 = salutaridine + NADP+ + 2 H2O among other reactions EC 1.14.14.1 | *Homo sapiens* | BC067432 |
| Thebaine 6-O demethylase | T6ODM | thebaine → neopinone EC 1.14.11.31 | *Papaver somniferum*, *Papaver* spp. | GQ500139.1 |
| Codeinone reductase | COR | codeinone → codeine EC 1.1.1.247, neopinone → neopine | *Papaver somniferum*, *Papaver* spp. | AF108432.1 AF108433.1 AF108434.1 AF108435.1 |
| Codeine O-demethylase | CODM | codeine → morphine EC 1.14.11.32, neopine → neomorphine | *Papaver somniferum*, *Papaver* spp. | GQ500141.1 |
| Morphine dehydrogenase | morA | morphine → morphinone EC 1.1.1.218, codeinone → codeine EC 1.1.1.247 | *Pseudomonas putida* | M94775.1 |
| Morphinone reductase | morB | codeinone → hydrocodone morphinone → hydromorphone EC 1.3.1.- | *Pseudomonas putida* | U37350.1 |
| Reticuline N-methyltransferase | RNMT | reticuline→tembetarine | *Papaver somniferum*, *Papaver* spp. | KX369612.1 |
| Papaverine 7-O-demethylase | P7OMT | papaverine→pacodine | *Papaver somniferum*, *Papaver* spp. | KT159979.1 |
| 3-O-demethylase | 3ODM | oxycodone→oxymorphone hydrocodone→hydromorphone dihydrocodeine→dihydromorphine 14-hydroxycodeine→14-hydroxymorphine codeinone→morphinone 14-hydroxycodeinone→14-hydroxymorphinone | *Papaver somniferum*, *Papaver bracteatum*, *Papaverrhoeas*, *Papaver* spp. | |
| N-demethylase | NDM | Codeine→Norcodeine Morphine→Normorphine Oxycodone→Noroxycodone Oxymorphone→Noroxymorphone Thebaine→Northebaine Oripavine→Nororipavine Hydrocodone→Norhydrocodone Hydromorphone→Norhydromorphone Dihydrocodeine→Nordihydrocodeine Dihydromorphine→Nordihydromorphine 14-hydroxycodeine→Nor-14-hydroxycodeine 14-hydroxymorphine→Nor-14-hydroxymorphine Codeinone→Norcodeinone Morphinone→Normorphinone 14-hydroxycodeinone→Nor-14-hydroxycodeinone 14-hydroxymorphinone→Nor-14-hydroxymorphinone | *Bacillus megaterium*, *Homo sapiens*, *Papaver somniferum*, *Papaver* spp., *Chelidonium majus*, *Stylophorum diphyllum*, *Nigella sativa*, *Hydrastis canadensis*, *Glaucium flavum*, *Eschscholzia californica*, *Menispermum canadense*, *Papaver bracteatum* | |
| N-methyltransferase | NMT | Norcodeine→codeine Normorphine→morphine Noroxycodone→oxycodone Noroxymorphone→noroxymorphone Northebaine→thebaine Nororipavine→oripavine Norhydrocodone→hydrocodone Norhydromorphone→Hydromorphone Nordihydrocodeine→Dihydrocodeine Nordihydromorphine→Dihydromorphine Nor-14-hydroxycodeine→14-hydroxycodeine Nor-14-hydroxymorphine→14-hydroxymorphine Norcodeineone→Codeineone Normorphinone→Morphinone | *Papaver* spp., *Chelidonium majus*, *Thalictrum flavum*, *Coptis japonica*, *Papaver somniferum*, *Eschscholzia californica*, *Papaver bracteatum*, *Argenome mexicana*, *Glaucium flavum*, *Sanguinaria canadensis*, *Corydalis chelanthifolia*, *Nigella sativa*, *Jeffersonia diphylla*, *Berberis thunbergii*, *Mahonia aquifolium*, *Menispermum canadense*, *Tinospora cordifolia*, | |

TABLE 2-continued

| Enzyme | Abbrev | Catalyzed Reactions | Source organisms | Genbank # |
|---|---|---|---|---|
| | | Nor-14-hydroxy-codeinone→ 14-hydroxy-codeinone → Nor-14-hydroxy-morphinone→14-hydroxymorphinone | *Cissampelos mucronata*, *Cocculus trilobus* | |
| N-allyltransferase | NAT | Norcodeine→N-allyl-norcodeine Normorphine→N-allyl-normorphine Noroxycodone→N-allyl-noroxycodone Noroxymorphone→N-allyl-nornoroxymorphone Northebaine→N-allyl-northebaine Nororipavine→N-allyl-nororipavine Norhydrocodone→N-allyl-norhydrocodone Norhydromorphone→ N-allyl-norhydromorphone Nordihydrocodeine→ N-allyl-nordihydrocodeine Nordihydromorphine→ N-allyl-nordihydromorphine Nor-14-hydroxycodeine→ N-allyl-nor-14-hydroxycodeine Nor-14-hydroxymorphine→ N-allyl-nor-14-hydroxymorphine Norcodeineone→ N-allyl-norcodeineone Normorphinone→ N-allyl-normorphinone Nor-14-hydroxy-codeinone→ N-allyl-nor-14-hydroxycodeinone Nor-14-hydroxy-morphinone→ N-allyl-nor-14-hydroxymorphinone | *Papaver* spp., *Chelidonium majus*, *Thalictrum flavum*, *Coptis japonica*, *Papaver somniferum*, *Eschscholzia californica*, *Papaver bracteatum*, *Argenome mexicana*, *Glaucium flavum*, *Sanguinaria canadensis*, *Corydalis chelanthifolia*, *Nigella sativa*, *Jeffersonia diphylla*, *Berberis thunbergii*, *Mahonia aquifolium*, *Menispermum canadense*, *Tinospora cordifolia*, *Cissampelos mucronata*, *Cocculus trilobus* | |
| N-cyclopropylmethyl-transferase | NCPMT | Norcodeine→N-(Cyclopropylmethyl)norcodeine Normorphine→N-(Cyclopropylmethyl)normorphine Noroxycodone→N-(Cyclopropylmethyl)noroxycodone Noroxymorphone→N-(Cyclopropylmethyl)nornoroxymorphone Northebaine→N-(Cyclopropylmethyl)northebaine Nororipavine→N-(Cyclopropylmethyl)nororipavine Norhydrocodone→N-(Cyclopropylmethyl)norhydrocodone Nordihydrocodeine→N-(Cyclopropylmethyl)nordihydrocodeine Nordihydromorphine→ N-(Cyclopropylmethyl)nordihydromorphine Nor-14-hydroxycodeine→ N-(Cyclopropylmethyl)nor-14-hydroxycodeine Nor-14-hydroxymorphine→ N-(Cyclopropylmethyl)nor-14-hydroxymorphine Norcodeineone→ N-(Cyclopropylmethyl)norcodeineone Normorphinone→ N-(Cyclopropylmethyl)normorphinone Nor-14-hydroxy-codeinone→ N-(Cyclopropylmethyl)nor-14-hydroxycodeinone Nor-14-hydroxy-morphinone→ N-(Cyclopropylmethyl)nor-14-hydroxymorphinone | *Papaver* spp., *Chelidonium majus*, *Thalictrum flavum*, *Coptis japonica*, *Papaver somniferum*, *Eschscholzia californica*, *Papaver bracteatum*, *Argenome mexicana*, *Glaucium flavum*, *Sanguinaria canadensis*, *Corydalis chelanthifolia*, *Nigella sativa*, *Jeffersonia diphylla*, *Berberis thunbergii*, *Mahonia aquifolium*, *Menispermum canadense*, *Tinospora cordifolia*, *Cissampelos mucronata*, *Cocculus trilobus* | |

TABLE 3

O-demethylase candidate enzymes

| Name | Sequence | SEQ ID NO: |
|---|---|---|
| T6ODM | MEKAKLMKLGNGMEIPSVQELAKLTLAEIPSRYVCANENLLLPMGA SVINDHETIPVIDIENLLSPEPIIGKLELDRLHFACKEWGFFQVVNHGV DASLVDSVKSEIQGFFNLSMDEKTKYEQEDGDVEGFGQGFIESEDQT LDWADIFMMFTLPLHLRKPHLFSKLPVPLRETIESYSSEMKKLSMVL FNKMEKALQVQAAEIKGMSEVFIDGTQAMRMNYYPPCPQPNLAIGL TSHSDFGGLTILLQINEVEGLQIKREGTWISVKPLPNAFVVNVGDILEI MTNGIYHSVDHRAVVNSTNERLSIATFHDPSLESVIGPISSLITPETPAL FKSGSTYGDLVEECKTRKLDGKSFLDSMRI | 16 |
| CODM | METPILIKLGNGLSIPSVQELAKLTLAEIPSRYTCTGESPLNNIGASVT DDETVPVIDLQNLLSPEPVVGKLELDKLHSACKEWGFFQLVNHGVD ALLMDNIKSEIKGFFNLPMNEKTKYGQQDGDFEGFGQPYIESEDQRL DWTEVFSMLSLPLHLRKPHLFPELPLPFRETLESYLSKMKKLSTVVFE MLEKSLQLVEIKGMTDLFEDGLQTMRMNYYPPCPRPELVLGLTSHS DFSGLTILLQLNEVEGLQIRKEERWISIKPLPDAFIVNVGDILEIMTNGI YRSVEHRAVVNSTKERLSIATFHDSKLESEIGPISSLVTPETPALFKRG RYEDILKENLSRKLDGKSFLDYMRM | 17 |
| PsP7ODM | MEKAKLMKLGNGLSIPSVQELAELTFAEVPSRYVCTNDENLLLMTM GASEIDDETVPVIDLQNLLSPEPAIGKSELDWLHYSCKEWGFFQLVN HGVDALLVDHVKSEIHSFFNLPLNEKTKYGQRDGDVEGFGQAFLVS ENQKLDWADMFFINTLPLHLRKPHLFPNLPLPLRETIESYSSEMKKLS MVLFEMMGKAIEVIDIKEAITEMFEDGMQSMRMNYYPPCPQPERVI GITPHSDFDGLTILLQLNEVEGLQIRKEDKWISIKPLPDAFIVNVGDIW EIMTNGVHRSVDHRGVINSTKERLSIATFHSPKLELEIGPISSLIRPETP AVFKSAGRFEDLLKEGLSRKLDGKSFLDCMRM | 18 |
| PsoDIOX1 | MEKAKLMKLGNGMEIPSVQELAKLTLAEIPSRYVCANENLLLPMGA SVINDHETIPVIDIENLLSPEPIIGKLELDRLHFACKEWGFFQVVNHGV DASLVDSVKSEIQGFFNLSMDEKTKYEQEDGDVEGFGQGFIESEDQT LDWADIFMMFTLPLHLRKPHLFSKLPVPLRETIESYSSEMKKLSMVL FNKMEKALQVQAAEIKGMSEVFIDGTQAMRMNYYPPCPQPNLAIGL TSHSDFGGLTILLQINEVEGLQIKREGTWISVKPLPNAFVVNVGDILEI MTNGIYHSVD | 19 |
| PsoDIOX2 | METAKLMKLGNGMSIPSVQELAKLTLAEIPSRYICTVENLQLPVGAS VIDDHETVPVIDIENLISSEPVTEKLELDRLHSACKEWGFFQVVNHGV DTSLVDNVKSDIQGFFNLSMNEKIKYGQKDGDVEGFGQAFVASEDQ TLDWADIFMILTLPLHLRKPHLFSKLPLPLRETIESYSSEMKKLSMVL FEKMEKALQVQAVEIKEISEVFKDMTQVMRMNYYPPCPQPELAIGL TPHSDFGGLTILLQLNEVEGLQIKNEGRWISVKPLPNAFVVNVGDVL EIMTNGMYRSVDHRAVVNSTKERLSIATFHDPNLESEIGPISSLITPNT PALFRSGSTYGELVEEFHSRKLDGKSFLDSMRM | 20 |
| PbrDIOX2 | METPKSIKLGGSLLVPSVQELAQQSFAEVPARYVRDDLEPLTDLSGV SMIDQTIPVIDLQKLQSPVPIIRELESEKLHSACKEWGFFQVVNHGVDI LLVEKTKSEIKDFFNLPMDEKKKFWQEEGDIQGFGQAFVQSEDQKL DWADIFLMVTLPRHTRNPRLFPKLPLPLRNTMDSYSSKLSKLASTLIE MMGKALHMETSVLAELFEDGRQTMRINYYPPCPQPKDVIGLTPHSD GGGLTILLQLNEVDGLQIRKEKIWIPIKPLPNAFVVNIGNILEIMTNGI YRSVEHRATIHSTKERLSVAAFHNPKVGVEIGPIVSMITPESPALFRTI EYDDYGKKYFSRKLDGKSSLDFMRIGEGDEENKAT | 21 |
| PbrDIOX3 | METPKLIKLGGSLLVPSVELTKQSPAEVPARYIRNDLEPMTDLSSAS LTDQTIPVIDLQNLLSPEPELELEKLHSGCKEWGFFQVVNHGVDILLV EKVKSEIQGFFNLPIDEKNKFWQEEGDLEGYGKAFVHSEDEKLDWA DMFFILTQPQYMRKPRVFPKLPLRLRETIESYSLELSKLGLTLLDLMG KALQIETGVMSELFEDGRQTMRMNYYPPCPQPEHVIGLTPHSDGGA LTILLQLNQVDGLQIRKEEIWVPIKPLPNAFVVNIGDILEIMSNGVYRS VEHRATINSSKERLSVAIFQSPKHGTEIGPILSMITPEAPALFKTIPYED YLRKFFSRKLGGKSFVDSMRIGESDEDNNTA | 22 |
| PbrDIOX4 | METQKQENFGASLSVPNVQELAKQSPEQVPDRYIRSDQDSSTNISCPS MTDQIPVIDLQSLLSPDPIIGELELERLHSACKEWGFFQVVNHGVDNL LVEEKVKSEIQGFFNLPMDEKKKFWQEEGDFEGFGQAFVFSEDQKLD WGDVFFILTQPQHMRKPRLFPKLPLPFRKTIESYSLETNKLSMTLLEL MEKALKIETGVMTELFEGGIQRMRMTYYPPCPQPKHVIGLTPHSDPD ALTILLQLNEVDGLQIRKEKIWVPIKPLSNAFVVNIGDILEIMSNGIYR SVEHRATVNSTKERLSVATFHSPRKDTEIGPILITPETPALFRTSGFED YFRKFFAHKLNGKSFLSSIRIGETDEGNNAT | 23 |
| PbrDIOX5 | MEAPKLIMLGGSLFVPSVQELAKQSLAEVPVRYVRDDQDTLGNNINI TPMSMIDQSIPVIDLEKLLSPEPIVGELELERLHSACKEWGFFQVVNH GVDSLLVEKVKSEIEGFFKLPMDEKTKFWQEEGDIEGFGQVFVHSQD QKLDWGDMFLMQTLPRHTRKPRLFPNLPLPLRQTIESYSSELSKLVL | 24 |

TABLE 3-continued

O-demethylase candidate enzymes

| Name | Sequence | SEQ ID NO: |
|---|---|---|
| | TLVDLMGKALQMESGVLTELFENGIQRMRMNYYPPCPQPEQVIGLT PHSDVGGLTILLQLNEVDGLQIKKDKVWVPIKPLANAFVVNVGDAL EIMSNGIYRSVEHRATINSTKERLSIATFHNPRADREIGPIPSMISPETP ALFKTTGYEEYFKKFFSRKLEGKSFLDSLRIREGDEHCGRLDVKGPCN | |
| PbrDIOX6 | MEIPNPIKIGSSLLVPSVQELAKQSFAEVPARYIRNDVDPLITKLSDVS LIDQTVPVIDLQKLLSPEPIVGELELERLHSACKEWGFFQVVNHGVD NLLVEKVKSEIQGFFNLPMEEKKKFWQEEGDFEGFGQMFVQSEEQK LDWGDMFFILTQPQHMRKPRLFSKLPLPLRETIESYSLELIKLGLTIIK LMEKALQIDAGVMAELFEDGIHTMRMNYYPPCPQPEHVIGLTPHSD GGGLTILLQLNEVDGLQIRRENIWVPIKPLPNAFVVNIGDILEILSNGI YRSVEHRSTVNATKERLSVATFQNPKQESVIGPNMITPERPALFRKIV YKDYMKKLFSRKLDGKSFLDSLRIGEGDERP | 25 |
| PbrDIOX8 | METLKTVKPGGSLFIPNGQELAKQSLEEVYVGNDQDTMLLIGQTIPVI DLQKLLSPEPITGDMELDKLHSACKEWGFFQVVNHGVDILLVEKVK SEVHDFFNIPMDEKKPFWQEEGDLEGFGQVFITSEDQQLDWGDMFF MVTLPKHMRKPRLFLKLPLPLRETIESYSLKLSKLGVTLVELMGKAL QMEDRIMSELFDDGRQTMRMNYYPPCPQPEQVIGLTPHSDPGGLTIL LELNEVNGLIRKENIWVPIIPLPNAFIVNIGDILEIMSNGIYHSVEHRAT INSTKERLSVAMFNSPKVDTEIGPIHSMITPETPALFRTIGYDEYLKIFF SRKLDGKSLLESMKI | 26 |
| PbrDIOX10 | MEAPKLIMLGGSLFVPSVQELAKQSLAEVPVRYVRDDQDTLGNNINI TPMSMIDQSIPVIDLEKLLSPEPIVGELELERLHSACKEWGFFQVVNH GVDSLLVEKVKSEIEGFFELPVDEKKKFWQEEGDIEGFGQIFVHSEDQ KLDWADMFYMLTLPPNMRKPRLFPNLPLPLRQTIDSYSSELSKLVLT LVDLMGKALQMESGVLTELFENGIQRMRMNYYPPCPQPEQVIGLTP HSDVGGLTILLQLNEVDGLQIKKDKIWVPIKPLRNAFVVNVGDALEI MSNGIYRSVEHRATINSTKERLSIATFHNPRADREIGPIPSMISPETPAL FKTTGYEEYFKKFFSRKLEGKSFLDSLRIGEGDEHCGRLXVKGXCN | 27 |
| PbrDIOX11 | METPKLMKLGGSLFVPSVQELAKQSLAEVPARYVRDDRDMVGNIIN VTPMSMIDQSIPVIDLEKLLSPDLIVGELELERLHSACKEWGFFQVVN HGVDSLLVEKVKSEIEGFFELPMDEKKKFWQEEGDAEGFAQFFVQS EDQKLDYSGDMFFMLNLPQHMRKPRLFLKLPLPLRETIESYSLKLSK LGVTLVELMGKALQMEDRIMSELFDDGRQTMRMNYYPPCPQPEQVI GLTPHSDPGGLTILLELNEVNGLIRKENIWVPIIPLPNAFIVNIGDILEI MSNGIYHSVEHRATINSTKERLSVAMFNSPKVDTEIGPIHSMITPETPA LFRTIGYDEYLKIFFSRKLDGKSLLESMKI | 28 |
| PbrDIOX13 | METPKLRDFGSFLPVPSVQELAKQVLTEIPPRYIRTDLEALNKLSCAS NTDQTVPIIDMQCLLSAEPEMELEKLHSACKEWGFFRVVNHGVDNL ESVKSEIESFLNLPVNAKNKYGQKQGDDQGFGSRFVLSEEQKLDWG DFFYMVTRPLYLRKPHLFPELPLPLRETIESYSSEVSKLAMALFEMM GKALKIETGVMTEIFEGGMQAMRMNYYPPCPRPDLVIGLNAHSDFG GLTILLQLNEVEGLEIRNKGEWVSVKPLANAFVVNVGDVMEILTNGI YHSVEHRATINSSKERLSVATFHYPKLETGIGPLPCMITPKTPALFGRI ERYELLLRKYYARKLNGKSTLDCMRIGNGFEDDNTA | 29 |
| PbrDIOX18 | MEAPKLIMLGGSLFVPSVQELAKQSLAEVPARYVRDDQDTLGNNINI TPMSMIDQSIPVIDLEKLLSPEPIVGELELERLHSACKEWGFFQVVNH GVDSLLVEKVKSEIEGFFELPVDEKKKFWQEEGDIEGFGQIFVHSEDQ KLDWADMFYMLTLPPNMRKPRLFPNLPLPLRQTIDSYSSELSKLVLT LVDLMGKALQMESGVLTELFENGIQRMRMNYYPPCPQPEQVIGLTP HSEVGGLTILLQLNEVDGLQIRKEKIWVPIKPLSNAFIVNIGDILEIMS NGIYRSVEHRATVNSTKERLSVATFHSPRKDTEIGPILITPETPALFRTS GFEDYFRKFFAHKLNGKSFLSSIRIGETDEGNNAT | 30 |
| PbrDIOX19 | MSMIDQSIPVIDLEKLLSPEPIVGELELERLHSACKEWGFFQVVNHGV DSLLVEKVKSEIEGFFELPVDEKKKFWQEEGDIEGFGQIFVHSEDQKL DWADMFYMLTLPPNMRKPRLFPNLPLPLRQTIDSYSSELSKLVLTLV DLMGKALQMESGVLTELFENGIQRMRMNYYPPCPQPEQVIGLTPHS DVGGLTILLQLNEVDGLQIRKEKIWVPIKPLSNAFIVNIGDILEIMSNGI YHSVEHRATINSTKERLSVAMFNSPKVDTEIGPIHSMITPETPALFRTI GYDEYLKIFFSRKLDGKSLLESMKI | 31 |
| PbrDIOX21 | METPKLVKSSGSSLFLSTSVQELAKQSLPEVPARYIRTNLEPLSNVSG DSQSVPVIDLQKLLSSEPIIGELELDKLHSACKEWGFFQVVNHGVDN LVMEKIKTEIQGFFNLSLDEKPWFKKEGDAEGFGQNFIESEDQKLD WGDTFGMFTLPIHMRNPRLFPELPLPLRETIESYSLDVRKLALALIGL MEKALKIKTSAMSELFEDGGQAMRMNYYPPCPQPEHVIGLTPHSDA GGLTILLQLNEVDGLQIKKDKIWVPIKPLPNAFVVNIGDILEIMTNGIY RSVEHRATINSSKERLSVAAFHSPKGDTLIGPMVSLITPETPALFRTIG YQDYMKKFMSRKLDGKSLVNSMRIGEGDEDK | 32 |

TABLE 3-continued

O-demethylase candidate enzymes

| Name | Sequence | SEQ ID NO: |
|---|---|---|
| PbrDIOX-ZSNV-2004018 | METPTLMKLGNGLSVPSVQELAKATLAEIPSRYICTDENLLTMGAST TDNETVPVIDLQNLLSPEPVIGMLELDRLHSACKEWGFFQLVNHGVD ALLVDNEVQGFFNLPMDEKTKYGQKDGDDEGFGQFFVISEDQKLD WADVFYMSTLPLHSRKPHLFPELPLPLRETMESYSSEMKKLSMVLFD MMGKALQVVEIKGITELFEDGAQQIRMNYYPPCPQPELVFGLTSHSD FDGLTILLQLGEVEGLQIKKEERWISIKPLPDAFIVNVGDILEIMTNGI YRSVDHRAVVNSIKERLTIATFHDPRLEAEIGPISSLITPETPALFKRGV FEDLLKEMFLRKLDGKSFLDCMRM | 33 |
| PrhDIOX-MVTX-2001522 | GNGLSVPSVQELAKQTLAEIPSRYICTDENPLITGASVVDDETVPVIN LQNLLSPEPVIGKLELDKLHSACKEWGFFQLVNHGVNDSLVDSVKS EIEGFFNLPANEKLKYGQKDGDVEGFGQHFVVSEDQKLDWADVFY MVTLPVRLRKPHLFPELPLPLRDTLDSYSSELNKLSMVLLEMMEKAL KLVECKGITDFFEDGFQQMRMNYYPPCPRPELVTGLTSHSDFGGLTI LLQLNDVEGLQIKKEERWISIKPLPNAFIVNIGDVLEIMSNGIYRSVDH RAVINSTKVRMSVATFHDPRLEAVIGPISSLITPETPALFKRGVFEDLL KEMFLRKLDGKSFLDCMRI | 34 |
| PseDIOX-JSVC-2005842 | LMKLANGMSVPIVQELAKLTVGEIPSRYICTDGNLLTMGASVIDYET VPVIDLQNLQSREPVIEKLELDRLHSACKEWGFFQLLNHGVDASLMD NVRSEIRGFFNLPISDKMKYGQKDGDEEGFGQHFIVSEDQKLDWVD AFMMFTLPLHSRNPRLTPEFPQPLRETVESYSSEMKKLSVLLFELME KALQVKGITEMFEDGLQSIRMNYYPPCPRPELAIGLTSHSDFDGLTIL LQLNEVEGLQIKKEERWISIKPLPNAFIVNVGDVLEVMTNGIYRSVD HRAVVNSTKERLSIATFHDPELESEIGPIASLITPETPALFKRGRFKDLL KENLSTKLDGKSFLDCIRM | 35 |
| CYP2D6 | MGLEALVPLAVIVAIFLLLVDLMHRRQRWAARYSPGPLPLPGLGNLL HVDFQNTPYCFDQLRRRFGDVFSLQLAWTPVVVLNGLAAVREALVT HGEDTADRPPVPITQILGFGPRSQGVFLARYGPAWREQRRFSVSTLR NLGLGKKSLEQWVTEEAACLCAAFANHSGRPFRPNGLLDKAVSNVI ASLTCGRRFEYDDPRFLRLLDLAQEGLKEESGFLREVLNAVPVLLHIP ALAGKVLRFQKAFLTQLDELLTEHRMTWDPAQPPRDLTEAFLAEME KAKGNPESSFNDENLRIVVADLFSAGMVTTSTTLAWGLLLMILHPDV QRRVQQEIDDVIGQVRRPEMGDQAHMPYTTAVIHEVQRFGDIVPLG VTHMTSRDIEVQGFRIPKGTTLITNLSSVLKDEAVWEKPFRFHPEHFL DAQGHFVKPEAFLPFSAGRRACLGEPLARMELFLFFTSLLQHFSFSVP TGQPRPSHHGVFAFLVTPSPYELCAVPR | 36 |

TABLE 4

N-demethylase candidate enzymes

| Name | Sequence | SEQ ID NO: |
|---|---|---|
| BM3 | MTIKEMPQPKTFGELKNLPLLNTDKPVQALMKIADELGEIFKFEAPG RVTRYLSSQRLIKEACDESRFDKNLSQAAKFARDFAGDGLVTSWTH EKNWKKAHNILLPSFSQQAMKGYHAMMVDIAVQLVQKWERLNA DEHIEVSEDMTRLTLDTIGLCGFNYRFNSFYRDQPHPFIISMVRAAD EVMNKLQRANPDDPAYDENKRQFQEDIKVMNDLVDKIIADRKARG EQSDDLLTQMLNGKDPETGEPLDDGNIRYQIITFLIAGHETTSGLLSF ALYFLVKNPHVLQKVAEEAARVLVDPVPSYKQVKQLKYVGMVLN EALRLWPTAPAFSLYAKEDTVLGGEYPLEKGDEVMVLIPQLHRDKT VWGDDVEEFRPERFENPSAIPQHAFKPFGNGQRACIGQQFALHEAT LVLGMMLKHFDFEDHTNYELDIKETLTLKPKGFVVKAKSKKIPLGG IPSPSTEQSAKKVRKKAENAHNTPLLVLYGSNMGTAEGTARDLADI AMSKGFAPQVATLDSHAGNLPREGAVLIVTASYNGHPPDNAKQFV DWLDQASADEVKGVRYSVFGCGDKNWATTYQKVPAFIDETLAAK GAENIADRGEADASDDFEGTYEEWREHMWSDVAAYFNLDIENSED NKSTLSLQFVDSAADMPLAKMHGAFSTNVVASKELQQPGSARSTR HLEIELPKEASYQEGDHLGVIPRNYEGIVNRVTARFGLDASQQIRLE AEEEKLAHLPLAKTVSVEELLQYVELQDPVTRTQLRAMAAKTVCPP HKVELEALLEKQAYKEQVLAKRLTMLELLEKYPACEMKFSEFIALL PSIRPRYYSISSSPRVDEKQASITVSVVSGEAWSGYGEYKGIASNYLA ELQEGDTITCFISTPQSEFTLPKDPETPLIMVGPGTGVAPFRGFVQAR KQLKEQGQSLGEAHLYFGCRSPHEDYLYQEELENAQSEGIITLHTAF SRMPNQPKTYVQHVMEQDGKKLIELLDQGAHFYICGDGSQMAPAV EATLMKSYADVHQVSEADARLWLQQLEEKGRYAKDVWAG | 37 |

TABLE 4-continued

N-demethylase candidate enzymes

| Name | Sequence | SEQ ID NO: |
|---|---|---|
| CYP3A4-1 | MALIPDLAMETWLLLAVSLVLLYLYGTHSHGLFKKLGIPGPTPLPFL GNILSYHKGFCMFDMECHKKYGKVWGFYDGQQPVLAITDPDMIKT VLVKECYSVFTNRRPFGPVGFMKSAISIAEDEEWKRLRSLLSPTFTS GKLKEMVPIIAQYGDVLVRNLRREAETGKPVTLKDVFGAYSMDVIT STSFGVNIDSLNNPQDPFVENTKKLLRFDFLDPFFLSITVFPFLIPILEV LNICVFPREVTNFLRKSVKRMKESRLEDTQKHRVDFLQLMIDSQNS KETESHKALSDLELVAQSIIFIFAGYETTSSVLSFIMYELATHPDVQQ KLQEEIDAVLPNKAPPTYDTVLQMEYLDMVVNETLRLFPIAMRLER VCKKDVEINGMFIPKGVVVMIPSYALHRDPKYWTEPEKFLPERFSK KNKDNIDPYIYTPFGSGPRNCIGMRFALMNMKLALIRVLQNFSFKPC KETQIPLKLSLGGLLQPEKPVVLKVESRDGTVSGA | 38 |
| CYP3A4-2 | MALIPDLAMETWLLLAVSLVLLYLYGTHSHGLFKKLGIPGPTPLPFL GNILSYHKGFCMFDMECHKKYGKVWGFYDGQQPVLAITDPDMIKT VLVKECYSVFTNRRPFGPVGFMKSAISIAEDEEWKRLRSLLSPTFTS GKLKEMVPIIAQYGDVLVRNLRREAETGKPVTLKDVFGAYSMDVIT STSFGVNIDSLNNPQDPFVENTKKLLRFDFLDPFFLSIIFPFLIPILEVL NICVFPREVTNFLRKSVKRMKESRLEDTQKHRVDFLQLMIDSQNSK ETESHKALSDLELVAQSIIFIFAGYETTSSVLSFIMYELATHPDVQQK LQEEIDAVLPNKAPPTYDTVLQMEYLDMVVNETLRLFPIAMRLERV CKKDVEINGMFIPKGVVVMIPSYALHRDPKYWTEPEKFLPERFSKK NKDNIDPYIYTPFGSGPRNCIGMRFALMNMKLALIRVLQNFSFKPCK ETQIPLKLSLGGLLQPEKPVVLKVESRDGTVSGA | 39 |
| McaCYP82-4 | MIMMFIDYYSSWLPQTLLLQSILLAVSLVIFINLFLTRRRSYSSKSHT NIIHPPKAAGALPVIGHLYTLFRGLSAGVPLYRQLDAMADRYGPAFI IHLGVYPTLVVTCRELAKECFTTNDQTFATRPSTCAGKYIGYNYAFF GFAPYGPYWREARKIATVELLSNYRLDSLRHVREAEVGRNVDELY ALHASSSTNKQNMMKIDMKQWFDQVTLNVILMMVVGKRCVTTGG NEEEVRVVKVLHEFFKHLGTLSVSDVVPYVEWMDLDGNIGRMKST AKELDCILGRWLEEHRRERRSDFMDAMLAMVEGIKIPYYDSDTVIK AICLNLLNAGSDTLGITMTWALSLLLNNRHVLKKVKDELDVHVGK NRQVEELDVKNLVYLHAVVKETLRLFPPAPLGVPHEAMEDCVVGG FHVAKGTRLVVNVWKLHRDPSVWSDPLAFKPERFLDNNTVDVRG QHFQLLPFGSGRRGCPGITFALQVAHLTLARLLHGFEWDTPDGAPV DMSEVSVLTTAKKNPVEVLFTPRLPAEVYTQN | 40 |
| NsaCYP82-4 | MLSIHDSTMVFLQLQAICGIFGFIIITWWTRWKSSNKMKAPEVAGA WPVIGHLHLLGGGRPLYQLLGDMSDKYGPAFTLRMGIQKALVVSS WEVAKECLTTNDRALATRPSSAGGKYMGYNNALIPFSPYGPYWRD MRKIATLELLSNHRLEELKHVREMEINTCISDMYKLCQVEDGVEIKP ISVDLSQWFADLTFNVVVMMITGKRYIGSTDAGDMNEIRHFQAALV KFMRLLRISLLVDVFPVLQWINYGGFKGVMKSTARDIDSVLENWLQ EHQRKRLSPDFNGNHDFIDVMISTLEGTEFSDYDHNTIIKAISMAMV VGGTDTTTTTLIWAISLLLNNPNAMKKVQEELEIHVGKERNVDGSD IQHLVYLQAVVKETLRLYPPVPLSVMHQAMEDCVIGSYNIQAGTRV LFNLWKLHRDSSVWSDPLEFRPERFLTSHVDVDVRGQHFELIPFGSG RRSCPGISFALQVIHLTIARLFHGFNLTTPGNSSVDMSEISGATLSKV TPLEVLVTPRLSSKLYN | 41 |
| HcaCYP82-10 | MDSLLQLQIIGALAALIFTYKLLKVICRSPMTDGMEAPEPPGAWPIIG HLHLLGGQDPIARTLGVMTDKYGPILKLRLGVHTGLVVSNWELAK ECFTTNDRVLASRPMGAAGKYLGYNYAIFGLAPHGPYWSEVRKIV LRELLSNQSLEKLKHVRISEINTCLKNLFSLNNGNTPIKVDMKQWFE RPMFNVVTMMIAGKRYFSMENDNEAMNFRKVATEFMYLTGVFVV SDALPYLEWLDLQGHVSAMKRTAKELDIHVGKWLEEHRRAKLLGE TKNEDDFVDVLLTILPEDLKDNQTYIHDRDTIIKATALALFLAASDT TAITLTWALSLILNNPDVLKRAQDELDKHVGKEKLVKESDIINLVYL QAIIKETLRLYPAAPLLLPHEAMEDCTVGGYHVPKGTRIFVNIWKLQ RDPRVWFDPNEFRPERFLTTHANVDFKGQHFEYIPFSSGRRVCPGIT FSTQIMHLTLAHLLHEFNIVTPTKSNAGVDMTESLGITMPKATPLEV LLTPRLPSNLYNQYRD | 42 |
| EcaCYP82-7 | MNLLIFFQFLLQFQVLVGLSVLLAFSYYLWVSKNPKINKFKGKGAL LAPQAAGAWPIVGHLPQLVGPKPLFRILGAMADNYGPIFMLRFGVH PTVVVSSWEMTKECFTTNDRHLASRPSNAASQYLIYEVYALFGFSL YGSSYWRDARKIATLELLSHRRLELLKHVPYTEIDTCIKQLHRLWT KNNKNQNNPELKVEMNQFFTDLTMNVILKLVVGKRFFNVDDAAD HEKEEARKIQGTIFEFFKLTEGSVSAGALPLLNWLDLNGQKRAMKR TAKKMDSIAEKLLDEHRQKRLSKEGVKGTHDHNDFMDVLLSILDA DQGDYSHHPFNYSRDHVIKATTLSMILSSMSISVSLSWALSLLLNNR HVLKKAQDELDMNVGKDRQVEEGDIKNLVYLQAIVKETFRMYPA NPLLLPHEAIEDCKIGGFNVPAGTRVVVNAWKLQHDPRVWSNPSEF KPERFLNDQAAKVVDVRGQNFEYLPFGSGRRVCPGISFSLQTIHMSL ARLVQAFELGTPSNERIDMTEGSGLTMPKTTPLHVLLNPRLPLPLYE | 43 |

TABLE 4-continued

N-demethylase candidate enzymes

| Name | Sequence | SEQ ID NO: |
|---|---|---|
| GflCYP82-8 | MELINSLEIQPITISILALLTVSILLYKIIWNHGSRKNNKSNKNNRKTS SSAGVVEIPGAWPIIGHLHLFNGSEQMFHKLGSLADQYGPAPFFIRF GSRKYVVVSNWELVKTCFTAQSQIFVSRPPMLAMNILFFPKDSLSYI QHGDHWRELRKISSTKLLSSHRVETQKHLIASEVDYCFKQLYKLSN NGEFTLVRLNTWCEDMALNVHVRMIAGMKNYVAAPGSGEYGGQ ARRYRKALEEALDLLNQFTITDVVPWLGWLDHFRDVVGRMKRCG AELDSIFATWVEEHRVKRASGKGGDVEPDFIDLCWESMEQLPGNDP ATVIKLMCKEHIFNGSGTSSLTLAWILSLIMNNPYVIKKAREELEKH VGNHRQVEESDLPNLLYIQAIIKEGMRLYTPGPFIDRNTTEDYEING VHIPAGTCLYVNLWKIHRDPNVYEDPLEFKPERFLKNNSDLDLKGQ NYQLLPFGAGRRICPGVSLALPLMYLTVSRLIHGFDMKLPKGVEKA DMTAHGGVINQRAYPLEVLLKPRLTFQQA | 44 |
| SdiCYP82-3 | MTIGALALLSFIYFLRVSVIKRTKYTNTAVTATNKLENDEDEANHSK RVVAPPEVAGAWPILGHLPQLVGLKQPLFRVLGDMADKYGPIFIVR FGMYPTLVVSSWEMAKECFTTNDRVLASRPASASGKYLTYNYAMF GFTNGPYWREIRKISMLELLSHRRVELLKHVPSTEIDSSIKQLYHLW VENQNQNKQGDHQVKVDMSQLLRDLTLNIVLKLVVGKRLFNNND MDHEQDEAARKLQKTMVELIKVAGASVASDALPFLGWLDVDGLK RTMKRIAKEIDVIAERWLQEHRQKKLTSNDKGGSNNIQGGGGDND FMDVMLSILDDDSNFFINYNRDTVIKATSLTMILAGSDTTTLSLTWA LTLLATNPGALRKAQDELDTKVGRDRQVDERDIKNLVYLQAIVKET LRMYPAAPLAIPHEATQDCIVGGYHVTAGTRVWVNLWKLQRDPH AWPNPSEFRPERFLAVENDCKQQGTCDGEAANMDFRGQHFEYMPF GSGRRMCPGINFAIQIIHMTLARLLHSFELRVPEEEVIDMAEDSGLTI SKVTPLELLLTPRLPLPLYI | 45 |
| SdiCYP82-6 | FCQFQGIVGILLAFLTFLYYLWRASITGLRTKPKHNDFKVTKAAPEA DGAWPIVGHFAQFIGPRPLFRILGDMADKYGSIFMVRFGMYPTLVV SSWEMAKECFTTNDRFLASRPASAAGKYLTYDFAMLSFSFYGPYW REIRKISMLELLSHRRVELLKHVPSTEIDSSIKQLYHLWVENQNQNK QGDHQVKVDMSQLLRDLTLNIVLKLVVGKRLFNNNDMDHEQDEA ARKLQKTMVELIKVAGASVASDALPFLGWLDVDGLKRTMKRIAKE IDVIAERWLQEHRQKKLTSNDKGGSNNIQGGGGDNDFMDVMLSIL DDDSNFFINYNRDTVIKATSLTMILAGSDTTTLSLTWALTLLATYPL CALRKAQDELDTKVGRDRQVDERDIKNLVYLQAIVKETLRMYPAA PLAIPHEATQDCIVGGYHVTAGTRVWVNLWKLQRDPHAWPNPSEF RPERFLAVENDCKQQGTCDGEAANMDFRGQHFEYMPFGSGRRMC PGINFAIQIIHMTLARLLHSFELRVPEEEVIDMAEDSGLTISKVTPLEL LLTPRLPLPLYI | 46 |
| CmaCYP82-6 | MDLFIFFSRFQYIVGLLAFLTFFYYLWRVSITGTRIKTNQNIMNGTN MMAPEAAGAWPIVGHLPQLVGPQPLFKILGDMADKYGSIFMVRFG MHPTLVVSSWEMAKECFTTNDKFLASRPTSAGGKYLTYDFAMPGF SFYGPYWREIRKISTLELLSHRRVELLKHVPYTEIGGSIKQLYKLWM ETQNQNKQRDDHQVKVDMSQVFGYLTLNTVLKLVVGKGLFNNND MNHEQEEGRKLHETVLEFFKLAGVSVASDALPFLGWLDVDGQKRS MKRIAKEMDLIAERWLQEHRQKRLTSNNKASSGHDDFMSVLLSILD DDSNFFYNYNRDTVIKATSLNLILAASDTTSVSLTWVLSLLVTNPGAL KKVQDELDTKVGRNRHVEERDIEKLVYLQATVKETLRMYPAGPLS VPHEATQDCTVGGYQVTAGTRLVVNVWKLQRDPRVWPNPSEFKP ERFLPDGCEVGCGEAANMDFRGQHFEYIPFGSGRRMCPGIDFAIQII HMTLACLLHAFEFQVPSSLDKHLVPAVIDMSEGSGLTMPKVTPLEV LLNPRLPLPLYEL | 47 |
| EcaCYP82-5 | MEKPILLQLQPGILGLLALMCFLYYVIKVSLSTRNCNQLVRHPPEAA GSWPIVGHLPQLVGSGKPLFRVLGDMADKFGPIFMVRFGVHPTLVV SSWEMAKECFTSNDKFLASRPPSAASIYMAYDHAMLGFSSYGPYW REIRKISTLHLLSHRRLELLKHVPHLEIHNFIKGLYGIWKDHQKQQQ QPTARDDQDSVMLEMSQLFGYLTLNIVLSLVVGKRVCNYHADGHL DDGEEAGQGQKLHQTITDFFKLSGVSVASDALPFLGLFDLDGQKKI MKRVAKEMDFVAERWLQDKKSSLLLSSKSNNKQNEAGEGDVDDF MDVLMSTLPDDDDSFFTKYSRDTVIKANSLSMVVAGSDTTSVSLT WALSLLLNNIQVLRKAQDELDTKVGRDRHVEEKDIDNLVYLQAIV KETLRMYPAGPLSVPHEAIEDCNVGGYHIKTGTRLLVNIWKLQRDP RVWSNPSEFRPERFLDNQSNGTLLDFRGQHFEYIPFGSRRMCPGV NLATPILHMTLARLLQSFDLTTPSSSPVDMTEGSGLTMPKVTPLKVL LTPRLPLPLYDY | 48 |
| PbrCYP82-5 | MDVAIIVDHHYLQPFVSIAGLLALLSFFYCIWVFIIRPRIIKSNLDERK LSPSSPPEVAGAWPIVGHLPQLIGSTPLFKILADMSNKYGPIFMVRFG MYPTLVVSSWEMSKECFTTNDRLFATRPPSAAGKYLTKALFAFSVY GPYWREIRKISTIHLLSLRRLELLKHGRYLEIDKCMKRLFEYWMEH HKNIISTTSSVKVNMSQVFAELSLNVVLKIIVGKTLFIKNGNEDYTKE | 49 |

TABLE 4-continued

N-demethylase candidate enzymes

| Name | Sequence | SEQ ID NO: |
|---|---|---|
| | EEEGQKLHKTILKFMELAGVSVASDVLPFLGWLDVDGQKKQMKR VYKEMNLIASKWLGEHRERKRLQIIQKRGAARGSNYDDGNDFMDV LMSILDEENDDLFFGYSRDTVIKSTCLQLIVAASDTTSLAMTWALSL LLTNPNVLQKAQDELDTKVGRDRIIEEHDIECLVYLQAIVKETLRLY PPAPLSLPHEAMEDCTVGGYQVKAGTRLVVNLWKLQRDPRVWSN PLEFKPERFLPQSDGGFGGEEARMDFRGQHFEYTPFGSGRRICPGIDF FLQTVHMALARLLQAFDFNTAGGLVIDMVEGPGLTMPKVTPLEVH LNP RLPVTLY | |
| PbrCYP82-6 | MQVDWPNILQKYYPIITCSLLTLLSFYYIWVSITKPSRNSKTKLPPPE VAGSWPIVGHLPQLVGSTPLFKILANMSDKYGPIFMVRFGMHPTLV VSSWEMSKECFTTNDKFLASRPPSASAKYLGYDNAMFVFSDYGPY WREIRKISTLQLLTHKRLDSLKNIPYLEINSCVKTLYTRWAKTQSQIK QNVGGAADDFVKVDMTEMFGHLNLNVVLRLVVGKPIFIQKDNAD EDYTKDGHNKEELGQKLHKTIIEFFELAGASVASDVLPYLGWLDVD GQKKRMKKIAMEMDLFAQKWLEEHRQKGINHDNENDFMAVLISV LGEGKDDHIFGYSRDTVIKATCLTLIVAATDTTLVSLTWALSLLLTN PRVLSKAQDELDTVVGKERNVEDRDVNHLVYLQAVIKETLRLYPPS PLAVPHEAIENCNVGGYEVKARTRLLVNLWKIHRDPRVWSNPLEFK PERFLPKLDGGTGEASKLDFKGQDFVYTPFGSGRRMCPGINFASQTL HMTLARLLHAFDFDIESNGLVIDMTEGSGLTMPKVTPLQVHLRPRL PATLY | 50 |
| McaCYP82-4 | MIMMFIDYYSSWLPQTLLLQSILLAVSLVIFINLFLTRRRSYSSKSHT NIIHPPKAAGALPVIGHLYTLFRGLSAGVPLYRQLDAMADRYGPAFI IHLGVYPTLVVTCRELAKECFTTNDQTFATRPSTCAGKYIGYNYAFF GFAPYGPYWREARKIATVELLSNYRLDSLRHVREAEVGRNVDELY ALHASSSTNKQNMMKIDMKQWFDQVTLNVILMMVVGKRCVTTGG NEEEVRVVKVLHEFFKHLGTLSVSDVVPYVEWMDLDGNIGRMKST AKELDCILGRWLEEHRRERRSDFMDAMLAMVEGIKIPYYDSDTVIK AICLNLLNAGSDTLGITMTWALSLLLNNRHVLKKVKDELDVHVGK NRQVEELDVKNLVYLHAVVKETLRLFPPAPLGVPHEAMEDCVVGG FHVAKGTRLVVNVWKLHRDPSVWSDPLAFKPERFLDNNTVDVRG QHFQLLPFGSGRRGCPGITFALQVAHLTLARLLHGFEWDTPDGAPV DMSEVSVLTTAKKNPVEVLFTPRLPAEVYTQN | 51 |
| NsaCYP82-4 | MLSIHDSTMVFLQLQAICGIFGFIIITWWTRWKSSNKMKAPEVAGA WPVIGHLHLLGGGRPLYQLLGDMSDKYGPAFTLRMGIQKALVVSS WEVAKECLTTNDRALATRPSSAGGKYMGYNNALIPFSPYGPYWRD MRKIATLELLSNHRLEELKHVREMEINTCISDMYKLCQVEDGVEIKP ISVDLSQWFADLTFNVVVMMITGKRYIGSTDAGDMNEIRHFQAALV KFMRLLRISLLVDVFPVLQWINYGGFKGVMKSTARDIDSVLENWLQ EHQRKRLSPDFNGNHDFIDVMISTLEGTEFSDYDHNTIIKAISMAMV VGGTDTTTTLIWAISLLLNNPNAMKKVQEELEIHVGKERNVDGSD IQHLVYLQAVVKETLRLYPPVPLSVMHQAMEDCVIGSYNIQAGTRV LFNLWKLHRDSSVWSDPLEFRPERFLTSHVDVDVRGQHFELIPFGSG RRSCPGISFALQVIHLTIARLFHGFNLTTPGNSSVDMSEISGATLSKV TPLEVLVTPRLSSKLYN | 52 |
| HcaCYP82-10 | MDSLLQLQIIGALAALIFTYKLLKVICRSPMTDGMEAPEPPGAWPIIG HLHLLGGQDPIARTLGVMTDKYGPILKLRLGVHTGLVVSNWELAK ECFTTNDRVLASRPMGAAGKYLGYNYAIFGLAPHGPYWSEVRKIV LRELLSNQSLEKLKHVRISEINTCLKNLFSLNNGNTPIKVDMKQWFE RPMFNVVTMMIAGKRYFSMENDNEAMNFRKVATEFMYLTGVFVV SDALPYLEWLDLQGHVSAMKRTAKELDIHVGKWLEEHRRAKLLGE TKNEDDFVDVLLTILPEDLKDNQTYIHDRDTIIKATALALFLAASDT TAITLTWALSLILNNPDVLKRAQDELDKHVGKEKLVKESDIINLVYL QAIIKETLRLYPAAPLLLPHEAMEDCTVGGYHVPKGTRIFVNIWKLQ RDPRVWFDPNEFRPERFLTTHANVDFKGQHFEYIPFSSGRRVCPGIT FSTQIMHLTLAHLLHEFNIVTPTKSNAGVDMTESLGITMPKATPLEV LLTPRLPSNLYNQYRD | 53 |
| EcaCYP82-7 | MNLLIFFQFLLQFQVLVGLSVLLAFSYYLWVSKNPKINKFKGKGAL LAPQAAGAWPIVGHLPQLVGPKPLFRILGAMADNYGPIFMLRFGVH PTVVVSSWEMTKECFTTNDRHLASRPSNAASQYLIYEVYALFGFSL YGSSYWRDARKIATLELLSHRRLELLKHVPYTEIDTCIKQLHRLWT KNNKNQNNPELKVEMNQFFTDLTMNVILKLVVGKRFFNVDDAAD HEKEEARKIQGTIFEFFKLTEGSVSAGALPLLNWLDLNGQKRAMKR TAKKMDSIAEKLLDEHRQKRLSKEGVKGTHDHNDFMDVLLSILDA DQGDYSHHPFNYSRDHVIKATTLSMILSSMSISVSLSWALSLLLNNR HVLKKAQDELDMNVGKDRQVEEGDIKNLVYLQAIVKETFRMYPA NPLLLLPHEAIEDCKIGGFNVPAGTRVVVNAWKLQHDPRVWSNPSEF KPERFLNDQAAKVVDVRGQNFEYLPFGSGRRVCPGISFSLQTIHMSL ARLVQAFELGTPSNERIDMTEGSGLTMPKTTPLHVLLNPRLPLPLYE | 54 |

TABLE 4-continued

N-demethylase candidate enzymes

| Name | Sequence | SEQ ID NO: |
|---|---|---|
| GflCYP82-8 | MELINSLEIQPITISILALLTVSILLYKIIWNHGSRKNNKSNKNNRKTS SSAGVVEIPGAWPIIGHLHLFNGSEQMFHKLGSLADQYGPAPFFIRF GSRKYVVVSNWELVKTCFTAQSQIFVSRPPMLAMNILFFPKDSLSYI QHGDHWRELRKISSTKLLSSHRVETQKHLIASEVDYCFKQLYKLSN NGEFTLVRLNTWCEDMALNVHVRMIAGMKNYVAAPGSGEYGGQ ARRYRKALEEALDLLNQFTITDVVPWLGWLDHFRDVVGRMKRCG AELDSIFATWVEEHRVKRASGKGGDVEPDFIDLCWESMEQLPGNDP ATVIKLMCKEHIFNGSGTSSLTLAWILSLIMNNPYVIKKAREELEKH VGNHRQVEESDLPNLLYIQAIIKEGMRLYTPGPFIDRNTTEDYEING VHIPAGTCLYVNLWKIHRDPNVYEDPLEFKPERFLKNNSDLDLKGQ NYQLLPFGAGRRICPGVSLALPLMYLTVSRLIHGFDMKLPKGVEKA DMTAHGGVINQRAYPLEVLLKPRLTFQQA | 55 |
| SdiCYP82-3 | MTIGALALLSFIYFLRVSVIKRTKYTNTAVTATNKLENDEDEANHSK RVVAPPEVAGAWPILGHLPQLVGLKQPLFRVLGDMADKYGPIFIVR FGMYPTLVVSSWEMAKECFTTNDRVLASRPASASGKYLTYNYAMF GFTNGPYWREIRKISMLELLSHRRVELLKHVPSTEIDSSIKQLYHLW VENQNQNKQGDHQVKVDMSQLLRDLTLNIVLKLVVGKRLFNNND MDHEQDEAARKLQKTMVELIKVAGASVASDALPFLGWLDVDGLK RTMKRIAKEIDVIAERWLQEHRQKKLTSNDKGGSNNIQGGGGDND FMDVMLSILDDDSNFFINYNRDTVIKATSLTMILAGSDTTTLSLTWA LTLLATNPGALRKAQDELDTKVGRDRQVDERDIKNLVYLQAIVKET LRMYPAAPLAIPHEATQDCIVGGYHVTAGTRVWVNLWKLQRDPH AWPNPSEFRPERFLAVENDCKQQGTCDGEAANMDFRGQHFEYMPF GSGRRMCPGINFAIQIIHMTLARLLHSFELRVPEEEVIDMAEDSGLTI SKVTPLELLLTPRLPLPLYI | 56 |
| SdiCYP82-6 | FCQFQGIVGILLAFLTFLYYLWRASITGLRTKPKHNDFKVTKAAPEA DGAWPIVGHFAQFIGPRPLFRILGDMADKYGSIFMVRFGMYPTLVV SSWEMAKECFTTNDRFLASRPASAAGKYLTYDFAMLSFSFYGPYW REIRKISMLELLSHRRVELLKHVPSTEIDSSIKQLYHLWVENQNQNK QGDHQVKVDMSQLLRDLTLNIVLKLVVGKRLFNNNDMDHEQDEA ARKLQKTMVELIKVAGASVASDALPFLGWLDVDGLKRTMKRIAKE IDVIAERWLQEHRQKKLTSNDKGGSNNIQGGGGDNDFMDVMLSIL DDDSNFFINYNRDTVIKATSLTMILAGSDTTTLSLTWALTLLATYPL CALRKAQDELDTKVGRDRQVDERDIKNLVYLQAIVKETLRMYPAA PLAIPHEATQDCIVGGYHVTAGTRVWVNLWKLQRDPHAWPNPSEF RPERFLAVENDCKQQGTCDGEAANMDFRGQHFEYMPFGSGRRMC PGINFAIQIIHMTLARLLHSFELRVPEEEVIDMAEDSGLTISKVTPLEL LLTPRLPLPLYI | 57 |
| CmaCYP82-6 | MDLFIFFSRFQYIVGLLAFLTFFYYLWRVSITGTRIKTNQNIMNGTN MMAPEAAGAWPIVGHLPQLVGPQPLFKILGDMADKYGSIFMVRFG MHPTLVVSSWEMAKECFTTNDKFLASRPTSAGGKYLTYDFAMPGF SFYGPYWREIRKISTLELLSHRRVELLKHVPYTEIGGSIKQLYKLWM ETQNQNKQRDDHQVKVDMSQVFGYLTLNTVLKLVVGKGLFNNND MNHEQEEGRKLHETVLEFFKLAGVSVASDALPFLGWLDVDGQKRS MKRIAKEMDLIAERWLQEHRQKRLTSNNKASSGHDDFMSVLLSILD DDSNFFNYNRDTVIKATSLNLILAASDTTSVSLTWVLSLLVTNPGAL KKVQDELDTKVGRNRHVEERDIEKLVYLQATVKETLRMYPAGPLS VPHEATQDCTVGGYQVTAGTRLVVNVWKLQRDPRVWPNPSEFKP ERFLPDGCEVGCGEAANMDFRGQHFEYIPFGSGRRMCPGIDFAIQII HMTLACLLHAFEFQVPSSLDKHLVPAVIDMSEGSGLTMPKVTPLEV LLNPRLPLPLYEL | 58 |
| EcaCYP82-5 | MEKPILLQLQPGILGLLALMCFLYYVIKVSLSTRNCNQLVRHPPEAA GSWPIVGHLPQLVGSGKPLFRVLGDMADKFGPIFMVRFGVHPTLVV SSWEMAKECFTSNDKFLASRPPSAASIYMAYDHAMLGFSSYGPYW REIRKISTLHLLSHRRLELLKHVPHLEIHNFIKGLYGIWKDHQKQQQ QPTARDDQDSVMLEMSQLFGYLTLNIVLSLVVGKRVCNYHADGHL DDGEEAGQGQKLHQTITDFFKLSGVSVASDALPFLGLFDLDGQKKI MKRVAKEMDFVAERWLQDKKSSLLLSSKSNNKQNEAGEGDVDDF MDVLMSTLPDDDDSFFTKYSRDTVIKANSLSMVVAGSDTTSVSLT WALSLLLNNIQVLRKAQDELDTKVGRDRHVEEKDIDNLVYLQAIV KETLRMYPAGPLSVPHEAIEDCNVGGYHIKTGTRLLVNIWKLQRDP RVWSNPSEFRPERFLDNQSNGTLLDFRGQHFEYIPFGSGRRMCPGV NLATPILHMTLARLLQSFDLTTPSSSPVDMTEGSGLTMPKVTPLKVL LTPRLPLPLYDY | 59 |
| PbrCYP82-5 | MDVAIIVDHHYLQPFVSIAGLLALLSFFYCIWVFIIRPRIIKSNLDERK LSPSSPPEVAGAWPIVGHLPQLIGSTPLFKILADMSNKYGPIFMVRFG MYPTLVVSSWEMSKECFTTNDRLFATRPPSAAGKYLTKALFAFSVY GPYWREIRKISTIHLLSLRRLELLKHGRYLEIDKCMKRLFEYWMEH HKNIISTTSSVKVNMSQVFAELSLNVVLKIIVGKTLFIKNGNEDYTKE | 60 |

TABLE 4-continued

N-demethylase candidate enzymes

| Name | Sequence | SEQ ID NO: |
|------|----------|------------|
| | EEEGQKLHKTILKFMELAGVSVASDVLPFLGWLDVDGQKKQMKR VYKEMNLIASKWLGEHRERKRLQIIQKRGAARGSNYDDGNDFMDV LMSILDEENDDLFFGYSRDTVIKSTCLQLIVAASDTTSLAMTWALSL LLTNPNVLQKAQDELDTKVGRDRIIEEHDIECLVYLQAIVKETLRLY PPAPLSLPHEAMEDCTVGGYQVKAGTRLVVNLWKLQRDPRVWSN PLEFKPERFLPQSDGGFGGEEARMDFRGQHFEYTPFGSGRRICPGIDF FLQTVHMALARLLQAFDFNTAGGLVIDMVEGPGLTMPKVTPLEVH LNPRLPVTLY | |
| PbrCYP82-6 | MQVDWPNILQKYYPIITCSLLTLLSFYYIWVSITKPSRNSKTKLPPPE VAGSWPIVGHLPQLVGSTPLFKILANMSDKYGPIFMVRFGMHPTLV VSSWEMSKECFTTNDKFLASRPPSASAKYLGYDNAMFVFSDYGPY WREIRKISTLQLLTHKRLDSLKNIPYLEINSCVKTLYTRWAKTQSQIK QNVGGAADDFVKVDMTEMFGHLNLNVVLRLVVGKPIFIQKDNAD EDYTKDGHNKEELGQKLHKTIIEFFELAGASVASDVLPYLGWLDVD GQKKRMKKIAMEMDLFAQKWLEEHRQKGINHDNENDFMAVLISV LGEGKDDHIFGYSRDTVIKATCLTLIVAATDTTLVSLTWALSLLLTN PRVLSKAQDELDTVVGKERNVEDRDVNHLVYLQAVIKETLRLYPPS PLAVPHEAIENCNVGGYEVKARTRLLVNLWKIHRDPRVWSNPLEFK PERFLPKLDGGTGEASKLDFKGQDFVYTPFGSGRRMCPGINFASQTL HMTLARLLHAFDFDIESNGLVIDMTEGSGLTMPKVTPLQVHLRPRL PATLY | 61 |
| PbrCYP82-7 | MMDLAMFIDQYFSLAKIAGLLALLSFFYYLWISTLWSPRNPKLSSVS PPEVAGAWPILGHLPQLLGSRPLFKILADMSDNYGPIFMVRFGMHPT LVVSSWEMAKECFTTNDRFLAGRPSGAANKYLTFALFGFSTYGPY WREIRKIATLHLLSHRRLELLKHVPDLEVTNCMKHLHRRWIDSQNQ IKQNDAAAGSVKVDMGRVFGELTLNVVLKLVAGKSIFFKNDNTRQ YDSKDGHNKEEEEGKKLHKTIIDFYSLAGASVASDVLPFLGWLDVD GQKKRMKRVAKDMDFIAAKWLEEHRHQKRQTVLSSSATLGSSNH DDAKDFMDVLMSILDGENDDLFFGYSRDTVIKTTCLQLIAAAADTT SVTMTWALALLITNPTILRKAQDELDTKVGKDRNIEERDINDLVYL QAIVKETLRMYPAGPLNVPHEAIADCNIGGYEVRAGTRLLVNLWK MHRDPRVWSNPSEFKPERFLPQLDGGSGGEAANLDFRGQDFEYLPF SAGRRMCPGIDFSLQTLHMTLARLLHGFDFNNDSAGIIIDMEEGSGL TMPKLTPLEIYLCPRLPAKLY | 62 |

TABLE 5

N-methyltransferase and N-modifying candidate enzymes

| Name | Sequence | SEQ ID NO: |
|------|----------|------------|
| TfCNMT | MAVEGKQVAPKKAIIVELLKKLELGLVPDDEIKKLIRIQLGRRLQWG CKSTYEEQIAQLVNLTHSLRQMKIATEVETLDDQMYEVPIDFLKIMN GSNLKGSCCYFKNDSTTLDEAEIAMLELYCERAQIKDGHSVLDLGCG QGALTLYVAQKYKNSRVTAVTNSVSQKEFIEEESRKRNLSNVEVLL ADITTHKMPDTYDRILVVELFEHMKNYELLLRKIKEWMAKDGLLFV EHICHKTFAYHYEPIDEDDWFTEYVFPAGTMIIPSASFFLYFQDDVSV VNHWTLSGKHFSRTNEEWLKRLDANVELIKPMFVTITGQCRQEAMK LINYWRGFCLSGMEMFGYNNGEEWMASHVLFKKK | 63 |
| CjCNMT | MAVEAKQTKKAAIVELLKQLELGLVPYDDIKQLIRRELARRLQWGY KPTYEEQIAEIQNLTHSLRQMKIATEVETLDSQLYEIPIEFLKIMNGSN LKGSCCYFKEDSTTLDEAEIAMLDLYCERAQIQDGQSVLDLGCGQG ALTLHVAQKYKNCRVTAVTNSVSQKEYIEEESRRRNLLNVEVKLAD ITTHEMAETYDRILVIELFEHMKNYELLLRKISEWISKDGLLFLEHICH KTFAYHYEPLDDDDWFTEYVFPAGTMIIPSASFFLYFQDDVSVVNH WTLSGKHFSRTNEEWLKRLDANLDVIKPMFETLMGNEEEAVKLINY WRGFCLSGMEMFGYNNGEEWMASHVLFKKK | 64 |
| PsCNMT | MQLKAKEELLRNMELGLIPDQEIRQLIRVELEKRLQWGYKETHEEQL SQLLDLVHSLKGMKMATEMENLDLKLYEAPMEFLKIQHGSNMKQS AGYYTDESTTLDEAEIAMLDLYMERAQIKDGQSVLDLGCGLGAVAL FGANKFKKCQFTGVTSSVEQKDYIEGKCKELKLTNVKVLLADITTYE TEERFDRIFAVELIEHMKNYQLLLKKISEWMKDDGLLFVEHVCHKTL AYHYEPVDAEDWYTNYIFPAGTLTLSSASMLLYFQDDVSVVNQWTL SGKHYSRSHEEWLKNMDKNIVEFKEIMRSITKTEKEAIKLLNFWRIFC MCGAELFGYKNGEEWMLTHLLFKKK | 65 |

TABLE 5-continued

N-methyltransferase and N-modifying candidate enzymes

| Name | Sequence | SEQ ID NO: |
|---|---|---|
| PsTNMT | MGSIDEVKKESAGETLGRLLKGEIKDEELKKLIKFQFEKRLQWGYKS SHQEQLSFNLDFIKSLKKMEMSGEIETMNKETYELPSEFLEAVFGKT VKQSMCYFTHESATIDEAEEAAHELYCERAQIKDGQTVLDIGCGQG GLVLYIAQKYKNCHVTGLTNSKAQVNYLLKQAEKLGLTNVDAILAD VTQYESDKTYDRLLMIEAIEHMKNLQLFMKKLSTWMTKESLLFVDH VCHKTFAHFFEAVDEDDWYSGFIFPPGCATILAANSLLYFQDDVSVV DHWVVNGMHMARSVDIWRKALDKNMEAAKEILLPGLGGSHETVN GVVTHIRTFCMGGYEQFSMNNGDEWMVAQLLFKKK | 66 |
| EcTNMT | MGSSAGEIMGRLMKGEIEDEELKKLIRHQWDRRIEWGYKPTHEKQL AFNLDFIKGLKEMVMSGEIDTMNKETYELPTAFLEAVFGKTVKQSC CYFKDENSTIDEAEEAAHELYCERAQIKDGQTVLDIGCGQGGLVLYI AEKYKNCHVTGLTNSKAQANYIEQQAEKLELTNVDVIFADVTKFDT DKTYDRILVVETIEHMKNIQLFMKKLSTWMTEDSLLFVDHISHKTFN HNFEALDEDDWYSGFIFPKGCVTILSSSTLLYFQDDVSALDHWVVNG MHMARSVEAWRKKLDETIEAAREILEPGLGSKEAVNQVITHIRTFCI GGYEQFSYNNGEEWMITQILFKKK | 67 |
| PsRNMT | MSTTMETTKISQQDDLWKNMELGQISDEEVRRLMKIGIEKRIKWGT KPTQQEQLAQLLDFNKSLRGMKMATEIDTLENHKIYETPESFNQIIGG KESAGLFTDETTTTMEEANTKMMDLYCERAGLKDGHTILDLGCGA GLLVLHLAKKYKKSKITGITNTSSHKEYILKQCKNLNLSNVEIILADV TKVDIESTFDRVFVIGLIEHMKNFELFLRKISKWMKDDGLLLLEHLC HKSFSDHWEPLSEDDWYAKNFFPSGTLVIPSATCLLYFQEDVTVIDH WILSGNNFARSNEVILKRIDGKIEEVKDIFMSFYGIGREEAVKLINWW RLLCITANELFKYNNGEEWLISQLLFKKKLMTCI | 68 |
| TfPNMT | METKQTKKEAVANLIKRIEHGEVSDEEIRGMMKIQVQKRLKWGYKP THEQQLAQLVTFAQSLKGMEMAEEVDTLDAELYEIPLPFLHIMCGKT LKFSPGYFKDESTTLDESEVYMMDLYCERAQIKDGQSILDLGCGHGS LTLHVAQKYRGCKVTGITNSVSQKEFIMDQCKKLDLSNVEIILEDVT KFETEITYDRIFAVALIEHMKNYELFLKKVSTWIAQYGLLFVEHHCH KVFAYQYEPLDEDDWYTEYIFPSGTLVMSSSSILLYFQEDVSVVNHW TLSGKHPSLGFKQWLKRLDDNIDEVKEIFESFYGSKEKAMKFITYWR VFCIAHSQMYSTNNGEEWMLSQVLFKKK | 69 |
| PbrTNMT1 | MGSIDEVKKESAGETLGRLLKGEIKDEELKKLIKFQFEKRLQWGYKS SHQEQLSFNLDFIKSLKKMEMSGEIETMNKETYELPSEFLEAVFGKT VKQSMCYFKHESATIDEAEEAAHELYCERAQIKDGQTVLDIGCGQG GLVLYIARKYKKCHVTGLTNSKAQVNYLLKQAEKLGLTNVDAILAD VTQYESDKTYDRLLMIEAIEHMKNLQLFMKKLSTWMTEESLLFVDH VCHKTFAHFFEAVDEDDWYSGFIFPPGCATILAANSLLYFQDDVSVV DHWVVNGMHMARSVDIWRKALDKNMEAAKEILLPGLGGSHEAVN GVVTHIRTFCMGGYEQFSMNDGDEWMVAQLLFKKK | 70 |
| PbrTNMT2 | MGSIEEVKKESAEETLGRLLRGEINDEELKKLIKYQLEKRLQWGYKS SHQEQLSFNLDFINSLKKMGMSGQVEAFTNEVYELPTECFEAAYGKS MKLSGCYFKHESSTIDEAEEASHELYCERAQIKDGQTVLDIGCGQGG LVLYVAQKYKNCHVTGLTNSKEQVNYILKQAEKLGLRNVDVILAD VTQYESDKTYDRILVIGVVEHMKNMQLFIKKLSTWMAEDSLLFVDH SCHKTFNHFFEALDEDDWYSGYIFPPGCATFLSADSLLYFQDDVSVV DHWVVNGMHFARTVDAWRKKLDKNMEAVKEILLPGLGGNHEAVN GVITHIRTCCVGGYVQFSLNDGDEWMNAQLLFKKK | 71 |
| AmeNMT1 | MCLFFAEKMGLMAEANNQQQLKKEDLLKNMELGLIPDEEIRKLIRV QLEKRLNWGYKSTHEQQLSQLLHLVHSLKKMKIATEMENLDLKLY EAPFSFVQIQHGSTIKESSGLFKDESTTLDEAEIAMLDLYTKRAKIEDG QSVLDLGCGLGAVTLYVAQKFKNCYVTGITSSVEQKDFIEGRCKELK LSNVKVILADITTYETEEKYNRIFAVELIEHMKNYELLLRKISEWMKQ DGLLFIEHVCHKTLAYHYEPLDEEDWYTNYIFPAGTLTLSSATLLLYF QDDVAVVDQWTLSGKHYSRSHEEWLKRIDGNIEEVKEIMKSITKSEE EAKKLLNFWRIFCMCGAELFGYKNGEEWMMTHILFKKK | 72 |
| GflNMT1 | MDLMATSKQVKKKEELLKNMELGLVPDEEIRRLIRIELEKRLKWGY KPTHQQQLAQLLDVHSLKKMKIATEMESLDLKLYEAPFSFVQIKHG STIKESSSYFKDESMTLDEAEIAMLDLYVERAQIEDGQSVLDLGCGL GAVTLHVAKKYKNCHVTGLTNSVEQKDFIEGCKELNLSNVKVILA DVTSHEMEDKFDRIFAVELIEHMKNYELLLRRISKWMKDDGLLFIEH VCHKTFAYHYEPIDEDDWYTEYIFPAGTLTLSSASLLLYFQDDVSVV NHWTLSGKHYSRSHEEWLKRIDGNMDAVKEIMKSITKTEEEAVKLI NFWRIFCMCGAELFGYKDGEEWMMSHVLFKKKQLLQQC | 73 |
| EcaNMT1 | MVDLKVEKEELLKSMELGLVPDEDIRKHIRSQLEKRLKWGYKPNHE QQLAQLLDVIHSLKKMKISKEYESFDLRLYEAPFDFPHKIQLGTHLKES CSYYKDESTTLDEAEGAMLDLYTQKAKIEDGQSILDLGCGVGAVTL | 74 |

TABLE 5-continued

N-methyltransferase and N-modifying candidate enzymes

| Name | Sequence | SEQ ID NO: |
|------|----------|------------|
| | FVANKYKNCKVTGITSCQWQKDFIENKCKELNLTNVRVIIGDVTAYE<br>MEETFDRIFAIELIEHMKNYELLLRKISKWMKDDGLLFIEHVCHKILA<br>YPYEPIDEEDWFTEYIFPGGTLTLSSASLLLYFQDDVSVVEHSSLNGK<br>HYSRSHGEWLKNIDANIDEVKGIMRSITKTEEEAVRLVNFWRIFCMC<br>GIELFGYNNGEEWMVSHILLKKK | |
| EcaNMT2 | MAADLVVKKWNNKKELIDEMELGLVGDEEIRELIRNDLEKRLKWG<br>YKSNHEQQLAQLLHFVHSLRGMKIAADEVESFNIKVYEAPFSFNKIQ<br>LGSSLKESSCYYKHDETTLDEGEIAMMELYTEKAQIKDGQSVLDLGC<br>GLGSLTLYVANKYPNCKVTGTTASLWHKDFIESKCKEQELTNVKIVL<br>GDATTHEMEERFDRILAIGLIEHLKNYGLLLGRISKWLKDDGFLFIQH<br>VCHKTLAYPLVPVDEEDWIGEYIFPGGTLTMPSASLLLYFQDELSVV<br>DHSTLNGKHFSRTHEEWLKNIDAKIDEVKEILKSVTKTEEEVVRLTN<br>FWRIFCMFGVEMFGYNEGEEWMLSQILFKKK | 75 |
| CmaNMT4 | MASGKVVDLLKRLDSGLVSDEELRRVIRFELERRLKWGYKPTHEQQ<br>LAELLNLAHATKQMEIATKIDTLNSTMYEVPNSFLEIQLGSTLKESCL<br>YFKDESTTVDEAEIAMMDLYLERAQIKDGQIILDLGCGLGALAFHIA<br>QKYTNCNVTSVTNSVKQKEFIEEKCKILNVSNVKVILTDICTLEMEAT<br>FDRIFAIGLIEHMKNYELLLRKFSAWMKQDGLLFIEHLCHKTLGYHN<br>EPIDEDDWYTAYFFPAGTLTFIPSSFLLYFQDDVSVVNHWTLSGKHFS<br>RSNEEWLKRMDNKIDEVKEIYKAAASETKDDDIMKLIRLWRFLSISA<br>AEMFGYKDGEEWMISQVLFKKK | 76 |
| EcNMT3 | MASLVEEGSFVNNKESVKERVSELVKRLKNGLVSDEELRKLMRVEL<br>EKRLEWGYKSTHEQQLSQLIDLAHSMKKMEIAMEIDALNSTVYEVP<br>LSFLQIIHGTTIKESCLYFKDESTTVDEAEIAMMDLYLERAQIKDGQSI<br>LDLGCGLGGFSFHIASKFTGCNITAVTNSVKQKEFIEEKCKTLNVPNI<br>KVILADICTTEIENVFDRIIAIGLIEHMKNYELLLKKFSKWMTQDGLLF<br>IEHLCHKTFGYHNEPLDEDDWYTTYFFPAGTLTFIPSSFLLYFQDDVS<br>VVDHWTLNGKHFARSNEEWLKRMDEKMDEVKQIFRSNLKSENEVT<br>KTIGEWRFLSMSAAEMFGYNNGEEWMVSQLLFKKK | 77 |
| GflNMT5 | MGSNETNGELKTKEMVPDLLKRLESGLVADEELRKLIRFELERRLK<br>WGYKPTHEQQLAELLKLAHSTKQMKIATETDSLNSTMYEVPIPFLQL<br>QFGSAIKESCCYFKDESTTLDEAEVAMMDLYLERTQIKDGQSILDLG<br>CGLGALAFHIVQKYPNCNVLAITNSVEQKEFIEEKCKIRKVENVKVS<br>LADICTLEMKTTFDRIFAIGLLEHMKNYQLLLKKFSNWMKQDGLLFI<br>EHLCHKTLAYHYEPLDEDDWYTEYFFPAGTLTIISSSFLLYFQDDVSI<br>VNHWSLSGKHFSRNEEWLKRMDMKIDEVKEILEAAFENKDHDITK<br>LINHWRFLAINATEMFGYNNGEEWMVSQVLFKKK | 78 |
| ScaNMT1 | MASDHEVSNKELKKKKEVITELLKRLESGLVSDEELRGLIRFELERRL<br>RWGYKPTHEQQLAQLLNLAHSMKQMKIATEIDALNSTMYEVPIPFL<br>QIQLGSTLKESCCYFKDESTTVDEAEIAMMDLYLERAQIKDGQSILDL<br>GCGLGALAFHIAQKYTNCNITAITNSVRQKEFIEEKCKILNVSNVKVS<br>LADICTLEMEATFDRIFAIGLIEHMKNYELLLKKFSEWMKQDGLIFIE<br>HLCHKTLAYHYEPLDEDDWYTEYFFPAGTLTLISSSFLLYFQDDVSV<br>VDHWTLSGKHFSRSNEEWLKRMDEKIDEVKEIFESVSDSKDDDVTK<br>LINHWRFFCISSAEMFGYNNGEEWMISQVLFKKK | 79 |
| CchNMT3 | MIKKSKIMAFSDHHHEVVKNHSKKEMIADLLKRLEAGLVPDEEMRN<br>LFRFELERRLQWGYKSIHQEQLSQLLKLAHSTKEMTIVAEMDALNSS<br>MYELPISFLQIQLGSNLKQSSLYFKDELTTVDEAEVAIMDLYLERAQI<br>EDGQSILDLGCGLGAFSFHVARKYTNCNITAVTNSLTQKEFIEKKSKI<br>LNIQNVKVIFADVTTVEMETTFDRVFAIGLIEHMQNYELFLKKLSKW<br>MKQDGLLFIEHFCHKTLAYHYKPIDEDDWFTNLLYPNGTVISSSLLL<br>YFQDDVSVVDHWSLSGKHFSRASEESLKRMDAKMDEMKEIFESITD<br>SKEEAMKLINQWRIFCISCAEMFGYNNGEEWMTSHFLFKKKL | 80 |
| CchNMT6 | MGSSTASDHEMVIMENDSKNKQVVIADLLKRLVGGLVPDEEMRNM<br>FRFELEKRLKWGYKSTHQQQLSQLLNLVELNKGIAKIAPEMDALNS<br>AMYEVPIPYLKLMLGSTLKQSCLYFKDESTTLDEAEIEMMDLYLERA<br>DIQDGQSILDLGCGLGGLGPHIAQKYISCNITALTNSLTQKEFIEEKCK<br>TLNIPNVKVILADVTTVEIETTFDRLFAIGLVEHMENYELFLRKLSKW<br>MKQDGLLFIEHLCHKTLAYHYKPIDEDDWYSNLLYPTGTLTSASFLL<br>YFQDDLSVVDHWSLSGKHFSRATEEWLKMIDANMDKIREIYESVTE<br>SKEEATRSINQWRIFCISCAEMFGYNDGEEWMISHFLFKNKKQIE | 81 |
| CchNMT1 | MATSDQEVKTSKMEMIADLLKRLEAGLVPDDEIRSLIRVELERRLKW<br>GYKSTHQEQLDQLLLNAHSIKKMKIASTEMDGLTSTMYEVPISLVQI<br>QLGSHLKESCLYFKDETTTVDEAEIAMMDLYLERAQIKDGQSILDLG<br>CGLGAVSFHIAQKYTSCNITAVTNSVRQKEFIEEKSKTLNVPNVKVL<br>LADITTLEMEHTFDRLFAISLIEHMENYELLLRKLSEWMKQDGLLFIE<br>HLCHKTLSYHFEPMDEDDWYTNLLFPAGTLTLVSASFLLYFQDDLS | 82 |

TABLE 5-continued

N-methyltransferase and N-modifying candidate enzymes

| Name | Sequence | SEQ ID NO: |
|---|---|---|
| | VVNQWVMSGKHFSRANEEWLKNMDAKMDEMREIFESITDSEEEVV KLINHWRIFCISSAEMFAYNDGEEWMNSHVLFKKKKQIQ | |
| CchNMT2 | MAGSGANKEMIADLLKRLEVGLVPDEEIRSLIRFQLKRRLKWGYKT THQEQLEQLLSLAHSIRKMKIATEMDALNSTMYEVPISFMQIVFGSTL KESCLYFKDEATTVNEAEIAMMDLYLERAQIKDGQSILDLGCMGS LCFHIARKYTNCNITAVTNSVSQKEFIEEKSKTLNLPNVKVILADITTL EMDDTYDCLFAIGLIEHMKNYELLLRKLSNWMKQDSLLFIDHVCHK TLAYHYEPIDEDDWYTNLLFPAGTLTLVSASFLLYFQDDLSLVDHWS MSGKHFSRTNKEWLKNIDGKMDKIREIVKSITDSEEEVVKLINHWR MLCINSSEMFGFNDGEEWMNSHVLFKKKKQI | 83 |
| ScaNMT2 | MEMIADLLKRLEAGLVPDDEIRSLIRVELERRRLKWGYKSTHQEQLDQ LLNLAHSIKKMKIASTEMDGLTSTMYEVPISLVQIQLGSHLKESCLYF KDETTTVDEAEIAMMDLYLERAQIKDGQSILDLGCGLGSVCFHIARK YTSCNITAVTNSVSQKEFIEEKSKTLNVPNVKVLLADITTLEMDDTFD CLFAIGLIEHMENYELLLRKLSDWMKQDGLLFIDHVCHKTLSYHFEP MDEDDWYTNLLFPAGTLTLVSASFLLYFQDDLSLVDHWSMSGKHFS RTNKEWLKNIDGKMDKIREIVKSITDSEEEVVKLINHWRMLCINSSE MFGFNDGEEWMNSHVLFKKKKQI | 84 |
| PbrNMT2 | MCTTMDTTKISQQDDLWKNMELGLISDEEVRRLMKIETEKRIKWGT KPTQQEQLAQLLDFNKSLRGMKMATEVHALENHKIYEIPDSFNQIIG GKESAGLFTDEATTTIEEANTKMMDLYCERAGLKDGQTILDIGCGA GLLVLHLAKKYKNCKITGVTNTSWHKEHILEQCKNLNLSNVEVILA DVTTVDIERTFDRVFVIGLIEHMKNFELFLRKISKWMKDDGLLFLEH LCHKSFSDHWEPLSEDDWYAKNFFPSGTLVIPSATCLLYFQEDVTVK DHWLLSGNNFARSNEAILKRIDSKIEEVKDIFMSFYGIGEEEAVKLIN WWRLLCITANELFKYNNGEEWLISQLLFKKKLMTCI | 85 |
| PbrNMT1 | MVKGDQFQTTTMEETKISQENDLWTNMELGLIPDEEVRRLMKIEIEK RIEWGMKPTQHQQLAQLLDFTKSLRGMKMATELDKLDSKLYETPHS FNQIVNGSTLKESSGLYTDVTTTMDEASIKMMDLYCERANIKDGQTI LDLGCGPGPLVLHIAKKYSNCKITGVTNAFSQREYILEECKKLSLSNV EIILADVTSLDLETTFDRVFVIGFIEHMKNFELFLRKISKWMKDDAVL FLEHFCHKSFSYHGEPLSEDDWYAKNFFAPGTLVIPSATCLLYFQEDL AVIDHWFLSGNHFARTNEEMLKGIDGKIEEIKDIFMSFYGINEAEAVK LINWWRLFCITGAEMFSYNNGEEWFISQLLFKKK | 86 |
| EcaNMT4 | MALEQEDSMSVPERNEGVADLIKRMELGLVNDEEIRRLMRIQIENRL KWGYKPTHDQQLAQHLHFINSLKEMKMATEMDSLDSQVYESPNSF QQIMCGRSMKESAGLFMDDVTTVEEAHIRMMDLYCDKATFEDGQK ILDLGCGHGSVVLHVAQKYKGCQVTGVTNSSAQKQYILEQCKKDDL SNVEIILADVTTLEMEEKFDRVIIIGLIEHMKNFKLFFQKVSKWMKEG GLLFLENYFHKDFAYHCEKIDEDDWYDGYIFPPGSLLMPSASTLLYF QEDLTVADHWVLPGTHFAKTFEEFLKKIDLRIEEVREIFEAFYGISKE EAMKLSNYWRNFCISAMEIFNYNNGQEWMISHLLYTKK | 87 |
| CmaNMT5 | METGKNNQNMKTTIDDLWNQMMLGIVPDKEIRRLMKIELKKRLDW GYRPTHQQQLSQLLDFAKGLCNYCWTALRCMKMSAEFDTLDSKVY ETPKSFQQIMCGTTIKESSGLFMNESTTLDQAQISMLDLYFDKAKIKD GQSILDLGCGHGALILYLAQKYQNCITGVTNSLSQKEFIVEKCKKKL GLSNVEILLADVTKLEMEDMFDRVFVIGLIEHMKNFELFLRKISEWM KPDGLLFLEHYCHKSFAHQWEPIDEEDWFSKYIFPPGTVIIPSASFLLY FQEDVKVIDHWTLSGNHFARTQEEWLKGIDGHIDEVEKTFESFYGIS KEEAVKLINFWRVFCLSGVEMFGYNNGEEWMISHLLFKKK | 88 |
| GflNMT4 | MTMEANNAKKEAIENLWEQMMMGLVPDHEITRLMKSELQKRLNW GYKPTHQQQISQLLDFAKSLRRMEMSLDFDNLELDTKMYETPESFQL IMSGTTLKESSGLFTDETATLDQTQIRMMDLYLEKAKIKDGQSILDL GCGHGALILHVAQKYRNCVTGVTNSIAQKEFIPKQCKKLGLSNVE MVLADVTKCEMKATFDHIFVIGLIEHMKNFELFLRKVSEWMKSDGL LFMEHYCHKSFAYQWEPMDDDDLFSKYVFPPGSAIIPSASFLLYFQD DLTVVDHWTLSGNHFARTHQEWLKRIDSQSDEIKGIFESFYGISKEEA VKLINYWRVFCLFGVEMFGYNNGEEWMISHLLFKKK | 89 |
| CchNMT5 | MEVVATSSARNPKKEIVDLWKRMELGLIPDEEIRDLMKIGLEKRLK WGYKPTHEQQLSQLLHFAKSLRSMKMASEMETLDDQMYETPTAFQ QLMCGSTIKESAGFFKDESTTLDEAEIKMLDLYCEKARIEDGQKILDL GCGHGAVMLHIAQKYKNCVTGVTNSISQQQFIVQRSKELNLSNVN MILADVTMLEMDATYDRIFIIGLIEHMKNFELFLRKISKWITKEGLLF LEHYCHKTFAYQCEPVDEDDWYNMFIFPPGTLILPSASFLLYFQDDLI VVDRWTLNGNHYARTQEEWLKRIDANVDGVKQMFESVCDGNKEE AVKLMNFWRIFCISGAEMLAYNNGEEWMISHYLFKKRN | 90 |

TABLE 5-continued

N-methyltransferase and N-modifying candidate enzymes

| Name | Sequence | SEQ ID NO: |
|---|---|---|
| NsNMT2 | MEATQITKKQGVAELIKRIENGQVPDEEITRMMKIQIQKRLKLGYKS THEQQLAQLLHFVHSLQKMEMAEEVDTLDSELYEIPLPFLHIMCGKA LKFSPGYFKDESTTLDESEVNMLDLYCERAQIEDGQTILDLGCGHGS LTLHVAKKYRGCKVTGITNSVSQKDFIMEECKKLNLSNVEIILEDVT KFETGTTYDRIFAVALIEHMKNYELFLKKVSAWMAQDGLLFVEHHC HKVFAYKYEPIDDDDWYTEYIFPTGTLVMSSSSILLYFQEDVSVVNH WTLSGKHPSLGFKQWLKRIDDNIDEIKEIFESFYGSKEKATKFITYWR VFCIAHSEMYATNGGEEWMLSQVLFKRK | 91 |
| ScaNMT5 | MGGVADLLKKMELGLVPEEEIRRLMRIIIEKRLEWGYKPTHAEQLDH LTNFIQCLRGMKMADEIDALDAKMYEIPLPFMQTICGSTLKFSPGYF KDESTTLDESEIHMMDLYCERAEVKDGHSILDLGCGHGGFVLHVAQ KYKNSIVTGVTNSVAEKEFIMTQCKKLCLSNVEIILADVTKFEPETTY DRVFAIALIEHMKNYELVLEKLSKWVAQDGLFVEHHCHKVFPYKY EPLDEDDWYTEYIFPGGTIVLPSASILLYFQKDVSVVNHWSLNGKHP ARGFKEWLKRLDENMDAVKAIFEPFYGSKEEAMKWITYWRVFCITH SEMYAYNNGEEWMLSQVLFKRK | 92 |
| JdiNMT1 | MSKGVAKLVERMELGLVSDDEVRRLMRILIEKRLWGYKPTHEEQL TYLTNFIQGLKGMKIAEEIDALDAKMYEIPIAFMQILCGYSLKFSPGFF EDESTTLDESETIMMDLYCERAQVDQGSILDLGCGHGGFVLHVAQ KYKNCKVTGVTNSVSETEYIMEQCKKLGLSNVEIIIADVTKFEPEVTY DRVFAIALIEHMKNYELVLQKLSKWVAQDGFLFVDHHCHKVFPYK YEPIDEDDWYTQYIFPGGTLVLPSASILLYFQEDVSIVNHWTLSGNHP ARGFKEWLKRLDDNMDEIKAIFEPFYGSKEEAMKWITYWRVFCITH SEMYAYNGGEEWMISQVLFKRK | 93 |
| BthNMT1 | MEVKQAGKEGVTELLVKRMELGLVPEEEIRRLMRIQIQKRLDWGYK PTHEEQLAHLTKFIQNIRGMKMADEIDALDAKMYEIPLPFLQTICGKT LKFSPGYFKDESTTLDESETLMMDLYCERAQVKDGQSILDLGCGHG GFVLHLAQKYRNSVVTGVTNSVSETEYIKEQCKKLGLSNVEIIADVT KFEPEVTYDRVFAIALIEHMKNYALVLNKISKWVAQDGYLFVEHHC HKVFPYKYEPLDEDDWYTNYIFPGGTLILPSASILLYFQEDVTVLNH WSLSGKHPSRGFIEWLKRLDENIDVIMGIFEPFYGSKEEATKWINYW RVFCMTHSEMYAYGNEEWMLSQVLLKRK | 94 |
| MaqNMT3 | MELGLVPEKEIRRLMRIQIQKRLEWGYKPTHEEQLAHLTKFIQNIRG MKMADEIDALDAKMYEIPLPFLQTICGKTLKFSPGYFKDESTTLDESE TLMMDLYCERAQVKDGQSILDLGCGHGGFVLHLAQKYRNSIVTGV TNSVSETEYIKEQCKKLGLSNVEIIIADVTKFEPEVTYDRVFAIALIEH MKNYALVLNKISKWVAQDGYLFVEHHCHKVFPYKYEPLDEDDWY TNYIFPGGTLILPSASILLYFQEDVTVLNHWSLSGKHPSRGFIEWLKRL DENIDVIMGIFEPFYGSKEEATKWINYWRVFCITHSEMYAYGNEEW MLSQVLLKRK | 95 |
| McaNMT4 | MDKANERELKRAELFKKLEDDLVTYDEIKQVMRTELAKRLEWGYK PTHQQQLAHLLDFAHALEGMKIANEVETLASEVYETPLPFXEIVLGP AKKXSSCLFEDESTTLEQAEIAMLDLYFERAQIRXGMSVLDLGCGXG SVGLHIARKYKNCXVTCITNSISQKQYIENQCKLYNLSNVKIILADIV AHDTDDTFDVVLVIGVIEHMKNYALLLNKISKWMAKDGLLFVEHLC HKTFPYHFEPLDEDDWYSNFVFPTGTLTMPSVSFLLYFQADVSILNH WILSGKNFSRTXEEFLKRIDANVDAIKDGLKPSLGSEGVAKLISYWR GFCLTGMEMFGYNNGEEWMVSQVLFKNK | 96 |
| TcoNMT3 | MEDNNNLLQEEMNVVELLQRPELGLVPDEKIRKLTRLQLQKRLKW GYKPTHEAQLSHLFQFIHSLPSLNMESEDENPKSWLYETPTSFLQLLY GDCIKESDTYYKEDTATLEEAVINMLELYCERARITEGLSVLDLGCG YGALTLHVAQKYKSCKVTGVTSSISQKQYIMEKCKKLNLTNVEIILA DVATIEIEAASYDRIFALGIFEHVNDYKLFLGKLSKWMKQDGLLFVE YLCHKTFPYQNKPLDGKDWYNEYVFPSGGLIIPSASFILYFQNDVS VVRQWTQGGQHSARTFEELLKRIDGNIDKIKEIFIESYGSKEDAVRFI NYWRVFLITGVEMFSYNDGEEWMGAHFLFKKKFIMQE | 97 |
| CmuNMT4 | MEVKQSKGDELRSRVAELLERPELGLVPDEEIRRLAKARLEKRLKW GYKATHGEQLSSLLQFVESLPSLNMASEDDSPKAWLYETPTSFLQLI YGDIIKESGSYYKDESTTLEEAMIHNMNLCCERANIKEGQSVVDLGC GYGAFILHVAQKYKTCRVTGITSSISQKHYIMEQCKKLNLSNVEVILA DVATIKLDATFDRVFAAGMFEHVNDYKSFLRKITNWMKPDGRLFVE HLCNKTFPYQNKPLDDGDNWGEYVFPSGGLIIPSASLLLYFQEDVSIV NHWTFSGKHAANKFEELLKRIDAKIDAIKRIFNECYGSKDSIRFINYW RVFLITAAEMFGYNNGEEWMGVHLLFKKK | 98 |
| CtrNMT2 | GLKSSVAELLERPELGLVPDGEIRKLTKTRLAKRLEWGYKATHEDQL SHLLRFIHSLPSLNMASEDDSPKAWLYETPTSFLQLIYGDIIKESGTYY KDESSTLEEAIIHNMDLCCERARIKEGQSVLDLGCGYGAFTLHVAQK | 99 |

TABLE 5-continued

N-methyltransferase and N-modifying candidate enzymes

| Name | Sequence | SEQ ID NO: |
|---|---|---|
| | YKSCSVTGITSSISQKDYIMEQCKKLNLSNVEVILADVATIKMNTTFD RVFALGMFEHINDYKLFLRRISNWMKHDGLLFVEHLCNKTFAYQNK PLDDGDDWFNEYVFPSAGLIIPSASLLLYFQEDVSIVHHWTFSGKHA AYKFEELLERIDAKIEAIKEIFIECYGSKEDAIRFINYWRVFLITAAEMF AYRDGEEWMGSHVLFKKK | |
| CmuNMT5 | MEAKQHESNNNIDEELKNRVNIGEQEERPGFEDEEIRRLAKAQLAKR LKWGYKPTHEQQLSHLLQFLQSLPSLNMASEDESSKAWLYETPTSFL QLLFGNVIKFSGYYYKHESSTFEESMIHNMDLCCERANIKEGQNVID LGCGYGAFVLHVAQKYKSCSVTGITCSITQKHHIMEECKKLNLCNV KVILADVATIELGTAFDRVFAFGMFEEINDYKLILRKISNWMKPDGLF FVEHLCHKTLAYQNKLIDDQDWYEEYIFPSGGLIVPSASLLLYFQDD LSVVYHWTYNGKHGARSFEKMLERTDANIDTIKDMFTEFYGSKEKA IKFINYWRVFFITAAEMFAYNDGEEWMCSQLLFKKK | 100 |
| CmuNMT8 | MEHKIEDIRKLKSRVEEQLERPELGLVKDEDIKTLAKAKLEKRLKWG YKPTYAEQLSNLLQFAQSLPSLKMENVDDQGSSKQWLYGVPSEFLQI IYGGIIKMSGSYYEDESTTLEESMIKDMDSCCEKANVKEGHSVLDIG CGYGSLIIHIAKKYRTCNVTGITNFVEQKQYIMEECKKLNSNVEVIV GDGTTINLNTTTFDRVFVTGMLEEINDYKLFLKSVSDWMKPDGLLL VTHFCHKTFAYQNNKALDDEDWHNEYIFPSGNLIVPSASLLLYFQED LSVVSHWATNGTHTGRTCKKLVERIDANIEKIKEIFSEFYGSKEDAIR MINYWRVLCITGAEMYTCKDGEEWMDVYYLFKKK | 101 |

TABLE 6

Variants of BM3 N-demethylase

| BM3 variant | | SEQ ID NO: |
|---|---|---|
| | Genotype | |
| 8F11 | L437A | |
| 4H9 | L181A, T260A, L437A | |
| 8C7 | L75A, L181A | |
| 4H5 | L75A, M177A, L181A | |
| 7A1 | L75A, M177A, L181A, T260A | |
| | Amino Acid Sequence | |
| 8F11 | MTIKEMPQPKTFGELKNLPLLNTDKPVQALMKIADELGEIFKFEA PGRVTRYLSSQRLIKEACDESRFDKNLSQALKFARDFAGDGLVTS WTHEKNWKKAHNILLPSFSQQAMKGYHAMMVDIAVQLVQKWE RLNADEHIEVSEDMTRLTLDTIGLCGFNYRFNSFYRDQPHPFIISM VRALDEVMNKLQRANPDDPAYDENKRQFQEDIKVMNDLVDKII ADRKARGEQSDDLLTQMLNGKDPETGEPLDDGNIRYQIITFLIAG HETTSGLLSFALYFLVKNPHVLQKVAEEAARVLVDPVPSYKQVK QLKYVGMVLNEALRLWPTAPAFSLYAKEDTVLGGEYPLEKGDE VMVLIPQLHRDKTVWGDDVEEFRPERFENPSAIPQHAFKPFGNG QRACIGQQFALHEATLVLGMMLKHFDFEDHTNYELDIKETATLK PKGFVVKAKSKKIPLGGIPSPSTEQSAKKVRKKAENAHNTPLLVL YGSNMGTAEGTARDLADIAMSKGFAPQVATLDSHAGNLPREGA VLIVTASYNGHPPDNAKQFVDWLDQASADEVKGVRYSVFGCGD KNWATTYQKVPAFIDETLAAKGAENIADRGEADASDDFEGTYEE WREHMWSDVAAYFNLDIENSEDNKSTLSLQFVDSAADMPLAKM HGAFSTNVVASKELQQPGSARSTRHLEIELPKEASYQEGDHLGVI PRNYEGIVNRVTARFGLDASQQIRLEAEEEKLAHLPLAKTVSVEE LLQYVELQDPVTRTQLRAMAAKTVCPPHKVELEALLEKQAYKE QVLAKRTLMLELLEKYPACEMKFSEFIALLPSIRPRYYSISSSPRV DEKQASITVSVVSGEAWSGYGEYKGIASNYLAELQEGDTITCFIST PQSEFTLPKDPETPLIMVGPGTGVAPFRGFVQARKQLKEQGQSLG EAHLYFGCRSPHEDYLYQEELENAQSEGIITLHTAFSRMPNQPKT YVQHVMEQDGKKLIELLDQGAHFYICGDGSQMAPAVEATLMKS YADVHQVSEADARLWLQQLEEKGRYAKDVWAG | 102 |
| 4H9 | MTIKEMPQPKTFGELKNLPLLNTDKPVQALMKIADELGEIFKFEA PGRVTRYLSSQRLIKEACDESRFDKNLSQALKFARDFAGDGLVTS | 103 |

TABLE 6-continued

Variants of BM3 N-demethylase

| BM3 variant | | SEQ ID NO: |
|---|---|---|
| | WTHEKNWKKAHNILLPSFSQQAMKGYHAMMVDIAVQLVQKWE RLNADEHIEVSEDMTRLTLDTIGLCGFNYRFNSFYRDQPHPFIISM VRAADEVMNKLQRANPDDPAYDENKRQFQEDIKVMNDLVDKII ADRKARGEQSDDLLTQMLNGKDPETGEPLDDGNIRYQIIAFLIAG HETTSGLLSFALYFLVKNPHVLQKVAEEEAARVLVDPVPSYKQVK QLKYVGMVLNEALRLWPTAPAFSLYAKEDTVLGGEYPLEKGDE VMVLIPQLHRDKTVWGDDVEEFRPERFENPSAIPQHAFKPFGNG QRACIGQQFALHEATLVLGMMLKHFDFEDHTNYELDIKETATLK PKGFVVKAKSKKIPLGGIPSPSTEQSAKKVRKKAENAHNTPLLVL YGSNMGTAEGTARDLADIAMSKGFAPQVATLDSHAGNLPREGA VLIVTASYNGHPPDNAKQFVDWLDQASADEVKGVRYSVFGCGD KNWATTYQKVPAFIDETLAAKGAENIADRGEADASDDFEGTYEE WREHMWSDVAAYFNLDIENSEDNKSTLSLQFVDSAADMPLAKM HGAFSTNVVASKELQQPGSARSTRHLEIELPKEASYQEGDHLGVI PRNYEGIVNRVTARFGLDASQQIRLEAEEEKLAHLPLAKTVSVEE LLQYVELQDPVTRTQLRAMAAKTVCPPHKVELEALLEKQAYKE QVLAKRTLMLELLEKYPACEMKFSEFIALLPSIRPRYYSISSSPRV DEKQASITVSVVSGEAWSGYGEYKGIASNYLAELQEGDTITCFIST PQSEFTLPKDPETPLIMVGPGTGVAPFRGFVQARKQLKEQGQSLG EAHLYFGCRSPHEDYLYQEELENAQSEGIITLHTAFSRMPNQPKT YVQHVMEQDGKKLIELLDQGAHFYICGDGSQMAPAVEATLMKS YADVHQVSEADARLWLQQLEEKGRYAKDVWAG | |
| 8C7 | MTIKEMPQPKTFGELKNLPLLNTDKPVQALMKIADELGEIFKFEA PGRVTRYLSSQRLIKEACDESRFDKNLSQAAKFARDFAGDGLVTS WTHEKNWKKAHNILLPSFSQQAMKGYHAMMVDIAVQLVQKWE RLNADEHIEVSEDMTRLTLDTIGLCGFNYRFNSFYRDQPHPFIISM VRAADEVMNKLQRANPDDPAYDENKRQFQEDIKVMNDLVDKII ADRKARGEQSDDLLTQMLNGKDPETGEPLDDGNIRYQIITFLIAG HETTSGLLSFALYFLVKNPHVLQKVAEEEAARVLVDPVPSYKQVK QLKYVGMVLNEALRLWPTAPAFSLYAKEDTVLGGEYPLEKGDE VMVLIPQLHRDKTVWGDDVEEFRPERFENPSAIPQHAFKPFGNG QRACIGQQFALHEATLVLGMMLKHFDFEDHTNYELDIKETLTLK PKGFVVKAKSKKIPLGGIPSPSTEQSAKKVRKKAENAHNTPLLVL YGSNMGTAEGTARDLADIAMSKGFAPQVATLDSHAGNLPREGA VLIVTASYNGHPPDNAKQFVDWLDQASADEVKGVRYSVFGCGD KNWATTYQKVPAFIDETLAAKGAENIADRGEADASDDFEGTYEE WREHMWSDVAAYFNLDIENSEDNKSTLSLQFVDSAADMPLAKM HGAFSTNVVASKELQQPGSARSTRHLEIELPKEASYQEGDHLGVI PRNYEGIVNRVTARFGLDASQQIRLEAEEEKLAHLPLAKTVSVEE LLQYVELQDPVTRTQLRAMAAKTVCPPHKVELEALLEKQAYKE QVLAKRTLMLELLEKYPACEMKFSEFIALLPSIRPRYYSISSSPRV DEKQASITVSVVSGEAWSGYGEYKGIASNYLAELQEGDTITCFIST PQSEFTLPKDPETPLIMVGPGTGVAPFRGFVQARKQLKEQGQSLG EAHLYFGCRSPHEDYLYQEELENAQSEGIITLHTAFSRMPNQPKT YVQHVMEQDGKKLIELLDQGAHFYICGDGSQMAPAVEATLMKS YADVHQVSEADARLWLQQLEEKGRYAKDVWAG | 104 |
| 4H5 | MTIKEMPQPKTFGELKNLPLLNTDKPVQALMKIADELGEIFKFEA PGRVTRYLSSQRLIKEACDESRFDKNLSQAAKFARDFAGDGLVTS WTHEKNWKKAHNILLPSFSQQAMKGYHAMMVDIAVQLVQKWE RLNADEHIEVSEDMTRLTLDTIGLCGFNYRFNSFYRDQPHPFIISA VRAADEVMNKLQRANPDDPAYDENKRQFQEDIKVMNDLVDKII ADRKARGEQSDDLLTQMLNGKDPETGEPLDDGNIRYQIITFLIAG HETTSGLLSFALYFLVKNPHVLQKVAEEEAARVLVDPVPSYKQVK QLKYVGMVLNEALRLWPTAPAFSLYAKEDTVLGGEYPLEKGDE VMVLIPQLHRDKTVWGDDVEEFRPERFENPSAIPQHAFKPFGNG QRACIGQQFALHEATLVLGMMLKHFDFEDHTNYELDIKETLTLK PKGFVVKAKSKKIPLGGIPSPSTEQSAKKVRKKAENAHNTPLLVL YGSNMGTAEGTARDLADIAMSKGFAPQVATLDSHAGNLPREGA VLIVTASYNGHPPDNAKQFVDWLDQASADEVKGVRYSVFGCGD KNWATTYQKVPAFIDETLAAKGAENIADRGEADASDDFEGTYEE WREHMWSDVAAYFNLDIENSEDNKSTLSLQFVDSAADMPLAKM HGAFSTNVVASKELQQPGSARSTRHLEIELPKEASYQEGDHLGVI PRNYEGIVNRVTARFGLDASQQIRLEAEEEKLAHLPLAKTVSVEE LLQYVELQDPVTRTQLRAMAAKTVCPPHKVELEALLEKQAYKE QVLAKRTLMLELLEKYPACEMKFSEFIALLPSIRPRYYSISSSPRV DEKQASITVSVVSGEAWSGYGEYKGIASNYLAELQEGDTITCFIST PQSEFTLPKDPETPLIMVGPGTGVAPFRGFVQARKQLKEQGQSLG EAHLYFGCRSPHEDYLYQEELENAQSEGIITLHTAFSRMPNQPKT YVQHVMEQDGKKLIELLDQGAHFYICGDGSQMAPAVEATLMKS YADVHQVSEADARLWLQQLEEKGRYAKDVWAG | 105 |
| 7A1 | MTIKEMPQPKTFGELKNLPLLNTDKPVQALMKIADELGEIFKFEA PGRVTRYLSSQRLIKEACDESRFDKNLSQAAKFARDFAGDGLVTS | 106 |

TABLE 6-continued

Variants of BM3 N-demethylase

| BM3 variant | | SEQ ID NO: |
|---|---|---|
| | WTHEKNWKKAHNILLPSFSQQAMKGYHAMMVDIAVQLVQKWE<br>RLNADEHIEVSEDMTRLTLDTIGLCGFNYRFNSFYRDQPHPFIISA<br>VRAADEVMNKLQRANPDDPAYDENKRQFQEDIKVMNDLVDKII<br>ADRKARGEQSDDLLTQMLNGKDPETGEPLDDGNIRYQIIAFLIAG<br>HETTSGLLSFALYFLVKNPHVLQKVAEEAARVLVDPVPSYKQVK<br>QLKYVGMVLNEALRLWPTAPAFSLYAKEDTVLGGEYPLEKGDE<br>VMVLIPQLHRDKTVWGDDVEEFRPERFENPSAIPQHAFKPFGNG<br>QRACIGQQFALHEATLVLGMMLKHFDFEDHTNYELDIKETLTLK<br>PKGFVVKAKSKKIPLGGIPSPSTEQSAKKVRKKAENAHNTPLLVL<br>YGSNMGTAEGTARDLADIAMSKGFAPQVATLDSHAGNLPREGA<br>VLIVTASYNGHPPDNAKQFVDWLDQASADEVKGVRYSVFGCGD<br>KNWATTYQKVPAFIDETLAAKGAENIADRGEADASDDFEGTYEE<br>WREHMWSDVAAYFNLDIENSEDNKSTLSLQFVDSAADMPLAKM<br>HGAFSTNVVASKELQQPGSARSTRHLEIELPKEASYQEGDHLGVI<br>PRNYEGIVNRVTARFGLDASQQIRLEAEEEKLAHLPLAKTVSVEE<br>LLQYVELQDPVTRTQLRAMAAKTVCPPHKVELEALLEKQAYKE<br>QVLAKRTLMLELLEKYPACEMKFSEFIALLPSIRPRYYSISSSPRV<br>DEKQASITVSVVSGEAWSGYGEYKGIASNYLAELQEGDTITCFIST<br>PQSEFTLPKDPETPLIMVGPGTGVAPFRGFVQARKQLKEQGQSLG<br>EAHLYFGCRSPHEDYLYQEELENAQSEGIIITLHTAFSRMPNQPKT<br>YVQHVMEQDGKKLIELLDQGAHFYICGDSQMAPAVEATLMKS<br>YADVHQVSEADARLWLQQLEEKGRYAKDVWAG | |

Nucleotide Sequence

| | | |
|---|---|---|
| 8F11 | ATGACCATCAAAGAAATGCCACAACCTAAGACTTTCGGTGAA<br>TTGAAGAATTTGCCTTTGTTGAACACCGATAAGCCAGTTCAAG<br>CTTTGATGAAGATTGCTGATGAATTGGGTGAAATCTTCAAGTT<br>TGAAGCTCCAGGTAGAGTCACTAGATACTTGTCATCTCAAAGA<br>TTGATCAAAGAAGCCTGCGACGAATCCAGATTTGATAAGAATT<br>TGTCTCAAGCTTTGAAGTTCGCTAGAGATTTTGCTGGTGATGG<br>TTTGGTTACTTCTTGGACTCACGAAAAGAATTGGAAGAAGGCC<br>CATAACATTTTGTTGCCATCTTTCTCACAACAAGCCATGAAGG<br>GTTATCATGCTATGATGGTTGATATCGCCGTTCAATTGGTTCA<br>AAAGTGGGAAAGATTGAACGCCGATGAACATATCGAAGTCTC<br>TGAAGATATGACCAGATTGACCTTGGATACCATTGGTTTGTGT<br>GGTTTCAACTACAGATTCAACTCCTTCTACAGAGATCAACCAC<br>ATCCATTCATCATCTCTATGGTTAGAGCTTTGGATGAAGTCAT<br>GAACAAATTGCAAAGAGCTAATCCAGACGATCCAGCTTATGA<br>CGAAAACAAGAGACAATTCCAAGAAGATATCAAGGTCATGAA<br>CGATTTGGTCGATAAGATTATCGCTGATAGAAAGGCTAGAGGT<br>GAACAATCTGATGATTTGTTGACCCAAATGTTGAACGGTAAGG<br>ATCCAGAAACTGGTGAACCATTGGATGATGGTAACATCAGAT<br>ACCAAATTATCGCCTTCTTGATTGCTGGTCACGAAACTACATC<br>TGGTTTGTTGTCTTTTGCCTTGTACTTTTTGGTTAAGAACCCAC<br>ACGTCTTGCAAAAGGTTGCTGAAGAAGCTGCAAGAGTTTTGGT<br>TGATCCAGTTCCATCTTACAAGCAAGTCAAGCAATTGAAGTAC<br>GTTGGTATGGTTTTGAACGAAGCTTTGAGATTGTGGCCAACTG<br>CTCCAGCTTTTTCATTATACGCTAAAGAAGATACCGTCTTGGG<br>TGGTGAATATCCATTGGAAAAAGGTGATGAAGTTATGGTCTTG<br>ATCCCACAATTGCATAGAGATAAGACTGTTTGGGGTGATGATG<br>TCGAAGAATTCAGACCAGAAAGATTCGAAAACCCATCTGCTA<br>TTCCACAACATGCTTTTAAGCCATTTGGTAACGGTCAAAGAGC<br>TTGCATTGGTCAACAATTCGCTTTACATGAAGCTACCTTGGTTT<br>TGGGTATGATGTTGAAACACTTCGACTTCGAAGATCACACCAA<br>CTACGAATTGGATATCAAAGAAACCGCTACCTTGAAGCCAAA<br>GGGTTTTGTTGTTAAGGCTAAGTCCAAAAAGATTCCATTGGGT<br>GGTATTCCATCTCCATCTACTGAACAATCCGCTAAGAAGGTTA<br>GAAAGAAAGCTGAAAACGCTCATAACACACCTTTGTTGGTCTT<br>GTACGGTTCTAATATGGGTACTGCTGAAGGTACAGCAAGAGA<br>TTTGGCAGATATTGCTATGTCTAAAGGTTTCGCTCCACAAGTT<br>GCTACTTTGGATTCTCATGCTGGTAATTTGCCAAGAGAAGGTG<br>CTGTTTTGATAGTTACTGCTTCTTACAATGGTCACCCACCAGAT<br>AATGCTAAGCAATTCGTTGATTGGTTGGATCAAGCTTCAGCTG<br>ATGAAGTAAAAGGTGTTAGATACTCTGTTTTCGGTTGCGGTGA<br>CAAAAATTGGGCTACTACTTATCAAAAGGTTCCAGCCTTTATT<br>GACGAAACTTTGGCTGCTAAAGGTGCTGAAAACATTGCTGAC<br>AGAGGTGAAGCTGATGCCTCCGACGACTTCGAAGGTACTTAC<br>GAAGAATGGAGAGAACACATGTGGTCTGACGTTGCTGCTTACT<br>TCAACTTGGACATCGAAACTCTGAAGCAACAAGTCCACTTT<br>GTCTTTGCAATTCGTTGACTCCGCTGCTGACATGCCATTGGCTA<br>AGATGCACGGTGCTTTCTCTACCAACGTCGTTGCCTCCAAGGA<br>ATTGCAACAACCAGGTTCTGCTAGATCTACTAGACACTTGGAA<br>ATCGAATTGCCAAAGGAAGCTTCCTACCAAGAAGGTGACCAC<br>TTGGGCGTTATTCCAAGAAACTACGAAGGTATCGTCAACAGA | 107 |

TABLE 6-continued

Variants of BM3 N-demethylase

| BM3 variant | | SEQ ID NO: |
|---|---|---|
| | GTTACTGCTAGATTCGGTTTGGATGCTTCTCAACAAATCAGAT<br>TAGAAGCTGAAGAAGAAAAGTTGGCTCACTTGCCATTAGCTA<br>AGACTGTCTCCGTTGAAGAATTGTTGCAATACGTCGAATTGCA<br>AGACCCAGTTACCAGAACCCAATTGAGAGCCATGGCTGCCAA<br>GACCGTCTGTCCACCACACAAGGTTGAATTGGAAGCCTTGTTG<br>GAAAAGCAAGCCTACAAGGAACAAGTTTTGGCTAAGAGATTG<br>ACCATGTTGGAATTGTTGGAAAAGTACCCAGCCTGCGAAATG<br>AAGTTCTCTGAATTTATCGCCTTGTTGCCATCTATCAGACCACG<br>TTACTACTCTATTTCTTCCTCTCCACGTGTTGACGAAAAGCAAG<br>CTTCTATTACTGTTTCCGTTGTCTCCGGTGAAGCTTGGTCCGGT<br>TACGGTGAATACAAGGGTATTGCTTCTAACTACTTGGCTGAAT<br>TGCAAGAAGGTGACACCATTACTTGTTTCATCTCTACTCCACA<br>ATCCGAATTTACTTTGCCAAAGGACCCAGAAACTCCATTGATC<br>ATGGTTGGTCCAGGTACTGGTGTCGCTCCATTCAGAGGTTTCG<br>TTCAAGCTAGAAAACAATTGAAGGAACAAGGTCAATCTTTGG<br>GTGAAGCTCACTTGTACTTCGGTTGTAGATCTCCACACGAAGA<br>CTACTTATACCAAGAAGAATTGGAAAACGCTCAATCCGAAGG<br>TATTATCACTTTGCACACCGCTTTCTCCAGAATGCCAAACCAA<br>CCAAAGACTTACGTCCAACACGTTATGGAACAAGACGGTAAG<br>AAGTTGATTGAATTGTTGGACCAAGGTGCTCACTTCTACATTT<br>GTGGTGATGGTTCTCAAATGGCTCCAGCCGTTGAAGCCACTTT<br>GATGAAGTCTTACGCTGATGTTCACCAAGTTTCCGAAGCCGAT<br>GCTAGATTATGGTTGCAACAATTGGAAGAAAAAGGTCGTTAC<br>GCTAAGGATGTCTGGGCCGGTTGA | | |
| 4H9 | ATGACCATCAAAGAAATGCCACAACCTAAGACTTTCGGTGAA<br>TTGAAGAATTTGCCTTTGTTGAACACCGATAAGCCAGTTCAAG<br>CTTTGATGAAGATTGCTGATGAATTGGGTGAAATCTTCAAGTT<br>TGAAGCTCCAGGTAGAGTCACTAGATACTTGTCATCTCAAAGA<br>TTGATCAAAGAAGCCTGCGACGAATCCAGATTTGATAAGAATT<br>TGTCTCAAGCTTTGAAGTTCGCTAGAGATTTTGCTGGTGATGG<br>TTTGGTTACTTCTTGGACTCACGAAAAGAATTGGAAGAAGGCC<br>CATAACATTTTGTTGCCATCTTTCTCACAACAAGCCATGAAGG<br>GTTATCATGCTATGATGGTTGATATCGCCGTTCAATTGGTTCA<br>AAAGTGGGAAAGATTGAACGCCGATGAACATATCGAAGTCTC<br>TGAAGATATGACCAGATTGACCTTGGATACCATTGGTTTGTGT<br>GGTTTCAACTACAGATTCAACTCCTTCTACAGAGATCAACCAC<br>ATCCATTCATCATCTCTATGGTTAGAGCTGCAGATGAAGTCAT<br>GAACAAATTGCAAAGAGCTAATCCAGACGATCCAGCTTATGA<br>CGAAAACAAGAGACAATTCCAAGAAGATATCAAGGTCATGAA<br>CGATTTGGTCGATAAGATTATCGCTGATAGAAAGGCTAGAGGT<br>GAACAATCTGATGATTTGTTGACCCAAATGTTGAACGGTAAGG<br>ATCCAGAAACTGGTGAACCATTGGATGATGGTAACATCAGAT<br>ACCAAATTATCGCTTTCTTGATTGCTGGTCACGAAACTACATC<br>TGGTTTGTTGTCTTTTGCCTTGTACTTTTTGGTTAAGAACCCAC<br>ACGTCTTGCAAAAGGTTGCTGAAGAAGCTGCAAGAGTTTTGGT<br>TGATCCAGTTCCATCTTACAAGCAAGTCAAGCAATTGAAGTAC<br>GTTGGTATGGTTTTGAACGAAGCTTTGAGATTGTGGCCAACTG<br>CTCCAGCTTTTTCATTATACGCTAAAGAAGATACCGTCTTGGG<br>TGGTGAATATCCATTGGAAAAAGGTGATGAAGTTATGGTCTTG<br>ATCCCACAATTGCATAGAGATAAGACTGTTTGGGGTGATGATG<br>TCGAAGAATTCAGACCAGAAAGATTCGAAAACCCATCTGCTA<br>TTCCACAACATGCTTTTAAGCCATTTGGTAACGGTCAAAGAGC<br>TTGCATTGGTCAACAATTCGCTTTACATGAAGCTACCTTGGTTT<br>TGGGTATGATGTTGAAACACTTCGACTTCGAAGATCACACCAA<br>CTACGAATTGGATATCAAAGAAACCGCTACCTTGAAGCCAAA<br>GGGTTTTGTTGTTAAGGCTAAGTCCAAAAAGATTCCATTGGGT<br>GGTATTCCATCTCCATCTACTGAACAATCCGCTAAGAAGGTTA<br>GAAAGAAAGCTGAAAACGCTCATAACACACCTTTGTTGGTCTT<br>GTACGGTTCTAATATGGGTACTGCTGAAGGTACAGCAAGAGA<br>TTTGGCAGATATTGCTATGTCTAAAGGTTTCGCTCCACAAGTT<br>GCTACTTTGGATTCTCATGCTGGTAATTTGCCAAGAGAAGGTG<br>CTGTTTTGATAGTTACTGCTTCTTACAATGGTCACCCACCAGAT<br>AATGCTAAGCAATTCGTTGATTGGTTGGATCAAGCTTCAGCTG<br>ATGAAGTAAAAGGTGTTAGATACTCTGTTTTCGGTTGCGGTGA<br>CAAAAATTGGGCTACTACTTATCAAAAGGTTCCAGCCTTTATT<br>GACGAAACTTTGGCTGCTAAAGGTGCTGAAAACATTGCTGAC<br>AGAGGTGAAGCTGATGCCTCCGACGACTTCGAAGGTACTTAC<br>GAAGAATGGAGAGAACACATGTGGTCTGACGTTGCTGCTTACT<br>TCAACTTGGACATCGAAAACTCTGAAGACAACAAGTCCACTTT<br>GTCTTTGCAATTCGTTGACTCCGCTGCTGACATGCCATTGGCTA<br>AGATGCACGGTGCTTTCTCTACCAACGTCGTTGCCTCCAAGGA<br>ATTGCAACAACCAGGTTCTGCTAGATCTACTAGACACTTGGAA<br>ATCGAATTGCCAAAGGAAGCTTCCTACCAAGAAGGTGACCAC<br>TTGGGCGTTATTCCAAGAAACTACGAAGGTATCGTCAACAGA | 108 |

TABLE 6-continued

Variants of BM3 N-demethylase

| BM3 variant | | SEQ ID NO: |
|---|---|---|
| | GTTACTGCTAGATTCGGTTTGGATGCTTCTCAACAAATCAGAT<br>TAGAAGCTGAAGAAGAAAAGTTGGCTCACTTGCCATTAGCTA<br>AGACTGTCTCCGTTGAAGAATTGTTGCAATACGTCGAATTGCA<br>AGACCCAGTTACCAGAACCCAATTGAGAGCCATGGCTGCCAA<br>GACCGTCTGTCCACCACACAAGGTTGAATTGGAAGCCTTGTTG<br>GAAAAGCAAGCCTACAAGGAACAAGTTTTGGCTAAGAGATTG<br>ACCATGTTGGAATTGTTGGAAAAGTACCCAGCCTGCGAAATG<br>AAGTTCTCTGAATTTATCGCCTTGTTGCCATCTATCAGACCACG<br>TTACTACTCTATTTCTTCCTCTCCACGTGTTGACGAAAAGCAAG<br>CTTCTATTACTGTTTCCGTTGTCTCCGGTGAAGCTTGGTCCGGT<br>TACGGTGAATACAAGGGTATTGCTTCTAACTACTTGGCTGAAT<br>TGCAAGAAGGTGACACCATTACTTGTTTCATCTCTACTCCACA<br>ATCCGAATTTACTTTGCCAAAGGACCCAGAAACTCCATTGATC<br>ATGGTTGGTCCAGGTACTGGTGTCGCTCCATTCAGAGGTTTCG<br>TTCAAGCTAGAAAACAATTGAAGGAACAAGGTCAATCTTTGG<br>GTGAAGCTCACTTGTACTTCGGTTGTAGATCTCCACACGAAGA<br>CTACTTATACCAAGAAGAATTGGAAAACGCTCAATCCGAAGG<br>TATTATCACTTTGCACACCGCTTTCTCCAGAATGCCAAACCAA<br>CCAAAGACTACGTCCAACACGTTATGAACAAGACGGTAAG<br>AAGTTGATTGAATTGTTGGACCAAGGTGCTCACTTCTACATTT<br>GTGGTGATGGTTCTCAAATGGCTCCAGCCGTTGAAGCCACTTT<br>GATGAAGTCTTACGCTGATGTTCACCAAGTTTCCGAAGCCGAT<br>GCTAGATTATGGTTGCAACAATTGGAAGAAAAAGGTCGTTAC<br>GCTAAGGATGTCTGGGCCGGTTGA | |
| 8C7 | ATGACCATCAAAGAAATGCCACAACCTAAGACTTTCGGTGAA<br>TTGAAGAATTTGCCTTTGTTGAACACCGATAAGCCAGTTCAAG<br>CTTTGATGAAGATTGCTGATGAATTGGGTGAAATCTTCAAGTT<br>TGAAGCTCCAGGTAGAGTCACTAGATACTTGTCATCTCAAAGA<br>TTGATCAAAGAAGCCTGCGACGAATCCAGATTTGATAAGAATT<br>TGTCTCAAGCTGCTAAGTTCGCTAGAGATTTTGCTGGTGATGG<br>TTTGGTTACTTCTTGGACTCACGAAAAGAATTGGAAGAAGGCC<br>CATAACATTTTGTTGCCATCTTTCTCACAACAAGCCATGAAGG<br>GTTATCATGCTATGATGGTTGATATCGCCGTTCAATTGGTTCA<br>AAAGTGGGAAAGATTGAACGCCGATGAACATATCGAAGTCTC<br>TGAAGATATGACCAGATTGACCTTGGATACCATTGGTTTGTGT<br>GGTTTCAACTACAGATTCAACTCCTTCTACAGAGATCAACCAC<br>ATCCATTCATCATCTCTATGGTTAGAGCTGCAGATGAAGTCAT<br>GAACAAATTGCAAAGAGCTAATCCAGACGATCCAGCTTATGA<br>CGAAAACAAGAGACAATTCCAAGAAGATATCAAGGTCATGAA<br>CGATTTGGTCGATAAGATTATCGCTGATAGAAAGGCTAGAGGT<br>GAACAATCTGATGATTTGTTGACCCAAATGTTGAACGGTAAGG<br>ATCCAGAAACTGGTGAACCATTGGATGATGGTAACATCAGAT<br>ACCAAATTATCACCTTCTTGATTGCTGGTCACGAAACTACATC<br>TGGTTTGTTGTCTTTTGCCTTGTACTTTTTGGTTAAGAACCCAC<br>ACGTCTTGCAAAAGGTTGCTGAAGAAGCTGCAAGAGTTTTGGT<br>TGATCCAGTTCCATCTTACAAGCAAGTCAAGCAATTGAAGTAC<br>GTTGGTATGGTTTTGAACGAAGCTTTGAGATTGTGGCCAACTG<br>CTCCAGCTTTTTCATTATACGCTAAAGAAGATACCGTCTTGGG<br>TGGTGAATATCCATTGGAAAAAGGTGATGAAGTTATGGTCTTG<br>ATCCCACAATTGCATAGAGATAAGACTGTTTGGGGTGATGATG<br>TCGAAGAATTCAGACCAGAAAGATTCGAAAACCCATCTGCTA<br>TTCCACAACATGCTTTTAAGCCATTTGGTAACGGTCAAAGAGC<br>TTGCATTGGTCAACAATTCGCTTTACATGAAGCTACCTTGGTTT<br>TGGGTATGATGTTGAAACACTTCGACTTCGAAGATCACACCAA<br>CTACGAATTGGATATCAAAGAAACCTTGACCTTGAAGCCAAA<br>GGGTTTTGTTGTTAAGGCTAAGTCCAAAAAGATTCCATTGGGT<br>GGTATTCCATCTCCATCTACTGAACAATCCGCTAAGAAGGTTA<br>GAAAGAAAGCTGAAAACGCTCATAACACACCTTTGTTGGTCTT<br>GTACGGTTCTAATATGGGTACTGCTGAAGGTACAGCAAGAGA<br>TTTGGCAGATATTGCTATGTCTAAAGGTTTCGCTCCACAAGTT<br>GCTACTTTGGATTCTCATGCTGGTAATTTGCCAAGAGAAGGTG<br>CTGTTTTGATAGTTACTGCTTCTTACAATGGTCACCCACCAGAT<br>AATGCTAAGCAATTCGTTGATTGGTTGGATCAAGCTTCAGCTG<br>ATGAAGTAAAAGGTGTTAGATACTCTGTTTTCGGTTGCGGTGA<br>CAAAAATTGGGCTACTACTTTATCAAAAGGTTCCAGCCTTTATT<br>GACGAAACTTTGGCTGCTAAAGGTGCTGAAAACATTGCTGAC<br>AGAGGTGAAGCTGATGCCTCCGACGACTTCGAAGGTACTTAC<br>GAAGAATGGAGAGAACACATGTGGTCTGACGTTGCTGCTTACT<br>TCAACTTGGACATCGAAAACTCTGAAGACAACAAGTCCACTTT<br>GTCTTTGCAATTCGTTGACTCCGCTGCTGACATGCCATTGGCTA<br>AGATGCACGGTGCTTTCTCTACCAACGTCGTTGCCTCCAAGGA<br>ATTGCAACAACCAGGTTCTGCTAGATCTACTAGACACTTGGAA<br>ATCGAATTGCCAAAGGAAGCTTCCTACCAAGAAGGTGACCAC<br>TTGGGCGTTATTCCAAGAAACTACGAAGGTATCGTCAACAGA | 109 |

TABLE 6-continued

Variants of BM3 N-demethylase

| BM3 variant | | SEQ ID NO: |
|---|---|---|
| | GTTACTGCTAGATTCGGTTTGGATGCTTCTCAACAAATCAGAT TAGAAGCTGAAGAAGAAAAGTTGGCTCACTTGCCATTAGCTA AGACTGTCTCCGTTGAAGAATTGTTGCAATACGTCGAATTGCA AGACCCAGTTACCAGAACCCAATTGAGAGCCATGGCTGCCAA GACCGTCTGTCCACCACACAAGGTTGAATTGGAAGCCTTGTTG GAAAAGCAAGCCTACAAGGAACAAGTTTTGGCTAAGAGATTG ACCATGTTGGAATTGTTGGAAAAGTACCCAGCCTGCGAAATG AAGTTCTCTGAATTTATCGCCTTGTTGCCATCTATCAGACCACG TTACTACTCTATTTCTTCCTCTCCACGTGTTGACGAAAAGCAAG CTTCTATTACTGTTTCCGTTGTCTCCGGTGAAGCTTGGTCCGGT TACGGTGAATACAAGGGTATTGCTTCTAACTACTTGGCTGAAT TGCAAGAAGGTGACACCATTACTTGTTTCATCTCTACTCCACA ATCCGAATTTACTTTGCCAAAGGACCCAGAAACTCCATTGATC ATGGTTGGTCCAGGTACTGGTGTCGCTCCATTCAGAGGTTTCG TTCAAGCTAGAAAACAATTGAAGGAACAAGGTCAATCTTTGG GTGAAGCTCACTTGTACTTCGGTTGTAGATCTCCACACGAAGA CTACTTATACCAAGAAGAATTGGAAAACGCTCAATCCGAAGG TATTATCACTTTGCACACCGCTTTCTCCAGAATGCCAAACCAA CCAAAGACTTACGTCCAACACGTTATGGAACAAGACGGTAAG AAGTTGATTGAATTGTTGGACCAAGGTGCTCACTTCTACATTT GTGGTGATGGTTCTCAAATGGCTCCAGCCGTTGAAGCCACTTT GATGAAGTCTTACGCTGATGTTCACCAAGTTTCCGAAGCCGAT GCTAGATTATGGTTGCAACAATTGGAAGAAAAAGGTCGTTAC GCTAAGGATGTCTGGGCCGGTTGA | |
| 4H5 | ATGACCATCAAAGAAATGCCACAACCTAAGACTTTCGGTGAA TTGAAGAATTTGCCTTTGTTGAACACCGATAAGCCAGTTCAAG CTTTGATGAAGATTGCTGATGAATTGGGTGAAATCTTCAAGTT TGAAGCTCCAGGTAGAGTCACTAGATACTTGTCATCTCAAAGA TTGATCAAAGAAGCCTGCGACGAATCCAGATTTGATAAGAATT TGTCTCAAGCTGCTAAGTTCGCTAGAGATTTTGCTGGTGATGG TTTGGTTACTTCTTGGACTCACGAAAAGAATTGGAAGAAGGCC CATAACATTTTGTTGCCATCTTTCTCACAACAAGCCATGAAGG GTTATCATGCTATGATGGTTGATATCGCCGTTCAATTGGTTCA AAAGTGGGAAAGATTGAACGCCGATGAACATATCGAAGTCTC TGAAGATATGACCAGATTGACCTTGGATACCATTGGTTTGTGT GGTTTCAACTACAGATTCAACTCCTTCTACAGAGATCAACCAC ATCCATTCATCATCTCTGCTGTTAGAGCTGCAGATGAAGTCAT GAACAAATTGCAAAGAGCTAATCCAGACGATCCAGCTTATGA CGAAAACAAGAGACAATTCCAAGAAGATATCAAGGTCATGAA CGATTTGGTCGATAAGATTATCGCTGATAGAAAGGCTAGAGGT GAACAATCTGATGATTTGTTGACCCAAATGTTGAACGGTAAGG ATCCAGAAACTGGTGAACCATTGGATGATGGTAACATCAGAT ACCAAATTATCACCTTCTTGATTGCTGGTCACGAAACTACATC TGGTTTGTTGTCTTTTGCCTTGTACTTTTTGGTTAAGAACCCAC ACGTCTTGCAAAAGGTTGCTGAAGAAGCTGCAAGAGTTTTGGT TGATCCAGTTCCATCTTACAAGCAAGTCAAGCAATTGAAGTAC GTTGGTATGGTTTTGAACGAAGCTTTGAGATTGTGGCCAACTG CTCCAGCTTTTTCATTATACGCTAAAGAAGATACCGTCTTGGG TGGTGAATATCCATTGGAAAAAGGTGATGAAGTTATGGTCTTG ATCCCACAATTGCATAGAGATAAGACTGTTTGGGGTGATGATG TCGAAGAATTCAGACCAGAAAGATTCGAAAACCCATCTGCTA TTCCACAACATGCTTTTAAGCCATTTGGTAACGGTCAAAGAGC TTGCATTGGTCAACAATTCGCTTTACATGAAGCTACCTTGGTTT TGGGTATGATGTTGAAACACTTCGACTTCGAAGATCACACCAA CTACGAATTGGATATCAAAGAAACCTTGACCTTGAAGCCAAA GGGTTTTGTTGTTAAGGCTAAGTCCAAAAAGATTCCATTGGGT GGTATTCCATCTCCATCTACTGAACAATCCGCTAAGAAGGTTA GAAAGAAAGCTGAAAACGCTCATAACACACCTTTGTTGGTCTT GTACGGTTCTAATATGGGTACTGCTGAAGGTACAGCAAGAGA TTTGGCAGATATTGCTATGTCTAAAGGTTTCGCTCCACAAGTT GCTACTTTGGATTCTCATGCTGGTAATTTGCCAAGAGAAGGTG CTGTTTTGATAGTTACTGCTTCTTACAATGGTCACCCACCAGAT AATGCTAAGCAATTCGTTGATTGGTTGGATCAAGCTTCAGCTG ATGAAGTAAAAGGTGTTAGATACTCTGTTTTCGGTTGCGGTGA CAAAAATTGGGCTACTACTTTATCAAAAGGTTCCAGCCTTTATT GACGAAACTTTTGGCTGCTAAAGGTGCTGAAAACATTGCTGAC AGAGGTGAAGCTGATGCCTCCGACGACTTCGAAGGTACTTAC GAAGAATGGAGAGAACACATGTGGTCTGACGTTGCTGCTTACT TCAACTTGGACATCGAAAACTCTGAAGACAACAAGTCCACTTT GTCTTTGCAATTCGTTGACTCCGCTGCTGACATGCCATTGGCTA AGATGCACGGTGCTTTCTCTACCAACGTCGTTGCCTCCAAGGA ATTGCAACAACCAGGTTCTGCTAGATCTACTAGACACTTGGAA ATCGAATTGCCAAAGGAAGCTTCCTACCAAGAAGGTGACCAC TTGGGCGTTATTCCAAGAAACTACGAAGGTATCGTCAACAGA | 110 |

TABLE 6-continued

Variants of BM3 N-demethylase

| BM3 variant | | SEQ ID NO: |
|---|---|---|
| | GTTACTGCTAGATTCGGTTTGGATGCTTCTCAACAAATCAGAT<br>TAGAAGCTGAAGAAGAAAAGTTGGCTCACTTGCCATTAGCTA<br>AGACTGTCTCCGTTGAAGAATTGTTGCAATACGTCGAATTGCA<br>AGACCCAGTTACCAGAACCCAATTGAGAGCCATGGCTGCCAA<br>GACCGTCTGTCCACCACACAAGGTTGAATTGGAAGCCTTGTTG<br>GAAAAGCAAGCCTACAAGGAACAAGTTTTGGCTAAGAGATTG<br>ACCATGTTGGAATTGTTGGAAAAGTACCCAGCCTGCGAAATG<br>AAGTTCTCTGAATTTATCGCCTTGTTGCCATCTATCAGACCACG<br>TTACTACTCTATTTCTTCCTCTCCACGTGTTGACGAAAAGCAAG<br>CTTCTATTACTGTTTCCGTTGTCTCCGGTGAAGCTTGGTCCGGT<br>TACGGTGAATACAAGGGTATTGCTTCTAACTACTTGGCTGAAT<br>TGCAAGAAGGTGACACCATTACTTGTTTCATCTCTACTCCACA<br>ATCCGAATTTACTTTGCCAAAGGACCCAGAAACTCCATTGATC<br>ATGGTTGGTCCAGGTACTGGTGTCGCTCCATTCAGAGGTTTCG<br>TTCAAGCTAGAAAACAATTGAAGGAACAAGGTCAATCTTTGG<br>GTGAAGCTCACTTGTACTTCGGTTGTAGATCTCCACACGAAGA<br>CTACTTATACCAAGAAGAATTGGAAAACGCTCAATCCGAAGG<br>TATTATCACTTTGCACACCGCTTTCTCCAGAATGCCAAACCAA<br>CCAAAGACTTACGTCCAACACGTTATGGAACAAGACGGTAAG<br>AAGTTGATTGAATTGTTGGACCAAGGTGCTCACTTCTACATTT<br>GTGGTGATGGTTCTCAAATGGCTCCAGCCGTTGAAGCCACTTT<br>GATGAAGTCTTACGCTGATGTTCACCAAGTTTCCGAAGCCGAT<br>GCTAGATTATGGTTGCAACAATTGGAAGAAAAAGGTCGTTAC<br>GCTAAGGATGTCTGGGCCGGTTGA | | |
| 7A1 | ATGACCATCAAAGAAATGCCACAACCTAAGACTTTCGGTGAA<br>TTGAAGAATTTGCCTTTGTTGAACACCGATAAGCCAGTTCAAG<br>CTTTGATGAAGATTGCTGATGAATTGGGTGAAATCTTCAAGTT<br>TGAAGCTCCAGGTAGAGTCACTAGATACTTGTCATCTCAAAGA<br>TTGATCAAAGAAGCCTGCGACGAATCCAGATTTGATAAGAATT<br>TGTCTCAAGCTGCTAAGTTCGCTAGAGATTTTGCTGGTGATGG<br>TTTGGTTACTTCTTGGACTCACGAAAAGAATTGGAAGAAGGCC<br>CATAACATTTTGTTGCCATCTTTCTCACAACAAGCCATGAAGG<br>GTTATCATGCTATGATGGTTGATATCGCCGTTCAATTGGTTCA<br>AAAGTGGGAAAGATTGAACGCCGATGAACATATCGAAGTCTC<br>TGAAGATATGACCAGATTGACCTTGGATACCATTGGTTTGTGT<br>GGTTTCAACTACAGATTCAACTCCTTCTACAGAGATCAACCAC<br>ATCCATTCATCATCTCTGCTGTTAGAGCTGCAGATGAAGTCAT<br>GAACAAATTGCAAAGAGCTAATCCAGACGATCCAGCTTATGA<br>CGAAAACAAGAGACAATTCCAAGAAGATATCAAGGTCATGAA<br>CGATTTGGTCGATAAGATTATCGCTGATAGAAAGGCTAGAGGT<br>GAACAATCTGATGATTTGTTGACCCAAATGTTGAACGGTAAGG<br>ATCCAGAAACTGGTGAACCATTGGATGATGGTAACATCAGAT<br>ACCAAATTATCGCTTTCTTGATTGCTGGTCACGAAACTACATC<br>TGGTTTGTTGTCTTTTGCCTTGTACTTTTTGGTTAAGAACCCAC<br>ACGTCTTGCAAAAGGTTGCTGAAGAAGCTGCAAGAGTTTTGGT<br>TGATCCAGTTCCATCTTACAAGCAAGTCAAGCAATTGAAGTAC<br>GTTGGTATGGTTTTGAACGAAGCTTTGAGATTGTGGCCAACTG<br>CTCCAGCTTTTTCATTATACGCTAAAGAAGATACCGTCTTGGG<br>TGGTGAATATCCATTGGAAAAAGGTGATGAAGTTATGGTCTTG<br>ATCCCACAATTGCATAGAGATAAGACTGTTTGGGGTGATGATG<br>TCGAAGAATTCAGACCAGAAAGATTCGAAAACCCATCTGCTA<br>TTCCACAACATGCTTTTAAGCCATTTGGTAACGGTCAAAGAGC<br>TTGCATTGGTCAACAATTCGCTTTACATGAAGCTACCTTGGTTT<br>TGGGTATGATGTTGAAACACTTCGACTTCGAAGATCACACCAA<br>CTACGAATTGGATATCAAAGAAACCTTGACCTTGAAGCCAAA<br>GGGTTTTGTTGTTAAGGCTAAGTCCAAAAAGATTCCATTGGGT<br>GGTATTCCATCTCCATCTACTGAACAATCCGCTAAGAAGGTTA<br>GAAAGAAAGCTGAAAACGCTCATAACACACCTTTGTTGGTCTT<br>GTACGGTTCTAATATGGGTACTGCTGAAGGTACAGCAAGAGA<br>TTTGGCAGATATTGCTATGTCTAAAGGTTTCGCTCCACAAGTT<br>GCTACTTTGGATTCTCATGCTGGTAATTTGCCAAGAGAAGGTG<br>CTGTTTTGATAGTTACTGCTTCTTACAATGGTCACCCACCAGAT<br>AATGCTAAGCAATTCGTTGATTGGTTGGATCAAGCTTCAGCTG<br>ATGAAGTAAAAGGTGTTAGATACTCTGTTTTCGGTTGCGGTGA<br>CAAAAATTGGGCTACTACTTATCAAAAGGTTCCAGCCTTTATT<br>GACGAAACTTTGGCTGCTAAAGGTGCTGAAAACATTGCTGAC<br>AGAGGTGAAGCTGATGCCTCCGACGACTTCGAAGGTACTTAC<br>GAAGAATGGAGAGAACACATGTGGTCTGACGTTGCTGCTTACT<br>TCAACTTGGACATCGAAAACTCTGAAGACAACAAGTCCACTTT<br>GTCTTTGCAATTCGTTGACTCCGCTGCTGACATGCCATTGGCTA<br>AGATGCACGGTGCTTTCTCTACCAACGTCGTTGCCTCCAAGGA<br>ATTGCAACAACCAGGTTCTGCTAGATCTACTAGACACTTGGAA<br>ATCGAATTGCCAAAGGAAGCTTCCTACCAAGAAGGTGACCAC<br>TTGGGCGTTATTCCAAGAAACTACGAAGGTATCGTCAACAGA | 111 |

TABLE 6-continued

Variants of BM3 N-demethylase

| BM3 variant | | SEQ ID NO: |
|---|---|---|
| | GTTACTGCTAGATTCGGTTTGGATGCTTCTCAACAAATCAGAT<br>TAGAAGCTGAAGAAGAAAAGTTGGCTCACTTGCCATTAGCTA<br>AGACTGTCTCCGTTGAAGAATTGTTGCAATACGTCGAATTGCA<br>AGACCCAGTTACCAGAACCCAATTGAGAGCCATGGCTGCCAA<br>GACCGTCTGTCCACCACACAAGGTTGAATTGGAAGCCTTGTTG<br>GAAAAGCAAGCCTACAAGGAACAAGTTTTGGCTAAGAGATTG<br>ACCATGTTGGAATTGTTGGAAAAGTACCCAGCCTGCGAAATG<br>AAGTTCTCTGAATTTATCGCCTTGTTGCCATCTATCAGACCACG<br>TTACTACTCTATTTCTTCCTCTCCACGTGTTGACGAAAAGCAAG<br>CTTCTATTACTGTTTCCGTTGTCTCCGGTGAAGCTTGGTCCGGT<br>TACGGTGAATACAAGGGTATTGCTTCTAACTACTTGGCTGAAT<br>TGCAAGAAGGTGACACCATTACTTGTTTCATCTCTACTCCACA<br>ATCCGAATTTACTTTGCCAAAGGACCCAGAAACTCCATTGATC<br>ATGGTTGGTCCAGGTACTGGTGTCGCTCCATTCAGAGGTTTCG<br>TTCAAGCTAGAAACAATTGAAGGACAAGGTCAATCTTTGG<br>GTGAAGCTCACTTGTACTTCGGTTGTAGATCTCCACACGAAGA<br>CTACTTATACCAAGAAGAATTGGAAAACGCTCAATCCGAGG<br>TATTATCACTTTGCACACCGCTTTCTCCAGAATGCCAAACCAA<br>CCAAAGACTTACGTCCAACACGTTATGGAACAAGACGGTAAG<br>AAGTTGATTGAATTGTTGGACCAAGGTGCTCACTTCTACATTT<br>GTGGTGATGGTTCTCAAATGGCTCCAGCCGTTGAAGCCACTTT<br>GATGAAGTCTTACGCTGATGTTCACCAAGTTTCCGAAGCCGAT<br>GCTAGATTATGGTTGCAACAATTGGAAGAAAAAGGTCGTTAC<br>GCTAAGGATGTCTGGGCCGGTTGA | |

TABLE 7 pA24, pA25, and pA26 sequences

| pA24 Sequence | cctcgccgcagttaattaaagtcagtgagcgaggaagcgcgtaactataacggtcctaaggtagcgaa<br>tcctgatgcggtattttctccttacgcatctgtgcggtatttcacaccgcatagatcggcaagtgcacaaa<br>caatacttaaataaatactactcagtaataacctatttcttagcattttgacgaaatttgctattttgttagagt<br>cttttacaccattttgtctccacacctccgcttacatcaacaccaataacgccatttaatctaagcgcatcac<br>caacattttctggcgtcagtccaccagctaacataaaatgtaagctttcggggctctcttgccttccaacc<br>cagtcagaaatcgagttccaatccaaaagttcacctgtcccacctgcttctgaatcaaacaagggaata<br>aacgaatgaggtttctgtgaagctgcactgagtagtatgttgcagtcttttggaaatacgagtcttttaata<br>actggcaaaccgaggaactcttggtattcttgccacgactcatctccatgcagtggagccaatcaattct<br>tgcggtcaactttggacgatatcaatgccgtaatcattgaccagagccaaaacatcctccttaagttgatt<br>acgaaacacgccaaccaagtatttcggagtgcctgaactatttttatatgcttttacaagacttgaaattttc<br>cttgcaataaccgggtcaattgttctctttctattgggcacacatataatacccagcaagtcagcatcgga<br>atctagagcacattctgcggcctctgtgctctgcaagccgcaaactttcaccaatggaccagaactacc<br>tgtgaaattaataacagacatactccaagctgcctttgtgtgcttaatcacgtatactcacgtgctcaatag<br>tcaccaatgccctccctcttggccctctcctttttcttttttcgaccgaattaattcttaatcggcaaaaaaag<br>aaaagctccggatcaagattgtacgtaaggtgacaagctattttttcaataaagaatatcttccactactgc<br>catctggcgtcataactgcaaagtacacatatattacgatgctgttctattaaatgcttcctatattatatata<br>tagtaatgtcgtgatctatggtgcactctcagtacaatctgctctgatgccgcatagttaagccagccccg<br>acacccgccaacacccgctgacgcgccctgacgggcttgtctgctcccggcatccgcttacagacaa<br>gctgtgaccgtctccgggagctgcatgtgtcagaggttttcaccgtcatcaccgaaacgcgcgagacg<br>aaagggcctcgtgatacgcctatttttataggttaatgtcatgataataatggtttcttagacggatcgcttg<br>cctgtaacttacacgcgcctcgtatctttaatgatggaataatttgggaatttactctgtgtttatttattttttat<br>gttttgtatttggatttttagaaagtaaataaagaaggtagaagagttacggaatgaagaaaaaaaataa<br>acaaaggtttaaaaaatttcaacaaaaagcgtacttttacatatatatttattagacaagaaaagcagattaa<br>atagatatacattcgattaacgataagtaaaatgtaaaatcacaggattttcgtgtgtggtcttctacacag<br>acaaggtgaaacaattcggcattaatacctgagagcaggaagagcaagataaaaggtagtatttgttg<br>gcgatccccctagagtcttttacatcttcggaaaacaaaaactattttttctttaattctttttttactttctattt<br>taatttatatatttatattaaaaaatttaaattataattattttttatagcacgtgatgaaaaggaccaggtggc<br>acttttcggggaaatgtgcgcggaacccctatttgttattttttctaaatacattcaaatatgtatccgctcat<br>gagacaataaccctgataaatgcttcaataatattgaaaaaggaagagtatgagtattcaactttccgtg<br>tcgcccttattcctctttttgcggcattttgccttcctgttttttgctcacccagaaacgctggtgaaagtaaaa<br>gatgctgaagatcagttgggtgcacgagtgggttacatcgaactggatctcaacagcggtaagatcgct<br>acccaaggttgccgggtgacgcacaccgtgggaaacggatgaaggcacgaacccagtggacataag<br>cctgttcggttcgtaagctgtaatgcaagtagcgtatgcgctcacgcaactggtccagaaccttgaccg<br>aacgcagcggtggtaacgcgcagtggcggttttcatggcttgttatgactgtttttttggggtacagtct<br>atgcctcgggcatccaagcagcaagcgcgttacgccgtgggtcgatgtttgatgttatggagcagcaa<br>cgatgttacgcagcagggcagtcgccctaaaacaaagttaaacattatgagggaagcggtgatcgcc<br>gaagtatcgactcaactatcagaggtagttggcgccatcgagcgccatctcgaaccgacgttgctggc<br>cgtacatttgtacggctccgcagtggatggcggcctgaagccacacagtgatattgatttgctggttacg<br>gtgaccgtaaggcttgatgaaacaacgcggcgaactttttgacgtgtgtggcagctctggcccgtgcgg<br>cctggagagagcgagattctccgcgctgtagaagtcaccattgttgtgcacgacgacatcattccgtgg<br>cgttatccagctaagcgcgaactgcaatttggagaatggcagcgcaatgacattcttgcaggtatcttcg<br>agccagccacgatcgacattgatctggctatcttgctgacaaaagcaagagaacatagcgttgccttgg<br>taggtccagcggcggaggaactctttgatccggttcctgaacaggatctatttgaggcgctaaatgaaa | SEQ ID NO: 112 |

TABLE 7-continued pA24, pA25, and pA26 sequences

|  |  |  |
|---|---|---|
|  | ccttaacgctatggaactcgccgcccgactgggctggcgatgagcgaaatgtagtgcttacgttgtccc<br>gcatttggtacagcgcagtaaccggcaaaatcgcgccgaaggatgtcgctgccggctgggcaatgg<br>agcgcctgccggcccagtatcagcccgtcatacttgaagctagacaggcttatcttggacaagaagaa<br>gatcgcttggcctcgcgcgcagatcagttggaagaatttgtccactacgtgaaaggcgagatcaccaa<br>ggtagtcggcaaataaccctcgagcattcaaggcgccttgattatttgacgtggtttgatggcctccacg<br>cacgttgtgatatgtagatgattcagttcgagtttatcattatcaatactgccatttcaaagaatacgtaaat<br>aattaatagtagtgattttcctaacttttatttagtcaaaaaattagccttttaattctgctgtaaccgtacatg<br>cccaaaataggggcgggttacacagaatatataacatcgtaggtgtctgggtgaacagtttattcctg<br>gcatccactaaatataatggagcccgcttttttaagctggcatccagaaaaaaaagaatcccagcacca<br>aaatattgttttcttcaccaaccatcagttcataggtccattctcttagcgcaactacagagaacaggggc<br>acaaacaggcaaaaaacgggcacaacctcaatggagtgatgcaacctgcctggagtaaatgatgac<br>acaaggcaattgacccacgcatgtatctatctcattttcttacaccttctattaccttctgctctctctgatttg<br>gaaaaagctgaaaaaaaggttgaaaccagttccctgaaattattcccctacttgactaataagtatataa<br>agacggtaggtattgattgtaattctgtaaatctatttcttaaacttcttaaattctacttttatagttagtctttttt<br>tttagttttaaaacaccaagaacttagtttcgaataaacacacataaacaaacaaaacaggccccttttcc<br>tttgtcgatatcatgtaattagttatgtcacgcttacattcacgccctcctcccacatccgctctaaccgaaa<br>aggaaggagttagacaacctgaagtctaggtccctatttatttttttaatagttatgttagtattaagaacgt<br>tatttatatttcaaatttttcttttttttctgtacaaacgcgtgtacgcatgtaacattatactgaaaaccttgctt<br>gagaaggttttgggacgctcgaaggctttaatttgtaatcattatcacttttacgggtcctttccggtgatcc<br>gacaggttacgggcggcgacctcgcgggttttcgctatttatgaaaattttccggtttaaggcgtttccg<br>ttcttcttcgtcataacttaatgttttttatttaaaatacctcgcgagtggcaacactgaaaatacccatggag<br>cggcgtaaccgtcgcacaggatctaggtgaagatcctttttgataatctcatgaccaaaatcccttaacg<br>tgagttttcgttccactgagcgtcagacccccgtgagaaagatcaaaggatcttcttgagatcctttttttctg<br>cgcgtaatctgctgcttgcaaacaaaaaaaccaccgctaccagcggtggtttgtttgccggatcaagag<br>ctaccaactctttttccgaaggtaactggcttcagcagagcgcagataccaaatactgtccttctagtgta<br>gccgtagttaggccaccacttcaagaactctgtagcaccgcctacatacctcgctctgctaatcctgtta<br>ccagtggctgctgccagtggcgataagtcgtgtcttaccgggttggactcaagacgatagttaccggat<br>aaggcgcagcggtcgggctgaacggggggttcgtgcacacagcccagcttggagcgaaccaccta<br>caccgaactgagataccctacagcgtgagctatgagaaagcgccacgcttcccgaagggagaaaggc<br>ggacaggtatccggtaagcggcagggtcggaacaggagagcgcacgagggagcttccaggggga<br>aacgcctggtatctttatagtcctgtcgggtttcgccacctctgacttgagcgtcgatttttgtgatgctcgt<br>caggggggcggagcctatggaaaaacgccagcaacgcggcagtggaacgtgcattatgaattagtt<br>acgctagggataacagggtaatatagaacccgaacgaccgagcgcagcggcggccgcgctgatac<br>cgccgc |  |
| pA25 sequence | aacgacctacaccgaactgagatacctacagcgtgagctatgagaaagcgccacgcttcccgaagg<br>gagaaaggcggacaggtatccggtaagcggcagggtcggaacaggagagcgcacgagggagctt<br>ccaggggaaacgcctggtatctttatagtcctgtcgggtttcgccacctctgacttgagcgtcgattttt<br>gtgatgctcgtcaggggggcggagcctatggaaaaacgccagcaacgcggcagtggaacgtgcatt<br>atgaattagttacgctagggataacagggtaatatagaacccgaacgaccgagcgcagcggcggccgc<br>gcgctgataccgccgcctcgccgcagttaattaaagtcagtgagcgaggaagcgcgtaactataac<br>ggtcctaaggtagcgaatcctgatgcggtattttctccttacgcatctgtgcggtatttcacaccgcatag<br>atcggcaagtgcacaaacaatacttaaataaatactactcagtaataacctattctttagcatttttgacga<br>aatttgctcatttttgttagagtcttttacaccattttgtctctccacacctccgcttacatcaacaccaataacgcca<br>tttaatctaagcgcatcaccaacattttctggcgtcagtccaccagctaacataaaatgtaagctttcggg<br>gctctcttgccttccaacccagtcagaaatcgagttccaatccaaaagttcacctgtcccacctgcttctg<br>aatcaaacaagggaataaacgaatgaggtttctgtgaagctgcactgagtagtatgttgcagtcttttgg<br>aaatacgagtcttttaataactggcaaaccgaggaactcttggtattcttgccacgactcatctccatgca<br>gtggagccaatcaattcttgcggtcaactttggacgatatcaatgccgtaatcattgaccagagccaaaa<br>catcctccttaagttgattacgaaacacgccaaccaagtatttcggagtgcctgaactatttttatatgcttt<br>tacaagacttgaaattttccttgcaataaccgggtcaattgttctctttctattgggcacacatataataccc<br>agcaagtcagcatcggaatctagagcacattctgcggcctctgtgctctgcaagccgcaaactttcacc<br>aatggaccagaactacctgtgaaattaatacagacatactccaagctgcctttgtgtgcttaatcacgta<br>tactcacgtgctcaatagtcaccaatgccctccctcttggccctctccttttctttttttcgaccgaattaattct<br>taatcggcaaaaaagaaaagctccggatcaagattgtacgtaaggtgacaagctatttttcaataaag<br>aatatcttccactactgccatctggcgtcataactgcaaagtacacatatattacgatgctgttctattaaat<br>gcttcctatattatatatatgtcgtatcgtatgttgcactctcagtacaatctgctctgatgccgcat<br>agttaagccagccccgacaccgccaacaccgctgacgcgcccgacgggcttgtctgctcccgg<br>catccgcttacagacaagctgtgaccgtctccgggagctgcatgtgtcagaggttttcaccgtcatcac<br>cgaaacgcgcgagacgaaagggcctcgtgatacgcctatttttataggttaatgtcatgataataatggt<br>ttcttagacggatcgcttgcctgtaactcacgcgcctcgtatcttttaatgatggaataatttgggaattt<br>actctgtgtttatttattttttatgtttgtatttggattttagaaagtaaataaagaaggtagaagagttacgga<br>atgaagaaaaaaaataaacaaaggtttaaaaaatttcaacaaaaagcgtactttacatatatatttattag<br>acaagaaaagcagattaaatagatatacattcgattaacgataagtaaaatgtaaaatcacaggattttc<br>gtgtgtggtcttctacacagacaaggtgaaacaattcggcattaatacctgagagcaggaagagcaag<br>ataaaaggtagtatttgttggcgatcccctagagtcttttacatcttcggaaaacaaaaactatttttctttt<br>aatttcttttttttactttctattttaatttatatttatattaaaaaatttaaattataattattttttatagcacgtgat<br>gaaaaggacccaggtggcacttttcggggaaatgtgcgcggaacccctatttgtttatttttctaaataca<br>ttcaaatatgtatccgctcatgagacaataacctgataaatgcttcaataatattgaaaaaggaagagta<br>tgagtattcaacatttccgtgtcgcccttattcccttttttgcggcattttgccttcctgtttttgctcacccaga<br>aacgctggtgaaagtaaaagatgctgaagatcagttgggacgcgtagtcctagaccagccaggacaga<br>aatgcctcgacttcgctgctacccaaggttgccgggtgacgcacaccgtggaaacggatgaaggcac<br>gaaccagtggacataagcctgttcgttcgtaagctgtaatgaagtagcgttgtgcgctcacgcaact<br>ggtccagaaccttgaccgaaccgcagcggtggtaacggcgcagtggcggttttcatgcttgttatgact<br>gtttttttggggtacagtctatgcctcgggcatccaagcagcaagcgcgttacgccgtgggtcgatgttt<br>gatgttatggagcagcaacgatgttacgcagcagggcagtcgccctaaaacaaagttaaacattatga<br>gggaagcggtgatcgccgaagtatcgactcaactatcagaggtagttggcgccatcgagcgccatct<br>cgaaccgacgttgctggccgtacatttgtacggctccgcagtggatggcggcctgaagccacacagt | SEQ ID<br>NO: 113 |

TABLE 7-continued pA24, pA25, and pA26 sequences

```
                  gatattgatttgctggttacggtgaccgtaaggcttgatgaaacaacgcggcgagctttgatcaacgac
                  cttttggaaacttcggcttccccctggagagagcgagattctccgcgctgtagaagtcaccattgttgtgc
                  acgacgacatcattccgtggcgttatccagctaagcgcgaactgcaatttggagaatggcagcgcaat
                  gacattcttgcaggtatcttcgagccagccacgatcgacattgatctggctatcttgctgacaaaagcaa
                  gagaacatagcgttgccttggtaggtccagcggcggaggaactctttgatccggttcctgaacaggat
                  ctatttgaggcgctaaatgaaaccttaacgctatggaactcgccgcccgactgggctggcgatgagcg
                  aaatgtagtgcttacgttgtcccgcatttggtacagcgcagtaaccgcaaaatcgcgccgaaggatgt
                  cgctgccggctgggcaatggagcgcctgccggcccagtatcagccgtcatacttgaagctagacag
                  gcttatcttggacaagaagaagatcgcttggcctcgcgcgcagatcagttggaagaatttgtccactac
                  gtgaaaggcgagatcaccaaggtagtcggcaaataaccctcgagcattcaaggcgccttgattatttg
                  acgtggtttgatggcctccacgcacgttgtgatatgtagatgagagcgttggttggtggtgatcaagccca
                  cgcgtaggcaatcctcgagcagatccgccaggcgtgtatatatagcgtggatggccaggcaactttag
                  tgctgacacatacaggcatatatatgtgtgcgacaacacatgatcatatggcatgcatgtgctctgtat
                  gtatataaaactcttgttttcttcttttctctaaatattctttccttatacattaggaccttgcagcataaattact
                  atacttctatagacacacaaacacaaatacacacactaaattaataacgagcccctttttccttttgtcgatat
                  catgtaattagttatgtcacgcttacattcacgccctccccccacatccgctctaaccgaaaaggaagga
                  gttagacaacctgaagtctaggtccctattatttttttatagttatgttagtattaagaacgttatttatatttca
                  aattttctttttttttctgtacaaacgcgtgtacgcatgtaacattatactgaaaaccttgcttgagaaggtttt
                  gggacgctcgaaggctttaatttgtaatcattatcacttttacgggtccttttccggtgatccgacaggttac
                  ggggcggcgacctcgcgggttttcgctattttatgaaaattttccggtttaaggcgtttccgttcttcttcgtc
                  ataacttaatgtttttatttaaaatacctcgcgagtggcaacactgaaaataccatgagcggcgtaacc
                  gtcgcacaggatctaggtgaagatccttttttgataatctcatgaccaaaatcccttaacgtgagttttcgtt
                  ccactgagcgtcagacccgtagaaaagatcaaaggatcttcttgagatcctttttttttctgcgcgtaatct
                  gctgcttgcaaacaaaaaaaccaccgctaccagcggtggtttgtttgccggatcaagagctaccaact
                  ctttttcgaaggtaactggcttcagcagagcgcagataccaaatactgtccttctagtgtagccgtagtt
                  aggccaccacttcaagaactctgtagcaccgcctacatacctcgctctgctaatcctgttaccagtggct
                  gctgccagtggcgataagtcgtgtcttaccgggttggactcaagacgatagttaccggataaggcgca
                  gcggtcgggctgaacggggggttcgtgcacacagcccagcttggagcg
pA26 sequence    acgacctacaccgaactgagatacctacagcgtgagctatgagaaagcgccacgcttcccgaaggg      SEQ ID
                  agaaaggcggacaggtatccggtaagcggcagggtcggaacaggagagcgcacgagggagcttc      NO: 114
                  caggggggaaacgcctggtatctttatagtcctgtcgggtttcgccacctctgacttgagcgtcgattttgt
                  gatgctcgtcaggggggcggagcctatgaaaaacgccagcaacgcggcagtggaacgtgcattat
                  gaattagttacgctagggataacagggtaatatagaacccgaacgaccgagcgcagcggcggccgc
                  gctgataccgcgcccctcgccgcagttaattaaagtcagtgagcgaggaagcgcgtaactataacggt
                  cctaaggtagcgaatcctgatgcggtatttctccttacgcatctgtgcggtatttcacaccgcatagatc
                  ggcaagtgcacaaacaatacttaaataaatactactcagtaataacctatttcttagcatttttgacgaaatt
                  tgctatttgttagagtcttttacaccatttgtctccacacctccgcttacatcaacaccaataacgccattta
                  atctaagcgcatcaccaacattttctggcgtcagtccaccagctaacataaaatgtaagctttcggggct
                  ctcttgccttccaaccagtcagaaatcgagttccaatccaaaagttcacctgtcccacctgcttctgaat
                  caaacaagggaataaacgaatgaggtttctgtgaagctgcactgagtagtatgttgcagtcttttggaaa
                  tacgagtcttttaataactggcaaaccgaggaactcttggtattcttgccacgactcatctccatgcagtg
                  gagccaatcaattcttgcggtcaactttggacgatatcaatgccgtaatcattgaccagagccaaaacat
                  cctccttaagttgattacgaaacacgccaaccaagtatttcgagtgcctgaactattttttatatgcttttac
                  aagacttgaaattttccttgcaataaccgggtcaattgttctcttttctattgggcacacatataataccagc
                  aagtcagcatcggaatctagagcacattctgcggcctctgtgctctgcaagccgcaaactttcaccaat
                  ggaccagaactacctgtgaaattaataacagacatactccaagctgcctttgtgtgcttaatcacgtatac
                  tcacgtgctcaatagtcaccaatgccctccctcttggccctctccttttcttttttcgaccgaattaattcttaa
                  tcggcaaaaaaagaaaagctccggatcaagattgtacgtaaggtgacaagctcattttcaataaagaat
                  atcttccactactgccatctggcgtcataactgcaaagtacacatatattacgatgctgttctattaaatgct
                  tcctatattatatatagtaatgtcgtgatctatggtgcactctcagtacaatctgctctgatgccgcatagt
                  taagccagccccgacacccgccaacaccgctgacgcgccctgacgggcttgtctgctcccggcat
                  ccgcttacagacaagctgtgaccgtctccgggagctgcatgtgtcagaggttttccaccgtcatcaccga
                  aacgcgcgagacgaaagggcctcgtgatacgcctatttttataggttaatgtcatgataataatggttctt
                  agacggatcgcttgcctgtaacttacacgcgcctcgtatcttttaatgatggaataatttgggaatttactct
                  gtgtttatttattttatgtttttgtatttggattttagaaagtaaataaagaaggtagaagagttacggaatgaa
                  gaaaaaaaaatcaaaggttaaaaaatttcaacaaaaagcgtactttacatatatatttattagacaa
                  gaaaagcagattaaatagatacattcgattaacgataagtaaaatgtaaaatcacaggattcgtgtg
                  tggtcttctacacagacaaggtgaaacaattcggcattaatacctgagagcaggaagagcaagataaa
                  aggtagtatttgttggcgatcccctagagtcttttacatcttcggaaaacaaaaactatttttctcttaatttc
                  tttttttacttttctattttttaattttataaaaatttttatatttatatttatagcacgtgatgaaaa
                  ggacccaggtggcacttttcgggaaatgtgcgcggaaccccctatttgtttatttttctaaatacattcaaa
                  tatgtatccgctcatgagacaataaccctgataaatgcttcaataatattgaaaaaggaagagtatgagta
                  ttcaacatttccgtgtcgcccttattccttttttgcggcattttgccttcctgtttttgctcaccagaaacgc
                  tggtgaaagtaaaagatgctgaagatcagttgggacgcgtagtctagaccagcagcagaaatgc
                  ctcgacttcgctgctacccaaggttgccgggtgacgcacaccgtggaaacggatgaaggcacgaac
                  ccagtggacataagcctgttcggttcgtaagctgtaatgcaagtagcgtatgcgctcacgcaactggtc
                  cagaaccttgaccgaacgcagcggtggtaacggcgcagtggcggttttcatggcttgttatgactgtttt
                  tttggggtacagtctatgcctcgggcatccaagcagcaagcgcgttacgccgtgggtcgatgtttgatg
                  ttatggagcagcaacgatgttacgcagcagggcagtcgccctaaaacaaagttaaacattatgagggga
                  agcggtgatcgccgaagtatcgactcaactatcagaggtagttggcgccatcgagcgccatctcgaac
                  cgacgttgctggccgtacatttgtacggctccgcagtggatggcggcctgaagccacacagtgatatt
                  gatttgctggttacggtgaccgtaaggcttgatgaaacaacgcggcgagctttgatcaacgaccttttgg
                  aaacttcggcttcccctggagagagcgagattctccgcgctgtagaagtcaccattgttgtgcacgacg
                  acatcattccgtggcgttatccagctaagcgcgaactgcaatttggagaatggcagcgcaatgacattc
                  ttgcaggtatcttcgagccagccacgatcgacattgatctggctatcttgctgacaaaagcaagagaac
                  atagcgttgccttggtaggtccagcggcggaggaactctttgatccggttcctgaacaggatctatttga
                  ggcgctaaatgaaaccttaacgctatggaactcgccgcccgactgggctggcgatgagcgaaatgta
```

TABLE 7-continued pA24, pA25, and pA26 sequences

```
gtgcttacgttgtcccgcatttggtacagcgcagtaaccggcaaaatcgcgccgaaggatgtcgctgc
cggctgggcaatggagcgcctgccggcccagtatcagcccgtcatacttgaagctagacaggcttat
cttggacaagaagaagatcgcttggcctcgcgcgcagatcagttggaagaatttgtccactacgtgaa
aggcgagatcaccaaggtagtcggcaaataaccctcgagcattcaaggcgccttgattatttgacgtg
gtttgatggcctccacgcacgttgtgatatgtagatgactcgtaggaacaatttcgggcccctgcgtgtt
cttctgaggttcatcttttacatttgcttctgctggataattttcagaggcaacaaggaaaaattagatggca
aaaagtcgtctttcaaggaaaaatccccaccatctttcgagatcccctgtaacttattggcaactgaaag
aatgaaaaggaggaaaatacaaaatatactagaactgaaaaaaaaaaagtataaatagagacgatata
tgccaatacttcacaatgttcgaatctattcttcatttgcagctattgtaaaataataaaacatcaagaacaa
acaagctcaacttgtcttttctaagaacaaagaataaacacaaaaacaaaaagttttttttaattttaatcaaa
aaacaggcccctttcctttgtcgatatcatgtaattagttatgtcacgcttacattcacgccctccccccac
atccgctctaaccgaaaaggaaggagttagacaacctgaagtctaggtccctatttattttttttatagttat
gttagtattaagaacgttatttatatttcaaatttttctttttttttctgtacaaacgcgtgtacgcatgtaacatta
tactgaaaaccttgcttgagaaggttttgggacgctcgaaggctttaatttgtaatcattatcactttacgg
gtccttttccggtgatccgacaggttacgggggcggcgacctcgcgggttttcgctattatgaaaattttcc
ggtttaaggcgtttccgttcttcttcgtcataacttaatgtttttatttaaaatacctcgcgagtggcaacact
gaaaatacccatggagcggcgtaaccgtcgcacaggatctaggtgaagatccttttttgataatctcatg
accaaaatcccttaacgtgagttttcgttccactgagcgtcagaccccgtagaaaagatcaaaggatctt
cttgagatccttttttctgcgcgtaatctgctgcttgcaaacaaaaaaaccaccgctaccagcggtggttt
gtttgccggatcaagagctaccaactcttttttccgaaggtaactggcttcagcagagcgcagataccaa
atactgtccttctagtgtagccgtagttaggccaccacttcaagaactctgtagcaccgcctacataccctc
gctctgctaatcctgttaccagtggctgctgccagtggcgataagtcgtgtcttaccgggttggactcaa
gacgatagttaccggataaggcgcagcggtcgggctgaacggggggttcgtgcacacagcccagct
tggagcga
```

25

TABLE 8

Tailoring enzymes

| Reaction Catalyzed | Enzyme | Species |
|---|---|---|
| Carbon-carbon coupling | Berberine bridge enzyme (BBE) | Ps, Ec, Cj, Bs, Tf |
| | Salutaridine synthase (SalSyn) | Ps |
| | Corytuberine synthase (CorSyn) | Cj |
| Oxidation | Tetrahydroprotoberberine oxidase (STOX) | Cj, Am, Bw |
| | Dihydrobenzophenanthridine oxidase (DBOX) | Ps |
| | Methylstylopine hydroxylase (MSH) | Ps |
| | Protopine 6-hydroxylase (P6H) | Ps, Ec |
| Methylenedioxy bridge formation | Stylopine synthase (StySyn) | Ps, Ec, Am |
| | Cheilanthifoline synthase (CheSyn) | Ps, Ec, Am |
| | Canadine synthase (CAS) | Tf, Cc |
| O-methylation | Norcoclaurine 6-O-methyltrarsferase (6OMT) | Ps, Tf, Cj, Pb |
| | 3'hydroxy-N-methylcoclaurine 4'-O-methyltransferase (4'OMT) | Ps, Tf, Cj, Cc |
| | Reticuline 7-O-methyltransfarase (7OMT) | Ps, Ec |
| | Scoulerine 9-O-methyltransferase (9OMT) | Ps, Tf, Cj, Cc |
| N-methylation | Coclaurine N-methyltransferase (CNMT) | Ps, Tf, Cj |
| | Tetrahydroprotoberberine N-methyltransferase (TMNT) | Ps, Ec, Pb |
| O-demethylation | Thebaine demethylase (T6ODM) | Ps |
| | Codeine demethylase (CODM) | Ps, Ga |
| Reduction | Salutaridine reductase (SalR) | Ps, Pb, Ga |
| | Codeinone reductase (COR) | Ps |
| | Sanguinarine reductase (SanR) | Ec |
| Acetylation | Salutaridine acetyltransferase (SalAT) | Ps |

TABLE 9

Comparison of impurities that may be present in concentrate of poppy straw and clarified yeast culture medium.

| Impurities: | | Concentrate of Poppy Straw | Clarified Yeast Culture Medium |
|---|---|---|---|
| Inorganic | Sodium | ✓ | ✓ |
| | Magnesium | ✓ | ✓ |
| | Silicon | ✓ | x (not in culture medium) |
| | Phosphorus | ✓ | ✓ |
| | Sulfur | ✓ | ✓ |
| | Chloride | ✓ | ✓ |
| | Potassium | ✓ | ✓ |
| | Calcium | ✓ | ✓ |
| | Copper | ✓ | ✓ |
| | Zinc | ✓ | ✓ |
| | Molybdenum | ✓ | ✓ (sodium molybdenite in medium) |

TABLE 9-continued

Comparison of impurities that may be present in concentrate of poppy straw and clarified yeast culture medium.

| | Impurities: | Concentrate of Poppy Straw | Clarified Yeast Culture Medium |
|---|---|---|---|
| | Iron | ✓ | ✓ |
| | Manganese | ✓ | ✓ |
| | Ammonium | ✓ | ✓ |
| | Boron | ✓ | ✓ |
| Organic | Polysaccharides (starch, cellulose, xylan) | ✓ | X (yeast fed simple sugars) |
| | Lignin (p-coumaryl, coniferyl, sinapyl, alcohols) | ✓ | x |
| | Pigments (chlorophyll, anthocyanins, carotenoids) | ✓ | x |
| | Flavonoids | ✓ | x |
| | Phenanthreoids | ✓ | x |
| | Latex, gum, and wax | ✓ | x |
| | Rubisco | ✓ | x |
| | Meconic acid | ✓ | x |
| | Pseudomorphine | ✓ | x |
| | Narceine | ✓ | x |
| | Thebaol | ✓ | x |
| Other | Pesticides | ✓ | x |
| | Pollen | ✓ | x |

TABLE 10

Distinct groups of molecules pesent in clarified yeast culture medium (CYCM). Unlike concentrate of poppy straw (CPS), yeast host strains may be engineered to produce molecules of a predetermined class of alkaloids (i.e., only one biosynthesis pathway per strain) such that other classes of alkaloids are not present. Therefore, the CYCM may contain molecules within a single biosenthesis pathway including a subset of molecules spanning one or two columns, whereas the CPS may contain a subset of molecules across many columns.

| 1-Benzylisoquinoline | Protoberberine and Phthalideisoquinoline | Morphinan | Isopavine | Aporphine | BisBIA |
|---|---|---|---|---|---|
| Tetrahydro-papaverine | Scoulerine | Salutaridine | Pavine | Magnoflorine | Dauricine |
| Dihydro-papverine | Stylopine | Salutaridnol | Caryachine | Coryluberine | Berbamunine |
| Papaverine | Cis-N-methylstylopine | Salutaridine-7-0-acetate | Bisnor-argemonine | Aparinorphine | Ligensinine |
| | Protopine | Thebaine | Isonor-aremonine | Boidine | Fangchinoline |
| | Dihydro-sanguinarine | Codeinone | | | Tetradrine |
| | Tetrahydro-columbarine | Oripavine | | | Curine |
| | N-methylcanadine | Morphinone | | | Cepharanthine |
| | Noscapine | Neopinone | | | Berbamine |
| | Berberine | Neopine | | | |
| | | Codeine | | | |
| | | Morphine | | | |
| | | Neomorphine | | | |
| | | Hydrocodone | | | |
| | | Oxycodone | | | |
| | | 14-hydroxycodeine | | | |
| | | Dihydromorphine | | | |
| | | Dihydrocodeine | | | |

TABLE 11

Impurities that may be present in chemical synthesis preparations of compounds

| Compound | Impurities |
|---|---|
| Buprenorphine | 15,16-Dehydrobuprenorphine, 17,18-Dehydrobuprenorphine, 18,19-demethylbuprenorphine, 19,19'-Ethylbuprenorphine, 2,2'-Bisbuprenorphine, 3-Deshydroxybuprenorphine, 3-O-Methylbuprenorphine, 3-O-Methyl-N-cyanonorbuprenorphine, 3-O-Methyl-N-methylnorbuprenorphine, 6-O-Desmethylbuprenorphine, Buprenorphine N-oxide, N-But-3-enylnorbuprenorphine, N-But-3-enylnormethylbuprenorphine, N-Butylnorbuprenorphine, N-Methylbuprenorphine, Norbuprenorphine, Tetramethylfuran buprenorphine |
| Oxymorphone | 1-Bromooxymorphone, 6-Beta oxymorphol, 10-Alpha-hydroxyoxymorphone, 10-Ketooxymorphone, 2,2-Bisoxymorphone, Noroxymorphone, Oxymorphone N-oxide, 10-Hydroxyoxymorphone, 4-Hydroxyoxymorphone, 8-Hydroxyoxymorphone, Hydromorphinol. |
| Naltrexone | 10-Hydroxynaltrexone, 10-Ketonaltrexone, 14-Hydroxy-17-cyclopropylmethylnormorphinone, 2,2'-Bisnaltrexone, 3-Cyclopropylmethylnaltrexone, 3-O-Methylnaltrexone, 8-Hydroxynaltrexone, N-(3-Butenyl)-noroxymorphone, Naltrexone aldol dimer, N-Formyl-noroxymorphone |

TABLE 11-continued

Impurities that may be present in chemical synthesis preparations of compounds

| Compound | Impurities |
|---|---|
| Naloxone | 10-Alpha-hydroxynaloxone, 10-Beta-hydroxynaloxone, 10-Ketonaloxone, 3-O-Allylnaloxone, 7,8-Didehydronaloxone, 2,2'-Bisnaloxone, Naloxone N-oxide |
| Nalbuphine | Beta-epimer of nalbuphine, 2,2'-Bisnalbuphine, 6-Ketonalbuphine, 10-Ketonalbuphine, Alpha-noroxymorphol, N-(Cyclobutylcarbonyl)-alpha-noroxymorphol, N-Formyl-6-alpha-noroxymophol. |

While preferred embodiments of the invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of altering an opioid to a nal-opioid, comprising:
    contacting the opioid with at least a first enzyme, wherein contacting the opioid with the at least a first enzyme converts the opioid to a nor-opioid through removal of a N-linked methyl group from the opioid; and
    contacting the nor-opioid with at least a second enzyme, wherein contacting the nor-opioid with the at least a second enzyme in the presence of a cofactor converts the nor-opioid to the nal-opioid through transfer of a sidechain from the cofactor.

2. A method of altering an opioid to a nal-opioid, comprising:
    contacting a first opioid with at least one enzyme, wherein contacting the first opioid with the at least one enzyme converts the first opioid to a second opioid through loss of an O-linked methyl group;
    contacting the second opioid with at least a second enzyme, wherein contacting the opioid with the at least a second enzyme converts the second opioid to the nor-opioid through loss of an N-linked methyl group; and
    contacting the nor-opioid with at least a third enzyme, wherein contacting the nor-opioid with the at least a third enzyme in the presence of a cofactor converts the nor-opioid to a nal-opioid through transfer of a sidechain from the cofactor.

3. The method of claim 1, wherein the nal-opioid is produced by culturing an engineered cell comprising a coding sequence for encoding the first enzyme and the second enzyme.

4. The method of claim 2, wherein the nor-opioid is produced by culturing an engineered cell comprising a coding sequence for encoding the first enzyme, the second enzyme, and the third enzyme.

5. The method of claim 3, further comprising:
    recovering the nal-opioid from the cell culture.

6. An engineered cell that produces a nor-opioid from an opioid produced from and present within the engineered cell, the engineered cell comprising a heterologous coding sequence encoding an N-demethylase produced by the engineered cell, wherein the N-demethylase converts the opioid within the engineered cell to the nor-opioid and wherein the nor-opioid is produced within the engineered cell.

7. The engineered cell of claim 6, further comprising heterologous coding sequence encoding an N-methyltransferase.

8. The engineered cell of claim 6, wherein the opioid is produced within the engineered cell by a metabolic pathway starting with L-tyrosine.

9. A method of altering a nor-opioid to a nal-opioid, comprising:

contacting said nor-opioid with at least one enzyme, wherein contacting said nor-opioid with said enzyme in the presence of a cofactor converts said nor-opioid to a nal-opioid through transfer of a sidechain from the cofactor.

10. A method for forming a product stream having a nor-opioid product, comprising:
 i. providing engineered cells and a feedstock including nutrients and water to a batch reactor, which engineered cells have at least one heterologous coding sequence comprising a N-demethylase enzyme;
 ii. in said batch reactor, subjecting said engineered cells to fermentation by incubating said engineered cells for a time period of at least about 5 minutes to produce a solution comprising said nor-opioid and cellular material; and
 iii. using at least one separation unit to separate said nor-opioid from said cellular material to provide said product stream comprising said nor-opioid.

11. The method of claim 4, further comprising: recovering the nal-opioid from the cell culture.

* * * * *

```
                          SEQUENCE LISTING

<160> NUMBER OF SEQ ID NOS: 117

<210> SEQ ID NO 1
<211> LENGTH: 901
<212> TYPE: PRT
<213> ORGANISM: Papaver somniferum

<400> SEQUENCE: 1

Met Glu Leu Gln Tyr Ile Ser Tyr Phe Gln Pro Thr Ser Ser Val Val
1               5                   10                  15

Ala Leu Leu Leu Ala Leu Val Ser Ile Leu Ser Ser Val Val Val Leu
            20                  25                  30

Arg Lys Thr Phe Leu Asn Asn Tyr Ser Ser Ser Pro Ala Ser Ser Thr
        35                  40                  45

Lys Thr Ala Val Leu Ser His Gln Arg Gln Gln Ser Cys Ala Leu Pro
    50                  55                  60

Ile Ser Gly Leu Leu His Ile Phe Met Asn Lys Asn Gly Leu Ile His
65                  70                  75                  80

Val Thr Leu Gly Asn Met Ala Asp Lys Tyr Gly Pro Ile Phe Ser Phe
                85                  90                  95

Pro Thr Gly Ser His Arg Thr Leu Val Val Ser Ser Trp Glu Met Val
            100                 105                 110

Lys Glu Cys Phe Thr Gly Asn Asn Asp Thr Ala Phe Ser Asn Arg Pro
        115                 120                 125

Ile Pro Leu Ala Phe Lys Thr Ile Phe Tyr Ala Cys Gly Gly Ile Asp
    130                 135                 140

Ser Tyr Gly Leu Ser Ser Val Pro Tyr Gly Lys Tyr Trp Arg Glu Leu
145                 150                 155                 160

Arg Lys Val Cys Val His Asn Leu Leu Ser Asn Gln Gln Leu Leu Lys
                165                 170                 175

Phe Arg His Leu Ile Ile Ser Gln Val Asp Thr Ser Phe Asn Lys Leu
            180                 185                 190

Tyr Glu Leu Cys Lys Asn Ser Glu Asp Asn His Gly Asn Tyr Thr Thr
        195                 200                 205

Thr Thr Thr Thr Ala Ala Gly Met Val Arg Ile Asp Asp Trp Leu Ala
    210                 215                 220

Glu Leu Ser Phe Asn Val Ile Gly Arg Ile Val Cys Gly Phe Gln Ser
225                 230                 235                 240
```

```
Gly Pro Lys Thr Gly Ala Pro Ser Arg Val Glu Gln Phe Lys Glu Ala
            245                 250                 255
Ile Asn Glu Ala Ser Tyr Phe Met Ser Thr Ser Pro Val Ser Asp Asn
        260                 265                 270
Val Pro Met Leu Gly Trp Ile Asp Gln Leu Thr Gly Leu Thr Arg Asn
    275                 280                 285
Met Lys His Cys Gly Lys Lys Leu Asp Leu Val Val Glu Ser Ile Ile
290                 295                 300
Asn Asp His Arg Gln Lys Arg Arg Phe Ser Arg Thr Lys Gly Gly Asp
305                 310                 315                 320
Glu Lys Asp Asp Glu Gln Asp Asp Phe Ile Asp Ile Cys Leu Ser Ile
                325                 330                 335
Met Glu Gln Pro Gln Leu Pro Gly Asn Asn Asn Pro Ser Gln Ile Pro
            340                 345                 350
Ile Lys Ser Ile Val Leu Asp Met Ile Gly Gly Thr Asp Thr Thr
        355                 360                 365
Lys Leu Thr Thr Ile Trp Thr Leu Ser Leu Leu Leu Asn Asn Pro His
    370                 375                 380
Val Leu Asp Lys Ala Lys Gln Glu Val Asp Ala His Phe Arg Thr Lys
385                 390                 395                 400
Arg Arg Ser Thr Asn Asp Ala Ala Ala Val Val Asp Phe Asp Asp
                405                 410                 415
Ile Arg Asn Leu Val Tyr Ile Gln Ala Ile Ile Lys Glu Ser Met Arg
            420                 425                 430
Leu Tyr Pro Ala Ser Pro Val Glu Arg Leu Ser Gly Glu Asp Cys
        435                 440                 445
Val Val Gly Gly Phe His Val Pro Ala Gly Thr Arg Leu Trp Ala Asn
    450                 455                 460
Val Trp Lys Met Gln Arg Asp Pro Lys Val Trp Asp Pro Leu Val
465                 470                 475                 480
Phe Arg Pro Asp Arg Phe Leu Ser Asp Glu Gln Lys Met Val Asp Val
                485                 490                 495
Arg Gly Gln Asn Tyr Glu Leu Leu Pro Phe Gly Ala Gly Arg Arg Val
            500                 505                 510
Cys Pro Gly Val Ser Phe Ser Leu Asp Leu Met Gln Leu Val Leu Thr
        515                 520                 525
Arg Leu Ile Leu Glu Phe Glu Met Lys Ser Pro Ser Gly Lys Val Asp
    530                 535                 540
Met Thr Ala Thr Pro Gly Leu Met Ser Tyr Lys Val Ile Pro Leu Asp
545                 550                 555                 560
Ile Leu Leu Thr His Arg Arg Ile Lys Pro Cys Val Gln Ser Ala Ala
                565                 570                 575
Ser Glu Arg Asp Met Glu Ser Ser Gly Val Pro Val Ile Thr Leu Gly
            580                 585                 590
Ser Gly Lys Val Met Pro Val Leu Gly Met Gly Thr Phe Glu Lys Val
        595                 600                 605
Gly Lys Gly Ser Glu Arg Glu Arg Leu Ala Ile Leu Lys Ala Ile Glu
    610                 615                 620
Val Gly Tyr Arg Tyr Phe Asp Thr Ala Ala Ala Tyr Glu Thr Glu Glu
625                 630                 635                 640
Val Leu Gly Glu Ala Ile Ala Glu Ala Leu Gln Leu Gly Leu Val Lys
                645                 650                 655
```

-continued

```
Ser Arg Asp Glu Leu Phe Ile Ser Ser Met Leu Trp Cys Thr Asp Ala
            660                 665                 670

His Ala Asp Arg Val Leu Leu Ala Leu Gln Asn Ser Leu Arg Asn Leu
        675                 680                 685

Lys Leu Glu Tyr Val Asp Leu Tyr Met Leu Pro Phe Pro Ala Ser Leu
    690                 695                 700

Lys Pro Gly Lys Ile Thr Met Asp Ile Pro Glu Glu Asp Ile Cys Arg
705                 710                 715                 720

Met Asp Tyr Arg Ser Val Trp Ala Ala Met Glu Glu Cys Gln Asn Leu
                725                 730                 735

Gly Phe Thr Lys Ser Ile Gly Val Ser Asn Phe Ser Cys Lys Lys Leu
            740                 745                 750

Gln Glu Leu Met Ala Thr Ala Asn Ile Pro Pro Ala Val Asn Gln Val
        755                 760                 765

Glu Met Ser Pro Ala Phe Gln Gln Lys Lys Leu Arg Glu Tyr Cys Asn
    770                 775                 780

Ala Asn Asn Ile Leu Val Ser Ala Ile Ser Val Leu Gly Ser Asn Gly
785                 790                 795                 800

Thr Pro Trp Gly Ser Asn Ala Val Leu Gly Ser Glu Val Leu Lys Lys
                805                 810                 815

Ile Ala Met Ala Lys Gly Lys Ser Val Ala Gln Val Ser Met Arg Trp
            820                 825                 830

Val Tyr Glu Gln Gly Ala Ser Leu Val Val Lys Ser Phe Ser Glu Glu
        835                 840                 845

Arg Leu Arg Glu Asn Leu Asn Ile Phe Asp Trp Glu Leu Thr Lys Glu
    850                 855                 860

Asp His Glu Lys Ile Gly Glu Ile Pro Gln Cys Arg Ile Leu Ser Ala
865                 870                 875                 880

Tyr Phe Leu Val Ser Pro Asn Gly Pro Phe Lys Ser Gln Glu Glu Leu
                885                 890                 895

Trp Asp Asp Glu Ala
            900

<210> SEQ ID NO 2
<211> LENGTH: 919
<212> TYPE: PRT
<213> ORGANISM: Papaver somniferum
<220> FEATURE:
<221> NAME/KEY: MOD_RES
<222> LOCATION: (209)..(209)
<223> OTHER INFORMATION: Any amino acid
<220> FEATURE:
<221> NAME/KEY: MOD_RES
<222> LOCATION: (226)..(226)
<223> OTHER INFORMATION: Any amino acid

<400> SEQUENCE: 2

Met Glu Leu Gln Tyr Ile Ser Tyr Phe Gln Pro Thr Ser Ser Val Val
1               5                   10                  15

Ala Leu Leu Leu Ala Leu Val Ser Ile Leu Ser Ser Val Val Val Leu
            20                  25                  30

Arg Lys Thr Phe Leu Asn Asn Tyr Ser Ser Ser Pro Ala Ser Ser Thr
        35                  40                  45

Lys Thr Ala Val Leu Ser His Gln Arg Gln Ser Cys Ala Leu Pro
    50                  55                  60

Ile Ser Gly Leu Leu His Ile Phe Met Asn Lys Asn Gly Leu Ile His
65                  70                  75                  80
```

```
Val Thr Leu Gly Asn Met Ala Asp Lys Tyr Gly Pro Ile Phe Ser Phe
                    85                  90                  95

Pro Thr Gly Ser His Arg Thr Leu Val Val Ser Ser Trp Glu Met Val
                100                 105                 110

Lys Glu Cys Phe Thr Gly Asn Asn Asp Thr Ala Phe Ser Asn Arg Pro
                115                 120                 125

Ile Pro Leu Ala Phe Lys Thr Ile Phe Tyr Ala Cys Gly Gly Ile Asp
                130                 135                 140

Ser Tyr Gly Leu Ser Ser Val Pro Tyr Gly Lys Tyr Trp Arg Glu Leu
145                 150                 155                 160

Arg Lys Val Cys Val His Asn Leu Leu Ser Asn Gln Gln Leu Leu Lys
                165                 170                 175

Phe Arg His Leu Ile Ile Ser Gln Val Asp Thr Ser Phe Asn Lys Leu
                180                 185                 190

Tyr Glu Leu Cys Lys Asn Ser Glu Asp Asn His Gly Asn Tyr Thr Thr
                195                 200                 205

Xaa Leu Leu Leu Pro Gln Leu Ala Trp Arg Gln Pro Trp Lys Leu Tyr
    210                 215                 220

Tyr Xaa Thr Thr Thr Thr Ala Ala Gly Met Val Arg Ile Asp Asp Trp
225                 230                 235                 240

Leu Ala Glu Leu Ser Phe Asn Val Ile Gly Arg Ile Val Cys Gly Phe
                245                 250                 255

Gln Ser Gly Pro Lys Thr Gly Ala Pro Ser Arg Val Glu Gln Phe Lys
                260                 265                 270

Glu Ala Ile Asn Glu Ala Ser Tyr Phe Met Ser Thr Ser Pro Val Ser
                275                 280                 285

Asp Asn Val Pro Met Leu Gly Trp Ile Asp Gln Leu Thr Gly Leu Thr
                290                 295                 300

Arg Asn Met Lys His Cys Gly Lys Lys Leu Asp Leu Val Val Glu Ser
305                 310                 315                 320

Ile Ile Asn Asp His Arg Gln Lys Arg Phe Ser Arg Thr Lys Gly
                325                 330                 335

Gly Asp Glu Lys Asp Asp Glu Gln Asp Asp Phe Ile Asp Ile Cys Leu
                340                 345                 350

Ser Ile Met Glu Gln Pro Gln Leu Pro Gly Asn Asn Asn Pro Ser Gln
                355                 360                 365

Ile Pro Ile Lys Ser Ile Val Leu Asp Met Ile Gly Gly Gly Thr Asp
                370                 375                 380

Thr Thr Lys Leu Thr Thr Ile Trp Thr Leu Ser Leu Leu Leu Asn Asn
385                 390                 395                 400

Pro His Val Leu Asp Lys Ala Lys Gln Glu Val Asp Ala His Phe Arg
                405                 410                 415

Thr Lys Arg Arg Ser Thr Asn Asp Ala Ala Ala Val Val Asp Phe
                420                 425                 430

Asp Asp Ile Arg Asn Leu Val Tyr Ile Gln Ala Ile Ile Lys Glu Ser
                435                 440                 445

Met Arg Leu Tyr Pro Ala Ser Pro Val Val Glu Arg Leu Ser Gly Glu
                450                 455                 460

Asp Cys Val Val Gly Gly Phe His Val Pro Ala Gly Thr Arg Leu Trp
465                 470                 475                 480

Ala Asn Val Trp Lys Met Gln Arg Asp Pro Lys Val Trp Asp Pro
                485                 490                 495

Leu Val Phe Arg Pro Asp Arg Phe Leu Ser Asp Glu Gln Lys Met Val
```

```
            500                 505                 510
Asp Val Arg Gly Gln Asn Tyr Glu Leu Leu Pro Phe Gly Ala Gly Arg
            515                 520                 525

Arg Val Cys Pro Gly Val Ser Phe Ser Leu Asp Leu Met Gln Leu Val
            530                 535                 540

Leu Thr Arg Leu Ile Leu Glu Phe Glu Met Lys Ser Pro Ser Gly Lys
545                 550                 555                 560

Val Asp Met Thr Ala Thr Pro Gly Leu Met Ser Tyr Lys Val Ile Pro
                565                 570                 575

Leu Asp Ile Leu Leu Thr His Arg Arg Ile Lys Pro Cys Val Gln Ser
            580                 585                 590

Ala Ala Ser Glu Arg Asp Met Glu Ser Ser Gly Val Pro Val Ile Thr
            595                 600                 605

Leu Gly Ser Gly Lys Val Met Pro Val Leu Gly Met Gly Thr Phe Glu
            610                 615                 620

Lys Val Gly Lys Gly Ser Glu Arg Glu Arg Leu Ala Ile Leu Lys Ala
625                 630                 635                 640

Ile Glu Val Gly Tyr Arg Tyr Phe Asp Thr Ala Ala Ala Tyr Glu Thr
                645                 650                 655

Glu Glu Val Leu Gly Glu Ala Ile Ala Glu Ala Leu Gln Leu Gly Leu
            660                 665                 670

Val Lys Ser Arg Asp Glu Leu Phe Ile Ser Ser Met Leu Trp Cys Thr
            675                 680                 685

Asp Ala His Ala Asp Arg Val Leu Leu Ala Leu Gln Asn Ser Leu Arg
            690                 695                 700

Asn Leu Lys Leu Glu Tyr Val Asp Leu Tyr Met Leu Pro Phe Pro Ala
705                 710                 715                 720

Ser Leu Lys Pro Gly Lys Ile Thr Met Asp Ile Pro Glu Glu Asp Ile
                725                 730                 735

Cys Arg Met Asp Tyr Arg Ser Val Trp Ala Ala Met Glu Glu Cys Gln
                740                 745                 750

Asn Leu Gly Phe Thr Lys Ser Ile Gly Val Ser Asn Phe Ser Cys Lys
            755                 760                 765

Lys Leu Gln Glu Leu Met Ala Thr Ala Asn Ile Pro Pro Ala Val Asn
770                 775                 780

Gln Val Glu Met Ser Pro Ala Phe Gln Gln Lys Lys Leu Arg Glu Tyr
785                 790                 795                 800

Cys Asn Ala Asn Asn Ile Leu Val Ser Ala Ile Ser Val Leu Gly Ser
                805                 810                 815

Asn Gly Thr Pro Trp Gly Ser Asn Ala Val Leu Gly Ser Glu Val Leu
            820                 825                 830

Lys Lys Ile Ala Met Ala Lys Gly Lys Ser Val Ala Gln Val Ser Met
            835                 840                 845

Arg Trp Val Tyr Glu Gln Gly Ala Ser Leu Val Val Lys Ser Phe Ser
            850                 855                 860

Glu Glu Arg Leu Arg Glu Asn Leu Asn Ile Phe Asp Trp Glu Leu Thr
865                 870                 875                 880

Lys Glu Asp His Glu Lys Ile Gly Glu Ile Pro Gln Cys Arg Ile Leu
                885                 890                 895

Ser Ala Tyr Phe Leu Val Ser Pro Asn Gly Pro Phe Lys Ser Gln Glu
            900                 905                 910

Glu Leu Trp Asp Asp Glu Ala
            915
```

<210> SEQ ID NO 3
<211> LENGTH: 732
<212> TYPE: PRT
<213> ORGANISM: Papaver somniferum
<220> FEATURE:
<221> NAME/KEY: MOD_RES
<222> LOCATION: (725)..(725)
<223> OTHER INFORMATION: Any amino acid

<400> SEQUENCE: 3

| | | | | | | | | | | | | | | | |
|---|---|---|---|---|---|---|---|---|---|---|---|---|---|---|---|
| Met | Glu | Leu | Gln | Tyr | Ile | Ser | Tyr | Phe | Gln | Pro | Thr | Ser | Ser | Val | Val |
| 1 | | | | 5 | | | | | 10 | | | | | 15 | |
| Ala | Leu | Leu | Leu | Ala | Leu | Val | Ser | Ile | Leu | Ser | Ser | Val | Val | Val | Leu |
| | | | 20 | | | | | 25 | | | | | 30 | | |
| Arg | Lys | Thr | Phe | Leu | Asn | Asn | Tyr | Ser | Ser | Ser | Pro | Ala | Ser | Ser | Thr |
| | | 35 | | | | | 40 | | | | | 45 | | | |
| Lys | Thr | Ala | Val | Leu | Ser | His | Gln | Arg | Gln | Gln | Ser | Cys | Ala | Leu | Pro |
| | 50 | | | | | 55 | | | | | 60 | | | | |
| Ile | Ser | Gly | Leu | Leu | His | Ile | Phe | Met | Asn | Lys | Asn | Gly | Leu | Ile | His |
| 65 | | | | | 70 | | | | | 75 | | | | | 80 |
| Val | Thr | Leu | Gly | Asn | Met | Ala | Asp | Lys | Tyr | Gly | Pro | Ile | Phe | Ser | Phe |
| | | | | 85 | | | | | 90 | | | | | 95 | |
| Pro | Thr | Gly | Ser | His | Arg | Thr | Leu | Val | Val | Ser | Ser | Trp | Glu | Met | Val |
| | | | 100 | | | | | 105 | | | | | 110 | | |
| Lys | Glu | Cys | Phe | Thr | Gly | Asn | Asn | Asp | Thr | Ala | Phe | Ser | Asn | Arg | Pro |
| | | 115 | | | | | 120 | | | | | 125 | | | |
| Ile | Pro | Leu | Ala | Phe | Lys | Thr | Ile | Phe | Tyr | Ala | Cys | Gly | Gly | Ile | Asp |
| | 130 | | | | | 135 | | | | | 140 | | | | |
| Ser | Tyr | Gly | Leu | Ser | Ser | Val | Pro | Tyr | Gly | Lys | Tyr | Trp | Arg | Glu | Leu |
| 145 | | | | | 150 | | | | | 155 | | | | | 160 |
| Arg | Lys | Val | Cys | Val | His | Asn | Leu | Leu | Ser | Asn | Gln | Gln | Leu | Leu | Lys |
| | | | | 165 | | | | | 170 | | | | | 175 | |
| Phe | Arg | His | Leu | Ile | Ile | Ser | Gln | Val | Asp | Thr | Ser | Phe | Asn | Lys | Leu |
| | | | 180 | | | | | 185 | | | | | 190 | | |
| Tyr | Glu | Leu | Cys | Lys | Asn | Ser | Glu | Asp | Asn | His | Gly | Asn | Tyr | Thr | Thr |
| | | 195 | | | | | 200 | | | | | 205 | | | |
| Thr | Thr | Thr | Thr | Ala | Ala | Gly | Met | Val | Arg | Ile | Asp | Asp | Trp | Leu | Ala |
| | 210 | | | | | 215 | | | | | 220 | | | | |
| Glu | Leu | Ser | Phe | Asn | Val | Ile | Gly | Arg | Ile | Val | Cys | Gly | Phe | Gln | Ser |
| 225 | | | | | 230 | | | | | 235 | | | | | 240 |
| Gly | Pro | Lys | Thr | Gly | Ala | Pro | Ser | Arg | Val | Glu | Gln | Phe | Lys | Glu | Ala |
| | | | | 245 | | | | | 250 | | | | | 255 | |
| Ile | Asn | Glu | Ala | Ser | Tyr | Phe | Met | Ser | Thr | Ser | Pro | Val | Ser | Asp | Asn |
| | | | 260 | | | | | 265 | | | | | 270 | | |
| Val | Pro | Met | Leu | Gly | Trp | Ile | Asp | Gln | Leu | Thr | Gly | Leu | Thr | Arg | Asn |
| | | 275 | | | | | 280 | | | | | 285 | | | |
| Met | Lys | His | Cys | Gly | Lys | Lys | Leu | Asp | Leu | Val | Val | Glu | Ser | Ile | Ile |
| | 290 | | | | | 295 | | | | | 300 | | | | |
| Asn | Asp | His | Arg | Gln | Lys | Arg | Arg | Phe | Ser | Arg | Thr | Lys | Gly | Gly | Asp |
| 305 | | | | | 310 | | | | | 315 | | | | | 320 |
| Glu | Lys | Asp | Asp | Glu | Gln | Asp | Phe | Ile | Asp | Ile | Cys | Leu | Ser | Ile |
| | | | | 325 | | | | | 330 | | | | | 335 |
| Met | Glu | Gln | Pro | Gln | Leu | Pro | Gly | Asn | Asn | Asn | Pro | Ser | Gln | Ile | Pro |
| | | | 340 | | | | | 345 | | | | | 350 | | |

```
Ile Lys Ser Ile Val Leu Asp Met Ile Gly Gly Thr Asp Thr Thr
            355                 360                 365
Lys Leu Thr Thr Ile Trp Thr Leu Ser Leu Leu Asn Asn Pro His
    370                 375                 380
Val Leu Asp Lys Ala Lys Gln Glu Val Asp Ala His Phe Arg Thr Lys
385                 390                 395                 400
Arg Arg Ser Thr Asn Asp Ala Ala Ala Val Val Asp Phe Asp Asp
                405                 410                 415
Ile Arg Asn Leu Val Tyr Ile Gln Ala Ile Ile Lys Glu Ser Met Arg
                420                 425                 430
Leu Tyr Pro Ala Ser Pro Val Val Glu Arg Leu Ser Gly Glu Asp Cys
            435                 440                 445
Val Val Gly Gly Phe His Val Pro Ala Gly Thr Arg Leu Trp Ala Asn
            450                 455                 460
Val Trp Lys Met Gln Arg Asp Pro Lys Val Trp Asp Asp Pro Leu Val
465                 470                 475                 480
Phe Arg Pro Asp Arg Phe Leu Ser Asp Glu Gln Lys Met Val Asp Val
                485                 490                 495
Arg Gly Gln Asn Tyr Glu Leu Leu Pro Phe Gly Ala Gly Arg Arg Val
                500                 505                 510
Cys Pro Gly Val Ser Phe Ser Leu Asp Leu Met Gln Leu Val Leu Thr
            515                 520                 525
Arg Leu Ile Leu Glu Phe Glu Met Lys Ser Pro Ser Gly Lys Val Asp
            530                 535                 540
Met Thr Ala Thr Pro Gly Leu Met Ser Tyr Lys Val Ile Pro Leu Asp
545                 550                 555                 560
Ile Leu Leu Thr His Arg Arg Ile Lys Pro Cys Val Gln Ser Ala Ala
                565                 570                 575
Ser Glu Arg Asp Met Glu Ser Ser Gly Val Pro Val Ile Thr Leu Gly
            580                 585                 590
Ser Gly Lys Val Met Pro Val Leu Gly Met Gly Thr Phe Glu Lys Val
            595                 600                 605
Gly Lys Gly Ser Glu Arg Glu Arg Leu Ala Ile Leu Lys Ala Ile Glu
    610                 615                 620
Val Gly Tyr Arg Tyr Phe Asp Thr Ala Ala Tyr Glu Thr Glu Glu
625                 630                 635                 640
Val Leu Gly Glu Ala Ile Ala Glu Ala Leu Gln Leu Gly Leu Val Lys
                645                 650                 655
Ser Arg Asp Glu Leu Phe Ile Ser Ser Met Leu Trp Cys Thr Asp Ala
            660                 665                 670
His Ala Asp Arg Val Leu Leu Ala Leu Gln Asn Ser Leu Arg Asn Leu
            675                 680                 685
Lys Leu Glu Tyr Val Asp Leu Tyr Met Leu Pro Phe Pro Ala Ser Leu
    690                 695                 700
Lys Pro Gly Lys Ile Thr Met Asp Ile Pro Glu Glu Asp Ile Cys Arg
705                 710                 715                 720
Met Asp Tyr Arg Xaa Val Ser Lys Pro Trp Leu His
                725                 730

<210> SEQ ID NO 4
<211> LENGTH: 764
<212> TYPE: PRT
<213> ORGANISM: Papaver somniferum
<220> FEATURE:
<221> NAME/KEY: MOD_RES
```

<222> LOCATION: (6)..(6)
<223> OTHER INFORMATION: Any amino acid

<400> SEQUENCE: 4

```
Met Arg Trp His Arg Xaa Ile Asp Ser Tyr Gly Leu Ser Ser Val Pro
1               5                   10                  15

Tyr Gly Lys Tyr Trp Arg Glu Leu Arg Lys Val Cys Val His Asn Leu
            20                  25                  30

Leu Ser Asn Gln Gln Leu Leu Lys Phe Arg His Leu Ile Ile Ser Gln
        35                  40                  45

Val Asp Thr Ser Phe Asn Lys Leu Tyr Glu Leu Cys Lys Asn Ser Glu
    50                  55                  60

Asp Asn Gln Gly Asn Tyr Pro Thr Thr Thr Ala Ala Gly Met Val
65                  70                  75                  80

Arg Ile Asp Asp Trp Leu Ala Glu Leu Ser Phe Asn Val Ile Gly Arg
                85                  90                  95

Ile Val Cys Gly Phe Gln Ser Gly Pro Lys Thr Gly Ala Pro Ser Arg
            100                 105                 110

Val Glu Gln Phe Lys Glu Ala Ile Asn Glu Ala Ser Tyr Phe Met Ser
        115                 120                 125

Thr Ser Pro Val Ser Asp Asn Val Pro Met Leu Gly Trp Ile Asp Gln
    130                 135                 140

Leu Thr Gly Leu Thr Arg Asn Met Lys His Cys Gly Lys Lys Leu Asp
145                 150                 155                 160

Leu Val Val Glu Ser Ile Ile Asn Asp His Arg Gln Lys Arg Arg Phe
                165                 170                 175

Ser Arg Thr Lys Gly Gly Asp Glu Lys Asp Asp Glu Gln Asp Asp Phe
            180                 185                 190

Ile Asp Ile Cys Leu Ser Ile Met Glu Gln Pro Gln Leu Pro Gly Asn
        195                 200                 205

Asn Asn Pro Ser Gln Ile Pro Ile Lys Ser Ile Val Leu Asp Met Ile
    210                 215                 220

Gly Gly Gly Thr Asp Thr Thr Lys Leu Thr Thr Ile Trp Thr Leu Ser
225                 230                 235                 240

Leu Leu Leu Asn Asn Pro His Val Leu Asp Lys Ala Lys Gln Glu Val
                245                 250                 255

Asp Ala His Phe Arg Thr Lys Arg Arg Ser Thr Asn Asp Ala Ala Ala
            260                 265                 270

Ala Val Val Asp Phe Asp Asp Ile Arg Asn Leu Val Tyr Ile Gln Ala
        275                 280                 285

Ile Ile Lys Glu Ser Met Arg Leu Tyr Pro Ala Ser Pro Val Val Glu
    290                 295                 300

Arg Leu Ser Gly Glu Asp Cys Val Val Gly Phe His Val Pro Ala
305                 310                 315                 320

Gly Thr Arg Leu Trp Ala Asn Val Trp Lys Met Gln Arg Asp Pro Lys
                325                 330                 335

Val Trp Asp Asp Pro Leu Val Phe Arg Pro Asp Arg Phe Leu Ser Asp
            340                 345                 350

Glu Gln Lys Met Val Asp Val Arg Gly Gln Asn Tyr Glu Leu Leu Pro
        355                 360                 365

Phe Gly Ala Gly Arg Arg Val Cys Pro Gly Val Ser Phe Ser Leu Asp
    370                 375                 380

Leu Met Gln Leu Val Leu Thr Arg Leu Ile Leu Glu Phe Glu Met Lys
385                 390                 395                 400
```

Ser Pro Ser Gly Lys Val Asp Met Thr Ala Thr Pro Gly Leu Met Ser
            405                 410                 415

Tyr Lys Val Ile Pro Leu Asp Ile Leu Leu Thr His Arg Arg Ile Lys
            420                 425                 430

Pro Cys Val Gln Ser Ala Ala Ser Glu Arg Asp Met Glu Ser Ser Gly
            435                 440                 445

Val Pro Val Ile Thr Leu Gly Ser Gly Lys Val Met Pro Val Leu Gly
450                 455                 460

Met Gly Thr Phe Glu Lys Val Gly Lys Gly Ser Glu Arg Glu Arg Leu
465                 470                 475                 480

Ala Ile Leu Lys Ala Ile Glu Val Gly Tyr Arg Tyr Phe Asp Thr Ala
            485                 490                 495

Ala Ala Tyr Glu Thr Glu Glu Val Leu Gly Glu Ala Ile Ala Glu Ala
            500                 505                 510

Leu Gln Leu Gly Leu Val Lys Ser Arg Asp Glu Leu Phe Ile Ser Ser
            515                 520                 525

Met Leu Trp Cys Thr Asp Ala His Ala Asp Arg Val Leu Leu Ala Leu
            530                 535                 540

Gln Asn Ser Leu Arg Asn Leu Lys Leu Glu Tyr Val Asp Leu Tyr Met
545                 550                 555                 560

Leu Pro Phe Pro Ala Ser Leu Lys Pro Gly Lys Ile Thr Met Asp Ile
            565                 570                 575

Pro Glu Glu Asp Ile Cys Arg Met Asp Tyr Arg Ser Val Trp Ala Ala
            580                 585                 590

Met Glu Glu Cys Gln Asn Leu Gly Phe Thr Lys Ser Ile Gly Val Ser
            595                 600                 605

Asn Phe Ser Cys Lys Lys Leu Gln Glu Leu Met Ala Thr Ala Asn Ile
            610                 615                 620

Pro Pro Ala Val Asn Gln Val Glu Met Ser Pro Ala Phe Gln Gln Lys
625                 630                 635                 640

Lys Leu Arg Glu Tyr Cys Asn Ala Asn Asn Ile Leu Val Ser Ala Ile
            645                 650                 655

Ser Val Leu Gly Ser Asn Gly Thr Pro Trp Gly Ser Asn Ala Val Leu
            660                 665                 670

Gly Ser Glu Val Leu Lys Lys Ile Ala Met Ala Lys Gly Lys Ser Val
            675                 680                 685

Ala Gln Val Ser Met Arg Trp Val Tyr Glu Gln Gly Ala Ser Leu Val
            690                 695                 700

Val Lys Ser Phe Ser Glu Arg Leu Arg Glu Asn Leu Asn Ile Phe
705                 710                 715                 720

Asp Trp Glu Leu Thr Lys Glu Asp His Glu Lys Ile Gly Glu Ile Pro
            725                 730                 735

Gln Cys Arg Ile Leu Ser Ala Tyr Phe Leu Val Ser Pro Asn Gly Pro
            740                 745                 750

Phe Lys Ser Gln Glu Glu Leu Trp Asp Asp Glu Ala
            755                 760

<210> SEQ ID NO 5
<211> LENGTH: 900
<212> TYPE: PRT
<213> ORGANISM: Papaver setigerum

<400> SEQUENCE: 5

Met Glu Leu Gln Tyr Ile Ser Tyr Phe Gln Pro Thr Ser Ser Val Val

-continued

```
1               5               10              15
Ala Leu Leu Ala Leu Val Ser Ile Leu Ser Ser Val Val Val Leu
            20              25              30
Arg Lys Thr Phe Leu Asn Asn Tyr Ser Ser Pro Ala Ser Ser Thr
            35              40              45
Lys Thr Ala Val Leu Ser His Gln Arg Gln Gln Ser Cys Ala Leu Pro
            50              55              60
Ile Ser Gly Leu Leu His Ile Phe Met Asn Lys Asn Gly Leu Ile His
65              70              75              80
Val Thr Leu Gly Asn Met Ala Asp Lys Tyr Gly Pro Ile Phe Ser Phe
            85              90              95
Pro Thr Gly Ser His Arg Thr Leu Val Val Ser Ser Trp Glu Met Val
            100             105             110
Lys Glu Cys Phe Thr Gly Asn Asn Asp Thr Ala Phe Ser Asn Arg Pro
            115             120             125
Ile Pro Leu Ala Phe Lys Thr Ile Phe Tyr Ala Cys Gly Gly Ile Asp
            130             135             140
Ser Tyr Gly Leu Ser Ser Val Pro Tyr Gly Lys Tyr Trp Arg Glu Leu
145             150             155             160
Arg Lys Val Cys Val His Asn Leu Leu Ser Asn Gln Gln Leu Leu Lys
            165             170             175
Phe Arg His Leu Ile Ile Ser Gln Val Asp Thr Ser Phe Asn Lys Leu
            180             185             190
Tyr Glu Leu Cys Lys Asn Ser Glu Asp Asn Gln Gly Asn Tyr Thr Thr
            195             200             205
Thr Thr Thr Ala Ala Gly Met Val Arg Ile Asp Asp Trp Leu Ala Glu
210             215             220
Leu Ser Phe Asn Val Ile Gly Arg Ile Val Cys Gly Phe Gln Ser Gly
225             230             235             240
Pro Lys Thr Gly Ala Pro Ser Arg Val Glu Gln Phe Lys Glu Ala Ile
            245             250             255
Asn Glu Ala Ser Tyr Phe Met Ser Thr Ser Pro Val Ser Asp Asn Val
            260             265             270
Pro Met Leu Gly Trp Ile Asp Gln Leu Thr Gly Leu Thr Arg Asn Met
            275             280             285
Lys His Cys Gly Lys Lys Leu Asp Leu Val Val Glu Ser Ile Ile Asn
            290             295             300
Asp His Arg Gln Lys Arg Arg Phe Ser Arg Thr Lys Gly Gly Asp Glu
305             310             315             320
Lys Asp Asp Glu Gln Asp Asp Phe Ile Asp Ile Cys Leu Ser Ile Met
            325             330             335
Glu Gln Pro Gln Leu Pro Gly Asn Asn Pro Ser Gln Ile Pro Ile
            340             345             350
Lys Ser Ile Val Leu Asp Met Ile Gly Gly Gly Thr Asp Thr Thr Lys
            355             360             365
Leu Thr Thr Ile Trp Thr Leu Ser Leu Leu Asn Asn Pro His Val
            370             375             380
Leu Asp Lys Ala Lys Gln Glu Val Asp Ala His Phe Arg Thr Lys Arg
385             390             395             400
Arg Ser Thr Asn Asp Ala Ala Ala Val Asp Phe Asp Ile
            405             410             415
Arg Asn Leu Val Tyr Ile Gln Ala Ile Ile Lys Glu Ser Met Arg Leu
            420             425             430
```

```
Tyr Pro Ala Ser Pro Val Val Glu Arg Leu Ser Gly Glu Asp Cys Val
            435                 440                 445

Val Gly Gly Phe His Val Pro Ala Gly Thr Arg Leu Trp Ala Asn Val
450                 455                 460

Trp Lys Met Gln Arg Asp Pro Lys Val Trp Asp Pro Leu Val Phe
465                 470                 475                 480

Arg Pro Asp Arg Phe Leu Ser Asp Glu Gln Lys Met Val Asp Val Arg
                485                 490                 495

Gly Gln Asn Tyr Glu Leu Leu Pro Phe Gly Ala Gly Arg Arg Val Cys
            500                 505                 510

Pro Gly Val Ser Phe Ser Leu Asp Leu Met Gln Leu Val Leu Thr Arg
            515                 520                 525

Leu Ile Leu Glu Phe Glu Met Lys Ser Pro Ser Gly Lys Val Asp Met
530                 535                 540

Thr Ala Thr Pro Gly Leu Met Ser Tyr Lys Val Ile Pro Leu Asp Ile
545                 550                 555                 560

Leu Leu Thr His Arg Arg Ile Lys Pro Cys Val Gln Ser Ala Ala Ser
                565                 570                 575

Glu Arg Asp Met Glu Ser Ser Gly Val Pro Val Ile Thr Leu Gly Ser
            580                 585                 590

Gly Lys Val Met Pro Val Leu Gly Met Gly Thr Phe Glu Lys Val Gly
            595                 600                 605

Lys Gly Ser Glu Arg Glu Arg Leu Ala Ile Leu Lys Ala Ile Glu Val
            610                 615                 620

Gly Tyr Arg Tyr Phe Asp Thr Ala Ala Ala Tyr Glu Thr Glu Glu Val
625                 630                 635                 640

Leu Gly Glu Ala Ile Ala Glu Ala Leu Gln Leu Gly Leu Val Lys Ser
                645                 650                 655

Arg Asp Glu Leu Phe Ile Ser Ser Met Leu Trp Cys Thr Asp Ala His
            660                 665                 670

Ala Asp Arg Val Leu Leu Ala Leu Gln Asn Ser Leu Arg Asn Leu Lys
            675                 680                 685

Leu Glu Tyr Val Asp Leu Tyr Met Leu Pro Phe Pro Ala Ser Leu Lys
            690                 695                 700

Pro Gly Lys Ile Thr Met Asp Ile Pro Glu Glu Asp Ile Cys Arg Met
705                 710                 715                 720

Asp Tyr Arg Ser Val Trp Ala Ala Met Glu Glu Cys Gln Asn Leu Gly
                725                 730                 735

Phe Thr Lys Ser Ile Gly Val Ser Asn Phe Ser Cys Lys Lys Leu Gln
            740                 745                 750

Glu Leu Met Ala Thr Ala Asn Ile Pro Pro Ala Val Asn Gln Val Glu
            755                 760                 765

Met Ser Pro Ala Phe Gln Gln Lys Lys Leu Arg Glu Tyr Cys Asn Ala
770                 775                 780

Asn Asn Ile Leu Val Ser Ala Ile Ser Val Leu Gly Ser Asn Gly Thr
785                 790                 795                 800

Pro Trp Gly Ser Asn Ala Val Leu Gly Ser Glu Val Leu Lys Lys Ile
                805                 810                 815

Ala Met Ala Lys Gly Lys Ser Val Ala Gln Val Ser Met Arg Trp Val
            820                 825                 830

Tyr Glu Gln Gly Ala Ser Leu Val Val Lys Ser Phe Ser Glu Glu Arg
            835                 840                 845
```

```
Leu Arg Glu Asn Leu Asn Ile Phe Asp Trp Glu Leu Thr Lys Glu Asp
    850                 855                 860

His Glu Lys Ile Gly Glu Ile Pro Gln Cys Arg Ile Leu Ser Ala Tyr
865                 870                 875                 880

Phe Leu Val Ser Pro Asn Gly Pro Phe Lys Ser Gln Glu Glu Leu Trp
                885                 890                 895

Asp Asp Glu Ala
            900

<210> SEQ ID NO 6
<211> LENGTH: 724
<212> TYPE: PRT
<213> ORGANISM: Papaver setigerum

<400> SEQUENCE: 6

Met Glu Leu Gln Tyr Ile Ser Tyr Phe Gln Pro Thr Ser Ser Val Val
1               5                   10                  15

Ala Leu Leu Leu Ala Leu Val Ser Ile Leu Ser Ser Val Val Val Leu
                20                  25                  30

Arg Lys Thr Phe Leu Asn Asn Tyr Ser Ser Ser Pro Ala Ser Ser Thr
            35                  40                  45

Lys Thr Ala Val Leu Ser His Gln Arg Gln Gln Ser Cys Ala Leu Pro
50                  55                  60

Ile Ser Gly Leu Leu His Ile Phe Met Asn Lys Asn Gly Leu Ile His
65                  70                  75                  80

Val Thr Leu Gly Asn Met Ala Asp Lys Tyr Gly Pro Ile Phe Ser Phe
                85                  90                  95

Pro Thr Gly Ser His Arg Thr Leu Val Val Ser Ser Trp Glu Met Val
                100                 105                 110

Lys Glu Cys Phe Thr Gly Asn Asn Asp Thr Ala Phe Ser Asn Arg Pro
            115                 120                 125

Ile Pro Leu Ala Phe Lys Thr Ile Phe Tyr Ala Cys Gly Gly Ile Asp
130                 135                 140

Ser Tyr Gly Leu Ser Ser Val Pro Tyr Gly Lys Tyr Trp Arg Glu Leu
145                 150                 155                 160

Arg Lys Val Cys Val His Asn Leu Leu Ser Asn Gln Gln Leu Leu Lys
                165                 170                 175

Phe Arg His Leu Ile Ile Ser Gln Val Asp Thr Ser Phe Asn Lys Leu
            180                 185                 190

Tyr Glu Leu Cys Lys Asn Ser Glu Asp Asn Gln Gly Asn Tyr Thr Thr
        195                 200                 205

Thr Thr Thr Ala Ala Gly Met Val Arg Ile Asp Asp Trp Leu Ala Glu
    210                 215                 220

Leu Ser Phe Asn Val Ile Gly Arg Ile Val Cys Gly Phe Gln Ser Gly
225                 230                 235                 240

Pro Lys Thr Gly Ala Pro Ser Arg Val Glu Gln Phe Lys Glu Ala Ile
                245                 250                 255

Asn Glu Ala Ser Tyr Phe Met Ser Thr Ser Pro Val Ser Asp Asn Val
            260                 265                 270

Pro Met Leu Gly Trp Ile Asp Gln Leu Thr Gly Leu Thr Arg Asn Met
        275                 280                 285

Lys His Cys Gly Lys Lys Leu Asp Leu Val Val Glu Ser Ile Ile Asn
    290                 295                 300

Asp His Arg Gln Lys Arg Phe Ser Arg Thr Lys Gly Gly Asp Glu
305                 310                 315                 320
```

-continued

```
Lys Asp Asp Glu Gln Asp Asp Phe Ile Asp Ile Cys Leu Ser Ile Met
                325                 330                 335
Glu Gln Pro Gln Leu Pro Gly Asn Asn Pro Ser Gln Ile Pro Ile
        340                 345                 350
Lys Ser Ile Val Leu Asp Met Ile Gly Gly Thr Asp Thr Thr Lys
            355                 360                 365
Leu Thr Thr Ile Trp Thr Leu Ser Leu Leu Asn Asn Pro His Val
    370                 375                 380
Leu Asp Lys Ala Lys Gln Glu Val Asp Ala His Phe Arg Thr Lys Arg
385                 390                 395                 400
Arg Ser Thr Asn Asp Ala Ala Ala Val Val Asp Phe Asp Asp Ile
                405                 410                 415
Arg Asn Leu Val Tyr Ile Gln Ala Leu Tyr Pro Ala Ser Pro Val Val
                420                 425                 430
Glu Arg Leu Ser Gly Glu Asp Cys Val Val Gly Gly Phe His Val Pro
                435                 440                 445
Ala Gly Thr Arg Leu Trp Ala Asn Val Trp Lys Met Gln Arg Asp Pro
        450                 455                 460
Lys Val Trp Asp Asp Pro Leu Val Phe Arg Pro Asp Arg Phe Leu Ser
465                 470                 475                 480
Asp Glu Gln Lys Met Val Asp Val Arg Gly Gln Asn Tyr Glu Leu Leu
                485                 490                 495
Pro Phe Gly Ala Gly Arg Arg Val Cys Pro Gly Val Ser Phe Ser Leu
                500                 505                 510
Asp Leu Met Gln Leu Val Leu Thr Arg Leu Ile Leu Glu Phe Glu Met
            515                 520                 525
Lys Ser Pro Ser Gly Lys Val Asp Met Thr Ala Thr Pro Gly Leu Met
    530                 535                 540
Ser Tyr Lys Val Ile Pro Leu Asp Ile Leu Thr His Arg Arg Ile
545                 550                 555                 560
Lys Pro Cys Val Gln Ser Ala Ala Ser Glu Arg Asp Met Glu Ser Ser
                565                 570                 575
Gly Val Pro Val Ile Thr Leu Gly Ser Gly Lys Val Met Pro Val Leu
            580                 585                 590
Gly Met Gly Thr Phe Glu Lys Val Gly Lys Gly Ser Glu Arg Glu Arg
        595                 600                 605
Leu Ala Ile Leu Lys Ala Ile Glu Val Gly Tyr Arg Tyr Phe Asp Thr
610                 615                 620
Ala Ala Ala Tyr Glu Thr Glu Glu Val Leu Gly Glu Ala Ile Ala Glu
625                 630                 635                 640
Ala Leu Gln Leu Gly Leu Val Lys Ser Arg Asp Glu Leu Phe Ile Ser
                645                 650                 655
Ser Met Leu Trp Cys Thr Asp Ala His Ala Asp Arg Val Leu Leu Ala
                660                 665                 670
Leu Gln Asn Ser Leu Arg Asn Leu Lys Leu Glu Tyr Val Asp Leu Tyr
        675                 680                 685
Met Leu Pro Phe Pro Ala Ser Leu Lys Pro Gly Lys Ile Thr Met Asp
    690                 695                 700
Ile Pro Glu Glu Asp Ile Cys Arg Met Asp Tyr Arg Ser Val Trp Ala
705                 710                 715                 720
Ala Met Glu Glu
```

```
<210> SEQ ID NO 7
<211> LENGTH: 889
<212> TYPE: PRT
<213> ORGANISM: Papaver bracteatum

<400> SEQUENCE: 7

Met Glu Leu Gln Tyr Phe Ser Tyr Phe Gln Pro Thr Ser Ser Val Val
1               5                   10                  15

Ala Leu Leu Ala Leu Val Ser Ile Leu Phe Ser Val Val Val Leu
            20                  25                  30

Arg Lys Thr Phe Ser Asn Asn Tyr Ser Ser Pro Ala Ser Ser Thr Glu
                35                  40                  45

Thr Ala Val Leu Cys His Gln Arg Gln Gln Ser Cys Ala Leu Pro Ile
        50                  55                  60

Ser Gly Leu Leu His Val Phe Met Asn Lys Asn Gly Leu Ile His Val
65                  70                  75                  80

Thr Leu Gly Asn Met Ala Asp Lys Tyr Gly Pro Ile Phe Ser Phe Pro
                85                  90                  95

Thr Gly Ser His Arg Thr Leu Val Val Ser Ser Trp Glu Met Val Lys
            100                 105                 110

Glu Cys Phe Thr Gly Asn Asn Asp Thr Ala Phe Ser Asn Arg Pro Ile
        115                 120                 125

Pro Leu Ala Phe Gln Thr Ile Phe Tyr Ala Cys Gly Gly Ile Asp Ser
    130                 135                 140

Tyr Gly Leu Ser Ser Val Pro Tyr Gly Lys Tyr Trp Arg Glu Leu Arg
145                 150                 155                 160

Lys Val Cys Val His Asn Leu Leu Ser Asn Gln Gln Leu Leu Lys Phe
                165                 170                 175

Arg His Leu Ile Ile Ser Gln Val Asp Thr Ser Phe Asn Lys Leu Tyr
            180                 185                 190

Glu Leu Cys Lys Asn Ser Glu Asp Asn Gln Gly Met Val Arg Met Asp
        195                 200                 205

Asp Trp Leu Ala Gln Leu Ser Phe Asn Val Ile Gly Arg Ile Val Cys
    210                 215                 220

Gly Phe Gln Ser Asp Pro Lys Thr Gly Ala Pro Ser Arg Val Glu Gln
225                 230                 235                 240

Phe Lys Glu Val Ile Asn Glu Ala Ser Tyr Phe Met Ser Thr Ser Pro
                245                 250                 255

Val Ser Asp Asn Val Pro Met Leu Gly Trp Ile Asp Gln Leu Thr Gly
            260                 265                 270

Leu Thr Arg Asn Met Lys His Cys Gly Lys Lys Leu Asp Leu Val Val
        275                 280                 285

Glu Ser Ile Ile Lys Asp His Arg Gln Lys Arg Arg Phe Ser Arg Thr
    290                 295                 300

Lys Gly Gly Asp Glu Lys Asp Asp Glu Gln Asp Asp Phe Ile Asp Ile
305                 310                 315                 320

Cys Leu Ser Ile Met Glu Gln Pro Gln Leu Pro Gly Asn Asn Ser Pro
                325                 330                 335

Pro Gln Ile Pro Ile Lys Ser Ile Val Leu Asp Met Ile Gly Gly Gly
            340                 345                 350

Thr Asp Thr Thr Lys Leu Thr Thr Ile Trp Thr Leu Ser Leu Leu Leu
        355                 360                 365

Asn Asn Pro His Val Leu Asp Lys Ala Lys Gln Glu Val Asp Ala His
    370                 375                 380
```

```
Phe Arg Lys Lys Arg Arg Ser Thr Asp Asp Ala Ala Ala Val Val
385                 390                 395                 400

Asp Phe Asp Asp Ile Arg Asn Leu Val Tyr Ile Gln Ala Ile Ile Lys
        405                 410                 415

Glu Ser Met Arg Leu Tyr Pro Ala Ser Pro Val Val Glu Arg Leu Ser
            420                 425                 430

Gly Glu Asp Cys Val Val Gly Phe His Val Pro Ala Gly Thr Arg
        435                 440                 445

Leu Trp Ala Asn Val Trp Lys Met Gln Arg Asp Pro Lys Val Trp Asp
    450                 455                 460

Asp Pro Leu Val Phe Arg Pro Glu Arg Phe Leu Ser Asp Glu Gln Lys
465                 470                 475                 480

Met Val Asp Val Arg Gly Gln Asn Tyr Glu Leu Leu Pro Phe Gly Ala
            485                 490                 495

Gly Arg Arg Ile Cys Pro Gly Val Ser Phe Ser Leu Asp Leu Met Gln
                500                 505                 510

Leu Val Leu Thr Arg Leu Ile Leu Glu Phe Glu Met Lys Ser Pro Ser
            515                 520                 525

Gly Lys Val Asp Met Thr Ala Thr Pro Gly Leu Met Ser Tyr Lys Val
        530                 535                 540

Val Pro Leu Asp Ile Leu Leu Thr His Arg Arg Ile Lys Ser Cys Val
545                 550                 555                 560

Gln Leu Ala Ser Ser Glu Arg Asp Met Glu Ser Ser Gly Val Pro Val
                565                 570                 575

Ile Thr Leu Ser Ser Gly Lys Val Met Pro Val Leu Gly Met Gly Thr
            580                 585                 590

Phe Glu Lys Val Gly Lys Gly Ser Glu Arg Glu Arg Leu Ala Ile Leu
        595                 600                 605

Lys Ala Ile Glu Val Gly Tyr Arg Tyr Phe Asp Thr Ala Ala Ala Tyr
610                 615                 620

Glu Thr Glu Glu Val Leu Gly Glu Ala Ile Ala Glu Ala Leu Gln Leu
625                 630                 635                 640

Gly Leu Ile Glu Ser Arg Asp Glu Leu Phe Ile Ser Ser Met Leu Trp
            645                 650                 655

Cys Thr Asp Ala His Pro Asp Arg Val Leu Leu Ala Leu Gln Asn Ser
            660                 665                 670

Leu Arg Asn Leu Lys Leu Glu Tyr Leu Asp Leu Tyr Met Leu Pro Phe
        675                 680                 685

Pro Ala Ser Leu Lys Pro Gly Lys Ile Thr Met Asp Ile Pro Glu Glu
        690                 695                 700

Asp Ile Cys Arg Met Asp Tyr Arg Ser Val Trp Ser Ala Met Glu Glu
705                 710                 715                 720

Cys Gln Asn Leu Gly Phe Thr Lys Ser Ile Gly Val Ser Asn Phe Ser
                725                 730                 735

Ser Lys Lys Leu Gln Glu Leu Met Ala Thr Ala Asn Ile Pro Pro Ala
            740                 745                 750

Val Asn Gln Val Glu Met Ser Pro Ala Phe Gln Gln Lys Lys Leu Arg
        755                 760                 765

Glu Tyr Cys Asn Ala Asn Asn Ile Leu Val Ser Ala Val Ser Ile Leu
        770                 775                 780

Gly Ser Asn Gly Thr Pro Trp Gly Ser Asn Ala Val Leu Gly Ser Glu
785                 790                 795                 800

Val Leu Lys Gln Ile Ala Met Ala Lys Gly Lys Ser Val Ala Gln Val
```

```
              805                 810                 815
Ser Met Arg Trp Val Tyr Glu Gln Gly Ala Ser Leu Val Val Lys Ser
            820                 825                 830

Phe Ser Glu Glu Arg Leu Arg Glu Asn Leu Asn Ile Phe Asp Trp Glu
            835                 840                 845

Leu Thr Lys Glu Asp Asn Glu Lys Ile Gly Glu Ile Pro Gln Cys Arg
            850                 855                 860

Ile Leu Thr Ala Tyr Phe Leu Val Ser Pro Asn Gly Pro Phe Lys Ser
865                 870                 875                 880

Gln Glu Glu Leu Trp Asp Asp Lys Ala
                885

<210> SEQ ID NO 8
<211> LENGTH: 889
<212> TYPE: PRT
<213> ORGANISM: Papaver bracteatum

<400> SEQUENCE: 8

Met Glu Leu Gln Tyr Phe Ser Tyr Phe Gln Pro Thr Ser Ser Val Val
1               5                   10                  15

Ala Leu Leu Leu Ala Leu Val Ser Ile Leu Phe Ser Val Val Val Leu
            20                  25                  30

Arg Lys Thr Phe Ser Asn Asn Tyr Ser Ser Pro Ala Ser Ser Thr Glu
            35                  40                  45

Thr Ala Val Leu Cys His Gln Arg Gln Gln Ser Cys Ala Leu Pro Ile
        50                  55                  60

Ser Gly Leu Leu His Val Phe Met Asn Lys Asn Gly Leu Ile His Val
65                  70                  75                  80

Thr Leu Gly Asn Met Ala Asp Lys Tyr Gly Pro Ile Phe Ser Phe Pro
                85                  90                  95

Thr Gly Ser His Arg Thr Leu Val Val Ser Ser Trp Glu Met Val Lys
            100                 105                 110

Glu Cys Phe Thr Gly Asn Asn Asp Thr Ala Phe Ser Asn Arg Pro Ile
            115                 120                 125

Pro Leu Ala Phe Gln Thr Ile Phe Tyr Ala Cys Gly Gly Ile Asp Ser
        130                 135                 140

Tyr Gly Leu Ser Ser Val Pro Tyr Gly Lys Tyr Trp Arg Glu Leu Arg
145                 150                 155                 160

Lys Val Cys Val His Asn Leu Leu Ser Asn Gln Gln Leu Leu Lys Phe
                165                 170                 175

Arg His Leu Ile Ile Ser Gln Val Asp Thr Ser Phe Asn Lys Leu Tyr
            180                 185                 190

Glu Leu Cys Lys Asn Ser Glu Asp Asn Gln Gly Met Val Arg Met Asp
            195                 200                 205

Asp Trp Leu Ala Gln Leu Ser Phe Asn Val Ile Gly Arg Ile Val Cys
        210                 215                 220

Gly Phe Gln Ser Asp Pro Lys Thr Gly Ala Pro Ser Arg Val Glu Gln
225                 230                 235                 240

Phe Lys Glu Val Ile Asn Glu Ala Ser Tyr Phe Met Ser Thr Ser Pro
                245                 250                 255

Val Ser Asp Asn Val Pro Met Leu Gly Trp Ile Asp Gln Leu Thr Gly
            260                 265                 270

Leu Thr Arg Asn Met Lys His Cys Gly Lys Lys Leu Asp Leu Val Val
            275                 280                 285
```

-continued

```
Glu Ser Ile Ile Lys Asp His Arg Gln Lys Arg Arg Phe Ser Arg Thr
    290                 295                 300
Lys Gly Gly Asp Glu Lys Asp Asp Glu Gln Asp Asp Phe Ile Asp Ile
305                 310                 315                 320
Cys Leu Ser Ile Met Glu Gln Pro Gln Leu Pro Gly Asn Asn Ser Pro
                325                 330                 335
Pro Gln Ile Pro Ile Lys Ser Ile Val Leu Asp Met Ile Gly Gly Gly
            340                 345                 350
Thr Asp Thr Thr Lys Leu Thr Thr Ile Trp Thr Leu Ser Leu Leu Leu
        355                 360                 365
Asn Asn Pro His Val Leu Asp Lys Ala Lys Gln Glu Val Asp Ala His
370                 375                 380
Phe Arg Lys Lys Arg Ser Thr Asp Ala Ala Ala Val Val
385                 390                 395                 400
Asp Phe Asp Asp Ile Arg Asn Leu Val Tyr Ile Gln Ala Ile Ile Lys
                405                 410                 415
Glu Ser Met Arg Leu Tyr Pro Ala Ser Pro Val Val Glu Arg Leu Ser
            420                 425                 430
Gly Glu Asp Cys Val Val Gly Gly Phe His Val Pro Ala Gly Thr Arg
        435                 440                 445
Leu Trp Ala Asn Val Trp Lys Met Gln Arg Asp Pro Lys Val Trp Asp
450                 455                 460
Asp Pro Leu Val Phe Arg Pro Glu Arg Phe Leu Ser Asp Glu Gln Lys
465                 470                 475                 480
Met Val Asp Val Arg Gly Gln Asn Tyr Glu Leu Leu Pro Phe Gly Ala
                485                 490                 495
Gly Arg Arg Ile Cys Pro Gly Val Ser Phe Ser Leu Asp Leu Met Gln
            500                 505                 510
Leu Val Leu Thr Arg Leu Ile Leu Glu Phe Glu Met Lys Ser Pro Ser
        515                 520                 525
Gly Lys Val Asp Met Thr Ala Thr Pro Gly Leu Met Ser Tyr Lys Val
530                 535                 540
Val Pro Leu Asp Ile Leu Leu Thr His Arg Arg Ile Lys Ser Cys Val
545                 550                 555                 560
Gln Leu Ala Ser Ser Glu Arg Asp Met Glu Ser Ser Gly Val Pro Val
                565                 570                 575
Ile Thr Leu Ser Ser Gly Lys Val Met Pro Val Leu Gly Met Gly Thr
            580                 585                 590
Phe Glu Lys Val Gly Lys Gly Ser Glu Arg Glu Arg Leu Ala Ile Leu
        595                 600                 605
Lys Ala Ile Glu Val Gly Tyr Arg Tyr Phe Asp Thr Ala Ala Ala Tyr
610                 615                 620
Glu Thr Glu Glu Val Leu Gly Glu Ala Ile Ala Glu Ala Leu Gln Leu
625                 630                 635                 640
Gly Leu Ile Glu Ser Arg Asp Glu Leu Phe Ile Ser Ser Met Leu Trp
                645                 650                 655
Cys Thr Asp Ala His Pro Asp Arg Val Leu Leu Ala Leu Gln Asn Ser
            660                 665                 670
Leu Arg Asn Leu Lys Leu Glu Tyr Leu Asp Leu Tyr Met Leu Pro Phe
        675                 680                 685
Pro Ala Ser Leu Lys Pro Gly Lys Ile Thr Met Asp Ile Pro Glu Glu
690                 695                 700
Asp Ile Cys Arg Met Asp Tyr Arg Ser Val Trp Ser Ala Met Glu Glu
```

```
            705                 710                 715                 720
Cys Gln Asn Leu Gly Phe Thr Lys Ser Ile Gly Val Ser Asn Phe Ser
                    725                 730                 735

Cys Lys Lys Leu Gln Glu Leu Met Ala Thr Ala Asn Ile Pro Pro Ala
                    740                 745                 750

Val Asn Gln Val Glu Met Ser Pro Ala Phe Gln Gln Lys Lys Leu Arg
                    755                 760                 765

Glu Tyr Cys Asn Ala Asn Ile Leu Val Ser Ala Val Ser Ile Leu
                770                 775                 780

Gly Ser Asn Gly Thr Pro Trp Gly Ser Asn Ala Val Leu Gly Ser Glu
785                 790                 795                 800

Val Leu Lys Gln Ile Ala Met Ala Lys Gly Lys Ser Val Ala Gln Val
                    805                 810                 815

Ser Met Arg Trp Val Tyr Glu Gln Gly Ala Ser Leu Val Val Lys Ser
                    820                 825                 830

Phe Ser Glu Glu Arg Leu Arg Glu Asn Leu Asn Ile Phe Asp Trp Glu
                    835                 840                 845

Leu Thr Lys Glu Asp Asn Glu Lys Ile Gly Glu Ile Pro Gln Cys Arg
                850                 855                 860

Ile Leu Thr Ala Tyr Phe Leu Val Ser Pro Asn Gly Pro Phe Lys Ser
865                 870                 875                 880

Gln Glu Glu Leu Trp Asp Asp Lys Ala
                    885

<210> SEQ ID NO 9
<211> LENGTH: 848
<212> TYPE: PRT
<213> ORGANISM: Papaver bracteatum

<400> SEQUENCE: 9

Ser Ser Pro Ala Ser Ser Thr Glu Thr Ala Val Leu Cys His Gln Arg
1               5                   10                  15

Gln Gln Ser Cys Ala Leu Pro Ile Ser Gly Leu Leu His Ile Phe Met
                    20                  25                  30

Asn Lys Asn Gly Leu Ile His Val Thr Leu Gly Asn Met Ala Asp Lys
                35                  40                  45

Tyr Gly Pro Ile Phe Ser Phe Pro Thr Gly Ser His Arg Ile Leu Val
            50                  55                  60

Val Ser Ser Trp Glu Met Val Lys Glu Cys Phe Thr Gly Asn Asn Asp
65              70                  75                  80

Thr Ala Phe Ser Asn Arg Pro Ile Pro Leu Ala Phe Lys Thr Ile Phe
                    85                  90                  95

Tyr Ala Cys Arg Gly Ile Asp Ser Tyr Gly Leu Ser Ser Val Pro Tyr
                    100                 105                 110

Gly Lys Tyr Trp Arg Glu Leu Arg Lys Val Cys Val His Asn Leu Leu
                    115                 120                 125

Ser Asn Gln Gln Leu Leu Lys Phe Arg His Leu Ile Ile Ser Gln Val
                130                 135                 140

Asp Thr Ser Phe Asn Lys Leu Tyr Glu Leu Cys Lys Asn Ser Glu Asp
145                 150                 155                 160

Asn Gln Gly Met Val Arg Met Asp Asp Trp Leu Ala Gln Leu Ser Phe
                    165                 170                 175

Ser Val Ile Gly Arg Ile Val Cys Gly Phe Gln Ser Asp Pro Lys Thr
                    180                 185                 190
```

-continued

Gly Ala Pro Ser Arg Val Glu Gln Phe Lys Glu Ala Ile Asn Glu Ala
        195                 200                 205

Ser Tyr Phe Met Ser Thr Ser Pro Val Ser Asp Asn Val Pro Met Leu
    210                 215                 220

Gly Trp Ile Asp Gln Leu Thr Gly Leu Thr Arg Asn Met Thr His Cys
225                 230                 235                 240

Gly Lys Lys Leu Asp Leu Val Val Glu Ser Ile Ile Asn Asp His Arg
                245                 250                 255

Gln Lys Arg Arg Phe Ser Arg Thr Lys Gly Gly Asp Glu Lys Asp Asp
                260                 265                 270

Glu Gln Asp Asp Phe Ile Asp Ile Cys Leu Ser Ile Met Glu Gln Pro
            275                 280                 285

Gln Leu Pro Gly Asn Asn Pro Pro Lys Ile Pro Ile Lys Ser Ile
        290                 295                 300

Val Leu Asp Met Ile Gly Ala Gly Thr Asp Thr Thr Lys Leu Thr Ile
305                 310                 315                 320

Ile Trp Thr Leu Ser Leu Leu Asn Asn Pro Asn Val Leu Ala Lys
                325                 330                 335

Ala Lys Gln Glu Val Asp Ala His Phe Glu Thr Lys Lys Arg Ser Thr
            340                 345                 350

Asn Glu Ala Ser Val Val Asp Phe Asp Asp Ile Gly Asn Leu Val
        355                 360                 365

Tyr Ile Gln Ala Ile Ile Lys Glu Ser Met Arg Leu Tyr Pro Val Ser
    370                 375                 380

Pro Val Glu Arg Leu Ser Ser Glu Asp Cys Val Val Gly Gly Phe
385                 390                 395                 400

His Val Pro Ala Gly Thr Arg Leu Trp Ala Asn Val Trp Lys Met Gln
                405                 410                 415

Arg Asp Pro Lys Val Trp Asp Pro Leu Val Phe Arg Pro Glu Arg
                420                 425                 430

Phe Leu Ser Asp Glu Gln Lys Met Val Asp Val Arg Gly Gln Asn Tyr
            435                 440                 445

Glu Leu Leu Pro Phe Gly Ala Gly Arg Arg Ile Cys Pro Gly Val Ser
        450                 455                 460

Phe Ser Leu Asp Leu Met Gln Leu Val Leu Thr Arg Leu Ile Leu Glu
465                 470                 475                 480

Phe Glu Met Lys Ser Pro Ser Gly Lys Val Asp Met Thr Ala Thr Pro
                485                 490                 495

Gly Leu Met Ser Tyr Lys Val Val Pro Leu Asp Ile Leu Leu Thr His
            500                 505                 510

Arg Arg Ile Lys Ser Cys Val Gln Leu Ala Ser Ser Glu Arg Asp Met
        515                 520                 525

Glu Ser Ser Gly Val Pro Val Ile Thr Leu Arg Ser Gly Lys Val Met
    530                 535                 540

Pro Val Leu Gly Met Gly Thr Phe Glu Lys Ala Gly Lys Gly Ser Glu
545                 550                 555                 560

Arg Glu Arg Leu Ala Ile Leu Lys Ala Ile Glu Val Gly Tyr Arg Tyr
                565                 570                 575

Phe Asp Thr Ala Ala Ala Tyr Glu Thr Glu Glu Val Leu Gly Glu Ala
            580                 585                 590

Ile Ala Glu Ala Leu Gln Leu Gly Leu Ile Lys Ser Arg Asp Glu Leu
        595                 600                 605

Phe Ile Ser Ser Met Leu Trp Cys Thr Asp Ala His Pro Asp Arg Val

```
                    610                 615                 620
Leu Leu Ala Leu Gln Asn Ser Leu Arg Asn Leu Lys Leu Glu Tyr Val
625                 630                 635                 640

Asp Leu Tyr Met Leu Pro Phe Pro Ala Ser Leu Lys Pro Gly Lys Ile
                    645                 650                 655

Thr Met Asp Ile Pro Glu Glu Asp Ile Cys Pro Met Asp Tyr Arg Ser
                660                 665                 670

Val Trp Ser Ala Met Glu Glu Cys Gln Asn Leu Gly Leu Thr Lys Ser
                675                 680                 685

Ile Gly Val Ser Asn Phe Ser Cys Lys Lys Leu Glu Glu Leu Met Ala
                690                 695                 700

Thr Ala Asn Ile Pro Pro Ala Val Asn Gln Val Glu Met Ser Pro Ala
705                 710                 715                 720

Phe Gln Gln Lys Lys Leu Arg Glu Tyr Cys Asn Ala Asn Asn Ile Leu
                    725                 730                 735

Val Ser Ala Val Ser Ile Leu Gly Ser Asn Gly Thr Pro Trp Gly Ser
                740                 745                 750

Asn Ala Val Leu Gly Ser Glu Val Leu Lys Lys Ile Ala Met Ala Lys
                755                 760                 765

Gly Lys Ser Val Ala Gln Val Ser Met Arg Trp Val Tyr Glu Gln Gly
                770                 775                 780

Ala Ser Leu Val Val Lys Ser Phe Ser Glu Glu Arg Leu Arg Glu Asn
785                 790                 795                 800

Leu Asn Ile Phe Asp Trp Gln Leu Thr Lys Glu Asp Asn Glu Lys Ile
                    805                 810                 815

Gly Glu Ile Pro Gln Cys Arg Ile Leu Ser Ala Tyr Phe Leu Val Ser
                820                 825                 830

Pro Lys Gly Pro Phe Lys Ser Gln Glu Glu Leu Trp Asp Asp Lys Ala
                835                 840                 845

<210> SEQ ID NO 10
<211> LENGTH: 847
<212> TYPE: PRT
<213> ORGANISM: Papaver bracteatum

<400> SEQUENCE: 10

Ser Ser Pro Ala Ser Ser Thr Glu Thr Ala Val Leu Cys His Gln Arg
1               5                   10                  15

Gln Gln Ser Cys Ala Leu Pro Ile Ser Gly Leu Leu His Ile Phe Met
                20                  25                  30

Asn Lys Asn Gly Leu Ile His Val Thr Leu Gly Asn Met Ala Asp Lys
            35                  40                  45

Tyr Gly Pro Ile Phe Ser Phe Pro Thr Gly Ser His Arg Ile Leu Val
        50                  55                  60

Val Ser Ser Trp Glu Met Val Lys Glu Cys Phe Thr Gly Asn Asn Asp
65                  70                  75                  80

Thr Phe Phe Ser Asn Arg Pro Ile Pro Leu Ala Phe Lys Ile Ile Phe
                85                  90                  95

Tyr Ala Gly Gly Val Asp Ser Tyr Gly Leu Ala Leu Val Pro Tyr Gly
            100                 105                 110

Lys Tyr Trp Arg Glu Leu Arg Lys Ile Cys Val His Asn Leu Leu Ser
        115                 120                 125

Asn Gln Gln Leu Leu Lys Phe Arg His Leu Ile Ile Ser Gln Val Asp
    130                 135                 140
```

```
Thr Ser Phe Asn Lys Leu Tyr Glu Leu Cys Lys Asn Ser Glu Asp Asn
145                 150                 155                 160

Gln Gly Met Val Arg Met Asp Asp Trp Leu Ala Gln Leu Ser Phe Ser
                165                 170                 175

Val Ile Gly Arg Ile Val Cys Gly Phe Gln Ser Asp Pro Lys Thr Gly
                180                 185                 190

Ala Pro Ser Arg Val Glu Gln Phe Lys Glu Ala Ile Asn Glu Ala Ser
            195                 200                 205

Tyr Phe Met Ser Thr Ser Pro Val Ser Asp Asn Val Pro Met Leu Gly
        210                 215                 220

Trp Ile Asp Gln Leu Thr Gly Leu Thr Arg Asn Met Thr His Cys Gly
225                 230                 235                 240

Lys Lys Leu Asp Leu Val Val Glu Ser Ile Ile Asn Asp His Arg Gln
                245                 250                 255

Lys Arg Arg Phe Ser Arg Thr Lys Gly Gly Asp Glu Lys Asp Asp Glu
                260                 265                 270

Gln Asp Asp Phe Ile Asp Ile Cys Leu Ser Ile Met Glu Gln Pro Gln
            275                 280                 285

Leu Pro Gly Asn Asn Pro Pro Lys Ile Pro Ile Lys Ser Ile Val
        290                 295                 300

Leu Asp Met Ile Gly Gly Gly Thr Asp Thr Thr Lys Leu Thr Thr Ile
305                 310                 315                 320

Trp Thr Leu Ser Leu Leu Asn Asn Pro His Val Leu Asp Lys Ala
                325                 330                 335

Lys Gln Glu Val Asp Ala His Phe Leu Thr Lys Arg Arg Ser Thr Asn
                340                 345                 350

Asp Ala Ala Val Val Asp Phe Asp Asp Ile Arg Asn Leu Val Tyr Ile
            355                 360                 365

Gln Ala Ile Ile Lys Glu Ser Met Arg Leu Tyr Pro Ala Ser Pro Val
        370                 375                 380

Val Glu Arg Leu Ser Gly Glu Asp Cys Val Val Gly Gly Phe His Val
385                 390                 395                 400

Pro Ala Gly Thr Arg Leu Trp Val Asn Val Trp Lys Met Gln Arg Asp
                405                 410                 415

Pro Asn Val Trp Ala Asp Pro Met Val Phe Arg Pro Glu Arg Phe Leu
                420                 425                 430

Ser His Gly Gln Lys Lys Met Val Asp Val Arg Gly Lys Asn Tyr Glu
            435                 440                 445

Leu Leu Pro Phe Gly Ala Gly Arg Arg Ile Cys Pro Gly Ile Ser Phe
        450                 455                 460

Ser Leu Asp Leu Met Gln Leu Val Leu Thr Arg Leu Ile Leu Glu Phe
465                 470                 475                 480

Glu Met Lys Ser Pro Ser Gly Lys Val Asp Met Thr Ala Thr Pro Gly
                485                 490                 495

Leu Met Ser Tyr Lys Val Val Pro Leu Asp Ile Leu Leu Thr His Arg
                500                 505                 510

Arg Ile Lys Ser Cys Val Gln Leu Ala Ser Ser Glu Arg Asp Met Glu
                515                 520                 525

Ser Ser Gly Val Pro Val Ile Thr Leu Arg Ser Gly Lys Val Met Pro
            530                 535                 540

Val Leu Gly Met Gly Thr Phe Glu Lys Ala Gly Lys Gly Ser Glu Arg
545                 550                 555                 560

Glu Arg Leu Ala Ile Leu Lys Ala Ile Glu Val Gly Tyr Arg Tyr Phe
```

```
                        565                 570                 575
Asp Thr Ala Ala Ala Tyr Glu Thr Glu Glu Val Leu Gly Glu Ala Ile
                    580                 585                 590

Ala Glu Ala Leu Gln Leu Gly Leu Ile Lys Ser Arg Asp Glu Leu Phe
                595                 600                 605

Ile Ser Ser Met Leu Trp Cys Thr Asp Ala His Pro Asp Arg Val Leu
610                 615                 620

Leu Ala Leu Gln Asn Ser Leu Arg Asn Leu Lys Leu Glu Tyr Val Asp
625                 630                 635                 640

Leu Tyr Met Leu Pro Phe Pro Ala Ser Leu Lys Pro Gly Lys Ile Thr
                645                 650                 655

Met Asp Ile Pro Glu Glu Asp Ile Cys Pro Met Asp Tyr Arg Ser Val
                660                 665                 670

Trp Ser Ala Met Glu Glu Cys Gln Asn Leu Gly Leu Thr Lys Ser Ile
                675                 680                 685

Gly Val Ser Asn Phe Ser Cys Lys Lys Leu Glu Glu Leu Met Ala Thr
                690                 695                 700

Ala Asn Ile Pro Pro Ala Val Asn Gln Val Glu Met Ser Pro Ala Phe
705                 710                 715                 720

Gln Gln Lys Lys Leu Arg Glu Tyr Cys Asn Ala Asn Ile Leu Val
                725                 730                 735

Ser Ala Val Ser Ile Leu Gly Ser Asn Gly Thr Pro Trp Gly Ser Asn
                740                 745                 750

Ala Val Leu Gly Ser Glu Val Leu Lys Lys Ile Ala Met Ala Lys Gly
                755                 760                 765

Lys Ser Val Ala Gln Val Ser Met Arg Trp Val Tyr Glu Gln Gly Ala
                770                 775                 780

Ser Leu Val Val Lys Ser Phe Ser Glu Glu Arg Leu Arg Glu Asn Leu
785                 790                 795                 800

Asn Ile Phe Asp Trp Gln Leu Thr Lys Glu Asp Asn Glu Lys Ile Gly
                805                 810                 815

Glu Ile Pro Gln Cys Arg Ile Leu Ser Ala Tyr Phe Leu Val Ser Pro
                820                 825                 830

Lys Gly Pro Phe Lys Ser Gln Glu Glu Leu Trp Asp Asp Lys Ala
                835                 840                 845

<210> SEQ ID NO 11
<211> LENGTH: 845
<212> TYPE: PRT
<213> ORGANISM: Papaver bracteatum

<400> SEQUENCE: 11

Ser Ser Pro Ala Ser Ser Thr Glu Thr Ala Val Leu Cys His Gln Arg
1               5                   10                  15

Gln Gln Ser Cys Ala Leu Pro Ile Ser Gly Leu Leu His Ile Phe Met
                20                  25                  30

Asn Lys Asn Gly Leu Ile His Val Thr Leu Gly Asn Met Ala Asp Lys
                35                  40                  45

Tyr Gly Pro Ile Phe Ser Phe Pro Thr Gly Ser His Arg Ile Leu Val
                50                  55                  60

Val Ser Ser Trp Glu Met Val Lys Glu Cys Phe Thr Gly Asn Asn Asp
65                  70                  75                  80

Thr Phe Phe Ser Asn Arg Pro Ile Pro Leu Ala Phe Lys Ile Ile Phe
                85                  90                  95
```

```
Tyr Ala Gly Gly Val Asp Ser Tyr Gly Leu Ala Leu Val Pro Tyr Gly
            100                 105                 110

Lys Tyr Trp Arg Glu Leu Arg Lys Ile Cys Val His Asn Leu Leu Ser
        115                 120                 125

Asn Gln Gln Leu Leu Asn Phe Arg His Leu Ile Ile Ser Gln Val Asp
    130                 135                 140

Thr Ser Phe Asn Lys Leu Tyr Asp Leu Ser Asn Lys Lys Asn Thr
145                 150                 155                 160

Thr Thr Asp Ser Gly Thr Val Arg Met Asp Asp Trp Leu Ala Gln Leu
                165                 170                 175

Ser Phe Asn Val Ile Gly Arg Ile Val Cys Gly Phe Gln Thr His Thr
            180                 185                 190

Glu Thr Ser Ala Thr Ser Ser Val Glu Arg Phe Thr Glu Ala Ile Asp
        195                 200                 205

Glu Ala Ser Arg Phe Met Ser Ile Ala Thr Val Ser Asp Thr Phe Pro
    210                 215                 220

Trp Leu Gly Trp Ile Asp Gln Leu Thr Gly Leu Thr Arg Lys Met Lys
225                 230                 235                 240

His Tyr Gly Lys Lys Leu Asp Leu Val Val Glu Ser Ile Ile Glu Asp
                245                 250                 255

His Arg Gln Asn Arg Arg Ile Ser Gly Thr Lys Gln Gly Asp Asp Phe
            260                 265                 270

Ile Asp Ile Cys Leu Ser Ile Met Glu Gln Pro Gln Ile Pro Gly
        275                 280                 285

Asn Asn Asp Pro Pro Arg Gln Ile Pro Ile Lys Ser Ile Val Leu Asp
    290                 295                 300

Met Ile Gly Gly Gly Thr Asp Thr Thr Lys Leu Thr Thr Thr Trp Thr
305                 310                 315                 320

Leu Ser Leu Leu Leu Asn Asn Pro His Val Leu Glu Lys Ala Arg Glu
                325                 330                 335

Glu Val Asp Ala His Phe Gly Thr Lys Arg Arg Pro Thr Asn Asp Asp
            340                 345                 350

Ala Val Met Val Glu Phe Asp Asp Ile Arg Asn Leu Val Tyr Ile Gln
        355                 360                 365

Ala Ile Ile Lys Glu Ser Met Arg Leu Tyr Pro Ala Ser Pro Val Val
    370                 375                 380

Glu Arg Leu Ser Gly Glu Asp Cys Val Val Gly Gly Phe His Val Pro
385                 390                 395                 400

Ala Gly Thr Arg Leu Trp Val Asn Val Trp Lys Met Gln Arg Asp Pro
                405                 410                 415

Asn Val Trp Ala Asp Pro Met Val Phe Arg Pro Glu Arg Phe Leu Ser
            420                 425                 430

Asp Glu Gln Lys Met Val Asp Val Arg Gly Gln Asn Tyr Glu Leu Leu
        435                 440                 445

Pro Phe Gly Ala Gly Arg Arg Ile Cys Pro Gly Val Ser Phe Ser Leu
    450                 455                 460

Asp Leu Met Gln Leu Val Leu Thr Arg Leu Ile Leu Glu Phe Glu Met
465                 470                 475                 480

Lys Ser Pro Ser Gly Lys Val Asp Met Thr Ala Thr Pro Gly Leu Met
                485                 490                 495

Ser Tyr Lys Val Val Pro Leu Asp Ile Leu Leu Thr His Arg Arg Ile
            500                 505                 510

Lys Ser Cys Val Gln Leu Ala Ser Ser Glu Arg Asp Met Glu Ser Ser
```

```
                515                 520                 525
Gly Val Pro Val Ile Thr Leu Arg Ser Gly Lys Val Met Pro Val Leu
            530                 535                 540

Gly Met Gly Thr Phe Glu Lys Ala Gly Lys Gly Ser Glu Arg Glu Arg
545                 550                 555                 560

Leu Ala Ile Leu Lys Ala Ile Glu Val Gly Tyr Arg Tyr Phe Asp Thr
                565                 570                 575

Ala Ala Ala Tyr Glu Thr Glu Val Leu Gly Glu Ala Ile Ala Glu
            580                 585                 590

Ala Leu Gln Leu Gly Leu Ile Lys Ser Arg Asp Glu Leu Phe Ile Ser
            595                 600                 605

Ser Met Leu Trp Cys Thr Asp Ala His Pro Asp Arg Val Leu Leu Ala
            610                 615                 620

Leu Gln Asn Ser Leu Arg Asn Leu Lys Leu Glu Tyr Val Asp Leu Tyr
625                 630                 635                 640

Met Leu Pro Phe Pro Ala Ser Leu Lys Pro Gly Lys Ile Thr Met Asp
                645                 650                 655

Ile Pro Glu Glu Asp Ile Cys Pro Met Asp Tyr Arg Ser Val Trp Ser
                660                 665                 670

Ala Met Glu Glu Cys Gln Asn Leu Gly Leu Thr Lys Ser Ile Gly Val
            675                 680                 685

Ser Asn Phe Ser Cys Lys Lys Leu Glu Glu Leu Met Ala Thr Ala Asn
            690                 695                 700

Ile Pro Pro Ala Val Asn Gln Val Glu Met Ser Pro Ala Phe Gln Gln
705                 710                 715                 720

Lys Lys Leu Arg Glu Tyr Cys Asn Ala Asn Asn Ile Leu Val Ser Ala
                725                 730                 735

Val Ser Ile Leu Gly Ser Asn Gly Thr Pro Trp Gly Ser Asn Ala Val
                740                 745                 750

Leu Gly Ser Glu Val Leu Lys Lys Ile Ala Met Ala Lys Gly Lys Ser
            755                 760                 765

Val Ala Gln Val Ser Met Arg Trp Val Tyr Glu Gln Gly Ala Ser Leu
            770                 775                 780

Val Val Lys Ser Phe Ser Glu Glu Arg Leu Arg Glu Asn Leu Asn Ile
785                 790                 795                 800

Phe Asp Trp Gln Leu Thr Lys Glu Asp Asn Glu Lys Ile Gly Glu Ile
                805                 810                 815

Pro Gln Cys Arg Ile Leu Ser Ala Tyr Phe Leu Val Ser Pro Lys Gly
                820                 825                 830

Pro Phe Lys Ser Gln Glu Glu Leu Trp Asp Asp Lys Ala
            835                 840                 845

<210> SEQ ID NO 12
<211> LENGTH: 869
<212> TYPE: PRT
<213> ORGANISM: Papaver bracteatum

<400> SEQUENCE: 12

Val Ala Leu Arg Lys Lys Ile Leu Lys Asn Tyr Tyr Ser Ser Ser Ser
1               5                   10                  15

Ser Thr Ala Thr Ala Val Ser His Gln Trp Pro Lys Ala Ser Arg Ala
                20                  25                  30

Leu Pro Leu Ile Asp Leu Leu His Val Phe Phe Asn Lys Thr Asp Leu
            35                  40                  45
```

```
Met His Val Thr Leu Gly Asn Met Ala Asp Lys Phe Gly Pro Ile Phe
    50                  55                  60
Ser Phe Pro Thr Gly Ser His Arg Thr Leu Val Val Ser Ser Trp Glu
65                  70                  75                  80
Lys Ala Lys Glu Cys Phe Thr Gly Asn Asn Asp Ile Val Phe Ser Gly
                85                  90                  95
Arg Pro Leu Pro Leu Ala Phe Lys Leu Ile Phe Tyr Ala Gly Gly Ile
            100                 105                 110
Asp Ser Tyr Gly Ile Ser Gln Val Pro Tyr Gly Lys Lys Trp Arg Glu
            115                 120                 125
Leu Arg Asn Ile Cys Val His Asn Ile Leu Ser Asn Gln Gln Leu Leu
        130                 135                 140
Lys Phe Arg His Leu Met Ile Ser Gln Val Asp Asn Ser Phe Asn Lys
145                 150                 155                 160
Leu Tyr Glu Val Cys Asn Ser Asn Lys Asp Glu Gly Asp Ser Ala Thr
                165                 170                 175
Ser Thr Thr Ala Ala Gly Ile Val Arg Met Asp Asp Trp Leu Gly Lys
            180                 185                 190
Leu Ala Phe Asp Val Ile Ala Arg Ile Val Cys Gly Phe Gln Ser Gln
        195                 200                 205
Thr Glu Thr Ser Thr Thr Ser Ser Met Glu Arg Phe Thr Glu Ala Met
    210                 215                 220
Asp Glu Ala Ser Arg Phe Met Ser Val Thr Ala Val Ser Asp Thr Val
225                 230                 235                 240
Pro Trp Leu Gly Trp Ile Asp Gln Leu Thr Gly Leu Lys Arg Asn Met
                245                 250                 255
Lys His Cys Gly Lys Lys Leu Asn Leu Val Val Lys Ser Ile Ile Glu
            260                 265                 270
Asp His Arg Gln Lys Arg Leu Ser Ser Thr Lys Lys Gly Asp Glu
        275                 280                 285
Asn Ile Ile Asp Glu Asp Gln Asp Phe Ile Asp Ile Cys Leu
        290                 295                 300
Ser Ile Met Glu Gln Pro Gln Leu Pro Gly Asn Asn Asn Pro Pro Lys
305                 310                 315                 320
Ile Pro Ile Lys Ser Ile Val Leu Asp Met Ile Gly Gly Thr Asp
                325                 330                 335
Thr Thr Lys Leu Thr Thr Ile Trp Thr Leu Ser Leu Leu Asn Asn
            340                 345                 350
Pro His Val Leu Asp Lys Ala Lys Gln Glu Val Asp Ala His Phe Leu
        355                 360                 365
Thr Lys Arg Arg Ser Thr Asn Asp Ala Ala Val Val Asp Phe Asp Asp
    370                 375                 380
Ile Arg Asn Leu Val Tyr Ile Gln Ala Ile Ile Lys Glu Ser Met Arg
385                 390                 395                 400
Leu Tyr Pro Ala Ser Pro Val Val Glu Arg Leu Ser Gly Glu Asp Cys
                405                 410                 415
Val Val Gly Gly Phe His Val Pro Ala Gly Thr Arg Leu Trp Val Asn
            420                 425                 430
Val Trp Lys Met Gln Arg Asp Pro Asn Val Trp Ala Asp Pro Met Val
        435                 440                 445
Phe Arg Pro Glu Arg Phe Leu Ser Asp Glu Gln Lys Met Val Asp Val
    450                 455                 460
Arg Gly Gln Asn Tyr Glu Leu Leu Pro Phe Gly Ala Gly Arg Arg Ile
```

```
            465                 470                 475                 480
        Cys Pro Gly Val Ser Phe Ser Leu Asp Leu Met Gln Leu Val Leu Thr
                        485                 490                 495
        Arg Leu Ile Leu Glu Phe Glu Met Lys Ser Pro Ser Gly Lys Val Asp
                        500                 505                 510
        Met Thr Ala Thr Pro Gly Leu Met Ser Tyr Lys Val Pro Leu Asp
                        515                 520                 525
        Ile Leu Leu Thr His Arg Arg Ile Lys Ser Cys Val Gln Leu Ala Ser
                        530                 535                 540
        Ser Glu Arg Asp Met Glu Ser Ser Gly Val Pro Val Ile Thr Leu Arg
        545                 550                 555                 560
        Ser Gly Lys Val Met Pro Val Leu Gly Met Gly Thr Phe Glu Lys Ala
                            565                 570                 575
        Gly Lys Gly Ser Glu Arg Glu Arg Leu Ala Ile Leu Lys Ala Ile Glu
                        580                 585                 590
        Val Gly Tyr Arg Tyr Phe Asp Thr Ala Ala Ala Tyr Glu Thr Glu Glu
                        595                 600                 605
        Val Leu Gly Glu Ala Ile Ala Glu Ala Leu Gln Leu Gly Leu Ile Lys
                        610                 615                 620
        Ser Arg Asp Glu Leu Phe Ile Ser Ser Met Leu Trp Cys Thr Asp Ala
        625                 630                 635                 640
        His Pro Asp Arg Val Leu Leu Ala Leu Gln Asn Ser Leu Arg Asn Leu
                            645                 650                 655
        Lys Leu Glu Tyr Val Asp Leu Tyr Met Leu Pro Phe Pro Ala Ser Leu
                        660                 665                 670
        Lys Pro Gly Lys Ile Thr Met Asp Ile Pro Glu Glu Asp Ile Cys Pro
                        675                 680                 685
        Met Asp Tyr Arg Ser Val Trp Ser Ala Met Glu Glu Cys Gln Asn Leu
                        690                 695                 700
        Gly Leu Thr Lys Ser Ile Gly Val Ser Asn Phe Ser Cys Lys Lys Leu
        705                 710                 715                 720
        Glu Glu Leu Met Ala Thr Ala Asn Ile Pro Pro Ala Val Asn Gln Val
                            725                 730                 735
        Glu Met Ser Pro Ala Phe Gln Gln Lys Lys Leu Arg Glu Tyr Cys Asn
                        740                 745                 750
        Ala Asn Asn Ile Leu Val Ser Ala Val Ser Ile Leu Gly Ser Asn Gly
                        755                 760                 765
        Thr Pro Trp Gly Ser Asn Ala Val Leu Gly Ser Glu Val Leu Lys Lys
                        770                 775                 780
        Ile Ala Met Ala Lys Gly Lys Ser Val Ala Gln Val Ser Met Arg Trp
        785                 790                 795                 800
        Val Tyr Glu Gln Gly Ala Ser Leu Val Val Lys Ser Phe Ser Glu Glu
                            805                 810                 815
        Arg Leu Arg Glu Asn Leu Asn Ile Phe Asp Trp Gln Leu Thr Lys Glu
                        820                 825                 830
        Asp Asn Glu Lys Ile Gly Glu Ile Pro Gln Cys Arg Ile Leu Ser Ala
                        835                 840                 845
        Tyr Phe Leu Val Ser Pro Lys Gly Pro Phe Lys Ser Gln Glu Glu Leu
                        850                 855                 860
        Trp Asp Asp Lys Ala
        865

<210> SEQ ID NO 13
```

<211> LENGTH: 858
<212> TYPE: PRT
<213> ORGANISM: Papaver bracteatum
<220> FEATURE:
<221> NAME/KEY: MOD_RES
<222> LOCATION: (822)..(822)
<223> OTHER INFORMATION: Any amino acid

<400> SEQUENCE: 13

```
Met Glu Leu Gln Tyr Phe Ser Tyr Phe Gln Pro Thr Ser Ser Val Val
1               5                   10                  15

Ala Leu Leu Leu Ala Leu Val Ser Ile Leu Phe Ser Val Val Val Leu
            20                  25                  30

Arg Lys Thr Phe Ser Asn Asn Tyr Ser Ser Pro Ala Ser Ser Thr Glu
        35                  40                  45

Thr Ala Val Leu Cys His Gln Arg Gln Gln Ser Cys Ala Leu Pro Ile
    50                  55                  60

Ser Gly Leu Leu His Val Phe Met Asn Lys Asn Gly Leu Ile His Val
65                  70                  75                  80

Thr Leu Gly Asn Met Ala Asp Lys Tyr Gly Pro Ile Phe Ser Phe Pro
                85                  90                  95

Thr Gly Ser His Arg Thr Leu Val Val Ser Ser Trp Glu Met Val Lys
            100                 105                 110

Glu Cys Phe Thr Gly Asn Asn Asp Thr Ala Phe Ser Asn Arg Pro Ile
        115                 120                 125

Pro Leu Ala Phe Gln Thr Ile Phe Tyr Ala Cys Gly Gly Ile Asp Ser
    130                 135                 140

Tyr Gly Leu Ser Ser Val Pro Tyr Gly Lys Tyr Trp Arg Glu Leu Arg
145                 150                 155                 160

Lys Val Cys Val His Asn Leu Leu Ser Asn Gln Gln Leu Leu Lys Phe
                165                 170                 175

Arg His Leu Ile Ile Ser Gln Val Asp Thr Ser Phe Asn Lys Leu Tyr
            180                 185                 190

Glu Leu Cys Lys Asn Ser Glu Asp Asn Gln Gly Met Val Arg Met Asp
        195                 200                 205

Asp Trp Leu Ala Gln Leu Ser Phe Asn Val Ile Gly Arg Ile Val Cys
    210                 215                 220

Gly Phe Gln Ser Asp Pro Lys Thr Gly Ala Pro Ser Arg Val Glu Gln
225                 230                 235                 240

Phe Lys Glu Val Ile Asn Glu Ala Ser Tyr Phe Met Ser Thr Ser Pro
                245                 250                 255

Val Ser Asp Asn Val Pro Met Leu Gly Trp Ile Asp Gln Leu Thr Gly
            260                 265                 270

Leu Thr Arg Asn Met Lys His Cys Gly Lys Lys Leu Asp Leu Val Val
        275                 280                 285

Glu Ser Ile Ile Lys Asp His Arg Gln Lys Arg Arg Phe Ser Arg Thr
    290                 295                 300

Lys Gly Gly Asp Glu Lys Asp Asp Glu Gln Asp Phe Ile Asp Ile
305                 310                 315                 320

Cys Leu Ser Ile Met Glu Gln Pro Gln Leu Pro Gly Asn Asn Ser Pro
                325                 330                 335

Pro Gln Ile Pro Ile Lys Ser Ile Val Leu Asp Met Ile Gly Gly Gly
            340                 345                 350

Thr Asp Thr Thr Lys Leu Thr Thr Ile Trp Thr Leu Ser Leu Leu Leu
        355                 360                 365
```

-continued

```
Asn Asn Pro His Val Leu Asp Lys Ala Lys Gln Glu Val Asp Ala His
    370                 375                 380

Phe Arg Lys Lys Arg Ser Thr Asp Ala Ala Ala Val Val
385                 390                 395                 400

Asp Phe Asp Ile Arg Asn Leu Val Tyr Ile Gln Ala Ile Ile Lys
                405                 410                 415

Glu Ser Met Arg Leu Tyr Pro Ala Ser Pro Val Val Glu Arg Leu Ser
            420                 425                 430

Gly Glu Asp Cys Val Val Gly Gly Phe His Val Pro Ala Gly Thr Arg
            435                 440                 445

Leu Trp Ala Asn Val Trp Lys Met Gln Arg Asp Pro Lys Val Trp Asp
450                 455                 460

Asp Pro Leu Val Phe Arg Pro Glu Arg Phe Leu Ser Asp Glu Gln Lys
465                 470                 475                 480

Met Val Asp Val Arg Gly Gln Asn Tyr Glu Leu Leu Pro Phe Gly Ala
                485                 490                 495

Gly Arg Arg Ile Cys Pro Gly Val Ser Phe Ser Leu Asp Leu Met Gln
                500                 505                 510

Leu Val Leu Thr Arg Leu Ile Leu Glu Phe Glu Met Lys Ser Pro Ser
            515                 520                 525

Gly Lys Val Asp Met Thr Ala Thr Pro Gly Leu Met Ser Tyr Lys Val
530                 535                 540

Val Pro Leu Asp Ile Leu Leu Thr His Arg Arg Ile Lys Ser Cys Val
545                 550                 555                 560

Gln Leu Ala Ser Ser Glu Arg Asp Met Glu Ser Ser Gly Val Pro Val
                565                 570                 575

Ile Thr Leu Ser Ser Gly Lys Val Met Pro Val Leu Gly Met Gly Thr
                580                 585                 590

Phe Glu Lys Val Gly Lys Gly Ser Glu Arg Glu Arg Leu Ala Ile Leu
            595                 600                 605

Lys Ala Ile Glu Val Gly Tyr Arg Tyr Phe Asp Thr Ala Ala Ala Tyr
            610                 615                 620

Glu Thr Glu Glu Val Leu Gly Glu Ala Ile Ala Glu Ala Leu Gln Leu
625                 630                 635                 640

Gly Leu Ile Glu Ser Arg Asp Glu Leu Phe Ile Ser Ser Met Leu Trp
                645                 650                 655

Cys Thr Asp Ala His Pro Asp Arg Val Leu Leu Ala Leu Gln Asn Ser
                660                 665                 670

Leu Arg Asn Leu Lys Leu Glu Tyr Leu Asp Leu Tyr Met Leu Pro Phe
            675                 680                 685

Pro Ala Ser Leu Lys Pro Gly Lys Ile Thr Met Asp Ile Pro Glu Glu
            690                 695                 700

Asp Ile Cys Arg Met Asp Tyr Arg Ser Val Trp Ser Ala Met Glu Glu
705                 710                 715                 720

Cys Gln Asn Leu Gly Phe Thr Lys Ser Ile Gly Val Ser Asn Phe Ser
                725                 730                 735

Ser Lys Lys Leu Gln Glu Leu Met Ala Thr Ala Asn Ile Pro Pro Ala
            740                 745                 750

Val Asn Gln Val Glu Met Ser Pro Ala Phe Gln Gln Lys Lys Leu Arg
            755                 760                 765

Glu Tyr Cys Asn Ala Asn Asn Ile Leu Val Ser Ala Val Ser Ile Leu
770                 775                 780

Gly Ser Asn Gly Thr Pro Trp Gly Ser Asn Ala Val Leu Gly Ser Glu
```

```
            785                 790                 795                 800
Val Leu Lys Gln Ile Ala Met Ala Lys Gly Lys Ser Val Ala Gln Val
                    805                 810                 815

Ser Met Arg Trp Val Xaa Lys Phe Ser Ala Tyr Ala Ile Val Trp Ser
                820                 825                 830

Leu Phe Phe Gly His Arg Ile Cys Ile Thr Leu Tyr Ser Phe Leu Ile
            835                 840                 845

Arg Asn Val Ala Tyr Ile Cys Ile Thr Tyr
        850                 855

<210> SEQ ID NO 14
<211> LENGTH: 716
<212> TYPE: PRT
<213> ORGANISM: Papaver bracteatum

<400> SEQUENCE: 14

Met Glu Leu Gln Tyr Phe Ser Tyr Phe Gln Pro Thr Ser Ser Val Val
1               5                   10                  15

Ala Leu Leu Leu Ala Leu Val Ser Ile Leu Phe Ser Val Val Val Leu
            20                  25                  30

Arg Lys Thr Phe Ser Asn Asn Tyr Ser Ser Pro Ala Ser Ser Thr Glu
        35                  40                  45

Thr Ala Val Leu Cys His Gln Arg Gln Gln Ser Cys Ala Leu Pro Ile
50                  55                  60

Ser Gly Leu Leu His Val Phe Met Asn Lys Asn Gly Leu Ile His Val
65                  70                  75                  80

Thr Leu Gly Asn Met Ala Asp Lys Tyr Gly Pro Ile Phe Ser Phe Pro
                85                  90                  95

Thr Gly Ser His Arg Thr Leu Val Val Ser Ser Trp Glu Met Val Lys
            100                 105                 110

Glu Cys Phe Thr Gly Asn Asn Asp Thr Ala Phe Ser Asn Arg Pro Ile
        115                 120                 125

Pro Leu Ala Phe Gln Thr Ile Phe Tyr Ala Cys Gly Gly Ile Asp Ser
    130                 135                 140

Tyr Gly Leu Ser Ser Val Pro Tyr Gly Lys Tyr Trp Arg Glu Leu Arg
145                 150                 155                 160

Lys Val Cys Val His Asn Leu Leu Ser Asn Gln Gln Leu Leu Lys Phe
                165                 170                 175

Arg His Leu Ile Ile Ser Gln Val Asp Thr Ser Phe Asn Lys Leu Tyr
            180                 185                 190

Glu Leu Cys Lys Asn Ser Glu Asp Asn Gln Gly Met Val Arg Met Asp
        195                 200                 205

Asp Trp Leu Ala Gln Leu Ser Phe Asn Val Ile Gly Arg Ile Val Cys
    210                 215                 220

Gly Phe Gln Ser Asp Pro Lys Thr Gly Ala Pro Ser Arg Val Glu Gln
225                 230                 235                 240

Phe Lys Glu Val Ile Asn Glu Ala Ser Tyr Phe Met Ser Thr Ser Pro
                245                 250                 255

Val Ser Asp Asn Val Pro Met Leu Gly Trp Ile Asp Gln Leu Thr Gly
            260                 265                 270

Leu Thr Arg Asn Met Lys His Cys Gly Lys Lys Leu Asp Leu Val Val
        275                 280                 285

Glu Ser Ile Ile Lys Asp His Arg Gln Lys Arg Phe Ser Arg Thr
    290                 295                 300
```

```
Lys Gly Gly Asp Glu Lys Asp Asp Glu Gln Asp Phe Ile Asp Ile
305                 310                 315                 320

Cys Leu Ser Ile Met Glu Gln Pro Gln Leu Pro Gly Asn Asn Ser Pro
                325                 330                 335

Pro Gln Ile Pro Ile Lys Ser Ile Val Leu Asp Met Ile Gly Gly Gly
            340                 345                 350

Thr Asp Thr Thr Lys Leu Thr Thr Ile Trp Thr Leu Ser Leu Leu Leu
        355                 360                 365

Asn Asn Pro His Val Leu Asp Lys Ala Lys Gln Glu Val Asp Ala His
    370                 375                 380

Phe Arg Lys Lys Arg Ser Thr Asp Ala Ala Ala Val Val
385             390                 395                 400

Asp Phe Asp Asp Ile Arg Asn Leu Val Tyr Ile Gln Ala Ile Ile Lys
                405                 410                 415

Glu Ser Met Arg Leu Tyr Pro Ala Ser Pro Val Val Glu Arg Leu Ser
            420                 425                 430

Gly Glu Asp Cys Val Val Gly Gly Phe His Val Pro Ala Gly Thr Arg
        435                 440                 445

Leu Trp Ala Asn Val Trp Lys Met Gln Arg Asp Pro Lys Val Trp Asp
450                 455                 460

Asp Pro Leu Val Phe Arg Pro Glu Arg Phe Leu Ser Asp Glu Gln Lys
465                 470                 475                 480

Met Val Asp Val Arg Gly Gln Asn Tyr Glu Leu Leu Pro Phe Gly Ala
                485                 490                 495

Gly Arg Arg Ile Cys Pro Gly Val Ser Phe Ser Leu Asp Leu Met Gln
            500                 505                 510

Leu Val Leu Thr Arg Leu Ile Leu Glu Phe Glu Met Lys Ser Pro Ser
        515                 520                 525

Gly Lys Val Asp Met Thr Ala Thr Pro Gly Leu Met Ser Tyr Lys Val
    530                 535                 540

Val Pro Leu Asp Ile Leu Leu Thr His Arg Arg Ile Lys Ser Cys Val
545                 550                 555                 560

Gln Leu Ala Ser Ser Glu Arg Asp Met Glu Ser Ser Gly Val Pro Val
                565                 570                 575

Ile Thr Leu Ser Ser Gly Lys Val Met Pro Val Leu Gly Met Gly Thr
            580                 585                 590

Phe Glu Lys Val Gly Lys Gly Ser Glu Arg Glu Arg Leu Ala Ile Leu
        595                 600                 605

Lys Ala Ile Glu Val Gly Tyr Arg Tyr Phe Asp Thr Ala Ala Ala Tyr
    610                 615                 620

Glu Thr Glu Glu Val Leu Gly Glu Ala Ile Ala Glu Ala Leu Gln Leu
625                 630                 635                 640

Gly Leu Ile Glu Ser Arg Asp Glu Leu Phe Ile Ser Ser Met Leu Trp
                645                 650                 655

Cys Thr Asp Ala His Pro Asp Arg Val Leu Leu Ala Leu Gln Asn Ser
            660                 665                 670

Leu Arg Gln Val Phe Leu Met Gln Ile Arg Leu Ile Tyr Ile Cys Thr
        675                 680                 685

Tyr Gln Gln Val His Leu Asn Ile Tyr Phe Gln Ile Asn Glu Phe Val
    690                 695                 700

Leu Cys Asp Met Tyr Arg Asn Leu Lys Leu Glu Tyr
705                 710                 715
```

<210> SEQ ID NO 15
<211> LENGTH: 864
<212> TYPE: PRT
<213> ORGANISM: Chelidonium majus

<400> SEQUENCE: 15

```
Leu Asn Asn Tyr Ser Ser Pro Ala Ser Thr Lys Thr Ala Val
 1               5                  10                  15

Leu Ser His Gln Arg Gln Ser Cys Ala Leu Pro Ile Ser Gly Leu
             20                  25                  30

Leu His Ile Phe Met Asn Lys Asn Gly Leu Ile His Val Thr Leu Gly
             35                  40                  45

Asn Met Ala Asp Lys Tyr Gly Pro Ile Phe Ser Phe Pro Thr Gly Ser
 50                      55                  60

His Arg Thr Leu Val Val Ser Ser Trp Glu Met Val Lys Glu Cys Phe
 65                  70                      75                  80

Thr Gly Asn Asn Asp Thr Ala Phe Ser Asn Arg Pro Ile Pro Leu Ala
                 85                  90                  95

Phe Lys Thr Ile Phe Tyr Ala Cys Gly Ile Asp Ser Tyr Gly Leu
                100                 105                 110

Ser Ser Val Pro Tyr Gly Lys Tyr Trp Arg Glu Leu Arg Lys Val Cys
            115                 120                 125

Val His Asn Leu Leu Ser Asn Gln Gln Leu Leu Lys Phe Arg His Leu
    130                 135                 140

Ile Ile Ser Gln Val Asp Thr Ser Phe Asn Lys Leu Tyr Glu Leu Cys
145                 150                 155                 160

Lys Asn Ser Glu Asp Asn Gln Gly Asn Tyr Pro Thr Thr Thr Thr Ala
                165                 170                 175

Ala Gly Met Val Arg Ile Asp Asp Trp Leu Ala Glu Leu Ser Phe Asn
            180                 185                 190

Val Ile Gly Arg Ile Val Cys Gly Phe Gln Ser Gly Pro Lys Thr Gly
        195                 200                 205

Ala Pro Ser Arg Val Glu Gln Phe Lys Glu Ala Ile Asn Glu Ala Ser
    210                 215                 220

Tyr Phe Met Ser Thr Ser Pro Val Ser Asp Asn Val Pro Met Leu Gly
225                 230                 235                 240

Trp Ile Asp Gln Leu Thr Gly Leu Thr Arg Asn Met Lys His Cys Gly
                245                 250                 255

Lys Lys Leu Asp Leu Val Val Glu Ser Ile Ile Asn Asp His Arg Gln
            260                 265                 270

Lys Arg Arg Phe Ser Arg Thr Lys Gly Gly Asp Glu Lys Asp Asp Glu
        275                 280                 285

Gln Asp Asp Phe Ile Asp Ile Cys Leu Ser Ile Met Glu Gln Pro Gln
    290                 295                 300

Leu Pro Gly Asn Asn Asn Pro Ser Gln Ile Pro Ile Lys Ser Ile Val
305                 310                 315                 320

Leu Asp Met Ile Gly Gly Gly Thr Asp Thr Thr Lys Leu Thr Thr Ile
                325                 330                 335

Trp Thr Leu Ser Leu Leu Leu Asn Asn Pro His Val Leu Asp Lys Ala
            340                 345                 350

Lys Gln Glu Val Asp Ala His Phe Arg Thr Lys Arg Ser Thr Asn
        355                 360                 365

Asp Ala Ala Ala Ala Val Val Asp Phe Asp Asp Ile Arg Asn Leu Val
    370                 375                 380
```

```
Tyr Ile Gln Ala Ile Ile Lys Glu Ser Met Arg Leu Tyr Pro Ala Ser
385                 390                 395                 400

Pro Val Val Glu Arg Leu Ser Gly Glu Asp Cys Val Val Gly Gly Phe
            405                 410                 415

His Val Pro Ala Gly Thr Arg Leu Trp Ala Asn Val Trp Lys Met Gln
        420                 425                 430

Arg Asp Pro Lys Val Trp Asp Pro Leu Val Phe Arg Pro Asp Arg
        435                 440                 445

Phe Leu Ser Asp Glu Gln Lys Met Val Asp Val Arg Gly Gln Asn Tyr
    450                 455                 460

Glu Leu Leu Pro Phe Gly Ala Gly Arg Arg Val Cys Pro Gly Val Ser
465                 470                 475                 480

Phe Ser Leu Asp Leu Met Gln Leu Val Leu Thr Arg Leu Ile Leu Glu
            485                 490                 495

Phe Glu Met Lys Ser Pro Ser Gly Lys Val Asp Met Thr Ala Thr Pro
            500                 505                 510

Gly Leu Met Ser Tyr Lys Val Ile Pro Leu Asp Ile Leu Leu Thr His
        515                 520                 525

Arg Arg Ile Lys Pro Cys Val Gln Ser Ala Ala Ser Glu Arg Asp Met
530                 535                 540

Glu Ser Ser Gly Val Pro Val Ile Thr Leu Gly Ser Gly Lys Val Met
545                 550                 555                 560

Pro Val Leu Gly Met Gly Thr Phe Glu Lys Val Gly Lys Gly Ser Glu
            565                 570                 575

Arg Glu Arg Leu Ala Phe Leu Lys Ala Ile Glu Val Gly Tyr Arg Tyr
        580                 585                 590

Phe Asp Thr Ala Ala Ala Tyr Glu Thr Glu Glu Phe Leu Gly Glu Ala
        595                 600                 605

Ile Ala Glu Ala Leu Gln Leu Gly Leu Ile Lys Ser Arg Asp Glu Leu
    610                 615                 620

Phe Ile Thr Ser Lys Leu Trp Pro Cys Asp Ala His Pro Asp Leu Val
625                 630                 635                 640

Val Pro Ala Leu Gln Asn Ser Leu Arg Asn Leu Lys Leu Glu Tyr Val
            645                 650                 655

Asp Leu Tyr Met Leu Pro Phe Pro Ala Ser Leu Lys Pro Gly Lys Ile
            660                 665                 670

Thr Met Asp Ile Pro Glu Glu Asp Ile Cys Arg Met Asp Tyr Arg Ser
        675                 680                 685

Val Trp Ala Ala Met Glu Glu Cys Gln Asn Leu Gly Phe Thr Lys Ser
        690                 695                 700

Ile Gly Val Ser Asn Phe Ser Cys Lys Lys Leu Gln Glu Leu Met Ala
705                 710                 715                 720

Thr Ala Asn Ile Pro Pro Ala Val Asn Gln Val Glu Met Ser Pro Ala
            725                 730                 735

Phe Gln Gln Lys Lys Leu Arg Glu Tyr Cys Asn Ala Asn Asn Ile Leu
            740                 745                 750

Val Ser Ala Ile Ser Val Leu Gly Ser Asn Gly Thr Pro Trp Gly Ser
        755                 760                 765

Asn Ala Val Leu Gly Ser Glu Val Leu Lys Lys Ile Ala Met Ala Lys
        770                 775                 780

Gly Lys Ser Val Ala Gln Val Ser Met Arg Trp Val Tyr Glu Gln Gly
785                 790                 795                 800

Ala Ser Leu Val Val Lys Ser Phe Ser Glu Glu Arg Leu Arg Glu Asn
```

```
                    805                 810                 815

Leu Asn Ile Phe Asp Trp Glu Leu Thr Lys Glu Asp His Glu Lys Ile
                820                 825                 830

Gly Glu Ile Pro Gln Cys Arg Ile Leu Ser Ala Tyr Phe Leu Val Ser
            835                 840                 845

Pro Asn Gly Pro Phe Lys Ser Gln Glu Glu Leu Trp Asp Asp Glu Ala
        850                 855                 860

<210> SEQ ID NO 16
<211> LENGTH: 364
<212> TYPE: PRT
<213> ORGANISM: Papaver somniferum

<400> SEQUENCE: 16

Met Glu Lys Ala Lys Leu Met Lys Leu Gly Asn Gly Met Glu Ile Pro
1               5                   10                  15

Ser Val Gln Glu Leu Ala Lys Leu Thr Leu Ala Glu Ile Pro Ser Arg
            20                  25                  30

Tyr Val Cys Ala Asn Glu Asn Leu Leu Pro Met Gly Ala Ser Val
        35                  40                  45

Ile Asn Asp His Glu Thr Ile Pro Val Ile Asp Ile Glu Asn Leu Leu
    50                  55                  60

Ser Pro Glu Pro Ile Ile Gly Lys Leu Glu Leu Asp Arg Leu His Phe
65                  70                  75                  80

Ala Cys Lys Glu Trp Gly Phe Phe Gln Val Val Asn His Gly Val Asp
                85                  90                  95

Ala Ser Leu Val Asp Ser Val Lys Ser Glu Ile Gln Gly Phe Phe Asn
            100                 105                 110

Leu Ser Met Asp Glu Lys Thr Lys Tyr Glu Gln Glu Asp Gly Asp Val
        115                 120                 125

Glu Gly Phe Gly Gln Gly Phe Ile Glu Ser Glu Asp Gln Thr Leu Asp
    130                 135                 140

Trp Ala Asp Ile Phe Met Met Phe Thr Leu Pro Leu His Leu Arg Lys
145                 150                 155                 160

Pro His Leu Phe Ser Lys Leu Pro Val Pro Leu Arg Glu Thr Ile Glu
                165                 170                 175

Ser Tyr Ser Ser Glu Met Lys Lys Leu Ser Met Val Leu Phe Asn Lys
            180                 185                 190

Met Glu Lys Ala Leu Gln Val Gln Ala Ala Glu Ile Lys Gly Met Ser
        195                 200                 205

Glu Val Phe Ile Asp Gly Thr Gln Ala Met Arg Met Asn Tyr Tyr Pro
    210                 215                 220

Pro Cys Pro Gln Pro Asn Leu Ala Ile Gly Leu Thr Ser His Ser Asp
225                 230                 235                 240

Phe Gly Gly Leu Thr Ile Leu Leu Gln Ile Asn Glu Val Glu Gly Leu
                245                 250                 255

Gln Ile Lys Arg Glu Gly Thr Trp Ile Ser Val Lys Pro Leu Pro Asn
            260                 265                 270

Ala Phe Val Val Asn Val Gly Asp Ile Leu Glu Ile Met Thr Asn Gly
        275                 280                 285

Ile Tyr His Ser Val Asp His Arg Ala Val Val Asn Ser Thr Asn Glu
    290                 295                 300

Arg Leu Ser Ile Ala Thr Phe His Asp Pro Ser Leu Glu Ser Val Ile
305                 310                 315                 320
```

```
Gly Pro Ile Ser Ser Leu Ile Thr Pro Glu Thr Pro Ala Leu Phe Lys
                325                 330                 335

Ser Gly Ser Thr Tyr Gly Asp Leu Val Glu Glu Cys Lys Thr Arg Lys
            340                 345                 350

Leu Asp Gly Lys Ser Phe Leu Asp Ser Met Arg Ile
        355                 360
```

<210> SEQ ID NO 17
<211> LENGTH: 360
<212> TYPE: PRT
<213> ORGANISM: Papaver somniferum

<400> SEQUENCE: 17

```
Met Glu Thr Pro Ile Leu Ile Lys Leu Gly Asn Gly Leu Ser Ile Pro
1               5                   10                  15

Ser Val Gln Glu Leu Ala Lys Leu Thr Leu Ala Glu Ile Pro Ser Arg
            20                  25                  30

Tyr Thr Cys Thr Gly Glu Ser Pro Leu Asn Asn Ile Gly Ala Ser Val
        35                  40                  45

Thr Asp Asp Glu Thr Val Pro Val Ile Asp Leu Gln Asn Leu Leu Ser
    50                  55                  60

Pro Glu Pro Val Val Gly Lys Leu Glu Leu Asp Lys Leu His Ser Ala
65                  70                  75                  80

Cys Lys Glu Trp Gly Phe Phe Gln Leu Val Asn His Gly Val Asp Ala
                85                  90                  95

Leu Leu Met Asp Asn Ile Lys Ser Glu Ile Lys Gly Phe Phe Asn Leu
            100                 105                 110

Pro Met Asn Glu Lys Thr Lys Tyr Gly Gln Gln Asp Gly Asp Phe Glu
        115                 120                 125

Gly Phe Gly Gln Pro Tyr Ile Glu Ser Glu Asp Gln Arg Leu Asp Trp
    130                 135                 140

Thr Glu Val Phe Ser Met Leu Ser Leu Pro Leu His Leu Arg Lys Pro
145                 150                 155                 160

His Leu Phe Pro Glu Leu Pro Leu Pro Phe Arg Glu Thr Leu Glu Ser
                165                 170                 175

Tyr Leu Ser Lys Met Lys Lys Leu Ser Thr Val Val Phe Glu Met Leu
            180                 185                 190

Glu Lys Ser Leu Gln Leu Val Glu Ile Lys Gly Met Thr Asp Leu Phe
        195                 200                 205

Glu Asp Gly Leu Gln Thr Met Arg Met Asn Tyr Tyr Pro Pro Cys Pro
    210                 215                 220

Arg Pro Glu Leu Val Leu Gly Leu Thr Ser His Ser Asp Phe Ser Gly
225                 230                 235                 240

Leu Thr Ile Leu Leu Gln Leu Asn Glu Val Glu Gly Leu Gln Ile Arg
                245                 250                 255

Lys Glu Glu Arg Trp Ile Ser Ile Lys Pro Leu Pro Asp Ala Phe Ile
            260                 265                 270

Val Asn Val Gly Asp Ile Leu Glu Ile Met Thr Asn Gly Ile Tyr Arg
        275                 280                 285

Ser Val Glu His Arg Ala Val Asn Ser Thr Lys Gly Arg Leu Ser
    290                 295                 300

Ile Ala Thr Phe His Asp Ser Lys Leu Glu Ser Glu Ile Gly Pro Ile
305                 310                 315                 320

Ser Ser Leu Val Thr Pro Glu Thr Pro Ala Leu Phe Lys Arg Gly Arg
                325                 330                 335
```

```
Tyr Glu Asp Ile Leu Lys Glu Asn Leu Ser Arg Lys Leu Asp Gly Lys
                340                 345                 350

Ser Phe Leu Asp Tyr Met Arg Met
            355                 360

<210> SEQ ID NO 18
<211> LENGTH: 364
<212> TYPE: PRT
<213> ORGANISM: Papaver somniferum

<400> SEQUENCE: 18

Met Glu Lys Ala Lys Leu Met Lys Leu Gly Asn Gly Leu Ser Ile Pro
1               5                   10                  15

Ser Val Gln Glu Leu Ala Glu Leu Thr Phe Ala Glu Val Pro Ser Arg
            20                  25                  30

Tyr Val Cys Thr Asn Asp Glu Asn Leu Leu Met Thr Met Gly Ala
        35                  40                  45

Ser Glu Ile Asp Asp Glu Thr Val Pro Val Ile Asp Leu Gln Asn Leu
    50                  55                  60

Leu Ser Pro Glu Pro Ala Ile Gly Lys Ser Glu Leu Asp Trp Leu His
65                  70                  75                  80

Tyr Ser Cys Lys Glu Trp Gly Phe Phe Gln Leu Val Asn His Gly Val
                85                  90                  95

Asp Ala Leu Leu Val Asp His Val Lys Ser Glu Ile His Ser Phe Phe
            100                 105                 110

Asn Leu Pro Leu Asn Glu Lys Thr Lys Tyr Gly Gln Arg Asp Gly Asp
        115                 120                 125

Val Glu Gly Phe Gly Gln Ala Phe Leu Val Ser Glu Asn Gln Lys Leu
    130                 135                 140

Asp Trp Ala Asp Met Phe Phe Ile Asn Thr Leu Pro Leu His Leu Arg
145                 150                 155                 160

Lys Pro His Leu Phe Pro Asn Leu Pro Leu Arg Glu Thr Ile
                165                 170                 175

Glu Ser Tyr Ser Ser Glu Met Lys Lys Leu Ser Met Val Leu Phe Glu
            180                 185                 190

Met Met Gly Lys Ala Ile Glu Val Ile Asp Ile Lys Glu Ala Ile Thr
        195                 200                 205

Glu Met Phe Glu Asp Gly Met Gln Ser Met Arg Met Asn Tyr Tyr Pro
    210                 215                 220

Pro Cys Pro Gln Pro Glu Arg Val Ile Gly Ile Thr Pro His Ser Asp
225                 230                 235                 240

Phe Asp Gly Leu Thr Ile Leu Leu Gln Leu Asn Glu Val Glu Gly Leu
                245                 250                 255

Gln Ile Arg Lys Glu Asp Lys Trp Ile Ser Lys Pro Leu Pro Asp
            260                 265                 270

Ala Phe Ile Val Asn Val Gly Asp Ile Trp Glu Ile Met Thr Asn Gly
        275                 280                 285

Val His Arg Ser Val Asp His Arg Gly Val Ile Asn Ser Thr Lys Glu
    290                 295                 300

Arg Leu Ser Ile Ala Thr Phe His Ser Pro Lys Leu Glu Leu Glu Ile
305                 310                 315                 320

Gly Pro Ile Ser Ser Leu Ile Arg Pro Glu Thr Pro Ala Val Phe Lys
                325                 330                 335

Ser Ala Gly Arg Phe Glu Asp Leu Leu Lys Glu Gly Leu Ser Arg Lys
```

```
                    340                 345                 350
Leu Asp Gly Lys Ser Phe Leu Asp Cys Met Arg Met
            355                 360

<210> SEQ ID NO 19
<211> LENGTH: 294
<212> TYPE: PRT
<213> ORGANISM: Papaver somniferum

<400> SEQUENCE: 19

Met Glu Lys Ala Lys Leu Met Lys Leu Gly Asn Gly Met Glu Ile Pro
1               5                   10                  15

Ser Val Gln Glu Leu Ala Lys Leu Thr Leu Ala Glu Ile Pro Ser Arg
            20                  25                  30

Tyr Val Cys Ala Asn Glu Asn Leu Leu Leu Pro Met Gly Ala Ser Val
        35                  40                  45

Ile Asn Asp His Glu Thr Ile Pro Val Ile Asp Ile Glu Asn Leu Leu
    50                  55                  60

Ser Pro Glu Pro Ile Ile Gly Lys Leu Glu Leu Asp Arg Leu His Phe
65                  70                  75                  80

Ala Cys Lys Glu Trp Gly Phe Phe Gln Val Val Asn His Gly Val Asp
                85                  90                  95

Ala Ser Leu Val Asp Ser Val Lys Ser Glu Ile Gln Gly Phe Phe Asn
            100                 105                 110

Leu Ser Met Asp Glu Lys Thr Lys Tyr Glu Gln Glu Asp Gly Asp Val
        115                 120                 125

Glu Gly Phe Gly Gln Gly Phe Ile Glu Ser Glu Asp Gln Thr Leu Asp
    130                 135                 140

Trp Ala Asp Ile Phe Met Met Phe Thr Leu Pro Leu His Leu Arg Lys
145                 150                 155                 160

Pro His Leu Phe Ser Lys Leu Pro Val Pro Leu Arg Glu Thr Ile Glu
                165                 170                 175

Ser Tyr Ser Ser Glu Met Lys Lys Leu Ser Met Val Leu Phe Asn Lys
            180                 185                 190

Met Glu Lys Ala Leu Gln Val Gln Ala Ala Glu Ile Lys Gly Met Ser
        195                 200                 205

Glu Val Phe Ile Asp Gly Thr Gln Ala Met Arg Met Asn Tyr Tyr Pro
    210                 215                 220

Pro Cys Pro Gln Pro Asn Leu Ala Ile Gly Leu Thr Ser His Ser Asp
225                 230                 235                 240

Phe Gly Gly Leu Thr Ile Leu Leu Gln Ile Asn Glu Val Glu Gly Leu
                245                 250                 255

Gln Ile Lys Arg Glu Gly Thr Trp Ile Ser Val Lys Pro Leu Pro Asn
            260                 265                 270

Ala Phe Val Val Asn Val Gly Asp Ile Leu Glu Ile Met Thr Asn Gly
        275                 280                 285

Ile Tyr His Ser Val Asp
    290

<210> SEQ ID NO 20
<211> LENGTH: 364
<212> TYPE: PRT
<213> ORGANISM: Papaver somniferum

<400> SEQUENCE: 20

Met Glu Thr Ala Lys Leu Met Lys Leu Gly Asn Gly Met Ser Ile Pro
```

```
             1               5                  10                 15
             Ser Val Gln Glu Leu Ala Lys Leu Thr Leu Ala Glu Ile Pro Ser Arg
                            20                 25                 30

Tyr Ile Cys Thr Val Glu Asn Leu Gln Leu Pro Val Gly Ala Ser Val
                            35                 40                 45

Ile Asp Asp His Glu Thr Val Pro Val Ile Asp Ile Glu Asn Leu Ile
                 50                     55                 60

Ser Ser Glu Pro Val Thr Glu Lys Leu Glu Leu Asp Arg Leu His Ser
             65                 70                     75                 80

Ala Cys Lys Glu Trp Gly Phe Phe Gln Val Val Asn His Gly Val Asp
                                85                 90                 95

Thr Ser Leu Val Asp Asn Val Lys Ser Asp Ile Gln Gly Phe Phe Asn
                            100                105                110

Leu Ser Met Asn Glu Lys Ile Lys Tyr Gly Gln Lys Asp Gly Asp Val
                            115                120                125

Glu Gly Phe Gly Gln Ala Phe Val Ala Ser Glu Asp Gln Thr Leu Asp
                            130                135                140

Trp Ala Asp Ile Phe Met Ile Leu Thr Leu Pro Leu His Leu Arg Lys
             145                150                155                160

Pro His Leu Phe Ser Lys Leu Pro Leu Pro Leu Arg Glu Thr Ile Glu
                                165                170                175

Ser Tyr Ser Ser Glu Met Lys Lys Leu Ser Met Val Leu Phe Glu Lys
                            180                185                190

Met Glu Lys Ala Leu Gln Val Gln Ala Val Glu Ile Lys Glu Ile Ser
                            195                200                205

Glu Val Phe Lys Asp Met Thr Gln Val Met Arg Met Asn Tyr Tyr Pro
                 210                     215                220

Pro Cys Pro Gln Pro Glu Leu Ala Ile Gly Leu Thr Pro His Ser Asp
             225                230                     235                240

Phe Gly Gly Leu Thr Ile Leu Leu Gln Leu Asn Glu Val Glu Gly Leu
                                245                250                255

Gln Ile Lys Asn Glu Gly Arg Trp Ile Ser Val Lys Pro Leu Pro Asn
                            260                265                270

Ala Phe Val Val Asn Val Gly Asp Val Leu Glu Ile Met Thr Asn Gly
                            275                280                285

Met Tyr Arg Ser Val Asp His Arg Ala Val Val Asn Ser Thr Lys Glu
                            290                295                300

Arg Leu Ser Ile Ala Thr Phe His Asp Pro Asn Leu Glu Ser Glu Ile
             305                310                315                320

Gly Pro Ile Ser Ser Leu Ile Thr Pro Asn Thr Pro Ala Leu Phe Arg
                            325                330                335

Ser Gly Ser Thr Tyr Gly Glu Leu Val Glu Glu Phe His Ser Arg Lys
                            340                345                350

Leu Asp Gly Lys Ser Phe Leu Asp Ser Met Arg Met
                            355                360

<210> SEQ ID NO 21
             <211> LENGTH: 369
             <212> TYPE: PRT
             <213> ORGANISM: Papaver bracteatum

<400> SEQUENCE: 21

Met Glu Thr Pro Lys Ser Ile Lys Leu Gly Gly Ser Leu Leu Val Pro
             1                  5                  10                 15
```

Ser Val Gln Glu Leu Ala Gln Gln Ser Phe Ala Glu Val Pro Ala Arg
                20                  25                  30

Tyr Val Arg Asp Asp Leu Glu Pro Leu Thr Asp Leu Ser Gly Val Ser
            35                  40                  45

Met Ile Asp Gln Thr Ile Pro Val Ile Asp Leu Gln Lys Leu Gln Ser
 50                  55                  60

Pro Val Pro Ile Ile Arg Glu Leu Glu Ser Glu Lys Leu His Ser Ala
 65                  70                  75                  80

Cys Lys Glu Trp Gly Phe Phe Gln Val Val Asn His Gly Val Asp Ile
                85                  90                  95

Leu Leu Val Glu Lys Thr Lys Ser Glu Ile Lys Asp Phe Phe Asn Leu
                100                 105                 110

Pro Met Asp Glu Lys Lys Lys Phe Trp Gln Glu Gly Asp Ile Gln
                115                 120                 125

Gly Phe Gly Gln Ala Phe Val Gln Ser Glu Asp Gln Lys Leu Asp Trp
    130                 135                 140

Ala Asp Ile Phe Leu Met Val Thr Leu Pro Arg His Thr Arg Asn Pro
145                 150                 155                 160

Arg Leu Phe Pro Lys Leu Pro Leu Pro Leu Arg Asn Thr Met Asp Ser
                165                 170                 175

Tyr Ser Ser Lys Leu Ser Lys Leu Ala Ser Thr Leu Ile Glu Met Met
                180                 185                 190

Gly Lys Ala Leu His Met Glu Thr Ser Val Leu Ala Glu Leu Phe Glu
                195                 200                 205

Asp Gly Arg Gln Thr Met Arg Ile Asn Tyr Tyr Pro Pro Cys Pro Gln
    210                 215                 220

Pro Lys Asp Val Ile Gly Leu Thr Pro His Ser Asp Gly Gly Leu
225                 230                 235                 240

Thr Ile Leu Leu Gln Leu Asn Glu Val Asp Gly Leu Gln Ile Arg Lys
                245                 250                 255

Glu Lys Ile Trp Ile Pro Ile Lys Pro Leu Pro Asn Ala Phe Val Val
                260                 265                 270

Asn Ile Gly Asn Ile Leu Glu Ile Met Thr Asn Gly Ile Tyr Arg Ser
                275                 280                 285

Val Glu His Arg Ala Thr Ile His Ser Thr Lys Glu Arg Leu Ser Val
                290                 295                 300

Ala Ala Phe His Asn Pro Lys Val Gly Val Glu Ile Gly Pro Ile Val
305                 310                 315                 320

Ser Met Ile Thr Pro Glu Ser Pro Ala Leu Phe Arg Thr Ile Glu Tyr
                325                 330                 335

Asp Asp Tyr Gly Lys Lys Tyr Phe Ser Arg Lys Leu Asp Gly Lys Ser
                340                 345                 350

Ser Leu Asp Phe Met Arg Ile Gly Glu Gly Asp Glu Glu Asn Lys Ala
                355                 360                 365

Thr

<210> SEQ ID NO 22
<211> LENGTH: 366
<212> TYPE: PRT
<213> ORGANISM: Papaver bracteatum

<400> SEQUENCE: 22

Met Glu Thr Pro Lys Leu Ile Lys Leu Gly Gly Ser Leu Leu Val Pro
1               5                   10                  15

```
Ser Val Leu Glu Leu Thr Lys Gln Ser Pro Ala Glu Val Pro Ala Arg
             20                  25                  30

Tyr Ile Arg Asn Asp Leu Glu Pro Met Thr Asp Leu Ser Ser Ala Ser
         35                  40                  45

Leu Thr Asp Gln Thr Ile Pro Val Ile Asp Leu Gln Asn Leu Leu Ser
 50                  55                  60

Pro Glu Pro Glu Leu Glu Leu Lys Leu His Ser Gly Cys Lys Glu
 65                  70                  75                  80

Trp Gly Phe Phe Gln Val Met Asn His Gly Val Asp Ile Leu Leu Val
                 85                  90                  95

Glu Lys Val Lys Ser Glu Ile Gln Gly Phe Phe Asn Leu Pro Ile Asp
             100                 105                 110

Glu Lys Asn Lys Phe Trp Gln Glu Gly Asp Leu Glu Gly Tyr Gly
         115                 120                 125

Lys Ala Phe Val His Ser Glu Asp Glu Lys Leu Asp Trp Ala Asp Met
130                 135                 140

Phe Phe Ile Leu Thr Gln Pro Gln Tyr Met Arg Lys Pro Arg Val Phe
145                 150                 155                 160

Pro Lys Leu Pro Leu Arg Leu Arg Glu Thr Ile Glu Ser Tyr Ser Leu
                 165                 170                 175

Glu Leu Ser Lys Leu Gly Leu Thr Leu Leu Asp Leu Met Gly Lys Ala
             180                 185                 190

Leu Gln Ile Glu Thr Gly Val Met Ser Glu Leu Phe Glu Asp Gly Arg
         195                 200                 205

Gln Thr Met Arg Met Asn Tyr Tyr Pro Pro Cys Pro Gln Pro Glu His
210                 215                 220

Val Ile Gly Leu Thr Pro His Ser Asp Gly Gly Ala Leu Thr Ile Leu
225                 230                 235                 240

Leu Gln Leu Asn Gln Val Asp Gly Leu Gln Ile Arg Lys Glu Glu Ile
                 245                 250                 255

Trp Val Pro Ile Lys Pro Leu Pro Asn Ala Phe Val Val Asn Ile Gly
             260                 265                 270

Asp Ile Leu Glu Ile Met Ser Asn Gly Val Tyr Arg Ser Val Glu His
         275                 280                 285

Arg Ala Thr Ile Asn Ser Ser Lys Glu Arg Leu Ser Val Ala Ile Phe
290                 295                 300

Gln Ser Pro Lys His Gly Thr Glu Ile Gly Pro Ile Leu Ser Met Ile
305                 310                 315                 320

Thr Pro Glu Ala Pro Ala Leu Phe Lys Thr Ile Pro Tyr Glu Asp Tyr
                 325                 330                 335

Leu Arg Lys Phe Phe Ser Arg Lys Leu Gly Gly Lys Ser Phe Val Asp
             340                 345                 350

Ser Met Arg Ile Gly Glu Ser Asp Glu Asp Asn Asn Thr Ala
         355                 360                 365

<210> SEQ ID NO 23
<211> LENGTH: 366
<212> TYPE: PRT
<213> ORGANISM: Papaver bracteatum

<400> SEQUENCE: 23

Met Glu Thr Gln Lys Gln Glu Asn Phe Gly Ala Ser Leu Ser Val Pro
1               5                   10                  15

Asn Val Gln Glu Leu Ala Lys Gln Ser Pro Glu Gln Val Pro Asp Arg
             20                  25                  30
```

Tyr Ile Arg Ser Asp Gln Asp Ser Thr Asn Ile Ser Cys Pro Ser
            35                  40                  45

Met Thr Asp Gln Ile Pro Val Ile Asp Leu Gln Ser Leu Leu Ser Pro
        50                  55                  60

Asp Pro Ile Ile Gly Glu Leu Glu Leu Glu Arg Leu His Ser Ala Cys
65                  70                  75                  80

Lys Glu Trp Gly Phe Phe Gln Val Val Asn His Gly Val Asp Asn Leu
                85                  90                  95

Leu Val Glu Lys Val Lys Ser Glu Ile Gln Gly Phe Phe Asn Leu Pro
            100                 105                 110

Met Asp Glu Lys Lys Phe Trp Gln Glu Gly Asp Phe Glu Gly
        115                 120                 125

Phe Gly Gln Ala Phe Val Phe Ser Glu Asp Gln Lys Leu Asp Trp Gly
        130                 135                 140

Asp Val Phe Phe Ile Leu Thr Gln Pro Gln His Met Arg Lys Pro Arg
145                 150                 155                 160

Leu Phe Pro Lys Leu Pro Leu Pro Phe Arg Lys Thr Ile Glu Ser Tyr
                165                 170                 175

Ser Leu Glu Thr Asn Lys Leu Ser Met Thr Leu Leu Glu Leu Met Glu
            180                 185                 190

Lys Ala Leu Lys Ile Glu Thr Gly Val Met Thr Glu Leu Phe Glu Gly
                195                 200                 205

Gly Ile Gln Arg Met Arg Met Thr Tyr Tyr Pro Pro Cys Pro Gln Pro
        210                 215                 220

Lys His Val Ile Gly Leu Thr Pro His Ser Asp Pro Asp Ala Leu Thr
225                 230                 235                 240

Ile Leu Leu Gln Leu Asn Glu Val Asp Gly Leu Gln Ile Arg Lys Glu
                245                 250                 255

Lys Ile Trp Val Pro Ile Lys Pro Leu Ser Asn Ala Phe Val Val Asn
                260                 265                 270

Ile Gly Asp Ile Leu Glu Ile Met Ser Asn Gly Ile Tyr Arg Ser Val
        275                 280                 285

Glu His Arg Ala Thr Val Asn Ser Thr Lys Glu Arg Leu Ser Val Ala
        290                 295                 300

Thr Phe His Ser Pro Arg Lys Asp Thr Glu Ile Gly Pro Ile Leu Ile
305                 310                 315                 320

Thr Pro Glu Thr Pro Ala Leu Phe Arg Thr Ser Gly Phe Glu Asp Tyr
                325                 330                 335

Phe Arg Lys Phe Phe Ala His Lys Leu Asn Gly Lys Ser Phe Leu Ser
                340                 345                 350

Ser Ile Arg Ile Gly Thr Asp Glu Gly Asn Asn Ala Thr
            355                 360                 365

<210> SEQ ID NO 24
<211> LENGTH: 379
<212> TYPE: PRT
<213> ORGANISM: Papaver bracteatum

<400> SEQUENCE: 24

Met Glu Ala Pro Lys Leu Ile Met Leu Gly Gly Ser Leu Phe Val Pro
1               5                   10                  15

Ser Val Gln Glu Leu Ala Lys Gln Ser Leu Ala Glu Val Pro Val Arg
            20                  25                  30

Tyr Val Arg Asp Asp Gln Asp Thr Leu Gly Asn Asn Ile Asn Ile Thr

```
                    35                  40                  45
Pro Met Ser Met Ile Asp Gln Ser Ile Pro Val Ile Asp Leu Glu Lys
 50                  55                  60

Leu Leu Ser Pro Glu Pro Ile Val Gly Glu Leu Glu Leu Glu Arg Leu
 65                  70                  75                  80

His Ser Ala Cys Lys Glu Trp Gly Phe Phe Gln Val Val Asn His Gly
                 85                  90                  95

Val Asp Ser Leu Leu Val Glu Lys Val Lys Ser Glu Ile Glu Gly Phe
            100                 105                 110

Phe Lys Leu Pro Met Asp Glu Lys Thr Lys Phe Trp Gln Glu Glu Gly
        115                 120                 125

Asp Ile Glu Gly Phe Gly Gln Val Phe Val His Ser Gln Asp Gln Lys
    130                 135                 140

Leu Asp Trp Gly Asp Met Phe Leu Met Gln Thr Leu Pro Arg His Thr
145                 150                 155                 160

Arg Lys Pro Arg Leu Phe Pro Asn Leu Pro Leu Pro Leu Arg Gln Thr
                165                 170                 175

Ile Glu Ser Tyr Ser Ser Glu Leu Ser Lys Leu Val Leu Thr Leu Val
            180                 185                 190

Asp Leu Met Gly Lys Ala Leu Gln Met Glu Ser Gly Val Leu Thr Glu
        195                 200                 205

Leu Phe Glu Asn Gly Ile Gln Arg Met Arg Met Asn Tyr Tyr Pro Pro
    210                 215                 220

Cys Pro Gln Pro Glu Gln Val Ile Gly Leu Thr Pro His Ser Asp Val
225                 230                 235                 240

Gly Gly Leu Thr Ile Leu Leu Gln Leu Asn Glu Val Asp Gly Leu Gln
                245                 250                 255

Ile Lys Lys Asp Lys Val Trp Val Pro Ile Lys Pro Leu Ala Asn Ala
            260                 265                 270

Phe Val Val Asn Val Gly Asp Ala Leu Glu Ile Met Ser Asn Gly Ile
        275                 280                 285

Tyr Arg Ser Val Glu His Arg Ala Thr Ile Asn Ser Thr Lys Glu Arg
    290                 295                 300

Leu Ser Ile Ala Thr Phe His Asn Pro Arg Ala Asp Arg Glu Ile Gly
305                 310                 315                 320

Pro Ile Pro Ser Met Ile Ser Pro Glu Thr Pro Ala Leu Phe Lys Thr
                325                 330                 335

Thr Gly Tyr Glu Glu Tyr Phe Lys Lys Phe Ser Arg Lys Leu Glu
            340                 345                 350

Gly Lys Ser Phe Leu Asp Ser Leu Arg Ile Arg Glu Gly Asp Glu His
        355                 360                 365

Cys Gly Arg Leu Asp Val Lys Gly Pro Cys Asn
    370                 375

<210> SEQ ID NO 25
<211> LENGTH: 365
<212> TYPE: PRT
<213> ORGANISM: Papaver bracteatum

<400> SEQUENCE: 25

Met Glu Ile Pro Asn Pro Ile Lys Ile Gly Ser Ser Leu Leu Val Pro
  1               5                  10                  15

Ser Val Gln Glu Leu Ala Lys Gln Ser Phe Ala Glu Val Pro Ala Arg
             20                  25                  30
```

```
Tyr Ile Arg Asn Asp Val Asp Pro Leu Ile Thr Lys Leu Ser Asp Val
             35                  40                  45

Ser Leu Ile Asp Gln Thr Val Pro Val Ile Asp Leu Gln Lys Leu Leu
 50                  55                  60

Ser Pro Glu Pro Ile Val Gly Glu Leu Glu Leu Glu Arg Leu His Ser
65                   70                  75                  80

Ala Cys Lys Glu Trp Gly Phe Phe Gln Val Val Asn His Gly Val Asp
                 85                  90                  95

Asn Leu Leu Val Glu Lys Val Lys Ser Glu Ile Gln Gly Phe Phe Asn
            100                 105                 110

Leu Pro Met Glu Glu Lys Lys Phe Trp Gln Glu Gly Asp Phe
            115                 120                 125

Glu Gly Phe Gly Gln Met Phe Val Gln Ser Glu Gln Lys Leu Asp
            130                 135                 140

Trp Gly Asp Met Phe Phe Ile Leu Thr Gln Pro Gln His Met Arg Lys
145                 150                 155                 160

Pro Arg Leu Phe Ser Lys Leu Pro Leu Pro Leu Arg Glu Thr Ile Glu
                165                 170                 175

Ser Tyr Ser Leu Glu Leu Ile Lys Leu Gly Leu Thr Ile Ile Lys Leu
                180                 185                 190

Met Glu Lys Ala Leu Gln Ile Asp Ala Gly Val Met Ala Glu Leu Phe
            195                 200                 205

Glu Asp Gly Ile His Thr Met Arg Met Asn Tyr Tyr Pro Pro Cys Pro
            210                 215                 220

Gln Pro Glu His Val Ile Gly Leu Thr Pro His Ser Asp Gly Gly Gly
225                 230                 235                 240

Leu Thr Ile Leu Leu Gln Leu Asn Glu Val Asp Gly Leu Gln Ile Arg
                245                 250                 255

Arg Glu Asn Ile Trp Val Pro Ile Lys Pro Leu Pro Asn Ala Phe Val
                260                 265                 270

Val Asn Ile Gly Asp Ile Leu Glu Ile Leu Ser Asn Gly Ile Tyr Arg
            275                 280                 285

Ser Val Glu His Arg Ser Thr Val Asn Ala Thr Lys Glu Arg Leu Ser
290                 295                 300

Val Ala Thr Phe Gln Asn Pro Lys Gln Glu Ser Val Ile Gly Pro Asn
305                 310                 315                 320

Met Ile Thr Pro Glu Arg Pro Ala Leu Phe Arg Lys Ile Val Tyr Lys
                325                 330                 335

Asp Tyr Met Lys Lys Leu Phe Ser Arg Lys Leu Asp Gly Lys Ser Phe
            340                 345                 350

Leu Asp Ser Leu Arg Ile Gly Glu Gly Asp Glu Arg Pro
            355                 360                 365

<210> SEQ ID NO 26
<211> LENGTH: 349
<212> TYPE: PRT
<213> ORGANISM: Papaver bracteatum

<400> SEQUENCE: 26

Met Glu Thr Leu Lys Thr Val Pro Gly Gly Ser Leu Phe Ile Pro
1               5                  10                  15

Asn Gly Gln Glu Leu Ala Lys Gln Ser Leu Glu Glu Val Tyr Val Gly
            20                  25                  30

Asn Asp Gln Asp Thr Met Leu Leu Ile Gly Gln Thr Ile Pro Val Ile
        35                  40                  45
```

```
Asp Leu Gln Lys Leu Leu Ser Pro Glu Pro Ile Thr Gly Asp Met Glu
        50                  55                  60

Leu Asp Lys Leu His Ser Ala Cys Lys Glu Trp Gly Phe Phe Gln Val
 65                  70                  75                  80

Val Asn His Gly Val Asp Ile Leu Leu Val Glu Lys Val Lys Ser Glu
                85                  90                  95

Val His Asp Phe Phe Asn Ile Pro Met Asp Glu Lys Lys Pro Phe Trp
            100                 105                 110

Gln Glu Glu Gly Asp Leu Glu Gly Phe Gly Gln Val Phe Ile Thr Ser
            115                 120                 125

Glu Asp Gln Gln Leu Asp Trp Gly Asp Met Phe Phe Met Val Thr Leu
        130                 135                 140

Pro Lys His Met Arg Lys Pro Arg Leu Phe Leu Lys Leu Pro Leu Pro
145                 150                 155                 160

Leu Arg Glu Thr Ile Glu Ser Tyr Ser Leu Lys Leu Ser Lys Leu Gly
                165                 170                 175

Val Thr Leu Val Glu Leu Met Gly Lys Ala Leu Gln Met Glu Asp Arg
            180                 185                 190

Ile Met Ser Glu Leu Phe Asp Asp Gly Arg Gln Thr Met Arg Met Asn
        195                 200                 205

Tyr Tyr Pro Pro Cys Pro Gln Pro Glu Gln Val Ile Gly Leu Thr Pro
        210                 215                 220

His Ser Asp Pro Gly Gly Leu Thr Ile Leu Leu Glu Leu Asn Glu Val
225                 230                 235                 240

Asn Gly Leu Ile Arg Lys Glu Asn Ile Trp Val Pro Ile Ile Pro Leu
                245                 250                 255

Pro Asn Ala Phe Ile Val Asn Ile Gly Asp Ile Leu Gln Ile Met Ser
            260                 265                 270

Asn Gly Ile Tyr His Ser Val Glu His Arg Ala Thr Ile Asn Ser Thr
        275                 280                 285

Lys Glu Arg Leu Ser Val Ala Met Phe Asn Ser Pro Lys Val Asp Thr
        290                 295                 300

Glu Ile Gly Pro Ile His Ser Met Ile Thr Pro Glu Thr Pro Ala Leu
305                 310                 315                 320

Phe Arg Thr Ile Gly Tyr Asp Glu Tyr Leu Lys Ile Phe Phe Ser Arg
                325                 330                 335

Lys Leu Asp Gly Lys Ser Leu Leu Glu Ser Met Lys Ile
            340                 345

<210> SEQ ID NO 27
<211> LENGTH: 379
<212> TYPE: PRT
<213> ORGANISM: Papaver bracteatum
<220> FEATURE:
<221> NAME/KEY: MOD_RES
<222> LOCATION: (373)..(373)
<223> OTHER INFORMATION: Any amino acid
<220> FEATURE:
<221> NAME/KEY: MOD_RES
<222> LOCATION: (377)..(377)
<223> OTHER INFORMATION: Any amino acid

<400> SEQUENCE: 27

Met Glu Ala Pro Lys Leu Ile Met Leu Gly Gly Ser Leu Phe Val Pro
1                5                  10                  15

Ser Val Gln Glu Leu Ala Lys Gln Ser Leu Ala Glu Val Pro Val Arg
                20                  25                  30
```

```
Tyr Val Arg Asp Asp Gln Asp Thr Leu Gly Asn Asn Ile Asn Ile Thr
             35                  40                  45

Pro Met Ser Met Ile Asp Gln Ser Ile Pro Val Ile Asp Leu Glu Lys
 50                  55                  60

Leu Leu Ser Pro Glu Pro Ile Val Gly Glu Leu Glu Leu Glu Arg Leu
 65                  70                  75                  80

His Ser Ala Cys Lys Glu Trp Gly Phe Phe Gln Val Val Asn His Gly
             85                  90                  95

Val Asp Ser Leu Leu Val Glu Lys Val Lys Ser Glu Ile Glu Gly Phe
            100                 105                 110

Phe Glu Leu Pro Val Asp Glu Lys Lys Phe Trp Gln Glu Glu Gly
            115                 120                 125

Asp Ile Glu Gly Phe Gly Gln Ile Phe Val His Ser Glu Asp Gln Lys
            130                 135                 140

Leu Asp Trp Ala Asp Met Phe Tyr Met Leu Thr Leu Pro Pro Asn Met
145                 150                 155                 160

Arg Lys Pro Arg Leu Phe Pro Asn Leu Pro Leu Pro Leu Arg Gln Thr
                    165                 170                 175

Ile Asp Ser Tyr Ser Ser Glu Leu Ser Lys Leu Val Leu Thr Leu Val
            180                 185                 190

Asp Leu Met Gly Lys Ala Leu Gln Met Glu Ser Gly Val Leu Thr Glu
            195                 200                 205

Leu Phe Glu Asn Gly Ile Gln Arg Met Arg Met Asn Tyr Tyr Pro Pro
210                 215                 220

Cys Pro Gln Pro Glu Gln Val Ile Gly Leu Thr Pro His Ser Asp Val
225                 230                 235                 240

Gly Gly Leu Thr Ile Leu Leu Gln Leu Asn Glu Val Asp Gly Leu Gln
                    245                 250                 255

Ile Lys Lys Asp Lys Ile Trp Val Pro Ile Lys Pro Leu Arg Asn Ala
            260                 265                 270

Phe Val Val Asn Val Gly Asp Ala Leu Glu Ile Met Ser Asn Gly Ile
            275                 280                 285

Tyr Arg Ser Val Glu His Arg Ala Thr Ile Asn Ser Thr Lys Glu Arg
            290                 295                 300

Leu Ser Ile Ala Thr Phe His Asn Pro Arg Ala Asp Arg Glu Ile Gly
305                 310                 315                 320

Pro Ile Pro Ser Met Ile Ser Pro Glu Thr Pro Ala Leu Phe Lys Thr
                    325                 330                 335

Thr Gly Tyr Glu Glu Tyr Phe Lys Lys Phe Phe Ser Arg Lys Leu Glu
            340                 345                 350

Gly Lys Ser Phe Leu Asp Ser Leu Arg Ile Gly Glu Gly Asp Glu His
            355                 360                 365

Cys Gly Arg Leu Xaa Val Lys Gly Xaa Cys Asn
370                 375

<210> SEQ ID NO 28
<211> LENGTH: 362
<212> TYPE: PRT
<213> ORGANISM: Papaver bracteatum

<400> SEQUENCE: 28

Met Glu Thr Pro Lys Leu Met Lys Leu Gly Gly Ser Leu Phe Val Pro
 1                   5                  10                  15

Ser Val Gln Glu Leu Ala Lys Gln Ser Leu Ala Glu Val Pro Ala Arg
```

```
            20                  25                  30
Tyr Val Arg Asp Asp Arg Asp Met Val Gly Asn Ile Ile Asn Val Thr
            35                  40                  45

Pro Met Ser Met Ile Asp Gln Ser Ile Pro Val Ile Asp Leu Glu Lys
 50                  55                  60

Leu Leu Ser Pro Asp Leu Ile Val Gly Glu Leu Glu Leu Glu Arg Leu
 65                  70                  75                  80

His Ser Ala Cys Lys Glu Trp Gly Phe Phe Gln Val Val Asn His Gly
                 85                  90                  95

Val Asp Ser Leu Leu Val Glu Lys Val Lys Ser Glu Ile Glu Gly Phe
                100                 105                 110

Phe Glu Leu Pro Met Asp Glu Lys Lys Phe Trp Gln Glu Glu Gly
             115                 120                 125

Asp Ala Glu Gly Phe Ala Gln Phe Phe Val Gln Ser Glu Asp Gln Lys
             130                 135                 140

Leu Asp Tyr Ser Gly Asp Met Phe Phe Met Leu Asn Leu Pro Gln His
145                 150                 155                 160

Met Arg Lys Pro Arg Leu Phe Leu Lys Leu Pro Leu Pro Leu Arg Glu
                165                 170                 175

Thr Ile Glu Ser Tyr Ser Leu Lys Leu Ser Lys Leu Gly Val Thr Leu
                180                 185                 190

Val Glu Leu Met Gly Lys Ala Leu Gln Met Glu Asp Arg Ile Met Ser
            195                 200                 205

Glu Leu Phe Asp Asp Gly Arg Gln Thr Met Arg Met Asn Tyr Tyr Pro
210                 215                 220

Pro Cys Pro Gln Pro Glu Gln Val Ile Gly Leu Thr Pro His Ser Asp
225                 230                 235                 240

Pro Gly Gly Leu Thr Ile Leu Leu Glu Leu Asn Glu Val Asn Gly Leu
                245                 250                 255

Ile Arg Lys Glu Asn Ile Trp Val Pro Ile Ile Pro Leu Pro Asn Ala
                260                 265                 270

Phe Ile Val Asn Ile Gly Asp Ile Leu Glu Ile Met Ser Asn Gly Ile
            275                 280                 285

Tyr His Ser Val Glu His Arg Ala Thr Ile Asn Ser Thr Lys Glu Arg
            290                 295                 300

Leu Ser Val Ala Met Phe Asn Ser Pro Lys Val Asp Thr Glu Ile Gly
305                 310                 315                 320

Pro Ile His Ser Met Ile Thr Pro Glu Thr Pro Ala Leu Phe Arg Thr
                325                 330                 335

Ile Gly Tyr Asp Glu Tyr Leu Lys Ile Phe Phe Ser Arg Lys Leu Asp
                340                 345                 350

Gly Lys Ser Leu Leu Glu Ser Met Lys Ile
            355                 360

<210> SEQ ID NO 29
<211> LENGTH: 365
<212> TYPE: PRT
<213> ORGANISM: Papaver bracteatum

<400> SEQUENCE: 29

Met Glu Thr Pro Lys Leu Arg Asp Phe Gly Ser Phe Leu Pro Val Pro
 1               5                  10                  15

Ser Val Gln Glu Leu Ala Lys Gln Val Leu Thr Glu Ile Pro Pro Arg
                20                  25                  30
```

Tyr Ile Arg Thr Asp Leu Glu Ala Leu Asn Lys Leu Ser Cys Ala Ser
            35                  40                  45

Asn Thr Asp Gln Thr Val Pro Ile Ile Asp Met Gln Cys Leu Leu Ser
 50                  55                  60

Ala Glu Pro Glu Met Glu Leu Glu Lys Leu His Ser Ala Cys Lys Glu
 65                  70                  75                  80

Trp Gly Phe Phe Arg Val Val Asn His Gly Val Asp Asn Leu Glu Ser
                 85                  90                  95

Val Lys Ser Glu Ile Glu Ser Phe Leu Asn Leu Pro Val Asn Ala Lys
            100                 105                 110

Asn Lys Tyr Gly Gln Lys Gln Gly Asp Asp Gln Gly Phe Gly Ser Arg
            115                 120                 125

Phe Val Leu Ser Glu Glu Gln Lys Leu Asp Trp Gly Asp Phe Phe Tyr
            130                 135                 140

Met Val Thr Arg Pro Leu Tyr Leu Arg Lys Pro His Leu Phe Pro Glu
145                 150                 155                 160

Leu Pro Leu Pro Leu Arg Glu Thr Ile Glu Ser Tyr Ser Ser Glu Val
                165                 170                 175

Ser Lys Leu Ala Met Ala Leu Phe Glu Met Met Gly Lys Ala Leu Lys
            180                 185                 190

Ile Glu Thr Gly Val Met Thr Glu Ile Phe Glu Gly Gly Met Gln Ala
            195                 200                 205

Met Arg Met Asn Tyr Tyr Pro Pro Cys Pro Arg Pro Asp Leu Val Ile
            210                 215                 220

Gly Leu Asn Ala His Ser Asp Phe Gly Gly Leu Thr Ile Leu Leu Gln
225                 230                 235                 240

Leu Asn Glu Val Glu Gly Leu Glu Ile Arg Asn Lys Gly Glu Trp Val
                245                 250                 255

Ser Val Lys Pro Leu Ala Asn Ala Phe Val Asn Val Gly Asp Val
            260                 265                 270

Met Glu Ile Leu Thr Asn Gly Ile Tyr His Ser Val Glu His Arg Ala
            275                 280                 285

Thr Ile Asn Ser Ser Lys Glu Arg Leu Ser Val Ala Thr Phe His Tyr
            290                 295                 300

Pro Lys Leu Glu Thr Gly Ile Gly Pro Leu Pro Cys Met Ile Thr Pro
305                 310                 315                 320

Lys Thr Pro Ala Leu Phe Gly Arg Ile Glu Arg Tyr Glu Leu Leu Leu
                325                 330                 335

Arg Lys Tyr Tyr Ala Arg Lys Leu Asn Gly Lys Ser Thr Leu Asp Cys
            340                 345                 350

Met Arg Ile Gly Asn Gly Phe Glu Asp Asp Asn Thr Ala
            355                 360                 365

<210> SEQ ID NO 30
<211> LENGTH: 370
<212> TYPE: PRT
<213> ORGANISM: Papaver bracteatum

<400> SEQUENCE: 30

Met Glu Ala Pro Lys Leu Ile Met Leu Gly Gly Ser Leu Phe Val Pro
 1               5                  10                  15

Ser Val Gln Glu Leu Ala Lys Gln Ser Leu Ala Glu Val Pro Ala Arg
             20                  25                  30

Tyr Val Arg Asp Asp Gln Asp Thr Leu Gly Asn Asn Ile Asn Ile Thr
             35                  40                  45

```
Pro Met Ser Met Ile Asp Gln Ser Ile Pro Val Ile Asp Leu Glu Lys
    50                  55                  60

Leu Leu Ser Pro Glu Pro Ile Val Gly Glu Leu Glu Leu Glu Arg Leu
 65                  70                  75                  80

His Ser Ala Cys Lys Glu Trp Gly Phe Phe Gln Val Val Asn His Gly
                 85                  90                  95

Val Asp Ser Leu Leu Val Glu Lys Val Lys Ser Glu Ile Glu Gly Phe
            100                 105                 110

Phe Glu Leu Pro Val Asp Glu Lys Lys Phe Trp Gln Glu Glu Gly
            115                 120                 125

Asp Ile Glu Gly Phe Gly Gln Ile Phe Val His Ser Glu Asp Gln Lys
    130                 135                 140

Leu Asp Trp Ala Asp Met Phe Tyr Met Leu Thr Leu Pro Pro Asn Met
145                 150                 155                 160

Arg Lys Pro Arg Leu Phe Pro Asn Leu Pro Leu Pro Leu Arg Gln Thr
                165                 170                 175

Ile Asp Ser Tyr Ser Ser Glu Leu Ser Lys Leu Val Leu Thr Leu Val
                180                 185                 190

Asp Leu Met Gly Lys Ala Leu Gln Met Glu Ser Gly Val Leu Thr Glu
    195                 200                 205

Leu Phe Glu Asn Gly Ile Gln Arg Met Arg Met Asn Tyr Tyr Pro Pro
    210                 215                 220

Cys Pro Gln Pro Glu Gln Val Ile Gly Leu Thr Pro His Ser Glu Val
225                 230                 235                 240

Gly Gly Leu Thr Ile Leu Leu Gln Leu Asn Glu Val Asp Gly Leu Gln
                245                 250                 255

Ile Arg Lys Glu Lys Ile Trp Val Pro Ile Lys Pro Leu Ser Asn Ala
                260                 265                 270

Phe Ile Val Asn Ile Gly Asp Ile Leu Glu Ile Met Ser Asn Gly Ile
            275                 280                 285

Tyr Arg Ser Val Glu His Arg Ala Thr Val Asn Ser Thr Lys Glu Arg
    290                 295                 300

Leu Ser Val Ala Thr Phe His Ser Pro Arg Lys Asp Thr Glu Ile Gly
305                 310                 315                 320

Pro Ile Leu Ile Thr Pro Glu Thr Pro Ala Leu Phe Arg Thr Ser Gly
                325                 330                 335

Phe Glu Asp Tyr Phe Arg Lys Phe Phe Ala His Lys Leu Asn Gly Lys
            340                 345                 350

Ser Phe Leu Ser Ser Ile Arg Ile Gly Glu Thr Asp Glu Gly Asn Asn
            355                 360                 365

Ala Thr
    370

<210> SEQ ID NO 31
<211> LENGTH: 313
<212> TYPE: PRT
<213> ORGANISM: Papaver bracteatum

<400> SEQUENCE: 31

Met Ser Met Ile Asp Gln Ser Ile Pro Val Ile Asp Leu Glu Lys Leu
  1               5                  10                  15

Leu Ser Pro Glu Pro Ile Val Gly Glu Leu Glu Leu Glu Arg Leu His
             20                  25                  30

Ser Ala Cys Lys Glu Trp Gly Phe Phe Gln Val Val Asn His Gly Val
```

```
        35                  40                  45
Asp Ser Leu Leu Val Glu Lys Val Lys Ser Glu Ile Glu Gly Phe Phe
 50                  55                  60
Glu Leu Pro Val Asp Glu Lys Lys Phe Trp Gln Glu Gly Asp
 65                  70                  75                  80
Ile Glu Gly Phe Gly Gln Ile Phe Val His Ser Glu Asp Gln Lys Leu
                     85                  90                  95
Asp Trp Ala Asp Met Phe Tyr Met Leu Thr Leu Pro Pro Asn Met Arg
                100                 105                 110
Lys Pro Arg Leu Phe Pro Asn Leu Pro Leu Pro Leu Arg Gln Thr Ile
                115                 120                 125
Asp Ser Tyr Ser Ser Glu Leu Ser Lys Leu Val Leu Thr Leu Val Asp
130                 135                 140
Leu Met Gly Lys Ala Leu Gln Met Glu Ser Gly Val Leu Thr Glu Leu
145                 150                 155                 160
Phe Glu Asn Gly Ile Gln Arg Met Arg Met Asn Tyr Tyr Pro Pro Cys
                    165                 170                 175
Pro Gln Pro Glu Gln Val Ile Gly Leu Thr Pro His Ser Asp Val Gly
                180                 185                 190
Gly Leu Thr Ile Leu Leu Gln Leu Asn Glu Val Asp Gly Leu Gln Ile
                195                 200                 205
Arg Lys Glu Lys Ile Trp Val Pro Ile Lys Pro Leu Ser Asn Ala Phe
210                 215                 220
Ile Val Asn Ile Gly Asp Ile Leu Glu Ile Met Ser Asn Gly Ile Tyr
225                 230                 235                 240
His Ser Val Glu His Arg Ala Thr Ile Asn Ser Thr Lys Glu Arg Leu
                    245                 250                 255
Ser Val Ala Met Phe Asn Ser Pro Lys Val Asp Thr Glu Ile Gly Pro
                260                 265                 270
Ile His Ser Met Ile Thr Pro Glu Thr Pro Ala Leu Phe Arg Thr Ile
                275                 280                 285
Gly Tyr Asp Glu Tyr Leu Lys Ile Phe Phe Ser Arg Lys Leu Asp Gly
                290                 295                 300
Lys Ser Leu Leu Glu Ser Met Lys Ile
305                 310
```

<210> SEQ ID NO 32
<211> LENGTH: 365
<212> TYPE: PRT
<213> ORGANISM: Papaver bracteatum

<400> SEQUENCE: 32

```
Met Glu Thr Pro Lys Leu Val Lys Ser Ser Gly Ser Ser Leu Phe Leu
 1               5                  10                  15
Ser Thr Ser Val Gln Glu Leu Ala Lys Gln Ser Leu Pro Glu Val Pro
                20                  25                  30
Ala Arg Tyr Ile Arg Thr Asn Leu Glu Pro Leu Ser Asn Val Ser Gly
                35                  40                  45
Asp Ser Gln Ser Val Pro Val Ile Asp Leu Gln Lys Leu Leu Ser Ser
 50                  55                  60
Glu Pro Ile Ile Gly Glu Leu Glu Leu Asp Lys Leu His Ser Ala Cys
 65                  70                  75                  80
Lys Glu Trp Gly Phe Phe Gln Val Val Asn His Gly Val Asp Asn Leu
                    85                  90                  95
```

```
Val Met Glu Lys Ile Lys Thr Glu Ile Gln Gly Phe Phe Asn Leu Ser
            100                 105                 110

Leu Asp Glu Lys Gln Lys Phe Trp Lys Lys Glu Gly Asp Ala Glu Gly
            115                 120                 125

Phe Gly Gln Asn Phe Ile Glu Ser Glu Asp Gln Lys Leu Asp Trp Gly
            130                 135                 140

Asp Thr Phe Gly Met Phe Thr Leu Pro Ile His Met Arg Asn Pro Arg
145                 150                 155                 160

Leu Phe Pro Glu Leu Pro Leu Pro Leu Arg Glu Thr Ile Glu Ser Tyr
                165                 170                 175

Ser Leu Asp Val Arg Lys Leu Ala Leu Ala Leu Ile Gly Leu Met Glu
            180                 185                 190

Lys Ala Leu Lys Ile Lys Thr Ser Ala Met Ser Glu Leu Phe Glu Asp
            195                 200                 205

Gly Gly Gln Ala Met Arg Met Asn Tyr Tyr Pro Pro Cys Pro Gln Pro
            210                 215                 220

Glu His Val Ile Gly Leu Thr Pro His Ser Asp Ala Gly Gly Leu Thr
225                 230                 235                 240

Ile Leu Leu Gln Leu Asn Glu Val Asp Gly Leu Gln Ile Lys Lys Asp
                245                 250                 255

Lys Ile Trp Val Pro Ile Lys Pro Leu Pro Asn Ala Phe Val Val Asn
            260                 265                 270

Ile Gly Asp Ile Leu Glu Ile Met Thr Asn Gly Ile Tyr Arg Ser Val
            275                 280                 285

Glu His Arg Ala Thr Ile Asn Ser Ser Lys Glu Arg Leu Ser Val Ala
            290                 295                 300

Ala Phe His Ser Pro Lys Gly Asp Thr Leu Ile Gly Pro Met Val Ser
305                 310                 315                 320

Leu Ile Thr Pro Glu Thr Pro Ala Leu Phe Arg Thr Ile Gly Tyr Gln
                325                 330                 335

Asp Tyr Met Lys Lys Phe Met Ser Arg Lys Leu Asp Gly Lys Ser Leu
            340                 345                 350

Val Asn Ser Met Arg Ile Gly Glu Gly Asp Glu Asp Lys
            355                 360                 365

<210> SEQ ID NO 33
<211> LENGTH: 356
<212> TYPE: PRT
<213> ORGANISM: Papaver bracteatum

<400> SEQUENCE: 33

Met Glu Thr Pro Thr Leu Met Lys Leu Gly Asn Gly Leu Ser Val Pro
1               5                   10                  15

Ser Val Gln Glu Leu Ala Lys Ala Thr Leu Ala Glu Ile Pro Ser Arg
            20                  25                  30

Tyr Ile Cys Thr Asp Glu Asn Leu Leu Thr Met Gly Ala Ser Thr Thr
            35                  40                  45

Asp Asn Glu Thr Val Pro Val Ile Asp Leu Gln Asn Leu Leu Ser Pro
50                  55                  60

Glu Pro Val Ile Gly Met Leu Glu Leu Asp Arg Leu His Ser Ala Cys
65                  70                  75                  80

Lys Glu Trp Gly Phe Phe Gln Leu Val Asn His Gly Val Asp Ala Leu
                85                  90                  95

Leu Val Asp Asn Glu Val Gln Gly Phe Phe Asn Leu Pro Met Asp Glu
            100                 105                 110
```

Lys Thr Lys Tyr Gly Gln Lys Asp Gly Asp Glu Gly Phe Gly Gln
            115                 120                 125

Phe Phe Val Ile Ser Glu Asp Gln Lys Leu Asp Trp Ala Asp Val Phe
130                 135                 140

Tyr Met Ser Thr Leu Pro Leu His Ser Arg Lys Pro His Leu Phe Pro
145                 150                 155                 160

Glu Leu Pro Leu Pro Leu Arg Glu Thr Met Glu Ser Tyr Ser Ser Glu
                165                 170                 175

Met Lys Lys Leu Ser Met Val Leu Phe Asp Met Met Gly Lys Ala Leu
            180                 185                 190

Gln Val Val Glu Ile Lys Gly Ile Thr Glu Leu Phe Glu Asp Gly Ala
            195                 200                 205

Gln Gln Ile Arg Met Asn Tyr Tyr Pro Pro Cys Pro Gln Pro Glu Leu
            210                 215                 220

Val Phe Gly Leu Thr Ser His Ser Asp Phe Asp Gly Leu Thr Ile Leu
225                 230                 235                 240

Leu Gln Leu Gly Glu Val Gly Leu Gln Ile Lys Lys Glu Glu Arg
                245                 250                 255

Trp Ile Ser Ile Lys Pro Leu Pro Asp Ala Phe Ile Val Asn Val Gly
            260                 265                 270

Asp Ile Leu Glu Ile Met Thr Asn Gly Ile Tyr Arg Ser Val Asp His
            275                 280                 285

Arg Ala Val Val Asn Ser Ile Lys Glu Arg Leu Thr Ile Ala Thr Phe
290                 295                 300

His Asp Pro Arg Leu Glu Ala Glu Ile Gly Pro Ile Ser Ser Leu Ile
305                 310                 315                 320

Thr Pro Glu Thr Pro Ala Leu Phe Lys Arg Gly Val Phe Glu Asp Leu
                325                 330                 335

Leu Lys Glu Met Phe Leu Arg Lys Leu Asp Gly Lys Ser Phe Leu Asp
            340                 345                 350

Cys Met Arg Met
            355

<210> SEQ ID NO 34
<211> LENGTH: 350
<212> TYPE: PRT
<213> ORGANISM: Papaver rhoeas

<400> SEQUENCE: 34

Gly Asn Gly Leu Ser Val Pro Ser Val Gln Glu Leu Ala Lys Gln Thr
1               5                   10                  15

Leu Ala Glu Ile Pro Ser Arg Tyr Ile Cys Thr Asp Glu Asn Pro Leu
            20                  25                  30

Ile Thr Gly Ala Ser Val Val Asp Asp Glu Thr Val Pro Val Ile Asn
            35                  40                  45

Leu Gln Asn Leu Leu Ser Pro Glu Pro Val Ile Gly Lys Leu Glu Leu
        50                  55                  60

Asp Lys Leu His Ser Ala Cys Lys Glu Trp Gly Phe Phe Gln Val Val
65                  70                  75                  80

Asn His Gly Val Asn Asp Ser Leu Val Asp Ser Val Lys Ser Glu Ile
                85                  90                  95

Glu Gly Phe Phe Asn Leu Pro Ala Asn Glu Lys Leu Lys Tyr Gly Gln
            100                 105                 110

Lys Asp Gly Asp Val Glu Gly Phe Gly Gln His Phe Val Val Ser Glu

```
                115                 120                 125
Asp Gln Lys Leu Asp Trp Ala Asp Val Phe Tyr Met Val Thr Leu Pro
    130                 135                 140

Val Arg Leu Arg Lys Pro His Leu Phe Pro Glu Leu Pro Leu Pro Leu
145                 150                 155                 160

Arg Asp Thr Leu Asp Ser Tyr Ser Ser Glu Leu Asn Lys Leu Ser Met
                165                 170                 175

Val Leu Leu Glu Met Met Glu Lys Ala Leu Lys Leu Val Glu Cys Lys
            180                 185                 190

Gly Ile Thr Asp Phe Phe Glu Asp Gly Phe Gln Gln Met Arg Met Asn
        195                 200                 205

Tyr Tyr Pro Pro Cys Pro Arg Pro Glu Leu Val Thr Gly Leu Thr Ser
    210                 215                 220

His Ser Asp Phe Gly Gly Leu Thr Ile Leu Leu Gln Leu Asn Asp Val
225                 230                 235                 240

Glu Gly Leu Gln Ile Lys Lys Glu Arg Trp Ile Ser Ile Lys Pro
                245                 250                 255

Leu Pro Asn Ala Phe Ile Val Asn Ile Gly Asp Val Leu Glu Ile Met
            260                 265                 270

Ser Asn Gly Ile Tyr Arg Ser Val Asp His Arg Ala Val Ile Asn Ser
        275                 280                 285

Thr Lys Val Arg Met Ser Val Ala Thr Phe His Asp Pro Arg Leu Glu
    290                 295                 300

Ala Val Ile Gly Pro Ile Ser Ser Leu Ile Thr Pro Glu Thr Pro Ala
305                 310                 315                 320

Leu Phe Lys Arg Gly Val Phe Glu Asp Leu Leu Lys Glu Met Phe Leu
                325                 330                 335

Arg Lys Leu Asp Gly Lys Ser Phe Leu Asp Cys Met Arg Ile
            340                 345                 350

<210> SEQ ID NO 35
<211> LENGTH: 351
<212> TYPE: PRT
<213> ORGANISM: Papaver setigerum

<400> SEQUENCE: 35

Leu Met Lys Leu Ala Asn Gly Met Ser Val Pro Ile Val Gln Glu Leu
1               5                   10                  15

Ala Lys Leu Thr Val Gly Glu Ile Pro Ser Arg Tyr Ile Cys Thr Asp
            20                  25                  30

Gly Asn Leu Leu Thr Met Gly Ala Ser Val Ile Asp Tyr Glu Thr Val
        35                  40                  45

Pro Val Ile Asp Leu Gln Asn Leu Gln Ser Arg Glu Pro Val Ile Glu
    50                  55                  60

Lys Leu Glu Leu Asp Arg Leu His Ser Ala Cys Lys Glu Trp Gly Phe
65                  70                  75                  80

Phe Gln Leu Leu Asn His Gly Val Asp Ala Ser Leu Met Asp Asn Val
                85                  90                  95

Arg Ser Glu Ile Arg Gly Phe Phe Asn Leu Pro Ile Ser Asp Lys Met
            100                 105                 110

Lys Tyr Gly Gln Lys Asp Gly Asp Glu Glu Gly Phe Gly Gln His Phe
        115                 120                 125

Ile Val Ser Glu Asp Gln Lys Leu Asp Trp Val Asp Ala Phe Met Met
    130                 135                 140
```

```
Phe Thr Leu Pro Leu His Ser Arg Asn Pro Arg Leu Thr Pro Glu Phe
145                 150                 155                 160

Pro Gln Pro Leu Arg Glu Thr Val Glu Ser Tyr Ser Ser Glu Met Lys
            165                 170                 175

Lys Leu Ser Val Leu Leu Phe Glu Leu Met Glu Lys Ala Leu Gln Val
            180                 185                 190

Lys Gly Ile Thr Glu Met Phe Glu Asp Gly Leu Gln Ser Ile Arg Met
            195                 200                 205

Asn Tyr Tyr Pro Pro Cys Pro Arg Pro Glu Leu Ala Ile Gly Leu Thr
210                 215                 220

Ser His Ser Asp Phe Asp Gly Leu Thr Ile Leu Leu Gln Leu Asn Glu
225                 230                 235                 240

Val Glu Gly Leu Gln Ile Lys Lys Glu Glu Arg Trp Ile Ser Ile Lys
            245                 250                 255

Pro Leu Pro Asn Ala Phe Ile Val Asn Val Gly Asp Val Leu Glu Val
            260                 265                 270

Met Thr Asn Gly Ile Tyr Arg Ser Val Asp His Arg Ala Val Val Asn
            275                 280                 285

Ser Thr Lys Glu Arg Leu Ser Ile Ala Thr Phe His Asp Pro Glu Leu
290                 295                 300

Glu Ser Glu Ile Gly Pro Ile Ala Ser Leu Ile Thr Pro Glu Thr Pro
305                 310                 315                 320

Ala Leu Phe Lys Arg Gly Arg Phe Lys Asp Leu Leu Lys Glu Asn Leu
            325                 330                 335

Ser Thr Lys Leu Asp Gly Lys Ser Phe Leu Asp Cys Ile Arg Met
            340                 345                 350

<210> SEQ ID NO 36
<211> LENGTH: 497
<212> TYPE: PRT
<213> ORGANISM: Homo sapiens

<400> SEQUENCE: 36

Met Gly Leu Glu Ala Leu Val Pro Leu Ala Val Ile Val Ala Ile Phe
1               5                   10                  15

Leu Leu Leu Val Asp Leu Met His Arg Arg Gln Arg Trp Ala Ala Arg
                20                  25                  30

Tyr Ser Pro Gly Pro Leu Pro Leu Pro Gly Leu Gly Asn Leu Leu His
            35                  40                  45

Val Asp Phe Gln Asn Thr Pro Tyr Cys Phe Asp Gln Leu Arg Arg Arg
50                  55                  60

Phe Gly Asp Val Phe Ser Leu Gln Leu Ala Trp Thr Pro Val Val Val
65                  70                  75                  80

Leu Asn Gly Leu Ala Ala Val Arg Glu Ala Leu Val Thr His Gly Glu
            85                  90                  95

Asp Thr Ala Asp Arg Pro Pro Val Pro Ile Thr Gln Ile Leu Gly Phe
            100                 105                 110

Gly Pro Arg Ser Gln Gly Val Phe Leu Ala Arg Tyr Gly Pro Ala Trp
        115                 120                 125

Arg Glu Gln Arg Arg Phe Ser Val Ser Thr Leu Arg Asn Leu Gly Leu
130                 135                 140

Gly Lys Lys Ser Leu Glu Gln Trp Val Thr Glu Glu Ala Ala Cys Leu
145                 150                 155                 160

Cys Ala Ala Phe Ala Asn His Ser Gly Arg Pro Phe Arg Pro Asn Gly
                165                 170                 175
```

```
Leu Leu Asp Lys Ala Val Ser Asn Val Ile Ala Ser Leu Thr Cys Gly
            180                 185                 190

Arg Arg Phe Glu Tyr Asp Asp Pro Arg Phe Leu Arg Leu Leu Asp Leu
        195                 200                 205

Ala Gln Glu Gly Leu Lys Glu Glu Ser Gly Phe Leu Arg Glu Val Leu
    210                 215                 220

Asn Ala Val Pro Val Leu Leu His Ile Pro Ala Leu Ala Gly Lys Val
225                 230                 235                 240

Leu Arg Phe Gln Lys Ala Phe Leu Thr Gln Leu Asp Glu Leu Leu Thr
                245                 250                 255

Glu His Arg Met Thr Trp Asp Pro Ala Gln Pro Pro Arg Asp Leu Thr
            260                 265                 270

Glu Ala Phe Leu Ala Glu Met Glu Lys Ala Lys Gly Asn Pro Glu Ser
        275                 280                 285

Ser Phe Asn Asp Glu Asn Leu Arg Ile Val Val Ala Asp Leu Phe Ser
    290                 295                 300

Ala Gly Met Val Thr Thr Ser Thr Thr Leu Ala Trp Gly Leu Leu Leu
305                 310                 315                 320

Met Ile Leu His Pro Asp Val Gln Arg Val Gln Gln Glu Ile Asp
                325                 330                 335

Asp Val Ile Gly Gln Val Arg Arg Pro Glu Met Gly Asp Gln Ala His
            340                 345                 350

Met Pro Tyr Thr Thr Ala Val Ile His Glu Val Gln Arg Phe Gly Asp
        355                 360                 365

Ile Val Pro Leu Gly Val Thr His Met Thr Ser Arg Asp Ile Glu Val
    370                 375                 380

Gln Gly Phe Arg Ile Pro Lys Gly Thr Thr Leu Ile Thr Asn Leu Ser
385                 390                 395                 400

Ser Val Leu Lys Asp Glu Ala Val Trp Glu Lys Pro Phe Arg Phe His
                405                 410                 415

Pro Glu His Phe Leu Asp Ala Gln Gly His Phe Val Lys Pro Glu Ala
            420                 425                 430

Phe Leu Pro Phe Ser Ala Gly Arg Arg Ala Cys Leu Gly Glu Pro Leu
        435                 440                 445

Ala Arg Met Glu Leu Phe Leu Phe Phe Thr Ser Leu Leu Gln His Phe
    450                 455                 460

Ser Phe Ser Val Pro Thr Gly Gln Pro Arg Pro Ser His His Gly Val
465                 470                 475                 480

Phe Ala Phe Leu Val Thr Pro Ser Pro Tyr Glu Leu Cys Ala Val Pro
                485                 490                 495

Arg

<210> SEQ ID NO 37
<211> LENGTH: 1049
<212> TYPE: PRT
<213> ORGANISM: Bacillus megaterium

<400> SEQUENCE: 37

Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Arg
        35                  40                  45
```

```
Val Thr Arg Tyr Leu Ser Ser Gln Arg Leu Ile Lys Glu Ala Cys Asp
 50                  55                  60

Glu Ser Arg Phe Asp Lys Asn Leu Ser Gln Ala Ala Lys Phe Ala Arg
 65                  70                  75                  80

Asp Phe Ala Gly Asp Gly Leu Val Thr Ser Trp Thr His Glu Lys Asn
                 85                  90                  95

Trp Lys Lys Ala His Asn Ile Leu Leu Pro Ser Phe Ser Gln Gln Ala
                100                 105                 110

Met Lys Gly Tyr His Ala Met Met Val Asp Ile Ala Val Gln Leu Val
            115                 120                 125

Gln Lys Trp Glu Arg Leu Asn Ala Asp Glu His Ile Glu Val Ser Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Ile
                165                 170                 175

Ser Met Val Arg Ala Ala Asp Glu Val Met Asn Lys Leu Gln Arg Ala
            180                 185                 190

Asn Pro Asp Asp Pro Ala Tyr Asp Glu Asn Lys Arg Gln Phe Gln Glu
    195                 200                 205

Asp Ile Lys Val Met Asn Asp Leu Val Asp Lys Ile Ile Ala Asp Arg
210                 215                 220

Lys Ala Arg Gly Glu Gln Ser Asp Asp Leu Leu Thr Gln Met Leu Asn
225                 230                 235                 240

Gly Lys Asp Pro Glu Thr Gly Glu Pro Leu Asp Asp Gly Asn Ile Arg
                245                 250                 255

Tyr Gln Ile Ile Thr Phe Leu Ile Ala Gly His Glu Thr Thr Ser Gly
            260                 265                 270

Leu Leu Ser Phe Ala Leu Tyr Phe Leu Val Lys Asn Pro His Val Leu
    275                 280                 285

Gln Lys Val Ala Glu Glu Ala Ala Arg Val Leu Val Asp Pro Val Pro
290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
                325                 330                 335

Lys Glu Asp Thr Val Leu Gly Gly Glu Tyr Pro Leu Glu Lys Gly Asp
            340                 345                 350

Glu Val Met Val Leu Ile Pro Gln Leu His Arg Asp Lys Thr Val Trp
    355                 360                 365

Gly Asp Asp Val Glu Glu Phe Arg Pro Glu Arg Phe Glu Asn Pro Ser
370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
            420                 425                 430

Asp Ile Lys Glu Thr Leu Thr Leu Lys Pro Lys Gly Phe Val Val Lys
    435                 440                 445

Ala Lys Ser Lys Lys Ile Pro Leu Gly Gly Ile Pro Ser Pro Ser Thr
450                 455                 460
```

-continued

```
Glu Gln Ser Ala Lys Lys Val Arg Lys Lys Ala Glu Asn Ala His Asn
465                 470                 475                 480

Thr Pro Leu Leu Val Leu Tyr Gly Ser Asn Met Gly Thr Ala Glu Gly
                485                 490                 495

Thr Ala Arg Asp Leu Ala Asp Ile Ala Met Ser Lys Gly Phe Ala Pro
            500                 505                 510

Gln Val Ala Thr Leu Asp Ser His Ala Gly Asn Leu Pro Arg Glu Gly
        515                 520                 525

Ala Val Leu Ile Val Thr Ala Ser Tyr Asn Gly His Pro Pro Asp Asn
    530                 535                 540

Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
                565                 570                 575

Thr Thr Tyr Gln Lys Val Pro Ala Phe Ile Asp Glu Thr Leu Ala Ala
            580                 585                 590

Lys Gly Ala Glu Asn Ile Ala Asp Arg Gly Glu Ala Asp Ala Ser Asp
        595                 600                 605

Asp Phe Glu Gly Thr Tyr Glu Glu Trp Arg Glu His Met Trp Ser Asp
    610                 615                 620

Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
                645                 650                 655

Ala Lys Met His Gly Ala Phe Ser Thr Asn Val Val Ala Ser Lys Glu
            660                 665                 670

Leu Gln Gln Pro Gly Ser Ala Arg Ser Thr Arg His Leu Glu Ile Glu
        675                 680                 685

Leu Pro Lys Glu Ala Ser Tyr Gln Glu Gly Asp His Leu Gly Val Ile
    690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Lys Leu
                725                 730                 735

Ala His Leu Pro Leu Ala Lys Thr Val Ser Val Glu Glu Leu Leu Gln
            740                 745                 750

Tyr Val Glu Leu Gln Asp Pro Val Thr Arg Thr Gln Leu Arg Ala Met
        755                 760                 765

Ala Ala Lys Thr Val Cys Pro Pro His Lys Val Glu Leu Glu Ala Leu
    770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Lys Phe Ser
                805                 810                 815

Glu Phe Ile Ala Leu Leu Pro Ser Ile Arg Pro Arg Tyr Tyr Ser Ile
            820                 825                 830

Ser Ser Ser Pro Arg Val Asp Glu Lys Gln Ala Ser Ile Thr Val Ser
        835                 840                 845

Val Val Ser Gly Glu Ala Trp Ser Gly Tyr Gly Glu Tyr Lys Gly Ile
    850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
```

```
                   885             890                 895
Thr Pro Leu Ile Met Val Gly Pro Gly Thr Gly Val Ala Pro Phe Arg
                900                 905                 910
Gly Phe Val Gln Ala Arg Lys Gln Leu Lys Glu Gln Gly Gln Ser Leu
                915                 920                 925
Gly Glu Ala His Leu Tyr Phe Gly Cys Arg Ser Pro His Glu Asp Tyr
            930                 935                 940
Leu Tyr Gln Glu Glu Leu Glu Asn Ala Gln Ser Glu Gly Ile Ile Thr
945                 950                 955                 960
Leu His Thr Ala Phe Ser Arg Met Pro Asn Gln Pro Lys Thr Tyr Val
                965                 970                 975
Gln His Val Met Glu Gln Asp Gly Lys Lys Leu Ile Glu Leu Leu Asp
            980                 985                 990
Gln Gly Ala His Phe Tyr Ile Cys Gly Asp Gly Ser Gln Met Ala Pro
            995                 1000                1005
Ala Val Glu Ala Thr Leu Met Lys Ser Tyr Ala Asp Val His Gln
    1010                1015                1020
Val Ser Glu Ala Asp Ala Arg Leu Trp Leu Gln Gln Leu Glu Glu
    1025                1030                1035
Lys Gly Arg Tyr Ala Lys Asp Val Trp Ala Gly
    1040                1045
```

<210> SEQ ID NO 38
<211> LENGTH: 503
<212> TYPE: PRT
<213> ORGANISM: Homo sapiens

<400> SEQUENCE: 38

```
Met Ala Leu Ile Pro Asp Leu Ala Met Glu Thr Trp Leu Leu Leu Ala
1               5                   10                  15
Val Ser Leu Val Leu Leu Tyr Leu Tyr Gly Thr His Ser His Gly Leu
                20                  25                  30
Phe Lys Lys Leu Gly Ile Pro Gly Pro Thr Pro Leu Pro Phe Leu Gly
            35                  40                  45
Asn Ile Leu Ser Tyr His Lys Gly Phe Cys Met Phe Asp Met Glu Cys
        50                  55                  60
His Lys Lys Tyr Gly Lys Val Trp Gly Phe Tyr Asp Gly Gln Gln Pro
65                  70                  75                  80
Val Leu Ala Ile Thr Asp Pro Asp Met Ile Lys Thr Val Leu Val Lys
                85                  90                  95
Glu Cys Tyr Ser Val Phe Thr Asn Arg Arg Pro Phe Gly Pro Val Gly
                100                 105                 110
Phe Met Lys Ser Ala Ile Ser Ile Ala Glu Asp Glu Glu Trp Lys Arg
            115                 120                 125
Leu Arg Ser Leu Leu Ser Pro Thr Phe Thr Ser Gly Lys Leu Lys Glu
        130                 135                 140
Met Val Pro Ile Ile Ala Gln Tyr Gly Asp Val Leu Val Arg Asn Leu
145                 150                 155                 160
Arg Arg Glu Ala Glu Thr Gly Lys Pro Val Thr Leu Lys Asp Val Phe
                165                 170                 175
Gly Ala Tyr Ser Met Asp Val Ile Thr Ser Thr Ser Phe Gly Val Asn
                180                 185                 190
Ile Asp Ser Leu Asn Asn Pro Gln Asp Pro Phe Val Glu Asn Thr Lys
            195                 200                 205
```

```
Lys Leu Leu Arg Phe Asp Phe Leu Asp Pro Phe Phe Leu Ser Ile Thr
    210                 215                 220

Val Phe Pro Phe Leu Ile Pro Ile Leu Glu Val Leu Asn Ile Cys Val
225                 230                 235                 240

Phe Pro Arg Glu Val Thr Asn Phe Leu Arg Lys Ser Val Lys Arg Met
                245                 250                 255

Lys Glu Ser Arg Leu Glu Asp Thr Gln Lys His Arg Val Asp Phe Leu
                260                 265                 270

Gln Leu Met Ile Asp Ser Gln Asn Ser Lys Thr Glu Ser His Lys
                275                 280                 285

Ala Leu Ser Asp Leu Glu Leu Val Ala Gln Ser Ile Ile Phe Ile Phe
    290                 295                 300

Ala Gly Tyr Glu Thr Thr Ser Ser Val Leu Ser Phe Ile Met Tyr Glu
305                 310                 315                 320

Leu Ala Thr His Pro Asp Val Gln Gln Lys Leu Gln Glu Glu Ile Asp
                325                 330                 335

Ala Val Leu Pro Asn Lys Ala Pro Pro Thr Tyr Asp Thr Val Leu Gln
                340                 345                 350

Met Glu Tyr Leu Asp Met Val Val Asn Glu Thr Leu Arg Leu Phe Pro
                355                 360                 365

Ile Ala Met Arg Leu Glu Arg Val Cys Lys Lys Asp Val Glu Ile Asn
370                 375                 380

Gly Met Phe Ile Pro Lys Gly Val Val Met Ile Pro Ser Tyr Ala
385                 390                 395                 400

Leu His Arg Asp Pro Lys Tyr Trp Thr Glu Pro Glu Lys Phe Leu Pro
                405                 410                 415

Glu Arg Phe Ser Lys Lys Asn Lys Asp Asn Ile Asp Pro Tyr Ile Tyr
                420                 425                 430

Thr Pro Phe Gly Ser Gly Pro Arg Asn Cys Ile Gly Met Arg Phe Ala
                435                 440                 445

Leu Met Asn Met Lys Leu Ala Leu Ile Arg Val Leu Gln Asn Phe Ser
                450                 455                 460

Phe Lys Pro Cys Lys Glu Thr Gln Ile Pro Leu Lys Leu Ser Leu Gly
465                 470                 475                 480

Gly Leu Leu Gln Pro Glu Lys Pro Val Val Leu Lys Val Glu Ser Arg
                485                 490                 495

Asp Gly Thr Val Ser Gly Ala
                500

<210> SEQ ID NO 39
<211> LENGTH: 502
<212> TYPE: PRT
<213> ORGANISM: Homo sapiens

<400> SEQUENCE: 39

Met Ala Leu Ile Pro Asp Leu Ala Met Glu Thr Trp Leu Leu Leu Ala
1               5                   10                  15

Val Ser Leu Val Leu Leu Tyr Leu Tyr Gly Thr His Ser His Gly Leu
                20                  25                  30

Phe Lys Lys Leu Gly Ile Pro Gly Pro Thr Pro Leu Pro Phe Leu Gly
                35                  40                  45

Asn Ile Leu Ser Tyr His Lys Gly Phe Cys Met Phe Asp Met Glu Cys
            50                  55                  60

His Lys Lys Tyr Gly Lys Val Trp Gly Phe Tyr Asp Gly Gln Gln Pro
65              70                  75                  80
```

```
Val Leu Ala Ile Thr Asp Pro Asp Met Ile Lys Thr Val Leu Val Lys
                85                  90                  95

Glu Cys Tyr Ser Val Phe Thr Asn Arg Arg Pro Phe Gly Pro Val Gly
            100                 105                 110

Phe Met Lys Ser Ala Ile Ser Ile Ala Glu Asp Glu Gly Trp Lys Arg
        115                 120                 125

Leu Arg Ser Leu Leu Ser Pro Thr Phe Thr Ser Gly Lys Leu Lys Glu
    130                 135                 140

Met Val Pro Ile Ile Ala Gln Tyr Gly Asp Val Leu Val Arg Asn Leu
145                 150                 155                 160

Arg Arg Glu Ala Glu Thr Gly Lys Pro Val Thr Leu Lys Asp Val Phe
                165                 170                 175

Gly Ala Tyr Ser Met Asp Val Ile Thr Ser Thr Ser Phe Gly Val Asn
            180                 185                 190

Ile Asp Ser Leu Asn Asn Pro Gln Asp Pro Phe Val Glu Asn Thr Lys
        195                 200                 205

Lys Leu Leu Arg Phe Asp Phe Leu Asp Pro Phe Phe Leu Ser Ile Ile
    210                 215                 220

Phe Pro Phe Leu Ile Pro Ile Leu Glu Val Leu Asn Ile Cys Val Phe
225                 230                 235                 240

Pro Arg Glu Val Thr Asn Phe Leu Arg Lys Ser Val Lys Arg Met Lys
                245                 250                 255

Glu Ser Arg Leu Glu Asp Thr Gln Lys His Arg Val Asp Phe Leu Gln
            260                 265                 270

Leu Met Ile Asp Ser Gln Asn Ser Lys Glu Thr Glu Ser His Lys Ala
        275                 280                 285

Leu Ser Asp Leu Glu Leu Val Ala Gln Ser Ile Ile Phe Ile Phe Ala
    290                 295                 300

Gly Tyr Glu Thr Thr Ser Ser Val Leu Ser Phe Ile Met Tyr Glu Leu
305                 310                 315                 320

Ala Thr His Pro Asp Val Gln Gln Lys Leu Gln Glu Glu Ile Asp Ala
                325                 330                 335

Val Leu Pro Asn Lys Ala Pro Pro Thr Tyr Asp Thr Val Leu Gln Met
            340                 345                 350

Glu Tyr Leu Asp Met Val Val Asn Glu Thr Leu Arg Leu Phe Pro Ile
        355                 360                 365

Ala Met Arg Leu Glu Arg Val Cys Lys Lys Asp Val Glu Ile Asn Gly
    370                 375                 380

Met Phe Ile Pro Lys Gly Val Val Val Met Ile Pro Ser Tyr Ala Leu
385                 390                 395                 400

His Arg Asp Pro Lys Tyr Trp Thr Glu Pro Glu Lys Phe Leu Pro Glu
                405                 410                 415

Arg Phe Ser Lys Lys Asn Lys Asp Asn Ile Asp Pro Tyr Ile Tyr Thr
            420                 425                 430

Pro Phe Gly Ser Gly Pro Arg Asn Cys Ile Gly Met Arg Phe Ala Leu
        435                 440                 445

Met Asn Met Lys Leu Ala Leu Ile Arg Val Leu Gln Asn Phe Ser Phe
    450                 455                 460

Lys Pro Cys Lys Glu Thr Gln Ile Pro Leu Lys Leu Ser Leu Gly Gly
465                 470                 475                 480

Leu Leu Gln Pro Glu Lys Pro Val Val Leu Lys Val Glu Ser Arg Asp
                485                 490                 495
```

```
Gly Thr Val Ser Gly Ala
            500

<210> SEQ ID NO 40
<211> LENGTH: 534
<212> TYPE: PRT
<213> ORGANISM: Menispermum canadense

<400> SEQUENCE: 40

Met Ile Met Met Phe Ile Asp Tyr Tyr Ser Ser Trp Leu Pro Gln Thr
 1               5                  10                  15

Leu Leu Leu Gln Ser Ile Leu Leu Ala Val Ser Leu Val Ile Phe Ile
            20                  25                  30

Asn Leu Phe Leu Thr Arg Arg Ser Tyr Ser Ser Lys Ser His Thr
        35                  40                  45

Asn Ile Ile His Pro Pro Lys Ala Ala Gly Ala Leu Pro Val Ile Gly
    50                  55                  60

His Leu Tyr Thr Leu Phe Arg Gly Leu Ser Ala Gly Val Pro Leu Tyr
65                  70                  75                  80

Arg Gln Leu Asp Ala Met Ala Asp Arg Tyr Gly Pro Ala Phe Ile Ile
                85                  90                  95

His Leu Gly Val Tyr Pro Thr Leu Val Val Thr Cys Arg Glu Leu Ala
            100                 105                 110

Lys Glu Cys Phe Thr Thr Asn Asp Gln Thr Phe Ala Thr Arg Pro Ser
        115                 120                 125

Thr Cys Ala Gly Lys Tyr Ile Gly Tyr Asn Tyr Ala Phe Phe Gly Phe
    130                 135                 140

Ala Pro Tyr Gly Pro Tyr Trp Arg Glu Ala Arg Lys Ile Ala Thr Val
145                 150                 155                 160

Glu Leu Leu Ser Asn Tyr Arg Leu Asp Ser Leu Arg His Val Arg Glu
                165                 170                 175

Ala Glu Val Gly Arg Asn Val Asp Glu Leu Tyr Ala Leu His Ala Ser
            180                 185                 190

Ser Ser Thr Asn Lys Gln Asn Met Met Lys Ile Asp Met Lys Gln Trp
        195                 200                 205

Phe Asp Gln Val Thr Leu Asn Val Ile Leu Met Met Val Val Gly Lys
    210                 215                 220

Arg Cys Val Thr Thr Gly Gly Asn Glu Glu Val Arg Val Val Lys
225                 230                 235                 240

Val Leu His Glu Phe Phe Lys His Leu Gly Thr Leu Ser Val Ser Asp
                245                 250                 255

Val Val Pro Tyr Val Glu Trp Met Asp Leu Asp Gly Asn Ile Gly Arg
            260                 265                 270

Met Lys Ser Thr Ala Lys Glu Leu Asp Cys Ile Leu Gly Arg Trp Leu
        275                 280                 285

Glu Glu His Arg Arg Glu Arg Arg Ser Asp Phe Met Asp Ala Met Leu
    290                 295                 300

Ala Met Val Glu Gly Ile Lys Ile Pro Tyr Tyr Asp Ser Asp Thr Val
305                 310                 315                 320

Ile Lys Ala Ile Cys Leu Asn Leu Leu Asn Ala Gly Ser Asp Thr Leu
                325                 330                 335

Gly Ile Thr Met Thr Trp Ala Leu Ser Leu Leu Leu Asn Asn Arg His
            340                 345                 350

Val Leu Lys Lys Val Lys Asp Glu Leu Asp Val His Val Gly Lys Asn
        355                 360                 365
```

```
Arg Gln Val Glu Glu Leu Asp Val Lys Asn Leu Val Tyr Leu His Ala
        370                 375                 380

Val Val Lys Glu Thr Leu Arg Leu Phe Pro Pro Ala Pro Leu Gly Val
385                 390                 395                 400

Pro His Glu Ala Met Glu Asp Cys Val Val Gly Gly Phe His Val Ala
                405                 410                 415

Lys Gly Thr Arg Leu Val Val Asn Val Trp Lys Leu His Arg Asp Pro
                420                 425                 430

Ser Val Trp Ser Asp Pro Leu Ala Phe Lys Pro Glu Arg Phe Leu Asp
            435                 440                 445

Asn Asn Thr Val Asp Val Arg Gly Gln His Phe Gln Leu Leu Pro Phe
        450                 455                 460

Gly Ser Gly Arg Arg Gly Cys Pro Gly Ile Thr Phe Ala Leu Gln Val
465                 470                 475                 480

Ala His Leu Thr Leu Ala Arg Leu Leu His Gly Phe Glu Trp Asp Thr
                485                 490                 495

Pro Asp Gly Ala Pro Val Asp Met Ser Glu Val Ser Val Leu Thr Thr
                500                 505                 510

Ala Lys Lys Asn Pro Val Glu Val Leu Phe Thr Pro Arg Leu Pro Ala
            515                 520                 525

Glu Val Tyr Thr Gln Asn
        530

<210> SEQ ID NO 41
<211> LENGTH: 527
<212> TYPE: PRT
<213> ORGANISM: Nigella sativa

<400> SEQUENCE: 41

Met Leu Ser Ile His Asp Ser Thr Met Val Phe Leu Gln Leu Gln Ala
1               5                   10                  15

Ile Cys Gly Ile Phe Gly Phe Ile Phe Ile Ile Thr Trp Trp Thr Arg
                20                  25                  30

Trp Lys Ser Ser Asn Lys Met Lys Ala Pro Glu Val Ala Gly Ala Trp
            35                  40                  45

Pro Val Ile Gly His Leu His Leu Leu Gly Gly Arg Pro Leu Tyr
        50                  55                  60

Gln Leu Leu Gly Asp Met Ser Asp Lys Tyr Gly Pro Ala Phe Thr Leu
65                  70                  75                  80

Arg Met Gly Ile Gln Lys Ala Leu Val Val Ser Ser Trp Glu Val Ala
                85                  90                  95

Lys Glu Cys Leu Thr Thr Asn Asp Arg Ala Leu Ala Thr Arg Pro Ser
            100                 105                 110

Ser Ala Gly Gly Lys Tyr Met Gly Tyr Asn Asn Ala Leu Ile Pro Phe
        115                 120                 125

Ser Pro Tyr Gly Pro Tyr Trp Arg Asp Met Arg Lys Ile Ala Thr Leu
    130                 135                 140

Glu Leu Leu Ser Asn His Arg Leu Glu Glu Leu Lys His Val Arg Glu
145                 150                 155                 160

Met Glu Ile Asn Thr Cys Ile Ser Asp Met Tyr Lys Leu Cys Gln Val
                165                 170                 175

Glu Asp Gly Val Glu Ile Lys Pro Ile Ser Val Asp Leu Ser Gln Trp
            180                 185                 190

Phe Ala Asp Leu Thr Phe Asn Val Val Val Met Met Ile Thr Gly Lys
```

```
                195                 200                 205
Arg Tyr Ile Gly Ser Thr Asp Ala Gly Asp Met Asn Glu Ile Arg His
    210                 215                 220

Phe Gln Ala Ala Leu Val Lys Phe Met Arg Leu Leu Arg Ile Ser Leu
225                 230                 235                 240

Leu Val Asp Val Phe Pro Val Leu Gln Trp Ile Asn Tyr Gly Gly Phe
                245                 250                 255

Lys Gly Val Met Lys Ser Thr Ala Arg Asp Ile Asp Ser Val Leu Glu
                260                 265                 270

Asn Trp Leu Gln Glu His Gln Arg Lys Arg Leu Ser Pro Asp Phe Asn
                275                 280                 285

Gly Asn His Asp Phe Ile Asp Val Met Ile Ser Thr Leu Glu Gly Thr
                290                 295                 300

Glu Phe Ser Asp Tyr Asp His Asn Thr Ile Ile Lys Ala Ile Ser Met
305                 310                 315                 320

Ala Met Val Val Gly Gly Thr Asp Thr Thr Thr Thr Leu Ile Trp
                325                 330                 335

Ala Ile Ser Leu Leu Leu Asn Asn Pro Asn Ala Met Lys Lys Val Gln
                340                 345                 350

Glu Glu Leu Glu Ile His Val Gly Lys Glu Arg Asn Val Asp Gly Ser
                355                 360                 365

Asp Ile Gln His Leu Val Tyr Leu Gln Ala Val Val Lys Glu Thr Leu
    370                 375                 380

Arg Leu Tyr Pro Pro Val Pro Leu Ser Val Met His Gln Ala Met Glu
385                 390                 395                 400

Asp Cys Val Ile Gly Ser Tyr Asn Ile Gln Ala Gly Thr Arg Val Leu
                405                 410                 415

Phe Asn Leu Trp Lys Leu His Arg Asp Ser Ser Val Trp Ser Asp Pro
                420                 425                 430

Leu Glu Phe Arg Pro Glu Arg Phe Leu Thr Ser His Val Asp Val Asp
                435                 440                 445

Val Arg Gly Gln His Phe Glu Leu Ile Pro Phe Gly Ser Gly Arg Arg
    450                 455                 460

Ser Cys Pro Gly Ile Ser Phe Ala Leu Gln Val Ile His Leu Thr Ile
465                 470                 475                 480

Ala Arg Leu Phe His Gly Phe Asn Leu Thr Thr Pro Gly Asn Ser Ser
                485                 490                 495

Val Asp Met Ser Glu Ile Ser Gly Ala Thr Leu Ser Lys Val Thr Pro
                500                 505                 510

Leu Glu Val Leu Val Thr Pro Arg Leu Ser Ser Lys Leu Tyr Asn
                515                 520                 525
```

<210> SEQ ID NO 42
<211> LENGTH: 525
<212> TYPE: PRT
<213> ORGANISM: Hydrastis canadensis

<400> SEQUENCE: 42

```
Met Asp Ser Leu Leu Gln Leu Gln Ile Ile Gly Ala Leu Ala Ala Leu
1               5                   10                  15

Ile Phe Thr Tyr Lys Leu Leu Lys Val Ile Cys Arg Ser Pro Met Thr
                20                  25                  30

Asp Gly Met Glu Ala Pro Glu Pro Pro Gly Ala Trp Pro Ile Ile Gly
                35                  40                  45
```

His Leu His Leu Leu Gly Gly Gln Asp Pro Ile Ala Arg Thr Leu Gly
 50                  55                  60

Val Met Thr Asp Lys Tyr Gly Pro Ile Leu Lys Leu Arg Leu Gly Val
 65                  70                  75                  80

His Thr Gly Leu Val Val Ser Asn Trp Glu Leu Ala Lys Glu Cys Phe
                 85                  90                  95

Thr Thr Asn Asp Arg Val Leu Ala Ser Arg Pro Met Gly Ala Ala Gly
            100                 105                 110

Lys Tyr Leu Gly Tyr Asn Tyr Ala Ile Phe Gly Leu Ala Pro His Gly
            115                 120                 125

Pro Tyr Trp Ser Glu Val Arg Lys Ile Val Leu Arg Glu Leu Leu Ser
130                 135                 140

Asn Gln Ser Leu Glu Lys Leu Lys His Val Arg Ile Ser Glu Ile Asn
145                 150                 155                 160

Thr Cys Leu Lys Asn Leu Phe Ser Leu Asn Asn Gly Asn Thr Pro Ile
                165                 170                 175

Lys Val Asp Met Lys Gln Trp Phe Glu Arg Pro Met Phe Asn Val Val
            180                 185                 190

Thr Met Met Ile Ala Gly Lys Arg Tyr Phe Ser Met Glu Asn Asp Asn
            195                 200                 205

Glu Ala Met Asn Phe Arg Lys Val Ala Thr Glu Phe Met Tyr Leu Thr
            210                 215                 220

Gly Val Phe Val Val Ser Asp Ala Leu Pro Tyr Leu Glu Trp Leu Asp
225                 230                 235                 240

Leu Gln Gly His Val Ser Ala Met Lys Arg Thr Ala Lys Glu Leu Asp
                245                 250                 255

Ile His Val Gly Lys Trp Leu Glu Glu His Arg Arg Ala Lys Leu Leu
            260                 265                 270

Gly Glu Thr Lys Asn Glu Asp Asp Phe Val Asp Val Leu Leu Thr Ile
            275                 280                 285

Leu Pro Glu Asp Leu Lys Asp Asn Gln Thr Tyr Ile His Asp Arg Asp
            290                 295                 300

Thr Ile Ile Lys Ala Thr Ala Leu Ala Leu Phe Leu Ala Ala Ser Asp
305                 310                 315                 320

Thr Thr Ala Ile Thr Leu Thr Trp Ala Leu Ser Leu Ile Leu Asn Asn
                325                 330                 335

Pro Asp Val Leu Lys Arg Ala Gln Asp Glu Leu Asp Lys His Val Gly
            340                 345                 350

Lys Glu Lys Leu Val Lys Glu Ser Asp Ile Ile Asn Leu Val Tyr Leu
            355                 360                 365

Gln Ala Ile Ile Lys Glu Thr Leu Arg Leu Tyr Pro Ala Ala Pro Leu
            370                 375                 380

Leu Leu Pro His Glu Ala Met Glu Asp Cys Thr Val Gly Gly Tyr His
385                 390                 395                 400

Val Pro Lys Gly Thr Arg Ile Phe Val Asn Ile Trp Lys Leu Gln Arg
                405                 410                 415

Asp Pro Arg Val Trp Phe Asp Pro Asn Glu Phe Arg Pro Glu Arg Phe
            420                 425                 430

Leu Thr Thr His Ala Asn Val Asp Phe Lys Gly Gln His Phe Glu Tyr
            435                 440                 445

Ile Pro Phe Ser Ser Gly Arg Arg Val Cys Pro Gly Ile Thr Phe Ser
450                 455                 460

Thr Gln Ile Met His Leu Thr Leu Ala His Leu Leu His Glu Phe Asn

```
                465            470            475          480
Ile Val Thr Pro Thr Lys Ser Asn Ala Gly Val Asp Met Thr Glu Ser
                485                        490                495

Leu Gly Ile Thr Met Pro Lys Ala Thr Pro Leu Glu Val Leu Leu Thr
                500                        505                510

Pro Arg Leu Pro Ser Asn Leu Tyr Asn Gln Tyr Arg Asp
                515                        520                525

<210> SEQ ID NO 43
<211> LENGTH: 550
<212> TYPE: PRT
<213> ORGANISM: Eschscholzia californica

<400> SEQUENCE: 43

Met Asn Leu Leu Ile Phe Phe Gln Phe Leu Gln Phe Gln Val Leu
 1               5                  10                  15

Val Gly Leu Ser Val Leu Leu Ala Phe Ser Tyr Tyr Leu Trp Val Ser
                20                  25                  30

Lys Asn Pro Lys Ile Asn Lys Phe Gly Lys Gly Ala Leu Leu Ala
                35                  40                  45

Pro Gln Ala Ala Gly Ala Trp Pro Ile Val Gly His Leu Pro Gln Leu
 50                          55                  60

Val Gly Pro Lys Pro Leu Phe Arg Ile Leu Gly Ala Met Ala Asp Asn
 65                  70                          75                  80

Tyr Gly Pro Ile Phe Met Leu Arg Phe Gly Val His Pro Thr Val Val
                    85                  90                  95

Val Ser Ser Trp Glu Met Thr Lys Glu Cys Phe Thr Thr Asn Asp Arg
                100                    105                    110

His Leu Ala Ser Arg Pro Ser Asn Ala Ala Ser Gln Tyr Leu Ile Tyr
                115                    120                    125

Glu Val Tyr Ala Leu Phe Gly Phe Ser Leu Tyr Gly Ser Ser Tyr Trp
                130                    135                    140

Arg Asp Ala Arg Lys Ile Ala Thr Leu Glu Leu Leu Ser His Arg Arg
145                    150                    155                    160

Leu Glu Leu Leu Lys His Val Pro Tyr Thr Glu Ile Asp Thr Cys Ile
                    165                    170                    175

Lys Gln Leu His Arg Leu Trp Thr Lys Asn Asn Lys Asn Gln Asn Asn
                180                    185                    190

Pro Glu Leu Lys Val Glu Met Asn Gln Phe Phe Thr Asp Leu Thr Met
                195                    200                    205

Asn Val Ile Leu Lys Leu Val Val Gly Lys Arg Phe Phe Asn Val Asp
                210                    215                    220

Asp Ala Ala Asp His Glu Lys Glu Ala Arg Lys Ile Gln Gly Thr
225                    230                    235                    240

Ile Phe Glu Phe Phe Lys Leu Thr Glu Gly Ser Val Ser Ala Gly Ala
                    245                    250                    255

Leu Pro Leu Leu Asn Trp Leu Asp Leu Asn Gly Gln Lys Arg Ala Met
                    260                    265                    270

Lys Arg Thr Ala Lys Lys Met Asp Ser Ile Ala Glu Lys Leu Leu Asp
                275                    280                    285

Glu His Arg Gln Lys Arg Leu Ser Lys Glu Gly Val Lys Gly Thr His
                290                    295                    300

Asp His Asn Asp Phe Met Asp Val Leu Leu Ser Ile Leu Asp Ala Asp
305                    310                    315                    320
```

```
Gln Gly Asp Tyr Ser His His Pro Phe Asn Tyr Ser Arg Asp His Val
            325                 330                 335

Ile Lys Ala Thr Thr Leu Ser Met Ile Leu Ser Ser Met Ser Ile Ser
        340                 345                 350

Val Ser Leu Ser Trp Ala Leu Ser Leu Leu Asn Asn Arg His Val
            355                 360                 365

Leu Lys Lys Ala Gln Asp Glu Leu Asp Met Asn Val Gly Lys Asp Arg
370                 375                 380

Gln Val Glu Glu Gly Asp Ile Lys Asn Leu Val Tyr Leu Gln Ala Ile
385                 390                 395                 400

Val Lys Glu Thr Phe Arg Met Tyr Pro Ala Asn Pro Leu Leu Leu Pro
                405                 410                 415

His Glu Ala Ile Glu Asp Cys Lys Ile Gly Gly Phe Asn Val Pro Ala
            420                 425                 430

Gly Thr Arg Val Val Asn Ala Trp Lys Leu Gln His Asp Pro Arg
            435                 440                 445

Val Trp Ser Asn Pro Ser Glu Phe Lys Pro Glu Arg Phe Leu Asn Asp
        450                 455                 460

Gln Ala Ala Lys Val Val Asp Val Arg Gly Gln Asn Phe Glu Tyr Leu
465                 470                 475                 480

Pro Phe Gly Ser Gly Arg Arg Val Cys Pro Gly Ile Ser Phe Ser Leu
                485                 490                 495

Gln Thr Ile His Met Ser Leu Ala Arg Leu Val Gln Ala Phe Glu Leu
            500                 505                 510

Gly Thr Pro Ser Asn Glu Arg Ile Asp Met Thr Glu Gly Ser Gly Leu
            515                 520                 525

Thr Met Pro Lys Thr Thr Pro Leu His Val Leu Leu Asn Pro Arg Leu
530                 535                 540

Pro Leu Pro Leu Tyr Glu
545                 550

<210> SEQ ID NO 44
<211> LENGTH: 537
<212> TYPE: PRT
<213> ORGANISM: Glaucium flavum

<400> SEQUENCE: 44

Met Glu Leu Ile Asn Ser Leu Glu Ile Gln Pro Ile Thr Ile Ser Ile
1               5                   10                  15

Leu Ala Leu Leu Thr Val Ser Ile Leu Leu Tyr Lys Ile Ile Trp Asn
            20                  25                  30

His Gly Ser Arg Lys Asn Asn Lys Ser Asn Lys Asn Asn Arg Lys Thr
        35                  40                  45

Ser Ser Ser Ala Gly Val Val Glu Ile Pro Gly Ala Trp Pro Ile Ile
50                  55                  60

Gly His Leu His Leu Phe Asn Gly Ser Glu Gln Met Phe His Lys Leu
65                  70                  75                  80

Gly Ser Leu Ala Asp Gln Tyr Gly Pro Ala Pro Phe Phe Ile Arg Phe
                85                  90                  95

Gly Ser Arg Lys Tyr Val Val Val Ser Asn Trp Glu Leu Val Lys Thr
            100                 105                 110

Cys Phe Thr Ala Gln Ser Gln Ile Phe Val Ser Arg Pro Pro Met Leu
        115                 120                 125

Ala Met Asn Ile Leu Phe Phe Pro Lys Asp Ser Leu Ser Tyr Ile Gln
130                 135                 140
```

His Gly Asp His Trp Arg Glu Leu Arg Lys Ile Ser Ser Thr Lys Leu
145                 150                 155                 160

Leu Ser Ser His Arg Val Glu Thr Gln Lys His Leu Ile Ala Ser Glu
            165                 170                 175

Val Asp Tyr Cys Phe Lys Gln Leu Tyr Lys Leu Ser Asn Asn Gly Glu
            180                 185                 190

Phe Thr Leu Val Arg Leu Asn Thr Trp Cys Glu Asp Met Ala Leu Asn
            195                 200                 205

Val His Val Arg Met Ile Ala Gly Met Lys Asn Tyr Val Ala Ala Pro
210                 215                 220

Gly Ser Gly Glu Tyr Gly Gly Gln Ala Arg Arg Tyr Arg Lys Ala Leu
225                 230                 235                 240

Glu Glu Ala Leu Asp Leu Leu Asn Gln Phe Thr Ile Thr Asp Val Val
            245                 250                 255

Pro Trp Leu Gly Trp Leu Asp His Phe Arg Asp Val Val Gly Arg Met
            260                 265                 270

Lys Arg Cys Gly Ala Glu Leu Asp Ser Ile Phe Ala Thr Trp Val Glu
            275                 280                 285

Glu His Arg Val Lys Arg Ala Ser Gly Lys Gly Gly Asp Val Glu Pro
            290                 295                 300

Asp Phe Ile Asp Leu Cys Trp Glu Ser Met Glu Gln Leu Pro Gly Asn
305                 310                 315                 320

Asp Pro Ala Thr Val Ile Lys Leu Met Cys Lys Glu His Ile Phe Asn
            325                 330                 335

Gly Ser Gly Thr Ser Ser Leu Thr Leu Ala Trp Ile Leu Ser Leu Ile
            340                 345                 350

Met Asn Asn Pro Tyr Val Ile Lys Lys Ala Arg Glu Glu Leu Glu Lys
            355                 360                 365

His Val Gly Asn His Arg Gln Val Glu Glu Ser Asp Leu Pro Asn Leu
            370                 375                 380

Leu Tyr Ile Gln Ala Ile Ile Lys Glu Gly Met Arg Leu Tyr Thr Pro
385                 390                 395                 400

Gly Pro Phe Ile Asp Arg Asn Thr Thr Glu Asp Tyr Glu Ile Asn Gly
            405                 410                 415

Val His Ile Pro Ala Gly Thr Cys Leu Tyr Val Asn Leu Trp Lys Ile
            420                 425                 430

His Arg Asp Pro Asn Val Tyr Glu Asp Pro Leu Glu Phe Lys Pro Glu
            435                 440                 445

Arg Phe Leu Lys Asn Asn Ser Asp Leu Asp Leu Lys Gly Gln Asn Tyr
450                 455                 460

Gln Leu Leu Pro Phe Gly Ala Gly Arg Arg Ile Cys Pro Gly Val Ser
465                 470                 475                 480

Leu Ala Leu Pro Leu Met Tyr Leu Thr Val Ser Arg Leu Ile His Gly
            485                 490                 495

Phe Asp Met Lys Leu Pro Lys Gly Val Glu Lys Ala Asp Met Thr Ala
            500                 505                 510

His Gly Gly Val Ile Asn Gln Arg Ala Tyr Pro Leu Glu Val Leu Leu
            515                 520                 525

Lys Pro Arg Leu Thr Phe Gln Gln Ala
530                 535

<210> SEQ ID NO 45
<211> LENGTH: 568

<212> TYPE: PRT
<213> ORGANISM: Stylophorum diphyllum

<400> SEQUENCE: 45

```
Met Thr Ile Gly Ala Leu Ala Leu Leu Ser Phe Ile Tyr Phe Leu Arg
1               5                   10                  15

Val Ser Val Ile Lys Arg Thr Lys Tyr Thr Asn Thr Ala Val Thr Ala
            20                  25                  30

Thr Asn Lys Leu Glu Asn Asp Glu Asp Glu Ala Asn His Ser Lys Arg
        35                  40                  45

Val Val Ala Pro Pro Glu Val Ala Gly Ala Trp Pro Ile Leu Gly His
    50                  55                  60

Leu Pro Gln Leu Val Gly Leu Lys Gln Pro Leu Phe Arg Val Leu Gly
65                  70                  75                  80

Asp Met Ala Asp Lys Tyr Gly Pro Ile Phe Ile Val Arg Phe Gly Met
                85                  90                  95

Tyr Pro Thr Leu Val Val Ser Ser Trp Glu Met Ala Lys Glu Cys Phe
            100                 105                 110

Thr Thr Asn Asp Arg Val Leu Ala Ser Arg Pro Ala Ser Ala Ser Gly
        115                 120                 125

Lys Tyr Leu Thr Tyr Asn Tyr Ala Met Phe Gly Phe Thr Asn Gly Pro
    130                 135                 140

Tyr Trp Arg Glu Ile Arg Lys Ile Ser Met Leu Glu Leu Leu Ser His
145                 150                 155                 160

Arg Arg Val Glu Leu Leu Lys His Val Pro Ser Thr Glu Ile Asp Ser
                165                 170                 175

Ser Ile Lys Gln Leu Tyr His Leu Trp Val Glu Asn Gln Asn Gln Asn
            180                 185                 190

Lys Gln Gly Asp His Gln Val Lys Val Asp Met Ser Gln Leu Leu Arg
        195                 200                 205

Asp Leu Thr Leu Asn Ile Val Leu Lys Leu Val Val Gly Lys Arg Leu
    210                 215                 220

Phe Asn Asn Asn Asp Met Asp His Glu Gln Asp Glu Ala Ala Arg Lys
225                 230                 235                 240

Leu Gln Lys Thr Met Val Glu Leu Ile Lys Val Ala Gly Ala Ser Val
                245                 250                 255

Ala Ser Asp Ala Leu Pro Phe Leu Gly Trp Leu Asp Val Asp Gly Leu
            260                 265                 270

Lys Arg Thr Met Lys Arg Ile Ala Lys Glu Ile Asp Val Ile Ala Glu
        275                 280                 285

Arg Trp Leu Gln Glu His Arg Gln Lys Lys Leu Thr Ser Asn Asp Lys
    290                 295                 300

Gly Gly Ser Asn Asn Ile Gln Gly Gly Gly Asp Asn Asp Phe Met
305                 310                 315                 320

Asp Val Met Leu Ser Ile Leu Asp Asp Ser Asn Phe Phe Ile Asn
                325                 330                 335

Tyr Asn Arg Asp Thr Val Ile Lys Ala Thr Ser Leu Thr Met Ile Leu
            340                 345                 350

Ala Gly Ser Asp Thr Thr Thr Leu Ser Leu Thr Trp Ala Leu Thr Leu
        355                 360                 365

Leu Ala Thr Asn Pro Gly Ala Leu Arg Lys Ala Gln Asp Glu Leu Asp
    370                 375                 380

Thr Lys Val Gly Arg Asp Arg Gln Val Asp Glu Arg Asp Ile Lys Asn
385                 390                 395                 400
```

```
Leu Val Tyr Leu Gln Ala Ile Val Lys Glu Thr Leu Arg Met Tyr Pro
                405                 410                 415

Ala Ala Pro Leu Ala Ile Pro His Glu Ala Thr Gln Asp Cys Ile Val
            420                 425                 430

Gly Gly Tyr His Val Thr Ala Gly Thr Arg Val Trp Val Asn Leu Trp
                435                 440                 445

Lys Leu Gln Arg Asp Pro His Ala Trp Pro Asn Pro Ser Glu Phe Arg
            450                 455                 460

Pro Glu Arg Phe Leu Ala Val Glu Asn Asp Cys Lys Gln Gln Gly Thr
465                 470                 475                 480

Cys Asp Gly Glu Ala Ala Asn Met Asp Phe Arg Gly Gln His Phe Glu
                485                 490                 495

Tyr Met Pro Phe Gly Ser Gly Arg Arg Met Cys Pro Gly Ile Asn Phe
                500                 505                 510

Ala Ile Gln Ile Ile His Met Thr Leu Ala Arg Leu Leu His Ser Phe
                515                 520                 525

Glu Leu Arg Val Pro Glu Glu Val Ile Asp Met Ala Glu Asp Ser
            530                 535                 540

Gly Leu Thr Ile Ser Lys Val Thr Pro Leu Glu Leu Leu Leu Thr Pro
545                 550                 555                 560

Arg Leu Pro Leu Pro Leu Tyr Ile
                565

<210> SEQ ID NO 46
<211> LENGTH: 561
<212> TYPE: PRT
<213> ORGANISM: Stylophorum diphyllum

<400> SEQUENCE: 46

Phe Cys Gln Phe Gln Gly Ile Val Gly Ile Leu Leu Ala Phe Leu Thr
1               5                   10                  15

Phe Leu Tyr Tyr Leu Trp Arg Ala Ser Ile Thr Gly Leu Arg Thr Lys
                20                  25                  30

Pro Lys His Asn Asp Phe Lys Val Thr Lys Ala Ala Pro Glu Ala Asp
            35                  40                  45

Gly Ala Trp Pro Ile Val Gly His Phe Ala Gln Phe Ile Gly Pro Arg
        50                  55                  60

Pro Leu Phe Arg Ile Leu Gly Asp Met Ala Asp Lys Tyr Gly Ser Ile
65              70                  75                  80

Phe Met Val Arg Phe Gly Met Tyr Pro Thr Leu Val Val Ser Ser Trp
                85                  90                  95

Glu Met Ala Lys Glu Cys Phe Thr Thr Asn Asp Arg Phe Leu Ala Ser
            100                 105                 110

Arg Pro Ala Ser Ala Ala Gly Lys Tyr Leu Thr Tyr Asp Phe Ala Met
        115                 120                 125

Leu Ser Phe Ser Phe Tyr Gly Pro Tyr Trp Arg Glu Ile Arg Lys Ile
130                 135                 140

Ser Met Leu Glu Leu Leu Ser His Arg Arg Val Glu Leu Leu Lys His
145                 150                 155                 160

Val Pro Ser Thr Glu Ile Asp Ser Ser Ile Lys Gln Leu Tyr His Leu
                165                 170                 175

Trp Val Glu Asn Gln Asn Gln Asn Lys Gln Gly Asp His Gln Val Lys
            180                 185                 190

Val Asp Met Ser Gln Leu Leu Arg Asp Leu Thr Leu Asn Ile Val Leu
```

```
                195                 200                 205
Lys Leu Val Val Gly Lys Arg Leu Phe Asn Asn Asn Asp Met Asp His
210                 215                 220

Glu Gln Asp Glu Ala Ala Arg Lys Leu Gln Lys Thr Met Val Glu Leu
225                 230                 235                 240

Ile Lys Val Ala Gly Ala Ser Val Ala Ser Asp Ala Leu Pro Phe Leu
                245                 250                 255

Gly Trp Leu Asp Val Asp Gly Leu Lys Arg Thr Met Lys Arg Ile Ala
                260                 265                 270

Lys Glu Ile Asp Val Ile Ala Glu Arg Trp Leu Gln Glu His Arg Gln
                275                 280                 285

Lys Lys Leu Thr Ser Asn Asp Lys Gly Gly Ser Asn Asn Ile Gln Gly
290                 295                 300

Gly Gly Gly Asp Asn Asp Phe Met Asp Val Met Leu Ser Ile Leu Asp
305                 310                 315                 320

Asp Asp Ser Asn Phe Phe Ile Asn Tyr Asn Arg Asp Thr Val Ile Lys
                325                 330                 335

Ala Thr Ser Leu Thr Met Ile Leu Ala Gly Ser Asp Thr Thr Thr Leu
                340                 345                 350

Ser Leu Thr Trp Ala Leu Thr Leu Leu Ala Thr Tyr Pro Leu Cys Ala
                355                 360                 365

Leu Arg Lys Ala Gln Asp Glu Leu Asp Thr Lys Val Gly Arg Asp Arg
370                 375                 380

Gln Val Asp Glu Arg Asp Ile Lys Asn Leu Val Tyr Leu Gln Ala Ile
385                 390                 395                 400

Val Lys Glu Thr Leu Arg Met Tyr Pro Ala Ala Pro Leu Ala Ile Pro
                405                 410                 415

His Glu Ala Thr Gln Asp Cys Ile Val Gly Gly Tyr His Val Thr Ala
                420                 425                 430

Gly Thr Arg Val Trp Val Asn Leu Trp Lys Leu Gln Arg Asp Pro His
                435                 440                 445

Ala Trp Pro Asn Pro Ser Glu Phe Arg Pro Glu Arg Phe Leu Ala Val
450                 455                 460

Glu Asn Asp Cys Lys Gln Gln Gly Thr Cys Asp Gly Glu Ala Ala Asn
465                 470                 475                 480

Met Asp Phe Arg Gly Gln His Phe Glu Tyr Met Pro Phe Gly Ser Gly
                485                 490                 495

Arg Arg Met Cys Pro Gly Ile Asn Phe Ala Ile Gln Ile Ile His Met
                500                 505                 510

Thr Leu Ala Arg Leu Leu His Ser Phe Glu Leu Arg Val Pro Glu Glu
                515                 520                 525

Glu Val Ile Asp Met Ala Glu Asp Ser Gly Leu Thr Ile Ser Lys Val
                530                 535                 540

Thr Pro Leu Glu Leu Leu Leu Thr Pro Arg Leu Pro Leu Pro Leu Tyr
545                 550                 555                 560

Ile

<210> SEQ ID NO 47
<211> LENGTH: 561
<212> TYPE: PRT
<213> ORGANISM: Chelidonium majus

<400> SEQUENCE: 47

Met Asp Leu Phe Ile Phe Phe Ser Arg Phe Gln Tyr Ile Val Gly Leu
```

```
1               5                   10                  15
Leu Ala Phe Leu Thr Phe Phe Tyr Tyr Leu Trp Arg Val Ser Ile Thr
                20                  25                  30
Gly Thr Arg Ile Lys Thr Asn Gln Asn Ile Met Asn Gly Thr Asn Met
                35                  40                  45
Met Ala Pro Glu Ala Ala Gly Ala Trp Pro Ile Val Gly His Leu Pro
            50                  55                  60
Gln Leu Val Gly Pro Gln Pro Leu Phe Lys Ile Leu Gly Asp Met Ala
65                  70                  75                  80
Asp Lys Tyr Gly Ser Ile Phe Met Val Arg Phe Gly Met His Pro Thr
                85                  90                  95
Leu Val Val Ser Ser Trp Glu Met Ala Lys Glu Cys Phe Thr Thr Asn
                100                 105                 110
Asp Lys Phe Leu Ala Ser Arg Pro Thr Ser Ala Gly Gly Lys Tyr Leu
                115                 120                 125
Thr Tyr Asp Phe Ala Met Phe Gly Phe Ser Phe Tyr Gly Pro Tyr Trp
            130                 135                 140
Arg Glu Ile Arg Lys Ile Ser Thr Leu Glu Leu Leu Ser His Arg Arg
145                 150                 155                 160
Val Glu Leu Leu Lys His Val Pro Tyr Thr Glu Ile Gly Gly Ser Ile
                165                 170                 175
Lys Gln Leu Tyr Lys Leu Trp Met Glu Thr Gln Asn Gln Asn Lys Gln
                180                 185                 190
Arg Asp Asp His Gln Val Lys Val Asp Met Ser Gln Val Phe Gly Tyr
                195                 200                 205
Leu Thr Leu Asn Thr Val Leu Lys Leu Val Val Gly Lys Gly Leu Phe
210                 215                 220
Asn Asn Asn Asp Met Asn His Glu Gln Glu Gly Arg Lys Leu His
225                 230                 235                 240
Glu Thr Val Leu Glu Phe Phe Lys Leu Ala Gly Val Ser Val Ala Ser
                245                 250                 255
Asp Ala Leu Pro Phe Leu Gly Trp Leu Asp Val Asp Gly Gln Lys Arg
                260                 265                 270
Ser Met Lys Arg Ile Ala Lys Glu Met Asp Leu Ile Ala Glu Arg Trp
                275                 280                 285
Leu Gln Glu His Arg Gln Lys Arg Leu Thr Ser Asn Asn Lys Ala Ser
                290                 295                 300
Ser Gly His Asp Asp Phe Met Ser Val Leu Leu Ser Ile Leu Asp Asp
305                 310                 315                 320
Asp Ser Asn Phe Phe Asn Tyr Asn Arg Asp Thr Val Ile Lys Ala Thr
                325                 330                 335
Ser Leu Asn Leu Ile Leu Ala Ala Ser Asp Thr Thr Ser Val Ser Leu
                340                 345                 350
Thr Trp Val Leu Ser Leu Leu Val Thr Asn Pro Gly Ala Leu Lys Lys
                355                 360                 365
Val Gln Asp Glu Leu Asp Thr Lys Val Gly Arg Asn Arg His Val Glu
                370                 375                 380
Glu Arg Asp Ile Glu Lys Leu Val Tyr Leu Gln Ala Thr Val Lys Glu
385                 390                 395                 400
Thr Leu Arg Met Tyr Pro Ala Gly Pro Leu Ser Val Pro His Glu Ala
                405                 410                 415
Thr Gln Asp Cys Thr Val Gly Gly Tyr Gln Val Thr Ala Gly Thr Arg
                420                 425                 430
```

Leu Val Val Asn Val Trp Lys Leu Gln Arg Asp Pro Arg Val Trp Pro
        435                 440                 445

Asn Pro Ser Glu Phe Lys Pro Glu Arg Phe Leu Pro Asp Gly Cys Glu
    450                 455                 460

Val Gly Cys Gly Glu Ala Ala Asn Met Asp Phe Arg Gly Gln His Phe
465                 470                 475                 480

Glu Tyr Ile Pro Phe Gly Ser Gly Arg Arg Met Cys Pro Gly Ile Asp
                485                 490                 495

Phe Ala Ile Gln Ile Ile His Met Thr Leu Ala Cys Leu Leu His Ala
            500                 505                 510

Phe Glu Phe Gln Val Pro Ser Ser Leu Asp Lys His Leu Val Pro Ala
        515                 520                 525

Val Ile Asp Met Ser Glu Gly Ser Gly Leu Thr Met Pro Lys Val Thr
    530                 535                 540

Pro Leu Glu Val Leu Leu Asn Pro Arg Leu Pro Leu Pro Leu Tyr Glu
545                 550                 555                 560

Leu

<210> SEQ ID NO 48
<211> LENGTH: 561
<212> TYPE: PRT
<213> ORGANISM: Eschscholzia californica

<400> SEQUENCE: 48

Met Glu Lys Pro Ile Leu Leu Gln Leu Gln Pro Gly Ile Leu Gly Leu
1               5                   10                  15

Leu Ala Leu Met Cys Phe Leu Tyr Tyr Val Ile Lys Val Ser Leu Ser
            20                  25                  30

Thr Arg Asn Cys Asn Gln Leu Val Arg His Pro Pro Glu Ala Ala Gly
        35                  40                  45

Ser Trp Pro Ile Val Gly His Leu Pro Gln Leu Val Gly Ser Gly Lys
    50                  55                  60

Pro Leu Phe Arg Val Leu Gly Asp Met Ala Asp Lys Phe Gly Pro Ile
65                  70                  75                  80

Phe Met Val Arg Phe Gly Val His Pro Thr Leu Val Val Ser Ser Trp
                85                  90                  95

Glu Met Ala Lys Glu Cys Phe Thr Ser Asn Asp Lys Phe Leu Ala Ser
            100                 105                 110

Arg Pro Pro Ser Ala Ala Ser Ile Tyr Met Ala Tyr Asp His Ala Met
        115                 120                 125

Leu Gly Phe Ser Ser Tyr Gly Pro Tyr Trp Arg Glu Ile Arg Lys Ile
    130                 135                 140

Ser Thr Leu His Leu Leu Ser His Arg Arg Leu Glu Leu Leu Lys His
145                 150                 155                 160

Val Pro His Leu Glu Ile His Asn Phe Ile Lys Gly Leu Tyr Gly Ile
                165                 170                 175

Trp Lys Asp His Gln Lys Gln Gln Gln Pro Thr Ala Arg Asp Asp
            180                 185                 190

Gln Asp Ser Val Met Leu Glu Met Ser Gln Leu Phe Gly Tyr Leu Thr
        195                 200                 205

Leu Asn Ile Val Leu Ser Leu Val Val Gly Lys Arg Val Cys Asn Tyr
    210                 215                 220

His Ala Asp Gly His Leu Asp Asp Gly Glu Glu Ala Gly Gln Gly Gln
225                 230                 235                 240

```
Lys Leu His Gln Thr Ile Thr Asp Phe Phe Lys Leu Ser Gly Val Ser
                245                 250                 255

Val Ala Ser Asp Ala Leu Pro Phe Leu Gly Leu Phe Asp Leu Asp Gly
            260                 265                 270

Gln Lys Lys Ile Met Lys Arg Val Ala Lys Glu Met Asp Phe Val Ala
        275                 280                 285

Glu Arg Trp Leu Gln Asp Lys Lys Ser Ser Leu Leu Leu Ser Ser Lys
    290                 295                 300

Ser Asn Asn Lys Gln Asn Glu Ala Gly Glu Gly Asp Val Asp Asp Phe
305                 310                 315                 320

Met Asp Val Leu Met Ser Thr Leu Pro Asp Asp Asp Ser Phe Phe
                325                 330                 335

Thr Lys Tyr Ser Arg Asp Thr Val Ile Lys Ala Asn Ser Leu Ser Met
                340                 345                 350

Val Val Ala Gly Ser Asp Thr Thr Ser Val Ser Leu Thr Trp Ala Leu
                355                 360                 365

Ser Leu Leu Leu Asn Asn Ile Gln Val Leu Arg Lys Ala Gln Asp Glu
            370                 375                 380

Leu Asp Thr Lys Val Gly Arg Asp Arg His Val Glu Glu Lys Asp Ile
385                 390                 395                 400

Asp Asn Leu Val Tyr Leu Gln Ala Ile Val Lys Glu Thr Leu Arg Met
                405                 410                 415

Tyr Pro Ala Gly Pro Leu Ser Val Pro His Glu Ala Ile Glu Asp Cys
                420                 425                 430

Asn Val Gly Gly Tyr His Ile Lys Thr Gly Thr Arg Leu Leu Val Asn
                435                 440                 445

Ile Trp Lys Leu Gln Arg Asp Pro Arg Val Trp Ser Asn Pro Ser Glu
        450                 455                 460

Phe Arg Pro Glu Arg Phe Leu Asp Asn Gln Ser Asn Gly Thr Leu Leu
465                 470                 475                 480

Asp Phe Arg Gly Gln His Phe Glu Tyr Ile Pro Phe Gly Ser Gly Arg
                485                 490                 495

Arg Met Cys Pro Gly Val Asn Leu Ala Thr Pro Ile Leu His Met Thr
                500                 505                 510

Leu Ala Arg Leu Leu Gln Ser Phe Asp Leu Thr Thr Pro Ser Ser Ser
            515                 520                 525

Pro Val Asp Met Thr Glu Gly Ser Gly Leu Thr Met Pro Lys Val Thr
            530                 535                 540

Pro Leu Lys Val Leu Leu Thr Pro Arg Leu Pro Leu Pro Leu Tyr Asp
545                 550                 555                 560

Tyr

<210> SEQ ID NO 49
<211> LENGTH: 567
<212> TYPE: PRT
<213> ORGANISM: Papaver bracteatum

<400> SEQUENCE: 49

Met Asp Val Ala Ile Ile Val Asp His His Tyr Leu Gln Pro Phe Val
1               5                   10                  15

Ser Ile Ala Gly Leu Leu Ala Leu Leu Ser Phe Phe Tyr Cys Ile Trp
            20                  25                  30

Val Phe Ile Ile Arg Pro Arg Ile Ile Lys Ser Asn Leu Asp Glu Arg
        35                  40                  45
```

```
Lys Leu Ser Pro Ser Ser Pro Pro Glu Val Ala Gly Ala Trp Pro Ile
    50                  55                  60

Val Gly His Leu Pro Gln Leu Ile Gly Ser Thr Pro Leu Phe Lys Ile
65                      70                  75                  80

Leu Ala Asp Met Ser Asn Lys Tyr Gly Pro Ile Phe Met Val Arg Phe
                85                  90                  95

Gly Met Tyr Pro Thr Leu Val Val Ser Ser Trp Glu Met Ser Lys Glu
            100                 105                 110

Cys Phe Thr Thr Asn Asp Arg Leu Phe Ala Thr Arg Pro Pro Ser Ala
        115                 120                 125

Ala Gly Lys Tyr Leu Thr Lys Ala Leu Phe Ala Phe Ser Val Tyr Gly
    130                 135                 140

Pro Tyr Trp Arg Glu Ile Arg Lys Ile Ser Thr Ile His Leu Leu Ser
145                 150                 155                 160

Leu Arg Arg Leu Glu Leu Leu Lys His Gly Arg Tyr Leu Glu Ile Asp
                165                 170                 175

Lys Cys Met Lys Arg Leu Phe Glu Tyr Trp Met Glu His His Lys Asn
            180                 185                 190

Ile Ile Ser Thr Thr Ser Ser Val Lys Val Asn Met Ser Gln Val Phe
        195                 200                 205

Ala Glu Leu Ser Leu Asn Val Val Leu Lys Ile Ile Val Gly Lys Thr
    210                 215                 220

Leu Phe Ile Lys Asn Gly Asn Glu Asp Tyr Thr Lys Glu Glu Glu
225                 230                 235                 240

Gly Gln Lys Leu His Lys Thr Ile Leu Lys Phe Met Glu Leu Ala Gly
                245                 250                 255

Val Ser Val Ala Ser Asp Val Leu Pro Phe Leu Gly Trp Leu Asp Val
            260                 265                 270

Asp Gly Gln Lys Lys Gln Met Lys Arg Val Tyr Lys Glu Met Asn Leu
        275                 280                 285

Ile Ala Ser Lys Trp Leu Gly Glu His Arg Glu Arg Lys Arg Leu Gln
    290                 295                 300

Ile Ile Gln Lys Arg Gly Ala Ala Arg Gly Ser Asn Tyr Asp Asp Gly
305                 310                 315                 320

Asn Asp Phe Met Asp Val Leu Met Ser Ile Leu Asp Glu Glu Asn Asp
                325                 330                 335

Asp Leu Phe Phe Gly Tyr Ser Arg Asp Thr Val Ile Lys Ser Thr Cys
            340                 345                 350

Leu Gln Leu Ile Val Ala Ala Ser Asp Thr Thr Ser Leu Ala Met Thr
        355                 360                 365

Trp Ala Leu Ser Leu Leu Leu Thr Asn Pro Asn Val Leu Gln Lys Ala
    370                 375                 380

Gln Asp Glu Leu Asp Thr Lys Val Gly Arg Asp Arg Ile Ile Glu Glu
385                 390                 395                 400

His Asp Ile Glu Cys Leu Val Tyr Leu Gln Ala Ile Val Lys Glu Thr
                405                 410                 415

Leu Arg Leu Tyr Pro Pro Ala Pro Leu Ser Leu Pro His Glu Ala Met
            420                 425                 430

Glu Asp Cys Thr Val Gly Gly Tyr Gln Val Lys Ala Gly Thr Arg Leu
        435                 440                 445

Val Val Asn Leu Trp Lys Leu Gln Arg Asp Pro Arg Val Trp Ser Asn
    450                 455                 460
```

```
Pro Leu Glu Phe Lys Pro Glu Arg Phe Leu Pro Gln Ser Asp Gly Gly
465                 470                 475                 480

Phe Gly Gly Glu Glu Ala Arg Met Asp Phe Arg Gly Gln His Phe Glu
            485                 490                 495

Tyr Thr Pro Phe Gly Ser Gly Arg Arg Ile Cys Pro Gly Ile Asp Phe
            500                 505                 510

Phe Leu Gln Thr Val His Met Ala Leu Ala Arg Leu Leu Gln Ala Phe
            515                 520                 525

Asp Phe Asn Thr Ala Gly Gly Leu Val Ile Asp Met Val Glu Gly Pro
            530                 535                 540

Gly Leu Thr Met Pro Lys Val Thr Pro Leu Glu Val His Leu Asn Pro
545                 550                 555                 560

Arg Leu Pro Val Thr Leu Tyr
                565

<210> SEQ ID NO 50
<211> LENGTH: 558
<212> TYPE: PRT
<213> ORGANISM: Papaver bracteatum

<400> SEQUENCE: 50

Met Gln Val Asp Trp Pro Asn Ile Leu Gln Lys Tyr Tyr Pro Ile Ile
1               5                   10                  15

Thr Cys Ser Leu Leu Thr Leu Leu Ser Phe Tyr Tyr Ile Trp Val Ser
                20                  25                  30

Ile Thr Lys Pro Ser Arg Asn Ser Lys Thr Lys Leu Pro Pro Pro Glu
            35                  40                  45

Val Ala Gly Ser Trp Pro Ile Val Gly His Leu Pro Gln Leu Val Gly
    50                  55                  60

Ser Thr Pro Leu Phe Lys Ile Leu Ala Asn Met Ser Asp Lys Tyr Gly
65                  70                  75                  80

Pro Ile Phe Met Val Arg Phe Gly Met His Pro Thr Leu Val Val Ser
                85                  90                  95

Ser Trp Glu Met Ser Lys Glu Cys Phe Thr Thr Asn Asp Lys Phe Leu
                100                 105                 110

Ala Ser Arg Pro Pro Ser Ala Ser Ala Lys Tyr Leu Gly Tyr Asp Asn
            115                 120                 125

Ala Met Phe Val Phe Ser Asp Tyr Gly Pro Tyr Trp Arg Glu Ile Arg
        130                 135                 140

Lys Ile Ser Thr Leu Gln Leu Leu Thr His Lys Arg Leu Asp Ser Leu
145                 150                 155                 160

Lys Asn Ile Pro Tyr Leu Glu Ile Asn Ser Cys Val Lys Thr Leu Tyr
                165                 170                 175

Thr Arg Trp Ala Lys Thr Gln Ser Gln Ile Lys Gln Asn Val Gly Gly
            180                 185                 190

Ala Ala Asp Asp Phe Val Lys Val Asp Met Thr Glu Met Phe Gly His
        195                 200                 205

Leu Asn Leu Asn Val Val Leu Arg Leu Val Val Gly Lys Pro Ile Phe
    210                 215                 220

Ile Gln Lys Asp Asn Ala Asp Glu Asp Tyr Thr Lys Asp Gly His Asn
225                 230                 235                 240

Lys Glu Glu Leu Gly Gln Lys Leu His Lys Thr Ile Ile Glu Phe Phe
                245                 250                 255

Glu Leu Ala Gly Ala Ser Val Ala Ser Asp Val Leu Pro Tyr Leu Gly
            260                 265                 270
```

```
Trp Leu Asp Val Asp Gly Gln Lys Lys Arg Met Lys Lys Ile Ala Met
            275                 280                 285

Glu Met Asp Leu Phe Ala Gln Lys Trp Leu Glu Glu His Arg Gln Lys
290                 295                 300

Gly Ile Asn His Asp Asn Glu Asn Asp Phe Met Ala Val Leu Ile Ser
305                 310                 315                 320

Val Leu Gly Glu Gly Lys Asp Asp His Ile Phe Gly Tyr Ser Arg Asp
                325                 330                 335

Thr Val Ile Lys Ala Thr Cys Leu Thr Leu Ile Val Ala Ala Thr Asp
                340                 345                 350

Thr Thr Leu Val Ser Leu Thr Trp Ala Leu Ser Leu Leu Leu Thr Asn
            355                 360                 365

Pro Arg Val Leu Ser Lys Ala Gln Asp Glu Leu Asp Thr Val Val Gly
            370                 375                 380

Lys Glu Arg Asn Val Glu Asp Arg Asp Val Asn His Leu Val Tyr Leu
385                 390                 395                 400

Gln Ala Val Ile Lys Glu Thr Leu Arg Leu Tyr Pro Pro Ser Pro Leu
                405                 410                 415

Ala Val Pro His Glu Ala Ile Glu Asn Cys Asn Val Gly Gly Tyr Glu
                420                 425                 430

Val Lys Ala Arg Thr Arg Leu Leu Val Asn Leu Trp Lys Ile His Arg
            435                 440                 445

Asp Pro Arg Val Trp Ser Asn Pro Leu Glu Phe Lys Pro Glu Arg Phe
            450                 455                 460

Leu Pro Lys Leu Asp Gly Gly Thr Gly Glu Ala Ser Lys Leu Asp Phe
465                 470                 475                 480

Lys Gly Gln Asp Phe Val Tyr Thr Pro Phe Gly Ser Gly Arg Arg Met
                485                 490                 495

Cys Pro Gly Ile Asn Phe Ala Ser Gln Thr Leu His Met Thr Leu Ala
            500                 505                 510

Arg Leu Leu His Ala Phe Asp Phe Asp Ile Glu Ser Asn Gly Leu Val
            515                 520                 525

Ile Asp Met Thr Glu Gly Ser Gly Leu Thr Met Pro Lys Val Thr Pro
530                 535                 540

Leu Gln Val His Leu Arg Pro Arg Leu Pro Ala Thr Leu Tyr
545                 550                 555

<210> SEQ ID NO 51
<211> LENGTH: 534
<212> TYPE: PRT
<213> ORGANISM: Menispermum canadense

<400> SEQUENCE: 51

Met Ile Met Met Phe Ile Asp Tyr Tyr Ser Ser Trp Leu Pro Gln Thr
1               5                   10                  15

Leu Leu Leu Gln Ser Ile Leu Leu Ala Val Ser Leu Val Ile Phe Ile
                20                  25                  30

Asn Leu Phe Leu Thr Arg Arg Arg Ser Tyr Ser Ser Lys Ser His Thr
            35                  40                  45

Asn Ile Ile His Pro Pro Lys Ala Ala Gly Ala Leu Pro Val Ile Gly
50                  55                  60

His Leu Tyr Thr Leu Phe Arg Gly Leu Ser Ala Gly Val Pro Leu Tyr
65                  70                  75                  80

Arg Gln Leu Asp Ala Met Ala Asp Arg Tyr Gly Pro Ala Phe Ile Ile
```

```
                            85                  90                  95
His Leu Gly Val Tyr Pro Thr Leu Val Val Thr Cys Arg Glu Leu Ala
            100                 105                 110

Lys Glu Cys Phe Thr Thr Asn Asp Gln Thr Phe Ala Thr Arg Pro Ser
            115                 120                 125

Thr Cys Ala Gly Lys Tyr Ile Gly Tyr Asn Tyr Ala Phe Phe Gly Phe
            130                 135                 140

Ala Pro Tyr Gly Pro Tyr Trp Arg Glu Arg Lys Ile Ala Thr Val
145                 150                 155                 160

Glu Leu Leu Ser Asn Tyr Arg Leu Asp Ser Leu Arg His Val Arg Glu
                165                 170                 175

Ala Glu Val Gly Arg Asn Val Asp Glu Leu Tyr Ala Leu His Ala Ser
            180                 185                 190

Ser Ser Thr Asn Lys Gln Asn Met Met Lys Ile Asp Met Lys Gln Trp
            195                 200                 205

Phe Asp Gln Val Thr Leu Asn Val Ile Leu Met Met Val Val Gly Lys
210                 215                 220

Arg Cys Val Thr Thr Gly Gly Asn Glu Glu Glu Val Arg Val Val Lys
225                 230                 235                 240

Val Leu His Glu Phe Phe Lys His Leu Gly Thr Leu Ser Val Ser Asp
                245                 250                 255

Val Val Pro Tyr Val Glu Trp Met Asp Leu Asp Gly Asn Ile Gly Arg
            260                 265                 270

Met Lys Ser Thr Ala Lys Glu Leu Asp Cys Ile Leu Gly Arg Trp Leu
            275                 280                 285

Glu Glu His Arg Arg Glu Arg Arg Ser Asp Phe Met Asp Ala Met Leu
290                 295                 300

Ala Met Val Glu Gly Ile Lys Ile Pro Tyr Tyr Asp Ser Asp Thr Val
305                 310                 315                 320

Ile Lys Ala Ile Cys Leu Asn Leu Leu Asn Ala Gly Ser Asp Thr Leu
                325                 330                 335

Gly Ile Thr Met Thr Trp Ala Leu Ser Leu Leu Asn Asn Arg His
            340                 345                 350

Val Leu Lys Lys Val Lys Asp Glu Leu Asp Val His Val Gly Lys Asn
            355                 360                 365

Arg Gln Val Glu Glu Leu Asp Val Lys Asn Leu Val Tyr Leu His Ala
            370                 375                 380

Val Val Lys Glu Thr Leu Arg Leu Phe Pro Ala Pro Leu Gly Val
385                 390                 395                 400

Pro His Glu Ala Met Glu Asp Cys Val Val Gly Gly Phe His Val Ala
                405                 410                 415

Lys Gly Thr Arg Leu Val Val Asn Val Trp Lys Leu His Arg Asp Pro
            420                 425                 430

Ser Val Trp Ser Asp Pro Leu Ala Phe Lys Pro Glu Arg Phe Leu Asp
            435                 440                 445

Asn Asn Thr Val Asp Val Arg Gly Gln His Phe Gln Leu Leu Pro Phe
450                 455                 460

Gly Ser Gly Arg Arg Gly Cys Pro Gly Ile Thr Phe Ala Leu Gln Val
465                 470                 475                 480

Ala His Leu Thr Leu Ala Arg Leu Leu His Gly Phe Glu Trp Asp Thr
                485                 490                 495

Pro Asp Gly Ala Pro Val Asp Met Ser Glu Val Ser Val Leu Thr Thr
            500                 505                 510
```

-continued

```
Ala Lys Lys Asn Pro Val Glu Val Leu Phe Thr Pro Arg Leu Pro Ala
        515                 520                 525

Glu Val Tyr Thr Gln Asn
    530

<210> SEQ ID NO 52
<211> LENGTH: 527
<212> TYPE: PRT
<213> ORGANISM: Nigella sativa

<400> SEQUENCE: 52

Met Leu Ser Ile His Asp Ser Thr Met Val Phe Leu Gln Leu Gln Ala
1               5                   10                  15

Ile Cys Gly Ile Phe Gly Phe Ile Phe Ile Ile Thr Trp Trp Thr Arg
            20                  25                  30

Trp Lys Ser Ser Asn Lys Met Lys Ala Pro Glu Val Ala Gly Ala Trp
        35                  40                  45

Pro Val Ile Gly His Leu His Leu Leu Gly Gly Arg Pro Leu Tyr
    50                  55                  60

Gln Leu Leu Gly Asp Met Ser Asp Lys Tyr Gly Pro Ala Phe Thr Leu
65                  70                  75                  80

Arg Met Gly Ile Gln Lys Ala Leu Val Val Ser Ser Trp Glu Val Ala
                85                  90                  95

Lys Glu Cys Leu Thr Thr Asn Asp Arg Ala Leu Ala Thr Arg Pro Ser
            100                 105                 110

Ser Ala Gly Gly Lys Tyr Met Gly Tyr Asn Asn Ala Leu Ile Pro Phe
        115                 120                 125

Ser Pro Tyr Gly Pro Tyr Trp Arg Asp Met Arg Lys Ile Ala Thr Leu
    130                 135                 140

Glu Leu Leu Ser Asn His Arg Leu Glu Glu Leu Lys His Val Arg Glu
145                 150                 155                 160

Met Glu Ile Asn Thr Cys Ile Ser Asp Met Tyr Lys Leu Cys Gln Val
                165                 170                 175

Glu Asp Gly Val Glu Ile Lys Pro Ile Ser Val Asp Leu Ser Gln Trp
            180                 185                 190

Phe Ala Asp Leu Thr Phe Asn Val Val Met Met Ile Thr Gly Lys
        195                 200                 205

Arg Tyr Ile Gly Ser Thr Asp Ala Gly Asp Met Asn Glu Ile Arg His
    210                 215                 220

Phe Gln Ala Ala Leu Val Lys Phe Met Arg Leu Leu Arg Ile Ser Leu
225                 230                 235                 240

Leu Val Asp Val Phe Pro Val Leu Gln Trp Ile Asn Tyr Gly Gly Phe
                245                 250                 255

Lys Gly Val Met Lys Ser Thr Ala Arg Asp Ile Asp Ser Val Leu Glu
            260                 265                 270

Asn Trp Leu Gln Glu His Gln Arg Lys Arg Leu Ser Pro Asp Phe Asn
        275                 280                 285

Gly Asn His Asp Phe Ile Asp Val Met Ile Ser Thr Leu Glu Gly Thr
    290                 295                 300

Glu Phe Ser Asp Tyr Asp His Asn Thr Ile Ile Lys Ala Ile Ser Met
305                 310                 315                 320

Ala Met Val Val Gly Gly Thr Asp Thr Thr Thr Thr Thr Leu Ile Trp
                325                 330                 335

Ala Ile Ser Leu Leu Leu Asn Asn Pro Asn Ala Met Lys Lys Val Gln
```

```
              340              345               350
Glu Glu Leu Glu Ile His Val Gly Lys Glu Arg Asn Val Asp Gly Ser
            355                 360               365

Asp Ile Gln His Leu Val Tyr Leu Gln Ala Val Val Lys Glu Thr Leu
        370                 375             380

Arg Leu Tyr Pro Pro Val Pro Leu Ser Val Met His Gln Ala Met Glu
385                 390                 395                 400

Asp Cys Val Ile Gly Ser Tyr Asn Ile Gln Ala Gly Thr Arg Val Leu
                405                 410                 415

Phe Asn Leu Trp Lys Leu His Arg Asp Ser Ser Val Trp Ser Asp Pro
            420                 425                 430

Leu Glu Phe Arg Pro Glu Arg Phe Leu Thr Ser His Val Asp Val Asp
        435                 440                 445

Val Arg Gly Gln His Phe Glu Leu Ile Pro Phe Gly Ser Gly Arg Arg
    450                 455                 460

Ser Cys Pro Gly Ile Ser Phe Ala Leu Gln Val Ile His Leu Thr Ile
465                 470                 475                 480

Ala Arg Leu Phe His Gly Phe Asn Leu Thr Thr Pro Gly Asn Ser Ser
                485                 490                 495

Val Asp Met Ser Glu Ile Ser Gly Ala Thr Leu Ser Lys Val Thr Pro
            500                 505                 510

Leu Glu Val Leu Val Thr Pro Arg Leu Ser Ser Lys Leu Tyr Asn
        515                 520                 525

<210> SEQ ID NO 53
<211> LENGTH: 525
<212> TYPE: PRT
<213> ORGANISM: Hydrastis canadensis

<400> SEQUENCE: 53

Met Asp Ser Leu Leu Gln Leu Gln Ile Ile Gly Ala Leu Ala Ala Leu
1               5                   10                  15

Ile Phe Thr Tyr Lys Leu Leu Lys Val Ile Cys Arg Ser Pro Met Thr
                20                  25                  30

Asp Gly Met Glu Ala Pro Glu Pro Pro Gly Ala Trp Pro Ile Ile Gly
            35                  40                  45

His Leu His Leu Leu Gly Gly Gln Asp Pro Ile Ala Arg Thr Leu Gly
        50                  55                  60

Val Met Thr Asp Lys Tyr Gly Pro Ile Leu Lys Leu Arg Leu Gly Val
65                  70                  75                  80

His Thr Gly Leu Val Val Ser Asn Trp Glu Leu Ala Lys Glu Cys Phe
                85                  90                  95

Thr Thr Asn Asp Arg Val Leu Ala Ser Arg Pro Met Gly Ala Ala Gly
            100                 105                 110

Lys Tyr Leu Gly Tyr Asn Tyr Ala Ile Phe Gly Leu Ala Pro His Gly
        115                 120                 125

Pro Tyr Trp Ser Glu Val Arg Lys Ile Val Leu Arg Glu Leu Leu Ser
    130                 135                 140

Asn Gln Ser Leu Glu Lys Leu Lys His Val Arg Ile Ser Glu Ile Asn
145                 150                 155                 160

Thr Cys Leu Lys Asn Leu Phe Ser Leu Asn Asn Gly Asn Thr Pro Ile
                165                 170                 175

Lys Val Asp Met Lys Gln Trp Phe Glu Arg Pro Met Phe Asn Val Val
            180                 185                 190
```

Thr Met Met Ile Ala Gly Lys Arg Tyr Phe Ser Met Glu Asn Asp Asn
            195                 200                 205

Glu Ala Met Asn Phe Arg Lys Val Ala Thr Glu Phe Met Tyr Leu Thr
        210                 215                 220

Gly Val Phe Val Val Ser Asp Ala Leu Pro Tyr Leu Glu Trp Leu Asp
225                 230                 235                 240

Leu Gln Gly His Val Ser Ala Met Lys Arg Thr Ala Lys Glu Leu Asp
                245                 250                 255

Ile His Val Gly Lys Trp Leu Glu Glu His Arg Arg Ala Lys Leu Leu
            260                 265                 270

Gly Glu Thr Lys Asn Glu Asp Asp Phe Val Asp Val Leu Leu Thr Ile
        275                 280                 285

Leu Pro Glu Asp Leu Lys Asp Asn Gln Thr Tyr Ile His Asp Arg Asp
    290                 295                 300

Thr Ile Ile Lys Ala Thr Ala Leu Ala Leu Phe Leu Ala Ala Ser Asp
305                 310                 315                 320

Thr Thr Ala Ile Thr Leu Thr Trp Ala Leu Ser Leu Ile Leu Asn Asn
                325                 330                 335

Pro Asp Val Leu Lys Arg Ala Gln Asp Glu Leu Asp Lys His Val Gly
            340                 345                 350

Lys Glu Lys Leu Val Lys Glu Ser Asp Ile Ile Asn Leu Val Tyr Leu
        355                 360                 365

Gln Ala Ile Ile Lys Glu Thr Leu Arg Leu Tyr Pro Ala Ala Pro Leu
    370                 375                 380

Leu Leu Pro His Glu Ala Met Glu Asp Cys Thr Val Gly Gly Tyr His
385                 390                 395                 400

Val Pro Lys Gly Thr Arg Ile Phe Val Asn Ile Trp Lys Leu Gln Arg
                405                 410                 415

Asp Pro Arg Val Trp Phe Asp Pro Asn Glu Phe Arg Pro Glu Arg Phe
            420                 425                 430

Leu Thr Thr His Ala Asn Val Asp Phe Lys Gly Gln His Phe Glu Tyr
        435                 440                 445

Ile Pro Phe Ser Ser Gly Arg Arg Val Cys Pro Gly Ile Thr Phe Ser
    450                 455                 460

Thr Gln Ile Met His Leu Thr Leu Ala His Leu Leu His Glu Phe Asn
465                 470                 475                 480

Ile Val Thr Pro Thr Lys Ser Asn Ala Gly Val Asp Met Thr Glu Ser
                485                 490                 495

Leu Gly Ile Thr Met Pro Lys Ala Thr Pro Leu Glu Val Leu Leu Thr
            500                 505                 510

Pro Arg Leu Pro Ser Asn Leu Tyr Asn Gln Tyr Arg Asp
        515                 520                 525

<210> SEQ ID NO 54
<211> LENGTH: 550
<212> TYPE: PRT
<213> ORGANISM: Eschscholzia californica

<400> SEQUENCE: 54

Met Asn Leu Leu Ile Phe Phe Gln Phe Leu Leu Gln Phe Gln Val Leu
1               5                   10                  15

Val Gly Leu Ser Val Leu Leu Ala Phe Ser Tyr Tyr Leu Trp Val Ser
                20                  25                  30

Lys Asn Pro Lys Ile Asn Lys Phe Lys Gly Lys Gly Ala Leu Leu Ala
            35                  40                  45

```
Pro Gln Ala Ala Gly Ala Trp Pro Ile Val Gly His Leu Pro Gln Leu
 50                  55                  60

Val Gly Pro Lys Pro Leu Phe Arg Ile Leu Gly Ala Met Ala Asp Asn
 65                  70                  75                  80

Tyr Gly Pro Ile Phe Met Leu Arg Phe Gly Val His Pro Thr Val Val
                     85                  90                  95

Val Ser Ser Trp Glu Met Thr Lys Glu Cys Phe Thr Thr Asn Asp Arg
                100                 105                 110

His Leu Ala Ser Arg Pro Ser Asn Ala Ala Ser Gln Tyr Leu Ile Tyr
                115                 120                 125

Glu Val Tyr Ala Leu Phe Gly Phe Ser Leu Tyr Gly Ser Ser Tyr Trp
130                 135                 140

Arg Asp Ala Arg Lys Ile Ala Thr Leu Glu Leu Leu Ser His Arg Arg
145                 150                 155                 160

Leu Glu Leu Leu Lys His Val Pro Tyr Thr Glu Ile Asp Thr Cys Ile
                165                 170                 175

Lys Gln Leu His Arg Leu Trp Thr Lys Asn Asn Lys Asn Gln Asn Asn
                180                 185                 190

Pro Glu Leu Lys Val Glu Met Asn Gln Phe Thr Asp Leu Thr Met
                195                 200                 205

Asn Val Ile Leu Lys Leu Val Val Gly Lys Arg Phe Phe Asn Val Asp
210                 215                 220

Asp Ala Ala Asp His Glu Lys Glu Ala Arg Lys Ile Gln Gly Thr
225                 230                 235                 240

Ile Phe Glu Phe Phe Lys Leu Thr Glu Gly Ser Val Ser Ala Gly Ala
                245                 250                 255

Leu Pro Leu Leu Asn Trp Leu Asp Leu Asn Gly Gln Lys Arg Ala Met
                260                 265                 270

Lys Arg Thr Ala Lys Lys Met Asp Ser Ile Ala Glu Lys Leu Leu Asp
                275                 280                 285

Glu His Arg Gln Lys Arg Leu Ser Lys Glu Gly Val Lys Gly Thr His
                290                 295                 300

Asp His Asn Asp Phe Met Asp Val Leu Leu Ser Ile Leu Asp Ala Asp
305                 310                 315                 320

Gln Gly Asp Tyr Ser His His Pro Phe Asn Tyr Ser Arg Asp His Val
                325                 330                 335

Ile Lys Ala Thr Thr Leu Ser Met Ile Leu Ser Ser Met Ser Ile Ser
                340                 345                 350

Val Ser Leu Ser Trp Ala Leu Ser Leu Leu Asn Asn Arg His Val
                355                 360                 365

Leu Lys Lys Ala Gln Asp Glu Leu Asp Met Asn Val Gly Lys Asp Arg
370                 375                 380

Gln Val Glu Glu Gly Asp Ile Lys Asn Leu Val Tyr Leu Gln Ala Ile
385                 390                 395                 400

Val Lys Glu Thr Phe Arg Met Tyr Pro Ala Asn Pro Leu Leu Leu Pro
                405                 410                 415

His Glu Ala Ile Glu Asp Cys Lys Ile Gly Gly Phe Asn Val Pro Ala
                420                 425                 430

Gly Thr Arg Val Val Val Asn Ala Trp Lys Leu Gln His Asp Pro Arg
                435                 440                 445

Val Trp Ser Asn Pro Ser Glu Phe Lys Pro Glu Arg Phe Leu Asn Asp
450                 455                 460
```

```
Gln Ala Ala Lys Val Val Asp Val Arg Gly Gln Asn Phe Glu Tyr Leu
465                 470                 475                 480

Pro Phe Gly Ser Gly Arg Arg Val Cys Pro Gly Ile Ser Phe Ser Leu
            485                 490                 495

Gln Thr Ile His Met Ser Leu Ala Arg Leu Val Gln Ala Phe Glu Leu
        500                 505                 510

Gly Thr Pro Ser Asn Glu Arg Ile Asp Met Thr Glu Gly Ser Gly Leu
            515                 520                 525

Thr Met Pro Lys Thr Thr Pro Leu His Val Leu Leu Asn Pro Arg Leu
        530                 535                 540

Pro Leu Pro Leu Tyr Glu
545                 550

<210> SEQ ID NO 55
<211> LENGTH: 537
<212> TYPE: PRT
<213> ORGANISM: Glaucium flavum

<400> SEQUENCE: 55

Met Glu Leu Ile Asn Ser Leu Glu Ile Gln Pro Ile Thr Ile Ser Ile
1               5                   10                  15

Leu Ala Leu Leu Thr Val Ser Ile Leu Leu Tyr Lys Ile Ile Trp Asn
                20                  25                  30

His Gly Ser Arg Lys Asn Asn Lys Ser Asn Lys Asn Asn Arg Lys Thr
            35                  40                  45

Ser Ser Ser Ala Gly Val Val Glu Ile Pro Gly Ala Trp Pro Ile Ile
        50                  55                  60

Gly His Leu His Leu Phe Asn Gly Ser Glu Gln Met Phe His Lys Leu
65                  70                  75                  80

Gly Ser Leu Ala Asp Gln Tyr Gly Pro Ala Pro Phe Phe Ile Arg Phe
                85                  90                  95

Gly Ser Arg Lys Tyr Val Val Val Ser Asn Trp Glu Leu Val Lys Thr
            100                 105                 110

Cys Phe Thr Ala Gln Ser Gln Ile Phe Val Ser Arg Pro Pro Met Leu
        115                 120                 125

Ala Met Asn Ile Leu Phe Phe Pro Lys Asp Ser Leu Ser Tyr Ile Gln
130                 135                 140

His Gly Asp His Trp Arg Glu Leu Arg Lys Ile Ser Ser Thr Lys Leu
145                 150                 155                 160

Leu Ser Ser His Arg Val Glu Thr Gln Lys His Leu Ile Ala Ser Glu
                165                 170                 175

Val Asp Tyr Cys Phe Lys Gln Leu Tyr Lys Leu Ser Asn Asn Gly Glu
            180                 185                 190

Phe Thr Leu Val Arg Leu Asn Thr Trp Cys Glu Asp Met Ala Leu Asn
        195                 200                 205

Val His Val Arg Met Ile Ala Gly Met Lys Asn Tyr Val Ala Ala Pro
210                 215                 220

Gly Ser Gly Glu Tyr Gly Gly Gln Ala Arg Arg Tyr Arg Lys Ala Leu
225                 230                 235                 240

Glu Glu Ala Leu Asp Leu Leu Asn Gln Phe Thr Ile Thr Asp Val Val
                245                 250                 255

Pro Trp Leu Gly Trp Leu Asp His Phe Arg Asp Val Val Gly Arg Met
            260                 265                 270

Lys Arg Cys Gly Ala Glu Leu Asp Ser Ile Phe Ala Thr Trp Val Glu
        275                 280                 285
```

```
Glu His Arg Val Lys Arg Ala Ser Gly Lys Gly Gly Asp Val Glu Pro
    290                 295                 300

Asp Phe Ile Asp Leu Cys Trp Glu Ser Met Glu Gln Leu Pro Gly Asn
305                 310                 315                 320

Asp Pro Ala Thr Val Ile Lys Leu Met Cys Lys Glu His Ile Phe Asn
                325                 330                 335

Gly Ser Gly Thr Ser Ser Leu Thr Leu Ala Trp Ile Leu Ser Leu Ile
                340                 345                 350

Met Asn Asn Pro Tyr Val Ile Lys Lys Ala Arg Glu Glu Leu Glu Lys
            355                 360                 365

His Val Gly Asn His Arg Gln Val Glu Glu Ser Asp Leu Pro Asn Leu
        370                 375                 380

Leu Tyr Ile Gln Ala Ile Ile Lys Glu Gly Met Arg Leu Tyr Thr Pro
385                 390                 395                 400

Gly Pro Phe Ile Asp Arg Asn Thr Thr Glu Asp Tyr Glu Ile Asn Gly
                405                 410                 415

Val His Ile Pro Ala Gly Thr Cys Leu Tyr Val Asn Leu Trp Lys Ile
            420                 425                 430

His Arg Asp Pro Asn Val Tyr Glu Asp Pro Leu Glu Phe Lys Pro Glu
        435                 440                 445

Arg Phe Leu Lys Asn Asn Ser Asp Leu Asp Leu Lys Gly Gln Asn Tyr
450                 455                 460

Gln Leu Leu Pro Phe Gly Ala Gly Arg Arg Ile Cys Pro Gly Val Ser
465                 470                 475                 480

Leu Ala Leu Pro Leu Met Tyr Leu Thr Val Ser Arg Leu Ile His Gly
                485                 490                 495

Phe Asp Met Lys Leu Pro Lys Gly Val Glu Lys Ala Asp Met Thr Ala
            500                 505                 510

His Gly Gly Val Ile Asn Gln Arg Ala Tyr Pro Leu Glu Val Leu Leu
        515                 520                 525

Lys Pro Arg Leu Thr Phe Gln Gln Ala
    530                 535

<210> SEQ ID NO 56
<211> LENGTH: 568
<212> TYPE: PRT
<213> ORGANISM: Stylophorum diphyllum

<400> SEQUENCE: 56

Met Thr Ile Gly Ala Leu Ala Leu Leu Ser Phe Ile Tyr Phe Leu Arg
1               5                   10                  15

Val Ser Val Ile Lys Arg Thr Lys Tyr Thr Asn Thr Ala Val Thr Ala
            20                  25                  30

Thr Asn Lys Leu Glu Asn Asp Glu Asp Glu Ala Asn His Ser Lys Arg
        35                  40                  45

Val Val Ala Pro Pro Glu Val Ala Gly Ala Trp Pro Ile Leu Gly His
    50                  55                  60

Leu Pro Gln Leu Val Gly Leu Lys Gln Pro Leu Phe Arg Val Leu Gly
65                  70                  75                  80

Asp Met Ala Asp Lys Tyr Gly Pro Ile Phe Ile Val Arg Phe Gly Met
                85                  90                  95

Tyr Pro Thr Leu Val Val Ser Ser Trp Glu Met Ala Lys Glu Cys Phe
            100                 105                 110

Thr Thr Asn Asp Arg Val Leu Ala Ser Arg Pro Ala Ser Ala Ser Gly
```

-continued

```
            115                 120                 125
Lys Tyr Leu Thr Tyr Asn Tyr Ala Met Phe Gly Phe Thr Asn Gly Pro
130                 135                 140

Tyr Trp Arg Glu Ile Arg Lys Ile Ser Met Leu Glu Leu Leu Ser His
145                 150                 155                 160

Arg Arg Val Glu Leu Leu Lys His Val Pro Ser Thr Glu Ile Asp Ser
                165                 170                 175

Ser Ile Lys Gln Leu Tyr His Leu Trp Val Glu Asn Gln Asn Gln Asn
            180                 185                 190

Lys Gln Gly Asp His Gln Val Lys Val Asp Met Ser Gln Leu Leu Arg
        195                 200                 205

Asp Leu Thr Leu Asn Ile Val Leu Lys Leu Val Val Gly Lys Arg Leu
    210                 215                 220

Phe Asn Asn Asn Asp Met Asp His Glu Gln Asp Glu Ala Ala Arg Lys
225                 230                 235                 240

Leu Gln Lys Thr Met Val Glu Leu Ile Lys Val Ala Gly Ala Ser Val
                245                 250                 255

Ala Ser Asp Ala Leu Pro Phe Leu Gly Trp Leu Asp Val Asp Gly Leu
            260                 265                 270

Lys Arg Thr Met Lys Arg Ile Ala Lys Glu Ile Asp Val Ile Ala Glu
        275                 280                 285

Arg Trp Leu Gln Glu His Arg Gln Lys Leu Thr Ser Asn Asp Lys
    290                 295                 300

Gly Gly Ser Asn Asn Ile Gln Gly Gly Gly Asp Asn Asp Phe Met
305                 310                 315                 320

Asp Val Met Leu Ser Ile Leu Asp Asp Ser Asn Phe Phe Ile Asn
                325                 330                 335

Tyr Asn Arg Asp Thr Val Ile Lys Ala Thr Ser Leu Thr Met Ile Leu
            340                 345                 350

Ala Gly Ser Asp Thr Thr Thr Leu Ser Leu Thr Trp Ala Leu Thr Leu
        355                 360                 365

Leu Ala Thr Asn Pro Gly Ala Leu Arg Lys Ala Gln Asp Glu Leu Asp
    370                 375                 380

Thr Lys Val Gly Arg Asp Arg Gln Val Asp Glu Arg Asp Ile Lys Asn
385                 390                 395                 400

Leu Val Tyr Leu Gln Ala Ile Val Lys Glu Thr Leu Arg Met Tyr Pro
                405                 410                 415

Ala Ala Pro Leu Ala Ile Pro His Glu Ala Thr Gln Asp Cys Ile Val
            420                 425                 430

Gly Gly Tyr His Val Thr Ala Gly Thr Arg Val Trp Val Asn Leu Trp
        435                 440                 445

Lys Leu Gln Arg Asp Pro His Ala Trp Pro Asn Pro Ser Glu Phe Arg
    450                 455                 460

Pro Glu Arg Phe Leu Ala Val Glu Asn Asp Cys Lys Gln Gln Gly Thr
465                 470                 475                 480

Cys Asp Gly Glu Ala Ala Asn Met Asp Phe Arg Gly Gln His Phe Glu
                485                 490                 495

Tyr Met Pro Phe Gly Ser Gly Arg Met Cys Pro Gly Ile Asn Phe
            500                 505                 510

Ala Ile Gln Ile Ile His Met Thr Leu Ala Arg Leu Leu His Ser Phe
        515                 520                 525

Glu Leu Arg Val Pro Glu Glu Val Ile Asp Met Ala Glu Asp Ser
    530                 535                 540
```

Gly Leu Thr Ile Ser Lys Val Thr Pro Leu Glu Leu Leu Thr Pro
545                 550                 555                 560

Arg Leu Pro Leu Pro Leu Tyr Ile
                565

<210> SEQ ID NO 57
<211> LENGTH: 561
<212> TYPE: PRT
<213> ORGANISM: Stylophorum diphyllum

<400> SEQUENCE: 57

Phe Cys Gln Phe Gln Gly Ile Val Gly Ile Leu Leu Ala Phe Leu Thr
1               5                   10                  15

Phe Leu Tyr Tyr Leu Trp Arg Ala Ser Ile Thr Gly Leu Arg Thr Lys
            20                  25                  30

Pro Lys His Asn Asp Phe Lys Val Thr Lys Ala Ala Pro Glu Ala Asp
        35                  40                  45

Gly Ala Trp Pro Ile Val Gly His Phe Ala Gln Phe Ile Gly Pro Arg
    50                  55                  60

Pro Leu Phe Arg Ile Leu Gly Asp Met Ala Asp Lys Tyr Gly Ser Ile
65                  70                  75                  80

Phe Met Val Arg Phe Gly Met Tyr Pro Thr Leu Val Val Ser Ser Trp
                85                  90                  95

Glu Met Ala Lys Glu Cys Phe Thr Thr Asn Asp Arg Phe Leu Ala Ser
            100                 105                 110

Arg Pro Ala Ser Ala Ala Gly Lys Tyr Leu Thr Tyr Asp Phe Ala Met
        115                 120                 125

Leu Ser Phe Ser Phe Tyr Gly Pro Tyr Trp Arg Glu Ile Arg Lys Ile
130                 135                 140

Ser Met Leu Glu Leu Leu Ser His Arg Arg Val Glu Leu Leu Lys His
145                 150                 155                 160

Val Pro Ser Thr Glu Ile Asp Ser Ser Ile Lys Gln Leu Tyr His Leu
                165                 170                 175

Trp Val Glu Asn Gln Asn Gln Asn Lys Gln Gly Asp His Gln Val Lys
            180                 185                 190

Val Asp Met Ser Gln Leu Leu Arg Asp Leu Thr Leu Asn Ile Val Leu
        195                 200                 205

Lys Leu Val Val Gly Lys Arg Leu Phe Asn Asn Asn Asp Met Asp His
210                 215                 220

Glu Gln Asp Glu Ala Ala Arg Lys Leu Gln Lys Thr Met Val Glu Leu
225                 230                 235                 240

Ile Lys Val Ala Gly Ala Ser Val Ala Ser Asp Ala Leu Pro Phe Leu
                245                 250                 255

Gly Trp Leu Asp Val Asp Gly Leu Lys Arg Thr Met Lys Arg Ile Ala
            260                 265                 270

Lys Glu Ile Asp Val Ile Ala Glu Arg Trp Leu Gln Glu His Arg Gln
        275                 280                 285

Lys Lys Leu Thr Ser Asn Asp Lys Gly Gly Ser Asn Asn Ile Gln Gly
    290                 295                 300

Gly Gly Gly Asp Asn Asp Phe Met Asp Val Met Leu Ser Ile Leu Asp
305                 310                 315                 320

Asp Asp Ser Asn Phe Phe Ile Asn Tyr Asn Arg Asp Thr Val Ile Lys
                325                 330                 335

Ala Thr Ser Leu Thr Met Ile Leu Ala Gly Ser Asp Thr Thr Thr Leu

```
              340                 345                 350
Ser Leu Thr Trp Ala Leu Thr Leu Leu Ala Thr Tyr Pro Leu Cys Ala
            355                 360                 365

Leu Arg Lys Ala Gln Asp Glu Leu Asp Thr Lys Val Gly Arg Asp Arg
370                 375                 380

Gln Val Asp Glu Arg Asp Ile Lys Asn Leu Val Tyr Leu Gln Ala Ile
385                 390                 395                 400

Val Lys Glu Thr Leu Arg Met Tyr Pro Ala Ala Pro Leu Ala Ile Pro
                405                 410                 415

His Glu Ala Thr Gln Asp Cys Ile Val Gly Gly Tyr His Val Thr Ala
            420                 425                 430

Gly Thr Arg Val Trp Val Asn Leu Trp Lys Leu Gln Arg Asp Pro His
        435                 440                 445

Ala Trp Pro Asn Pro Ser Glu Phe Arg Pro Glu Arg Phe Leu Ala Val
    450                 455                 460

Glu Asn Asp Cys Lys Gln Gln Gly Thr Cys Asp Gly Glu Ala Ala Asn
465                 470                 475                 480

Met Asp Phe Arg Gly Gln His Phe Glu Tyr Met Pro Phe Gly Ser Gly
                485                 490                 495

Arg Arg Met Cys Pro Gly Ile Asn Phe Ala Ile Gln Ile Ile His Met
            500                 505                 510

Thr Leu Ala Arg Leu Leu His Ser Phe Glu Leu Arg Val Pro Glu Glu
        515                 520                 525

Glu Val Ile Asp Met Ala Glu Asp Ser Gly Leu Thr Ile Ser Lys Val
    530                 535                 540

Thr Pro Leu Glu Leu Leu Leu Thr Pro Arg Leu Pro Leu Pro Leu Tyr
545                 550                 555                 560

Ile

<210> SEQ ID NO 58
<211> LENGTH: 561
<212> TYPE: PRT
<213> ORGANISM: Chelidonium majus

<400> SEQUENCE: 58

Met Asp Leu Phe Ile Phe Phe Ser Arg Phe Gln Tyr Ile Val Gly Leu
1               5                   10                  15

Leu Ala Phe Leu Thr Phe Phe Tyr Tyr Leu Trp Arg Val Ser Ile Thr
                20                  25                  30

Gly Thr Arg Ile Lys Thr Asn Gln Asn Ile Met Asn Gly Thr Asn Met
            35                  40                  45

Met Ala Pro Glu Ala Ala Gly Ala Trp Pro Ile Val Gly His Leu Pro
        50                  55                  60

Gln Leu Val Gly Pro Gln Pro Leu Phe Lys Ile Leu Gly Asp Met Ala
65                  70                  75                  80

Asp Lys Tyr Gly Ser Ile Phe Met Val Arg Phe Gly Met His Pro Thr
                85                  90                  95

Leu Val Val Ser Ser Trp Glu Met Ala Lys Glu Cys Phe Thr Thr Asn
            100                 105                 110

Asp Lys Phe Leu Ala Ser Arg Pro Thr Ser Ala Gly Gly Lys Tyr Leu
        115                 120                 125

Thr Tyr Asp Phe Ala Met Phe Gly Phe Ser Phe Tyr Gly Pro Tyr Trp
    130                 135                 140

Arg Glu Ile Arg Lys Ile Ser Thr Leu Glu Leu Leu Ser His Arg Arg
```

```
            145                 150                 155                 160
        Val Glu Leu Leu Lys His Val Pro Tyr Thr Glu Ile Gly Gly Ser Ile
                        165                 170                 175

Lys Gln Leu Tyr Lys Leu Trp Met Glu Thr Gln Asn Gln Asn Lys Gln
                        180                 185                 190

Arg Asp Asp His Gln Val Lys Val Asp Met Ser Gln Val Phe Gly Tyr
                        195                 200                 205

Leu Thr Leu Asn Thr Val Leu Lys Leu Val Gly Lys Gly Leu Phe
            210                 215                 220

Asn Asn Asn Asp Met Asn His Glu Gln Glu Glu Gly Arg Lys Leu His
        225                 230                 235                 240

Glu Thr Val Leu Glu Phe Phe Lys Leu Ala Gly Val Ser Val Ala Ser
                        245                 250                 255

Asp Ala Leu Pro Phe Leu Gly Trp Leu Asp Val Asp Gly Gln Lys Arg
                        260                 265                 270

Ser Met Lys Arg Ile Ala Lys Glu Met Asp Leu Ile Ala Glu Arg Trp
                        275                 280                 285

Leu Gln Glu His Arg Gln Lys Arg Leu Thr Ser Asn Asn Lys Ala Ser
            290                 295                 300

Ser Gly His Asp Asp Phe Met Ser Val Leu Leu Ser Ile Leu Asp Asp
        305                 310                 315                 320

Asp Ser Asn Phe Phe Asn Tyr Asn Arg Asp Thr Val Ile Lys Ala Thr
                        325                 330                 335

Ser Leu Asn Leu Ile Leu Ala Ala Ser Asp Thr Thr Ser Val Ser Leu
                        340                 345                 350

Thr Trp Val Leu Ser Leu Leu Val Thr Asn Pro Gly Ala Leu Lys Lys
                        355                 360                 365

Val Gln Asp Glu Leu Asp Thr Lys Val Gly Arg Asn Arg His Val Glu
            370                 375                 380

Glu Arg Asp Ile Glu Lys Leu Val Tyr Leu Gln Ala Thr Val Lys Glu
        385                 390                 395                 400

Thr Leu Arg Met Tyr Pro Ala Gly Pro Leu Ser Val Pro His Glu Ala
                        405                 410                 415

Thr Gln Asp Cys Thr Val Gly Gly Tyr Gln Val Thr Ala Gly Thr Arg
                        420                 425                 430

Leu Val Val Asn Val Trp Lys Leu Gln Arg Asp Pro Arg Val Trp Pro
                        435                 440                 445

Asn Pro Ser Glu Phe Lys Pro Glu Arg Phe Leu Pro Asp Gly Cys Glu
        450                 455                 460

Val Gly Cys Gly Glu Ala Ala Asn Met Asp Phe Arg Gly Gln His Phe
        465                 470                 475                 480

Glu Tyr Ile Pro Phe Gly Ser Gly Arg Arg Met Cys Pro Gly Ile Asp
                        485                 490                 495

Phe Ala Ile Gln Ile Ile His Met Thr Leu Ala Cys Leu Leu His Ala
                        500                 505                 510

Phe Glu Phe Gln Val Pro Ser Ser Leu Asp Lys His Leu Val Pro Ala
                        515                 520                 525

Val Ile Asp Met Ser Glu Gly Ser Gly Leu Thr Met Pro Lys Val Thr
            530                 535                 540

Pro Leu Glu Val Leu Leu Asn Pro Arg Leu Pro Leu Pro Leu Tyr Glu
        545                 550                 555                 560

Leu
```

```
<210> SEQ ID NO 59
<211> LENGTH: 561
<212> TYPE: PRT
<213> ORGANISM: Eschscholzia californica

<400> SEQUENCE: 59
```

| | | | | | | | | | | | | | | | |
|---|---|---|---|---|---|---|---|---|---|---|---|---|---|---|---|
| Met | Glu | Lys | Pro | Ile | Leu | Leu | Gln | Leu | Gln | Pro | Gly | Ile | Leu | Gly | Leu |
| 1 | | | | 5 | | | | | 10 | | | | | 15 | |
| Leu | Ala | Leu | Met | Cys | Phe | Leu | Tyr | Tyr | Val | Ile | Lys | Val | Ser | Leu | Ser |
| | | | 20 | | | | | 25 | | | | | 30 | | |
| Thr | Arg | Asn | Cys | Asn | Gln | Leu | Val | Arg | His | Pro | Pro | Glu | Ala | Ala | Gly |
| | | 35 | | | | | 40 | | | | | 45 | | | |
| Ser | Trp | Pro | Ile | Val | Gly | His | Leu | Pro | Gln | Leu | Val | Gly | Ser | Gly | Lys |
| | 50 | | | | | 55 | | | | | 60 | | | | |
| Pro | Leu | Phe | Arg | Val | Leu | Gly | Asp | Met | Ala | Asp | Lys | Phe | Gly | Pro | Ile |
| 65 | | | | | 70 | | | | | 75 | | | | | 80 |
| Phe | Met | Val | Arg | Phe | Gly | Val | His | Pro | Thr | Leu | Val | Val | Ser | Ser | Trp |
| | | | | 85 | | | | | 90 | | | | | 95 | |
| Glu | Met | Ala | Lys | Glu | Cys | Phe | Thr | Ser | Asn | Asp | Lys | Phe | Leu | Ala | Ser |
| | | | 100 | | | | | 105 | | | | | 110 | | |
| Arg | Pro | Pro | Ser | Ala | Ala | Ser | Ile | Tyr | Met | Ala | Tyr | Asp | His | Ala | Met |
| | | 115 | | | | | 120 | | | | | 125 | | | |
| Leu | Gly | Phe | Ser | Ser | Tyr | Gly | Pro | Tyr | Trp | Arg | Glu | Ile | Arg | Lys | Ile |
| | 130 | | | | | 135 | | | | | 140 | | | | |
| Ser | Thr | Leu | His | Leu | Leu | Ser | His | Arg | Arg | Leu | Glu | Leu | Leu | Lys | His |
| 145 | | | | | 150 | | | | | 155 | | | | | 160 |
| Val | Pro | His | Leu | Glu | Ile | His | Asn | Phe | Ile | Lys | Gly | Leu | Tyr | Gly | Ile |
| | | | | 165 | | | | | 170 | | | | | 175 | |
| Trp | Lys | Asp | His | Gln | Lys | Gln | Gln | Gln | Pro | Thr | Ala | Arg | Asp | Asp |
| | | | 180 | | | | | 185 | | | | | 190 | | |
| Gln | Asp | Ser | Val | Met | Leu | Glu | Met | Ser | Gln | Leu | Phe | Gly | Tyr | Leu | Thr |
| | | 195 | | | | | 200 | | | | | 205 | | | |
| Leu | Asn | Ile | Val | Leu | Ser | Leu | Val | Val | Gly | Lys | Arg | Val | Cys | Asn | Tyr |
| | 210 | | | | | 215 | | | | | 220 | | | | |
| His | Ala | Asp | Gly | His | Leu | Asp | Asp | Gly | Glu | Glu | Ala | Gly | Gln | Gly | Gln |
| 225 | | | | | 230 | | | | | 235 | | | | | 240 |
| Lys | Leu | His | Gln | Thr | Ile | Thr | Asp | Phe | Phe | Lys | Leu | Ser | Gly | Val | Ser |
| | | | | 245 | | | | | 250 | | | | | 255 | |
| Val | Ala | Ser | Asp | Ala | Leu | Pro | Phe | Leu | Gly | Leu | Phe | Asp | Leu | Asp | Gly |
| | | | 260 | | | | | 265 | | | | | 270 | | |
| Gln | Lys | Lys | Ile | Met | Lys | Arg | Val | Ala | Lys | Glu | Met | Asp | Phe | Val | Ala |
| | | 275 | | | | | 280 | | | | | 285 | | | |
| Glu | Arg | Trp | Leu | Gln | Asp | Lys | Ser | Ser | Leu | Leu | Leu | Ser | Ser | Lys |
| | 290 | | | | | 295 | | | | | 300 | | | | |
| Ser | Asn | Asn | Lys | Gln | Asn | Glu | Ala | Gly | Glu | Gly | Asp | Val | Asp | Asp | Phe |
| 305 | | | | | 310 | | | | | 315 | | | | | 320 |
| Met | Asp | Val | Leu | Met | Ser | Thr | Leu | Pro | Asp | Asp | Asp | Ser | Phe | Phe |
| | | | | 325 | | | | | 330 | | | | | 335 | |
| Thr | Lys | Tyr | Ser | Arg | Asp | Thr | Val | Ile | Lys | Ala | Asn | Ser | Leu | Ser | Met |
| | | | 340 | | | | | 345 | | | | | 350 | | |
| Val | Val | Ala | Gly | Ser | Asp | Thr | Thr | Ser | Val | Ser | Leu | Thr | Trp | Ala | Leu |
| | | 355 | | | | | 360 | | | | | 365 | | | |
| Ser | Leu | Leu | Leu | Asn | Asn | Ile | Gln | Val | Leu | Arg | Lys | Ala | Gln | Asp | Glu |
| | 370 | | | | | 375 | | | | | 380 | | | | |

```
Leu Asp Thr Lys Val Gly Arg Asp Arg His Val Glu Glu Lys Asp Ile
385                 390                 395                 400

Asp Asn Leu Val Tyr Leu Gln Ala Ile Val Lys Glu Thr Leu Arg Met
            405                 410                 415

Tyr Pro Ala Gly Pro Leu Ser Val Pro His Glu Ala Ile Glu Asp Cys
            420                 425                 430

Asn Val Gly Gly Tyr His Ile Lys Thr Gly Thr Arg Leu Leu Val Asn
            435                 440                 445

Ile Trp Lys Leu Gln Arg Asp Pro Arg Val Trp Ser Asn Pro Ser Glu
            450                 455                 460

Phe Arg Pro Glu Arg Phe Leu Asp Asn Gln Ser Asn Gly Thr Leu Leu
465                 470                 475                 480

Asp Phe Arg Gly Gln His Phe Glu Tyr Ile Pro Phe Gly Ser Gly Arg
            485                 490                 495

Arg Met Cys Pro Gly Val Asn Leu Ala Thr Pro Ile Leu His Met Thr
            500                 505                 510

Leu Ala Arg Leu Leu Gln Ser Phe Asp Leu Thr Thr Pro Ser Ser Ser
            515                 520                 525

Pro Val Asp Met Thr Glu Gly Ser Gly Leu Thr Met Pro Lys Val Thr
            530                 535                 540

Pro Leu Lys Val Leu Leu Thr Pro Arg Leu Pro Leu Pro Leu Tyr Asp
545                 550                 555                 560

Tyr

<210> SEQ ID NO 60
<211> LENGTH: 567
<212> TYPE: PRT
<213> ORGANISM: Papaver bracteatum

<400> SEQUENCE: 60

Met Asp Val Ala Ile Ile Val Asp His His Tyr Leu Gln Pro Phe Val
1               5                   10                  15

Ser Ile Ala Gly Leu Leu Ala Leu Leu Ser Phe Phe Tyr Cys Ile Trp
            20                  25                  30

Val Phe Ile Ile Arg Pro Arg Ile Ile Lys Ser Asn Leu Asp Glu Arg
            35                  40                  45

Lys Leu Ser Pro Ser Ser Pro Pro Glu Val Ala Gly Ala Trp Pro Ile
50                  55                  60

Val Gly His Leu Pro Gln Leu Ile Gly Ser Thr Pro Leu Phe Lys Ile
65                  70                  75                  80

Leu Ala Asp Met Ser Asn Lys Tyr Gly Pro Ile Phe Met Val Arg Phe
                85                  90                  95

Gly Met Tyr Pro Thr Leu Val Val Ser Ser Trp Glu Met Ser Lys Glu
            100                 105                 110

Cys Phe Thr Thr Asn Asp Arg Leu Phe Ala Thr Arg Pro Pro Ser Ala
            115                 120                 125

Ala Gly Lys Tyr Leu Thr Lys Ala Leu Phe Ala Phe Ser Val Tyr Gly
            130                 135                 140

Pro Tyr Trp Arg Glu Ile Arg Lys Ile Ser Thr Ile His Leu Leu Ser
145                 150                 155                 160

Leu Arg Arg Leu Glu Leu Leu Lys His Gly Arg Tyr Leu Glu Ile Asp
                165                 170                 175

Lys Cys Met Lys Arg Leu Phe Glu Tyr Trp Met Glu His His Lys Asn
            180                 185                 190
```

Ile Ile Ser Thr Thr Ser Ser Val Lys Val Asn Met Ser Gln Val Phe
            195                 200                 205

Ala Glu Leu Ser Leu Asn Val Val Leu Lys Ile Ile Val Gly Lys Thr
210                 215                 220

Leu Phe Ile Lys Asn Gly Asn Glu Asp Tyr Thr Lys Glu Glu Glu Glu
225                 230                 235                 240

Gly Gln Lys Leu His Lys Thr Ile Leu Lys Phe Met Glu Leu Ala Gly
                245                 250                 255

Val Ser Val Ala Ser Asp Val Leu Pro Phe Leu Gly Trp Leu Asp Val
                260                 265                 270

Asp Gly Gln Lys Gln Met Lys Arg Val Tyr Lys Glu Met Asn Leu
                275                 280                 285

Ile Ala Ser Lys Trp Leu Gly Glu His Arg Glu Arg Lys Leu Gln
290                 295                 300

Ile Ile Gln Lys Arg Gly Ala Ala Arg Gly Ser Asn Tyr Asp Asp Gly
305                 310                 315                 320

Asn Asp Phe Met Asp Val Leu Met Ser Ile Leu Asp Glu Asn Asp
                325                 330                 335

Asp Leu Phe Phe Gly Tyr Ser Arg Asp Thr Val Ile Lys Ser Thr Cys
                340                 345                 350

Leu Gln Leu Ile Val Ala Ala Ser Asp Thr Thr Ser Leu Ala Met Thr
                355                 360                 365

Trp Ala Leu Ser Leu Leu Leu Thr Asn Pro Asn Val Leu Gln Lys Ala
370                 375                 380

Gln Asp Glu Leu Asp Thr Lys Val Gly Arg Asp Arg Ile Ile Glu Glu
385                 390                 395                 400

His Asp Ile Glu Cys Leu Val Tyr Leu Gln Ala Ile Val Lys Glu Thr
                405                 410                 415

Leu Arg Leu Tyr Pro Pro Ala Pro Leu Ser Leu Pro His Glu Ala Met
                420                 425                 430

Glu Asp Cys Thr Val Gly Gly Tyr Gln Val Lys Ala Gly Thr Arg Leu
                435                 440                 445

Val Val Asn Leu Trp Lys Leu Gln Arg Asp Pro Arg Val Trp Ser Asn
450                 455                 460

Pro Leu Glu Phe Lys Pro Glu Arg Phe Leu Pro Gln Ser Asp Gly Gly
465                 470                 475                 480

Phe Gly Gly Glu Glu Ala Arg Met Asp Phe Arg Gly Gln His Phe Glu
                485                 490                 495

Tyr Thr Pro Phe Gly Ser Gly Arg Arg Ile Cys Pro Gly Ile Asp Phe
                500                 505                 510

Phe Leu Gln Thr Val His Met Ala Leu Ala Arg Leu Leu Gln Ala Phe
                515                 520                 525

Asp Phe Asn Thr Ala Gly Gly Leu Val Ile Asp Met Val Glu Gly Pro
                530                 535                 540

Gly Leu Thr Met Pro Lys Val Thr Pro Leu Glu Val His Leu Asn Pro
545                 550                 555                 560

Arg Leu Pro Val Thr Leu Tyr
                565

<210> SEQ ID NO 61
<211> LENGTH: 558
<212> TYPE: PRT
<213> ORGANISM: Papaver bracteatum

```
<400> SEQUENCE: 61

Met Gln Val Asp Trp Pro Asn Ile Leu Gln Lys Tyr Tyr Pro Ile Ile
1               5                   10                  15

Thr Cys Ser Leu Leu Thr Leu Leu Ser Phe Tyr Tyr Ile Trp Val Ser
            20                  25                  30

Ile Thr Lys Pro Ser Arg Asn Ser Lys Thr Lys Leu Pro Pro Pro Glu
            35                  40                  45

Val Ala Gly Ser Trp Pro Ile Val Gly His Leu Pro Gln Leu Val Gly
    50                  55                  60

Ser Thr Pro Leu Phe Lys Ile Leu Ala Asn Met Ser Asp Lys Tyr Gly
65                  70                  75                  80

Pro Ile Phe Met Val Arg Phe Gly Met His Pro Thr Leu Val Val Ser
                85                  90                  95

Ser Trp Glu Met Ser Lys Glu Cys Phe Thr Thr Asn Asp Lys Phe Leu
            100                 105                 110

Ala Ser Arg Pro Pro Ser Ala Ser Ala Lys Tyr Leu Gly Tyr Asp Asn
            115                 120                 125

Ala Met Phe Val Phe Ser Asp Tyr Gly Pro Tyr Trp Arg Glu Ile Arg
130                 135                 140

Lys Ile Ser Thr Leu Gln Leu Leu Thr His Lys Arg Leu Asp Ser Leu
145                 150                 155                 160

Lys Asn Ile Pro Tyr Leu Glu Ile Asn Ser Cys Val Lys Thr Leu Tyr
                165                 170                 175

Thr Arg Trp Ala Lys Thr Gln Ser Gln Ile Lys Gln Asn Val Gly Gly
            180                 185                 190

Ala Ala Asp Asp Phe Val Lys Val Asp Met Thr Glu Met Phe Gly His
            195                 200                 205

Leu Asn Leu Asn Val Val Leu Arg Leu Val Gly Lys Pro Ile Phe
210                 215                 220

Ile Gln Lys Asp Asn Ala Asp Glu Asp Tyr Thr Lys Asp Gly His Asn
225                 230                 235                 240

Lys Glu Glu Leu Gly Gln Lys Leu His Lys Thr Ile Ile Glu Phe Phe
                245                 250                 255

Glu Leu Ala Gly Ala Ser Val Ala Ser Asp Val Leu Pro Tyr Leu Gly
            260                 265                 270

Trp Leu Asp Val Asp Gly Gln Lys Lys Arg Met Lys Lys Ile Ala Met
            275                 280                 285

Glu Met Asp Leu Phe Ala Gln Lys Trp Leu Glu Glu His Arg Gln Lys
290                 295                 300

Gly Ile Asn His Asp Asn Glu Asn Asp Phe Met Ala Val Leu Ile Ser
305                 310                 315                 320

Val Leu Gly Glu Gly Lys Asp Asp His Ile Phe Gly Tyr Ser Arg Asp
                325                 330                 335

Thr Val Ile Lys Ala Thr Cys Leu Thr Leu Ile Val Ala Ala Thr Asp
            340                 345                 350

Thr Thr Leu Val Ser Leu Thr Trp Ala Leu Ser Leu Leu Leu Thr Asn
            355                 360                 365

Pro Arg Val Leu Ser Lys Ala Gln Asp Glu Leu Asp Thr Val Val Gly
            370                 375                 380

Lys Glu Arg Asn Val Glu Asp Arg Asp Val Asn His Leu Val Tyr Leu
385                 390                 395                 400

Gln Ala Val Ile Lys Glu Thr Leu Arg Leu Tyr Pro Pro Ser Pro Leu
                405                 410                 415
```

```
Ala Val Pro His Glu Ala Ile Glu Asn Cys Asn Val Gly Gly Tyr Glu
            420                 425                 430

Val Lys Ala Arg Thr Arg Leu Leu Val Asn Leu Trp Lys Ile His Arg
        435                 440                 445

Asp Pro Arg Val Trp Ser Asn Pro Leu Glu Phe Lys Pro Glu Arg Phe
    450                 455                 460

Leu Pro Lys Leu Asp Gly Gly Thr Gly Glu Ala Ser Lys Leu Asp Phe
465                 470                 475                 480

Lys Gly Gln Asp Phe Val Tyr Thr Pro Phe Gly Ser Gly Arg Arg Met
                485                 490                 495

Cys Pro Gly Ile Asn Phe Ala Ser Gln Thr Leu His Met Thr Leu Ala
            500                 505                 510

Arg Leu Leu His Ala Phe Asp Phe Asp Ile Glu Ser Asn Gly Leu Val
        515                 520                 525

Ile Asp Met Thr Glu Gly Ser Gly Leu Thr Met Pro Lys Val Thr Pro
530                 535                 540

Leu Gln Val His Leu Arg Pro Arg Leu Pro Ala Thr Leu Tyr
545                 550                 555

<210> SEQ ID NO 62
<211> LENGTH: 571
<212> TYPE: PRT
<213> ORGANISM: Papaver bracteatum

<400> SEQUENCE: 62

Met Met Asp Leu Ala Met Phe Ile Asp Gln Tyr Phe Ser Leu Ala Lys
1               5                   10                  15

Ile Ala Gly Leu Leu Ala Leu Leu Ser Phe Phe Tyr Tyr Leu Trp Ile
            20                  25                  30

Ser Thr Leu Trp Ser Pro Arg Asn Pro Lys Leu Ser Ser Val Ser Pro
        35                  40                  45

Pro Glu Val Ala Gly Ala Trp Pro Ile Leu Gly His Leu Pro Gln Leu
    50                  55                  60

Leu Gly Ser Arg Pro Leu Phe Lys Ile Leu Ala Asp Met Ser Asp Asn
65                  70                  75                  80

Tyr Gly Pro Ile Phe Met Val Arg Phe Gly Met His Pro Thr Leu Val
                85                  90                  95

Val Ser Ser Trp Glu Met Ala Lys Glu Cys Phe Thr Thr Asn Asp Arg
            100                 105                 110

Phe Leu Ala Gly Arg Pro Ser Gly Ala Ala Asn Lys Tyr Leu Thr Phe
        115                 120                 125

Ala Leu Phe Gly Phe Ser Thr Tyr Gly Pro Tyr Trp Arg Glu Ile Arg
    130                 135                 140

Lys Ile Ala Thr Leu His Leu Leu Ser His Arg Arg Leu Glu Leu Leu
145                 150                 155                 160

Lys His Val Pro Asp Leu Glu Val Thr Asn Cys Met Lys His Leu His
                165                 170                 175

Arg Arg Trp Ile Asp Ser Gln Asn Gln Ile Lys Gln Asn Asp Ala Ala
            180                 185                 190

Ala Gly Ser Val Lys Val Asp Met Gly Arg Val Phe Gly Glu Leu Thr
        195                 200                 205

Leu Asn Val Val Leu Lys Leu Val Ala Gly Lys Ser Ile Phe Phe Lys
    210                 215                 220

Asn Asp Asn Thr Arg Gln Tyr Asp Ser Lys Asp Gly His Asn Lys Glu
```

```
                    225                 230                 235                 240
Glu Glu Glu Gly Lys Lys Leu His Lys Thr Ile Ile Asp Phe Tyr Ser
                245                 250                 255
Leu Ala Gly Ala Ser Val Ala Ser Asp Val Leu Pro Phe Leu Gly Trp
                260                 265                 270
Leu Asp Val Asp Gly Gln Lys Lys Arg Met Lys Arg Val Ala Lys Asp
                275                 280                 285
Met Asp Phe Ile Ala Ala Lys Trp Leu Glu Glu His Arg His Gln Lys
                290                 295                 300
Arg Gln Thr Val Leu Ser Ser Ser Ala Thr Leu Gly Ser Ser Asn His
305                 310                 315                 320
Asp Asp Ala Lys Asp Phe Met Asp Val Leu Met Ser Ile Leu Asp Gly
                325                 330                 335
Glu Asn Asp Asp Leu Phe Phe Gly Tyr Ser Arg Asp Thr Val Ile Lys
                340                 345                 350
Thr Thr Cys Leu Gln Leu Ile Ala Ala Ala Asp Thr Thr Ser Val
                355                 360                 365
Thr Met Thr Trp Ala Leu Ala Leu Leu Ile Thr Asn Pro Thr Ile Leu
370                 375                 380
Arg Lys Ala Gln Asp Glu Leu Asp Thr Lys Val Gly Lys Asp Arg Asn
385                 390                 395                 400
Ile Glu Glu Arg Asp Ile Asn Asp Leu Val Tyr Leu Gln Ala Ile Val
                405                 410                 415
Lys Glu Thr Leu Arg Met Tyr Pro Ala Gly Pro Leu Asn Val Pro His
                420                 425                 430
Glu Ala Ile Ala Asp Cys Asn Ile Gly Gly Tyr Glu Val Arg Ala Gly
                435                 440                 445
Thr Arg Leu Leu Val Asn Leu Trp Lys Met His Arg Asp Pro Arg Val
                450                 455                 460
Trp Ser Asn Pro Ser Glu Phe Lys Pro Glu Arg Phe Leu Pro Gln Leu
465                 470                 475                 480
Asp Gly Gly Ser Gly Gly Glu Ala Ala Asn Leu Asp Phe Arg Gly Gln
                485                 490                 495
Asp Phe Glu Tyr Leu Pro Phe Ser Ala Gly Arg Arg Met Cys Pro Gly
                500                 505                 510
Ile Asp Phe Ser Leu Gln Thr Leu His Met Thr Leu Ala Arg Leu Leu
                515                 520                 525
His Gly Phe Asp Phe Asn Asn Asp Ser Ala Gly Ile Ile Ile Asp Met
                530                 535                 540
Glu Glu Gly Ser Gly Leu Thr Met Pro Lys Leu Thr Pro Leu Glu Ile
545                 550                 555                 560
Tyr Leu Cys Pro Arg Leu Pro Ala Lys Leu Tyr
                565                 570

<210> SEQ ID NO 63
<211> LENGTH: 361
<212> TYPE: PRT
<213> ORGANISM: Thalictrum flavum

<400> SEQUENCE: 63

Met Ala Val Glu Gly Lys Gln Val Ala Pro Lys Lys Ala Ile Ile Val
1               5                   10                  15
Glu Leu Leu Lys Lys Leu Glu Leu Gly Leu Val Pro Asp Asp Glu Ile
                20                  25                  30
```

Lys Lys Leu Ile Arg Ile Gln Leu Gly Arg Arg Leu Gln Trp Gly Cys
            35                  40                  45

Lys Ser Thr Tyr Glu Glu Gln Ile Ala Gln Leu Val Asn Leu Thr His
 50                  55                  60

Ser Leu Arg Gln Met Lys Ile Ala Thr Glu Val Glu Thr Leu Asp Asp
 65                  70                  75                  80

Gln Met Tyr Glu Val Pro Ile Asp Phe Leu Lys Ile Met Asn Gly Ser
                 85                  90                  95

Asn Leu Lys Gly Ser Cys Cys Tyr Phe Lys Asn Asp Ser Thr Thr Leu
            100                 105                 110

Asp Glu Ala Glu Ile Ala Met Leu Glu Leu Tyr Cys Glu Arg Ala Gln
            115                 120                 125

Ile Lys Asp Gly His Ser Val Leu Asp Leu Gly Cys Gly Gln Gly Ala
130                 135                 140

Leu Thr Leu Tyr Val Ala Gln Lys Tyr Lys Asn Ser Arg Val Thr Ala
145                 150                 155                 160

Val Thr Asn Ser Val Ser Gln Lys Glu Phe Ile Glu Glu Ser Arg
                165                 170                 175

Lys Arg Asn Leu Ser Asn Val Glu Val Leu Leu Ala Asp Ile Thr Thr
            180                 185                 190

His Lys Met Pro Asp Thr Tyr Asp Arg Ile Leu Val Val Glu Leu Phe
            195                 200                 205

Glu His Met Lys Asn Tyr Glu Leu Leu Arg Lys Ile Lys Glu Trp
            210                 215                 220

Met Ala Lys Asp Gly Leu Leu Phe Val Glu His Ile Cys His Lys Thr
225                 230                 235                 240

Phe Ala Tyr His Tyr Glu Pro Ile Asp Glu Asp Asp Trp Phe Thr Glu
                245                 250                 255

Tyr Val Phe Pro Ala Gly Thr Met Ile Ile Pro Ser Ala Ser Phe Phe
                260                 265                 270

Leu Tyr Phe Gln Asp Asp Val Ser Val Asn His Trp Thr Leu Ser
            275                 280                 285

Gly Lys His Phe Ser Arg Thr Asn Glu Glu Trp Leu Lys Arg Leu Asp
            290                 295                 300

Ala Asn Val Glu Leu Ile Lys Pro Met Phe Val Thr Ile Thr Gly Gln
305                 310                 315                 320

Cys Arg Gln Glu Ala Met Lys Leu Ile Asn Tyr Trp Arg Gly Phe Cys
                325                 330                 335

Leu Ser Gly Met Glu Met Phe Gly Tyr Asn Asn Gly Glu Trp Met
            340                 345                 350

Ala Ser His Val Leu Phe Lys Lys Lys
        355                 360

<210> SEQ ID NO 64
<211> LENGTH: 358
<212> TYPE: PRT
<213> ORGANISM: Coptis japonica

<400> SEQUENCE: 64

Met Ala Val Glu Ala Lys Gln Thr Lys Lys Ala Ile Val Glu Leu
1                5                  10                  15

Leu Lys Gln Leu Glu Leu Gly Leu Val Pro Tyr Asp Asp Ile Lys Gln
            20                  25                  30

Leu Ile Arg Arg Glu Leu Ala Arg Arg Leu Gln Trp Gly Tyr Lys Pro
            35                  40                  45

Thr Tyr Glu Glu Gln Ile Ala Glu Ile Gln Asn Leu Thr His Ser Leu
            50                  55                  60

Arg Gln Met Lys Ile Ala Thr Glu Val Glu Thr Leu Asp Ser Gln Leu
65                  70                  75                  80

Tyr Glu Ile Pro Ile Glu Phe Leu Lys Ile Met Asn Gly Ser Asn Leu
                85                  90                  95

Lys Gly Ser Cys Cys Tyr Phe Lys Glu Asp Ser Thr Thr Leu Asp Glu
            100                 105                 110

Ala Glu Ile Ala Met Leu Asp Leu Tyr Cys Glu Arg Ala Gln Ile Gln
            115                 120                 125

Asp Gly Gln Ser Val Leu Asp Leu Gly Cys Gly Gln Gly Ala Leu Thr
            130                 135                 140

Leu His Val Ala Gln Lys Tyr Lys Asn Cys Arg Val Thr Ala Val Thr
145                 150                 155                 160

Asn Ser Val Ser Gln Lys Glu Tyr Ile Glu Glu Ser Arg Arg Arg
            165                 170                 175

Asn Leu Leu Asn Val Glu Val Lys Leu Ala Asp Ile Thr Thr His Glu
            180                 185                 190

Met Ala Glu Thr Tyr Asp Arg Ile Leu Val Ile Glu Leu Phe Glu His
            195                 200                 205

Met Lys Asn Tyr Glu Leu Leu Leu Arg Lys Ile Ser Glu Trp Ile Ser
210                 215                 220

Lys Asp Gly Leu Leu Phe Leu Glu His Ile Cys His Lys Thr Phe Ala
225                 230                 235                 240

Tyr His Tyr Glu Pro Leu Asp Asp Asp Trp Phe Thr Glu Tyr Val
            245                 250                 255

Phe Pro Ala Gly Thr Met Ile Ile Pro Ser Ala Ser Phe Phe Leu Tyr
            260                 265                 270

Phe Gln Asp Asp Val Ser Val Val Asn His Trp Thr Leu Ser Gly Lys
            275                 280                 285

His Phe Ser Arg Thr Asn Glu Glu Trp Leu Lys Arg Leu Asp Ala Asn
            290                 295                 300

Leu Asp Val Ile Lys Pro Met Phe Glu Thr Leu Met Gly Asn Glu Glu
305                 310                 315                 320

Glu Ala Val Lys Leu Ile Asn Tyr Trp Arg Gly Phe Cys Leu Ser Gly
            325                 330                 335

Met Glu Met Phe Gly Tyr Asn Asn Gly Glu Glu Trp Met Ala Ser His
            340                 345                 350

Val Leu Phe Lys Lys Lys
            355

<210> SEQ ID NO 65
<211> LENGTH: 351
<212> TYPE: PRT
<213> ORGANISM: Papaver somniferum

<400> SEQUENCE: 65

Met Gln Leu Lys Ala Lys Glu Glu Leu Leu Arg Asn Met Glu Leu Gly
1               5                   10                  15

Leu Ile Pro Asp Gln Glu Ile Arg Gln Leu Ile Arg Val Glu Leu Glu
                20                  25                  30

Lys Arg Leu Gln Trp Gly Tyr Lys Glu Thr His Glu Glu Gln Leu Ser
            35                  40                  45

Gln Leu Leu Asp Leu Val His Ser Leu Lys Gly Met Lys Met Ala Thr

```
                50                  55                  60
Glu Met Glu Asn Leu Asp Leu Lys Leu Tyr Glu Ala Pro Met Glu Phe
 65                  70                  75                  80

Leu Lys Ile Gln His Gly Ser Asn Met Lys Gln Ser Ala Gly Tyr Tyr
                 85                  90                  95

Thr Asp Glu Ser Thr Thr Leu Asp Glu Ala Glu Ile Ala Met Leu Asp
                100                 105                 110

Leu Tyr Met Glu Arg Ala Gln Ile Lys Asp Gly Gln Ser Val Leu Asp
                115                 120                 125

Leu Gly Cys Gly Leu Gly Ala Val Ala Leu Phe Gly Ala Asn Lys Phe
130                 135                 140

Lys Lys Cys Gln Phe Thr Gly Val Thr Ser Ser Val Glu Gln Lys Asp
145                 150                 155                 160

Tyr Ile Glu Gly Lys Cys Lys Glu Leu Lys Leu Thr Asn Val Lys Val
                165                 170                 175

Leu Leu Ala Asp Ile Thr Thr Tyr Glu Thr Glu Glu Arg Phe Asp Arg
                180                 185                 190

Ile Phe Ala Val Glu Leu Ile Glu His Met Lys Asn Tyr Gln Leu Leu
                195                 200                 205

Leu Lys Lys Ile Ser Glu Trp Met Lys Asp Asp Gly Leu Leu Phe Val
210                 215                 220

Glu His Val Cys His Lys Thr Leu Ala Tyr His Tyr Glu Pro Val Asp
225                 230                 235                 240

Ala Glu Asp Trp Tyr Thr Asn Tyr Ile Phe Pro Ala Gly Thr Leu Thr
                245                 250                 255

Leu Ser Ser Ala Ser Met Leu Leu Tyr Phe Gln Asp Asp Val Ser Val
                260                 265                 270

Val Asn Gln Trp Thr Leu Ser Gly Lys His Tyr Ser Arg Ser His Glu
                275                 280                 285

Glu Trp Leu Lys Asn Met Asp Lys Asn Ile Val Glu Phe Lys Glu Ile
290                 295                 300

Met Arg Ser Ile Thr Lys Thr Glu Lys Glu Ala Ile Lys Leu Leu Asn
305                 310                 315                 320

Phe Trp Arg Ile Phe Cys Met Cys Gly Ala Glu Leu Phe Gly Tyr Lys
                325                 330                 335

Asn Gly Glu Glu Trp Met Leu Thr His Leu Leu Phe Lys Lys Lys
                340                 345                 350

<210> SEQ ID NO 66
<211> LENGTH: 358
<212> TYPE: PRT
<213> ORGANISM: Papaver somniferum

<400> SEQUENCE: 66

Met Gly Ser Ile Asp Glu Val Lys Lys Glu Ser Ala Gly Glu Thr Leu
 1               5                  10                  15

Gly Arg Leu Leu Lys Gly Glu Ile Lys Asp Glu Leu Lys Lys Leu
                20                  25                  30

Ile Lys Phe Gln Phe Glu Lys Arg Leu Gln Trp Gly Tyr Lys Ser Ser
                35                  40                  45

His Gln Glu Gln Leu Ser Phe Asn Leu Asp Phe Ile Lys Ser Leu Lys
                50                  55                  60

Lys Met Glu Met Ser Gly Glu Ile Glu Thr Met Asn Lys Glu Thr Tyr
 65                  70                  75                  80
```

```
Glu Leu Pro Ser Glu Phe Leu Glu Ala Val Phe Gly Lys Thr Val Lys
                85                  90                  95

Gln Ser Met Cys Tyr Phe Thr His Glu Ser Ala Thr Ile Asp Glu Ala
            100                 105                 110

Glu Glu Ala Ala His Glu Leu Tyr Cys Glu Arg Ala Gln Ile Lys Asp
        115                 120                 125

Gly Gln Thr Val Leu Asp Ile Gly Cys Gly Gln Gly Leu Val Leu
    130                 135                 140

Tyr Ile Ala Gln Lys Tyr Lys Asn Cys His Val Thr Gly Leu Thr Asn
145                 150                 155                 160

Ser Lys Ala Gln Val Asn Tyr Leu Leu Lys Gln Ala Glu Lys Leu Gly
                165                 170                 175

Leu Thr Asn Val Asp Ala Ile Leu Ala Asp Val Thr Gln Tyr Glu Ser
            180                 185                 190

Asp Lys Thr Tyr Asp Arg Leu Leu Met Ile Glu Ala Ile Glu His Met
        195                 200                 205

Lys Asn Leu Gln Leu Phe Met Lys Lys Leu Ser Thr Trp Met Thr Lys
210                 215                 220

Glu Ser Leu Leu Phe Val Asp His Val Cys His Lys Thr Phe Ala His
225                 230                 235                 240

Phe Phe Glu Ala Val Asp Glu Asp Asp Trp Tyr Ser Gly Phe Ile Phe
                245                 250                 255

Pro Pro Gly Cys Ala Thr Ile Leu Ala Ala Asn Ser Leu Leu Tyr Phe
            260                 265                 270

Gln Asp Asp Val Ser Val Asp His Trp Val Val Asn Gly Met His
        275                 280                 285

Met Ala Arg Ser Val Asp Ile Trp Arg Lys Ala Leu Asp Lys Asn Met
290                 295                 300

Glu Ala Ala Lys Glu Ile Leu Leu Pro Gly Leu Gly Gly Ser His Glu
305                 310                 315                 320

Thr Val Asn Gly Val Val Thr His Ile Arg Thr Phe Cys Met Gly Gly
                325                 330                 335

Tyr Glu Gln Phe Ser Met Asn Asn Gly Asp Glu Trp Met Val Ala Gln
            340                 345                 350

Leu Leu Phe Lys Lys Lys
        355

<210> SEQ ID NO 67
<211> LENGTH: 350
<212> TYPE: PRT
<213> ORGANISM: Eschscholzia californica

<400> SEQUENCE: 67

Met Gly Ser Ser Ala Gly Glu Ile Met Gly Arg Leu Met Lys Gly Glu
1               5                   10                  15

Ile Glu Asp Glu Glu Leu Lys Lys Leu Ile Arg His Gln Trp Asp Arg
            20                  25                  30

Arg Ile Glu Trp Gly Tyr Lys Pro Thr His Glu Lys Gln Leu Ala Phe
        35                  40                  45

Asn Leu Asp Phe Ile Lys Gly Leu Lys Glu Met Val Met Ser Gly Glu
    50                  55                  60

Ile Asp Thr Met Asn Lys Glu Thr Tyr Glu Leu Pro Thr Ala Phe Leu
65                  70                  75                  80

Glu Ala Val Phe Gly Lys Thr Val Lys Gln Ser Cys Cys Tyr Phe Lys
                85                  90                  95
```

Asp Glu Asn Ser Thr Ile Asp Glu Ala Glu Ala Ala His Glu Leu
            100                 105                 110

Tyr Cys Glu Arg Ala Gln Ile Lys Asp Gly Gln Thr Val Leu Asp Ile
                115                 120                 125

Gly Cys Gly Gln Gly Gly Leu Val Leu Tyr Ile Ala Glu Lys Tyr Lys
            130                 135                 140

Asn Cys His Val Thr Gly Leu Thr Asn Ser Lys Ala Gln Ala Asn Tyr
145                 150                 155                 160

Ile Glu Gln Gln Ala Glu Lys Leu Glu Leu Thr Asn Val Asp Val Ile
                165                 170                 175

Phe Ala Asp Val Thr Lys Phe Asp Thr Asp Lys Thr Tyr Asp Arg Ile
            180                 185                 190

Leu Val Val Glu Thr Ile Glu His Met Lys Asn Ile Gln Leu Phe Met
                195                 200                 205

Lys Lys Leu Ser Thr Trp Met Thr Glu Asp Ser Leu Leu Phe Val Asp
            210                 215                 220

His Ile Ser His Lys Thr Phe Asn His Asn Phe Glu Ala Leu Asp Glu
225                 230                 235                 240

Asp Asp Trp Tyr Ser Gly Phe Ile Phe Pro Lys Gly Cys Val Thr Ile
                245                 250                 255

Leu Ser Ser Ser Thr Leu Leu Tyr Phe Gln Asp Asp Val Ser Ala Leu
            260                 265                 270

Asp His Trp Val Val Asn Gly Met His Met Ala Arg Ser Val Glu Ala
            275                 280                 285

Trp Arg Lys Lys Leu Asp Glu Thr Ile Glu Ala Ala Arg Glu Ile Leu
            290                 295                 300

Glu Pro Gly Leu Gly Ser Lys Glu Ala Val Asn Gln Val Ile Thr His
305                 310                 315                 320

Ile Arg Thr Phe Cys Ile Gly Gly Tyr Glu Gln Phe Ser Tyr Asn Asn
                325                 330                 335

Gly Glu Glu Trp Met Ile Thr Gln Ile Leu Phe Lys Lys Lys
            340                 345                 350

<210> SEQ ID NO 68
<211> LENGTH: 363
<212> TYPE: PRT
<213> ORGANISM: Papaver somniferum

<400> SEQUENCE: 68

Met Ser Thr Thr Met Glu Thr Thr Lys Ile Ser Gln Gln Asp Asp Leu
1               5                   10                  15

Trp Lys Asn Met Glu Leu Gly Gln Ile Ser Asp Glu Glu Val Arg Arg
                20                  25                  30

Leu Met Lys Ile Gly Ile Glu Lys Arg Ile Lys Trp Gly Thr Lys Pro
            35                  40                  45

Thr Gln Gln Glu Gln Leu Ala Gln Leu Leu Asp Phe Asn Lys Ser Leu
        50                  55                  60

Arg Gly Met Lys Met Ala Thr Glu Ile Asp Thr Leu Glu Asn His Lys
65                  70                  75                  80

Ile Tyr Glu Thr Pro Glu Ser Phe Asn Gln Ile Ile Gly Gly Lys Glu
                85                  90                  95

Ser Ala Gly Leu Phe Thr Asp Glu Thr Thr Thr Met Glu Glu Ala
            100                 105                 110

Asn Thr Lys Met Met Asp Leu Tyr Cys Glu Arg Ala Gly Leu Lys Asp

```
            115                 120                 125
Gly His Thr Ile Leu Asp Leu Gly Cys Gly Ala Gly Leu Leu Val Leu
    130                 135                 140

His Leu Ala Lys Lys Tyr Lys Lys Ser Lys Ile Thr Gly Ile Thr Asn
145                 150                 155                 160

Thr Ser Ser His Lys Glu Tyr Ile Leu Lys Gln Cys Lys Asn Leu Asn
                165                 170                 175

Leu Ser Asn Val Glu Ile Ile Leu Ala Asp Val Thr Lys Val Asp Ile
            180                 185                 190

Glu Ser Thr Phe Asp Arg Val Phe Val Ile Gly Leu Ile Glu His Met
        195                 200                 205

Lys Asn Phe Glu Leu Phe Leu Arg Lys Ile Ser Lys Trp Met Lys Asp
    210                 215                 220

Asp Gly Leu Leu Leu Glu His Leu Cys His Lys Ser Phe Ser Asp
225                 230                 235                 240

His Trp Glu Pro Leu Ser Glu Asp Asp Trp Tyr Ala Lys Asn Phe Phe
                245                 250                 255

Pro Ser Gly Thr Leu Val Ile Pro Ser Ala Thr Cys Leu Leu Tyr Phe
            260                 265                 270

Gln Glu Asp Val Thr Val Ile Asp His Trp Ile Leu Ser Gly Asn Asn
        275                 280                 285

Phe Ala Arg Ser Asn Glu Val Ile Leu Lys Arg Ile Asp Gly Lys Ile
    290                 295                 300

Glu Glu Val Lys Asp Ile Phe Met Ser Phe Tyr Gly Ile Gly Arg Glu
305                 310                 315                 320

Glu Ala Val Lys Leu Ile Asn Trp Trp Arg Leu Leu Cys Ile Thr Ala
                325                 330                 335

Asn Glu Leu Phe Lys Tyr Asn Asn Gly Glu Glu Trp Leu Ile Ser Gln
            340                 345                 350

Leu Leu Phe Lys Lys Lys Leu Met Thr Cys Ile
        355                 360

<210> SEQ ID NO 69
<211> LENGTH: 356
<212> TYPE: PRT
<213> ORGANISM: Thalictrum flavum

<400> SEQUENCE: 69

Met Glu Thr Lys Gln Thr Lys Lys Glu Ala Val Ala Asn Leu Ile Lys
1               5                   10                  15

Arg Ile Glu His Gly Glu Val Ser Asp Glu Ile Arg Gly Met Met
            20                  25                  30

Lys Ile Gln Val Gln Lys Arg Leu Lys Trp Gly Tyr Lys Pro Thr His
        35                  40                  45

Glu Gln Gln Leu Ala Gln Leu Val Thr Phe Ala Gln Ser Leu Lys Gly
    50                  55                  60

Met Glu Met Ala Glu Glu Val Asp Thr Leu Asp Ala Glu Leu Tyr Glu
65                  70                  75                  80

Ile Pro Leu Pro Phe Leu His Ile Met Cys Gly Lys Thr Leu Lys Phe
                85                  90                  95

Ser Pro Gly Tyr Phe Lys Asp Glu Ser Thr Thr Leu Asp Glu Ser Glu
            100                 105                 110

Val Tyr Met Met Asp Leu Tyr Cys Glu Arg Ala Gln Ile Lys Asp Gly
        115                 120                 125
```

```
Gln Ser Ile Leu Asp Leu Gly Cys Gly His Gly Ser Leu Thr Leu His
    130                 135                 140

Val Ala Gln Lys Tyr Arg Gly Cys Lys Val Thr Gly Ile Thr Asn Ser
145                 150                 155                 160

Val Ser Gln Lys Glu Phe Ile Met Asp Gln Cys Lys Lys Leu Asp Leu
                165                 170                 175

Ser Asn Val Glu Ile Ile Leu Glu Asp Val Thr Lys Phe Glu Thr Glu
                180                 185                 190

Ile Thr Tyr Asp Arg Ile Phe Ala Val Ala Leu Ile Glu His Met Lys
            195                 200                 205

Asn Tyr Glu Leu Phe Leu Lys Lys Val Ser Thr Trp Ile Ala Gln Tyr
210                 215                 220

Gly Leu Leu Phe Val Glu His His Cys His Lys Val Phe Ala Tyr Gln
225                 230                 235                 240

Tyr Glu Pro Leu Asp Glu Asp Trp Tyr Thr Glu Tyr Ile Phe Pro
                245                 250                 255

Ser Gly Thr Leu Val Met Ser Ser Ser Ile Leu Leu Tyr Phe Gln
                260                 265                 270

Glu Asp Val Ser Val Val Asn His Trp Thr Leu Ser Gly Lys His Pro
            275                 280                 285

Ser Leu Gly Phe Lys Gln Trp Leu Lys Arg Leu Asp Asp Asn Ile Asp
290                 295                 300

Glu Val Lys Glu Ile Phe Glu Ser Phe Tyr Gly Ser Lys Glu Lys Ala
305                 310                 315                 320

Met Lys Phe Ile Thr Tyr Trp Arg Val Phe Cys Ile Ala His Ser Gln
                325                 330                 335

Met Tyr Ser Thr Asn Asn Gly Glu Glu Trp Met Leu Ser Gln Val Leu
                340                 345                 350

Phe Lys Lys Lys
            355

<210> SEQ ID NO 70
<211> LENGTH: 358
<212> TYPE: PRT
<213> ORGANISM: Papaver bracteatum

<400> SEQUENCE: 70

Met Gly Ser Ile Asp Glu Val Lys Lys Glu Ser Ala Gly Glu Thr Leu
1               5                   10                  15

Gly Arg Leu Leu Lys Gly Glu Ile Lys Asp Glu Glu Leu Lys Lys Leu
                20                  25                  30

Ile Lys Phe Gln Phe Glu Lys Arg Leu Gln Trp Gly Tyr Lys Ser Ser
            35                  40                  45

His Gln Glu Gln Leu Ser Phe Asn Leu Asp Phe Ile Lys Ser Leu Lys
        50                  55                  60

Lys Met Glu Met Ser Gly Glu Ile Glu Thr Met Asn Lys Glu Thr Tyr
65                  70                  75                  80

Glu Leu Pro Ser Glu Phe Leu Glu Ala Val Phe Gly Lys Thr Val Lys
                85                  90                  95

Gln Ser Met Cys Tyr Phe Lys His Glu Ser Ala Thr Ile Asp Glu Ala
            100                 105                 110

Glu Glu Ala Ala His Glu Leu Tyr Cys Glu Arg Ala Gln Ile Lys Asp
        115                 120                 125

Gly Gln Thr Val Leu Asp Ile Gly Cys Gly Gln Gly Gly Leu Val Leu
130                 135                 140
```

-continued

```
Tyr Ile Ala Arg Lys Tyr Lys Cys His Val Thr Gly Leu Thr Asn
145                 150                 155                 160

Ser Lys Ala Gln Val Asn Tyr Leu Leu Lys Gln Ala Glu Lys Leu Gly
            165                 170                 175

Leu Thr Asn Val Asp Ala Ile Leu Ala Asp Val Thr Gln Tyr Glu Ser
            180                 185                 190

Asp Lys Thr Tyr Asp Arg Leu Leu Met Ile Glu Ala Ile Glu His Met
            195                 200                 205

Lys Asn Leu Gln Leu Phe Met Lys Lys Leu Ser Thr Trp Met Thr Glu
210                 215                 220

Glu Ser Leu Leu Phe Val Asp His Val Cys His Lys Thr Phe Ala His
225                 230                 235                 240

Phe Phe Glu Ala Val Asp Glu Asp Trp Tyr Ser Gly Phe Ile Phe
            245                 250                 255

Pro Pro Gly Cys Ala Thr Ile Leu Ala Ala Asn Ser Leu Leu Tyr Phe
            260                 265                 270

Gln Asp Asp Val Ser Val Val Asp His Trp Val Val Asn Gly Met His
            275                 280                 285

Met Ala Arg Ser Val Asp Ile Trp Arg Lys Ala Leu Asp Lys Asn Met
290                 295                 300

Glu Ala Ala Lys Glu Ile Leu Leu Pro Gly Leu Gly Gly Ser His Glu
305                 310                 315                 320

Ala Val Asn Gly Val Val Thr His Ile Arg Thr Phe Cys Met Gly Gly
                325                 330                 335

Tyr Glu Gln Phe Ser Met Asn Asp Gly Asp Glu Trp Met Val Ala Gln
            340                 345                 350

Leu Leu Phe Lys Lys Lys
            355

<210> SEQ ID NO 71
<211> LENGTH: 358
<212> TYPE: PRT
<213> ORGANISM: Papaver bracteatum

<400> SEQUENCE: 71

Met Gly Ser Ile Glu Glu Val Lys Lys Glu Ser Ala Glu Thr Leu
1               5                   10                  15

Gly Arg Leu Leu Arg Gly Glu Ile Asn Asp Glu Glu Leu Lys Lys Leu
            20                  25                  30

Ile Lys Tyr Gln Leu Glu Lys Arg Leu Gln Trp Gly Tyr Lys Ser Ser
        35                  40                  45

His Gln Glu Gln Leu Ser Phe Asn Leu Asp Phe Ile Asn Ser Leu Lys
    50                  55                  60

Lys Met Gly Met Ser Gly Gln Val Glu Ala Phe Thr Asn Glu Val Tyr
65                  70                  75                  80

Glu Leu Pro Thr Glu Cys Phe Glu Ala Ala Tyr Gly Lys Ser Met Lys
                85                  90                  95

Leu Ser Gly Cys Tyr Phe Lys His Glu Ser Ser Thr Ile Asp Glu Ala
            100                 105                 110

Glu Glu Ala Ser His Glu Leu Tyr Cys Glu Arg Ala Gln Ile Lys Asp
            115                 120                 125

Gly Gln Thr Val Leu Asp Ile Gly Cys Gly Gln Gly Leu Val Leu
            130                 135                 140

Tyr Val Ala Gln Lys Tyr Lys Asn Cys His Val Thr Gly Leu Thr Asn
```

```
                145                 150                 155                 160
Ser Lys Glu Gln Val Asn Tyr Ile Leu Lys Gln Ala Glu Lys Leu Gly
                165                 170                 175

Leu Arg Asn Val Asp Val Ile Leu Ala Asp Val Thr Gln Tyr Glu Ser
            180                 185                 190

Asp Lys Thr Tyr Asp Arg Ile Leu Val Ile Gly Val Glu His Met
        195                 200                 205

Lys Asn Met Gln Leu Phe Ile Lys Lys Leu Ser Thr Trp Met Ala Glu
    210                 215                 220

Asp Ser Leu Leu Phe Val Asp His Ser Cys His Lys Thr Phe Asn His
225                 230                 235                 240

Phe Phe Glu Ala Leu Asp Glu Asp Trp Tyr Ser Gly Tyr Ile Phe
                245                 250                 255

Pro Pro Gly Cys Ala Thr Phe Leu Ser Ala Asp Ser Leu Leu Tyr Phe
            260                 265                 270

Gln Asp Asp Val Ser Val Asp His Trp Val Val Asn Gly Met His
        275                 280                 285

Phe Ala Arg Thr Val Asp Ala Trp Arg Lys Lys Leu Asp Lys Asn Met
    290                 295                 300

Glu Ala Val Lys Glu Ile Leu Leu Pro Gly Leu Gly Gly Asn His Glu
305                 310                 315                 320

Ala Val Asn Gly Val Ile Thr His Ile Arg Thr Cys Cys Val Gly Gly
                325                 330                 335

Tyr Val Gln Phe Ser Leu Asn Asp Gly Asp Glu Trp Met Asn Ala Gln
            340                 345                 350

Leu Leu Phe Lys Lys Lys
        355

<210> SEQ ID NO 72
<211> LENGTH: 368
<212> TYPE: PRT
<213> ORGANISM: Argenome mexicana

<400> SEQUENCE: 72

Met Cys Leu Phe Phe Ala Glu Lys Met Gly Leu Met Ala Glu Ala Asn
1               5                   10                  15

Asn Gln Gln Gln Leu Lys Lys Glu Asp Leu Leu Lys Asn Met Glu Leu
            20                  25                  30

Gly Leu Ile Pro Asp Glu Glu Ile Arg Lys Leu Ile Arg Val Gln Leu
        35                  40                  45

Glu Lys Arg Leu Asn Trp Gly Tyr Lys Ser Thr His Glu Gln Gln Leu
    50                  55                  60

Ser Gln Leu Leu His Leu Val His Ser Leu Lys Lys Met Lys Ile Ala
65                  70                  75                  80

Thr Glu Met Glu Asn Leu Asp Leu Lys Leu Tyr Glu Ala Pro Phe Ser
                85                  90                  95

Phe Val Gln Ile Gln His Gly Ser Thr Ile Lys Glu Ser Ser Gly Leu
            100                 105                 110

Phe Lys Asp Glu Ser Thr Thr Leu Asp Glu Ala Glu Ile Ala Met Leu
        115                 120                 125

Asp Leu Tyr Thr Lys Arg Ala Lys Ile Glu Asp Gly Gln Ser Val Leu
    130                 135                 140

Asp Leu Gly Cys Gly Leu Gly Ala Val Thr Leu Tyr Val Ala Gln Lys
145                 150                 155                 160
```

Phe Lys Asn Cys Tyr Val Thr Gly Ile Thr Ser Ser Val Glu Gln Lys
                165                 170                 175

Asp Phe Ile Glu Gly Arg Cys Lys Glu Leu Lys Leu Ser Asn Val Lys
            180                 185                 190

Val Ile Leu Ala Asp Ile Thr Thr Tyr Glu Thr Glu Lys Tyr Asn
        195                 200                 205

Arg Ile Phe Ala Val Glu Leu Ile Glu His Met Lys Asn Tyr Glu Leu
    210                 215                 220

Leu Leu Arg Lys Ile Ser Glu Trp Met Lys Gln Asp Gly Leu Leu Phe
225                 230                 235                 240

Ile Glu His Val Cys His Lys Thr Leu Ala Tyr His Tyr Glu Pro Leu
                245                 250                 255

Asp Glu Glu Asp Trp Tyr Thr Asn Tyr Ile Phe Pro Ala Gly Thr Leu
            260                 265                 270

Thr Leu Ser Ser Ala Thr Leu Leu Tyr Phe Gln Asp Asp Val Ala
        275                 280                 285

Val Val Asp Gln Trp Thr Leu Ser Gly Lys His Tyr Ser Arg Ser His
    290                 295                 300

Glu Glu Trp Leu Lys Arg Ile Asp Gly Asn Ile Glu Glu Val Lys Glu
305                 310                 315                 320

Ile Met Lys Ser Ile Thr Lys Ser Glu Glu Ala Lys Lys Leu Leu
                325                 330                 335

Asn Phe Trp Arg Ile Phe Cys Met Cys Gly Ala Glu Leu Phe Gly Tyr
            340                 345                 350

Lys Asn Gly Glu Glu Trp Met Met Thr His Ile Leu Phe Lys Lys Lys
        355                 360                 365

<210> SEQ ID NO 73
<211> LENGTH: 364
<212> TYPE: PRT
<213> ORGANISM: Glaucium flavum

<400> SEQUENCE: 73

Met Asp Leu Met Ala Thr Ser Lys Gln Val Lys Lys Glu Glu Leu
1               5                   10                  15

Leu Lys Asn Met Glu Leu Gly Leu Val Pro Asp Glu Glu Ile Arg Arg
            20                  25                  30

Leu Ile Arg Ile Glu Leu Glu Lys Arg Leu Lys Trp Gly Tyr Lys Pro
        35                  40                  45

Thr His Gln Gln Gln Leu Ala Gln Leu Leu Asp Leu Val His Ser Leu
    50                  55                  60

Lys Lys Met Lys Ile Ala Thr Glu Met Glu Ser Leu Asp Leu Lys Leu
65                  70                  75                  80

Tyr Glu Ala Pro Phe Ser Phe Val Gln Ile Lys His Gly Ser Thr Ile
                85                  90                  95

Lys Glu Ser Ser Ser Tyr Phe Lys Asp Glu Ser Met Thr Leu Asp Glu
            100                 105                 110

Ala Glu Ile Ala Met Leu Asp Leu Tyr Val Glu Arg Ala Gln Ile Glu
        115                 120                 125

Asp Gly Gln Ser Val Leu Asp Leu Gly Cys Gly Leu Gly Ala Val Thr
    130                 135                 140

Leu His Val Ala Lys Lys Tyr Lys Asn Cys His Val Thr Gly Leu Thr
145                 150                 155                 160

Asn Ser Val Glu Gln Lys Asp Phe Ile Glu Gly Lys Cys Lys Glu Leu
                165                 170                 175

```
Asn Leu Ser Asn Val Lys Val Ile Leu Ala Asp Val Thr Ser His Glu
            180                 185                 190

Met Glu Asp Lys Phe Asp Arg Ile Phe Ala Val Glu Leu Ile Glu His
        195                 200                 205

Met Lys Asn Tyr Glu Leu Leu Leu Arg Arg Ile Ser Lys Trp Met Lys
210                 215                 220

Asp Asp Gly Leu Leu Phe Ile Glu His Val Cys His Lys Thr Phe Ala
225                 230                 235                 240

Tyr His Tyr Glu Pro Ile Asp Glu Asp Trp Tyr Thr Glu Tyr Ile
            245                 250                 255

Phe Pro Ala Gly Thr Leu Thr Leu Ser Ser Ala Ser Leu Leu Leu Tyr
            260                 265                 270

Phe Gln Asp Asp Val Ser Val Val Asn His Trp Thr Leu Ser Gly Lys
        275                 280                 285

His Tyr Ser Arg Ser His Glu Glu Trp Leu Lys Arg Ile Asp Gly Asn
    290                 295                 300

Met Asp Ala Val Lys Glu Ile Met Lys Ser Ile Thr Lys Thr Glu Glu
305                 310                 315                 320

Glu Ala Val Lys Leu Ile Asn Phe Trp Arg Ile Phe Cys Met Cys Gly
                325                 330                 335

Ala Glu Leu Phe Gly Tyr Lys Asp Gly Glu Glu Trp Met Met Ser His
            340                 345                 350

Val Leu Phe Lys Lys Lys Gln Leu Leu Gln Gln Cys
            355                 360

<210> SEQ ID NO 74
<211> LENGTH: 353
<212> TYPE: PRT
<213> ORGANISM: Eschscholzia californica

<400> SEQUENCE: 74

Met Val Asp Leu Lys Val Glu Lys Glu Leu Leu Lys Ser Met Glu
1               5                   10                  15

Leu Gly Leu Val Pro Asp Glu Ile Arg Lys His Ile Arg Ser Gln
            20                  25                  30

Leu Glu Lys Arg Leu Lys Trp Gly Tyr Lys Pro Asn His Glu Gln Gln
        35                  40                  45

Leu Ala Gln Leu Leu Asp Val Ile His Ser Leu Lys Lys Met Lys Ile
    50                  55                  60

Ser Lys Glu Tyr Glu Ser Phe Asp Leu Arg Leu Tyr Glu Ala Pro Phe
65                  70                  75                  80

Asp Phe His Lys Ile Gln Leu Gly Thr His Leu Lys Glu Ser Cys Ser
                85                  90                  95

Tyr Tyr Lys Asp Glu Ser Thr Thr Leu Asp Glu Ala Glu Gly Ala Met
            100                 105                 110

Leu Asp Leu Tyr Thr Gln Lys Ala Lys Ile Glu Asp Gly Gln Ser Ile
        115                 120                 125

Leu Asp Leu Gly Cys Gly Val Gly Ala Val Thr Leu Phe Val Ala Asn
    130                 135                 140

Lys Tyr Lys Asn Cys Lys Val Thr Gly Ile Thr Ser Cys Gln Trp Gln
145                 150                 155                 160

Lys Asp Phe Ile Glu Asn Lys Cys Lys Glu Leu Asn Leu Thr Asn Val
                165                 170                 175

Arg Val Ile Ile Gly Asp Val Thr Ala Tyr Glu Met Glu Glu Thr Phe
```

```
                180                 185                 190
Asp Arg Ile Phe Ala Ile Glu Leu Ile Glu His Met Lys Asn Tyr Glu
            195                 200                 205
Leu Leu Leu Arg Lys Ile Ser Lys Trp Met Lys Asp Asp Gly Leu Leu
            210                 215                 220
Phe Ile Glu His Val Cys His Lys Ile Leu Ala Tyr Pro Tyr Glu Pro
225                 230                 235                 240
Ile Asp Glu Glu Asp Trp Phe Thr Glu Tyr Ile Phe Pro Gly Gly Thr
                245                 250                 255
Leu Thr Leu Ser Ser Ala Ser Leu Leu Leu Tyr Phe Gln Asp Asp Val
            260                 265                 270
Ser Val Val Glu His Ser Ser Leu Asn Gly Lys His Tyr Ser Arg Ser
            275                 280                 285
His Gly Glu Trp Leu Lys Asn Ile Asp Ala Asn Ile Asp Glu Val Lys
            290                 295                 300
Gly Ile Met Arg Ser Ile Thr Lys Thr Glu Glu Ala Val Arg Leu
305                 310                 315                 320
Val Asn Phe Trp Arg Ile Phe Cys Met Cys Gly Ile Glu Leu Phe Gly
                325                 330                 335
Tyr Asn Asn Gly Glu Glu Trp Met Val Ser His Ile Leu Leu Lys Lys
                340                 345                 350
Lys

<210> SEQ ID NO 75
<211> LENGTH: 359
<212> TYPE: PRT
<213> ORGANISM: Eschscholzia californica

<400> SEQUENCE: 75

Met Ala Ala Asp Leu Val Val Lys Lys Trp Asn Asn Lys Lys Glu Leu
1               5                   10                  15
Ile Asp Glu Met Glu Leu Gly Leu Val Gly Asp Glu Glu Ile Arg Glu
                20                  25                  30
Leu Ile Arg Asn Asp Leu Glu Lys Arg Leu Lys Trp Gly Tyr Lys Ser
            35                  40                  45
Asn His Glu Gln Gln Leu Ala Gln Leu Leu His Phe Val His Ser Leu
        50                  55                  60
Arg Gly Met Lys Ile Ala Ala Asp Glu Val Glu Ser Phe Asn Ile Lys
65                  70                  75                  80
Val Tyr Glu Ala Pro Phe Ser Phe Asn Lys Ile Gln Leu Gly Ser Ser
                85                  90                  95
Leu Lys Glu Ser Ser Cys Tyr Tyr Lys His Asp Glu Thr Thr Leu Asp
                100                 105                 110
Glu Gly Glu Ile Ala Met Met Glu Leu Tyr Thr Glu Lys Ala Gln Ile
            115                 120                 125
Lys Asp Gly Gln Ser Val Leu Asp Leu Gly Cys Gly Leu Gly Ser Leu
        130                 135                 140
Thr Leu Tyr Val Ala Asn Lys Tyr Pro Asn Cys Lys Val Thr Gly Thr
145                 150                 155                 160
Thr Ala Ser Leu Trp His Lys Asp Phe Ile Glu Ser Lys Cys Lys Glu
                165                 170                 175
Gln Glu Leu Thr Asn Val Lys Ile Val Leu Gly Asp Ala Thr Thr His
                180                 185                 190
Glu Met Glu Glu Arg Phe Asp Arg Ile Leu Ala Ile Gly Leu Ile Glu
```

```
               195                 200                 205
    His Leu Lys Asn Tyr Gly Leu Leu Gly Arg Ile Ser Lys Trp Leu
        210                 215                 220

Lys Asp Asp Gly Phe Leu Phe Ile Gln His Val Cys His Lys Thr Leu
    225                 230                 235                 240

Ala Tyr Pro Leu Val Pro Val Asp Glu Glu Asp Trp Ile Gly Glu Tyr
                        245                 250                 255

Ile Phe Pro Gly Gly Thr Leu Thr Met Pro Ser Ala Ser Leu Leu Leu
                    260                 265                 270

Tyr Phe Gln Asp Glu Leu Ser Val Val Asp His Ser Thr Leu Asn Gly
                275                 280                 285

Lys His Phe Ser Arg Thr His Glu Glu Trp Leu Lys Asn Ile Asp Ala
                290                 295                 300

Lys Ile Asp Glu Val Lys Glu Ile Leu Lys Ser Val Thr Lys Thr Glu
    305                 310                 315                 320

Glu Glu Val Val Arg Leu Thr Asn Phe Trp Arg Ile Phe Cys Met Phe
                        325                 330                 335

Gly Val Glu Met Phe Gly Tyr Asn Glu Gly Glu Glu Trp Met Leu Ser
                    340                 345                 350

Gln Ile Leu Phe Lys Lys Lys
            355

<210> SEQ ID NO 76
<211> LENGTH: 353
<212> TYPE: PRT
<213> ORGANISM: Chelidonium majus

<400> SEQUENCE: 76

Met Ala Ser Gly Lys Val Val Asp Leu Leu Lys Arg Leu Asp Ser Gly
    1               5                   10                  15

Leu Val Ser Asp Glu Glu Leu Arg Arg Val Ile Arg Phe Glu Leu Glu
                    20                  25                  30

Arg Arg Leu Lys Trp Gly Tyr Lys Pro Thr His Glu Gln Gln Leu Ala
                35                  40                  45

Glu Leu Leu Asn Leu Ala His Ala Thr Lys Gln Met Glu Ile Ala Thr
        50                  55                  60

Lys Ile Asp Thr Leu Asn Ser Thr Met Tyr Glu Val Pro Asn Ser Phe
    65                  70                  75                  80

Leu Glu Ile Gln Leu Gly Ser Thr Leu Lys Glu Ser Cys Leu Tyr Phe
                    85                  90                  95

Lys Asp Glu Ser Thr Thr Val Asp Glu Ala Glu Ile Ala Met Met Asp
                    100                 105                 110

Leu Tyr Leu Glu Arg Ala Gln Ile Lys Asp Gly Gln Ile Ile Leu Asp
                115                 120                 125

Leu Gly Cys Gly Leu Gly Ala Leu Ala Phe His Ile Ala Gln Lys Tyr
        130                 135                 140

Thr Asn Cys Asn Val Thr Ser Val Thr Asn Ser Val Lys Gln Lys Glu
    145                 150                 155                 160

Phe Ile Glu Glu Lys Cys Lys Ile Leu Asn Val Ser Asn Val Lys Val
                    165                 170                 175

Ile Leu Thr Asp Ile Cys Thr Leu Glu Met Glu Ala Thr Phe Asp Arg
                    180                 185                 190

Ile Phe Ala Ile Gly Leu Ile Glu His Met Lys Asn Tyr Glu Leu Leu
                195                 200                 205
```

```
Leu Arg Lys Phe Ser Ala Trp Met Lys Gln Asp Gly Leu Leu Phe Ile
    210                 215                 220

Glu His Leu Cys His Lys Thr Leu Gly Tyr His Asn Glu Pro Ile Asp
225                 230                 235                 240

Glu Asp Asp Trp Tyr Thr Ala Tyr Phe Phe Pro Ala Gly Thr Leu Thr
                245                 250                 255

Phe Ile Pro Ser Ser Phe Leu Leu Tyr Phe Gln Asp Asp Val Ser Val
            260                 265                 270

Val Asn His Trp Thr Leu Ser Gly Lys His Phe Ser Arg Ser Asn Glu
            275                 280                 285

Glu Trp Leu Lys Arg Met Asp Asn Lys Ile Asp Glu Val Lys Glu Ile
    290                 295                 300

Tyr Lys Ala Ala Ala Ser Glu Thr Lys Asp Asp Asp Ile Met Lys Leu
305                 310                 315                 320

Ile Arg Leu Trp Arg Phe Leu Ser Ile Ser Ala Ala Glu Met Phe Gly
                325                 330                 335

Tyr Lys Asp Gly Glu Glu Trp Met Ile Ser Gln Val Leu Phe Lys Lys
            340                 345                 350

Lys

<210> SEQ ID NO 77
<211> LENGTH: 366
<212> TYPE: PRT
<213> ORGANISM: Eschscholzia californica

<400> SEQUENCE: 77

Met Ala Ser Leu Val Glu Glu Gly Ser Phe Val Asn Asn Lys Glu Ser
1               5                   10                  15

Val Lys Glu Arg Val Ser Glu Leu Val Lys Arg Leu Lys Asn Gly Leu
            20                  25                  30

Val Ser Asp Glu Glu Leu Arg Lys Leu Met Arg Val Glu Leu Glu Lys
        35                  40                  45

Arg Leu Glu Trp Gly Tyr Lys Ser Thr His Glu Gln Gln Leu Ser Gln
    50                  55                  60

Leu Ile Asp Leu Ala His Ser Met Lys Lys Met Glu Ile Ala Met Glu
65                  70                  75                  80

Ile Asp Ala Leu Asn Ser Thr Val Tyr Glu Val Pro Leu Ser Phe Leu
                85                  90                  95

Gln Ile Ile His Gly Thr Thr Ile Lys Glu Ser Cys Leu Tyr Phe Lys
            100                 105                 110

Asp Glu Ser Thr Thr Val Asp Glu Ala Glu Ile Ala Met Met Asp Leu
        115                 120                 125

Tyr Leu Glu Arg Ala Gln Ile Lys Asp Gly Gln Ser Ile Leu Asp Leu
    130                 135                 140

Gly Cys Gly Leu Gly Gly Phe Ser Phe His Ile Ala Ser Lys Phe Thr
145                 150                 155                 160

Gly Cys Asn Ile Thr Ala Val Thr Asn Ser Val Lys Gln Lys Glu Phe
                165                 170                 175

Ile Glu Glu Lys Cys Lys Thr Leu Asn Val Pro Asn Ile Lys Val Ile
            180                 185                 190

Leu Ala Asp Ile Cys Thr Thr Glu Ile Glu Asn Val Phe Asp Arg Ile
        195                 200                 205

Ile Ala Ile Gly Leu Ile Glu His Met Lys Asn Tyr Glu Leu Leu Leu
    210                 215                 220
```

```
Lys Lys Phe Ser Lys Trp Met Thr Gln Asp Gly Leu Leu Phe Ile Glu
225                 230                 235                 240

His Leu Cys His Lys Thr Phe Gly Tyr His Asn Glu Pro Leu Asp Glu
            245                 250                 255

Asp Asp Trp Tyr Thr Thr Tyr Phe Phe Pro Ala Gly Thr Leu Thr Phe
        260                 265                 270

Ile Pro Ser Ser Phe Leu Leu Tyr Phe Gln Asp Asp Val Ser Val Val
    275                 280                 285

Asp His Trp Thr Leu Asn Gly Lys His Phe Ala Arg Ser Asn Glu Glu
290                 295                 300

Trp Leu Lys Arg Met Asp Glu Lys Met Asp Glu Val Lys Gln Ile Phe
305                 310                 315                 320

Arg Ser Asn Leu Lys Ser Glu Asn Glu Val Thr Lys Thr Ile Gly Glu
            325                 330                 335

Trp Arg Phe Leu Ser Met Ser Ala Ala Glu Met Phe Gly Tyr Asn Asn
        340                 345                 350

Gly Glu Glu Trp Met Val Ser Gln Leu Leu Phe Lys Lys Lys
        355                 360                 365

<210> SEQ ID NO 78
<211> LENGTH: 362
<212> TYPE: PRT
<213> ORGANISM: Glaucium flavum

<400> SEQUENCE: 78

Met Gly Ser Asn Glu Thr Asn Gly Glu Leu Lys Thr Lys Glu Met Val
1               5                   10                  15

Pro Asp Leu Leu Lys Arg Leu Glu Ser Gly Leu Val Ala Asp Glu Glu
                20                  25                  30

Leu Arg Lys Leu Ile Arg Phe Glu Leu Glu Arg Arg Leu Lys Trp Gly
            35                  40                  45

Tyr Lys Pro Thr His Glu Gln Gln Leu Ala Glu Leu Leu Lys Leu Ala
        50                  55                  60

His Ser Thr Lys Gln Met Lys Ile Ala Thr Glu Thr Asp Ser Leu Asn
65                  70                  75                  80

Ser Thr Met Tyr Glu Val Pro Ile Pro Phe Leu Gln Leu Gln Phe Gly
                85                  90                  95

Ser Ala Ile Lys Glu Ser Cys Cys Tyr Phe Lys Asp Glu Ser Thr Thr
                100                 105                 110

Leu Asp Glu Ala Glu Val Ala Met Met Asp Leu Tyr Leu Glu Arg Thr
            115                 120                 125

Gln Ile Lys Asp Gly Gln Ser Ile Leu Asp Leu Gly Cys Gly Leu Gly
        130                 135                 140

Ala Leu Ala Phe His Ile Val Gln Lys Tyr Pro Asn Cys Asn Val Leu
145                 150                 155                 160

Ala Ile Thr Asn Ser Val Glu Gln Lys Glu Phe Ile Glu Glu Lys Cys
                165                 170                 175

Lys Ile Arg Lys Val Glu Asn Val Lys Val Ser Leu Ala Asp Ile Cys
                180                 185                 190

Thr Leu Glu Met Lys Thr Thr Phe Asp Arg Ile Phe Ala Ile Gly Leu
            195                 200                 205

Leu Glu His Met Lys Asn Tyr Gln Leu Leu Leu Lys Lys Phe Ser Asn
        210                 215                 220

Trp Met Lys Gln Asp Gly Leu Leu Phe Ile Glu His Leu Cys His Lys
225                 230                 235                 240
```

```
Thr Leu Ala Tyr His Tyr Glu Pro Leu Asp Glu Asp Trp Tyr Thr
            245                 250                 255

Glu Tyr Phe Phe Pro Ala Gly Thr Leu Thr Ile Ile Ser Ser Ser Phe
        260                 265                 270

Leu Leu Tyr Phe Gln Asp Val Ser Ile Val Asn His Trp Ser Leu
        275                 280                 285

Ser Gly Lys His Phe Ser Arg Ser Asn Glu Glu Trp Leu Lys Arg Met
290                 295                 300

Asp Met Lys Ile Asp Glu Val Lys Glu Ile Leu Glu Ala Ala Phe Glu
305                 310                 315                 320

Asn Lys Asp His Asp Ile Thr Lys Leu Ile Asn His Trp Arg Phe Leu
                325                 330                 335

Ala Ile Asn Ala Thr Glu Met Phe Gly Tyr Asn Asn Gly Glu Glu Trp
            340                 345                 350

Met Val Ser Gln Val Leu Phe Lys Lys Lys
            355                 360

<210> SEQ ID NO 79
<211> LENGTH: 365
<212> TYPE: PRT
<213> ORGANISM: Sanguinaria canadensis

<400> SEQUENCE: 79

Met Ala Ser Asp His Glu Val Ser Asn Lys Glu Leu Lys Lys Lys Lys
1               5                   10                  15

Glu Val Ile Thr Glu Leu Leu Lys Arg Leu Glu Ser Gly Leu Val Ser
            20                  25                  30

Asp Glu Glu Leu Arg Gly Leu Ile Arg Phe Glu Leu Glu Arg Arg Leu
        35                  40                  45

Arg Trp Gly Tyr Lys Pro Thr His Glu Gln Gln Leu Ala Gln Leu Leu
    50                  55                  60

Asn Leu Ala His Ser Met Lys Gln Met Lys Ile Ala Thr Glu Ile Asp
65                  70                  75                  80

Ala Leu Asn Ser Thr Met Tyr Glu Val Pro Ile Pro Phe Leu Gln Ile
                85                  90                  95

Gln Leu Gly Ser Thr Leu Lys Glu Ser Cys Cys Tyr Phe Lys Asp Glu
            100                 105                 110

Ser Thr Thr Val Asp Glu Ala Glu Ile Ala Met Met Asp Leu Tyr Leu
        115                 120                 125

Glu Arg Ala Gln Ile Lys Asp Gly Gln Ser Ile Leu Asp Leu Gly Cys
    130                 135                 140

Gly Leu Gly Ala Leu Ala Phe His Ile Ala Gln Lys Tyr Thr Asn Cys
145                 150                 155                 160

Asn Ile Thr Ala Ile Thr Asn Ser Val Arg Gln Lys Glu Phe Ile Glu
                165                 170                 175

Glu Lys Cys Lys Ile Leu Asn Val Ser Asn Val Lys Val Ser Leu Ala
            180                 185                 190

Asp Ile Cys Thr Leu Glu Met Glu Ala Thr Phe Asp Arg Ile Phe Ala
        195                 200                 205

Ile Gly Leu Ile Glu His Met Lys Asn Tyr Glu Leu Leu Lys Lys
    210                 215                 220

Phe Ser Glu Trp Met Lys Gln Asp Gly Leu Ile Phe Ile Glu His Leu
225                 230                 235                 240

Cys His Lys Thr Leu Ala Tyr His Tyr Glu Pro Leu Asp Glu Asp
```

```
                        245                 250                 255
Trp Tyr Thr Glu Tyr Phe Phe Pro Ala Gly Thr Leu Thr Leu Ile Ser
            260                 265                 270

Ser Ser Phe Leu Leu Tyr Phe Gln Asp Asp Val Ser Val Val Asp His
        275                 280                 285

Trp Thr Leu Ser Gly Lys His Phe Ser Arg Ser Asn Glu Glu Trp Leu
    290                 295                 300

Lys Arg Met Asp Glu Lys Ile Asp Glu Val Lys Glu Ile Phe Glu Ser
305                 310                 315                 320

Val Ser Asp Ser Lys Asp Asp Val Thr Lys Leu Ile Asn His Trp
                325                 330                 335

Arg Phe Phe Cys Ile Ser Ser Ala Glu Met Phe Gly Tyr Asn Asn Gly
                340                 345                 350

Glu Glu Trp Met Ile Ser Gln Val Leu Phe Lys Lys Lys
                355                 360                 365

<210> SEQ ID NO 80
<211> LENGTH: 371
<212> TYPE: PRT
<213> ORGANISM: Corydalis chelanthifolia

<400> SEQUENCE: 80

Met Ile Lys Lys Ser Lys Ile Met Ala Phe Ser Asp His His Glu
1               5                   10                  15

Val Val Lys Asn His Ser Lys Lys Glu Met Ile Ala Asp Leu Leu Lys
            20                  25                  30

Arg Leu Glu Ala Gly Leu Val Pro Asp Glu Glu Met Arg Asn Leu Phe
        35                  40                  45

Arg Phe Glu Leu Glu Arg Arg Leu Gln Trp Gly Tyr Lys Ser Ile His
    50                  55                  60

Gln Glu Gln Leu Ser Gln Leu Leu Lys Leu Ala His Ser Thr Lys Glu
65                  70                  75                  80

Met Thr Ile Val Ala Glu Met Asp Ala Leu Asn Ser Ser Met Tyr Glu
                85                  90                  95

Leu Pro Ile Ser Phe Leu Gln Ile Gln Leu Gly Ser Asn Leu Lys Gln
            100                 105                 110

Ser Ser Leu Tyr Phe Lys Asp Glu Leu Thr Thr Val Asp Glu Ala Glu
        115                 120                 125

Val Ala Ile Met Asp Leu Tyr Leu Glu Arg Ala Gln Ile Glu Asp Gly
    130                 135                 140

Gln Ser Ile Leu Asp Leu Gly Cys Gly Leu Gly Ala Phe Ser Phe His
145                 150                 155                 160

Val Ala Arg Lys Tyr Thr Asn Cys Asn Ile Thr Ala Val Thr Asn Ser
                165                 170                 175

Leu Thr Gln Lys Glu Phe Ile Glu Lys Lys Ser Lys Ile Leu Asn Ile
            180                 185                 190

Gln Asn Val Lys Val Ile Phe Ala Asp Val Thr Thr Val Glu Met Glu
        195                 200                 205

Thr Thr Phe Asp Arg Val Phe Ala Ile Gly Leu Ile Glu His Met Gln
    210                 215                 220

Asn Tyr Glu Leu Phe Leu Lys Lys Leu Ser Lys Trp Met Lys Gln Asp
225                 230                 235                 240

Gly Leu Leu Phe Ile Glu His Phe Cys His Lys Thr Leu Ala Tyr His
                245                 250                 255
```

```
Tyr Lys Pro Ile Asp Glu Asp Trp Phe Thr Asn Leu Leu Tyr Pro
            260                 265                 270

Asn Gly Thr Val Ile Ser Ser Leu Leu Tyr Phe Gln Asp Asp
        275                 280                 285

Val Ser Val Asp His Trp Ser Leu Ser Gly Lys His Phe Ser Arg
    290                 295                 300

Ala Ser Glu Glu Ser Leu Lys Arg Met Asp Ala Lys Met Asp Glu Met
305                 310                 315                 320

Lys Glu Ile Phe Glu Ser Ile Thr Asp Ser Lys Glu Glu Ala Met Lys
                325                 330                 335

Leu Ile Asn Gln Trp Arg Ile Phe Cys Ile Ser Cys Ala Glu Met Phe
            340                 345                 350

Gly Tyr Asn Asn Gly Glu Glu Trp Met Thr Ser His Phe Leu Phe Lys
            355                 360                 365

Lys Lys Leu
        370

<210> SEQ ID NO 81
<211> LENGTH: 373
<212> TYPE: PRT
<213> ORGANISM: Corydalis chelanthifolia

<400> SEQUENCE: 81

Met Gly Ser Ser Thr Ala Ser Asp His Glu Met Val Ile Met Glu Asn
1               5                   10                  15

Asp Ser Lys Asn Lys Gln Val Val Ile Ala Asp Leu Leu Lys Arg Leu
            20                  25                  30

Val Gly Gly Leu Val Pro Asp Glu Glu Met Arg Asn Met Phe Arg Phe
        35                  40                  45

Glu Leu Glu Lys Arg Leu Lys Trp Gly Tyr Lys Ser Thr His Gln Gln
    50                  55                  60

Gln Leu Ser Gln Leu Leu Asn Leu Val Glu Leu Asn Lys Gly Ile Ala
65                  70                  75                  80

Lys Ile Ala Pro Glu Met Asp Ala Leu Asn Ser Ala Met Tyr Glu Val
                85                  90                  95

Pro Ile Pro Tyr Leu Lys Leu Met Leu Gly Ser Thr Leu Lys Gln Ser
            100                 105                 110

Cys Leu Tyr Phe Lys Asp Glu Ser Thr Thr Leu Asp Glu Ala Glu Ile
        115                 120                 125

Glu Met Met Asp Leu Tyr Leu Glu Arg Ala Asp Ile Gln Asp Gly Gln
    130                 135                 140

Ser Ile Leu Asp Leu Gly Cys Gly Leu Gly Gly Leu Gly Phe His Ile
145                 150                 155                 160

Ala Gln Lys Tyr Ile Ser Cys Asn Ile Thr Ala Leu Thr Asn Ser Leu
                165                 170                 175

Thr Gln Lys Glu Phe Ile Glu Glu Lys Cys Lys Thr Leu Asn Ile Pro
            180                 185                 190

Asn Val Lys Val Ile Leu Ala Asp Val Thr Thr Val Glu Ile Glu Thr
        195                 200                 205

Thr Phe Asp Arg Leu Phe Ala Ile Gly Leu Val Glu His Met Glu Asn
    210                 215                 220

Tyr Glu Leu Phe Leu Arg Lys Leu Ser Lys Trp Met Lys Gln Asp Gly
225                 230                 235                 240

Leu Leu Phe Ile Glu His Leu Cys His Lys Thr Leu Ala Tyr His Tyr
                245                 250                 255
```

```
Lys Pro Ile Asp Glu Asp Asp Trp Tyr Ser Asn Leu Leu Tyr Pro Thr
            260                 265                 270

Gly Thr Leu Thr Ser Ala Ser Phe Leu Leu Tyr Phe Gln Asp Asp Leu
        275                 280                 285

Ser Val Val Asp His Trp Ser Leu Ser Gly Lys His Phe Ser Arg Ala
290                 295                 300

Thr Glu Glu Trp Leu Lys Met Ile Asp Ala Asn Met Asp Lys Ile Arg
305                 310                 315                 320

Glu Ile Tyr Glu Ser Val Thr Glu Ser Lys Glu Ala Thr Arg Ser
                325                 330                 335

Ile Asn Gln Trp Arg Ile Phe Cys Ile Ser Cys Ala Glu Met Phe Gly
            340                 345                 350

Tyr Asn Asp Gly Glu Glu Trp Met Ile Ser His Phe Leu Phe Lys Asn
            355                 360                 365

Lys Lys Gln Ile Glu
            370

<210> SEQ ID NO 82
<211> LENGTH: 366
<212> TYPE: PRT
<213> ORGANISM: Corydalis chelanthifolia

<400> SEQUENCE: 82

Met Ala Thr Ser Asp Gln Glu Val Lys Thr Ser Lys Met Glu Met Ile
1               5                   10                  15

Ala Asp Leu Leu Lys Arg Leu Glu Ala Gly Leu Val Pro Asp Asp Glu
            20                  25                  30

Ile Arg Ser Leu Ile Arg Val Glu Leu Glu Arg Arg Leu Lys Trp Gly
        35                  40                  45

Tyr Lys Ser Thr His Gln Glu Gln Leu Asp Gln Leu Leu Asn Leu Ala
    50                  55                  60

His Ser Ile Lys Lys Met Lys Ile Ala Ser Thr Glu Met Asp Gly Leu
65                  70                  75                  80

Thr Ser Thr Met Tyr Glu Val Pro Ile Ser Leu Val Gln Ile Gln Leu
                85                  90                  95

Gly Ser His Leu Lys Glu Ser Cys Leu Tyr Phe Lys Asp Glu Thr Thr
            100                 105                 110

Thr Val Asp Glu Ala Glu Ile Ala Met Met Asp Leu Tyr Leu Glu Arg
        115                 120                 125

Ala Gln Ile Lys Asp Gly Gln Ser Ile Leu Asp Leu Gly Cys Gly Leu
    130                 135                 140

Gly Ala Val Ser Phe His Ile Ala Gln Lys Tyr Thr Ser Cys Asn Ile
145                 150                 155                 160

Thr Ala Val Thr Asn Ser Val Arg Gln Lys Glu Phe Ile Glu Glu Lys
                165                 170                 175

Ser Lys Thr Leu Asn Val Pro Asn Val Lys Val Leu Leu Ala Asp Ile
            180                 185                 190

Thr Thr Leu Glu Met Glu His Thr Phe Asp Arg Leu Phe Ala Ile Ser
        195                 200                 205

Leu Ile Glu His Met Glu Asn Tyr Glu Leu Leu Arg Lys Leu Ser
    210                 215                 220

Glu Trp Met Lys Gln Asp Gly Leu Leu Phe Ile Glu His Leu Cys His
225                 230                 235                 240

Lys Thr Leu Ser Tyr His Phe Glu Pro Met Asp Glu Asp Asp Trp Tyr
```

```
                       245                 250                 255
Thr Asn Leu Leu Phe Pro Ala Gly Thr Leu Thr Leu Val Ser Ala Ser
                260                 265                 270

Phe Leu Leu Tyr Phe Gln Asp Asp Leu Ser Val Val Asn Gln Trp Val
            275                 280                 285

Met Ser Gly Lys His Phe Ser Arg Ala Asn Glu Glu Trp Leu Lys Asn
        290                 295                 300

Met Asp Ala Lys Met Asp Glu Met Arg Glu Ile Phe Glu Ser Ile Thr
305                 310                 315                 320

Asp Ser Glu Glu Glu Val Val Lys Leu Ile Asn His Trp Arg Ile Phe
                325                 330                 335

Cys Ile Ser Ser Ala Glu Met Phe Ala Tyr Asn Asp Gly Glu Glu Trp
                340                 345                 350

Met Asn Ser His Val Leu Phe Lys Lys Lys Gln Ile Gln
                355                 360                 365

<210> SEQ ID NO 83
<211> LENGTH: 359
<212> TYPE: PRT
<213> ORGANISM: Corydalis chelanthifolia

<400> SEQUENCE: 83

Met Ala Gly Ser Gly Ala Asn Lys Glu Met Ile Ala Asp Leu Leu Lys
1               5                   10                  15

Arg Leu Glu Val Gly Leu Val Pro Asp Glu Ile Arg Ser Leu Ile
            20                  25                  30

Arg Phe Gln Leu Lys Arg Arg Leu Lys Trp Gly Tyr Lys Thr Thr His
        35                  40                  45

Gln Glu Gln Leu Glu Gln Leu Leu Ser Leu Ala His Ser Ile Arg Lys
    50                  55                  60

Met Lys Ile Ala Thr Glu Met Asp Ala Leu Asn Ser Thr Met Tyr Glu
65                  70                  75                  80

Val Pro Ile Ser Phe Met Gln Ile Val Phe Gly Ser Thr Leu Lys Glu
                85                  90                  95

Ser Cys Leu Tyr Phe Lys Asp Glu Ala Thr Thr Val Asn Glu Ala Glu
            100                 105                 110

Ile Ala Met Met Asp Leu Tyr Leu Glu Arg Ala Gln Ile Lys Asp Gly
        115                 120                 125

Gln Ser Ile Leu Asp Leu Gly Cys Gly Met Gly Ser Leu Cys Phe His
    130                 135                 140

Ile Ala Arg Lys Tyr Thr Asn Cys Asn Ile Thr Ala Val Thr Asn Ser
145                 150                 155                 160

Val Ser Gln Lys Glu Phe Ile Glu Lys Ser Lys Thr Leu Asn Leu
                165                 170                 175

Pro Asn Val Lys Val Ile Leu Ala Asp Ile Thr Thr Leu Glu Met Asp
            180                 185                 190

Asp Thr Tyr Asp Cys Leu Phe Ala Ile Gly Leu Ile Glu His Met Lys
        195                 200                 205

Asn Tyr Glu Leu Leu Leu Arg Lys Leu Ser Asn Trp Met Lys Gln Asp
    210                 215                 220

Ser Leu Leu Phe Ile Asp His Val Cys His Lys Thr Leu Ala Tyr His
225                 230                 235                 240

Tyr Glu Pro Ile Asp Glu Asp Asp Trp Tyr Thr Asn Leu Leu Phe Pro
                245                 250                 255
```

Ala Gly Thr Leu Thr Leu Val Ser Ala Ser Phe Leu Leu Tyr Phe Gln
            260                 265                 270

Asp Asp Leu Ser Leu Val Asp His Trp Ser Met Ser Gly Lys His Phe
            275                 280                 285

Ser Arg Thr Asn Lys Glu Trp Leu Lys Asn Ile Asp Gly Lys Met Asp
            290                 295                 300

Lys Ile Arg Glu Ile Val Lys Ser Ile Thr Asp Ser Glu Glu Glu Val
305                 310                 315                 320

Val Lys Leu Ile Asn His Trp Arg Met Leu Cys Ile Asn Ser Ser Glu
            325                 330                 335

Met Phe Gly Phe Asn Asp Gly Glu Glu Trp Met Asn Ser His Val Leu
            340                 345                 350

Phe Lys Lys Lys Lys Gln Ile
            355

<210> SEQ ID NO 84
<211> LENGTH: 353
<212> TYPE: PRT
<213> ORGANISM: Sanguinaria canadensis

<400> SEQUENCE: 84

Met Glu Met Ile Ala Asp Leu Leu Lys Arg Leu Glu Ala Gly Leu Val
1               5                   10                  15

Pro Asp Asp Glu Ile Arg Ser Leu Ile Arg Val Glu Leu Glu Arg Arg
            20                  25                  30

Leu Lys Trp Gly Tyr Lys Ser Thr His Gln Glu Gln Leu Asp Gln Leu
            35                  40                  45

Leu Asn Leu Ala His Ser Ile Lys Lys Met Lys Ile Ala Ser Thr Glu
        50                  55                  60

Met Asp Gly Leu Thr Ser Thr Met Tyr Glu Val Pro Ile Ser Leu Val
65                  70                  75                  80

Gln Ile Gln Leu Gly Ser His Leu Lys Glu Ser Cys Leu Tyr Phe Lys
                85                  90                  95

Asp Glu Thr Thr Thr Val Asp Glu Ala Glu Ile Ala Met Met Asp Leu
            100                 105                 110

Tyr Leu Glu Arg Ala Gln Ile Lys Asp Gly Gln Ser Ile Leu Asp Leu
            115                 120                 125

Gly Cys Gly Leu Gly Ser Val Cys Phe His Ile Ala Arg Lys Tyr Thr
        130                 135                 140

Ser Cys Asn Ile Thr Ala Val Thr Asn Ser Val Ser Gln Lys Glu Phe
145                 150                 155                 160

Ile Glu Glu Lys Ser Lys Thr Leu Asn Val Pro Asn Val Lys Val Leu
                165                 170                 175

Leu Ala Asp Ile Thr Thr Leu Glu Met Asp Thr Phe Asp Cys Leu
            180                 185                 190

Phe Ala Ile Gly Leu Ile Glu His Met Glu Asn Tyr Glu Leu Leu Leu
            195                 200                 205

Arg Lys Leu Ser Asp Trp Met Lys Gln Asp Gly Leu Leu Phe Ile Asp
        210                 215                 220

His Val Cys His Lys Thr Leu Ser Tyr His Phe Glu Pro Met Asp Glu
225                 230                 235                 240

Asp Asp Trp Tyr Thr Asn Leu Leu Phe Pro Ala Gly Thr Leu Thr Leu
                245                 250                 255

Val Ser Ala Ser Phe Leu Leu Tyr Phe Gln Asp Asp Leu Ser Leu Val
            260                 265                 270

```
Asp His Trp Ser Met Ser Gly Lys His Phe Ser Arg Thr Asn Lys Glu
            275                 280                 285

Trp Leu Lys Asn Ile Asp Gly Lys Met Asp Lys Ile Arg Glu Ile Val
        290                 295                 300

Lys Ser Ile Thr Asp Ser Glu Glu Val Val Lys Leu Ile Asn His
305                 310                 315                 320

Trp Arg Met Leu Cys Ile Asn Ser Ser Glu Met Phe Gly Phe Asn Asp
                325                 330                 335

Gly Glu Glu Trp Met Asn Ser His Val Leu Phe Lys Lys Lys Gln
                340                 345                 350

Ile

<210> SEQ ID NO 85
<211> LENGTH: 363
<212> TYPE: PRT
<213> ORGANISM: Papaver bracteatum

<400> SEQUENCE: 85

Met Cys Thr Thr Met Asp Thr Thr Lys Ile Ser Gln Gln Asp Asp Leu
1               5                   10                  15

Trp Lys Asn Met Glu Leu Gly Leu Ile Ser Asp Glu Glu Val Arg Arg
                20                  25                  30

Leu Met Lys Ile Glu Thr Glu Lys Arg Ile Lys Trp Gly Thr Lys Pro
            35                  40                  45

Thr Gln Gln Glu Gln Leu Ala Gln Leu Leu Asp Phe Asn Lys Ser Leu
        50                  55                  60

Arg Gly Met Lys Met Ala Thr Glu Val His Ala Leu Glu Asn His Lys
65              70                  75                  80

Ile Tyr Glu Ile Pro Asp Ser Phe Asn Gln Ile Gly Gly Lys Glu
                85                  90                  95

Ser Ala Gly Leu Phe Thr Asp Glu Ala Thr Thr Thr Ile Glu Glu Ala
            100                 105                 110

Asn Thr Lys Met Met Asp Leu Tyr Cys Glu Arg Ala Gly Leu Lys Asp
        115                 120                 125

Gly Gln Thr Ile Leu Asp Ile Gly Cys Gly Ala Gly Leu Leu Val Leu
    130                 135                 140

His Leu Ala Lys Lys Tyr Lys Asn Cys Lys Ile Thr Gly Val Thr Asn
145                 150                 155                 160

Thr Ser Trp His Lys Glu His Ile Leu Glu Gln Cys Lys Asn Leu Asn
                165                 170                 175

Leu Ser Asn Val Glu Val Ile Leu Ala Asp Val Thr Thr Val Asp Ile
            180                 185                 190

Glu Arg Thr Phe Asp Arg Val Phe Val Ile Gly Leu Ile Glu His Met
        195                 200                 205

Lys Asn Phe Glu Leu Phe Leu Arg Lys Ile Ser Lys Trp Met Lys Asp
    210                 215                 220

Asp Gly Leu Leu Phe Leu Glu His Leu Cys His Lys Ser Phe Ser Asp
225                 230                 235                 240

His Trp Glu Pro Leu Ser Glu Asp Trp Tyr Ala Lys Asn Phe Phe
                245                 250                 255

Pro Ser Gly Thr Leu Val Ile Pro Ser Ala Thr Cys Leu Leu Tyr Phe
            260                 265                 270

Gln Glu Asp Val Thr Val Lys Asp His Trp Leu Leu Ser Gly Asn Asn
        275                 280                 285
```

-continued

```
Phe Ala Arg Ser Asn Glu Ala Ile Leu Lys Arg Ile Asp Ser Lys Ile
    290                 295                 300

Glu Glu Val Lys Asp Ile Phe Met Ser Phe Tyr Gly Ile Gly Glu Glu
305                 310                 315                 320

Glu Ala Val Lys Leu Ile Asn Trp Trp Arg Leu Leu Cys Ile Thr Ala
            325                 330                 335

Asn Glu Leu Phe Lys Tyr Asn Asn Gly Glu Glu Trp Leu Ile Ser Gln
            340                 345                 350

Leu Leu Phe Lys Lys Lys Leu Met Thr Cys Ile
            355                 360

<210> SEQ ID NO 86
<211> LENGTH: 366
<212> TYPE: PRT
<213> ORGANISM: Papaver bracteatum

<400> SEQUENCE: 86

Met Val Lys Gly Asp Gln Phe Gln Thr Thr Thr Met Glu Glu Thr Lys
1               5                   10                  15

Ile Ser Gln Glu Asn Asp Leu Trp Thr Asn Met Glu Leu Gly Leu Ile
            20                  25                  30

Pro Asp Glu Glu Val Arg Arg Leu Met Lys Ile Glu Ile Glu Lys Arg
        35                  40                  45

Ile Glu Trp Gly Met Lys Pro Thr Gln His Gln Gln Leu Ala Gln Leu
    50                  55                  60

Leu Asp Phe Thr Lys Ser Leu Arg Gly Met Lys Met Ala Thr Glu Leu
65                  70                  75                  80

Asp Lys Leu Asp Ser Lys Leu Tyr Glu Thr Pro His Ser Phe Asn Gln
                85                  90                  95

Ile Val Asn Gly Ser Thr Leu Lys Glu Ser Ser Gly Leu Tyr Thr Asp
            100                 105                 110

Val Thr Thr Thr Met Asp Glu Ala Ser Ile Lys Met Met Asp Leu Tyr
        115                 120                 125

Cys Glu Arg Ala Asn Ile Lys Asp Gly Gln Thr Ile Leu Asp Leu Gly
    130                 135                 140

Cys Gly Pro Gly Pro Leu Val Leu His Ile Ala Lys Lys Tyr Ser Asn
145                 150                 155                 160

Cys Lys Ile Thr Gly Val Thr Asn Ala Phe Ser Gln Arg Glu Tyr Ile
                165                 170                 175

Leu Glu Glu Cys Lys Lys Leu Ser Leu Ser Asn Val Glu Ile Ile Leu
            180                 185                 190

Ala Asp Val Thr Ser Leu Asp Leu Glu Thr Thr Phe Asp Arg Val Phe
        195                 200                 205

Val Ile Gly Phe Ile Glu His Met Lys Asn Phe Glu Leu Phe Leu Arg
    210                 215                 220

Lys Ile Ser Lys Trp Met Lys Asp Asp Ala Val Leu Phe Leu Glu His
225                 230                 235                 240

Phe Cys His Lys Ser Phe Ser Tyr His Gly Glu Pro Leu Ser Glu Asp
                245                 250                 255

Asp Trp Tyr Ala Lys Asn Phe Phe Ala Pro Gly Thr Leu Val Ile Pro
            260                 265                 270

Ser Ala Thr Cys Leu Leu Tyr Phe Gln Glu Asp Leu Ala Val Ile Asp
        275                 280                 285

His Trp Phe Leu Ser Gly Asn His Phe Ala Arg Thr Asn Glu Glu Met
```

```
                290                 295                 300
Leu Lys Gly Ile Asp Gly Lys Ile Glu Glu Ile Lys Asp Ile Phe Met
305                 310                 315                 320

Ser Phe Tyr Gly Ile Asn Glu Ala Glu Ala Val Lys Leu Ile Asn Trp
                325                 330                 335

Trp Arg Leu Phe Cys Ile Thr Gly Ala Glu Met Phe Ser Tyr Asn Asn
                340                 345                 350

Gly Glu Glu Trp Phe Ile Ser Gln Leu Leu Phe Lys Lys Lys
            355                 360                 365

<210> SEQ ID NO 87
<211> LENGTH: 364
<212> TYPE: PRT
<213> ORGANISM: Eschscholzia californica

<400> SEQUENCE: 87

Met Ala Leu Glu Gln Glu Asp Ser Met Ser Val Pro Glu Arg Asn Glu
1               5                   10                  15

Gly Val Ala Asp Leu Ile Lys Arg Met Glu Leu Gly Leu Val Asn Asp
                20                  25                  30

Glu Glu Ile Arg Arg Leu Met Arg Ile Gln Ile Glu Asn Arg Leu Lys
            35                  40                  45

Trp Gly Tyr Lys Pro Thr His Asp Gln Gln Leu Ala Gln His Leu His
    50                  55                  60

Phe Ile Asn Ser Leu Lys Glu Met Lys Met Ala Thr Glu Met Asp Ser
65                  70                  75                  80

Leu Asp Ser Gln Val Tyr Glu Ser Pro Asn Ser Phe Gln Gln Ile Met
                85                  90                  95

Cys Gly Arg Ser Met Lys Glu Ser Ala Gly Leu Phe Met Asp Asp Val
                100                 105                 110

Thr Thr Val Glu Glu Ala His Ile Arg Met Met Asp Leu Tyr Cys Asp
            115                 120                 125

Lys Ala Thr Phe Glu Asp Gly Gln Lys Ile Leu Asp Leu Gly Cys Gly
    130                 135                 140

His Gly Ser Val Val Leu His Val Ala Gln Lys Tyr Lys Gly Cys Gln
145                 150                 155                 160

Val Thr Gly Val Thr Asn Ser Ser Ala Gln Lys Gln Tyr Ile Leu Glu
                165                 170                 175

Gln Cys Lys Lys Leu Asp Leu Ser Asn Val Glu Ile Ile Leu Ala Asp
                180                 185                 190

Val Thr Thr Leu Glu Met Glu Glu Lys Phe Asp Arg Val Ile Ile Ile
            195                 200                 205

Gly Leu Ile Glu His Met Lys Asn Phe Lys Leu Phe Phe Gln Lys Val
    210                 215                 220

Ser Lys Trp Met Lys Glu Gly Gly Leu Leu Phe Leu Glu Asn Tyr Phe
225                 230                 235                 240

His Lys Asp Phe Ala Tyr His Cys Glu Lys Ile Asp Glu Asp Asp Trp
                245                 250                 255

Tyr Asp Gly Tyr Ile Phe Pro Pro Gly Ser Leu Leu Met Pro Ser Ala
                260                 265                 270

Ser Thr Leu Leu Tyr Phe Gln Glu Asp Leu Thr Val Ala Asp His Trp
            275                 280                 285

Val Leu Pro Gly Thr His Phe Ala Lys Thr Phe Glu Glu Phe Leu Lys
    290                 295                 300
```

```
Lys Ile Asp Leu Arg Ile Glu Glu Val Arg Glu Ile Phe Glu Ala Phe
305                 310                 315                 320

Tyr Gly Ile Ser Lys Glu Glu Ala Met Lys Leu Ser Asn Tyr Trp Arg
            325                 330                 335

Asn Phe Cys Ile Ser Ala Met Glu Ile Phe Asn Tyr Asn Asn Gly Gln
            340                 345                 350

Glu Trp Met Ile Ser His Leu Leu Tyr Thr Lys Lys
            355                 360

<210> SEQ ID NO 88
<211> LENGTH: 368
<212> TYPE: PRT
<213> ORGANISM: Chelidonium majus

<400> SEQUENCE: 88

Met Glu Thr Gly Lys Asn Asn Gln Asn Met Lys Thr Thr Ile Asp Asp
1               5                   10                  15

Leu Trp Asn Gln Met Met Leu Gly Ile Val Pro Asp Lys Glu Ile Arg
            20                  25                  30

Arg Leu Met Lys Ile Glu Leu Lys Lys Arg Leu Asp Trp Gly Tyr Arg
        35                  40                  45

Pro Thr His Gln Gln Leu Ser Gln Leu Leu Asp Phe Ala Lys Gly
    50                  55                  60

Leu Cys Asn Tyr Cys Trp Thr Ala Leu Arg Cys Met Lys Met Ser Ala
65              70                  75                  80

Glu Phe Asp Thr Leu Asp Ser Lys Val Tyr Glu Thr Pro Lys Ser Phe
                85                  90                  95

Gln Gln Ile Met Cys Gly Thr Thr Ile Lys Glu Ser Ser Gly Leu Phe
            100                 105                 110

Met Asn Glu Ser Thr Thr Leu Asp Gln Ala Gln Ile Ser Met Leu Asp
        115                 120                 125

Leu Tyr Phe Asp Lys Ala Lys Ile Lys Asp Gly Gln Ser Ile Leu Asp
    130                 135                 140

Leu Gly Cys Gly His Gly Ala Leu Ile Leu Tyr Leu Ala Gln Lys Tyr
145                 150                 155                 160

Gln Asn Cys Asn Ile Thr Gly Val Thr Asn Ser Leu Ser Gln Lys Glu
                165                 170                 175

Phe Ile Val Glu Lys Cys Lys Lys Leu Gly Leu Ser Asn Val Glu Ile
            180                 185                 190

Leu Leu Ala Asp Val Thr Lys Leu Glu Met Glu Asp Met Phe Asp Arg
        195                 200                 205

Val Phe Val Ile Gly Leu Ile Glu His Met Lys Asn Phe Glu Leu Phe
    210                 215                 220

Leu Arg Lys Ile Ser Glu Trp Met Lys Pro Asp Gly Leu Leu Phe Leu
225                 230                 235                 240

Glu His Tyr Cys His Lys Ser Phe Ala His Gln Trp Glu Pro Ile Asp
                245                 250                 255

Glu Glu Asp Trp Phe Ser Lys Tyr Ile Phe Pro Pro Gly Thr Val Ile
            260                 265                 270

Ile Pro Ser Ala Ser Phe Leu Leu Tyr Phe Gln Glu Asp Val Lys Val
        275                 280                 285

Ile Asp His Trp Thr Leu Ser Gly Asn His Phe Ala Arg Thr Gln Glu
    290                 295                 300

Glu Trp Leu Lys Gly Ile Asp Gly His Ile Asp Glu Val Glu Lys Thr
305                 310                 315                 320
```

Phe Glu Ser Phe Tyr Gly Ile Ser Lys Glu Glu Ala Val Lys Leu Ile
              325                 330                 335

Asn Phe Trp Arg Val Phe Cys Leu Ser Gly Val Glu Met Phe Gly Tyr
              340                 345                 350

Asn Asn Gly Glu Glu Trp Met Ile Ser His Leu Leu Phe Lys Lys Lys
              355                 360                 365

<210> SEQ ID NO 89
<211> LENGTH: 361
<212> TYPE: PRT
<213> ORGANISM: Glaucium flavum

<400> SEQUENCE: 89

Met Thr Met Glu Ala Asn Asn Ala Lys Lys Glu Ala Ile Glu Asn Leu
1               5                   10                  15

Trp Glu Gln Met Met Gly Leu Val Pro Asp His Glu Ile Thr Arg
              20                  25                  30

Leu Met Lys Ser Glu Leu Gln Lys Arg Leu Asn Trp Gly Tyr Lys Pro
              35                  40                  45

Thr His Gln Gln Gln Ile Ser Gln Leu Leu Asp Phe Ala Lys Ser Leu
          50                  55                  60

Arg Arg Met Glu Met Ser Leu Asp Phe Asp Asn Leu Glu Leu Asp Thr
65              70                  75                  80

Lys Met Tyr Glu Thr Pro Glu Ser Phe Gln Leu Ile Met Ser Gly Thr
              85                  90                  95

Thr Leu Lys Glu Ser Ser Gly Leu Phe Thr Asp Glu Thr Ala Thr Leu
              100                 105                 110

Asp Gln Thr Gln Ile Arg Met Met Asp Leu Tyr Leu Glu Lys Ala Lys
          115                 120                 125

Ile Lys Asp Gly Gln Ser Ile Leu Asp Leu Gly Cys Gly His Gly Ala
              130                 135                 140

Leu Ile Leu His Val Ala Gln Lys Tyr Arg Asn Cys Asn Val Thr Gly
145             150                 155                 160

Val Thr Asn Ser Ile Ala Gln Lys Glu Phe Ile Phe Lys Gln Cys Lys
              165                 170                 175

Lys Leu Gly Leu Ser Asn Val Glu Met Val Leu Ala Asp Val Thr Lys
              180                 185                 190

Cys Glu Met Lys Ala Thr Phe Asp His Ile Phe Val Ile Gly Leu Ile
          195                 200                 205

Glu His Met Lys Asn Phe Glu Leu Phe Leu Arg Lys Val Ser Glu Trp
              210                 215                 220

Met Lys Ser Asp Gly Leu Leu Phe Met Glu His Tyr Cys His Lys Ser
225             230                 235                 240

Phe Ala Tyr Gln Trp Glu Pro Met Asp Asp Asp Leu Phe Ser Lys
              245                 250                 255

Tyr Val Phe Pro Pro Gly Ser Ala Ile Ile Pro Ser Ala Ser Phe Leu
              260                 265                 270

Leu Tyr Phe Gln Asp Asp Leu Thr Val Val Asp His Trp Thr Leu Ser
          275                 280                 285

Gly Asn His Phe Ala Arg Thr His Gln Glu Trp Leu Lys Arg Ile Asp
              290                 295                 300

Ser Gln Ser Asp Glu Ile Lys Gly Ile Phe Glu Ser Phe Tyr Gly Ile
305             310                 315                 320

Ser Lys Glu Glu Ala Val Lys Leu Ile Asn Tyr Trp Arg Val Phe Cys

```
                        325                 330                 335
Leu Phe Gly Val Glu Met Phe Gly Tyr Asn Asn Gly Glu Glu Trp Met
                340                 345                 350
Ile Ser His Leu Leu Phe Lys Lys Lys
            355                 360

<210> SEQ ID NO 90
<211> LENGTH: 363
<212> TYPE: PRT
<213> ORGANISM: Corydalis chelanthifolia

<400> SEQUENCE: 90

Met Glu Val Val Ala Thr Ser Ser Ala Arg Asn Pro Lys Lys Glu Ile
1               5                   10                  15
Val Asp Leu Trp Lys Arg Met Glu Leu Gly Leu Ile Pro Asp Glu Glu
                20                  25                  30
Ile Arg Asp Leu Met Lys Ile Gly Leu Glu Lys Arg Leu Lys Trp Gly
            35                  40                  45
Tyr Lys Pro Thr His Glu Gln Gln Leu Ser Gln Leu Leu His Phe Ala
        50                  55                  60
Lys Ser Leu Arg Ser Met Lys Met Ala Ser Glu Met Glu Thr Leu Asp
65                  70                  75                  80
Asp Gln Met Tyr Glu Thr Pro Thr Ala Phe Gln Gln Leu Met Cys Gly
                85                  90                  95
Ser Thr Ile Lys Glu Ser Ala Gly Phe Phe Lys Asp Glu Ser Thr Thr
                100                 105                 110
Leu Asp Glu Ala Glu Ile Lys Met Leu Asp Leu Tyr Cys Glu Lys Ala
            115                 120                 125
Arg Ile Glu Asp Gly Gln Lys Ile Leu Asp Leu Gly Cys Gly His Gly
        130                 135                 140
Ala Val Met Leu His Ile Ala Gln Lys Tyr Lys Asn Cys Asn Val Thr
145                 150                 155                 160
Gly Val Thr Asn Ser Ile Ser Gln Gln Gln Phe Ile Val Gln Arg Ser
                165                 170                 175
Lys Glu Leu Asn Leu Ser Asn Val Asn Met Ile Leu Ala Asp Val Thr
                180                 185                 190
Met Leu Glu Met Asp Ala Thr Tyr Asp Arg Ile Phe Ile Ile Gly Leu
            195                 200                 205
Ile Glu His Met Lys Asn Phe Glu Leu Phe Leu Arg Lys Ile Ser Lys
        210                 215                 220
Trp Ile Thr Lys Glu Gly Leu Leu Phe Leu Glu His Tyr Cys His Lys
225                 230                 235                 240
Thr Phe Ala Tyr Gln Cys Glu Pro Val Asp Glu Asp Trp Tyr Asn
                245                 250                 255
Met Phe Ile Phe Pro Pro Gly Thr Leu Ile Leu Pro Ser Ala Ser Phe
                260                 265                 270
Leu Leu Tyr Phe Gln Asp Asp Leu Ile Val Val Asp Arg Trp Thr Leu
            275                 280                 285
Asn Gly Asn His Tyr Ala Arg Thr Gln Glu Glu Trp Leu Lys Arg Ile
        290                 295                 300
Asp Ala Asn Val Asp Gly Val Lys Gln Met Phe Glu Ser Val Cys Asp
305                 310                 315                 320
Gly Asn Lys Glu Glu Ala Val Lys Leu Met Asn Phe Trp Arg Ile Phe
                325                 330                 335
```

```
Cys Ile Ser Gly Ala Glu Met Leu Ala Tyr Asn Asn Gly Glu Glu Trp
            340                 345                 350

Met Ile Ser His Tyr Leu Phe Lys Lys Arg Asn
            355                 360

<210> SEQ ID NO 91
<211> LENGTH: 357
<212> TYPE: PRT
<213> ORGANISM: Nigella sativa

<400> SEQUENCE: 91

Met Glu Ala Thr Gln Ile Thr Lys Lys Gln Gly Val Ala Glu Leu Ile
1               5                   10                  15

Lys Arg Ile Glu Asn Gly Gln Val Pro Asp Glu Ile Thr Arg Met
            20                  25                  30

Met Lys Ile Gln Ile Gln Lys Arg Leu Lys Leu Gly Tyr Lys Ser Thr
            35                  40                  45

His Glu Gln Gln Leu Ala Gln Leu Leu His Phe Val His Ser Leu Gln
        50                  55                  60

Lys Met Glu Met Ala Glu Val Asp Thr Leu Asp Ser Glu Leu Tyr
65                  70                  75                  80

Glu Ile Pro Leu Pro Phe Leu His Ile Met Cys Gly Lys Ala Leu Lys
                85                  90                  95

Phe Ser Pro Gly Tyr Phe Lys Asp Glu Ser Thr Thr Leu Asp Glu Ser
            100                 105                 110

Glu Val Asn Met Leu Asp Leu Tyr Cys Glu Arg Ala Gln Ile Glu Asp
            115                 120                 125

Gly Gln Thr Ile Leu Asp Leu Gly Cys Gly His Gly Ser Leu Thr Leu
        130                 135                 140

His Val Ala Lys Lys Tyr Arg Gly Cys Lys Val Thr Gly Ile Thr Asn
145                 150                 155                 160

Ser Val Ser Gln Lys Asp Phe Ile Met Glu Glu Cys Lys Lys Leu Asn
                165                 170                 175

Leu Ser Asn Val Glu Ile Ile Leu Glu Asp Val Thr Lys Phe Glu Thr
            180                 185                 190

Gly Thr Thr Tyr Asp Arg Ile Phe Ala Val Ala Leu Ile Glu His Met
            195                 200                 205

Lys Asn Tyr Glu Leu Phe Leu Lys Lys Val Ser Ala Trp Met Ala Gln
        210                 215                 220

Asp Gly Leu Leu Phe Val Glu His His Cys His Lys Val Phe Ala Tyr
225                 230                 235                 240

Lys Tyr Glu Pro Ile Asp Asp Asp Trp Tyr Thr Glu Tyr Ile Phe
                245                 250                 255

Pro Thr Gly Thr Leu Val Met Ser Ser Ser Ile Leu Leu Tyr Phe
            260                 265                 270

Gln Glu Asp Val Ser Val Val Asn His Trp Thr Leu Ser Gly Lys His
            275                 280                 285

Pro Ser Leu Gly Phe Lys Gln Trp Leu Lys Arg Ile Asp Asp Asn Ile
        290                 295                 300

Asp Glu Ile Lys Glu Ile Phe Glu Ser Phe Tyr Gly Ser Lys Glu Lys
305                 310                 315                 320

Ala Thr Lys Phe Ile Thr Tyr Trp Arg Val Phe Cys Ile Ala His Ser
                325                 330                 335

Glu Met Tyr Ala Thr Asn Gly Gly Glu Glu Trp Met Leu Ser Gln Val
            340                 345                 350
```

Leu Phe Lys Arg Lys
        355

<210> SEQ ID NO 92
<211> LENGTH: 349
<212> TYPE: PRT
<213> ORGANISM: Sanguinaria canadensis

<400> SEQUENCE: 92

Met Gly Gly Val Ala Asp Leu Leu Lys Lys Met Glu Leu Gly Leu Val
1               5                   10                  15

Pro Glu Glu Glu Ile Arg Arg Leu Met Arg Ile Ile Ile Glu Lys Arg
            20                  25                  30

Leu Glu Trp Gly Tyr Lys Pro Thr His Ala Glu Gln Leu Asp His Leu
        35                  40                  45

Thr Asn Phe Ile Gln Cys Leu Arg Gly Met Lys Met Ala Asp Glu Ile
    50                  55                  60

Asp Ala Leu Asp Ala Lys Met Tyr Glu Ile Pro Leu Pro Phe Met Gln
65                  70                  75                  80

Thr Ile Cys Gly Ser Thr Leu Lys Phe Ser Pro Gly Tyr Phe Lys Asp
                85                  90                  95

Glu Ser Thr Thr Leu Asp Glu Ser Glu Ile His Met Met Asp Leu Tyr
            100                 105                 110

Cys Glu Arg Ala Glu Val Lys Asp Gly His Ser Ile Leu Asp Leu Gly
        115                 120                 125

Cys Gly His Gly Gly Phe Val Leu His Val Ala Gln Lys Tyr Lys Asn
    130                 135                 140

Ser Ile Val Thr Gly Val Thr Asn Ser Val Ala Glu Lys Glu Phe Ile
145                 150                 155                 160

Met Thr Gln Cys Lys Lys Leu Cys Leu Ser Asn Val Glu Ile Ile Leu
                165                 170                 175

Ala Asp Val Thr Lys Phe Glu Pro Glu Thr Thr Tyr Asp Arg Val Phe
            180                 185                 190

Ala Ile Ala Leu Ile Glu His Met Lys Asn Tyr Glu Leu Val Leu Glu
        195                 200                 205

Lys Leu Ser Lys Trp Val Ala Gln Asp Gly Phe Leu Phe Val Glu His
    210                 215                 220

His Cys His Lys Val Phe Pro Tyr Lys Tyr Glu Pro Leu Asp Glu Asp
225                 230                 235                 240

Asp Trp Tyr Thr Glu Tyr Ile Phe Pro Gly Gly Thr Ile Val Leu Pro
                245                 250                 255

Ser Ala Ser Ile Leu Leu Tyr Phe Gln Lys Asp Val Ser Val Val Asn
            260                 265                 270

His Trp Ser Leu Asn Gly Lys His Pro Ala Arg Gly Phe Lys Glu Trp
        275                 280                 285

Leu Lys Arg Leu Asp Glu Asn Met Asp Ala Val Lys Ala Ile Phe Glu
    290                 295                 300

Pro Phe Tyr Gly Ser Lys Glu Glu Ala Met Lys Trp Ile Thr Tyr Trp
305                 310                 315                 320

Arg Val Phe Cys Ile Thr His Ser Glu Met Tyr Ala Tyr Asn Asn Gly
                325                 330                 335

Glu Glu Trp Met Leu Ser Gln Val Leu Phe Lys Arg Lys
            340                 345

<210> SEQ ID NO 93
<211> LENGTH: 350
<212> TYPE: PRT
<213> ORGANISM: Jeffersonia diphylla

<400> SEQUENCE: 93

Met Ser Lys Gly Val Ala Lys Leu Val Glu Arg Met Glu Leu Gly Leu
1               5                   10                  15

Val Ser Asp Asp Glu Val Arg Arg Leu Met Arg Ile Leu Ile Glu Lys
            20                  25                  30

Arg Leu Lys Trp Gly Tyr Lys Pro Thr His Glu Glu Gln Leu Thr Tyr
        35                  40                  45

Leu Thr Asn Phe Ile Gln Gly Leu Lys Gly Met Lys Ile Ala Glu Glu
    50                  55                  60

Ile Asp Ala Leu Asp Ala Lys Met Tyr Glu Ile Pro Ile Ala Phe Met
65                  70                  75                  80

Gln Ile Leu Cys Gly Tyr Ser Leu Lys Phe Ser Pro Gly Phe Phe Glu
                85                  90                  95

Asp Glu Ser Thr Thr Leu Asp Glu Ser Glu Thr Ile Met Met Asp Leu
            100                 105                 110

Tyr Cys Glu Arg Ala Gln Val Gln Asp Gly Gln Ser Ile Leu Asp Leu
        115                 120                 125

Gly Cys Gly His Gly Gly Phe Val Leu His Val Ala Gln Lys Tyr Lys
    130                 135                 140

Asn Cys Lys Val Thr Gly Val Thr Asn Ser Val Ser Glu Thr Glu Tyr
145                 150                 155                 160

Ile Met Glu Gln Cys Lys Lys Leu Gly Leu Ser Asn Val Glu Ile Ile
                165                 170                 175

Ile Ala Asp Val Thr Lys Phe Glu Pro Glu Val Thr Tyr Asp Arg Val
            180                 185                 190

Phe Ala Ile Ala Leu Ile Glu His Met Lys Asn Tyr Glu Leu Val Leu
        195                 200                 205

Gln Lys Leu Ser Lys Trp Val Ala Gln Asp Gly Phe Leu Phe Val Asp
    210                 215                 220

His His Cys His Lys Val Phe Pro Tyr Lys Tyr Glu Pro Ile Asp Glu
225                 230                 235                 240

Asp Asp Trp Tyr Thr Gln Tyr Ile Phe Pro Gly Gly Thr Leu Val Leu
                245                 250                 255

Pro Ser Ala Ser Ile Leu Leu Tyr Phe Gln Glu Asp Val Ser Ile Val
            260                 265                 270

Asn His Trp Thr Leu Ser Gly Asn His Pro Ala Arg Gly Phe Lys Glu
        275                 280                 285

Trp Leu Lys Arg Leu Asp Asp Asn Met Asp Glu Ile Lys Ala Ile Phe
    290                 295                 300

Glu Pro Phe Tyr Gly Ser Lys Glu Glu Ala Met Lys Trp Ile Thr Tyr
305                 310                 315                 320

Trp Arg Val Phe Cys Ile Thr His Ser Glu Met Tyr Ala Tyr Asn Gly
                325                 330                 335

Gly Glu Glu Trp Met Ile Ser Gln Val Leu Phe Lys Arg Lys
            340                 345                 350

<210> SEQ ID NO 94
<211> LENGTH: 357
<212> TYPE: PRT
<213> ORGANISM: Berberis thunbergii

<400> SEQUENCE: 94

Met Glu Val Lys Gln Ala Gly Lys Glu Gly Val Thr Glu Leu Leu Val
1               5                   10                  15

Lys Arg Met Glu Leu Gly Leu Val Pro Glu Glu Ile Arg Arg Leu
            20                  25                  30

Met Arg Ile Gln Ile Gln Lys Arg Leu Asp Trp Gly Tyr Lys Pro Thr
        35                  40                  45

His Glu Glu Gln Leu Ala His Leu Thr Lys Phe Ile Gln Asn Ile Arg
    50                  55                  60

Gly Met Lys Met Ala Asp Glu Ile Asp Ala Leu Asp Ala Lys Met Tyr
65                  70                  75                  80

Glu Ile Pro Leu Pro Phe Leu Gln Thr Ile Cys Gly Lys Thr Leu Lys
                85                  90                  95

Phe Ser Pro Gly Tyr Phe Lys Asp Glu Ser Thr Thr Leu Asp Glu Ser
            100                 105                 110

Glu Thr Leu Met Met Asp Leu Tyr Cys Glu Arg Ala Gln Val Lys Asp
        115                 120                 125

Gly Gln Ser Ile Leu Asp Leu Gly Cys Gly His Gly Gly Phe Val Leu
130                 135                 140

His Leu Ala Gln Lys Tyr Arg Asn Ser Val Val Thr Gly Val Thr Asn
145                 150                 155                 160

Ser Val Ser Glu Thr Glu Tyr Ile Lys Glu Gln Cys Lys Lys Leu Gly
                165                 170                 175

Leu Ser Asn Val Glu Ile Ile Ala Asp Val Thr Lys Phe Glu Pro
            180                 185                 190

Glu Val Thr Tyr Asp Arg Val Phe Ala Ile Ala Leu Ile Glu His Met
        195                 200                 205

Lys Asn Tyr Ala Leu Val Leu Asn Lys Ile Ser Lys Trp Val Ala Gln
210                 215                 220

Asp Gly Tyr Leu Phe Val Glu His His Cys His Lys Val Phe Pro Tyr
225                 230                 235                 240

Lys Tyr Glu Pro Leu Asp Glu Asp Trp Tyr Thr Asn Tyr Ile Phe
                245                 250                 255

Pro Gly Gly Thr Leu Ile Leu Pro Ser Ala Ser Ile Leu Leu Tyr Phe
            260                 265                 270

Gln Glu Asp Val Thr Val Leu Asn His Trp Ser Leu Ser Gly Lys His
        275                 280                 285

Pro Ser Arg Gly Phe Ile Glu Trp Leu Lys Arg Leu Asp Glu Asn Ile
290                 295                 300

Asp Val Ile Met Gly Ile Phe Glu Pro Phe Tyr Gly Ser Lys Glu Glu
305                 310                 315                 320

Ala Thr Lys Trp Ile Asn Tyr Trp Arg Val Phe Cys Met Thr His Ser
                325                 330                 335

Glu Met Tyr Ala Tyr Gly Asn Gly Glu Glu Trp Met Leu Ser Gln Val
            340                 345                 350

Leu Leu Lys Arg Lys
        355

<210> SEQ ID NO 95
<211> LENGTH: 339
<212> TYPE: PRT
<213> ORGANISM: Mahonia aquifolium

<400> SEQUENCE: 95

```
Met Glu Leu Gly Leu Val Pro Glu Lys Glu Ile Arg Arg Leu Met Arg
1               5                   10                  15

Ile Gln Ile Gln Lys Arg Leu Glu Trp Gly Tyr Lys Pro Thr His Glu
            20                  25                  30

Glu Gln Leu Ala His Leu Thr Lys Phe Ile Gln Asn Ile Arg Gly Met
        35                  40                  45

Lys Met Ala Asp Glu Ile Asp Ala Leu Asp Lys Met Tyr Glu Ile
    50                  55                  60

Pro Leu Pro Phe Leu Gln Thr Ile Cys Gly Lys Thr Leu Lys Phe Ser
65                  70                  75                  80

Pro Gly Tyr Phe Lys Asp Glu Ser Thr Thr Leu Asp Glu Ser Glu Thr
                85                  90                  95

Leu Met Met Asp Leu Tyr Cys Glu Arg Ala Gln Val Lys Asp Gly Gln
                100                 105                 110

Ser Ile Leu Asp Leu Gly Cys Gly His Gly Phe Val Leu His Leu
            115                 120                 125

Ala Gln Lys Tyr Arg Asn Ser Ile Val Thr Gly Val Thr Asn Ser Val
    130                 135                 140

Ser Glu Thr Glu Tyr Ile Lys Glu Gln Cys Lys Lys Leu Gly Leu Ser
145                 150                 155                 160

Asn Val Glu Ile Ile Ile Ala Asp Val Thr Lys Phe Glu Pro Glu Val
                165                 170                 175

Thr Tyr Asp Arg Val Phe Ala Ile Ala Leu Ile Glu His Met Lys Asn
                180                 185                 190

Tyr Ala Leu Val Leu Asn Lys Ile Ser Lys Trp Val Ala Gln Asp Gly
    195                 200                 205

Tyr Leu Phe Val Glu His His Cys His Lys Val Phe Pro Tyr Lys Tyr
    210                 215                 220

Glu Pro Leu Asp Glu Asp Trp Tyr Thr Asn Tyr Ile Phe Pro Gly
225                 230                 235                 240

Gly Thr Leu Ile Leu Pro Ser Ala Ser Ile Leu Leu Tyr Phe Gln Glu
                245                 250                 255

Asp Val Thr Val Leu Asn His Trp Ser Leu Ser Gly Lys His Pro Ser
                260                 265                 270

Arg Gly Phe Ile Glu Trp Leu Lys Arg Leu Asp Glu Asn Ile Asp Val
            275                 280                 285

Ile Met Gly Ile Phe Glu Pro Phe Tyr Gly Ser Lys Glu Glu Ala Thr
            290                 295                 300

Lys Trp Ile Asn Tyr Trp Arg Val Phe Cys Ile Thr His Ser Glu Met
305                 310                 315                 320

Tyr Ala Tyr Gly Asn Gly Glu Glu Trp Met Leu Ser Gln Val Leu Leu
                325                 330                 335

Lys Arg Lys

<210> SEQ ID NO 96
<211> LENGTH: 355
<212> TYPE: PRT
<213> ORGANISM: Menispermum canadense
<220> FEATURE:
<221> NAME/KEY: MOD_RES
<222> LOCATION: (86)..(86)
<223> OTHER INFORMATION: Any amino acid
<220> FEATURE:
<221> NAME/KEY: MOD_RES
<222> LOCATION: (96)..(96)
<223> OTHER INFORMATION: Any amino acid
<220> FEATURE:
```

```
<221> NAME/KEY: MOD_RES
<222> LOCATION: (127)..(127)
<223> OTHER INFORMATION: Any amino acid
<220> FEATURE:
<221> NAME/KEY: MOD_RES
<222> LOCATION: (138)..(138)
<223> OTHER INFORMATION: Any amino acid
<220> FEATURE:
<221> NAME/KEY: MOD_RES
<222> LOCATION: (153)..(153)
<223> OTHER INFORMATION: Any amino acid
<220> FEATURE:
<221> NAME/KEY: MOD_RES
<222> LOCATION: (292)..(292)
<223> OTHER INFORMATION: Any amino acid

<400> SEQUENCE: 96

Met Asp Lys Ala Asn Glu Arg Glu Leu Lys Arg Ala Glu Leu Phe Lys
1               5                   10                  15

Lys Leu Glu Asp Asp Leu Val Thr Tyr Asp Glu Ile Lys Gln Val Met
            20                  25                  30

Arg Thr Glu Leu Ala Lys Arg Leu Glu Trp Gly Tyr Lys Pro Thr His
        35                  40                  45

Gln Gln Gln Leu Ala His Leu Leu Asp Phe Ala His Ala Leu Glu Gly
    50                  55                  60

Met Lys Ile Ala Asn Glu Val Glu Thr Leu Ala Ser Glu Val Tyr Glu
65                  70                  75                  80

Thr Pro Leu Pro Phe Xaa Glu Ile Val Leu Gly Pro Ala Lys Lys Xaa
                85                  90                  95

Ser Ser Cys Leu Phe Glu Asp Glu Ser Thr Thr Leu Glu Gln Ala Glu
            100                 105                 110

Ile Ala Met Leu Asp Leu Tyr Phe Glu Arg Ala Gln Ile Arg Xaa Gly
        115                 120                 125

Met Ser Val Leu Asp Leu Gly Cys Gly Xaa Gly Ser Val Gly Leu His
    130                 135                 140

Ile Ala Arg Lys Tyr Lys Asn Cys Xaa Val Thr Cys Ile Thr Asn Ser
145                 150                 155                 160

Ile Ser Gln Lys Gln Tyr Ile Glu Asn Gln Cys Lys Leu Tyr Asn Leu
                165                 170                 175

Ser Asn Val Lys Ile Ile Leu Ala Asp Ile Val Ala His Asp Thr Asp
            180                 185                 190

Asp Thr Phe Asp Val Val Leu Val Ile Gly Val Ile Glu His Met Lys
        195                 200                 205

Asn Tyr Ala Leu Leu Leu Asn Lys Ile Ser Lys Trp Met Ala Lys Asp
    210                 215                 220

Gly Leu Leu Phe Val Glu His Leu Cys His Lys Thr Phe Pro Tyr His
225                 230                 235                 240

Phe Glu Pro Leu Asp Glu Asp Trp Tyr Ser Asn Phe Val Phe Pro
                245                 250                 255

Thr Gly Thr Leu Thr Met Pro Ser Val Ser Phe Leu Leu Tyr Phe Gln
            260                 265                 270

Ala Asp Val Ser Ile Leu Asn His Trp Ile Leu Ser Gly Lys Asn Phe
        275                 280                 285

Ser Arg Thr Xaa Glu Glu Phe Leu Lys Arg Ile Asp Ala Asn Val Asp
    290                 295                 300

Ala Ile Lys Asp Gly Leu Lys Pro Ser Leu Gly Ser Glu Gly Val Ala
305                 310                 315                 320

Lys Leu Ile Ser Tyr Trp Arg Gly Phe Cys Leu Thr Gly Met Glu Met
```

```
                      325                 330                 335
Phe Gly Tyr Asn Asn Gly Glu Glu Trp Met Val Ser Gln Val Leu Phe
                  340                 345                 350
Lys Asn Lys
        355

<210> SEQ ID NO 97
<211> LENGTH: 366
<212> TYPE: PRT
<213> ORGANISM: Tinospora cordifolia

<400> SEQUENCE: 97

Met Glu Asp Asn Asn Asn Leu Leu Gln Glu Glu Met Asn Val Val Glu
1               5                   10                  15
Leu Leu Gln Arg Pro Glu Leu Gly Leu Val Pro Asp Glu Lys Ile Arg
            20                  25                  30
Lys Leu Thr Arg Leu Gln Leu Gln Lys Arg Leu Lys Trp Gly Tyr Lys
        35                  40                  45
Pro Thr His Glu Ala Gln Leu Ser His Leu Phe Gln Phe Ile His Ser
    50                  55                  60
Leu Pro Ser Leu Asn Met Glu Ser Glu Asp Glu Asn Pro Lys Ser Trp
65                  70                  75                  80
Leu Tyr Glu Thr Pro Thr Ser Phe Leu Gln Leu Leu Tyr Gly Asp Cys
                85                  90                  95
Ile Lys Glu Ser Asp Thr Tyr Tyr Lys Glu Asp Thr Ala Thr Leu Glu
            100                 105                 110
Glu Ala Val Ile Asn Met Leu Glu Leu Tyr Cys Glu Arg Ala Arg Ile
        115                 120                 125
Thr Glu Gly Leu Ser Val Leu Asp Leu Gly Cys Gly Tyr Gly Ala Leu
    130                 135                 140
Thr Leu His Val Ala Gln Lys Tyr Lys Ser Cys Lys Val Thr Gly Val
145                 150                 155                 160
Thr Ser Ser Ile Ser Gln Lys Gln Tyr Ile Met Glu Lys Cys Lys Lys
                165                 170                 175
Leu Asn Leu Thr Asn Val Glu Ile Ile Leu Ala Asp Val Ala Thr Ile
            180                 185                 190
Glu Ile Glu Ala Ala Ser Tyr Asp Arg Ile Phe Ala Leu Gly Ile Phe
        195                 200                 205
Glu His Val Asn Asp Tyr Lys Leu Phe Leu Gly Lys Leu Ser Lys Trp
    210                 215                 220
Met Lys Gln Asp Gly Leu Leu Phe Val Glu Tyr Leu Cys His Lys Thr
225                 230                 235                 240
Phe Pro Tyr Gln Asn Lys Pro Leu Asp Lys Gly Asp Lys Trp Tyr Asn
                245                 250                 255
Glu Tyr Val Phe Pro Ser Gly Gly Leu Ile Ile Pro Ser Ala Ser Phe
            260                 265                 270
Ile Leu Tyr Phe Gln Asn Asp Val Ser Val Val Arg Gln Trp Thr Gln
        275                 280                 285
Gly Gly Gln His Ser Ala Arg Thr Phe Glu Glu Leu Leu Lys Arg Ile
    290                 295                 300
Asp Gly Asn Ile Asp Lys Ile Lys Glu Ile Phe Ile Glu Ser Tyr Gly
305                 310                 315                 320
Ser Lys Glu Asp Ala Val Arg Phe Ile Asn Tyr Trp Arg Val Phe Leu
                325                 330                 335
```

```
Ile Thr Gly Val Glu Met Phe Ser Tyr Asn Asp Gly Glu Glu Trp Met
                    340                 345                 350

Gly Ala His Phe Leu Phe Lys Lys Lys Phe Ile Met Gln Glu
            355                 360                 365

<210> SEQ ID NO 98
<211> LENGTH: 359
<212> TYPE: PRT
<213> ORGANISM: Cissampelos mucronata

<400> SEQUENCE: 98

Met Glu Val Lys Gln Ser Lys Gly Asp Glu Leu Arg Ser Arg Val Ala
1               5                   10                  15

Glu Leu Leu Glu Arg Pro Glu Leu Gly Leu Val Pro Asp Glu Glu Ile
            20                  25                  30

Arg Arg Leu Ala Lys Ala Arg Leu Glu Lys Arg Leu Lys Trp Gly Tyr
        35                  40                  45

Lys Ala Thr His Gly Glu Gln Leu Ser Ser Leu Leu Gln Phe Val Glu
50                  55                  60

Ser Leu Pro Ser Leu Asn Met Ala Ser Glu Asp Asp Ser Pro Lys Ala
65                  70                  75                  80

Trp Leu Tyr Glu Thr Pro Thr Ser Phe Leu Gln Leu Ile Tyr Gly Asp
                85                  90                  95

Ile Ile Lys Glu Ser Gly Ser Tyr Tyr Lys Asp Glu Ser Thr Thr Leu
            100                 105                 110

Glu Glu Ala Met Ile His Asn Met Asn Leu Cys Cys Glu Arg Ala Asn
        115                 120                 125

Ile Lys Glu Gly Gln Ser Val Val Asp Leu Gly Cys Gly Tyr Gly Ala
130                 135                 140

Phe Ile Leu His Val Ala Gln Lys Tyr Lys Thr Cys Arg Val Thr Gly
145                 150                 155                 160

Ile Thr Ser Ser Ile Ser Gln Lys His Tyr Ile Met Glu Gln Cys Lys
                165                 170                 175

Lys Leu Asn Leu Ser Asn Val Glu Val Ile Leu Ala Asp Val Ala Thr
            180                 185                 190

Ile Lys Leu Asp Ala Thr Phe Asp Arg Val Phe Ala Ala Gly Met Phe
        195                 200                 205

Glu His Val Asn Asp Tyr Lys Ser Phe Leu Arg Lys Ile Thr Asn Trp
210                 215                 220

Met Lys Pro Asp Gly Arg Leu Phe Val Glu His Leu Cys Asn Lys Thr
225                 230                 235                 240

Phe Pro Tyr Gln Asn Lys Pro Leu Asp Asp Gly Asp Asn Trp Gly Glu
                245                 250                 255

Tyr Val Phe Pro Ser Gly Gly Leu Ile Ile Pro Ser Ala Ser Leu Leu
            260                 265                 270

Leu Tyr Phe Gln Glu Asp Val Ser Ile Val Asn His Trp Thr Phe Ser
        275                 280                 285

Gly Lys His Ala Ala Asn Lys Phe Glu Glu Leu Leu Lys Arg Ile Asp
290                 295                 300

Ala Lys Ile Asp Ala Ile Lys Arg Ile Phe Asn Glu Cys Tyr Gly Ser
305                 310                 315                 320

Lys Asp Ser Ile Arg Phe Ile Asn Tyr Trp Arg Val Phe Leu Ile Thr
                325                 330                 335

Ala Ala Glu Met Phe Gly Tyr Asn Asn Gly Glu Glu Trp Met Gly Val
            340                 345                 350
```

His Leu Leu Phe Lys Lys Lys
        355

<210> SEQ ID NO 99
<211> LENGTH: 352
<212> TYPE: PRT
<213> ORGANISM: Cocculus trilobus

<400> SEQUENCE: 99

Gly Leu Lys Ser Ser Val Ala Glu Leu Leu Glu Arg Pro Glu Leu Gly
1               5                   10                  15

Leu Val Pro Asp Gly Glu Ile Arg Lys Leu Thr Lys Thr Arg Leu Ala
            20                  25                  30

Lys Arg Leu Glu Trp Gly Tyr Lys Ala Thr His Glu Asp Gln Leu Ser
        35                  40                  45

His Leu Leu Arg Phe Ile His Ser Leu Pro Ser Leu Asn Met Ala Ser
    50                  55                  60

Glu Asp Asp Ser Pro Lys Ala Trp Leu Tyr Glu Thr Pro Thr Ser Phe
65                  70                  75                  80

Leu Gln Leu Ile Tyr Gly Asp Ile Ile Lys Glu Ser Gly Thr Tyr Tyr
                85                  90                  95

Lys Asp Glu Ser Ser Thr Leu Glu Glu Ala Ile Ile His Asn Met Asp
            100                 105                 110

Leu Cys Cys Glu Arg Ala Arg Ile Lys Glu Gly Gln Ser Val Leu Asp
        115                 120                 125

Leu Gly Cys Gly Tyr Gly Ala Phe Thr Leu His Val Ala Gln Lys Tyr
    130                 135                 140

Lys Ser Cys Ser Val Thr Gly Ile Thr Ser Ser Ile Ser Gln Lys Asp
145                 150                 155                 160

Tyr Ile Met Glu Gln Cys Lys Lys Leu Asn Leu Ser Asn Val Glu Val
                165                 170                 175

Ile Leu Ala Asp Val Ala Thr Ile Lys Met Asn Thr Thr Phe Asp Arg
            180                 185                 190

Val Phe Ala Leu Gly Met Phe Glu His Ile Asn Asp Tyr Lys Leu Phe
        195                 200                 205

Leu Arg Arg Ile Ser Asn Trp Met Lys His Asp Gly Leu Leu Phe Val
    210                 215                 220

Glu His Leu Cys Asn Lys Thr Phe Ala Tyr Gln Asn Lys Pro Leu Asp
225                 230                 235                 240

Asp Gly Asp Asp Trp Phe Asn Glu Tyr Val Phe Pro Ser Ala Gly Leu
                245                 250                 255

Ile Ile Pro Ser Ala Ser Leu Leu Tyr Phe Gln Glu Asp Val Ser
            260                 265                 270

Ile Val His His Trp Thr Phe Ser Gly Lys His Ala Ala Tyr Lys Phe
        275                 280                 285

Glu Glu Leu Leu Glu Arg Ile Asp Ala Lys Ile Glu Ala Ile Lys Glu
    290                 295                 300

Ile Phe Ile Glu Cys Tyr Gly Ser Lys Glu Asp Ala Ile Arg Phe Ile
305                 310                 315                 320

Asn Tyr Trp Arg Val Phe Leu Ile Thr Ala Ala Glu Met Phe Ala Tyr
                325                 330                 335

Arg Asp Gly Glu Glu Trp Met Gly Ser His Val Leu Phe Lys Lys Lys
            340                 345                 350

<210> SEQ ID NO 100
<211> LENGTH: 364
<212> TYPE: PRT
<213> ORGANISM: Cissampelos mucronata

<400> SEQUENCE: 100

| Met | Glu | Ala | Lys | Gln | His | Glu | Ser | Asn | Asn | Ile | Asp | Glu | Leu |
|-----|-----|-----|-----|-----|-----|-----|-----|-----|-----|-----|-----|-----|-----|
| 1   |     |     |     | 5   |     |     |     |     | 10  |     |     |     | 15  |

Lys Asn Arg Val Asn Ile Gly Glu Gln Glu Arg Pro Gly Phe Glu
                20                  25                  30

Asp Glu Glu Ile Arg Arg Leu Ala Lys Ala Gln Leu Ala Lys Arg Leu
            35                  40                  45

Lys Trp Gly Tyr Lys Pro Thr His Glu Gln Gln Leu Ser His Leu Leu
 50                      55                      60

Gln Phe Leu Gln Ser Leu Pro Ser Leu Asn Met Ala Ser Glu Asp Glu
 65                  70                  75                  80

Ser Ser Lys Ala Trp Leu Tyr Glu Thr Pro Thr Ser Phe Leu Gln Leu
                85                  90                  95

Leu Phe Gly Asn Val Ile Lys Phe Ser Gly Tyr Tyr Lys His Glu
                100                 105                 110

Ser Ser Thr Phe Glu Glu Ser Met Ile His Asn Met Asp Leu Cys Cys
            115                 120                 125

Glu Arg Ala Asn Ile Lys Glu Gly Gln Asn Val Ile Asp Leu Gly Cys
130                 135                 140

Gly Tyr Gly Ala Phe Val Leu His Val Ala Gln Lys Tyr Lys Ser Cys
145                 150                 155                 160

Ser Val Thr Gly Ile Thr Cys Ser Ile Thr Gln Lys His His Ile Met
                165                 170                 175

Glu Glu Cys Lys Lys Leu Asn Leu Cys Asn Val Lys Val Ile Leu Ala
            180                 185                 190

Asp Val Ala Thr Ile Glu Leu Gly Thr Ala Phe Asp Arg Val Phe Ala
        195                 200                 205

Phe Gly Met Phe Glu Glu Ile Asn Asp Tyr Lys Leu Ile Leu Arg Lys
210                 215                 220

Ile Ser Asn Trp Met Lys Pro Asp Gly Leu Phe Phe Val Glu His Leu
225                 230                 235                 240

Cys His Lys Thr Leu Ala Tyr Gln Asn Lys Leu Ile Asp Asp Gln Asp
                245                 250                 255

Trp Tyr Glu Glu Tyr Ile Phe Pro Ser Gly Leu Ile Val Pro Ser
            260                 265                 270

Ala Ser Leu Leu Leu Tyr Phe Gln Asp Asp Leu Ser Val Val Tyr His
        275                 280                 285

Trp Thr Tyr Asn Gly Lys His Gly Ala Arg Ser Phe Glu Lys Met Leu
290                 295                 300

Glu Arg Thr Asp Ala Asn Ile Asp Thr Ile Lys Asp Met Phe Thr Glu
305                 310                 315                 320

Phe Tyr Gly Ser Lys Glu Lys Ala Ile Lys Phe Ile Asn Tyr Trp Arg
                325                 330                 335

Val Phe Phe Ile Thr Ala Ala Glu Met Phe Ala Tyr Asn Asp Gly Glu
            340                 345                 350

Glu Trp Met Cys Ser Gln Leu Leu Phe Lys Lys Lys
        355                 360

<210> SEQ ID NO 101
<211> LENGTH: 364

```
<212> TYPE: PRT
<213> ORGANISM: Cissampelos mucronata

<400> SEQUENCE: 101
```

| | | | | | | | | | | | | | | |
|---|---|---|---|---|---|---|---|---|---|---|---|---|---|---|
| Met | Glu | His | Lys | Ile | Glu | Asp | Ile | Arg | Lys | Leu | Lys | Ser | Arg | Val | Glu |
| 1 | | | | 5 | | | | | 10 | | | | | 15 | |

Glu Gln Leu Glu Arg Pro Glu Leu Gly Leu Val Lys Asp Glu Asp Ile
             20                  25                  30

Lys Thr Leu Ala Lys Ala Lys Leu Glu Lys Arg Leu Lys Trp Gly Tyr
         35                  40                  45

Lys Pro Thr Tyr Ala Glu Gln Leu Ser Asn Leu Leu Gln Phe Ala Gln
     50                  55                  60

Ser Leu Pro Ser Leu Lys Met Glu Asn Val Asp Asp Gln Gly Ser Ser
65                  70                  75                  80

Lys Gln Trp Leu Tyr Gly Val Pro Ser Glu Phe Leu Gln Ile Ile Tyr
                 85                  90                  95

Gly Gly Ile Ile Lys Met Ser Gly Ser Tyr Tyr Glu Asp Glu Ser Thr
            100                 105                 110

Thr Leu Glu Glu Ser Met Ile Lys Asp Met Asp Ser Cys Cys Glu Lys
        115                 120                 125

Ala Asn Val Lys Glu Gly His Ser Val Leu Asp Ile Gly Cys Gly Tyr
    130                 135                 140

Gly Ser Leu Ile Ile His Ile Ala Lys Lys Tyr Arg Thr Cys Asn Val
145                 150                 155                 160

Thr Gly Ile Thr Asn Phe Val Glu Gln Lys Gln Tyr Ile Met Glu Glu
                165                 170                 175

Cys Lys Lys Leu Asn Leu Ser Asn Val Glu Val Ile Val Gly Asp Gly
            180                 185                 190

Thr Thr Ile Asn Leu Asn Thr Thr Thr Phe Asp Arg Val Phe Val Thr
        195                 200                 205

Gly Met Leu Glu Glu Ile Asn Asp Tyr Lys Leu Phe Leu Lys Ser Val
    210                 215                 220

Ser Asp Trp Met Lys Pro Asp Gly Leu Leu Leu Val Thr His Phe Cys
225                 230                 235                 240

His Lys Thr Phe Ala Tyr Gln Asn Asn Lys Ala Leu Asp Asp Glu Asp
                245                 250                 255

Trp His Asn Glu Tyr Ile Phe Pro Ser Gly Asn Leu Ile Val Pro Ser
            260                 265                 270

Ala Ser Leu Leu Leu Tyr Phe Gln Glu Asp Leu Ser Val Val Ser His
        275                 280                 285

Trp Ala Thr Asn Gly Thr His Thr Gly Arg Thr Cys Lys Lys Leu Val
    290                 295                 300

Glu Arg Ile Asp Ala Asn Ile Glu Lys Ile Lys Glu Ile Phe Ser Glu
305                 310                 315                 320

Phe Tyr Gly Ser Lys Glu Asp Ala Ile Arg Met Ile Asn Tyr Trp Arg
                325                 330                 335

Val Leu Cys Ile Thr Gly Ala Glu Met Tyr Thr Cys Lys Asp Gly Glu
            340                 345                 350

Glu Trp Met Asp Val Tyr Tyr Leu Phe Lys Lys Lys
        355                 360

```
<210> SEQ ID NO 102
<211> LENGTH: 1049
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 102

Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Arg
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Leu Lys Phe Ala Arg
65                  70                  75                  80

Asp Phe Ala Gly Asp Gly Leu Val Thr Ser Trp Thr His Glu Lys Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Val
        115                 120                 125

Gln Lys Trp Glu Arg Leu Asn Ala Asp Glu His Ile Glu Val Ser Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Ile
                165                 170                 175

Ser Met Val Arg Ala Leu Asp Glu Val Met Asn Lys Leu Gln Arg Ala
            180                 185                 190

Asn Pro Asp Asp Pro Ala Tyr Asp Glu Asn Lys Arg Gln Phe Gln Glu
        195                 200                 205

Asp Ile Lys Val Met Asn Asp Leu Val Asp Lys Ile Ile Ala Asp Arg
    210                 215                 220

Lys Ala Arg Gly Glu Gln Ser Asp Asp Leu Leu Thr Gln Met Leu Asn
225                 230                 235                 240

Gly Lys Asp Pro Glu Thr Gly Glu Pro Leu Asp Asp Gly Asn Ile Arg
                245                 250                 255

Tyr Gln Ile Ile Thr Phe Leu Ile Ala Gly His Glu Thr Thr Ser Gly
            260                 265                 270

Leu Leu Ser Phe Ala Leu Tyr Phe Leu Val Lys Asn Pro His Val Leu
        275                 280                 285

Gln Lys Val Ala Glu Glu Ala Ala Arg Val Leu Val Asp Pro Val Pro
    290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
                325                 330                 335

Lys Glu Asp Thr Val Leu Gly Gly Glu Tyr Pro Leu Glu Lys Gly Asp
            340                 345                 350

Glu Val Met Val Leu Ile Pro Gln Leu His Arg Asp Lys Thr Val Trp
        355                 360                 365

Gly Asp Asp Val Glu Glu Phe Arg Pro Glu Arg Phe Glu Asn Pro Ser
    370                 375                 380

Ala Ile Pro Gln His Ala Phe Lys Pro Phe Gly Asn Gly Gln Arg Ala
```

```
                385                 390                 395                 400
            Cys Ile Gly Gln Gln Phe Ala Leu His Glu Ala Thr Leu Val Leu Gly
                            405                 410                 415

Met Met Leu Lys His Phe Asp Phe Glu Asp His Thr Asn Tyr Glu Leu
                            420                 425                 430

Asp Ile Lys Glu Thr Ala Thr Leu Lys Pro Lys Gly Phe Val Val Lys
                            435                 440                 445

Ala Lys Ser Lys Lys Ile Pro Leu Gly Gly Ile Pro Ser Pro Ser Thr
                450                 455                 460

Glu Gln Ser Ala Lys Lys Val Arg Lys Ala Glu Asn Ala His Asn
            465                 470                 475                 480

Thr Pro Leu Leu Val Leu Tyr Gly Ser Asn Met Gly Thr Ala Glu Gly
                            485                 490                 495

Thr Ala Arg Asp Leu Ala Asp Ile Ala Met Ser Lys Gly Phe Ala Pro
                            500                 505                 510

Gln Val Ala Thr Leu Asp Ser His Ala Gly Asn Leu Pro Arg Glu Gly
                            515                 520                 525

Ala Val Leu Ile Val Thr Ala Ser Tyr Asn Gly His Pro Pro Asp Asn
                530                 535                 540

Ala Lys Gln Phe Val Asp Trp Leu Asp Gln Ala Ser Ala Asp Glu Val
            545                 550                 555                 560

Lys Gly Val Arg Tyr Ser Val Phe Gly Cys Gly Asp Lys Asn Trp Ala
                            565                 570                 575

Thr Thr Tyr Gln Lys Val Pro Ala Phe Ile Asp Glu Thr Leu Ala Ala
                            580                 585                 590

Lys Gly Ala Glu Asn Ile Ala Asp Arg Gly Glu Ala Asp Ala Ser Asp
                            595                 600                 605

Asp Phe Glu Gly Thr Tyr Glu Glu Trp Arg Glu His Met Trp Ser Asp
                610                 615                 620

Val Ala Ala Tyr Phe Asn Leu Asp Ile Glu Asn Ser Glu Asp Asn Lys
            625                 630                 635                 640

Ser Thr Leu Ser Leu Gln Phe Val Asp Ser Ala Ala Asp Met Pro Leu
                            645                 650                 655

Ala Lys Met His Gly Ala Phe Ser Thr Asn Val Val Ala Ser Lys Glu
                            660                 665                 670

Leu Gln Gln Pro Gly Ser Ala Arg Ser Thr Arg His Leu Glu Ile Glu
                            675                 680                 685

Leu Pro Lys Glu Ala Ser Tyr Gln Glu Gly Asp His Leu Gly Val Ile
                690                 695                 700

Pro Arg Asn Tyr Glu Gly Ile Val Asn Arg Val Thr Ala Arg Phe Gly
            705                 710                 715                 720

Leu Asp Ala Ser Gln Gln Ile Arg Leu Glu Ala Glu Glu Lys Leu
                            725                 730                 735

Ala His Leu Pro Leu Ala Lys Thr Val Ser Val Glu Glu Leu Leu Gln
                            740                 745                 750

Tyr Val Glu Leu Gln Asp Pro Val Thr Arg Thr Gln Leu Arg Ala Met
                            755                 760                 765

Ala Ala Lys Thr Val Cys Pro Pro His Lys Val Glu Leu Glu Ala Leu
                770                 775                 780

Leu Glu Lys Gln Ala Tyr Lys Glu Gln Val Leu Ala Lys Arg Leu Thr
            785                 790                 795                 800

Met Leu Glu Leu Leu Glu Lys Tyr Pro Ala Cys Glu Met Lys Phe Ser
                            805                 810                 815
```

-continued

```
Glu Phe Ile Ala Leu Leu Pro Ser Ile Arg Pro Arg Tyr Tyr Ser Ile
                820                 825                 830

Ser Ser Ser Pro Arg Val Asp Glu Lys Gln Ala Ser Ile Thr Val Ser
            835                 840                 845

Val Val Ser Gly Glu Ala Trp Ser Gly Tyr Gly Glu Tyr Lys Gly Ile
850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
                885                 890                 895

Thr Pro Leu Ile Met Val Gly Pro Gly Thr Gly Val Ala Pro Phe Arg
            900                 905                 910

Gly Phe Val Gln Ala Arg Lys Gln Leu Lys Glu Gln Gly Gln Ser Leu
        915                 920                 925

Gly Glu Ala His Leu Tyr Phe Gly Cys Arg Ser Pro His Glu Asp Tyr
930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
                965                 970                 975

Gln His Val Met Glu Gln Asp Gly Lys Lys Leu Ile Glu Leu Leu Asp
            980                 985                 990

Gln Gly Ala His Phe Tyr Ile Cys Gly Asp Gly Ser Gln Met Ala Pro
        995                1000                1005

Ala Val Glu Ala Thr Leu Met Lys Ser Tyr Ala Asp Val His Gln
       1010                1015                1020

Val Ser Glu Ala Asp Ala Arg Leu Trp Leu Gln Gln Leu Glu Glu
       1025                1030                1035

Lys Gly Arg Tyr Ala Lys Asp Val Trp Ala Gly
       1040                1045
```

<210> SEQ ID NO 103
<211> LENGTH: 1049
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

```
Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Arg
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Leu Lys Phe Ala Arg
65                  70                  75                  80

Asp Phe Ala Gly Asp Gly Leu Val Thr Ser Trp Thr His Glu Lys Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Val
```

-continued

```
            115                 120                 125
Gln Lys Trp Glu Arg Leu Asn Ala Asp Glu His Ile Glu Val Ser Glu
130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Ile
                165                 170                 175

Ser Met Val Arg Ala Ala Asp Glu Val Met Asn Lys Leu Gln Arg Ala
                180                 185                 190

Asn Pro Asp Asp Pro Ala Tyr Asp Glu Asn Lys Arg Gln Phe Gln Glu
                195                 200                 205

Asp Ile Lys Val Met Asn Asp Leu Val Asp Lys Ile Ala Asp Arg
210                 215                 220

Lys Ala Arg Gly Glu Gln Ser Asp Asp Leu Leu Thr Gln Met Leu Asn
225                 230                 235                 240

Gly Lys Asp Pro Glu Thr Gly Glu Pro Leu Asp Asp Gly Asn Ile Arg
                245                 250                 255

Tyr Gln Ile Ile Ala Phe Leu Ile Ala Gly His Glu Thr Thr Ser Gly
                260                 265                 270

Leu Leu Ser Phe Ala Leu Tyr Phe Leu Val Lys Asn Pro His Val Leu
                275                 280                 285

Gln Lys Val Ala Glu Glu Ala Ala Arg Val Leu Val Asp Pro Val Pro
290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
                325                 330                 335

Lys Glu Asp Thr Val Leu Gly Gly Glu Tyr Pro Leu Glu Lys Gly Asp
                340                 345                 350

Glu Val Met Val Leu Ile Pro Gln Leu His Arg Asp Lys Thr Val Trp
                355                 360                 365

Gly Asp Asp Val Glu Glu Phe Arg Pro Glu Arg Phe Glu Asn Pro Ser
370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
                420                 425                 430

Asp Ile Lys Glu Thr Ala Thr Leu Lys Pro Lys Gly Phe Val Val Lys
                435                 440                 445

Ala Lys Ser Lys Lys Ile Pro Leu Gly Gly Ile Pro Ser Pro Ser Thr
450                 455                 460

Glu Gln Ser Ala Lys Lys Val Arg Lys Lys Ala Glu Asn Ala His Asn
465                 470                 475                 480

Thr Pro Leu Leu Val Leu Tyr Gly Ser Asn Met Gly Thr Ala Glu Gly
                485                 490                 495

Thr Ala Arg Asp Leu Ala Asp Ile Ala Met Ser Lys Gly Phe Ala Pro
                500                 505                 510

Gln Val Ala Thr Leu Asp Ser His Ala Gly Asn Leu Pro Arg Glu Gly
                515                 520                 525

Ala Val Leu Ile Val Thr Ala Ser Tyr Asn Gly His Pro Pro Asp Asn
530                 535                 540
```

```
Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
            565                 570                 575

Thr Thr Tyr Gln Lys Val Pro Ala Phe Ile Asp Glu Thr Leu Ala Ala
            580                 585                 590

Lys Gly Ala Glu Asn Ile Ala Asp Arg Gly Glu Ala Asp Ala Ser Asp
            595                 600                 605

Asp Phe Glu Gly Thr Tyr Glu Glu Trp Arg Glu His Met Trp Ser Asp
610                 615                 620

Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
                645                 650                 655

Ala Lys Met His Gly Ala Phe Ser Thr Asn Val Val Ala Ser Lys Glu
            660                 665                 670

Leu Gln Gln Pro Gly Ser Ala Arg Ser Thr Arg His Leu Glu Ile Glu
            675                 680                 685

Leu Pro Lys Glu Ala Ser Tyr Gln Glu Gly Asp His Leu Gly Val Ile
690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Lys Leu
                725                 730                 735

Ala His Leu Pro Leu Ala Lys Thr Val Ser Val Glu Glu Leu Leu Gln
            740                 745                 750

Tyr Val Glu Leu Gln Asp Pro Val Thr Arg Thr Gln Leu Arg Ala Met
            755                 760                 765

Ala Ala Lys Thr Val Cys Pro Pro His Lys Val Glu Leu Glu Ala Leu
            770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Lys Phe Ser
                805                 810                 815

Glu Phe Ile Ala Leu Leu Pro Ser Ile Arg Pro Arg Tyr Tyr Ser Ile
                820                 825                 830

Ser Ser Ser Pro Arg Val Asp Glu Lys Gln Ala Ser Ile Thr Val Ser
            835                 840                 845

Val Val Ser Gly Glu Ala Trp Ser Gly Tyr Gly Glu Tyr Lys Gly Ile
            850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
                885                 890                 895

Thr Pro Leu Ile Met Val Gly Pro Gly Thr Gly Val Ala Pro Phe Arg
            900                 905                 910

Gly Phe Val Gln Ala Arg Lys Gln Leu Lys Glu Gln Gly Gln Ser Leu
            915                 920                 925

Gly Glu Ala His Leu Tyr Phe Gly Cys Arg Ser Pro His Glu Asp Tyr
            930                 935                 940

Leu Tyr Gln Glu Glu Leu Glu Asn Ala Gln Ser Glu Gly Ile Ile Thr
945                 950                 955                 960
```

-continued

```
Leu His Thr Ala Phe Ser Arg Met Pro Asn Gln Pro Lys Thr Tyr Val
                965                 970                 975

Gln His Val Met Glu Gln Asp Gly Lys Lys Leu Ile Glu Leu Leu Asp
            980                 985                 990

Gln Gly Ala His Phe Tyr Ile Cys Gly Asp Gly Ser Gln Met Ala Pro
        995                 1000                1005

Ala Val Glu Ala Thr Leu Met Lys Ser Tyr Ala Asp Val His Gln
   1010                1015                1020

Val Ser Glu Ala Asp Ala Arg Leu Trp Leu Gln Gln Leu Glu Glu
   1025                1030                1035

Lys Gly Arg Tyr Ala Lys Asp Val Trp Ala Gly
   1040                1045
```

<210> SEQ ID NO 104
<211> LENGTH: 1049
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 104

```
Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Arg
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Ala Lys Phe Ala Arg
65                  70                  75                  80

Asp Phe Ala Gly Asp Gly Leu Val Thr Ser Trp Thr His Glu Lys Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Val
        115                 120                 125

Gln Lys Trp Glu Arg Leu Asn Ala Asp Glu His Ile Glu Val Ser Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Ile
                165                 170                 175

Ser Met Val Arg Ala Ala Asp Glu Val Met Asn Lys Leu Gln Arg Ala
            180                 185                 190

Asn Pro Asp Asp Pro Ala Tyr Asp Glu Asn Lys Arg Gln Phe Gln Glu
        195                 200                 205

Asp Ile Lys Val Met Asn Asp Leu Val Asp Lys Ile Ile Ala Asp Arg
    210                 215                 220

Lys Ala Arg Gly Glu Gln Ser Asp Asp Leu Leu Thr Gln Met Leu Asn
225                 230                 235                 240

Gly Lys Asp Pro Glu Thr Gly Glu Pro Leu Asp Asp Gly Asn Ile Arg
                245                 250                 255

Tyr Gln Ile Ile Thr Phe Leu Ile Ala Gly His Glu Thr Thr Ser Gly
            260                 265                 270
```

```
Leu Leu Ser Phe Ala Leu Tyr Phe Leu Val Lys Asn Pro His Val Leu
        275                 280                 285

Gln Lys Val Ala Glu Ala Ala Arg Val Leu Val Asp Pro Val Pro
    290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
                325                 330                 335

Lys Glu Asp Thr Val Leu Gly Gly Glu Tyr Pro Leu Glu Lys Gly Asp
            340                 345                 350

Glu Val Met Val Leu Ile Pro Gln Leu His Arg Asp Lys Thr Val Trp
        355                 360                 365

Gly Asp Asp Val Glu Glu Phe Arg Pro Glu Arg Phe Glu Asn Pro Ser
    370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
            420                 425                 430

Asp Ile Lys Glu Thr Leu Thr Leu Lys Pro Lys Gly Phe Val Val Lys
        435                 440                 445

Ala Lys Ser Lys Lys Ile Pro Leu Gly Gly Ile Pro Ser Pro Ser Thr
    450                 455                 460

Glu Gln Ser Ala Lys Lys Val Arg Lys Lys Ala Glu Asn Ala His Asn
465                 470                 475                 480

Thr Pro Leu Leu Val Leu Tyr Gly Ser Asn Met Gly Thr Ala Glu Gly
                485                 490                 495

Thr Ala Arg Asp Leu Ala Asp Ile Ala Met Ser Lys Gly Phe Ala Pro
            500                 505                 510

Gln Val Ala Thr Leu Asp Ser His Ala Gly Asn Leu Pro Arg Glu Gly
        515                 520                 525

Ala Val Leu Ile Val Thr Ala Ser Tyr Asn Gly His Pro Pro Asp Asn
    530                 535                 540

Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
                565                 570                 575

Thr Thr Tyr Gln Lys Val Pro Ala Phe Ile Asp Glu Thr Leu Ala Ala
            580                 585                 590

Lys Gly Ala Glu Asn Ile Ala Asp Arg Gly Glu Ala Asp Ala Ser Asp
        595                 600                 605

Asp Phe Glu Gly Thr Tyr Glu Glu Trp Arg Glu His Met Trp Ser Asp
    610                 615                 620

Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
                645                 650                 655

Ala Lys Met His Gly Ala Phe Ser Thr Asn Val Val Ala Ser Lys Glu
            660                 665                 670

Leu Gln Gln Pro Gly Ser Ala Arg Ser Thr Arg His Leu Glu Ile Glu
        675                 680                 685
```

Leu Pro Lys Glu Ala Ser Tyr Gln Glu Gly Asp His Leu Gly Val Ile
690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Lys Leu
            725                 730                 735

Ala His Leu Pro Leu Ala Lys Thr Val Ser Val Glu Leu Leu Gln
            740                 745                 750

Tyr Val Glu Leu Gln Asp Pro Val Thr Arg Thr Gln Leu Arg Ala Met
            755                 760                 765

Ala Ala Lys Thr Val Cys Pro Pro His Lys Val Glu Leu Glu Ala Leu
770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Lys Phe Ser
                805                 810                 815

Glu Phe Ile Ala Leu Leu Pro Ser Ile Arg Pro Arg Tyr Tyr Ser Ile
            820                 825                 830

Ser Ser Ser Pro Arg Val Asp Glu Lys Gln Ala Ser Ile Thr Val Ser
835                 840                 845

Val Val Ser Gly Glu Ala Trp Ser Gly Tyr Gly Glu Tyr Lys Gly Ile
850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
            885                 890                 895

Thr Pro Leu Ile Met Val Gly Pro Gly Thr Gly Val Ala Pro Phe Arg
                900                 905                 910

Gly Phe Val Gln Ala Arg Lys Gln Leu Lys Glu Gln Gly Gln Ser Leu
            915                 920                 925

Gly Glu Ala His Leu Tyr Phe Gly Cys Arg Ser Pro His Glu Asp Tyr
930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
            965                 970                 975

Gln His Val Met Glu Gln Asp Gly Lys Lys Leu Ile Glu Leu Leu Asp
            980                 985                 990

Gln Gly Ala His Phe Tyr Ile Cys Gly Asp Gly Ser Gln Met Ala Pro
            995                 1000                1005

Ala Val Glu Ala Thr Leu Met Lys Ser Tyr Ala Asp Val His Gln
    1010                1015                1020

Val Ser Glu Ala Asp Ala Arg Leu Trp Leu Gln Gln Leu Glu Glu
    1025                1030                1035

Lys Gly Arg Tyr Ala Lys Asp Val Trp Ala Gly
    1040                1045

<210> SEQ ID NO 105
<211> LENGTH: 1049
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

```
Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Arg
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Ala Lys Phe Ala Arg
65                  70                  75                  80

Asp Phe Ala Gly Asp Gly Leu Val Thr Ser Trp Thr His Glu Lys Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Val
        115                 120                 125

Gln Lys Trp Glu Arg Leu Asn Ala Asp Glu His Ile Glu Val Ser Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Ile
                165                 170                 175

Ser Ala Val Arg Ala Ala Asp Glu Val Met Asn Lys Leu Gln Arg Ala
            180                 185                 190

Asn Pro Asp Asp Pro Ala Tyr Asp Glu Asn Lys Arg Gln Phe Gln Glu
        195                 200                 205

Asp Ile Lys Val Met Asn Asp Leu Val Asp Lys Ile Ile Ala Asp Arg
    210                 215                 220

Lys Ala Arg Gly Glu Gln Ser Asp Asp Leu Leu Thr Gln Met Leu Asn
225                 230                 235                 240

Gly Lys Asp Pro Glu Thr Gly Glu Pro Leu Asp Asp Gly Asn Ile Arg
                245                 250                 255

Tyr Gln Ile Ile Thr Phe Leu Ile Ala Gly His Glu Thr Thr Ser Gly
            260                 265                 270

Leu Leu Ser Phe Ala Leu Tyr Phe Leu Val Lys Asn Pro His Val Leu
        275                 280                 285

Gln Lys Val Ala Glu Glu Ala Ala Arg Val Leu Val Asp Pro Val Pro
    290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
                325                 330                 335

Lys Glu Asp Thr Val Leu Gly Gly Glu Tyr Pro Leu Glu Lys Gly Asp
            340                 345                 350

Glu Val Met Val Leu Ile Pro Gln Leu His Arg Asp Lys Thr Val Trp
        355                 360                 365

Gly Asp Asp Val Glu Glu Phe Arg Pro Glu Arg Phe Glu Asn Pro Ser
    370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415
```

```
Met Met Leu Lys His Phe Asp Phe Glu Asp His Thr Asn Tyr Glu Leu
            420                 425                 430

Asp Ile Lys Glu Thr Leu Thr Leu Lys Pro Lys Gly Phe Val Val Lys
            435                 440                 445

Ala Lys Ser Lys Lys Ile Pro Leu Gly Gly Ile Pro Ser Pro Ser Thr
        450                 455                 460

Glu Gln Ser Ala Lys Lys Val Arg Lys Lys Ala Glu Asn Ala His Asn
465                 470                 475                 480

Thr Pro Leu Leu Val Leu Tyr Gly Ser Asn Met Gly Thr Ala Glu Gly
                485                 490                 495

Thr Ala Arg Asp Leu Ala Asp Ile Ala Met Ser Lys Gly Phe Ala Pro
            500                 505                 510

Gln Val Ala Thr Leu Asp Ser His Ala Gly Asn Leu Pro Arg Glu Gly
            515                 520                 525

Ala Val Leu Ile Val Thr Ala Ser Tyr Asn Gly His Pro Pro Asp Asn
        530                 535                 540

Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
                565                 570                 575

Thr Thr Tyr Gln Lys Val Pro Ala Phe Ile Asp Glu Thr Leu Ala Ala
            580                 585                 590

Lys Gly Ala Glu Asn Ile Ala Asp Arg Gly Glu Ala Asp Ala Ser Asp
            595                 600                 605

Asp Phe Glu Gly Thr Tyr Glu Glu Trp Arg Glu His Met Trp Ser Asp
    610                 615                 620

Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
                645                 650                 655

Ala Lys Met His Gly Ala Phe Ser Thr Asn Val Val Ala Ser Lys Glu
            660                 665                 670

Leu Gln Gln Pro Gly Ser Ala Arg Ser Thr Arg His Leu Glu Ile Glu
        675                 680                 685

Leu Pro Lys Glu Ala Ser Tyr Gln Glu Gly Asp His Leu Gly Val Ile
    690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Lys Leu
            725                 730                 735

Ala His Leu Pro Leu Ala Lys Thr Val Ser Val Glu Glu Leu Leu Gln
            740                 745                 750

Tyr Val Glu Leu Gln Asp Pro Val Thr Arg Thr Gln Leu Arg Ala Met
        755                 760                 765

Ala Ala Lys Thr Val Cys Pro Pro His Lys Val Glu Leu Glu Ala Leu
            770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Lys Phe Ser
                805                 810                 815

Glu Phe Ile Ala Leu Leu Pro Ser Ile Arg Pro Arg Tyr Tyr Ser Ile
            820                 825                 830

Ser Ser Ser Pro Arg Val Asp Glu Lys Gln Ala Ser Ile Thr Val Ser
```

```
              835                 840                 845
Val Val Ser Gly Glu Ala Trp Ser Gly Tyr Gly Glu Tyr Lys Gly Ile
    850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
                885                 890                 895

Thr Pro Leu Ile Met Val Gly Pro Gly Thr Gly Val Ala Pro Phe Arg
            900                 905                 910

Gly Phe Val Gln Ala Arg Lys Gln Leu Lys Glu Gln Gly Gln Ser Leu
        915                 920                 925

Gly Glu Ala His Leu Tyr Phe Gly Cys Arg Ser Pro His Glu Asp Tyr
    930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
                965                 970                 975

Gln His Val Met Glu Gln Asp Gly Lys Lys Leu Ile Glu Leu Leu Asp
            980                 985                 990

Gln Gly Ala His Phe Tyr Ile Cys Gly Asp Gly Ser Gln Met Ala Pro
        995                 1000                1005

Ala Val Glu Ala Thr Leu Met Lys Ser Tyr Ala Asp Val His Gln
    1010                1015                1020

Val Ser Glu Ala Asp Ala Arg Leu Trp Leu Gln Gln Leu Glu Glu
    1025                1030                1035

Lys Gly Arg Tyr Ala Lys Asp Val Trp Ala Gly
    1040                1045

<210> SEQ ID NO 106
<211> LENGTH: 1049
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Arg
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Ala Lys Phe Ala Arg
65                  70                  75                  80

Asp Phe Ala Gly Asp Gly Leu Val Thr Ser Trp Thr His Glu Lys Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Val
        115                 120                 125

Gln Lys Trp Glu Arg Leu Asn Ala Asp Glu His Ile Glu Val Ser Glu
    130                 135                 140
```

```
Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Ile
                165                 170                 175

Ser Ala Val Arg Ala Ala Asp Glu Val Met Asn Lys Leu Gln Arg Ala
            180                 185                 190

Asn Pro Asp Asp Pro Ala Tyr Asp Glu Asn Lys Arg Gln Phe Gln Glu
        195                 200                 205

Asp Ile Lys Val Met Asn Asp Leu Val Asp Lys Ile Ala Asp Arg
210                 215                 220

Lys Ala Arg Gly Glu Gln Ser Asp Asp Leu Leu Thr Gln Met Leu Asn
225                 230                 235                 240

Gly Lys Asp Pro Glu Thr Gly Glu Pro Leu Asp Asp Gly Asn Ile Arg
                245                 250                 255

Tyr Gln Ile Ile Ala Phe Leu Ile Ala Gly His Glu Thr Thr Ser Gly
                260                 265                 270

Leu Leu Ser Phe Ala Leu Tyr Phe Leu Val Lys Asn Pro His Val Leu
            275                 280                 285

Gln Lys Val Ala Glu Glu Ala Ala Arg Val Leu Val Asp Pro Val Pro
290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
                325                 330                 335

Lys Glu Asp Thr Val Leu Gly Gly Glu Tyr Pro Leu Glu Lys Gly Asp
                340                 345                 350

Glu Val Met Val Leu Ile Pro Gln Leu His Arg Asp Lys Thr Val Trp
                355                 360                 365

Gly Asp Asp Val Glu Glu Phe Arg Pro Glu Arg Phe Glu Asn Pro Ser
                370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
                420                 425                 430

Asp Ile Lys Glu Thr Leu Thr Leu Lys Pro Lys Gly Phe Val Val Lys
                435                 440                 445

Ala Lys Ser Lys Lys Ile Pro Leu Gly Gly Ile Pro Ser Pro Ser Thr
450                 455                 460

Glu Gln Ser Ala Lys Lys Val Arg Lys Lys Ala Glu Asn Ala His Asn
465                 470                 475                 480

Thr Pro Leu Leu Val Leu Tyr Gly Ser Asn Met Gly Thr Ala Glu Gly
                485                 490                 495

Thr Ala Arg Asp Leu Ala Asp Ile Ala Met Ser Lys Gly Phe Ala Pro
                500                 505                 510

Gln Val Ala Thr Leu Asp Ser His Ala Gly Asn Leu Pro Arg Glu Gly
                515                 520                 525

Ala Val Leu Ile Val Thr Ala Ser Tyr Asn Gly His Pro Pro Asp Asn
                530                 535                 540

Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
```

-continued

```
                565                 570                 575
Thr Thr Tyr Gln Lys Val Pro Ala Phe Ile Asp Glu Thr Leu Ala Ala
            580                 585                 590
Lys Gly Ala Glu Asn Ile Ala Asp Arg Gly Glu Ala Asp Ala Ser Asp
            595                 600                 605
Asp Phe Glu Gly Thr Tyr Glu Glu Trp Arg Glu His Met Trp Ser Asp
    610                 615                 620
Val Ala Ala Tyr Phe Asn Leu Asp Ile Glu Asn Ser Glu Asp Asn Lys
625                 630                 635                 640
Ser Thr Leu Ser Leu Gln Phe Val Asp Ser Ala Ala Asp Met Pro Leu
                645                 650                 655
Ala Lys Met His Gly Ala Phe Ser Thr Asn Val Val Ala Ser Lys Glu
            660                 665                 670
Leu Gln Gln Pro Gly Ser Ala Arg Ser Thr Arg His Leu Glu Ile Glu
            675                 680                 685
Leu Pro Lys Glu Ala Ser Tyr Gln Glu Gly Asp His Leu Gly Val Ile
            690                 695                 700
Pro Arg Asn Tyr Glu Gly Ile Val Asn Arg Val Thr Ala Arg Phe Gly
705                 710                 715                 720
Leu Asp Ala Ser Gln Gln Ile Arg Leu Glu Ala Glu Glu Lys Leu
                725                 730                 735
Ala His Leu Pro Leu Ala Lys Thr Val Ser Val Glu Glu Leu Leu Gln
            740                 745                 750
Tyr Val Glu Leu Gln Asp Pro Val Thr Arg Thr Gln Leu Arg Ala Met
            755                 760                 765
Ala Ala Lys Thr Val Cys Pro Pro His Lys Val Glu Leu Glu Ala Leu
    770                 775                 780
Leu Glu Lys Gln Ala Tyr Lys Glu Gln Val Leu Ala Lys Arg Leu Thr
785                 790                 795                 800
Met Leu Glu Leu Leu Glu Lys Tyr Pro Ala Cys Glu Met Lys Phe Ser
                805                 810                 815
Glu Phe Ile Ala Leu Leu Pro Ser Ile Arg Pro Arg Tyr Tyr Ser Ile
            820                 825                 830
Ser Ser Ser Pro Arg Val Asp Glu Lys Gln Ala Ser Ile Thr Val Ser
            835                 840                 845
Val Val Ser Gly Glu Ala Trp Ser Gly Tyr Gly Glu Tyr Lys Gly Ile
            850                 855                 860
Ala Ser Asn Tyr Leu Ala Glu Leu Gln Glu Gly Asp Thr Ile Thr Cys
865                 870                 875                 880
Phe Ile Ser Thr Pro Gln Ser Glu Phe Thr Leu Pro Lys Asp Pro Glu
                885                 890                 895
Thr Pro Leu Ile Met Val Gly Pro Gly Thr Gly Val Ala Pro Phe Arg
                900                 905                 910
Gly Phe Val Gln Ala Arg Lys Gln Leu Lys Glu Gln Gly Gln Ser Leu
            915                 920                 925
Gly Glu Ala His Leu Tyr Phe Gly Cys Arg Ser Pro His Glu Asp Tyr
            930                 935                 940
Leu Tyr Gln Glu Glu Leu Glu Asn Ala Gln Ser Glu Gly Ile Ile Thr
945                 950                 955                 960
Leu His Thr Ala Phe Ser Arg Met Pro Asn Gln Pro Lys Thr Tyr Val
                965                 970                 975
Gln His Val Met Glu Gln Asp Gly Lys Lys Leu Ile Glu Leu Leu Asp
            980                 985                 990
```

Gln Gly Ala His Phe Tyr Ile Cys Gly Asp Gly Ser Gln Met Ala Pro
            995                1000                    1005

Ala Val Glu Ala Thr Leu Met Lys Ser Tyr Ala Asp Val His Gln
    1010                1015                    1020

Val Ser Glu Ala Asp Ala Arg Leu Trp Leu Gln Gln Leu Glu Glu
    1025                1030                    1035

Lys Gly Arg Tyr Ala Lys Asp Val Trp Ala Gly
    1040                1045

<210> SEQ ID NO 107
<211> LENGTH: 3150
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 107

| | | | | | |
|---|---|---|---|---|---|
| atgaccatca | agaaatgcc | acaacctaag | actttcggtg | aattgaagaa | tttgcctttg | 60 |
| ttgaacaccg | ataagccagt | tcaagctttg | atgaagattg | ctgatgaatt | gggtgaaatc | 120 |
| ttcaagtttg | aagctccagg | tagagtcact | agatacttgt | catctcaaag | attgatcaaa | 180 |
| gaagcctgcg | acgaatccag | atttgataag | aatttgtctc | aagctttgaa | gttcgctaga | 240 |
| gattttgctg | gtgatggttt | ggttacttct | tggactcacg | aaaagaattg | aagaaggcc | 300 |
| cataacattt | tgttgccatc | tttctcacaa | caagccatga | agggttatca | tgctatgatg | 360 |
| gttgatatcg | ccgttcaatt | ggttcaaaag | tgggaaagat | tgaacgccga | tgaacatatc | 420 |
| gaagtctctg | aagatatgac | cagattgacc | ttggatacca | ttggtttgtg | tggtttcaac | 480 |
| tacagattca | actccttcta | cagagatcaa | ccacatccat | tcatcatctc | tatggttaga | 540 |
| gctttggatg | aagtcatgaa | caaattgcaa | agagctaatc | agacgatcc | agcttatgac | 600 |
| gaaaacaaga | gacaattcca | agaagatatc | aaggtcatga | cgatttggt | cgataagatt | 660 |
| atcgctgata | gaaaggctag | aggtgaacaa | tctgatgatt | tgttgaccca | aatgttgaac | 720 |
| ggtaaggatc | cagaaactgg | tgaaccattg | gatgatggta | acatcagata | ccaaattatc | 780 |
| accttcttga | ttgctggtca | cgaaactaca | tctggtttgt | tgtcttttgc | cttgtacttt | 840 |
| ttggttaaga | acccacacgt | cttgcaaaag | gttgctgaag | aagctgcaag | agttttggtt | 900 |
| gatccagttc | catcttacaa | gcaagtcaag | caattgaagt | acgttggtat | ggttttgaac | 960 |
| gaagctttga | gattgtggcc | aactgctcca | gctttttcat | tatacgctaa | gaagatacc | 1020 |
| gtcttgggtg | gtgaatatcc | attggaaaaa | ggtgatgaag | ttatggtctt | gatcccacaa | 1080 |
| ttgcatagag | ataagactgt | ttggggtgat | gatgtcgaag | aattcagacc | agaaagattc | 1140 |
| gaaaacccat | ctgctattcc | acaacatgct | tttaagccat | tggtaacgg | tcaaagagct | 1200 |
| tgcattggtc | aacaattcgc | tttacatgaa | gctaccttgg | ttttgggtat | gatgttgaaa | 1260 |
| cacttcgact | tcgaagatca | caccaactac | gaattggata | tcaaagaaac | cgctaccttg | 1320 |
| aagccaaagg | ttttgttgt | taaggctaag | tccaaaaaga | ttccattggg | tggtattcca | 1380 |
| tctccatcta | ctgaacaatc | cgctaagaag | gttagaaaga | aagctgaaaa | cgctcataac | 1440 |
| acacctttgt | tggtcttgta | cggttctaat | atgggtactg | ctgaaggtac | agcaagagat | 1500 |
| ttggcagata | ttgctatgtc | taaaggtttc | gctccacaag | ttgctacttt | ggattctcat | 1560 |
| gctggtaatt | tgccaagaga | aggtgctgtt | ttgatagtta | ctgcttctta | caatggtcac | 1620 |
| ccaccagata | tgctaagca | attcgttgat | tggttggatc | aagcttcagc | tgatgaagta | 1680 |

```
aaaggtgtta gatactctgt tttcggttgc ggtgacaaaa attgggctac tacttatcaa    1740
aaggttccag cctttattga cgaaactttg gctgctaaag gtgctgaaaa cattgctgac    1800
agaggtgaag ctgatgcctc cgacgacttc gaaggtactt acgaagaatg gagagaacac    1860
atgtggtctg acgttgctgc ttacttcaac ttggacatcg aaaactctga agacaacaag    1920
tccactttgt ctttgcaatt cgttgactcc gctgctgaca tgccattggc taagatgcac    1980
ggtgctttct ctaccaacgt cgttgcctcc aaggaattgc aacaaccagg ttctgctaga    2040
tctactagac acttggaaat cgaattgcca aggaagcttc ctaccaaga aggtgaccac     2100 ttgggcgtta ttccaagaaa ctacgaaggt atcgtcaaca gagttactgc tagattcggt    2160
ttggatgctt ctcaacaaat cagattagaa gctgaagaag aaaagttggc tcacttgcca    2220
ttagctaaga ctgtctccgt tgaagaattg ttgcaatacg tcgaattgca agacccagtt    2280
accagaaccc aattgagagc catggctgcc aagaccgtct gtccaccaca caaggttgaa    2340
ttggaagcct tgttggaaaa gcaagcctac aaggaacaag ttttggctaa gagattgacc    2400
atgttggaat tgttggaaaa gtacccagcc tgcgaaatga agttctctga atttatcgcc    2460
ttgttgccat ctatcagacc acgttactac tctatttctt cctctccacg tgttgacgaa    2520
aagcaagctt ctattactgt ttccgttgtc tccggtgaag cttggtccgg ttacggtgaa    2580
tacaagggta ttgcttctaa ctacttggct gaattgcaag aaggtgacac cattacttgt    2640
ttcatctcta ctccacaatc cgaatttact ttgccaaagg acccagaaac tccattgatc    2700
atggttggtc caggtactgg tgtcgctcca ttcagaggtt cgttcaagc tagaaaacaa     2760 ttgaaggaac aaggtcaatc tttgggtgaa gctcacttgt acttcggttg tagatctcca    2820
cacgaagact acttatacca agaagaattg gaaaacgctc aatccgaagg tattatcact    2880
ttgcacaccg ctttctccag aatgccaaac caaccaaaga cttacgtcca acacgttatg    2940
gaacaagacg gtaagaagtt gattgaattg ttggaccaag gtgctcactt ctacatttgt    3000
ggtgatggtt ctcaaatggc tccagccgtt gaagccactt tgatgaagtc ttacgctgat    3060
gttcaccaag tttccgaagc cgatgctaga ttatggttgc aacaattgga gaaaaaggt    3120 cgttacgcta aggatgtctg ggccggttga                                    3150

<210> SEQ ID NO 108
<211> LENGTH: 3150
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 108
atgaccatca agaaatgcc acaacctaag actttcggtg aattgaagaa tttgcctttg       60
ttgaacaccg ataagccagt tcaagctttg atgaagattg ctgatgaatt gggtgaaatc     120
ttcaagtttg aagctccagg tagagtcact agatacttgt catctcaaag attgatcaaa    180
gaagcctgcg acgaatccag atttgataag aatttgtctc aagctttgaa gttcgctaga    240
gattttgctg gtgatggttt ggttacttct tggactcacg aaaagaattg gaagaaggcc    300
cataacattt tgttgccatc tttctcacaa caagccatga agggttatca tgctatgatg    360
gttgatatcg ccgttcaatt ggttcaaaag tgggaaagat gaacgccga tgaacatatc     420 gaagtctctg aagtatgac cagattgacc ttggatacca ttggtttgtg tggtttcaac    480
tacagattca actccttcta cagagatcaa ccacatccat tcatcatctc tatggttaga    540
```

```
gctgcagatg aagtcatgaa caaattgcaa agagctaatc cagacgatcc agcttatgac    600
gaaaacaaga gacaattcca agaagatatc aaggtcatga acgatttggt cgataagatt    660
atcgctgata gaaaggctag aggtgaacaa tctgatgatt tgttgaccca aatgttgaac    720
ggtaaggatc cagaaactgg tgaaccattg gatgatggta acatcagata ccaaattatc    780
gctttcttga ttgctggtca cgaaactaca tctggtttgt tgtcttttgc cttgtacttt    840
ttggttaaga acccacacgt cttgcaaaag gttgctgaag aagctgcaag agttttggtt    900
gatccagttc catcttacaa gcaagtcaag caattgaagt acgttggtat ggttttgaac    960
gaagctttga gattgtggcc aactgctcca gcttttcat tatacgctaa agaagatacc     1020
gtcttgggtg gtgaatatcc attggaaaaa ggtgatgaag ttatggtctt gatcccacaa    1080
ttgcatagag ataagactgt ttgggggtgat gatgtcgaag aattcagacc agaaagattc    1140
gaaaacccat ctgctattcc acaacatgct tttaagccat ttggtaacgg tcaaagagct    1200
tgcattggtc aacaattcgc tttacatgaa gctaccttgg ttttgggtat gatgttgaaa    1260
cacttcgact tcgaagatca caccaactac gaattggata tcaaagaaac cgctaccttg    1320
aagccaaagg ttttgttgt taaggctaag tccaaaaaga ttccattggg tggtattcca    1380
tctccatcta ctgaacaatc cgctaagaag gttagaaaga aagctgaaaa cgctcataac    1440
acacctttgt tggtcttgta cggttctaat atgggtactg ctgaaggtac agcaagagat    1500
ttggcagata ttgctatgtc taaaggtttc gctccacaag ttgctacttt ggattctcat    1560
gctggtaatt tgccaagaga aggtgctgtt ttgatagtta ctgcttctta caatggtcac    1620
ccaccagata atgctaagca attcgttgat tggttggatc aagcttcagc tgatgaagta    1680
aaaggtgtta gatactctgt tttcggttgc ggtgacaaaa attgggctac tacttatcaa    1740
aaggttccag cctttattga cgaaactttg gctgctaaag gtgctgaaaa cattgctgac    1800
agaggtgaag ctgatgcctc cgacgacttc gaaggtactt acgaagaatg gagagaacac    1860
atgtggtctg acgttgctgc ttacttcaac ttggacatcg aaaactctga agacaacaag    1920
tccactttgt ctttgcaatt cgttgactcc gctgctgaca tgccattggc taagatgcac    1980
ggtgctttct ctaccaacgt cgttgcctcc aaggaattgc aacaaccagg ttctgctaga    2040
tctactagac acttggaaat cgaattgcca aaggaagctt cctaccaaga aggtgaccac    2100
ttgggcgtta ttccaagaaa ctacgaaggt atcgtcaaca gagttactgc tagattcggt    2160
ttggatgctt ctcaacaaat cagattgaaa gctgaagaag aaaagttggc tcacttgcca    2220
ttagctaaga ctgtctccgt tgaagaattg ttgcaatacg tcgaattgca agacccagtt    2280
accagaaccc aattgagagc catggctgcc aagaccgtct gtccaccaca caaggttgaa    2340
ttggaagcct tgtggaaaaa gcaagcctac aaggaacaag ttttggctaa gagattgacc    2400
atgttggaat tgttggaaaa gtacccagcc tgcgaaatga agttctctga atttatcgcc    2460
ttgttgccat ctatcagacc acgttactac tctatttctt cctctccacg tgttgacgaa    2520
aagcaagctt ctattactgt ttccgttgtc tccggtgaag cttggtccgg ttacggtgaa    2580
tacaagggta ttgcttctaa ctacttggct gaattgcaag aaggtgacac cattacttgt    2640
ttcatctcta ctccacaatc cgaatttact ttgccaaagg acccagaaac tccattgatc    2700
atggttggtc aggtactggt tgtcgctcca ttcagaggtt tcgttcaagc tagaaaacaa    2760
ttgaaggaac aaggtcaatc tttgggtgaa gctcacttgt acttcggttg tagatctcca    2820
cacgaagact acttatacca agaagaattg gaaaacgctc aatccgaagg tattatcact    2880
```

```
ttgcacaccg ctttctccag aatgccaaac caaccaaaga cttacgtcca acacgttatg    2940
gaacaagacg gtaagaagtt gattgaattg ttggaccaag gtgctcactt ctacatttgt    3000
ggtgatggtt ctcaaatggc tccagccgtt gaagccactt tgatgaagtc ttacgctgat    3060
gttcaccaag tttccgaagc cgatgctaga ttatggttgc aacaattgga agaaaaaggt    3120
cgttacgcta aggatgtctg ggccggttga                                     3150
```

<210> SEQ ID NO 109
<211> LENGTH: 3150
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 109

```
atgaccatca agaaatgcc acaacctaag actttcggtg aattgaagaa tttgcctttg      60
ttgaacaccg ataagccagt tcaagctttg atgaagattg ctgatgaatt gggtgaaatc    120
ttcaagtttg aagctccagg tagagtcact agatacttgt catctcaaag attgatcaaa    180
gaagcctgcg acgaatccag atttgataag aatttgtctc aagctgctaa gttcgctaga    240
gattttgctg gtgatggttt ggttacttct tggactcacg aaaagaattg aagaaggcc     300 cataacattt tgttgccatc tttctcacaa caagccatga agggttatca tgctatgatg    360
gttgatatcg ccgttcaatt ggttcaaaag tgggaaagat tgaacgccga tgaacatatc    420
gaagtctctg aagatatgac cagattgacc ttggatacca ttggtttgtg tggtttcaac    480
tacagattca actccttcta cagagatcaa ccacatccat tcatcatctc tatggttaga    540
gctgcagatg aagtcatgaa caaattgcaa agagctaatc cagacgatcc agcttatgac    600
gaaaacaaga gacaattcca agaagatatc aaggtcatga acgatttggt cgataagatt    660
atcgctgata aaaggctag aggtgaacaa tctgatgatt tgttgaccca atgttgaac     720 ggtaaggatc cagaaactgg tgaaccattg gatgatggta acatcagata ccaaattatc    780
accttcttga ttgctggtca cgaaactaca tctggttttgt tgtcttttgc cttgtacttt    840
ttggttaaga cccacacgt cttgcaaaag gttgctgaag aagctgcaag agttttggtt    900
gatccagttc catcttacaa gcaagtcaag caattgaagt acgttggtat ggttttgaac    960
gaagctttga gattgtggcc aactgctcca gcttttcat tatacgctaa agaagatacc   1020
gtcttgggtg gtgaatatcc attggaaaaa ggtgatgaag ttatggtctt gatcccacaa   1080
ttgcatagaa ataagactgt ttgggtgat gatgtcgaag aattcagacc agaaagattc   1140
gaaaacccat ctgctattcc acaacatgct tttaagccat tggtaacgg tcaaagagct   1200 tgcattggtc aacaattcgc tttacatgaa gctaccttgg ttttgggtat gatgttgaaa   1260
cacttcgact cgaagatca caccaactac gaattggata tcaaagaaac cttgaccttg   1320
aagccaaagg gttttgttgt taaggctaag tccaaaaaga ttccattggg tggtattcca   1380
tctccatcta ctgaacaatc cgctaagaag gttagaaaga aagctgaaaa cgctcataac   1440
acacctttgt tggtcttgta cggttctaat atgggtactg ctgaaggtac agcaagagat   1500
ttggcagata ttgctatgtc taaggtttc gctccacaag ttgctacttt ggattctcat   1560
gctggtaatt tgccaagaga aggtgctgtt ttgatagtta ctgcttctta caatggtcac   1620
ccaccagata tgctaagca attcgttgat tggttggatc aagcttcagc tgatgaagta   1680
aaaggtgtta gatactctgt tttcggttgc ggtgacaaaa attgggctac tacttatcaa   1740
```

```
aaggttccag cctttattga cgaaactttg gctgctaaag gtgctgaaaa cattgctgac    1800
agaggtgaag ctgatgcctc cgacgacttc gaaggtactt acgaagaatg gagagaacac    1860
atgtggtctg acgttgctgc ttacttcaac ttggacatcg aaaactctga agacaacaag    1920
tccactttgt ctttgcaatt cgttgactcc gctgctgaca tgccattggc taagatgcac    1980
ggtgctttct ctaccaacgt cgttgcctcc aaggaattgc aacaaccagg ttctgctaga    2040
tctactagac acttggaaat cgaattgcca aggaagcttc ctaccaaga aggtgaccac    2100 ttgggcgtta ttccaagaaa ctacgaaggt atcgtcaaca gagttactgc tagattcggt    2160
ttggatgctt ctcaacaaat cagattagaa gctgaagaag aaaagttggc tcacttgcca    2220
ttagctaaga ctgtctccgt tgaagaattg ttgcaatacg tcgaattgca agacccagtt    2280
accagaaccc aattgagagc catggctgcc aagaccgtct gtccaccaca caaggttgaa    2340
ttggaagcct tgttggaaaa gcaagcctac aaggaacaag ttttggctaa gagattgacc    2400
atgttggaat tgttggaaaa gtacccagcc tgcgaaatga gttctctga atttatcgcc    2460 ttgttgccat ctatcagacc acgttactac tctatttctt cctctccacg tgttgacgaa    2520
aagcaagctt ctattactgt ttccgttgtc tccggtgaag cttggtccgg ttacggtgaa    2580
tacaagggta ttgcttctaa ctacttggct gaattgcaag aaggtgacac cattacttgt    2640
ttcatctcta ctccacaatc cgaatttact ttgccaaagg acccagaaac tccattgatc    2700
atggttggtc aggtactgg tgtcgctcca ttcagaggtt tcgttcaagc tagaaaacaa    2760
ttgaaggaac aaggtcaatc tttgggtgaa gctcacttgt acttcggttg tagatctcca    2820
cacgaagact acttatacca agaagaattg gaaaacgctc aatccgaagg tattatcact    2880
ttgcacaccg ctttctccag aatgccaaac caaccaaaga cttacgtcca acacgttatg    2940
gaacaagacg gtaagaagtt gattgaattg ttggaccaag gtgctcactt ctacatttgt    3000
ggtgatggtt ctcaaatggc tccagccgtt gaagccactt tgatgaagtc ttacgctgat    3060
gttcaccaag tttccgaagc cgatgctaga ttatggttgc aacaattgga agaaaaaggt    3120
cgttacgcta aggatgtctg ggccggttga                                     3150
```

<210> SEQ ID NO 110
<211> LENGTH: 3150
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 110

```
atgaccatca agaaatgcc acaacctaag actttcggtg aattgaagaa tttgcctttg      60
ttgaacaccg ataagccagt tcaagctttg atgaagattg ctgatgaatt gggtgaaatc     120
ttcaagtttg aagctccagg tagagtcact agatacttgt catctcaaag attgatcaaa     180
gaagcctgcg acgaatccag atttgataag aatttgtctc aagctgctaa gttcgctaga     240
gattttgctg gtgatggttt ggttacttct tggactcacg aaaagaattg gaagaaggcc     300
cataacattt tgttgccatc tttctcacaa caagccatga gggttatca tgctatgatg     360 gttgatatcg ccgttcaatt ggttcaaaag tgggaaagat gaacgccga tgaacatatc     420 gaagtctctg aagatatgac cagattgacc ttggatacca ttggtttgtg tggtttcaac     480
tacagattca actccttcta cagagatcaa ccacatccat tcatcatctc tgctgttaga     540
gctgcagatg aagtcatgaa caaattgcaa agagctaatc cagacgatcc agcttatgac     600
```

```
gaaaacaaga gacaattcca agaagatatc aaggtcatga acgatttggt cgataagatt    660
atcgctgata gaaaggctag aggtgaacaa tctgatgatt tgttgaccca aatgttgaac    720
ggtaaggatc cagaaactgg tgaaccattg gatgatggta acatcagata ccaaattatc    780
accttcttga ttgctggtca cgaaactaca tctggtttgt tgtcttttgc cttgtacttt    840
ttggttaaga acccacacgt cttgcaaaag gttgctgaag aagctgcaag agttttggtt    900
gatccagttc catcttacaa gcaagtcaag caattgaagt acgttggtat ggttttgaac    960
gaagctttga gattgtggcc aactgctcca gcttttttcat tatacgctaa agaagatacc   1020
gtcttgggtg gtgaatatcc attggaaaaa ggtgatgaag ttatggtctt gatcccacaa   1080
ttgcatagag ataagactgt ttggggtgat gatgtcgaag aattcagacc agaaagattc   1140
gaaaacccat ctgctattcc acaacatgct tttaagccat tggtaacgg tcaaagagct    1200 tgcattggtc aacaattcgc tttacatgaa gctaccttgg ttttgggtat gatgttgaaa   1260
cacttcgact tcgaagatca caccaactac gaattggata tcaaagaaac cttgaccttg   1320
aagccaaagg gttttgttgt taaggctaag tccaaaaaga ttccattggg tggtattcca   1380
tctccatcta ctgaacaatc cgctaagaag gttagaaaga aagctgaaaa cgctcataac   1440
acacctttgt tggtcttgta cggttctaat atgggtactg ctgaaggtac agcaagagat   1500
ttggcagata ttgctatgtc taaaggtttc gctccacaag ttgctacttt ggattctcat   1560
gctggtaatt tgccaagaga aggtgctgtt ttgatagtta ctgcttctta caatggtcac   1620
ccaccagata atgctaagca attcgttgat tggttggatc aagcttcagc tgatgaagta   1680
aaaggtgtta gatactctgt tttcggttgc ggtgacaaaa attgggctac tacttatcaa   1740
aaggttccag cctttattga cgaaactttg gctgctaaag gtgctgaaaa cattgctgac   1800
agaggtgaag ctgatgcctc cgacgacttc gaaggtactt acgaagaatg gagagaaac    1860 atgtggtctg acgttgctgc ttacttcaac ttggacatcg aaaactctga agacaacaag   1920
tccactttgt ctttgcaatt cgttgactcc gctgctgaca tgccattggc taagatgcac   1980
ggtgctttct ctaccaacgt cgttgcctcc aaggaattgc aacaaccagg ttctgctaga   2040
tctactagac acttggaaat cgaattgcca aaggaagctt cctaccaaga aggtgaccac   2100
ttgggcgtta ttccaagaaa ctacgaaggt atcgtcaaca gagttactgc tagattcggt   2160
ttggatgctt ctcaacaaat cagattagaa gctgaagaag aaaagttggc tcacttgcca   2220
ttagctaaga ctgtctccgt tgaagaattg ttgcaatacg tcgaattgca agacccagtt   2280
accagaaccc aattgagagc catggctgcc aagaccgtct gtccaccaca caaggttgaa   2340
ttggaagcct tgttggaaaa gcaagcctac aaggaacaag ttttggctaa gagattgacc   2400 atgtggaat tgtggaaaaa gtacccagcc tgcgaaatga agttctctga atttatcgcc    2460 tgttgccat ctatcagacc acgttactac tctatttctt cctctccacg tgttgacgaa    2520
aagcaagctt ctattactgt ttccgttgtc tccggtgaag cttggtccgg ttacggtgaa   2580
tacaagggta ttgcttctaa ctacttggct gaattgcaag aaggtgacac cattacttgt   2640
ttcatctcta ctccacaatc cgaatttact ttgccaaagg acccagaaac tccattgatc   2700
atggttggtc caggtactgg tgtcgctcca ttcagaggtt tcgttcaagc tagaaaacaa   2760
ttgaaggaac aaggtcaatc tttgggtgaa gctcacttgt acttcggttg tagatctcca   2820
cacgaagact acttataccac agaagaattg gaaaacgctc aatccgaagg tattatcact   2880
ttgcacaccg ctttctccag aatgccaaac caaccaaaga cttacgtcca acacgttatg   2940
gaacaagacg gtaagaagtt gattgaattg ttggaccaag gtgctcactt ctacatttgt   3000
```

| ggtgatggtt ctcaaatggc tccagccgtt gaagccactt tgatgaagtc ttacgctgat | 3060 |
| gttcaccaag tttccgaagc cgatgctaga ttatggttgc aacaattgga agaaaaaggt | 3120 |
| cgttacgcta aggatgtctg gccggttga | 3150 |

<210> SEQ ID NO 111
<211> LENGTH: 3150
<212> TYPE: DNA
<213> ORGANISM: Artificial Sequence
<220> FEATURE:
<223> OTHER INFORMATION: Description of Artificial Sequence: Synthetic polynucleotide
<400> SEQUENCE: 111

| atgaccatca aagaaatgcc acaacctaag actttcggtg aattgaagaa tttgcctttg | 60 |
| ttgaacaccg ataagccagt tcaagctttg atgaagattg ctgatgaatt gggtgaaatc | 120 |
| ttcaagtttg aagctccagg tagagtcact agatacttgt catctcaaag attgatcaaa | 180 |
| gaagcctgcg acgaatccag atttgataag aatttgtctc aagctgctaa gttcgctaga | 240 |
| gattttgctg gtgatggttt ggttacttct tggactcacg aaaagaattg gaagaaggcc | 300 |
| cataacattt tgttgccatc tttctcacaa caagccatga agggttatca tgctatgatg | 360 |
| gttgatatcg ccgttcaatt ggttcaaaag tgggaaagat gaacgccga tgaacatatc | 420 |
| gaagtctctg aagatatgac cagattgacc ttggatacca ttggtttgtg tggtttcaac | 480 |
| tacagattca actccttcta cagagatcaa ccacatccat tcatcatctc tgctgttaga | 540 |
| gctgcagatg aagtcatgaa caaattgcaa agagctaatc cagacgatcc agcttatgac | 600 |
| gaaaacaaga gacaattcca agaagatatc aaggtcatga acgatttggt cgataagatt | 660 |
| atcgctgata gaaaggctag aggtgaacaa tctgatgatt tgttgaccca aatgttgaac | 720 |
| ggtaaggatc cagaaactgg tgaaccattg gatgatggta acatcagata ccaaattatc | 780 |
| gctttcttga ttgctggtca cgaaactaca tctggttttg tgtctttttgc cttgtacttt | 840 |
| ttggttaaga acccacacgt cttgcaaaag gttgctgaag aagctgcaag agttttggtt | 900 |
| gatccagttc catcttacaa gcaagtcaag caattgaagt acgttggtat ggttttgaac | 960 |
| gaagctttga gattgtggcc aactgctcca gcttttttcat tatacgctaa gaagatacc | 1020 |
| gtcttgggtg gtaatatcc attggaaaaa ggtgatgaag ttatggtctt gatcccacaa | 1080 |
| ttgcatagag ataagactgt ttgggggtgat gatgtcgaag aattcagacc agaaagattc | 1140 |
| gaaaacccat ctgctattcc acaacatgct tttaagccat ttggtaacgg tcaaagagct | 1200 |
| tgcattggtc aacaattcgc tttacatgaa gctaccttgg ttttgggtat gatgttgaaa | 1260 |
| cacttcgact tcgaagatca caccaactac gaattggata tcaaagaaac cttgaccttg | 1320 |
| aagccaaagg ttttgttgt taaggctaag tccaaaaaga ttccattggg tggtattcca | 1380 |
| tctccatcta ctgaacaatc cgctaagaag gttagaaaga agctgaaaaa cgctcataac | 1440 |
| acacctttgt tggtcttgta cggttctaat atgggtactg ctgaaggtac agcaagagat | 1500 |
| ttggcagata ttgctatgtc taaaggtttc gctccacaag ttgctacttt ggattctcat | 1560 |
| gctggtaatt tgccaagaga aggtgctgtt ttgatagtta ctgcttctta caatggtcac | 1620 |
| ccaccagata atgctaagca attcgttgat tggttggatc aagcttcagc tgatgaagta | 1680 |
| aaaggtgtta gatactctgt tttcggttgc ggtgacaaaa attgggctac tacttatcaa | 1740 |
| aaggttccag ccttattga cgaaactttg gctgctaaag gtgctgaaaa cattgctgac | 1800 |
| agaggtgaag ctgatgcctc cgacgacttc gaaggtactt acgaagaatg gagagaacac | 1860 |

```
atgtggtctg acgttgctgc ttacttcaac ttggacatcg aaaactctga agacaacaag    1920
tccactttgt ctttgcaatt cgttgactcc gctgctgaca tgccattggc taagatgcac    1980
ggtgctttct ctaccaacgt cgttgcctcc aaggaattgc aacaaccagg ttctgctaga    2040
tctactagac acttggaaat cgaattgcca aggaagctt cctaccaaga aggtgaccac     2100
ttgggcgtta ttccaagaaa ctacgaaggt atcgtcaaca gagttactgc tagattcggt    2160
ttggatgctt ctcaacaaat cagattagaa gctgaagaag aaaagttggc tcacttgcca    2220
ttagctaaga ctgtctccgt tgaagaattg ttgcaatacg tcgaattgca agacccagtt    2280
accagaaccc aattgagagc catggctgcc aagaccgtct gtccaccaca caaggttgaa    2340
ttggaagcct tgttggaaaa gcaagcctac aaggaacaag ttttggctaa gagattgacc    2400
atgttggaat gtggaaaaa gtacccagcc tgcgaaatga agttctctga atttatcgcc     2460
ttgttgccat ctatcagacc acgttactac tctatttctt cctctccacg tgttgacgaa    2520
aagcaagctt ctattactgt ttccgttgtc tccggtgaag cttggtccgg ttacggtgaa    2580
tacaagggta ttgcttctaa ctacttggct gaattgcaag aaggtgacac cattacttgt    2640
ttcatctcta ctccacaatc cgaatttact ttgccaaagg acccagaaac tccattgatc    2700
atggttggtc caggtactgg tgtcgctcca ttcagaggtt tcgttcaagc tagaaaacaa    2760
ttgaaggaac aaggtcaatc tttgggtgaa gctcacttgt acttcggttg tagatctcca    2820
cacgaagact acttatacca agaagaattg gaaaacgctc aatccgaagg tattatcact    2880
ttgcacaccg ctttctccag aatgccaaac caaccaaaga cttacgtcca acacgttatg    2940
gaacaagacg gtaagaagtt gattgaattg ttggaccaag gtgctcactt ctacatttgt    3000
ggtgatggtt ctcaaatggc tccagccgtt gaagccactt tgatgaagtc ttacgctgat    3060
gttcaccaag tttccgaagc cgatgctaga ttatggttgc aacaattgga agaaaaggt    3120
cgttacgcta aggatgtctg ggccggttga                                     3150
```

<210> SEQ ID NO 112  
<211> LENGTH: 5372  
<212> TYPE: DNA  
<213> ORGANISM: Artificial Sequence  
<220> FEATURE:  
<223> OTHER INFORMATION: Description of Artificial Sequence: Synthetic polynucleotide

<400> SEQUENCE: 112

```
cctcgccgca gttaattaaa gtcagtgagc gaggaagcgc gtaactataa cggtcctaag     60
gtagcgaatc ctgatgcggt atttctcct tacgcatctg tgcggtattt cacaccgcat     120
agatcggcaa gtgcacaaac aatacttaaa taaatactac tcagtaataa cctatttctt    180
agcattttg acgaaatttg ctattttgtt agagtctttt acaccatttg tctccacacc     240
tccgcttaca tcaacaccaa taacgccatt aatctaagc gcatcaccaa catttctgg      300
cgtcagtcca ccagctaaca taaatgtaa gctttcgggg ctctcttgcc ttccaaccca     360
gtcagaaatc gagttccaat ccaaaagttc acctgtccca cctgcttctg aatcaaacaa    420
gggaataaac gaatgaggtt tctgtgaagc tgcactgagt agtatgttgc agtcttttgg    480
aaatacgagt cttttaataa ctggcaaacc gaggaactct tggtattctt gccacgactc    540
atctccatgc agtggagcca atcaattctt gcggtcaact ttggacgata tcaatgccgt    600
aatcattgac cagagccaaa acatcctcct taagttgatt acgaaacacg ccaaccaagt    660
atttcggagt gcctgaacta ttttatatg cttttacaag acttgaaatt tccttgcaa     720
```

```
taaccgggtc aattgttctc tttctattgg gcacacatat aatacccagc aagtcagcat     780
cggaatctag agcacattct gcggcctctg tgctctgcaa gccgcaaact ttcaccaatg     840
gaccagaact acctgtgaaa ttaataacag acatactcca agctgccttt gtgtgcttaa     900
tcacgtatac tcacgtgctc aatagtcacc aatgccctcc ctcttggccc tctccttttc     960
ttttttcgac cgaattaatt cttaatcggc aaaaaagaa aagctccgga tcaagattgt     1020
acgtaaggtg acaagctatt tttcaataaa gaatatcttc cactactgcc atctggcgtc     1080
ataactgcaa agtacacata tattacgatg ctgttctatt aaatgcttcc tatattatat     1140
atatagtaat gtcgtgatct atggtgcact ctcagtacaa tctgctctga tgccgcatag     1200
ttaagccagc cccgacaccc gccaacaccc gctgacgcgc cctgacgggc ttgtctgctc     1260
ccggcatccg cttacagaca agctgtgacc gtctccggga gctgcatgtg tcagaggttt     1320
tcaccgtcat caccgaaacg cgcgagacga agggcctcg tgatacgcct atttttatag     1380
gttaatgtca tgataataat ggtttcttag acggatcgct tgcctgtaac ttacacgcgc     1440
ctcgtatctt ttaatgatgg aataatttgg gaatttactc tgtgtttatt tatttttatg     1500
ttttgtattt ggattttaga aagtaaataa agaaggtaga agagttacgg aatgaagaaa     1560
aaaaaataaa caaaggttta aaaaatttca acaaaaagcg tactttacat atatatttat     1620
tagacaagaa aagcagatta aatagatata cattcgatta acgataagta aaatgtaaaa     1680
tcacaggatt ttcgtgtgtg gtcttctaca cagacaaggt gaaacaattc ggcattaata     1740
cctgagagca ggaagagcaa gataaaaggt agtatttgtt ggcgatcccc ctagagtctt     1800
ttacatcttc ggaaaacaaa aactatttt tctttaattt ctttttttac tttctatttt     1860
taatttatat atttatatta aaaaatttaa attataatta tttttatagc acgtgatgaa     1920
aaggacccag gtggcacttt cggggaaat gtgcgcggaa ccctatttg tttattttc      1980
taaatacatt caaatatgta tccgctcatg agacaataac cctgataaat gcttcaataa     2040
tattgaaaaa ggaagagtat gagtattcaa catttccgtg tcgcccttat tccctttttt     2100
gcggcatttt gccttcctgt ttttgctcac ccagaaacgc tggtgaaagt aaaagatgct     2160
gaagatcagt tgggacgcgt agtctagacc agccaggaca gaaatgcctc gacttcgctg     2220
ctacccaagg ttgccgggtg acgcacaccg tggaaacgga tgaaggcacg aacccagtgg     2280
acataagcct gttcggttcg taagctgtaa tgcaagtagc gtatgcgctc acgcaactgg     2340
tccagaacct tgaccgaacg cagcggtggt aacggcgcag tggcggtttt catggcttgt     2400
tatgactgtt ttttggggt acagtctatg cctcgggcat ccaagcagca agcgcgttac     2460
gccgtgggtc gatgtttgat gttatggagc agcaacgatg ttacgcagca gggcagtcgc     2520
cctaaaacaa agttaaacat tatgagggaa gcggtgatcg ccgaagtatc gactcaacta     2580
tcagaggtag ttggcgccat cgagcgccat ctcgaaccga cgttgctggc cgtacatttg     2640
tacggctccg cagtggatgg cggcctgaag ccacacagtg atattgattt gctggttacg     2700
gtgaccgtaa ggcttgatga aacaacgcgg cgagctttga tcaacgacct tttggaaact     2760
tcggcttccc ctggagagag cgagattctc cgcgctgtag aagtcaccat tgttgtgcac     2820
gacgacatca ttccgtggcg ttatccagct aagcgcgaac tgcaatttgg agaatggcag     2880
cgcaatgaca ttcttgcagg tatcttcgag ccagccacga tcgacattga tctggctatc     2940
ttgctgacaa aagcaagaga acatagcgtt gccttggtag tccagcggc ggaggaactc      3000
tttgatccgg ttcctgaaca ggatctattt gaggcgctaa atgaaacctt aacgctatgg     3060
```

```
aactcgccgc ccgactgggc tggcgatgag cgaaatgtag tgcttacgtt gtcccgcatt    3120
tggtacagcg cagtaaccgg caaaatcgcg ccgaaggatg tcgctgccgg ctgggcaatg    3180
gagcgcctgc cggcccagta tcagcccgtc atacttgaag ctagacaggc ttatcttgga    3240
caagaagaag atcgcttggc ctcgcgcgca gatcagttgg aagaatttgt ccactacgtg    3300
aaaggcgaga tcaccaaggt agtcggcaaa taaccctcga gcattcaagg cgccttgatt    3360
atttgacgtg gtttgatggc ctccacgcac gttgtgatat gtagatgatt cagttcgagt    3420
ttatcattat caatactgcc atttcaaaga atacgtaaat aattaatagt agtgattttc    3480
ctaactttat ttagtcaaaa aattagcctt ttaattctgc tgtaacccgt acatgcccaa    3540
aatagggggc gggttacaca gaatatataa catcgtaggt gtctgggtga acagtttatt    3600
cctggcatcc actaaatata atggagcccg ctttttaagc tggcatccag aaaaaaaaag    3660
aatcccagca ccaaaatatt gttttcttca ccaaccatca gttcataggt ccattctctt    3720
agcgcaacta cagagaacag gggcacaaac aggcaaaaaa cgggcacaac ctcaatggag    3780
tgatgcaacc tgcctggagt aaatgatgac acaaggcaat tgacccacgc atgtatctat    3840
ctcattttct tacaccttct attaccttct gctctctctg atttggaaaa agctgaaaaa    3900
aaaggttgaa accagttccc tgaaattatt cccctacttg actaataagt atataaagac    3960
ggtaggtatt gattgtaatt ctgtaaatct atttcttaaa cttcttaaat tctactttta    4020
tagttagtct ttttttttagt tttaaaacac caagaactta gttcgaata aacacacata    4080 aacaaacaaa acaggcccct tttcctttgt cgatatcatg taattagtta tgtcacgctt    4140
acattcacgc cctcctccca catccgctct aaccgaaaag gaaggagtta gacaacctga    4200
agtctaggtc cctatttatt ttttttaata gttatgttag tattaagaac gttatttata    4260
tttcaaattt ttctttttt tctgtacaaa cgcgtgtacg catgtaacat tatactgaaa    4320
accttgcttg agaaggtttt gggacgctcg aaggctttaa tttgtaatca ttatcacttt    4380
acgggtcctt tccggtgatc cgacaggtta cggggcggcg acctcgcggg ttttcgctat    4440
ttatgaaaat tttccggttt aaggcgtttc cgttcttctt cgtcataact taatgttttt    4500
atttaaaata cctcgcgagt ggcaacactg aaaatacccca tggagcggcg taaccgtcgc    4560
acaggatcta ggtgaagatc cttttttgata atctcatgac caaaatccct taacgtgagt    4620
tttcgttcca ctgagcgtca gaccccgtag aaaagatcaa aggatcttct tgagatcctt    4680 ttttttctgcg cgtaatctgc tgcttgcaaa caaaaaaacc accgctacca gcggtggttt    4740
gtttgccgga tcaagagcta ccaactcttt ttccgaaggt aactggcttc agcagagcgc    4800
agataccaaa tactgtcctt ctagtgtagc cgtagttagg ccaccacttc aagaactctg    4860
tagcaccgcc tacatacctc gctctgctaa tcctgttacc agtggctgct gccagtggcg    4920
ataagtcgtg tcttaccggg ttggactcaa gacgatagtt accggataag cgcagcggt    4980 cgggctgaac ggggggttcg tgcacacagc ccagcttgga gcgaacgacc tacaccgaac    5040
tgagatacct acagcgtgag ctatgagaaa gcgccacgct tcccgaaggg agaaaggcgg    5100
acaggtatcc ggtaagcggc agggtcggaa caggagagcg cacgagggag cttccagggg    5160
gaaacgcctg gtatctttat agtcctgtcg ggtttcgcca cctctgactt gagcgtcgat    5220
ttttgtgatg ctcgtcaggg gggcggagcc tatgaaaaa cgccagcaac gcggcagtgg    5280
aacgtgcatt atgaattagt tacgctaggg ataacaggt aatatagaac ccgaacgacc    5340
gagcgcagcg cgcgccgcgc tgataccgcc gc                                 5372
```

```
<210> SEQ ID NO 113
<211> LENGTH: 4977
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 113
aacgacctac accgaactga gatacctaca gcgtgagcta tgagaaagcg ccacgcttcc      60
cgaagggaga aaggcggaca ggtatccggt aagcggcagg gtcggaacag gagagcgcac     120
gagggagctt ccaggggggaa acgcctggta tctttatagt cctgtcgggt ttcgccacct    180
ctgacttgag cgtcgatttt tgtgatgctc gtcaggggg cggagcctat ggaaaaacgc     240
cagcaacgcg gcagtggaac gtgcattatg aattagttac gctagggata cagggtaat      300 atagaacccg aacgaccgag cgcagcggcg gccgcgctga taccgccgcc ctcgccgcag     360
ttaattaaag tcagtgagcg aggaagcgcg taactataac ggtcctaagg tagcgaatcc     420
tgatgcggta ttttctcctt acgcatctgt gcggtatttc acaccgcata gatcggcaag     480
tgcacaaaca atacttaaat aaatactact cagtaataac ctatttctta gcattttttga    540 cgaaatttgc tattttgtta gagtctttta caccattgt ctccacacct ccgcttacat      600
caacaccaat aacgccattt aatctaagcg catcaccaac attttctggc gtcagtccac     660
cagctaacat aaaatgtaag cttttcgggggc tctcttgcct tccaacccag tcagaaatcg   720
agttccaatc caaaagttca cctgtcccac ctgcttctga atcaaacaag ggaataaacg     780
aatgaggttt ctgtgaagct gcactgagta gtatgttgca gtcttttgga aatacgagtc     840
ttttaataac tggcaaaccg aggaactctt ggtattcttg ccacgactca tctccatgca     900
gtggagccaa tcaattcttg cggtcaactt tggacgatat caatgccgta atcattgacc     960
agagccaaaa catcctcctt aagttgatta cgaaacacgc caaccaagta tttcggagtg    1020
cctgaactat ttttatatgc ttttacaaga cttgaaattt tccttgcaat aaccgggtca    1080
attgttctct ttctattggg cacacatata atacccagca agtcagcatc ggaatctaga    1140
gcacattctg cggcctctgt gctctgcaag ccgcaaactt tcaccaatgg accagaacta    1200
cctgtgaaat taataacaga catactccaa gctgcctttg tgtgcttaat cacgtatact    1260
cacgtgctca atagtcacca atgccctccc tcttggccct ctccttttct ttttcgacc     1320 gaattaattc ttaatcggca aaaaagaaa agctccggat caagattgta cgtaaggtga    1380
caagctattt ttcaataaag aatatcttcc actactgcca tctggcgtca taactgcaaa    1440
gtacacatat attacgatgc tgttctatta aatgcttcct atattatata tatagtaatg    1500
tcgtgatcta tggtgcactc tcagtacaat ctgctctgat gccgcatagt taagccagcc    1560
ccgacacccg ccaacacccg ctgacgcgcc ctgacgggct tgtctgctcc cggcatccgc    1620
ttacagacaa gctgtgaccg tctccgggag ctgcatgtgt cagaggtttt caccgtcatc    1680
accgaaacgc gcgagacgaa agggcctcgt gatacgccta ttttttatagg ttaatgtcat    1740 gataataatg gtttcttaga cggatcgctt gcctgtaact tacacgcgcc tcgtatcttt    1800
taatgatgga ataatttggg aatttactct gtgtttattt attttttatgt tttgtatttg    1860 gatttttagaa agtaaataaa gaaggtagaa gagttacgga atgaagaaaa aaaaataaac    1920
aaaggtttaa aaaatttcaa caaaaagcgt actttacata tatatttatt agacaagaaa     1980
agcagattaa atagatatac attcgattaa cgataagtaa aatgtaaaat cacaggattt    2040
tcgtgtgtgg tcttctacac agacaaggtg aaacaattcg gcattaatac ctgagagcag    2100
```

```
gaagagcaag ataaaaggta gtatttgttg gcgatccccc tagagtcttt tacatcttcg    2160
gaaaacaaaa actattttt ctttaatttc tttttttact ttctatttt aatttatata     2220 tttatattaa aaaatttaaa ttataattat ttttatagca cgtgatgaaa aggacccagg   2280
tggcactttt cggggaaatg tgcgcggaac ccctatttgt ttattttct aaatacattc    2340 aaatatgtat ccgctcatga gacaataacc ctgataaatg cttcaataat attgaaaaag  2400
gaagagtatg agtattcaac atttccgtgt cgcccttatt cccttttttg cggcattttg  2460
ccttcctgtt tttgctcacc cagaaacgct ggtgaaagta aaagatgctg aagatcagtt  2520
gggacgcgta gtctagacca gccaggacag aaatgcctcg acttcgctgc tacccaaggt  2580
tgccgggtga cgcacaccgt ggaaacggat gaaggcacga acccagtgga cataagcctg  2640
ttcggttcgt aagctgtaat gcaagtagcg tatgcgctca cgcaactggt ccagaacctt  2700
gaccgaacgc agcggtggta acggcgcagt ggcggttttc atggcttgtt atgactgttt  2760
ttttggggta cagtctatgc ctcgggcatc caagcagcaa gcgcgttacg ccgtgggtcg  2820
atgtttgatg ttatggagca gcaacgatgt tacgcagcag ggcagtcgcc ctaaaacaaa  2880
gttaaacatt atgagggaag cggtgatcgc cgaagtatcg actcaactat cagaggtagt  2940
tggcgccatc gagcgccatc tcgaaccgac gttgctggcc gtacatttgt acggctccgc  3000
agtggatggc ggcctgaagc cacacagtga tattgatttg ctggttacgg tgaccgtaag  3060
gcttgatgaa acaacgcggc gagctttgat caacgacctt ttggaaactt cggcttcccc  3120
tggagagagc gagattctcc gcgctgtaga agtcaccatt gttgtgcacg acgacatcat  3180
tccgtggcgt tatccagcta agcgcgaact gcaatttgga gaatggcagc gcaatgacat  3240
tcttgcaggt atcttcgagc cagccacgat cgacattgat ctggctatct tgctgacaaa  3300
agcaagagaa catagcgttg ccttggtagg tccagcggcg gaggaactct tgatccggt   3360 tcctgaacag gatctatttg aggcgctaaa tgaaacctta acgctatgga actcgccgcc  3420
cgactgggct ggcgatgagc gaaatgtagt gcttacgttg tcccgcattt ggtacagcgc  3480
agtaaccggc aaaatcgcgc cgaaggatgt cgctgccggc tgggcaatgg agcgcctgcc  3540
ggcccagtat cagcccgtca tacttgaagc tagacaggct tatcttggac aagaagaaga  3600
tcgcttggcc tcgcgcgcag atcagttgga agaatttgtc cactacgtga aaggcgagat  3660
caccaaggta gtcggcaaat aaccctcgag cattcaaggc gccttgatta tttgacgtgg  3720
tttgatggcc tccacgcacg ttgtgatatg tagatgagag cgttggttgg tggatcaagc  3780
ccacgcgtag gcaatcctcg agcagatccg ccaggcgtgt atatatagcg tggatggcca  3840
ggcaacttta gtgctgacac atacaggcat atatatgt gtgcgacaac acatgatcat   3900
atggcatgca tgtgctctgt atgtatataa aactcttgtt ttcttctttt ctctaaatat  3960
tctttcctta tacattagga cctttgcagc ataaattact atacttctat agacacacaa  4020
acacaaatac acacactaaa ttaataacag gcccctttc ctttgtcgat atcatgtaat   4080
tagttatgtc acgcttacat tcacgccctc cccccacatc cgctctaacc gaaaaggaag  4140
gagttagaca acctgaagtc taggtcccta tttatttttt tatagttatg ttagtattaa  4200
gaacgttatt tatatttcaa attttctttt ttttctgta caaacgcgtg tacgcatgta   4260
acattatact gaaaaccttg cttgagaagg ttttgggacg ctcgaaggct taatttgta   4320 atcattatca ctttacgggt cctttccggt gatccgacag gttacggggc ggcgacctcg  4380
cgggttttcg ctatttatga aaattttccg gtttaaggcg tttccgttct tcttcgtcat  4440
```

```
aacttaatgt ttttatttaa aatacctcgc gagtggcaac actgaaaata cccatggagc      4500
ggcgtaaccg tcgcacagga tctaggtgaa gatccttttt gataatctca tgaccaaaat      4560
cccttaacgt gagttttcgt tccactgagc gtcagacccc gtagaaaaga tcaaaggatc      4620
ttcttgagat cctttttttc tgcgcgtaat ctgctgcttg caaacaaaaa aaccaccgct      4680
accagcggtg gtttgtttgc cggatcaaga gctaccaact cttttttccga aggtaactgg      4740 cttcagcaga gcgcagatac caaatactgt ccttctagtg tagccgtagt taggccacca      4800
cttcaagaac tctgtagcac cgcctacata cctcgctctg ctaatcctgt taccagtggc      4860
tgctgccagt ggcgataagt cgtgtcttac cgggttggac tcaagacgat agttaccgga      4920
taaggcgcag cggtcgggct gaacggggggg ttcgtgcaca cagcccagct tggagcg       4977

<210> SEQ ID NO 114
<211> LENGTH: 5079
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 114
acgacctaca ccgaactgag atacctacag cgtgagctat gagaaagcgc cacgcttccc        60
gaagggagaa aggcggacag gtatccggta agcggcaggg tcggaacagg agagcgcacg       120
agggagcttc caggggggaaa cgcctggtat ctttatagtc ctgtcgggtt tcgccacctc       180
tgacttgagc gtcgattttt gtgatgctcg tcagggggggc ggagcctatg gaaaaacgcc       240
agcaacgcgg cagtggaacg tgcattatga attagttacg ctagggataa cagggtaata       300
tagaacccga cgaccgagc gcagcggcgg ccgcgctgat accgccgccc tcgccgcagt       360
taattaaagt cagtgagcga ggaagcgcgt aactataacg gtcctaaggt agcgaatcct       420
gatgcggtat tttctcctta cgcatctgtg cggtatttca caccgcatag atcggcaagt       480
gcacaaacaa tacttaaata aatactactc agtaataacc tatttcttag cattttttgac       540 gaaatttgct atttttgttag agtcttttac accatttgtc tccacacctc cgcttacatc       600
aacaccaata acgccattta atctaagcgc atcaccaaca ttttctggcg tcagtccacc       660
agctaacata aaatgtaagc tttcgggggct ctcttgcctt ccaacccagt cagaaatcga       720
gttccaatcc aaaagttcac ctgtcccacc tgcttctgaa tcaaacaagg gaataaacga       780
atgaggtttc tgtgaagctg cactgagtag tatgttgcag tcttttggaa atacgagtct       840
tttaataact ggcaaaccga ggaactcttg gtattcttgc cacgactcat ctccatgcag       900
tggagccaat caattcttgc ggtcaacttt ggacgatatc aatgccgtaa tcattgacca       960
gagccaaaac atcctcctta agttgattac gaaacacgcc aaccaagtat tcggagtgc       1020 ctgaactatt tttatatgct tttacaagac ttgaaatttt ccttgcaata accgggtcaa      1080
ttgttctctt tctattgggc acacatataa tacccagcaa gtcagcatcg gaatctagag      1140
cacattctgc ggcctctgtg ctctgcaagc cgcaaacttt caccaatgga ccagaactac      1200
ctgtgaaatt aataacagac atactccaag ctgcctttgt gtgcttaatc acgtatactc      1260
acgtgctcaa tagtcaccaa tgccctccct cttggccctc tccttttctt ttttcgaccg      1320
aattaattct taatcggcaa aaaagaaaa gctccggatc aagattgtac gtaaggtgac      1380
aagctatttt tcaataaaga atatcttcca ctactgccat ctggcgtcat aactgcaaag      1440
tacacatata ttacgatgct gttctattaa atgcttccta tattatatat atagtaatgt      1500
```

```
cgtgatctat ggtgcactct cagtacaatc tgctctgatg ccgcatagtt aagccagccc    1560
cgacacccgc caacacccgc tgacgcgccc tgacgggctt gtctgctccc ggcatccgct    1620
tacagacaag ctgtgaccgt ctccgggagc tgcatgtgtc agaggttttc accgtcatca    1680
ccgaaacgcg cgagacgaaa gggcctcgtg atacgcctat ttttataggt taatgtcatg    1740
ataataatgg tttcttagac ggatcgcttg cctgtaactt acacgcgcct cgtatctttt    1800
aatgatggaa taatttggga atttactctg tgtttattta tttttatgtt ttgtatttgg    1860
attttagaaa gtaaataaag aaggtagaag agttacggaa tgaagaaaaa aaaataaaca    1920
aaggtttaaa aaatttcaac aaaaagcgta ctttacatat atatttatta gacaagaaaa    1980
gcagattaaa tagatataca ttcgattaac gataagtaaa atgtaaaatc acaggatttt    2040
cgtgtgtggt cttctacaca gacaaggtga acaattcgg cattaatacc tgagagcagg    2100
aagagcaaga taaaggtag tatttgttgg cgatccccct agagtctttt acatcttcgg    2160
aaaacaaaaa ctattttttc tttaatttct tttttactt tctattttta atttatatat    2220
ttatattaaa aaatttaaat tataattatt tttatagcac gtgatgaaaa ggacccaggt    2280 ggcactttc ggggaaatgt gcgcggaacc cctatttgtt tattttctct aatacattca    2340
aatatgtatc cgctcatgag acaataaccc tgataaatgc ttcaataata ttgaaaaagg    2400
aagagtatga gtattcaaca tttccgtgtc gcccttattc ccttttttgc ggcattttgc    2460
cttcctgttt ttgctcaccc agaaacgctg gtgaaagtaa aagatgctga agatcagttg    2520
ggacgcgtag tctagaccag ccaggacaga atgcctcga cttcgctgct acccaaggtt    2580
gccgggtgac gcacaccgtg aaacggatg aaggcacgaa cccagtggac ataagcctgt    2640
tcggttcgta agctgtaatg caagtagcgt atgcgctcac gcaactggtc cagaaccttg    2700
accgaacgca gcgtggtaa cggcgcagtg gcggttttca tggcttgtta tgactgtttt    2760
tttggggtac agtctatgcc tcgggcatcc aagcagcaag cgcgttacgc cgtgggtcga    2820
tgtttgatgt tatggagcag caacgatgtt acgcagcagg gcagtcgccc taaaacaaag    2880
ttaaacatta tgagggaagc ggtgatcgcc gaagtatcga ctcaactatc agaggtagtt    2940
ggcgccatcg agcgccatct cgaaccgacg ttgctggccg tacatttgta cggctccgca    3000
gtggatggcg gcctgaagcc acacagtgat attgatttgc tggttacggt gaccgtaagg    3060
cttgatgaaa caacgcggcg agctttgatc aacgaccttt tggaaacttc ggcttcccct    3120
ggagagagcg agattctccg cgctgtagaa gtcaccattg ttgtgcacga cgacatcatt    3180
ccgtggcgtt atccagctaa gcgcgaactg caatttggag aatggcagcg caatgacatt    3240
cttgcaggta tcttcgagcc agccacgatc gacattgatc tggctatctt gctgacaaaa    3300
gcaagagaac atagcgttgc cttggtaggt ccagcggcgg aggaactctt tgatccggtt    3360
cctgaacagg atctatttga ggcgctaaat gaaaccttaa cgctatggaa ctcgccgccc    3420
gactgggctg gcgatgagcg aaatgtagtg cttacgttgt cccgcatttg gtacagcgca    3480
gtaaccggca aaatcgcgcc gaaggatgtc gctgccggct gggcaatgga gcgcctgccg    3540
gcccagtatc agcccgtcat acttgaagct agacaggctt atcttggaca agaagaagat    3600
cgcttggcct cgcgcgcaga tcagttggaa gaatttgtcc actacgtgaa aggcgagatc    3660
accaaggtag tcggcaaata accctcgagc attcaaggcg ccttgattat tgacgtggt    3720 ttgatggcct ccacgcacgt tgtgatatgt agatgactcg taggaacaat tcgggcccc    3780 tgcgtgttct tctgaggttc atcttttaca tttgcttctg ctggataatt ttcagaggca    3840
acaaggaaaa attagatggc aaaaagtcgt ctttcaagga aaaatcccca ccatctttcg    3900
```

```
agatcccctg taacttattg gcaactgaaa gaatgaaaag gaggaaaata caaatatac    3960 tagaactgaa aaaaaaaaag tataaataga gacgatatat gccaatactt cacaatgttc    4020
gaatctattc ttcatttgca gctattgtaa aataataaaa catcaagaac aaacaagctc    4080
aacttgtctt ttctaagaac aaagaataaa cacaaaaaca aaaagttttt ttaattttaa    4140
tcaaaaaaca ggcccctttt cctttgtcga tatcatgtaa ttagttatgt cacgcttaca    4200
ttcacgccct cccccacat ccgctctaac cgaaaaggaa ggagttagac aacctgaagt    4260
ctaggtccct atttattttt ttatagttat gttagtatta agaacgttat ttatatttca    4320
aatttttctt ttttttctgt acaaacgcgt gtacgcatgt aacattatac tgaaaacctt    4380
gcttgagaag gttttgggac gctcgaaggc tttaatttgt aatcattatc actttacggg    4440
tcctttccgg tgatccgaca ggttacgggg cggcgacctc gcgggttttc gctatttatg    4500
aaaattttcc ggtttaaggc gtttccgttc ttcttcgtca taacttaatg ttttttattta    4560 aaatacctcg cgagtggcaa cactgaaaat acccatggag cggcgtaacc gtcgcacagg    4620
atctaggtga agatcctttt tgataatctc atgaccaaaa tcccttaacg tgagttttcg    4680
ttccactgag cgtcagaccc cgtagaaaag atcaaaggat cttcttgaga tcctttttt    4740 ctgcgcgtaa tctgctgctt gcaaacaaaa aaaccaccgc taccagcggt ggtttgtttg    4800
ccggatcaag agctaccaac tctttttccg aaggtaactg gcttcagcag agcgcagata    4860
ccaaatactg tccttctagt gtagccgtag ttaggccacc acttcaagaa ctctgtagca    4920
ccgcctacat acctcgctct gctaatcctg ttaccagtgg ctgctgccag tggcgataag    4980
tcgtgtctta ccgggttgga ctcaagacga tagttaccgg ataaggcgca gcggtcgggc    5040
tgaacggggg gttcgtgcac acagcccagc ttggagcga    5079
```

<210> SEQ ID NO 115
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 115

Met Glu Glu Ser Leu Trp Val Val Thr Ala Thr Val Val Val Phe
1               5                   10                  15

Ala Leu Ala Lys Leu Leu Lys Lys Ser Ser Ile Ser Thr Met Glu
            20                  25                  30

Trp Pro Lys Gly Pro Lys Lys Leu Pro Ile Ile Gly Asn Leu His Gln
        35                  40                  45

Leu Gly Gly Glu Ala Phe His Val Val Leu Ala Asn Leu Ala Lys Ile
    50                  55                  60

His Gly Thr Val Met Thr Ile Trp Val Gly Ala Trp Arg Pro Met Ile
65                  70                  75                  80

Val Ile Ser Asp Ile Asp Lys Ala Trp Glu Val Leu Val Asn Lys Ser
                85                  90                  95

Ser Asp Tyr Ala Gly Arg Asp Phe Pro Glu Ile Thr Lys Ile Ile Ser
            100                 105                 110

Ala Asn Trp Lys Asn Ile Ser Cys
        115                 120

<210> SEQ ID NO 116
<211> LENGTH: 120

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Met Ala Pro Ile Asn Ile Glu Gly Asn Asp Phe Trp Met Leu Ala Cys
1               5                   10                  15

Thr Val Ile Leu Val Phe Ala Leu Val Lys Phe Met Phe Ser Lys Ile
            20                  25                  30

Ser Phe Tyr Gln Ser Ala Asn Thr Thr Glu Trp Pro Ala Gly Pro Lys
        35                  40                  45

Thr Leu Pro Ile Ile Gly Asn Leu His Gln Leu Gly Gly Val Pro
    50                  55                  60

Leu Gln Val Ala Leu Ala Asn Leu Ala Lys Val Tyr Gly Gly Ala Phe
65                  70                  75                  80

Thr Ile Trp Ile Gly Ser Trp Val Pro Met Ile Val Ile Ser Asp Ile
                85                  90                  95

Asp Asn Ala Arg Glu Val Leu Val Asn Lys Ser Ala Asp Tyr Ser Ala
            100                 105                 110

Arg Asp Val Pro Asp Ile Leu Lys
        115                 120

<210> SEQ ID NO 117
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Met Glu Glu Ser Leu Trp Val Val Thr Ala
1               5                   10
```